(12) United States Patent
Bräuer et al.

(10) Patent No.: US 9,062,041 B2
(45) Date of Patent: Jun. 23, 2015

(54) 2H-INDAZOLES AS EP$_2$ RECEPTOR ANTAGONISTS

(71) Applicant: Bayer Intellectual Property GmbH, Monheim (DE)

(72) Inventors: Nico Bräuer, Falkensee (DE); Anne Mengel, Berlin (DE); Ulrike Charlotte Röhn, Berlin (DE); Andrea Rotgeri, Berlin (DE); Bernd Buchmann, Hohen Neuendorf (DE); Bernhard Lindenthal, Berlin (DE); Antonius Ter Laak, Berlin (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 14/361,213

(22) PCT Filed: Nov. 26, 2012

(86) PCT No.: PCT/EP2012/073556
§ 371 (c)(1),
(2) Date: May 28, 2014

(87) PCT Pub. No.: WO2013/079425
PCT Pub. Date: Jun. 6, 2013

(65) Prior Publication Data
US 2014/0336172 A1 Nov. 13, 2014

(30) Foreign Application Priority Data

Nov. 28, 2011 (DE) .......................... 10 2011 087 170
Apr. 24, 2012 (DE) .......................... 10 2012 206 715

(51) Int. Cl.

| | | |
|---|---|---|
| A61K 31/397 | (2006.01) |
| A61K 31/5377 | (2006.01) |
| A61K 31/505 | (2006.01) |
| A61K 31/445 | (2006.01) |
| C07D 413/02 | (2006.01) |
| C07D 239/02 | (2006.01) |
| C07D 211/68 | (2006.01) |
| C07D 231/56 | (2006.01) |
| C07D 417/14 | (2006.01) |
| C07D 401/14 | (2006.01) |
| C07D 413/14 | (2006.01) |
| C07D 401/06 | (2006.01) |
| C07D 403/06 | (2006.01) |
| C07D 403/14 | (2006.01) |
| C07D 407/14 | (2006.01) |
| A61K 45/06 | (2006.01) |
| A61K 31/416 | (2006.01) |
| A61K 31/454 | (2006.01) |
| A61K 31/4545 | (2006.01) |
| A61K 31/506 | (2006.01) |
| A61K 31/513 | (2006.01) |
| C07D 405/14 | (2006.01) |

(52) U.S. Cl.
CPC ............ *C07D 417/14* (2013.01); *C07D 401/14* (2013.01); *C07D 413/14* (2013.01); *C07D 401/06* (2013.01); *C07D 403/06* (2013.01); *C07D 403/14* (2013.01); *C07D 407/14* (2013.01); *A61K 45/06* (2013.01); *A61K 31/416* (2013.01); *A61K 31/454* (2013.01); *A61K 31/4545* (2013.01); *A61K 31/506* (2013.01); *A61K 31/513* (2013.01); *A61K 31/5377* (2013.01); *C07D 405/14* (2013.01)

(58) Field of Classification Search
USPC ......... 514/210.18, 234.5, 256, 274, 318, 322; 544/130, 316; 546/194, 199; 548/362.5
See application file for complete search history.

(56) References Cited

U.S. PATENT DOCUMENTS

| | | |
|---|---|---|
| 5,861,419 A | 1/1999 | Dube et al. |
| 2005/0059742 A1 | 3/2005 | Jabbour et al. |
| 2005/0124577 A1 | 6/2005 | Tani et al. |

FOREIGN PATENT DOCUMENTS

| | | |
|---|---|---|
| DE | 122009049662 A1 | 4/2011 |
| WO | 9803484 A1 | 1/1998 |
| WO | 03016254 A1 | 2/2003 |
| WO | 03030911 A1 | 4/2003 |

(Continued)

OTHER PUBLICATIONS

Matsumoto et al., "Diversification of Cyclooxygenase-2-Derived Prostaglandins in Ovulation and Implantation1," Biology of Reproduction, 2001, 64:1557-1565.

(Continued)

*Primary Examiner* — Samantha Shterengarts

(57) ABSTRACT

The present invention relates to novel 2H-indazoles of the general formula (I), methods for the preparation thereof and the use thereof for the production of pharmaceutical agents for the treatment of diseases and indications which are linked with the EP$_2$-receptor.

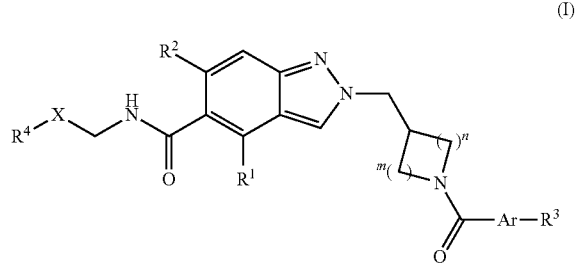

(I)

9 Claims, No Drawings

(56) References Cited

FOREIGN PATENT DOCUMENTS

| | | |
|---|---|---|
| WO | 03035064 A1 | 5/2003 |
| WO | 03053923 A2 | 7/2003 |
| WO | 03064391 A1 | 8/2003 |
| WO | 2004032964 A1 | 4/2004 |
| WO | 2007057232 A1 | 5/2007 |
| WO | 2007071456 A1 | 6/2007 |
| WO | 2007091107 A1 | 8/2007 |
| WO | 2008028689 A1 | 3/2008 |
| WO | 2008028690 A1 | 3/2008 |
| WO | 2008028691 A1 | 3/2008 |
| WO | 2008070599 A1 | 6/2008 |
| WO | 2008139287 A1 | 11/2008 |
| WO | 2008152094 A2 | 12/2008 |
| WO | 2008152097 A1 | 12/2008 |
| WO | 2008152099 A2 | 12/2008 |
| WO | 2009007421 A1 | 1/2009 |
| WO | 2009007422 A1 | 1/2009 |
| WO | 2009063365 A1 | 5/2009 |
| WO | 2010008777 A2 | 1/2010 |
| WO | 2010052625 A1 | 5/2010 |
| WO | 2013079425 A1 | 6/2013 |

OTHER PUBLICATIONS

Hizaki et al, "Abortive expansion of the cumulus and impaired fertility in mice lacking the prostaglandin E receptor subtype EP2," Proc. Natl. Acad. Sci., USA, Aug. 1999, 96(18):10501-10506.

Forselles et al., "In vitro and in vivo characterization of PF-04418948, a novel, potent and selective prostaglandin EP2 receptor antagonist," British Journal of Pharmacology, 2011, 164:1847-1856.

Roveto et al., "Discovery of novel thiazole EP2 antagonists," ACS Nattional Meeting of the Division of Medicinal Chemistry, Mar. 21-25, 2010, San Francisco CA, USA, MEDI 173.

Merck Index online: "Etoricoxib," downloaded from https://www.rsc.org/Merck-Index on Jan. 22, 2015.

2H-INDAZOLES AS EP$_2$ RECEPTOR ANTAGONISTS

The present invention relates to novel EP$_2$ receptor antagonists, the production thereof and the use thereof as drugs, and pharmaceutical preparations which contain the new 2H-indazoles.

It has already long been known that prostaglandins are key molecules in the processes of female reproductive biology, such as for example the regulation of ovulation and fertilization. Effects on uterine contractions, implantation, deciduation (e.g. placenta formation) and menstruation have also been described, or are the subject of scientific studies. Prostaglandins also play an important part in pathological changes in the reproductive tract, including menorrhagia, dysmenorrhoea, endometriosis, fibroids (myomas) and cancer, and in general in inflammatory (e.g. Crohn disease), infections (e.g. bacterial infections) and neurodegenerative processes (e.g. Alzheimer, ALS), and functions in the immune defence, angiogenesis, pain, wound healing and interactions with the endocrine system (e.g. aromatase induction) are known. Hitherto, the mechanism through which prostaglandins effect the changes has not been completely elucidated. Recent findings indicate that prostaglandins, their receptors and their signal transduction paths are involved in processes such as angiogenesis, apoptosis, proliferation and in inflammatory/anti-inflammatory processes.

The effects of the prostaglandins are mediated through their G protein coupled receptors, which are located in the cell membrane. Of particular interest is prostaglandin E$_2$ (PGE$_2$), which effects a great variety of cellular actions by binding to functionally different receptor subtypes, namely the EP$_1$, EP$_2$, EP$_3$ and EP$_4$ receptors. The receptor subtypes to which prostaglandin E$_2$ binds appear to be of particular importance for the receptor-mediated actions which are involved in the regulation of fertility. Thus it could be shown that the reproductive functions are impaired in EP$_2$ knockout mice (EP$_2^{-/-}$), e.g. in mice which no longer have a functional PGE$_2$ receptor subtype EP$_2$, and that these animals have a smaller "litter" (Matsumoto et al., 2001, Biology of Reproduction 64, 1557-1565). Likewise it could be shown that these EP$_2$ knockout mice (Hizaki et al., 1999, Proc Natl Acad Sci U.S.A. August 31; 96(18):10501-10506) display markedly decreased cumulus expansion and severe subfertility, which is to be regarded as being causally linked with decreased reproductive processes such as ovulation and fertilization.

Accordingly, the EP$_2$ receptor is an important target for the development of drugs for the regulation of female fertility. The existence of the 4 subclasses of the PGE$_2$ receptor opens up the possibility of targeted development of selectively active compounds. Previously, however, hardly any selective EP$_2$ receptor antagonists were known, since most known compounds also bind to the other PGE$_2$ receptor subtypes, such as for example to the EP$_4$ receptor or other prostaglandin receptors such as the DP receptor.

EP$_2$ receptor antagonists are for example described in the application US2005059742 and EP$_{1467738}$ (Jabbour, Medical Research Council). A method is claimed wherein an EP$_2$ and/or an EP$_4$ antagonist can be used for the treatment of menorrhagia and dysmenorrhoea. AH6809 is disclosed as an antagonist of the EP$_2$ or EP$_4$ receptor, and no other specific antagonists and no new compounds are disclosed.

In the application WO03/016254, Ono Pharmaceutical claims the production of arylcarboxylic acids or saturated carboxylic acid derivatives which are aryl group or heterocycle-substituted inter alia as PGE$_2$ receptor antagonists. The disclosed compounds are claimed for the treatment of a large number of diseases, also including allergic diseases, Alzheimer's disease, pain, abortion, menstrual problems, menorrhagia and dysmenorrhoea, endometriosis, diseases of the bones, ischaemia etc. However, the compounds described are characterized by a particularly high affinity for the EP$_3$ receptor. In a further application (WO04/032964), newer compounds are described which are also characterized by a particularly high affinity for the EP$_3$ receptor, but also find use as EP$_2$ antagonists, for the treatment and prophylaxis of allergic diseases.

In the applications from the company Applied Research Systems WO03/053923 (substituted pyrrolidines) or WO03/035064 (substituted pyrazolidiones), compounds for the treatment of diseases which are associated with prostaglandins, such as for example infertility, hypertension and osteoporosis, are claimed. The compounds bind to the EP$_4$ and the EP$_2$ receptor subtypes.

In the application WO03/064391 (Pfizer Products), metabolites of [3-[[N-(4-tert-butylbenzyl)-(pyridin-3-ylsulphonyl)amino]methyl]acetic acid are described, which inhibit the binding of [$^3$H] prostaglandin E$_2$ to the EP$_2$ receptor. The use of these metabolites for the treatment of osteoporosis is disclosed.

In the application US2005124577, Tani et al. claim 8-aza-prostaglandin derivatives for the treatment of immunological diseases, allergic diseases, premature labour, abortion, etc. The compounds bind to the EP$_2$ and the EP$_4$ receptor.

In the patent applications from Bayer Schering Pharma AG (WO2007/057232, WO2007/071456, WO2008/028689, WO2008/028690 WO2008/028691, WO2008/0152099, WO2008/0152097, WO2008/0152094, WO2009/007421, WO2009/007422) and DE 10 2009 049 662 A1, selective antagonists of the EP$_2$ receptors are for the first time claimed.

In the applications from Summit Corporation PLC (WO2007/091107) and C M Sun et al. (WO2008/070599) 2H-indazoles are disclosed, but not for the treatment of fertility disorders.

In the applications from Pfizer WO2009/063365 and WO2008/139287, azetidines and in WO2010/052625 pyrrolidones as antagonists of the EP$_2$ receptor, and the use thereof for the treatment of EP$_2$-mediated conditions such as endometriosis and leiomyomata are claimed.

In a publication (British Journal of Pharmacology (2011), 164, 1847-1856), Forselles et al. (Pfizer) describe selective antagonists of the EP$_2$ receptors. The compounds are azetidines which display an in-vivo influence on the blood flow. The compounds display high protein binding.

In a publication by P. M. Roveto et al. (239. ACS National Meeting of the Division of Medicinal Chemistry, 21.-25. March 2010, San Francisco, USA; MEDI 173), novel thiazoles are described as EP$_2$ antagonists.

EP$_2$ receptor antagonists are also described in the application by Ligand Pharmaceuticals Inc. (WO2010/008777). These compounds are bicyclic pyridine derivatives. The compounds are claimed for the treatment of pain, but also for the treatment of Alzheimer's disease, multiple sclerosis and fertility disorders.

For the regulation of the processes which are ultimately responsible for ovulation and fertilization and which thus contribute to the inhibition of fertility, other in vivo active antagonists of the EP$_2$ receptor with improved properties are needed.

Hence the purpose of the present invention was to provide other antagonists of the EP$_2$ receptor with improved properties which are available in vivo, and thus effective, and stable.

This problem was solved through the compounds of the general formula I,

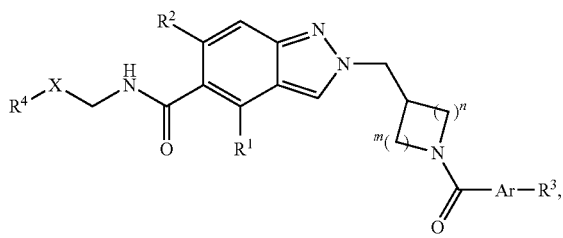

(I)

wherein
$R^1$: means H, $C_1$-$C_2$ alkyl or $C_1$-$C_2$ alkyloxy;
$R^2$: H or methyl;
  subject to the proviso that one of the two residues $R^1$ or $R^2$ equals H;
X: —$(CH_2)_l$—, —$(CH_2)_k$—O—, —$CH_2$—S—, $CH_2$—$S(O)_2$—, —$CH(CH_3)$—, —$CH(CH_3)$—O— or —$C(CH_3)_2$—O—;
k: 1 or 2;
l: 0, 1 or 2;
$R^4$: H, $C_1$-$C_4$ alkyl, $C_3$-$C_4$ cycloalkyl, or $CH_2$—$C_3$-$C_4$ cycloalkyl;
and in the case of X: —$CH_2$— or —$CH(CH_3)$—
$R^4$: additionally a 4-6-membered heterocyclyl residue;
and in the case of X: —$(CH_2)_1$— or —$CH(CH_3)$—
$R^4$: additionally CN;
or
X together with $R^4$ form a 4-6-membered heterocyclyl residue via a ring carbon linkage;
m: 1 or 2;
n: 1 or 2;
Ar: a 6-10-membered aryl or 5-10-membered hetaryl residue,
$R^3$: halogen, CN, $SF_5$, $C_1$-$C_4$ alkyl, $C_3$-$C_6$ cycloalkyl, $C_4$-$C_6$ heterocyclyl, O—$C_1$-$C_4$ alkyl, O—$C_3$-$C_6$ cycloalkyl, O—$C_4$-$C_6$ heterocyclyl, S—$C_1$-$C_4$ alkyl, $S(O)_2$—$C_1$-$C_4$ alkyl, Ar', O—Ar', $C(CH_3)_2$—CN or $C(CH_3)_2$—OH;
Ar': an optionally singly or doubly substituted 6-membered aryl or 5-6-membered heteroaryl residue;
  wherein the substituents are selected from F, Cl, CN, $C_1$-$C_4$ alkyl, O—$C_1$-$C_4$ alkyl, $C(CH_3)_2$—CN, $C(CH_3)_2$—OH and $C(O)NH_2$;
and isomers, diastereomers, enantiomers and salts or cyclodextrin clathrates thereof, for the production of drugs which overcome the known disadvantages and have improved properties such as good in-vivo activity, good solubility and stability.

The compounds according to the invention have an antagonistic action on the $EP_2$ receptor and thus inter alia serve for female fertility control.

$C_1$-$C_2$ alkyl or $C_1$-$C_4$ alkyl should each be understood to mean a linear or branched alkyl residue, such as for example methyl, ethyl, propyl, isopropyl, butyl, isobutyl, sec-butyl or tert-butyl.

The alkyl residues can optionally be singly or multiply substituted with fluorine.

The hydrogen atoms can optionally be replaced by deuterium.

$C_1$-$C_2$ alkoxy or $C_1$-$C_4$ alkoxy should be understood to mean a linear or branched residue of the formula alkyl-O—, such as for example methoxy, ethoxy, n-propoxy, isopropoxy, n-butoxy, sec-butoxy, isobutoxy or tert-butyloxy.

The alkoxy residues can optionally be singly or multiply substituted with fluorine.

$C_3$-$C_6$ cycloalkyl should be understood to mean monocyclic alkyl rings such as cyclopropyl, cyclobutyl, cyclopentyl and cyclohexyl.

The cycloalkyl residues can optionally be singly or multiply substituted with fluorine. 4-6-membered heterocyclyl should be understood to mean monocyclic rings which instead of the carbon atoms contain one or more hetero atoms, such as oxygen, sulphur and/or nitrogen or a hetero group such as —S(O)— or —$SO_2$—. The linking bond can be at any carbon atom or at a nitrogen atom.

For example, azetidinyl, pyrrolidinyl, piperidinyl, piperazinyl, 1,4-diazepanyl, morpholinyl, thiomorpholinyl, oxetanyl, tetrahydrofuranyl, tetrahydropyranyl, 1,4-dioxanyl and 2-oxo-oxazolidinyl may be mentioned.

The heterocyclyl residues can optionally be singly or multiply substituted with fluorine, hydroxy, methoxy or with oxo.

Halogen should in each case be understood to mean fluorine, chlorine, bromine or iodine.

The $C_6$-$C_{10}$-membered aryl residue in each case comprises 6-10 carbon atoms and can be benzo-condensed. Phenyl and naphthyl may be mentioned The $C_6$-$C_{10}$-membered aryl residue can optionally be singly substituted with fluorine, chlorine or a methyl group.

The $C_5$-$C_{10}$ heteroaryl residue should be understood to mean mono- or bicyclic ring systems which each contain 5-10 ring atoms and which instead of the carbon can contain one or more identical or different hetero atoms, such as oxygen, sulphur or nitrogen. The linking bond can be at any carbon atom or at a nitrogen atom.

For example, thienyl, thiazolyl, furyl, pyrrolyl, oxazolyl, imidazolyl, pyrazolyl, isoxazolyl, isothiazolyl, oxadiazolyl, triazolyl, thiadiazolyl, tetrazolyl, pyridyl, pyridazinyl, pyrimidinyl, pyrazinyl, triazinyl, phthalidyl, thiophthalidyl, indolyl, isoindolyl, indazolyl, benzothiazolyl, benzofuryl, benzothienyl, benzimidazolyl, benzoxazolyl, azocinyl, indolizinyl, purinyl, isoquinolinyl, quinolinyl, quinolizinyl, quinazolinyl, quinoxalinyl, cinnolinyl, phthalazinyl, 1,7- or 1,8-naphthyridinyl and pteridinyl may be mentioned.

The $C_5$-$C_{10}$-membered heteroaryl residue can optionally be singly substituted by fluorine, chlorine or a methyl group.

If a basic functional group is contained, the physiologically compatible salts of organic and inorganic acids, such as inter alia hydrochloric acid, sulphuric acid, phosphoric acid, citric acid and tartaric acid, are suitable Preferred are compounds of the formula I, wherein
$R^1$, $R^2$: mean H or methyl;
  subject to the proviso that one of the two residues $R^1$ or $R^2$ equals H;
X: —$(CH_2)_1$— or —$(CH_2)_k$—O—;
k: 1 or 2;
l: 0, 1 or 2;
$R^4$: $C_1$-$C_4$ alkyl, $C_3$-$C_4$ cycloalkyl or $CH_2$—$C_3$-$C_4$ cycloalkyl;
m, n: 2;
and isomers, diastereomers, enantiomers and salts or cyclodextrin clathrates thereof and $R^3$, Ar and Ar' have the aforesaid meanings.

Also preferred are compounds of the formula I, wherein
$R^1$, $R^2$: mean H or methyl;
  subject to the proviso that one of the two residues $R^1$ or $R^2$ equals H;
X: —$(CH_2)_1$— or —$(CH_2)_k$—O—;
k: 1 or 2;
l: 0, 1 or 2;
$R^4$: $C_1$-$C_4$ alkyl, —$C_3$-$C_4$ cycloalkyl or $CH_2$—$C_3$-$C_4$ cycloalkyl;
m, n: 1;

and isomers, diastereomers, enantiomers and salts or cyclodextrin clathrates thereof and R³, Ar and Ar' have the aforesaid meanings.

Also preferred are compounds of the formula I, wherein
R¹: means a methyl group;
R²: H;
X: —(CH$_2$)$_l$— or —(CH$_2$)$_k$—O—;
k: 1;
l: 0 or 1;
R⁴: C$_1$-C$_4$ alkyl, C$_3$-C$_4$ cycloalkyl or CH$_2$—C$_3$-C$_4$ cycloalkyl;
m, n: 2;
Ar: a phenyl residue;
and isomers, diastereomers, enantiomers and salts or cyclodextrin clathrates thereof and R³ and Ar' have the aforesaid meanings.

Additionally preferred are compounds of the formula I, wherein
R¹: means a methyl group;
R²: H;
X: —(CH$_2$)$_l$— or —(CH$_2$)$_k$—O—;
k: 1;
l: 0 or 1;
R⁴: C$_1$-C$_4$ alkyl, C$_3$-C$_4$ cycloalkyl or CH$_2$—C$_3$-C$_4$ cycloalkyl;
m, n: 1;
Ar: a phenyl residue;
and isomers, diastereomers, enantiomers and salts or cyclodextrin clathrates thereof and R³ and Ar' have the aforesaid meanings.

The following compounds according to the present invention are quite particularly preferred:

1. 2-{[1-(4-cyano-2-fluorobenzoyl)piperidin-4-yl]methyl}-N-(2-methoxyethyl)-4-methyl-2H-indazol-5-carboxamide
2. 2-{[1-(4-tert-butoxybenzoyl)piperidin-4-yl]methyl}-N-(2-methoxyethyl)-4-methyl-2H-indazol-5-carboxamide
3. 2-({1-[4-(4-fluorophenoxy)benzoyl]piperidin-4-yl}methyl)-N-(2-methoxyethyl)-4-methyl-2H-indazol-5-carboxamide
4. N-(2-methoxyethyl)-4-methyl-2-{[1-(4-morpholinobenzoyl)piperidin-4-yl]methyl}-2H-indazol-5-carboxamide
5. 2-({1-[(4'-fluorobiphenyl-4-yl)carbonyl]piperidin-4-yl}methyl)-N-(2-methoxyethyl)-4-methyl-2H-indazol-5-carboxamide
6. 2-{[1-(2-fluoro-4-mesylbenzoyl)piperidin-4-yl]methyl}-N-(2-methoxyethyl)-4-methyl-2H-indazol-5-carboxamide
7. 2-{[1-(2-fluoro-4-methoxybenzoyl)piperidin-4-yl]methyl}-N-(2-methoxyethyl)-4-methyl-2H-indazol-5-carboxamide
8. 2-{[1-(4-bromo-2-fluorobenzoyl)piperidin-4-yl]methyl}-N-(2-methoxyethyl)-4-methyl-2H-indazol-5-carboxamide
9. 2-{[1-(2-fluoro-4-methylbenzoyl)piperidin-4-yl]methyl}-N-(2-methoxyethyl)-4-methyl-2H-indazol-5-carboxamide
10. 2-({1-[2-fluoro-4-(trifluoromethyl)benzoyl]piperidin-4-yl}methyl)-N-(2-methoxyethyl)-4-methyl-2H-indazol-5-carboxamide
11. N-(2-methoxyethyl)-4-methyl-2-({1-[4-(pentafluoro-λ⁶-sulphanyl)benzoyl]piperidin-4-yl}methyl)-2H-indazol-5-carboxamide
12. N-(2-methoxyethyl)-4-methyl-2-{[1-(4-methylbenzoyl)piperidin-4-yl]methyl}-2H-indazol-5-carboxamide
13. 2-({1-[4-(4-chlorophenoxy)benzoyl]piperidin-4-yl}methyl)-N-(2-methoxyethyl)-4-methyl-2H-indazol-5-carboxamide
14. N-(2-methoxyethyl)-4-methyl-2-({1-[4-(4-methylphenoxy)benzoyl]piperidin-4-yl}-methyl)-2H-indazol-5-carboxamide
15. 2-({1-[4-(4-tert-butylphenoxy)benzoyl]piperidin-4-yl}methyl)-N-(2-methoxyethyl)-4-methyl-2H-indazol-5-carboxamide
16. N-(2-methoxyethyl)-4-methyl-2-[(1-{4-[4-(trifluoromethyl)phenoxy]benzoyl}piperidin-4-yl)methyl]-2H-indazol-5-carboxamide
17. N-(2-methoxyethyl)-2-({1-[4-(4-methoxyphenoxy)benzoyl]piperidin-4-yl}methyl)-4-methyl-2H-indazol-5-carboxamide
18. N-(2-methoxyethyl)-4-methyl-2-{[1-(4-phenoxybenzoyl)piperidin-4-yl]methyl}-2H-indazol-5-carboxamide
19. 2-{[1-(4-cyclopropylbenzoyl)piperidin-4-yl]methyl}-N-(2-methoxyethyl)-4-methyl-2H-indazol-5-carboxamide
20. 2-{[1-(4-methoxybenzoyl)piperidin-4-yl]methyl}-N-(2-methoxyethyl)-4-methyl-2H-indazol-5-carboxamide
21. 2-{[1-(4-fluorobenzoyl)piperidin-4-yl]methyl}-N-(2-methoxyethyl)-4-methyl-2H-indazol-5-carboxamide
22. N-(2-methoxyethyl)-4-methyl-2-({1-[4-(trifluoromethyl)benzoyl]piperidin-4-yl}-methyl)-2H-indazol-5-carboxamide
23. 2-{[1-(2-methoxybenzoyl)piperidin-4-yl]methyl}-N-(2-methoxyethyl)-4-methyl-2H-indazol-5-carboxamide
24. N-(2-methoxyethyl)-4-methyl-2-[(1-{4-[(trifluoromethyl)sulphonyl]benzoyl}piperidin-4-yl)methyl]-2H-indazol-5-carboxamide
25. N-(2-methoxyethyl)-4-methyl-2-({1-[3-(trifluoromethyl)benzoyl]piperidin-4-yl}-methyl)-2H-indazol-5-carboxamide
26. N-(2-methoxyethyl)-4-methyl-2-{[1-(3-methylbenzoyl)piperidin-4-yl]methyl}-2H-indazol-5-carboxamide
27. 2-{[1-(3-chlorobenzoyl)piperidin-4-yl]methyl}-N-(2-methoxyethyl)-4-methyl-2H-indazol-5-carboxamide
28. 2-({1-[4-(4-carbamoylphenoxy)benzoyl]piperidin-4-yl}methyl)-N-(2-methoxyethyl)-4-methyl-2H-indazol-5-carboxamide
29. 2-({1-[4-(cyclopentyloxy)benzoyl]piperidin-4-yl}methyl)-N-(2-methoxyethyl)-4-methyl-2H-indazol-5-carboxamide
30. 2-({1-[4-(difluoromethyl)benzoyl]piperidin-4-yl}methyl)-N-(2-methoxyethyl)-4-methyl-2H-indazol-5-carboxamide
31. 2-{[1-(4-cyanobenzoyl)piperidin-4-yl]methyl}-N-(2-methoxyethyl)-4-methyl-2H-indazol-5-carboxamide
32. 2-({1-[4-(1H-imidazol-1-yl)benzoyl]piperidin-4-yl}methyl)-N-(2-methoxyethyl)-4-methyl-2H-indazol-5-carboxamide
33. N-(2-methoxyethyl)-4-methyl-2-({1-[4-(oxazol-2-yl)benzoyl]piperidin-4-yl}methyl)-2H-indazol-5-carboxamide
34. N-(2-methoxyethyl)-4-methyl-2-({1-[4-(oxazol-5-yl)benzoyl]piperidin-4-yl}methyl)-2H-indazol-5-carboxamide
35. N-(2-methoxyethyl)-4-methyl-2-({1-[4-(isoxazol-5-yl)benzoyl]piperidin-4-yl}methyl)-2H-indazol-5-carboxamide
36. N-(2-methoxyethyl)-4-methyl-2-({1-[4-(1H-pyrazol-1-yl)benzoyl]piperidin-4-yl}-methyl)-2H-indazol-5-carboxamide
37. N-(2-methoxyethyl)-4-methyl-2-({1-[4-(1H-1,2,4-triazol-1-yl)benzoyl]piperidin-4-yl}-methyl)-2H-indazol-5-carboxamide 38. 2-({1-[4-(difluoromethoxy)-2-fluorobenzoyl]piperidin-4-yl}methyl)-N-(2-methoxy-ethyl)-4-methyl-2H-indazol-5-carboxamide
39. 2-({1-[2-fluoro-4-(pyrrolidin-1-yl)benzoyl]piperidin-4-yl}methyl)-N-(2-methoxyethyl)-4-methyl-2H-indazol-5-carboxamide
40. 2-({1-[(3,4'-difluorobiphenyl-4-yl)carbonyl]piperidin-4-yl}methyl)-N-(2-methoxyethyl)-4-methyl-2H-indazol-5-carboxamide
41. 2-({1-[(3-fluoro-4'-methoxybiphenyl-4-yl)carbonyl]piperidin-4-yl}methyl)-N-(2-methoxyethyl)-4-methyl-2H-indazol-5-carboxamide
42. 2-({1-[(3-fluoro-4'-methylbiphenyl-4-yl)carbonyl]piperidin-4-yl}methyl)-N-(2-methoxyethyl)-4-methyl-2H-indazol-5-carboxamide
43. 2-[(1-{[3-fluoro-3'-(trifluoromethyl)biphenyl-4-yl]carbonyl}piperidin-4-yl)methyl]-N-(2-methoxyethyl)-4-methyl-2H-indazol-5-carboxamide
44. 2-[(1-{[3-fluoro-2'-(trifluoromethoxy)biphenyl-4-yl]carbonyl}piperidin-4-yl)methyl]-N-(2-methoxyethyl)-4-methyl-2H-indazol-5-carboxamide
45. 2-({1-[(2'-fluorobiphenyl-4-yl)carbonyl]piperidin-4-yl}methyl)-N-(2-methoxyethyl)-4-methyl-2H-indazol-5-carboxamide
46. 2-({1-[(2',4'-difluorobiphenyl-4-yl)carbonyl]piperidin-4-yl}methyl)-N-(2-methoxy-ethyl)-4-methyl-2H-indazol-5-carboxamide
47. 2-({1-[(2-fluorobiphenyl-4-yl)carbonyl]piperidin-4-yl}methyl)-N-(2-methoxyethyl)-4-methyl-2H-indazol-5-carboxamide
48. N-(2-methoxyethyl)-4-methyl-2-({1-[(2'-methylbiphenyl-4-yl)carbonyl]piperidin-4-yl}-methyl)-2H-indazol-5-carboxamide
49. N-(2-methoxyethyl)-4-methyl-2-({1-[4-(4-pyridyloxy)benzoyl]piperidin-4-yl}methyl)-2H-indazol-5-carboxamide
50. N-(2-methoxyethyl)-4-methyl-2-({1-[4-(4H-1,2,4-triazol-4-yl)benzoyl]piperidin-4-yl}-methyl)-2H-indazol-5-carboxamide
51. 2-{[1-(2-fluoro-4-morpholinobenzoyl)piperidin-4-yl]methyl}-N-(2-methoxyethyl)-4-methyl-2H-indazol-5-carboxamide
52. 2-{[1-(4-bromobenzoyl)piperidin-4-yl]methyl}-N-(2-methoxyethyl)-4-methyl-2H-indazol-5-carboxamide
53. N-(2-methoxyethyl)-4-methyl-2-({1-[4-(trifluoromethoxy)benzoyl]piperidin-4-yl}-methyl)-2H-indazol-5-carboxamide
54. 2-{[1-(4-chlorobenzoyl)piperidin-4-yl]methyl}-N-(2-methoxyethyl)-4-methyl-2H-indazol-5-carboxamide
55. N-(2-methoxyethyl)-4-methyl-2-[(1-{4-[(trifluoromethyl)sulphanyl]benzoyl}piperidin-4-yl)methyl]-2H-indazol-5-carboxamide
56. 4-methyl-2-({1-[4-(pentafluoro-$\lambda^6$-sulphanyl)benzoyl]piperidin-4-yl}methyl)-N-(2,2,2-trifluoroethyl)-2H-indazol-5-carboxamide
57. 2-{[1-(4-chlorobenzoyl)piperidin-4-yl]methyl}-4-methyl-N-(2,2,2-trifluoroethyl)-2H-indazol-5-carboxamide
58. 4-methyl-N-(2,2,2-trifluoroethyl)-2-({1-[4-(trifluoromethoxy)benzoyl]piperidin-4-yl}methyl)-2H-indazol-5-carboxamide
59. 2-{[1-(4-chlorobenzoyl)piperidin-4-yl]methyl}-N-[2-(cyclopropylmethoxy)ethyl]-4-methyl-2H-indazole-5-carboxamide
60. N-[2-(cyclopropylmethoxy)ethyl]-4-methyl-2-{[1-(4-methylbenzoyl)piperidin-4-yl]-methyl}-2H-indazol-5-carboxamide
61. N-[2-(cyclopropylmethoxy)ethyl]-2-({1-[4-(4-fluorophenoxy)benzoyl]piperidin-4-yl}-methyl)-4-methyl-2H-indazol-5-carboxamide
62. N-[2-(cyclopropylmethoxy)ethyl]-4-methyl-2-({1-[4-(trifluoromethyl)benzoyl]piperidin-4-yl}methyl)-2H-indazol-5-carboxamide
63. N-[2-(cyclopropylmethoxy)ethyl]-2-({1-[(4'-fluorobiphenyl-4-yl)carbonyl]piperidin-4-yl}methyl)-4-methyl-2H-indazol-5-carboxamide
64. 2-{[1-(4-cyclopropylbenzoyl)piperidin-4-yl]methyl}-N-[2-(cyclopropylmethoxy)ethyl]-4-methyl-2H-indazol-5-carboxamide
65. 2-{[1-(4-chlorobenzoyl)piperidin-4-yl]methyl}-4-methyl-N-[2-(2,2,2-trifluoroethoxy)-ethyl]-2H-indazol-5-carboxamide
66. 4-methyl-2-{[1-(4-methylbenzoyl)piperidin-4-yl]methyl}-N-[2-(2,2,2-trifluoroethoxy)-ethyl]-2H-indazol-5-carboxamide
67. 2-({1-[4-(4-fluorophenoxy)benzoyl]piperidin-4-yl}methyl)-4-methyl-N-[2-(2,2,2-trifluoroethoxy)ethyl]-2H-indazol-5-carboxamide
68. 4-methyl-N-[2-(2,2,2-trifluoroethoxy)ethyl]-2-({1-[4-(trifluoromethyl)benzoyl]-piperidin-4-yl}methyl)-2H-indazol-5-carboxamide
69. 2-({1-[(4'-fluorobiphenyl-4-yl)carbonyl]piperidin-4-yl}methyl)-4-methyl-N-[2-(2,2,2-trifluoroethoxy)ethyl]-2H-indazol-5-carboxamide
70. 2-{[1-(4-cyclopropylbenzoyl)piperidin-4-yl]methyl}-4-methyl-N-[2-(2,2,2-trifluoro-ethoxy)ethyl]-2H-indazol-5-carboxamide
71. 2-{[1-(4-chlorobenzoyl)piperidin-4-yl]methyl}-N-(2-isopropoxyethyl)-4-methyl-2H-indazol-5-carboxamide
72. N-(2-isopropoxyethyl)-4-methyl-2-{[1-(4-methylbenzoyl)piperidin-4-yl]methyl}-2H-indazol-5-carboxamide
73. 2-({1-[4-(4-fluorophenoxy)benzoyl]piperidin-4-yl}methyl)-N-(2-isopropoxyethyl)-4-methyl-2H-indazol-5-carboxamide
74. N-(2-isopropoxyethyl)-4-methyl-2-({1-[4-(trifluoromethyl)benzoyl]piperidin-4-yl}-methyl)-2H-indazol-5-carboxamide
75. 2-({1-[(4'-fluorobiphenyl-4-yl)carbonyl]piperidin-4-yl}methyl)-N-(2-isopropoxyethyl)-4-methyl-2H-indazol-5-carboxamide
76. 2-{[1-(4-cyclopropylbenzoyl)piperidin-4-yl]methyl}-N-(2-isopropoxyethyl)-4-methyl-2H-indazol-5-carboxamide
77. 2-{[1-(4-chlorobenzoyl)piperidin-4-yl]methyl}-4-methyl-N-[2-(trifluoromethoxy)ethyl]-2H-indazol-5-carboxamide
78. 2-({1-[4-(4-fluorophenoxy)benzoyl]piperidin-4-yl}methyl)-4-methyl-N-[2-(trifluoro-methoxy)ethyl]-2H-indazol-5-carboxamide
79. 2-({1-[(4'-fluorobiphenyl-4-yl)carbonyl]piperidin-4-yl}methyl)-4-methyl-N-[2-(trifluoromethoxy)ethyl]-2H-indazol-5-carboxamide
80. 4-methyl-N-[2-(trifluoromethoxy)ethyl]-2-[(1-{4-[4-(trifluoromethyl)phenoxy]-benzoyl}piperidin-4-yl)methyl]-2H-indazol-5-carboxamide
81. N-(2-tert-butoxyethyl)-2-{[1-(4-chlorobenzoyl)piperidin-4-yl]methyl}-4-methyl-2H-indazol-5-carboxamide
82. N-(2-tert-butoxyethyl)-2-({1-[4-(4-fluorophenoxy)benzoyl]piperidin-4-yl}methyl)-4-methyl-2H-indazol-5-carboxamide
83. N-(2-tert-butoxyethyl)-2-({1-[(4'-fluorobiphenyl-4-yl)carbonyl]piperidin-4-yl}methyl)-4-methyl-2H-indazol-5-carboxamide 84. N-(2-tert-butoxyethyl)-4-methyl-2-[(1-{4-[4-(trifluoromethyl)phenoxy]benzoyl}-piperidin-4-yl)methyl]-2H-indazol-5-carboxamide
85. 2-{[1-(4-chlorobenzoyl)piperidin-4-yl]methyl}-4-methyl-N-{2-[($^2$H3)methyloxy]-($^2$H4)ethyl}-2H-indazol-5-carboxamide
86. 2-({1-[4-(4-fluorophenoxy)benzoyl]piperidin-4-yl}methyl)-4-methyl-N-{2-[($^2$H3)methyloxy] ($^2$H4)ethyl}-2H-indazol-5-carboxamide
87. 2-{[1-(4-chlorobenzoyl)azetidin-3-yl]methyl}-N-(2-methoxyethyl)-4-methyl-2H-indazol-5-carboxamide
88. N-(2-methoxyethyl)-4-methyl-2-[(1-{4-[(trifluoromethyl)sulphanyl]benzoyl}azetidin-3-yl)methyl]-2H-indazol-5-carboxamide
89. N-(2-methoxyethyl)-4-methyl-2-({1-[4-(trifluoromethoxy)benzoyl]azetidin-3-yl}-methyl)-2H-indazol-5-carboxamide
90. 2-({1-[2-fluoro-4-(trifluoromethyl)benzoyl]azetidin-3-yl}methyl)-N-(2-methoxyethyl)-4-methyl-2H-indazol-5-carboxamide
91. 2-{[1-(4-chloro-2-fluorobenzoyl)azetidin-3-yl]methyl}-N-(2-methoxyethyl)-4-methyl-2H-indazol-5-carboxamide
92. 2-({1-[3-fluoro-4-(trifluoromethyl)benzoyl]azetidin-3-yl}methyl)-N-(2-methoxyethyl)-4-methyl-2H-indazol-5-carboxamide
93. 2-({1-[4-chloro-3-(trifluoromethyl)benzoyl]azetidin-3-yl}methyl)-N-(2-methoxyethyl)-4-methyl-2H-indazol-5-carboxamide
94. 2-{[1-(4-cyclopropylbenzoyl)azetidin-3-yl]methyl}-N-(2-methoxyethyl)-4-methyl-2H-indazol-5-carboxamide
95. N-(2-methoxyethyl)-4-methyl-2-[(1-{4-[4-(trifluoromethyl)phenoxy]benzoyl}azetidin-3-yl)methyl]-2H-indazol-5-carboxamide
96. 2-{[1-(4-chlorobenzoyl)azetidin-3-yl]methyl}-4-methyl-N-(2,2,2-trifluoroethyl)-2H-indazol-5-carboxamide
97. 4-methyl-N-(2,2,2-trifluoroethyl)-2-({1-[4-(trifluoromethoxy)benzoyl]azetidin-3-yl}-methyl)-2H-indazol-5-carboxamide
98. 2-({1-[2-fluoro-4-(trifluoromethyl)benzoyl]azetidin-3-yl}methyl)-4-methyl-N-(2,2,2-trifluoroethyl)-2H-indazol-5-carboxamide
99. 4-methyl-2-({1-[4-(pentafluoro-λ$^6$-sulphanyl)benzoyl]azetidin-3-yl}methyl)-N-(2,2,2-trifluoroethyl)-2H-indazol-5-carboxamide
100. N-[2-(cyclopropyloxy)ethyl]-4-methyl-2-({1-[4-(trifluoromethoxy)benzoyl]azetidin-3-yl}methyl)-2H-indazol-5-carboxamide
101. N-[2-(cyclobutyloxy)ethyl]-4-methyl-2-({1-[4-(trifluoromethoxy)benzoyl]azetidin-3-yl}methyl)-2H-indazol-5-carboxamide
102. 2-{[1-(4-chlorobenzoyl)azetidin-3-yl]methyl}-N-[2-(cyclopropylmethoxy)ethyl]-4-methyl-2H-indazol-5-carboxamide
103. N-[2-(cyclopropylmethoxy)ethyl]-2-({1-[4-(4-fluorophenoxy)benzoyl]azetidin-3-yl}-methyl)-4-methyl-2H-indazol-5-carboxamide
104. N-[2-(cyclopropylmethoxy)ethyl]-4-methyl-2-{[1-(4-methylbenzoyl)azetidin-3-yl]-methyl}-2H-indazol-5-carboxamide
105. 2-{[1-(4-chlorobenzoyl)azetidin-3-yl]methyl}-4-methyl-N-[2-(trifluoromethoxy)ethyl]-2H-indazol-5-carboxamide
106. N-(2-tert-butoxyethyl)-2-{[1-(4-chlorobenzoyl)azetidin-3-yl]methyl}-4-methyl-2H-indazol-5-carboxamide
107. N-[2-(cyclopropylmethoxy)ethyl]-2-({1-[(4'-fluorobiphenyl-4-yl)carbonyl]azetidin-3-yl}methyl)-4-methyl-2H-indazol-5-carboxamide
108. 2-({1-[(4'-fluorobiphenyl-4-yl)carbonyl]azetidin-3-yl}methyl)-N-(2-methoxyethyl)-4-methyl-2H-indazol-5-carboxamide
109. 2-({1-[4-(4-fluorophenoxy)benzoyl]azetidin-3-yl}methyl)-N-(2-methoxyethyl)-4-methyl-2H-indazol-5-carboxamide
110. 2-({1-[4-(4-fluorophenoxy)benzoyl]azetidin-3-yl}methyl)-4-methyl-N-(2,2,2-trifluoroethyl)-2H-indazol-5-carboxamide
111. 2-({1-[(4'-fluorobiphenyl-4-yl)carbonyl]azetidin-3-yl}methyl)-4-methyl-N-(2,2,2-trifluoroethyl)-2H-indazol-5-carboxamide
112. 2-{[1-(4-chlorobenzoyl)azetidin-3-yl]methyl}-4-methyl-N-[2-(2,2,2-trifluoroethoxy)-ethyl]-2H-indazol-5-carboxamide
113. 4-methyl-N-[2-(2,2,2-trifluoroethoxy)ethyl]-2-[(1-{4-[4-(trifluoromethyl)phenoxy]-benzoyl}azetidin-3-yl)methyl]-2H-indazol-5-carboxamide
114. 4-methyl-N-(2,2,2-trifluoroethyl)-2-[(1-{4-[4-(trifluoromethyl)phenoxy]benzoyl}-azetidin-3-yl)methyl]-2H-indazol-5-carboxamide
115. 2-({1-[4-(4-chlorophenoxy)benzoyl]azetidin-3-yl}methyl)-4-methyl-N-(2,2,2-trifluoro-ethyl)-2H-indazol-5-carboxamide
116. 2-({1-[4-(4-chlorophenoxy)benzoyl]azetidin-3-yl}methyl)-N-(2-methoxyethyl)-4-methyl-2H-indazol-5-carboxamide
117. N-(2-methoxyethyl)-4-methyl-2-{[1-(4-{[5-(trifluoromethyl)pyridin-2-yl]oxy}benzoyl)-azetidin-3-yl]methyl}-2H-indazol-5-carboxamide
118. 4-methyl-N-(2,2,2-trifluoroethyl)-2-{[1-(4-{[5-(trifluoromethyl)pyridin-2-yl]oxy}benzoyl)azetidin-3-yl]methyl}-2H-indazol-5-carboxamide
119. 2-{[1-(4-chlorobenzoyl)piperidin-4-yl]methyl}-N-ethyl-4-methyl-2H-indazol-5-carboxamide
120. 2-({1-[4-(4-fluorophenoxy)benzoyl]piperidin-4-yl}methyl)-4-methyl-N-(2,2,2-trifluoro-ethyl)-2H-indazol-5-carboxamide
121. 2-({1-[4-(4-chlorophenoxy)benzoyl]piperidin-4-yl}methyl)-4-methyl-N-(2,2,2-trifluoro-ethyl)-2H-indazol-5-carboxamide
122. 4-methyl-2-({1-[4-(4-methylphenoxy)benzoyl]piperidin-4-yl}methyl)-N-(2,2,2-trifluoroethyl)-2H-indazol-5-carboxamide
123. 2-({1-[(4'-fluorobiphenyl-4-yl)carbonyl]piperidin-4-yl}methyl)-4-methyl-N-(2,2,2-trifluoroethyl)-2H-indazol-5-carboxamide
124. 4-methyl-2-{[1-(4-morpholinobenzoyl)piperidin-4-yl]methyl}-N-(2,2,2-trifluoroethyl)-2H-indazol-5-carboxamide
125. 4-methyl-N-(2,2,2-trifluoroethyl)-2-[(1-{4-[(trifluoromethyl)sulphanyl]benzoyl}-piperidin-4-yl)methyl]-2H-indazol-5-carboxamide
126. 4-methyl-N-(2,2,2-trifluoroethyl)-2-[(1-{4-[4-(trifluoromethyl)phenoxy]benzoyl}-piperidin-4-yl)methyl]-2H-indazol-5-carboxamide
127. 4-methyl-N-(2,2,2-trifluoroethyl)-2-{[1-(4-{[5-(trifluoromethyl)pyridin-2-yl]oxy}-benzoyl)piperidin-4-yl]methyl}-2H-indazol-5-carboxamide
128. 4-methyl-N-(2,2,2-trifluoroethyl)-2-{[1-(4-{[6-(trifluoromethyl)pyridin-3-yl]oxy}-benzoyl)piperidin-4-yl]methyl}-2H-indazol-5-carboxamide 129. 4-methyl-N-(2,2,2-trifluoroethyl)-2-{[1-(4-{[6-(trifluoromethyl)pyridin-2-yl]oxy}-benzoyl)piperidin-4-yl]methyl}-2H-indazol-5-carboxamide
130. 2-({1-[4-(4-cyanophenoxy)benzoyl]piperidin-4-yl}methyl)-4-methyl-N-(2,2,2-trifluoro-ethyl)-2H-indazol-5-carboxamide
131. 2-({1-[4-(3-fluorophenoxy)benzoyl]piperidin-4-yl}methyl)-4-methyl-N-(2,2,2-trifluoro-ethyl)-2H-indazol-5-carboxamide
132. 4-methyl-N-(2,2,2-trifluoroethyl)-2-[(1-{4-[3-(trifluoromethyl)phenoxy]benzoyl}-piperidin-4-yl)methyl]-2H-indazol-5-carboxamide
133. 2-[(1-{4-[(5-cyanopyridin-2-yl)oxy]benzoyl}piperidin-4-yl)methyl]-4-methyl-N-(2,2,2-trifluoroethyl)-2H-indazol-5-carboxamide
134. 2-[(1-{4-[(5-chloropyridin-2-yl)oxy]benzoyl}piperidin-4-yl)methyl]-4-methyl-N-(2,2,2-trifluoroethyl)-2H-indazol-5-carboxamide
135. 4-methyl-N-(2,2,2-trifluoroethyl)-2-[(1-{4-[5-(trifluoromethyl)pyridin-2-yl]benzoyl}-piperidin-4-yl)methyl]-2H-indazol-5-carboxamide
136. 2-({1-[4-(2,4-difluorophenoxy)benzoyl]piperidin-4-yl}methyl)-4-methyl-N-(2,2,2-trifluoroethyl)-2H-indazol-5-carboxamide
137. 2-({1-[4-(3,4-difluorophenoxy)benzoyl]piperidin-4-yl}methyl)-4-methyl-N-(2,2,2-trifluoroethyl)-2H-indazol-5-carboxamide
138. 4-methyl-N-(2,2,2-trifluoroethyl)-2-[(1-{[4'-(trifluoromethyl)biphenyl-4-yl]carbonyl}-piperidin-4-yl)methyl]-2H-indazol-5-carboxamide
139. 2-{[1-(4-bromobenzoyl)piperidin-4-yl]methyl}-4-methyl-N-(2,2,2-trifluoroethyl)-2H-indazol-5-carboxamide
140. 2-({1-[4-(5-chloropyridin-2-yl)benzoyl]piperidin-4-yl}methyl)-4-methyl-N-(2,2,2-trifluoroethyl)-2H-indazol-5-carboxamide
141. 2-({1-[(4'-methoxy-2'-methylbiphenyl-4-yl)carbonyl]piperidin-4-yl}methyl)-4-methyl-N-(2,2,2-trifluoroethyl)-2H-indazol-5-carboxamide
142. 4-methyl-2-({1-[4-(6-methylpyridin-3-yl)benzoyl]piperidin-4-yl}methyl)-N-(2,2,2-trifluoroethyl)-2H-indazol-5-carboxamide
143. 2-({1-[(4'-fluoro-2'-methoxybiphenyl-4-yl)carbonyl]piperidin-4-yl}methyl)-4-methyl-N-(2,2,2-trifluoroethyl)-2H-indazol-5-carboxamide
144. 4-methyl-N-(2,2,2-trifluoroethyl)-2-[(1-{4-[6-(trifluoromethyl)pyridin-3-yl]benzoyl}-piperidin-4-yl)methyl]-2H-indazol-5-carboxamide
145. 2-({1-[4-(6-methoxypyridin-3-yl)benzoyl]piperidin-4-yl}methyl)-4-methyl-N-(2,2,2-trifluoroethyl)-2H-indazol-5-carboxamide
146. 2-({1-[4-(6-methoxypyridin-2-yl)benzoyl]piperidin-4-yl}methyl)-4-methyl-N-(2,2,2-trifluoroethyl)-2H-indazol-5-carboxamide
147. 4-methyl-2-({1-[4-(5-methylpyridin-2-yl)benzoyl]piperidin-4-yl}methyl)-N-(2,2,2-trifluoroethyl)-2H-indazol-5-carboxamide
148. 2-({1-[4-(5-fluoropyridin-2-yl)benzoyl]piperidin-4-yl}methyl)-4-methyl-N-(2,2,2-trifluoroethyl)-2H-indazol-5-carboxamide
149. 2-({1-[4-(5-methoxypyridin-2-yl)benzoyl]piperidin-4-yl}methyl)-4-methyl-N-(2,2,2-trifluoroethyl)-2H-indazol-5-carboxamide
150. 4-methyl-2-({1-[4-(2-methylpyrimidin-5-yl)benzoyl]piperidin-4-yl}methyl)-N-(2,2,2-trifluoroethyl)-2H-indazol-5-carboxamide
151. 4-methyl-N-(2,2,2-trifluoroethyl)-2-[(1-{4-[2-(trifluoromethyl)pyrimidin-5-yl]benzoyl}-piperidin-4-yl)methyl]-2H-indazol-5-carboxamide
152. 4-methyl-N-(2,2,2-trifluoroethyl)-2-[(1-{4-[6-(trifluoromethyl)pyridin-2-yl]benzoyl}-piperidin-4-yl)methyl]-2H-indazol-5-carboxamide
153. 2-({1-[4-(4-cyanophenoxy)benzoyl]piperidin-4-yl}methyl)-N-(2-methoxyethyl)-4-methyl-2H-indazol-5-carboxamide
154. 2-{[1-(4-bromo-3-methylbenzoyl)piperidin-4-yl]methyl}-N-(2-methoxyethyl)-4-methyl-2H-indazol-5-carboxamide
155. 2-{[1-(4-tert-butylbenzoyl)piperidin-4-yl]methyl}-N-(2-methoxyethyl)-4-methyl-2H-indazol-5-carboxamide
156. 2-({1-[4-(1-hydroxy-1-methylethyl)benzoyl]piperidin-4-yl}methyl)-N-(2-methoxy-ethyl)-4-methyl-2H-indazol-5-carboxamide
157. 2-{[1-(4-cyclohexylbenzoyl)piperidin-4-yl]methyl}-N-(2-methoxyethyl)-4-methyl-2H-indazol-5-carboxamide
158. 2-({1-[4-(1-cyano-1-methylethyl)benzoyl]piperidin-4-yl}methyl)-N-(2-methoxyethyl)-4-methyl-2H-indazol-5-carboxamide
159. N-(2-methoxyethyl)-4-methyl-2-({1-[4-(pyrimidin-2-yloxy)benzoyl]piperidin-4-yl}-methyl)-2H-indazol-5-carboxamide
160. N-(2-methoxyethyl)-4-methyl-2-({1-[4-(3-pyridyloxy)benzoyl]piperidin-4-yl}methyl)-2H-indazol-5-carboxamide
161. N-(2-methoxyethyl)-4-methyl-2-{[1-(4-{[5-(trifluoromethyl)pyridin-2-yl]oxy}benzoyl)-piperidin-4-yl]methyl}-2H-indazol-5-carboxamide
162. N-(2-methoxyethyl)-4-methyl-2-({1-[4-(2-pyridyloxy)benzoyl]piperidin-4-yl}methyl)-2H-indazol-5-carboxamide
163. N-(2-methoxyethyl)-4-methyl-2-{[1-(4-{[4-(trifluoromethyl)pyrimidin-2-yl]oxy}-benzoyl)piperidin-4-yl]methyl}-2H-indazol-5-carboxamide
164. N-(2-methoxyethyl)-4-methyl-2-{[1-(4-{[6-(trifluoromethyl)pyridin-3-yl]oxy}benzoyl)-piperidin-4-yl]methyl}-2H-indazol-5-carboxamide
165. N-(2-methoxyethyl)-4-methyl-2-{[1-(4-{[6-(trifluoromethyl)pyridin-2-yl]oxy}benzoyl)-piperidin-4-yl]methyl}-2H-indazol-5-carboxamide
166. 2-({1-[(4'-methoxybiphenyl-4-yl)carbonyl]piperidin-4-yl}methyl)-N-(2-methoxyethyl)-4-methyl-2H-indazol-5-carboxamide
167. N-(2-methoxyethyl)-4-methyl-2-({1-[4-(3,4,5,6-tetrahydro-2H-pyran-4-yloxy)benzoyl]-piperidin-4-yl}methyl)-2H-indazol-5-carboxamide
168. N-(2-methoxyethyl)-4-methyl-2-[(1-{4-[3-(trifluoromethyl)phenoxy]benzoyl}piperidin-4-yl)methyl]-2H-indazol-5-carboxamide
169. 2-[(1-{4-[(5-cyanopyridin-2-yl)oxy]benzoyl}piperidin-4-yl)methyl]-N-(2-methoxy-ethyl)-4-methyl-2H-indazol-5-carboxamide
170. 2-[(1-{4-[(5-chloropyridin-2-yl)oxy]benzoyl}piperidin-4-yl)methyl]-N-(2-methoxy-ethyl)-4-methyl-2H-indazol-5-carboxamide
171. 2-({1-[4-(2,4-difluorophenoxy)benzoyl]piperidin-4-yl}methyl)-N-(2-methoxyethyl)-4-methyl-2H-indazol-5-carboxamide
172. 2-({1-[4-(3,4-difluorophenoxy)benzoyl]piperidin-4-yl}methyl)-N-(2-methoxyethyl)-4-methyl-2H-indazol-5-carboxamide
173. N-(2-methoxyethyl)-4-methyl-2-[(1-{[4'-(trifluoromethyl)biphenyl-4-yl]carbonyl}-piperidin-4-yl)methyl]-2H-indazol-5-carboxamide 174. 2-({1-[4-(3-fluorophenoxy)benzoyl]piperidin-4-yl}methyl)-N-(2-methoxyethyl)-4-methyl-2H-indazol-5-carboxamide
175. 2-{[1-(2-fluoro-4-isopropoxybenzoyl)piperidin-4-yl]methyl}-N-(2-methoxyethyl)-4-methyl-2H-indazol-5-carboxamide
176. 2-({1-[(3-fluoro-3',4'-dimethylbiphenyl-4-yl)carbonyl]piperidin-4-yl}methyl)-N-(2-methoxyethyl)-4-methyl-2H-indazol-5-carboxamide
177. 2-({1-[(2',3-difluoro-4'-methoxybiphenyl-4-yl)carbonyl]piperidin-4-yl}methyl)-N-(2-methoxyethyl)-4-methyl-2H-indazol-5-carboxamide
178. 2-({1-[4-(difluoromethoxy)benzoyl]piperidin-4-yl}methyl)-N-(2-methoxyethyl)-4-methyl-2H-indazol-5-carboxamide
179. 2-({1-[4-(2-fluorophenoxy)benzoyl]piperidin-4-yl}methyl)-N-(2-methoxyethyl)-4-methyl-2H-indazol-5-carboxamide
180. 2-({1-[(4'-cyano-2'-methylbiphenyl-4-yl)carbonyl]piperidin-4-yl}methyl)-N-(2-methoxyethyl)-4-methyl-2H-indazol-5-carboxamide
181. 2-({1-[4-(5-chloropyridin-2-yl)benzoyl]piperidin-4-yl}methyl)-N-(2-methoxyethyl)-4-methyl-2H-indazol-5-carboxamide
182. N-(2-methoxyethyl)-4-methyl-2-[(1-{4-[6-(trifluoromethyl)pyridin-2-yl]benzoyl}-piperidin-4-yl)methyl]-2H-indazol-5-carboxamide
183. N-(2-methoxyethyl)-2-({1-[(4'-methoxy-2'-methylbiphenyl-4-yl)carbonyl]piperidin-4-yl}methyl)-4-methyl-2H-indazol-5-carboxamide
184. 2-({1-[(4'-chloro-2'-methylbiphenyl-4-yl)carbonyl]piperidin-4-yl}methyl)-N-(2-methoxyethyl)-4-methyl-2H-indazol-5-carboxamide
185. 2-[(1-{[4'-(1-cyano-1-methylethyl)biphenyl-4-yl]carbonyl}piperidin-4-yl)methyl]-N-(2-methoxyethyl)-4-methyl-2H-indazol-5-carboxamide
186. N-(2-methoxyethyl)-2-({1-[4-(5-methoxypyridin-2-yl)benzoyl]piperidin-4-yl}methyl)-4-methyl-2H-indazol-5-carboxamide
187. N-(2-methoxyethyl)-4-methyl-2-[(1-{4-[6-(trifluoromethyl)pyridin-3-yl]benzoyl}-piperidin-4-yl)methyl]-2H-indazol-5-carboxamide
188. N-(2-methoxyethyl)-2-({1-[4-(6-methoxypyridin-3-yl)benzoyl]piperidin-4-yl}methyl)-4-methyl-2H-indazol-5-carboxamide
189. 2-({1-[(4'-fluoro-2'-methylbiphenyl-4-yl)carbonyl]piperidin-4-yl}methyl)-N-(2-methoxyethyl)-4-methyl-2H-indazol-5-carboxamide
190. N-(2-methoxyethyl)-4-methyl-2-({1-[4-(6-methylpyridin-3-yl)benzoyl]piperidin-4-yl}methyl)-2H-indazol-5-carboxamide
191. N-(2-methoxyethyl)-2-({1-[4-(6-methoxypyridin-2-yl)benzoyl]piperidin-4-yl}methyl)-4-methyl-2H-indazol-5-carboxamide
192. N-(2-methoxyethyl)-4-methyl-2-({1-[4-(2-methylpyrimidin-5-yl)benzoyl]piperidin-4-yl}methyl)-2H-indazol-5-carboxamide
193. 2-({1-[(4'-fluoro-2'-methoxybiphenyl-4-yl)carbonyl]piperidin-4-yl}methyl)-N-(2-methoxyethyl)-4-methyl-2H-indazol-5-carboxamide
194. 2-({1-[(4'-chloro-2'-methoxybiphenyl-4-yl)carbonyl]piperidin-4-yl}methyl)-N-(2-methoxyethyl)-4-methyl-2H-indazol-5-carboxamide
195. N-(2-methoxyethyl)-4-methyl-2-[(1-{4-[2-(trifluoromethyl)pyrimidin-5-yl]benzoyl}-piperidin-4-yl)methyl]-2H-indazol-5-carboxamide
196. 2-({1-[(4'-chloro-2'-fluorobiphenyl-4-yl)carbonyl]piperidin-4-yl}methyl)-N-(2-methoxy-ethyl)-4-methyl-2H-indazol-5-carboxamide
197. 2-({1-[(2'-chloro-4'-fluorobiphenyl-4-yl)carbonyl]piperidin-4-yl}methyl)-N-(2-methoxy-ethyl)-4-methyl-2H-indazol-5-carboxamide
198. 2-({1-[4-(5-chloropyridin-3-yl)benzoyl]piperidin-4-yl}methyl)-N-(2-methoxyethyl)-4-methyl-2H-indazol-5-carboxamide
199. 2-({1-[4-(5-fluoropyridin-3-yl)benzoyl]piperidin-4-yl}methyl)-N-(2-methoxyethyl)-4-methyl-2H-indazol-5-carboxamide
200. N-(2-methoxyethyl)-4-methyl-2-[(1-{4-[5-(trifluoromethyl)pyridin-3-yl]benzoyl}-piperidin-4-yl)methyl]-2H-indazol-5-carboxamide
201. 2-[(1-{[4'-(1-hydroxy-1-methylethyl)biphenyl-4-yl]carbonyl}piperidin-4-yl)methyl]-N-(2-methoxyethyl)-4-methyl-2H-indazol-5-carboxamide
202. 2-({1-[(3',5'-difluorobiphenyl-4-yl)carbonyl]piperidin-4-yl}methyl)-N-(2-methoxy-ethyl)-4-methyl-2H-indazol-5-carboxamide
203. 2-({1-[(4'-fluoro-2-methylbiphenyl-4-yl)carbonyl]piperidin-4-yl}methyl)-N-(2-methoxyethyl)-4-methyl-2H-indazol-5-carboxamide
204. 2-({1-[(3',5'-difluoro-2-methylbiphenyl-4-yl)carbonyl]piperidin-4-yl}methyl)-N-(2-methoxyethyl)-4-methyl-2H-indazol-5-carboxamide
205. N-(2-methoxyethyl)-4-methyl-2-({1-[3-methyl-4-(3-pyridyl)benzoyl]piperidin-4-yl}-methyl)-2H-indazol-5-carboxamide
206. N-(2-methoxyethyl)-4-methyl-2-({1-[3-methyl-4-(4-pyridyl)benzoyl]piperidin-4-yl}-methyl)-2H-indazol-5-carboxamide
207. N-(2-methoxyethyl)-4-methyl-2-({1-[(2-methylbiphenyl-4-yl)carbonyl]piperidin-4-yl}-methyl)-2H-indazol-5-carboxamide A subject of the present invention is the use of the compounds according to the invention for the production of drugs which contain at least one of the compounds according to formula I.

Also a subject of the present invention are drugs which contain the compounds according to the invention, with suitable formulation and carrier substances.

Compared to known prostaglandin $EP_2$ antagonists, the new $EP_2$ antagonists are characterized by improved properties such as better availability and stability.

A subject of the present invention are drugs for fertility control/contraception and for the treatment and prophylaxis of diseases, which include infectious diseases, cancer, cardiovascular diseases, angiogenic diseases, uterine contraction disorders, pain, inflammatory diseases, neuroinflammatory diseases, neurodegenerative diseases, autoimmune diseases, immuno-dependent diseases/therapies, nephrological diseases and ophthalmological diseases.

Infectious diseases should be understood to mean diseases caused by unicellular parasites (e.g. *Klebsiella* or *Streptococcus*). With infectious diseases, the drugs can have an immunomodulatory action such that the diseases can be treated prophylactically (diminution of the infection risk, such as for example in bone marrow transplants) or therapeutically. Cancer should be understood to mean solid tumours and leukaemias; viral infections e.g. cytomegalus infections, hepatitis, hepatitis B and C and HIV diseases; cardiovascular diseases ischaemic reperfusion disease, stenoses, arterioscleroses, restenoses, arthritis, Kawasaki syndrome and aneurysms; angiogenic diseases e.g. endometriosis and fibrosis and fibroids in the uterus; uterine contraction disorders e.g.

menstrual problems; pain, for example inflammatory hyperalgesia and arthritis, inflammatory diseases, for example inflammatory intestinal diseases; neuroinflammatory and neuro-degenerative diseases e.g. multiple sclerosis, Alzheimer, Parkinson, ALS and stroke; immuno-dependent diseases/therapies e.g. transplants in which immunomodulation increases the therapeutic success; autoimmune diseases for example the ophthalmological disease Graves' disease, and nephrological diseases polycystic kidney diseases and glomerulonephritis.

Also a subject of the present invention are drugs for treatment and prophylaxis of the diseases listed above which contain at least one compound according to the general formula I, and drugs with suitable formulation and carrier substances.

For the use of the compounds according to the invention as drugs, these are converted into the form of a pharmaceutical preparation which as well as the active substance contains pharmaceutical, organic or inorganic inert carrier materials suitable for enteral or parenteral administration, such as for example water, gelatine, gum Arabic, lactose, starch, magnesium stearate, talc, plant oils, polyalkylene glycols etc. The pharmaceutical preparations can be in solid form, for example as tablets, coated tablets or capsules, in semisolid form, for example as ointments, creams, gels or suppositories or in liquid form, for example as solutions, suspensions or emulsions.

They optionally contain additives, which are for example intended to function as fillers, binders, disintegrants, lubricants, solvents, solution mediators, masking flavours, colorant, or emulsifiers. Types of additive in the sense of the invention are for example saccharides (mono-, di-, tri-, oligo-, and/or polysaccharides), fats, waxes, oils, hydrocarbons, anionic, nonionic, cationic, natural, synthetic or semisynthetic surfactants. In addition, they optionally contain additives such as preservatives, stabilizers, wetting agents or emulsifiers; salts for alteration of the osmotic pressure or buffers.

These pharmaceutical preparations are also a subject of the present invention.

For inhalation, aerosol solutions, or else suitable solid substance preparations for inhalation, are advantageously prepared.

For oral use, tablets, coated tablets or capsules with talc and/or hydrocarbon carriers or binders, such as for example lactose, maize or potato starch are particularly suitable. Use is also possible in liquid form, such as for example as syrup, to which a sweetener is optionally added. Likewise, for the oral use of such compounds, clathrates are also suitable, for example the clathrates with alpha, beta or gamma cyclodextrin or else beta-hydroxypropyl cyclodextrin may be mentioned.

For parenteral administration, sterile, injectable, aqueous or oily solutions are used. Injection solutions or suspensions are particularly suitable, in particular aqueous solutions of the active compounds in polyethoxylated castor oil.

For vaginal application, for example suppositories, tampons, gels, foams or intrauterine pessaries are suitable and usual.

For intraarticular injection, suitably prepared crystal suspensions can be used.

For intramuscular injection, aqueous and oily injection solutions or suspensions and corresponding depot preparations can be used.

For rectal application, the new compounds can be used in the form of suppositories, capsules, solutions (e.g. in the form of enemas) and ointments both for systemic and also for local therapy.

For pulmonary application of the new compounds, these can be used in the form of aerosols and inhalation formulations.

For local use on eyes, external auditory canal, middle ear, nostrils and paranasal sinuses, the new compounds can be used as drops, ointments and tinctures in appropriate pharmaceutical preparations.

For topical application, formulations in gels, ointments, fatty ointments, creams, pastes, powders, milk and tinctures are possible. The dosage of the compounds of the general formula I in these preparations should be 0.01%-20% in order to achieve an adequate pharmacological action.

The dosage of the active substances can vary depending on the administration route, age and weight of the patient, nature and severity of the disease to be treated and similar factors. The treatment can be effected by single doses or by a large number of doses over a longer period. The daily dose is 0.5-1000 mg, preferably 50-200 mg, and the dose can be given as a single dose for administration once or subdivided into 2 or more daily doses.

As carrier systems, surface-active additives such as salts of the bile acids or animal or plant phospholipids, but also mixtures thereof and liposomes or components thereof can also be used.

The formulations and presentations described above are also a subject of the present invention.

The administration of the compounds according to the invention can be effected by any conventional method, including oral and parenteral, e.g. by subcutaneous or intramuscular injections, and various inhalation techniques. The enteral, parenteral, vaginal, intrauterine and oral applications are also a subject of the present invention.

The compounds according to the invention of the general formula I bind to the $EP_2$ receptor and have an antagonistic action. The antagonistic action can be determined by an antagonism test (see Example 1.2.1 of the biological examples).

Antagonists should be understood to mean molecules which bind to their appropriate receptors and which inhibit the initiation of the signal transduction pathway(s) coupled with the receptor through the naturally occurring ligand(s). Normally, the antagonists compete with the naturally occurring ligand of the receptors for the binding to the receptor. However, other modifications of the receptor by molecules which prevent the signal transduction pathways coupled with the receptor from being activated by the naturally occurring ligand(s) are also possible (e.g. non-competitive, steric modifications of the receptor).

More preferably, the antagonists bind reversibly to their corresponding receptors.

The $EP_2$ receptor antagonist has a preferential affinity for the $EP_2$ receptor compared to any other EP receptor. The antagonism is measured in the presence of the natural agonist ($PGE_2$).

For the determination of the selectivity, the action of the $EP_2$ antagonist on a human $EP_4$ receptor (Example 2.2.1) or PGD receptor (Example 3.2.1) can be determined (Table 1).

Furthermore, the substances according to the invention are more stable in vivo than the $EP_2$ receptor antagonists which are described in the closest state of the art (DE 10 2009 049 662 A1), and this results in higher half-lives (see Table 3).

Also a subject of the present invention is the use of the substances according to the invention as $EP_2$ receptor antagonists for the treatment of diseases which are caused by disorders in the signal transduction chain in which the $EP_2$ receptor is involved, such as for example pain and fertility disorders. The $EP_2$ receptor antagonists are also suitable for fertility control.

In the pre-ovulatory antral follicle, the oocyte is surrounded by cumulus cells which form a dense cell crown around the oocyte. After the peak of the luteinizing hormone (LH peak), a series of processes is activated, which results in a marked morphological change in this cell crown of cumulus cells. During this, the cumulus cells form an extracellular matrix, which leads to the so-called cumulus expansion (Vanderhyden et al. 1990, Dev Biol., August; 140(2):307-317). This cumulus expansion is an important component of the ovulatory process and the subsequent possibility of fertilization.

During the cumulus expansion, prostaglandins and here prostaglandin $E_2$, synthesis whereof is induced by the LH peak, are of decisive importance. Prostanoid $EP_2$ knockout mice (Hizaki et al., 1999, Proc Natl Acad Sci USA., August 31; 96(18):10501-6.) show a markedly decreased cumulus expansion and severe subfertility, which demonstrates the importance of the prostanoid $EP_2$ receptors for this process.

The action of an $EP_2$ antagonist on cumulus expansion can be measured in a cumulus expansion test (see Example 4.2).

The substances according to the invention have inhibitory effects in cumulus expansion tests and an influence on the fertilizability of ovulated cumulus-oocyte complexes (see Example 4.3 and Table 4). The substances according to the invention have a contraceptive effect in non-human primates (Cynomolgus), where they cause a markedly decreased pregnancy rate without having an influence on the cycle (length of the cycle and hormones) (see Example 4.4 and Table 5). This for the first time shows a contraceptive effect of $EP_2$ receptor antagonists in non-human primates. This effect is based on non-hormonal mechanisms, which demonstrates the possibility of hormone-free contraception with the substances according to the invention.

A subject of the present invention is the use of the substances according to the invention for fertility control.

While the $EP_2$ receptor antagonist AH6809 first suppresses the expansion of the cumulus, by only ca. 30%, at a concentration of 100-200 µM, in the presence of the substance according to the invention according to Example 17a ca. 70% suppression of the cumulus expansion can already be attained at a 100-200 times lower concentration (0.5 µM; $IC_{50}$: 3.4 nM, see Table 1). In these experiments, the test substances compete with the natural $EP_2$ receptor agonist $PGE_2$ (0.3 µM).

By administration of the substance of example 62 from the application DE 10 2009 049 662 A1, a ca. 70% suppression of the cumulus expansion can likewise be achieved, however for this a concentration of 10 µM is necessary, which represents a 10-20 times lower concentration in comparison to AH6809. However, this is markedly higher than the concentration of 0.5 µM for Example 17 from the present invention (see Table 2).

Example 17 according to the invention from the present invention is also characterized by a better terminal half-life. While example 62 from the application DE 10 2009 049 662 A1 has a $t_{1/2}$ of 0.4 hours, for Example 17 this is 2.5 hours (see Table 3).

Accordingly substance 17 of the present invention is markedly superior to this compound known from the state of the art.

A subject of the present invention is the use of the substances according to the invention for the inhibition of cumulus expansion and thereby of ovulation and fertilization for contraception.

A particular form of contraception is emergency protection (also known as "morning-after pill"). This should be understood to mean the taking of one or more substances which is intended to prevent a possible pregnancy after unprotected sexual intercourse and in the event of a presumable failure of the protective method.

A subject of the present invention is the use of the substances according to the invention for emergency protection.

Also a subject of the present invention is the use of the substances according to the invention as $EP_2$ receptor antagonists for the prophylaxis and direct treatment of diseases which are causally linked with the $EP_2$ receptor or of diseases which can be treated by influencing the $EP_2$ receptor.

Prostaglandins play an important part in angiogenesis (Sales, Jabbour, 2003, Reproduction 126, 559-567; Kuwano et al., 2004, FASEB J. 18, 300-310; Kamiyama et al., 2006, Oncogene 25, 7019-7028; Chang et al., 2005, prostaglandins & other Lipid Mediators 76, 48-58).

Endometriosis is a chronic disease wherein inflammatory, immunomodulatory and angiogenic processes are involved. Together with other factors, prostaglandins and here in particular the $PGE_2$ and the $EP_2$ receptor are of particular importance (Banu et al., 2009, Molecular Endocrinology 23: 1291-1305; Bulun 2009, N Engl J Med; 360, 268-279).

Circa 10% of women suffer regularly from severe bleeding during menstruation, caused by changes in the blood vessels of the endometrium. Additionally, structural differences in the blood vessels have been observed, such as for example the incomplete formation of the smooth muscle layer (Abberton et al., 1999, Hum. Reprod. 14, 1072-1079, Rogers et al. 2003, Microsc Res Tech. 60(4), 412-419). Since the blood loss during menstruation is partly regulated by the constriction of the blood vessels, it is obvious that the defects in the smooth musculature contribute substantially to the bleeding.

A subject of the present invention is the use of the substances of the general formula I for the prophylaxis and treatment of endometriosis.

Prostaglandins play an important part in uterine contraction, and excessively strong contractions are responsible for menstrual problems (Sales, Jabbour, 2003, Reproduction 126, 559-567). Prostaglandins and here especially the $EP_2$ and the $EP_4$ receptor have been linked with severe menstrual bleeding (Smith et al., 2007 (Human Reproduction, Vol. 22, No. 5 pp. 1450-1456).

A subject of the present invention is the use of the substances of the general formula I for the prophylaxis and treatment of menstrual problems and severe menstrual bleeding and pains during menstruation.

Fibroids (myomas) are benign tumours in the uterus with a high dissemination rate. Via the stimulation of aromatase by a $PGE_2$/cAMP-mediated signal pathway, and by other possible mechanisms, there is a link to the prostaglandin metabolism (Imir et al., 2007, J Clin Endocrinol Metab 92, 1979-1982).

A subject of the present invention is the use of the substances of the general formula I for the prophylaxis and treatment of fibroids (myomas).

An increasing number of research results also confirm the importance of the EP receptors, and in particular also of the $EP_2$ receptor in a large number of cancer types (e.g. breast cancer, colon carcinoma, lung cancer, prostate cancer, leukaemia and skin cancer), which points to future possibilities for the use of modulators (antagonists or agonists) of the $EP_2$ receptor for the therapy and prevention (prophylactic and/or adjuvant) of cancer (Fulton et al., 2006, Cancer Res; 66(20): 9794-7; Castellone et al., 2005, Science Vol 310, 1504-1510; Chang et al., 2005, Cancer Res; 65(11): 4496-9); Hull et al., 2004, Mol Cancer Ther; 3(8):1031-9; Richards et al., 2003, J Clin Endocrinol Metab 88: 2810-2816; Sinha et al., 2007, Cancer Res; 67(9): 4507-13; Wang et al., 2004, Seminars in Oncology, Vol 31, No 1, Suppl 3: pp 64-73), Yu et al., 2008; JPET Published on June 26, as DOI:10.1124/jpet.108.141275, Denizot et al., 2005, Int. J. Cancer: 115, 499-501; Fiancette et al., 2011, J Oncol. pii: 389021, Chun et al., 2011, Mol. Carcinog. 50(6):439-48).

A subject of the present invention is the use of the substances of the general formula I for the treatment and prevention of cancer diseases.

The activation of endothelial cells plays an important part in the pathogenic process of arteriosclerosis. Here oxidation products of low density lipoprotein (LDL) are significant in the onset and development of arteriosclerotic diseases. More recent researches indicate involvement of the $EP_2$ receptor (Li et al., 2006; Circ Res. 98:642-650).

A subject of the present invention is the use of the substances of the general formula I for the treatment and prevention of arteriosclerosis.

More recent scientific publications show that in neurodegenerative, neuroinflammatory and ischaemic diseases (Alzheimer, Parkinson, ALS and stroke), prostaglandins and the $EP_2$ receptor are important components of the pathological process (Hoshino et al., 2007, J Biol. Chem.; 282(45): 32676-88; Liang et al., 2005, The Journal of Neuroscience; 25(44): 10180-10187; Jin et al., 2007, J Neuroinflammation. January 4; 4:2.; Liang et al., 2008, Ann Neurol; 64: 304-314; Cimino et al., 2008, Current Medicinal Chemistry, 1863-1869).

Multiple sclerosis is a chronic inflammation of the nervous system. Prostaglandins, especially $PGE_2$, and effects mediated via the $EP_2$ receptor are causally linked with the pathological processes in multiple sclerosis (Palumbo et al., 2011, Prostaglandins, Leukotrienes and Essential Fatty Acids 85: 29-35; Palumbo et al., 2011, J. Neurochem. 10.1111/j.1471-4159, Kihara et al., 2009, Proc Natl Acad Sci U.S.A, 106, No. 51: 21807-21812).

A subject of the present invention is the use of the substances of the general formula I for the treatment and prevention of neurodegenerative, neuroinflammatory and ischaemic diseases such as for example Alzheimer's, Parkinson's, ALS and stroke and for the treatment of multiple sclerosis.

Polycystic kidney diseases are also linked with the $EP_2$ receptor (Song et al., 2009, Human Molecular Genetics, 18, No. 13: 2328-2343; Elberg et al., 2007, Am J Physiol Renal Physiol 293: F1622-F1632.)

A subject of the present invention is the use of the substances of the general formula I for the treatment and prevention of polycystic kidney diseases.

Reinold et al. (J. Clin. Invest. 115, 673-679 (2005)) describe $PGE_2$ receptors of the $EP_2$ subtype as the key signal elements in inflammatory hyperalgesia. Mice which no longer carry this receptor ($EP_2^{-/-}$) feel no spinal inflammatory pain. There are indications that an inflammatory, increased sensitivity to pain can be treated by specifically modulating $EP_2$ receptors. Furthermore, the $EP_2$ receptor is linked with other types of pain (Zeilhofer, 2007, Biochemical Pharmacology 73; 165-174), inter alia in facial nerves (Patwardhan et al. (J Dent Res 87(3):262-266, 2008)).

A subject of the present invention is the use of the substances according to the invention for the treatment and prevention of pain of various origins such as for example inflammatory hyperalgesia.

Recent scientific publications refer to a use of $EP_2$ inhibitors for the prevention and/or treatment of infections of the respiratory tract. Serezani et al. (Am Respir Cell Mol Biol Vol 37. pp 562-570, 2007) states that the ability of macrophages of the respiratory tract to destroy bacteria is impaired via the activation of the $EP_2$ receptor by $PGE_2$. Bacterial infections lead to increased production of prostaglandins, inter alia $PGE_2$, which via this mechanism weakens the endogenous defence against bacteria. As shown in this publication, this ability to combat bacteria can be restored by inactivation of the $EP_2$ receptor (and of the $EP_4$ receptor). Further relevant publications which explain these connections are: Sadikot et al., 2007, Eur. J. Immunol. 37: 1001-1009; Aronoff et al., 2004, The Journal of Immunology, 173: 559-565 and Medeiros et al., 2009, J Exp Med. 206(1):61-68.

A subject of the present invention is the use of the substances according to the invention for the prevention and treatment of infectious diseases of the lung.

Fibroblasts and here in particular their functions in the restoration of damaged tissue play a decisive part in chronic obstructive pulmonary disease. During this, an excess of $PGE_2$ suppresses important repair functions of the fibroblasts (Togo et al., 2008, Am J Respir Crit Care Med, 178: 248-260).

A subject of the present invention is the use of the substances according to the invention for prophylaxis and treatment in chronic obstructive pulmonary diseases.

Intestinal inflammatory diseases (e.g. Crohn's disease) are also linked with the prostaglandin $EP_2$ receptor (Sheibanie et al., 2007, The Journal of Immunology, 178: 8138-8147).

A subject of the present invention is the use of the substances according to the invention for the prevention and treatment of intestinal inflammatory diseases.

During bone marrow transplantation, complications often occur through infections, wherein an overproduction of $PGE_2$ is linked with decreased immune defence (Ballinger et al., 2006, The Journal of Immunology, 177: 5499-5508).

A subject of the present invention is the use of the substances according to the invention for prophylaxis and treatment in bone marrow transplantation.

Graves' disease is an autoimmune disease of the thyroid, in which the clinical picture can also include pathological changes in the eye (endocrine orbitopathy; protrusion of the eyeballs (exophthalmus)). During this, invading lymphocytes activate fibroblasts that are present, which leads inter alia to an accumulation of mucopolysaccharides. Possible consequences are impairment of the vision even extending to blindness. Studies show that interleukin-6 is of decisive importance for the pathological mechanisms and that interleukin-6 is induced via $PGE_2$ and the $EP_2$ receptor (Raychaudhuri et al., 2010, PloS ONE, 5: e15296; Wang et al., 1995, J Clin Endocrinol Metab 80: 3553-3560).

A subject of the present invention is the use of the substances according to the invention for prophylaxis and treatment in orbitopathy in connection with Graves' disease or other pathological diseases of the eye.

Aneurysms are vascular dilations with the risk of leading with vascular ruptures to haemorrhages with grave and life-threatening effects, e.g. paralysis, loss or impairment of speech, cognitive limitations and other neurological consequences in case of cerebral haemorrhages. Even without ruptures, cerebral aneurysms can cause severe neurological symptoms through the pressure on nerve fibres. Cerebral aneurysms are found in about 1-5% of the population, there being a higher incidence in women. Ruptures of aneurysms in the peripheral blood vessels involve a high risk of thromboses, cardiac infarctions, pain and a number of other clinical pictures. Pharmacological therapies mainly comprise the limitation of risk factors such as hypertension.

Recent scientific studies were able to show that the $EP_2$ receptor plays a substantial part in the pathogenesis of cerebral aneurysms. In this, via the cascade COX-2-$PGE_2$-$EP_2$-NF-κ-β an inflammatory state is created which is causally involved in aneurysm formation (Aoki et al., 2011, British Journal of Pharmacology 163: 1237-1249; Aoki et al. 2007, 116:2830-2840).

A subject of the present invention is the use of the substances according to the invention for the prophylaxis and treatment of aneurysms.

Kawasaki syndrome is an acute, systemic feverish disease, by which children under 5 years are predominantly affected. Long-term damage can include changes in the blood vessels, in particular the coronary blood vessels (e.g. formation of aneurysms) and diseases connected therewith such as cardiac rhythm disorders and cardiac infarction. The incidence differs regionally, thus for example 185 out of 100000 children under 5 years in Japan and about 9 out of 100000 children in Germany. Prostaglandin $E_2$ is elevated in the acute phase of the disease (Lee et al., 1988, Prostaglandins Leukot Essent Fatty Acids, 31(2):53-57). Through recent research studies it could be shown that l31 integrin is activated by $PGE_2$ and mediated via the $EP_2$ receptor, which is causally linked with the vascular damage (Kajimoto et al., 2009, Inflamm. Res. 58: 224-228).

A subject of the present invention is the use of the substances according to the invention for the prophylaxis and treatment of Kawasaki syndrome, in particular also for the prevention and avoidance of vascular damage.

Recent researches show that the $EP_2$ receptor has an important role in arthritis and here exerts an influence on the pathogenesis of this disease via immunomodulatory mechanisms (Harizi et al., 2010, Immunology and Cell Biology, 1-8).

A subject of the present invention is the use of the substances according to the invention for the prophylaxis and treatment of arthritis.

The natural ligand (agonist) of the $EP_2$ receptor is $PGE_2$, the synthesis whereof is mediated via cyclooxygenases (COX) enzymes (COX-1, COX-2). These enzymes are mostly involved in the said clinical pictures and indications and the onset thereof via increased expression and activity. Hence in all the use possibilities mentioned, a combination of a COX inhibitor (COX-2 and/or COX-1) is possible, with the aim of
 a) achieving a higher and more effective pharmacological activity than with one substance class and
 b) enabling a lower dosage of one of the two or of both substance classes, which leads to a reduction of possible side effects and better tolerance.

Hence drugs containing a compound of the general formula (I) in combination with a COX inhibitor for the treatment of diseases (combination preparations) are also a subject of the present invention. As COX inhibitors, for example the non-selective COX inhibitors such as aspirin, naproxen, indomethacin, ibuprofen and the selective COX inhibitors meloxicam, ketoprofen, piroxicam, tenoxicam, nimesulide, mefanemic acid, ketoralac, celecoxib (4-[5-(4-methylphenyl)-3-(trifluoromethyl)-1H-pyrazol-1-yl]benzenesulphonamide) parecoxib (N-[4-(5-methyl-3-phenyl-4-isoxazolyl)phenyl]sulphonylpropionamide), rofecoxib (4-(4-mesylphenyl)-3-phenylfuran-2(5H)-one), valdecoxib (4-[5-methyl-3-phenyl-4-isoxazoyl)benzenesulphonamide), NS-398 (N-methyl-2-cyclohexanoxy-4-nitrobenzenesulphonamide), lumiracoxib [2-(2'-chloro-6'-fluoro-phenyl)-amino-5-methylbenzeneacetic acid], ceracoxib and etoricoxib may be mentioned.

These combination preparations can be used for the treatment of the following diseases: infectious diseases, cancer, cardiovascular diseases, angiogenic diseases, uterine contraction disorders, pain, inflammatory diseases, neuroinflammatory diseases, neurodegenerative diseases, autoimmune diseases, immunodependent diseases/therapies, nephrological diseases and ophthalmological diseases.

They can also be used for fertility control.

In addition, the invention relates to a process for the production of the compounds according to the invention of the general formula I.

For this, for example a carboxylic acid of the formula VIII is reacted with an amine of the general formula XI by methods known to those skilled in the art to give the compounds according to the invention of the general formula I (Scheme 1).

The reaction takes place in that for example a carboxylic acid of the formula VIII is converted with isobutyl chloroformate in the presence of a tertiary amine, for example triethylamine, into a mixed anhydride, which reacts with an alkali metal salt of the appropriate amine XI in an inert solvent or solvent mixture, for example tetrahydrofuran, N,N-dimethylformamide or dimethoxyethane at temperatures between −30° C. and +60° C. to give the target compounds of the formula I.

It is also possible to activate a carboxylic acid VIII with reagents such as for example dicyclohexylcarbodiimide (DCC), 1-(3-dimethylaminopropyl)-3-ethylcarbodiimide (EDCI), N-hydroxybenzotriazole (HOBT) or N-[(dimethylamino)-(3H-[1,2,3]triazolo[4,5-b]pyridin-3-yloxy)methyliden]-N-methylmethanaminium hexafluorophosphate (HATU). For example the reaction with HATU takes place in an inert solvent, for example N,N-dimethylformamide or dimethyl sulphoxide in the presence of the appropriate amine XI and a tertiary amine, for example triethylamine or diisopropylamine, at temperatures between −30° C. and +60° C.

It is also possible, to convert a carboxylic acid of the formula VIII into the corresponding carboxylic acid chloride with an inorganic acid chloride, for example phosphorus pentachloride, phosphorus trichloride or thionyl chloride and then into the target compounds of the general formula I in pyridine or an inert solvent, such as for example N,N-dimethylformamide, in the presence of the appropriate amine XI and a tertiary amine, for example triethylamine, at temperatures between −30° C. and +60° C.

The compounds according to the invention of the general formula I can also be obtained from bromoindazoles of the general formula VI under palladium(0) catalysis by reaction with an appropriate amine XI and carbon monoxide (CO) or a carbon monoxide source, such as for example molybdenum hexacarbonyl in a suitable solvent or solvent mixture, for example 1,4-dioxan/water or tetrahydrofuran, addition of a base such as for example sodium carbonate or 1,8-diazabicyclo(5.4.0)undec-7-ene (DBU) and a catalyst-ligand mixture, for example palladium(II) acetate or trans bis(acetato)bis[o-(di-o-tolylphosphino)benzyl]-dipalladium(II)/tri-tert-butylphosphinotetrafluoroborate at temperatures between 80° C. and 160° C. (optionally with microwave irradiation between 80-200 watts), and in case of the use of carbon monoxide at a CO pressure of 5-15 bar (Scheme 1).

The compounds according to the invention of the general formula I can also be obtained from amines of the general formula XV by reaction with carboxylic acids (Y=OH), chlorides (Y=Cl) or anhydrides (e.g. Y=O—C(O)—O—$CH_2(CH)_3CH_3$) of the formula IX in the manner described for the production of the compounds I from the compounds VIII and XI (Scheme 2).

Likewise, the compounds of the general formula I can be obtained from compounds of the general formula XVI, wherein LG' for example means Br or I, by reaction with compounds of the formula XVIII (Scheme 2).

Compounds of the formula XVIII are for example (Het)Arylboronic acids ($R^3$-Met=(Het)Ar—B(OH)$_2$) or boronic acid pinacol esters ($R^3$-Met=(Het)Ar—BPin), which are converted to biaryl compounds of the formula I by methods known to those skilled in the art in a suitable solvent, for example N,N-dimethylformamide, tetrahydrofuran, dimethoxyethane and optionally water and addition of a base, for example triethylamine, potassium carbonate, caesium carbonate and a catalyst-ligand mixture, for example of palladium(II) acetate/triphenylphosphine, bis(diphenylphosphino)ferrocenedichloropalladium (II) (/1,1'-bis(diphenylphosphino)ferrocene/Cu(I)Cl) at temperatures between 20° C. and 120° C.

Compounds of the formula XVIII can also be (Het)Arylalcohols ($R^3$-Met=(Het)ArO—H), which are converted into biaryl ethers of the formula I by methods known to those skilled in the art in a suitable solvent, for example N,N-dimethylformamide or dimethyl sulphoxide with addition of a base, for example potassium carbonate, caesium carbonate under copper-(I) catalysis e.g. with copper(I) bromide at temperatures between 60° C. and 120° C.

The carboxylic acids of the general formula VIII can for example be obtained from esters of the formula VII by ester saponification in a suitable solvent or solvent mixture, for example methanol, ethanol or tetrahydrofuran, water with addition of an aqueous solution of an alkali metal hydroxide, for example sodium hydroxide or lithium hydroxide at temperatures between 20° C. and 60° C. (Scheme 1).

In the same manner, the carboxylic acids XIII can be obtained from the esters XII (Scheme 2, PG: e.g. Boc (tert-butyloxycarbonyl) and the carboxylic acids XXI from the esters XX (Scheme 3, LG': e.g. Br or I).

The esters of the general formula VII can be obtained from bromoindazoles of the general formula VI under palladium (0) catalysis by reaction with carbon monoxide or a carbon monoxide source, such as for example molybdenum hexacarbonyl, and methanol in a suitable solvent, for example dimethyl sulphoxide, N,N-dimethylformamide or tetrahydrofuran and addition of a base, for example triethylamine or 1,8-diazabicyclo(5.4.0)undec-7-ene and a catalyst-ligand mixture, for example of palladium(II) acetate/bis-1,3-diphenylphosphino-propane or trans bis(acetato)bis[o-(di-o-tolylphosphino)benzyl]dipalladium(II)/tri-tert-butylphosphinotetrafluoroborate at temperatures between 20° C. and 140° C. (optionally with microwave irradiation between 80-200 watts), and in case of the use of carbon monoxide at a CO pressure of 5-15 bar (Scheme 1).

This method is not restricted to methyl esters, i.e. to the use of methanol, but can also be extended to other esters. Thus for example by use of ethanol instead of methanol in this manner, the corresponding ethyl esters can be synthesized.

In the same manner, the esters XII can be obtained from the bromides IV (Scheme 2, -PG: e.g. -Boc).

The amides of the general formula VII can also be obtained from the amines of the general formula XIX by reaction with compounds of the general formula IX (Scheme 3), analogously to the synthesis of the compounds I from the compounds XV (Scheme 2).

The compounds of the general formula VII can also be obtained from compounds of the formula XX and reaction with compounds of the formula XVIII (Scheme 3), analogously to the described conversion of the compounds XVI to the compounds of the formula I (Scheme 2).

The amides of the general formula VI can be obtained from amines of the general formula V by reaction with carboxylic acids (Y=OH), chlorides (Y=Cl) or anhydrides (e.g. Y=O—C(O)—O—$CH_2(CH)_3CH_3$) of the formula IX (Scheme 1), as described for the conversion of amines XV to amides I (Scheme 2).

The amides of the general formula XVI can be obtained in analogous manner from amines XV and carboxylic acids or carboxylic acid derivatives XVII (Y: e.g. OH, Cl or O—C(O)—$CH_2(CH)_3CH_3$; LG': e.g. Br or I) (Scheme 2).

Analogously, amines XX (LG': e.g. Br or I) can be obtained from amines XIX and carboxylic acids or carboxylic acid derivatives XVII (Y: e.g. OH, Cl or O—C(O)—O—$CH_2$ $(CH)_3CH_3$; LG': e.g. Br or I) (Scheme 3).

Likewise, carboxylic acids XIII (PG: e.g. Boc) can be converted with amines XI to amides XIV (Scheme 2) and carboxylic acids XXI (LG': e.g. Br, I) with amines XI to amides XVI (Scheme 3) in this manner.

The secondary amines V can be obtained from the corresponding carbamates IV (PG: e.g. Boc) by methods known to those skilled in the art (Scheme 1).

Thus for example tert-butyl carbamates can be converted into the amines V in an acidic medium with the use of e.g. trifluoroacetic acid or hydrochloric acid in a suitable solvent or solvent mixture such as for example dichloromethane, dioxan or acetone/water. In an anhydrous medium the amines V are formed as the corresponding salts.

Analogously, the amines XV can be obtained from the carbamates XIV (Scheme 2) and the amines XIX from the carbamates XII (Scheme 3).

The 2H-indazoles of the general formulae IV and VI can be produced in various ways.

For example, 2H-indazoles IV can be obtained from 1H-indazoles of the general formula II by alkylation with compounds of the general formula III (PG: e.g. Boc, LG: e.g. Br, I, O-Ts (tosyloxy) or O-Ms (mesyloxy)) in a suitable solvent, for example N,N-dimethylformamide, N,N-dimethylacetamide, dimethyl sulphoxide or else THF, 1,4-dioxan and addition of a base such as for example potassium carbonate or caesium carbonate (optionally with addition of tetrabutylammonium iodide) or else sodium bis(trimethylsilyl)amide, at temperatures between 25° C. and 100° C. or else in case of the use of sodium bis(trimethylsilyl)amide 0° C. and 25° C. (Scheme 1).

Analogously the 2H-indazoles of the general formula VI can be obtained from 1H-indazoles of the general formula II and compounds of the general formula X (LG: e.g. Br, I, O-Ts or O-Ms) (Scheme 1).

The 2H-indazoles of the general formula IV can also be obtained from ortho-nitrobenzaldehydes of the general formula XXVII by reaction with an appropriate amine XXVIII (PG: e.g. Boc) in a suitable solvent, for example 1,4-dioxan and addition of a reducing agent such as for example triethyl phosphite, possibly with addition of potassium carbonate or caesium carbonate or powdered molecular sieve, at temperatures between 100° C. and 160° C. (Scheme 4).

Analogously, the 2H-indazoles of the general formula VI can be obtained from ortho-nitrobenzaldehydes XXVII by reaction with amines XXIX (Scheme 4).

The compounds of the general formula XIV (PG: e.g. Boc) can also be obtained from bromoindazoles of the general formula IV (PG: e.g. Boc) under palladium(0) catalysis by reaction with an appropriate amine XI and carbon monoxide or a carbon monoxide source, such as for example molybdenum hexacarbonyl (Scheme 2), analogously to the described process for the conversion of the bromoindazoles VI to the compounds of the general formula I, (Scheme 1).

The ortho-nitrobenzaldehydes of the general formula XXVII can be produced from the ortho-nitrotoluenes of the general formula XXVI by methods known to those skilled in the art in two reaction steps (Scheme 4).

For this, an ortho-nitrotoluene XXVI is dissolved in a suitable solvent such as N,N-dimethyl-formamide and converted with N,N-dimethylformamide dimethyl acetal at temperatures of 100-140° C. to the corresponding enamine, which is immediately oxidized at temperatures of 0° C.-20° C. to the corresponding ortho-nitrobenzaldehyde with a suitable oxidizing agent such as for example $NaIO_4$ in a suitable aqueous solvent mixture such as water/N,N-dimethylformamide and optionally with addition of a base such as for example triethylamine, N,N-diisopropylethylamine, sodium hydrogen carbonate or sodium carbonate.

The ortho-nitrotoluenes of the general formula XXVI can be produced from the ortho-methylanilines of the general formula XXV by methods known to those skilled in the art (Scheme 4).

For this, an ortho-methylaniline XXV is dissolved in a suitable solvent such as dichloromethane or chloroform, treated with zirconium(IV) tert-butoxide, ground molecular sieve 3 Å and tert-butyl hydroperoxide and reacted at temperatures of 20-40° C.

The 1H-indazoles of the general formula II can be liberated from the acetamides of the general formula XXIV by methods known to those skilled in the art (Scheme 4).

For this, for example an acetamide XXIV is reacted in a suitable solvent such as methanol or ethanol and addition of 37% hydrochloric acid at temperatures of 40-80° C.

Analogously thereto, the anilines of the formula XXV can be liberated from the acetanilides of the formula XXIII (Scheme 4).

The acetamides of the general formula XXIV can be produced from the ortho-methyl-acetanilides of the general formula XXIII by methods known to those skilled in the art (Scheme 4).

For this, the ortho-methyl-acetanilides XXIII are dissolved in a suitable solvent such as chloroform or toluene, treated with acetic anhydride, isopentyl or tert-butyl nitrite, and optionally potassium acetate and 18-crown-6, and reacted at temperatures of 60-100° C.

The ortho-methyl-acetanilides XXIII can be produced from the acetanilides of the general formula XXII by bromination by methods known to those skilled in the art (Scheme 4).

For this, the acetanilides XXII, which can for example be obtained from the corresponding anilines by reaction with acetic anhydride in a suitable solvent (e.g. toluene) at temperatures of 80-110° C., is reacted with bromine in glacial acetic acid at temperatures of 10-25° C.

The compounds of the general formula III wherein LG means —OTs or —OMs can be produced by methods known to those skilled in the art from the corresponding alcohols.

For this, the alcohols are reacted with p-toluenesulphonyl chloride or methanesulphonyl chloride at temperatures between 0° C. and 40° C. in a suitable solvent, e.g. dichloromethane or tetrahydrofuran or toluene and addition of a suitable base, e.g. pyridine or triethylamine.

The compounds of the general formula X, wherein LG means —OTs or —OMs, can be produced from the corresponding amino alcohols XXX by methods known to those skilled in the art (Scheme 4).

For this, in a first step the amino alcohols XXX are converted to the corresponding amides XXXI in a suitable solvent, e.g. dichloromethane, with arylcarboxylic acid chlorides of the formula Cl—C(O)—Ar—$R^3$ and addition of a suitable base, e.g. triethylamine, at temperatures between 0° C. and 25° C. Optionally, corresponding esters formed as by-products can be separated or else saponified to the corresponding alcohols XXXI under standard conditions, e.g. with use of a base, e.g. potassium hydroxide, in a suitable solvent mixture, e.g. ethanol/water, at temperatures between 20° C. and 40° C.

The N-protected alcohols XXXI thus obtained can be converted into the compounds of the formula X with LG: —OTs or —OMs analogously to the process described for the synthesis of the compounds III. Compounds of the formula X with LG: —Br can be obtained from the corresponding alcohols XXXI by methods known to those skilled in the art by reaction with a brominating agent such as for example $CBr_4$ with addition of $PPh_3$ as an oxophile in a suitable solvent, e.g. chloroform, at temperatures between 20° C. and 40° C.

The compounds of the general formula XXIX, can be produced by methods known to those skilled in the art for example from the amines of the formula XXXII (Scheme 4).

For this, in a first step, the amines XXXII are converted to the corresponding amides XXXIII analogously to the synthesis of the compounds I from the compounds XV.

The tert-butyloxycarbonyl group in compounds of the formula XXXIII is cleaved analogously to the conversion of the compounds IV to the compounds V, hence the compounds of the formula XXIX can be obtained.

Scheme 1
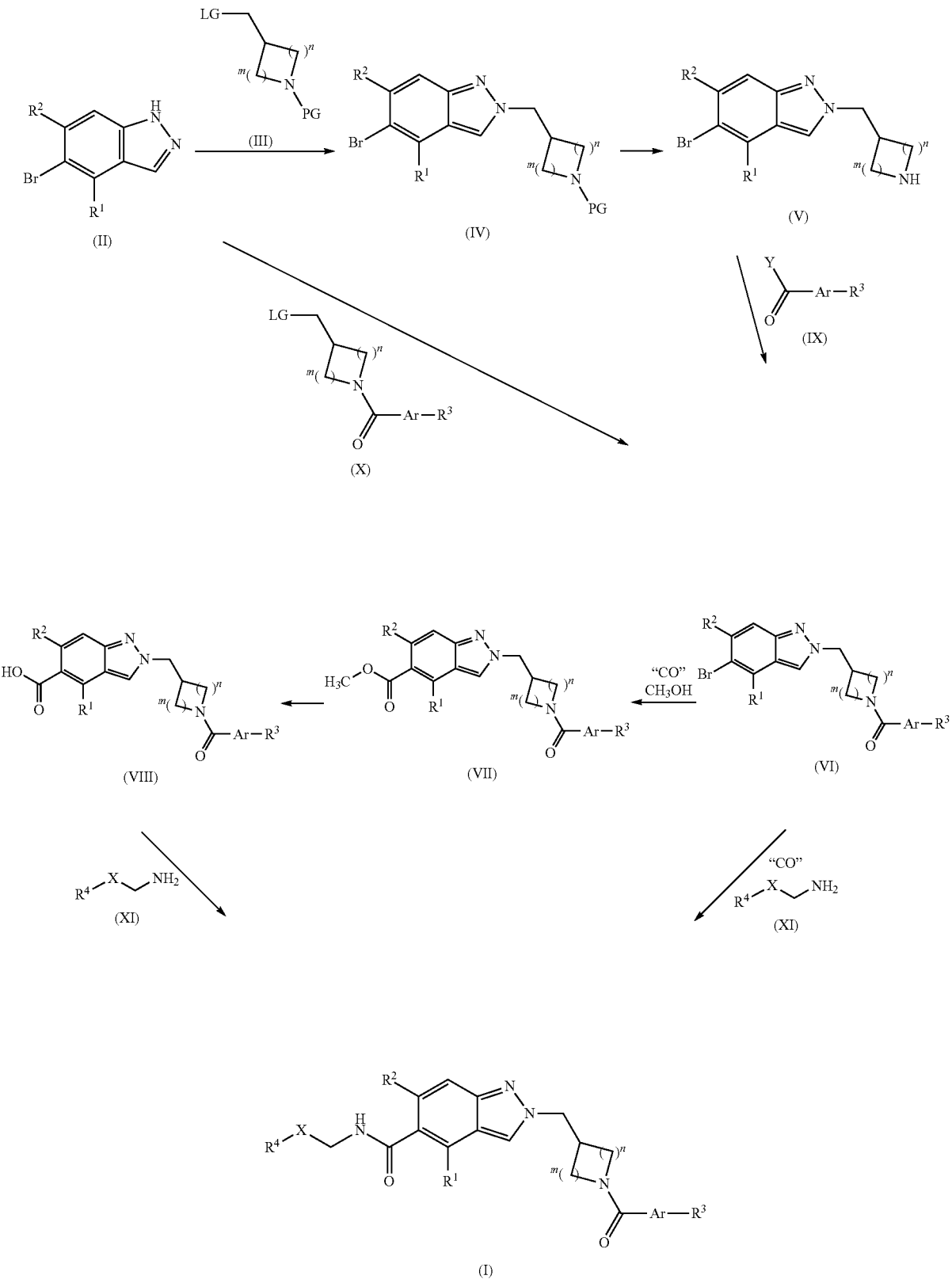

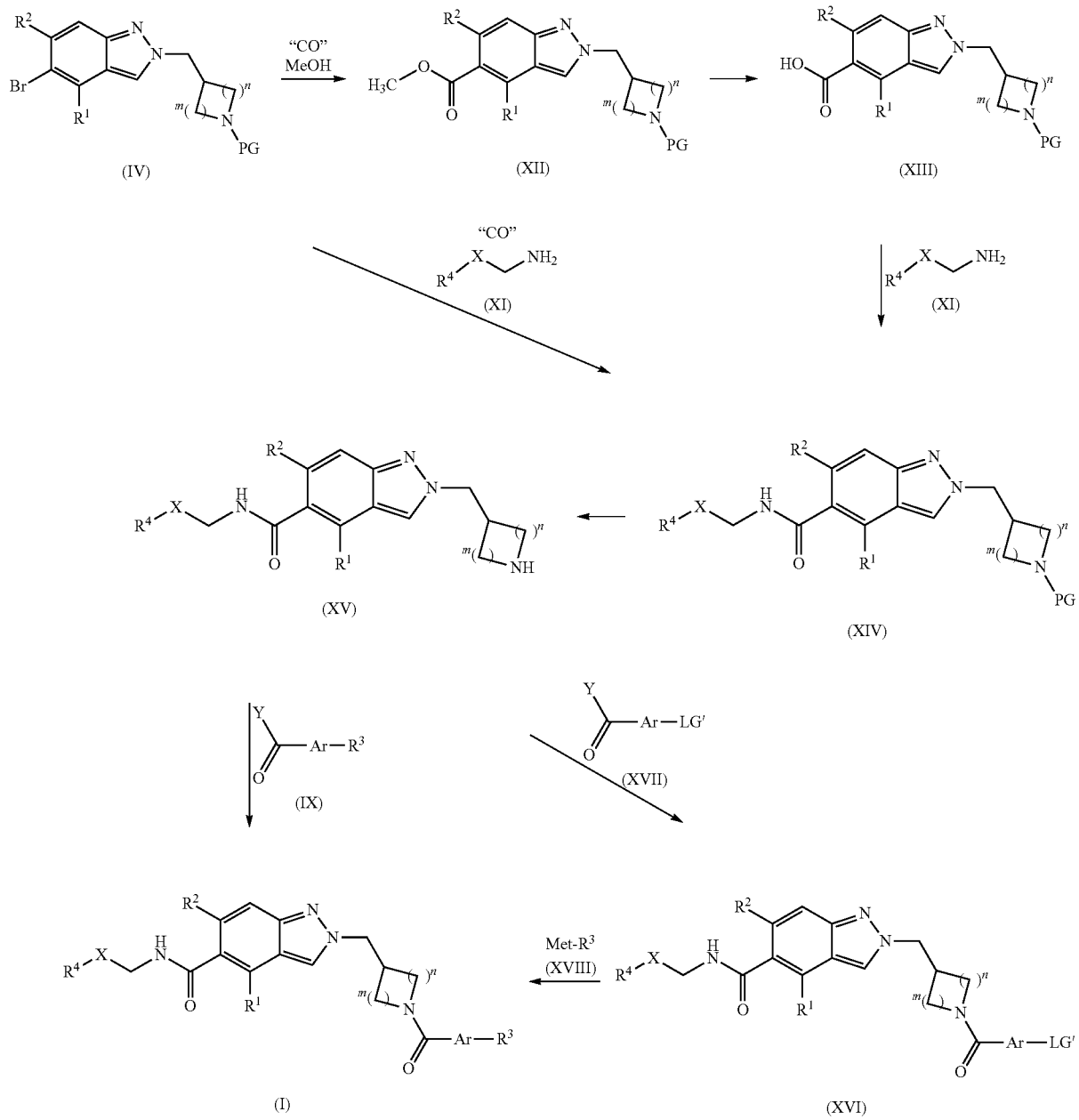
Scheme 2
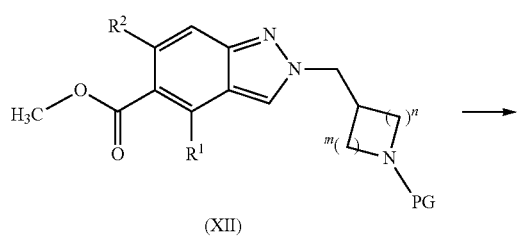
Scheme 3

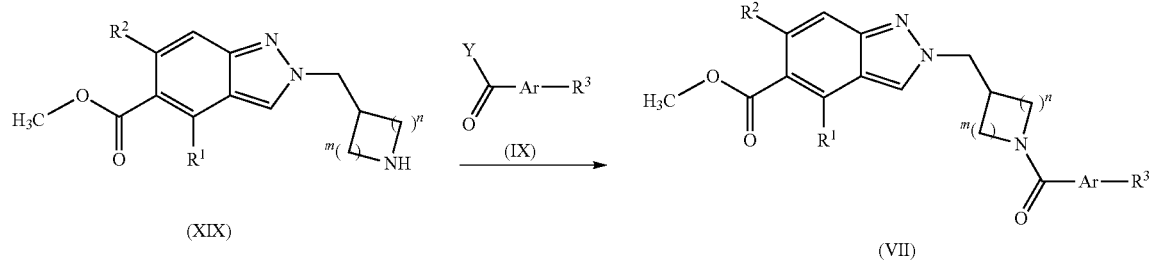
-continued
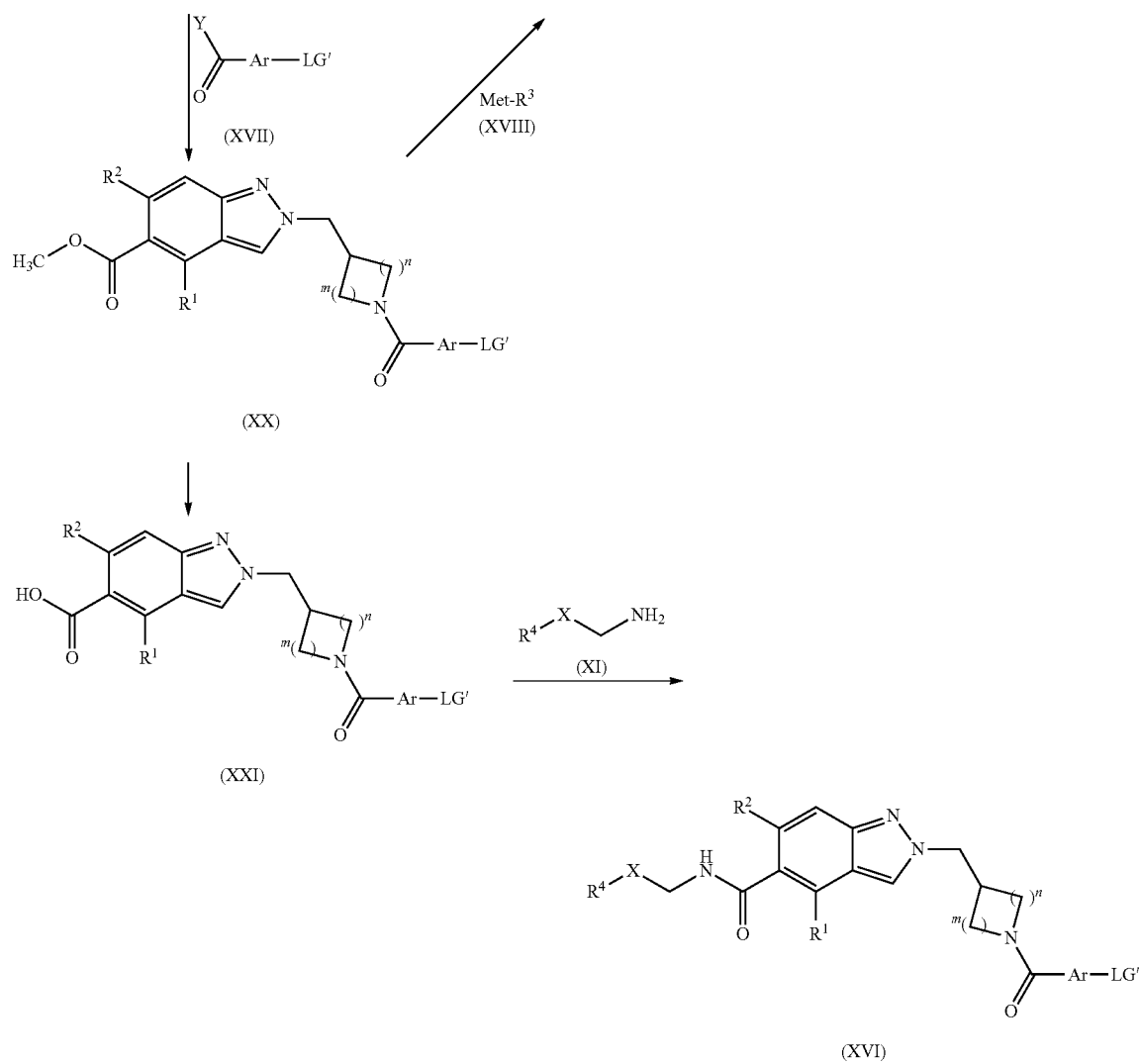
Scheme 4
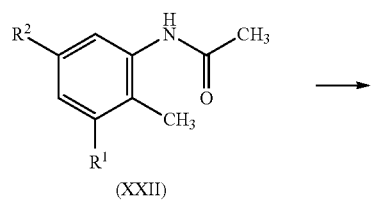

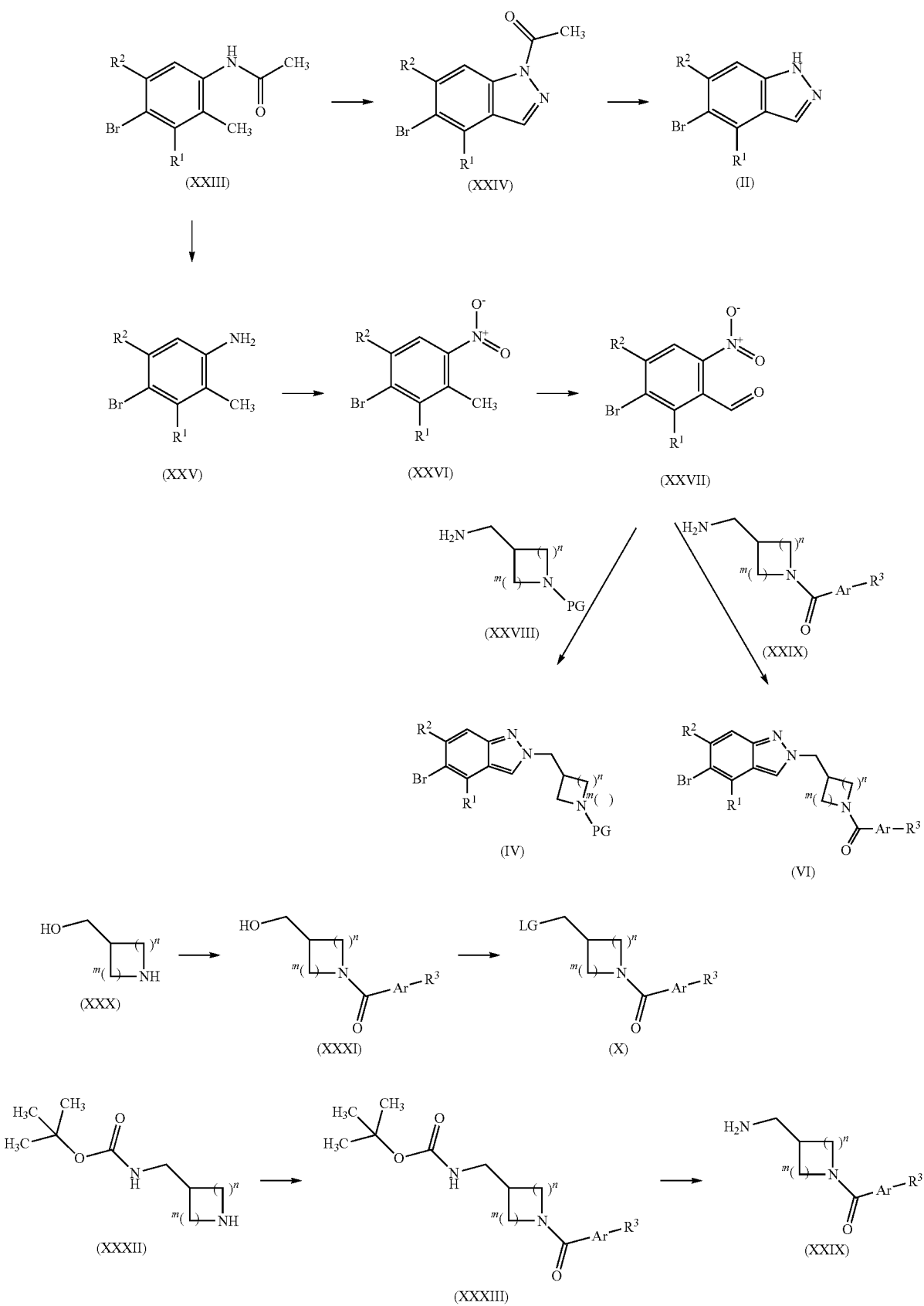

Production of the Compounds According to the Invention

The following examples illustrate the production of the compounds according to the invention of the general formula (I), without limiting the range of the claimed compounds to these examples.

The compounds according to the invention of the general formula (I) can be produced and characterized as described below.

LC-MS: Waters Acquity HPLC/MS 100-800 Daltons; 20 V (Micromass/Waters ZQ 4000); Column: BEHC 18 (Waters), 2.1×50 mm, BEH 1.7 µm; Mobile phase: A: $H_2O$/0.05% HCOOH, B: $CH_3CN$/0.05% HCOOH. Gradient: 10-90% B in 1.7 min, 90% B for 0.2 min, 98-2% B in 0.6 min; Flow rate: 1.3 ml/min, Detection: UV=200-400 nm.

Chiral HPLC Separation Method A:

Preparative chiral HPLC: System: Dionex: Pump P 580, Gilson: Liquid Handler 215, Knauer: UV detector K-2501 Column: Chiralpak AD-H 5 µm 250×20 mm; Solvent: hexane/ethanol 50:50; Flow rate: 15 ml/min; injection volume: 0.5 ml; Detection: UV 254 nm.

Analytical chiral HPLC: System: Waters: Alliance 2695, DAD 996, ESA: Corona; Column: Chiralpak AD-H 5 µm 150×4.6 mm Solvent: hexane/ethanol 50:50; Flow rate: 1.0 ml/min; Temperature: 25° C.; injection: 5 µl; Detection: DAD 254 nm.

Chiral HPLC Separation Method B:

Preparative chiral HPLC: System: Dionex: Pump P 580, Gilson: Liquid Handler 215, Knauer: UV detector K-2501 Column: Chiralpak IC 5 µm 250×30 mm; Solvent: ethanol/methanol 50:50; Flow rate: 30 ml/min; injection volume: 0.5 ml; Detection: UV 254 nm.

Analytical chiral HPLC: System: Waters: Alliance 2695, DAD 996, ESA: Corona; Column: Chiralpak IC 5 µm 150×4.6 mm Solvent: ethanol/methanol 50:50; Flow rate: 1.0 ml/min; Temperature: 25° C.; injection: 5 µl; Detection: DAD 254 nm.

Chiral HPLC Separation Method C:

Preparative chiral HPLC: System: Dionex: Pump P 580, Gilson: Liquid Handler 215, Knauer: UV detector K-2501 Column: Chiralpak AD-H 5 µm 250×20 mm; Solvent: hexane/2-propanol 50:50; Flow rate: 15 ml/min; injection volume: 0.25 ml; Detection: UV 254 nm.

Analytical chiral HPLC: System: Waters: Alliance 2695, DAD 996, ESA: Corona; Column: Chiralpak AD-H 5 µm 150×4.6 mm Solvent: hexane/2-propanol 50:50; Flow rate: 1.0 ml/min; Temperature: 25° C.; injection: 5 µl; Detection: DAD 254 nm.

Chiral HPLC Separation Method D:

Preparative chiral HPLC: System: Dionex: Pump P 580, Gilson: Liquid Handler 215, Knauer: UV detector K-2501 Column: Chiralpak IB 5 µm 250×20 mm; Solvent: hexane/ethanol 70:30; Flow rate: 20 ml/min; injection volume: 0.1 ml; Detection: UV 210 nm.

Analytical chiral HPLC: System: Waters: Alliance 2695, DAD 996, ESA: Corona; Column: Chiralpak IB 5 µm 150×4.6 mm Solvent: hexane/ethanol 70:30; Flow rate: 1.0 ml/min; Temperature: 25° C.; injection: 5 µl; Detection: DAD 230 nm.

Chiral HPLC separation method E:

Preparative chiral HPLC: System: Dionex: Pump P 580, Gilson: Liquid Handler 215, Knauer: UV detector K-2501 Column: Chiralpak IC 5 µm 250×20 mm; Solvent: ethanol/methanol 50:50; Flow rate: 15 ml/min; injection volume: 0.3 ml; Detection: UV 230 nm.

Analytical chiral HPLC: System: Waters: Alliance 2695, DAD 996, ESA: Corona; Column: Chiralpak IC 5 µm 150×4.6 mm Solvent: ethanol/methanol 50:50; Flow rate: 1.0 ml/min; Temperature: 25° C.; injection: 5 µl; Detection: DAD 230 nm.

Abbreviations

Boc tert-butoxycarbonyl
CO carbon monoxide
DBU 1,8-diazabicyclo[5.4.0]undec-7-ene
DCM dichloromethane
DMF N,N-dimethylformamide
DMSO dimethyl sulphoxide
ESI; ES+ electrospray ionization (in MS); positive charged ion trace
hr(s) hour(s)
HATU N—[(dimethylamino)-1H-1,2,3-triazolo[4,5-b]pyridin-1-ylmethylen]-N-methylmethanaminium hexafluorophosphate N-oxide
HPLC high pressure, high performance liquid chromatography
conc. concentrated
LC-MS liquid chromatography-coupled mass spectroscopy
M molar
min(s) minute(s)
MS mass spectroscopy
N normal
NMR nuclear resonance spectroscopy
$R_t$ retention time (in HPLC and LC)
RT room temperature
tert tertiary
THF tetrahydrofuran

EXAMPLE 1

2-{[1-(4-cyano-2-fluorobenzoyl)piperidin-4-yl]methyl}-N-(2-methoxyethyl)-4-methyl-2H-indazol-5-carboxamide

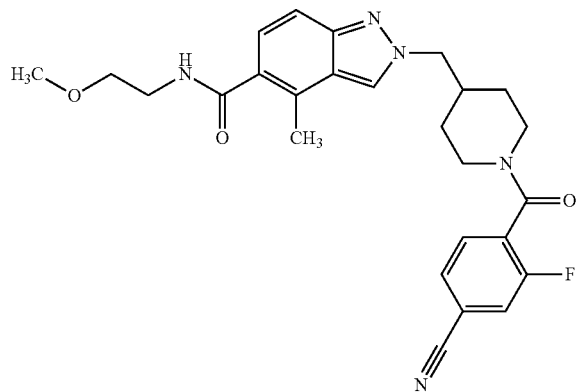 [SMILES: COCCNC(=O)c1ccc2nn(CC3CCN(C(=O)c4ccc(C#N)cc4F)CC3)cc2c1C]

To a solution of 33.7 mg of 4-cyano-2-fluorobenzoic acid in 1.0 ml dimethyl sulphoxide were added 85.5 mg of HATU, 75 mg of the amine prepared in Example 1a and 0.071 ml of N,N-diisopropylethylamine and this was stirred for 1 hour at 25° C. The mixture was concentrated in vacuo and the residue thus obtained purified by HPLC. Yield: 43.3 mg of the title compound.

$^1$H-NMR (400 MHz, DMSO-d$_6$): δ [ppm]=1.07-1.28 (2H), 1.30-1.44 (1H), 1.47-1.61 (1H), 2.18-2.34 (1H), 2.49 (3H), 2.71-2.83 (1H), 2.92-3.08 (1H), 3.32 (4H), 3.36 (2H), 3.42

(2H), 4.31 (2H), 4.39-4.51 (1H), 7.14 (1H), 7.38 (1H), 7.50-7.63 (1H), 7.71-7.79 (1H), 7.95 (1H), 8.09-8.15 (1H), 8.47 (1H).

The starting material for the above title compound was prepared as follows:

EXAMPLE 1a

N-(2-methoxyethyl)-4-methyl-2-(4-piperidylmethyl)-2H-indazol-5-carboxamide hydrochloride

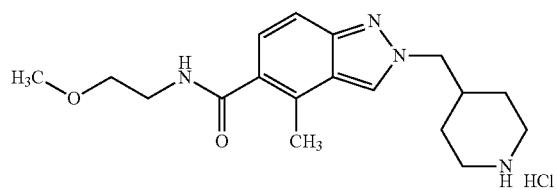 [SMILES: COCCNC(=O)c1ccc2nn(CC3CCNCC3)cc2c1C ; Cl]

To 855.1 mg of 1b were added 4.5 ml of 4M hydrochloric acid in dioxan and 1 ml dioxan. An oily mass was formed, which dissolved on vigorous stirring and gentle warming. The mixture was stirred for 1 hr at ca. 30° C. The reaction mixture was concentrated. Yield: 764.7 mg of the title compound, which was further reacted without further purification.

$^1$H-NMR (300 MHz, DMSO-d$_6$): δ [ppm]=1.33-1.50 (2H), 1.52-1.62 (2H), 2.17-2.31 (1H), 2.32-2.38 (1H), 2.49 (3H), 2.67-2.86 (2H), 3.13-3.28 (5H), 3.31-3.46 (4H), 4.33 (2H), 7.16 (1H), 7.38 (1H), 8.13 (1H), 8.53 (1H), 8.71-8.88 (1H), 8.99-9.11 (1H).

EXAMPLE 1b

Tert-butyl 4-({5-[N-(2-methoxyethyl)carbamoyl]-4-methyl-2H-indazol-2-yl}-methyl)piperidin-1-carboxylate

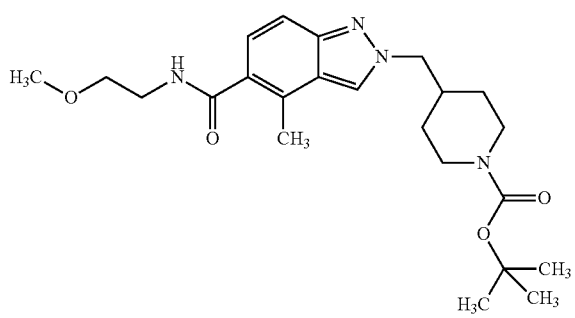 [SMILES: COCCNC(=O)c1ccc2nn(CC3CCN(C(=O)OC(C)(C)C)CC3)cc2c1C]

Version A: 2820 mg of 1c, 1556 mg of 2-methoxyethylamine, 1823 mg of molybdenum hexacarbonyl, 200.4 mg of tri-tert-butylphosphine tetrafluoroborate and 647.5 mg of trans-bis(acetato)-bis[o-(di-o-tolylphosphino)benzyl]dipalladium(II) were placed in portions in three microwave tubes and suspended with 56 ml THF. Then 3.1 ml of DBU were added and the mixtures stirred for 20 mins at 125° C. and 200 watts in the microwave. The reaction mixtures were combined, filtered and diluted with some ethyl acetate and the organic phase washed twice with water and once with saturated sodium chloride solution. This was dried over sodium sulphate, filtered and concentrated. The residue was chromatographed on the Biotage SP4. Gradient: ethyl acetate/methanol 0-10%. Yield: 885.1 mg of the title compound.

Version B: 780 mg of 1d and 1747 mg of HATU were first dissolved in 10 ml DMSO. Next, 314 mg of 2-methoxyethylamine and 1080 mg of N,N-diisopropylethylamine were added. The mixture was stirred for 1 hr at RT. The reaction mixture was poured into water and extracted three times with ethyl acetate. The combined organic phases were washed with saturated sodium chloride solution, dried over sodium sulphate, filtered and concentrated. The residue was purified chromatographically on the Biotage SP4. Gradient: ethyl acetate/methanol 0-10%. Yield: 740 mg of the title compound.

$^1$H-NMR (400 MHz, DMSO-d$_6$): δ [ppm]=1.01-1.13 (2H), 1.34 (9H), 1.36-1.43 (2H), 2.06-2.19 (1H), 2.49 (3H), 2.59-2.70 (2H), 3.29 (3H), 3.33-3.39 (2H), 3.40-3.45 (2H), 3.82-3.93 (2H), 4.28 (2H), 7.14 (1H), 7.38 (1H), 8.09-8.14 (1H), 8.46 (1H).

EXAMPLE 1c

Tert-butyl 4-[(5-bromo-4-methyl-2H-indazol-2-yl)methyl]piperidin-1-carboxylate

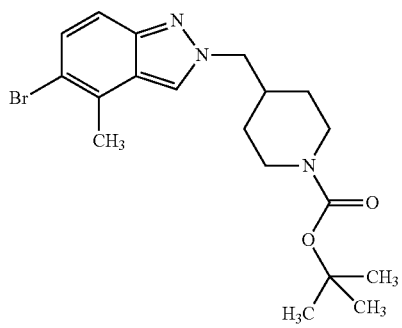 [SMILES: Cc1c(Br)ccc2nn(CC3CCN(C(=O)OC(C)(C)C)CC3)cc12]

5 g of 5-bromo-4-methyl-1H-indazole was dissolved in 110 ml DMF and treated with 11.5 g of caesium carbonate and 7.9 g of N-Boc-4-(bromomethyl)piperidine. The mixture was stirred for 3 hrs at 60° C. and overnight at RT. The reaction mixture was next diluted with ethyl acetate, and the organic phase was washed twice with water, dried over sodium sulphate, filtered and concentrated. The residue was purified chromatographically on the Biotage SP4 via a 65i-Si column Gradient: hexane/ethyl acetate 0-100%. Yield: 3.53 g of the title compound.

$^1$H-NMR (300 MHz, DMSO-d$_6$): δ [ppm]=0.99-1.12 (2H), 1.34 (9H), 1.36-1.44 (2H), 2.04-2.19 (1H), 2.47 (3H), 2.54-2.72 (2H), 3.82-3.93 (2H), 4.27 (2H), 7.29 (1H), 7.34 (1H), 8.46 (1H).

EXAMPLE 1d

2-{[1-(tert-butoxycarbonyl)piperidin-4-yl]methyl}-4-methyl-2H-indazol-5-carboxylic acid

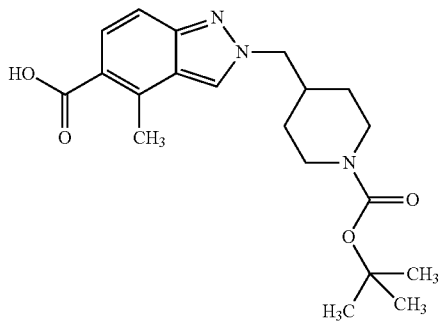 [SMILES: Cc1c(C(=O)O)ccc2nn(CC3CCN(C(=O)OC(C)(C)C)CC3)cc12]

1080 mg of 1e were dissolved in 8 ml methanol and treated with 1235 mg of lithium hydroxide in 10 ml water. A further 2 ml THF were added as solubilizer. The mixture was stirred for 24 hrs at RT. Next the methanol and THF were distilled off. The aqueous residue was diluted with water and washed once with ethyl acetate. The aqueous phase was acidified with 10% sulphuric acid and extracted twice with ethyl acetate. The combined organic phases were dried over sodium sulphate, filtered and concentrated. Yield: 880 mg of the title compound.

$^1$H-NMR (300 MHz, DMSO-$d_6$): δ [ppm]=0.99-1.18 (2H), 1.37-1.48 (2H), 1.34 (9H), 2.05-2.21 (1H), 2.53-2.70 (2H), 2.73 (3H), 3.81-3.94 (2H), 4.29 (2H), 7.39 (1H), 7.62 (1H), 8.62 (1H), 11.92-12.31 (1H).

EXAMPLE 1e

Methyl 2-{[1-(tert-butoxycarbonyl)piperidin-4-yl]methyl)}-4-methyl-2H-indazol-5-carboxylate

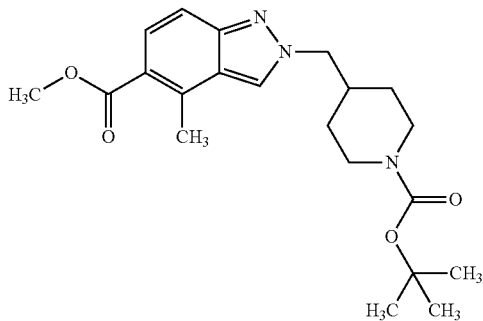 [SMILES: COC(=O)c1ccc2nn(CC3CCN(C(=O)OC(C)(C)C)CC3)cc2c1C]

666 mg of 1c, 156.8 mg of methanol, 645.8 mg of molybdenum hexacarbonyl, 47.3 mg of tri-tert-butylphosphine tetrafluoroborate and 123.5 mg of trans-bis(acetato)-bis[o-(di-o-tolyl-phosphino)benzyl]dipalladium(II) were placed in a microwave tube and suspended in 15 ml THF. Then 0.7 ml of DBU were added and the mixture was stirred for 20 mins at 125° C. and 150 watts in the microwave. Next, it was concentrated, taken up in ethyl acetate and the organic phase washed twice with water and once with saturated sodium chloride solution. It was dried over sodium sulphate, filtered and concentrated. The residue was chromatographed on the Biotage SP4. Gradient: hexane/ethyl acetate 0-100%. Yield: 363 mg of the title compound.

$^1$H-NMR (400 MHz, DMSO-$d_6$): δ [ppm]=1.01-1.12 (2H), 1.34 (9H), 1.37-1.45 (2H), 2.08-2.19 (1H), 2.53-2.69 (2H), 2.73 (3H), 3.79 (3H), 3.83-3.93 (2H), 4.30 (2H), 7.42 (1H), 7.62 (1H), 8.67 (1H).

EXAMPLE 2

2-({1-[4-tert-(butoxy)benzoyl]piperidin-4-yl}methyl)-N-(2-methoxyethyl)-4-methyl-2H-indazol-5-carboxamide

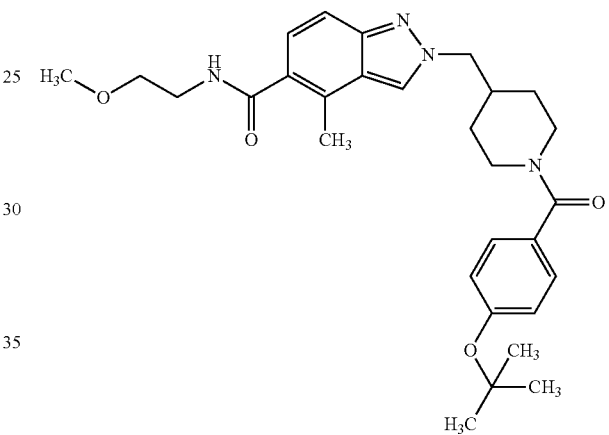

Analogously to Example 1, 35.9 mg of the title compound was obtained from 75 mg of the amine prepared in Example 1a and 39.7 mg of 4-(tert-butoxy)benzoic acid.

$^1$H-NMR (300 MHz, DMSO-$d_6$): δ [ppm]=1.09-1.26 (2H), 1.29 (9H), 1.35-1.58 (2H), 2.15-2.35 (1H), 2.49 (3H), 2.69-2.97 (2H), 3.24 (3H), 3.32-3.47 (4H), 4.23-4.40 (2H), 6.98 (2H), 7.14 (1H), 7.23 (2H), 7.38 (1H), 8.10 (1H), 8.47 (1H).

EXAMPLE 3

2-({1-[4-(4-fluorophenoxy)benzoyl]piperidin-4-yl}methyl)-N-(2-methoxyethyl)-4-methyl-2H-indazol-5-carboxamide

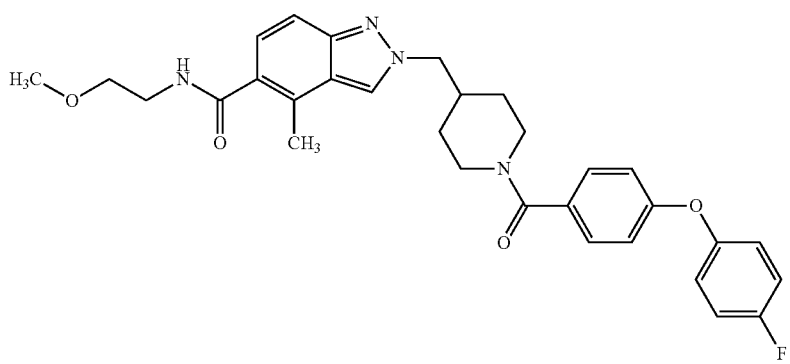 [SMILES: COCCNC(=O)c1ccc2nn(CC3CCN(C(=O)c4ccc(Oc5ccc(F)cc5)cc4)CC3)cc2c1C]

Analogously to Example 1, 51.6 mg of the title compound was obtained from 75 mg of the amine prepared in Example 1a and 47.5 mg of 4-(4-fluorophenoxy)benzoic acid.

$^1$H-NMR (300 MHz, DMSO-d$_6$): δ [ppm]=1.10-1.30 (2H), 1.32-1.58 (2H), 2.19-2.35 (1H), 2.49 (3H), 2.71-3.02 (2H), 3.25 (3H), 3.32-3.39 (2H), 3.40-3.47 (2H), 4.32 (2H), 6.95 (2H), 7.06-7.14 (3H), 7.15-7.27 (3H), 7.31-7.42 (3H), 8.07-8.15 (1H), 8.47 (1H).

EXAMPLE 4

N-(2-methoxyethyl)-4-methyl-2-{[1-(4-morpholinobenzoyl)piperidin-4-yl]methyl}-2H-indazol-5-carboxamide

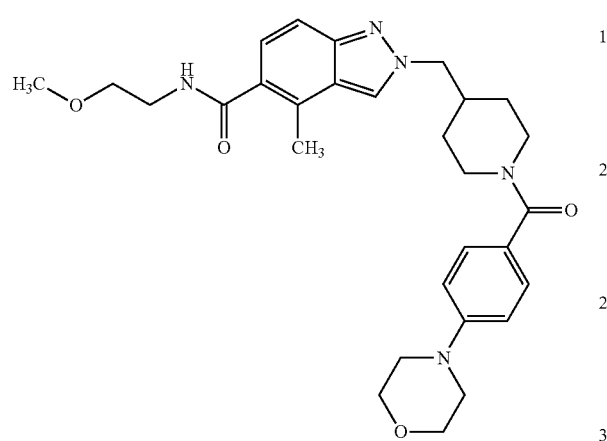

Analogously to Example 1, 48.1 mg of the title compound was obtained from 75 mg of the amine prepared in Example 1a and 42.3 mg of 4-morpholinobenzoic acid.

$^1$H-NMR (300 MHz, DMSO-d$_6$): δ [ppm]=1.09-1.29 (2H), 1.36-1.53 (2H), 2.16-2.34 (1H), 2.49 (3H), 2.72-2.94 (2H), 3.13 (4H), 3.24 (3H), 3.42 (4H), 3.64-3.75 (4H), 3.92-4.15 (1H), 4.32 (2H), 6.92 (2H), 7.14 (1H), 7.20 (2H), 7.38 (1H), 8.07-8.15 (1H), 8.47 (1H).

EXAMPLE 5

2-({1-[(4'-fluorobiphenyl-4-yl)carbonyl]piperidin-4-yl}methyl)-N-(2-methoxy-ethyl)-4-methyl-2H-indazol-5-carboxamide

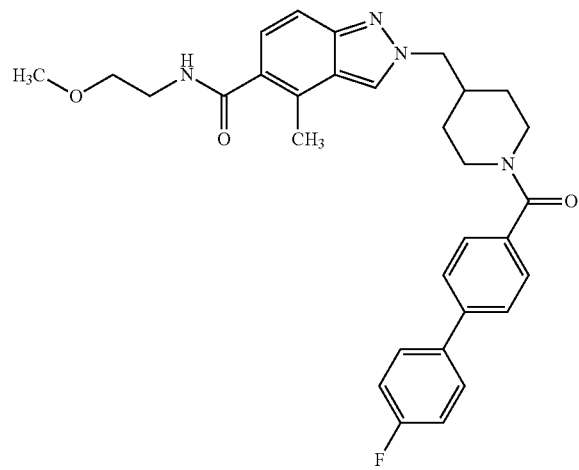 [SMILES: COCCNC(=O)c1ccc2nn(CC3CCN(C(=O)c4ccc(-c5ccc(F)cc5)cc4)CC3)cc2c1C]

Analogously to Example 1, 50.1 mg of the title compound was obtained from 75 mg of the amine prepared in Example 1a and 44.2 mg of 4-(4-fluorophenyl)benzoic acid.

$^1$H-NMR (300 MHz, DMSO-d$_6$): δ [ppm]=1.11-1.32 (2H), 1.32-1.64 (2H), 2.20-2.36 (1H), 2.49 (3H), 2.63-3.08 (2H), 3.24 (3H), 3.42 (4H), 3.50-3.73 (1H), 4.24-4.55 (3H), 7.10-7.20 (1H), 7.27 2H), 7.41 (3H), 7.67 (4H), 8.03-8.16 (1H), 8.48 (1H).

EXAMPLE 6

2-{[1-(2-fluoro-4-mesylbenzoyl)piperidin-4-yl]methyl}-N-(2-methoxyethyl)-4-methyl-2H-indazol-5-carboxamide

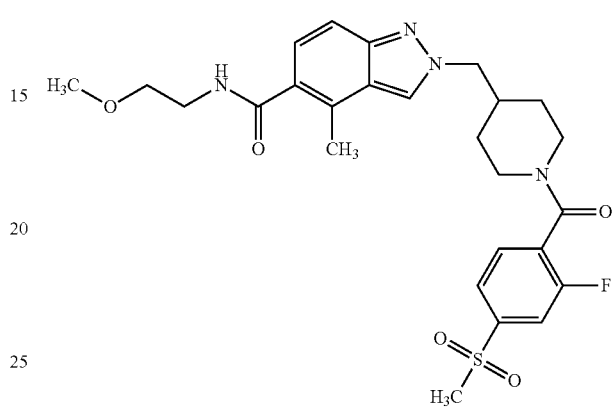

Analogously to Example 1, 40.1 mg of the title compound was obtained from 75 mg of the amine prepared in Example 1a and 44.6 mg of 2-fluoro-4-mesylbenzoic acid.

$^1$H-NMR (300 MHz, DMSO-d$_6$): δ [ppm]=1.06-1.30 (2H), 1.31-1.45 (1H), 1.51-1.64 (1H), 2.20-2.37 (1H), 2.49 (3H), 2.71-2.85 (1H), 2.91-3.10 (1H), 3.24 (3H), 3.26 (3H), 3.33-3.39 (2H), 3.42 (2H), 4.24-4.39 (2H), 4.40-4.51 (1H), 7.14 (1H), 7.38 (1H), 7.59-7.69 (1H), 7.76-7.89 (2H), 8.07-8.14 (1H), 8.47 (1H).

EXAMPLE 7

2-{[1-(2-fluoro-4-methoxybenzoyl)piperidin-4-yl]methyl}-N-(2-methoxyethyl)-4-methyl-2H-indazol-5-carboxamide

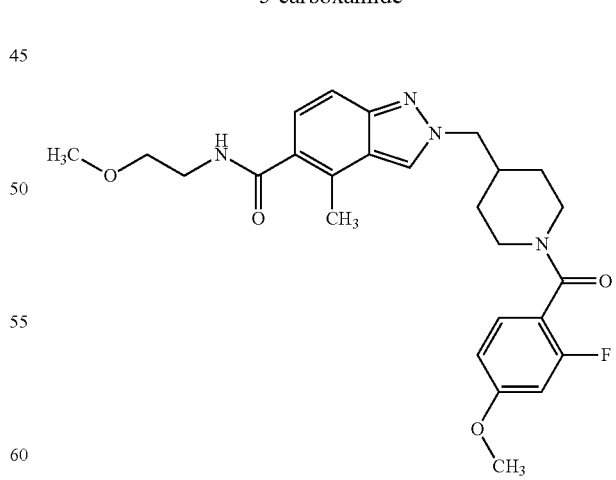

Analogously to Example 1, 43.1 mg of the title compound was obtained from 75 mg of the amine prepared in Example 1a and 34.8 mg of 2-fluoro-4-methoxybenzoic acid.

$^1$H-NMR (300 MHz, DMSO-d$_6$): δ [ppm]=1.05-1.25 (2H), 1.32-1.44 (1H), 1.48-1.61 (1H), 2.18-2.33 (1H), 2.49 (3H), 2.63-2.79 (1H), 2.88-3.05 (1H), 3.24 (3H), 3.42 (d, 5H), 3.75 (3H), 4.27-4.35 (2H), 4.37-4.49 (1H), 6.77-6.89 (2H), 7.14 (1H), 7.24 (1H), 7.38 (1H), 8.07-8.15 (1H), 8.47 (1H).

EXAMPLE 8

2-{[1-(4-bromo-2-fluorobenzoyl)piperidin-4-yl]methyl}-N-(2-methoxyethyl)-4-methyl-2H-indazol-5-carboxamide

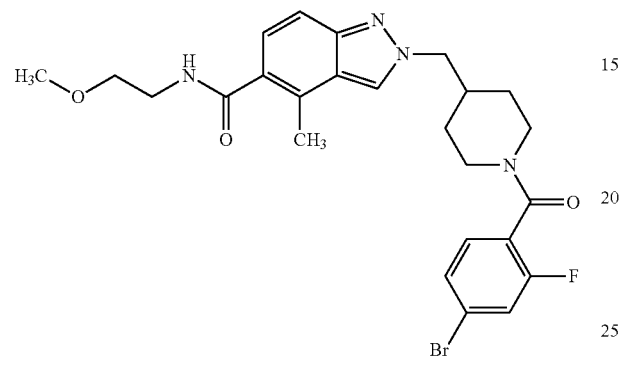

Analogously to Example 1, 51.8 mg of the title compound was obtained from 75 mg of the amine prepared in Example 1a and 44.7 mg of 4-bromo-2-fluorobenzoic acid.

$^1$H-NMR (300 MHz, DMSO-d$_6$): δ [ppm]=1.04-1.27 (2H), 1.32-1.43 (1H), 1.49-1.61 (1H), 2.20-2.33 (1H), 2.48 (3H), 2.67-2.80 (1H), 2.91-3.05 (1H), 3.24 (3H), 3.33-3.46 (5H), 4.24-4.36 (2H), 4.38-4.49 (1H), 7.15 (1H), 7.27-7.34 (1H), 7.35-7.41 (1H), 7.44-7.50 (1H), 7.60-7.66 (1H), 8.07-8.15 (1H), 8.47 (1H).

EXAMPLE 9

2-{[1-(2-fluoro-4-methylbenzoyl)piperidin-4-yl]methyl}-N-(2-methoxyethyl)-4-methyl-2H-indazol-5-carboxamide

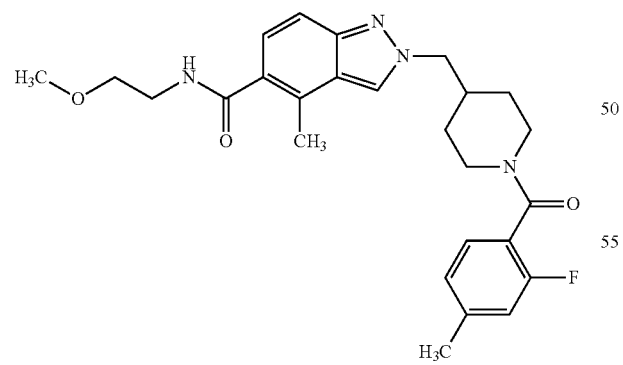

Analogously to Example 1, 38.3 mg of the title compound was obtained from 75 mg of the amine prepared in Example 1a and 31.5 mg of 2-fluoro-4-methylbenzoic acid.

$^1$H-NMR (300 MHz, DMSO-d$_6$): δ [ppm]=1.04-1.26 (2H), 1.31-1.43 (1H), 1.48-1.60 (1H), 2.18-2.35 (4H), 2.48 (3H), 2.64-2.79 (1H), 2.89-3.04 (1H), 3.24 (3H), 3.33-3.39 (3H), 3.39-3.45 (2H), 4.23-4.36 (2H), 4.39-4.49 (1H), 7.01-7.10 (2H), 7.13 (1H), 7.16-7.24 (1H), 7.38 (1H), 8.07-8.14 (1H), 8.47 (1H).

EXAMPLE 10

2-({1-[2-fluoro-4-(trifluoromethyl)benzoyl]piperidin-4-yl}methyl)-N-(2-methoxy-ethyl)-4-methyl-2H-indazol-5-carboxamide

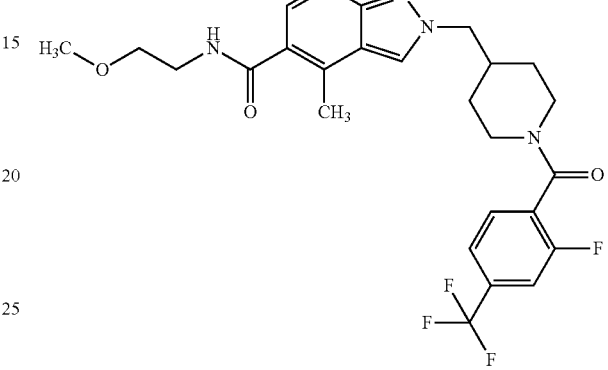

Analogously to Example 1, 57.8 mg of the title compound was obtained from 75 mg of the amine prepared in Example 1a and 42.5 mg of 2-fluoro-4-(trifluoromethyl)benzoic acid.

$^1$H-NMR (300 MHz, DMSO-d$_6$): δ [ppm]=1.07-1.29 (2H), 1.32-1.44 (1H), 1.52-1.62 (1H), 2.20-2.36 (1H), 2.49 (3H), 2.67-2.84 (1H), 2.93-3.07 (1H), 3.24 (3H), 3.32-3.39 (3H), 3.39-3.46 (2H), 4.24-4.39 (2H), 4.40-4.51 (1H), 7.14 (1H), 7.38 (1H), 7.56-7.68 (2H), 7.76 (1H), 8.07-8.14 (1H), 8.47 (1H).

EXAMPLE 11

N-(2-methoxyethyl)-4-methyl-2-({1-[4-(pentafluoro-λ$^6$-sulphanyl)benzoyl]piperidin-4-yl}methyl)-2H-indazol-5-carboxamide

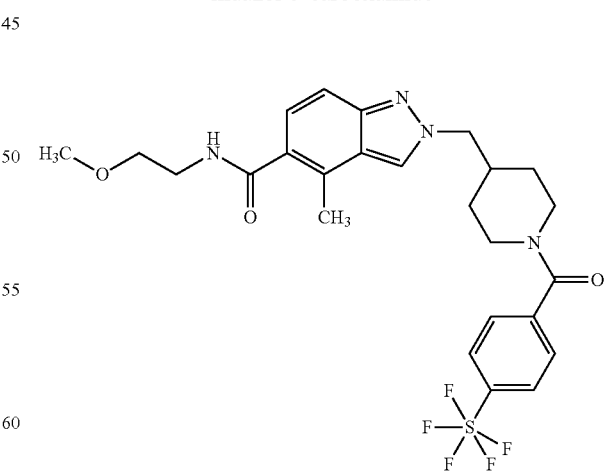

Analogously to Example 1, 135.1 mg of the title compound was obtained from 150 mg of the amine prepared in Example 1a and 101.5 mg of 4-(pentafluoro-λ$^6$-sulphanyl)benzoic acid.

¹H-NMR (300 MHz, DMSO-d₆): δ [ppm]=1.10-1.30 (2H), 1.31-1.42 (1H), 1.50-1.62 (1H), 2.20-2.33 (1H), 2.49 (3H), 2.67-2.83 (1H), 2.91-3.06 (1H), 3.24 (3H), 3.32-3.39 (2H), 3.41 (3H), 4.32 (2H), 4.37-4.48 (1H), 7.14 (1H), 7.38 (1H), 7.55 (2H), 7.94 (2H), 8.12 (1H), 8.47 (1H).

The following compounds were prepared analogously:

| Ex. | Structure | IUPAC name | Analysis |
|---|---|---|---|
| 12 | 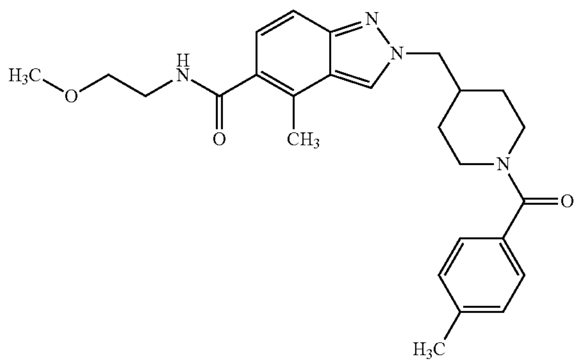 [SMILES: COCCNC(=O)c1ccc2nn(CC3CCN(C(=O)c4ccc(C)cc4)CC3)cc2c1C] | N-(2-methoxyethyl)-4-methyl-2-{[1-(4-methylbenzoyl)-piperidin-4-yl]-methyl)-2H-indazol-5-carboxamide | ¹H-NMR (400 MHz, DMSO-d₆): δ [ppm] = 1.20 (2H), 1.42 (2H), 2.29 (4H), 2.49 (3H), 2.73 (1H), 2.93 (1H), 3.25 (3H), 3.37 (2H), 3.43 (2H), 3.57 (1H), 4.31 (2H), 4.40 (1H), 7.14 (1H), 7.21 (4H), 7.38 (1H), 8.09 (1H), 8.46 (1H). |
| 13 | 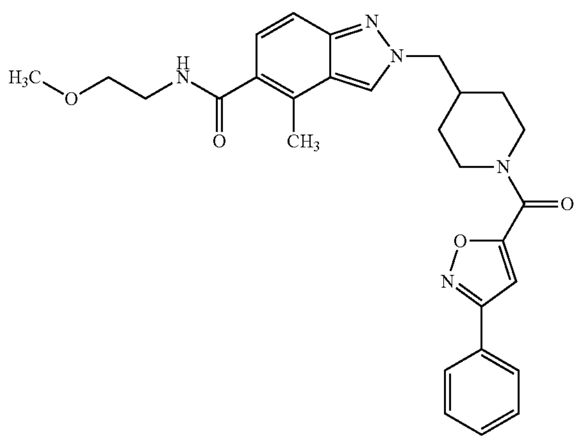 [SMILES: COCCNC(=O)c1ccc2nn(CC3CCN(C(=O)c4cc(-c5ccccc5)no4)CC3)cc2c1C] | N-(2-methoxyethyl)-4-methyl-2-({1-[(3-phenylisoxazol-5-yl)carbonyl]piperidin-4-yl}methyl)-2H-indazol-5-carboxamide | ¹H-NMR (300 MHz, DMSO-d₆): δ [ppm] = 1.25 (2H), 1.55 (2H), 2.34 (1H), 2.49 (3H), 2.83 (1H), 3.15 (1H), 3.24 (3H), 3.40 (4H), 3.87 (1H), 4.35 (3H), 7.15 (1H), 7.40 (1H), 7.46 (1H), 7.50 (3H), 7.90 (2H), 8.13 (1H), 8.49 (1H). |
| 14 | 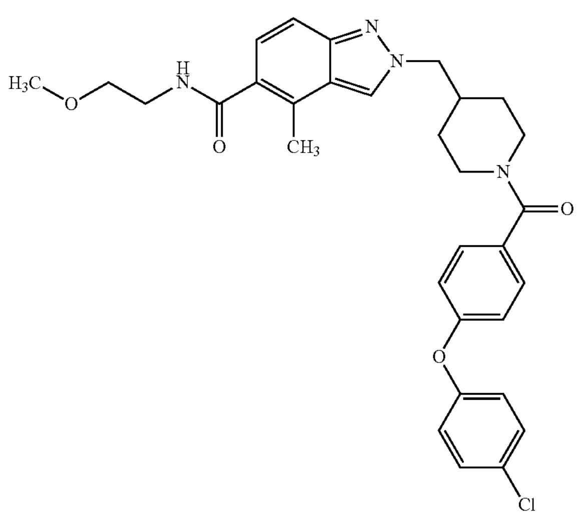 [SMILES: COCCNC(=O)c1ccc2nn(CC3CCN(C(=O)c4ccc(Oc5ccc(Cl)cc5)cc4)CC3)cc2c1C] | 2-({1-[4-(4-chlorophenoxy)benzoyl]-piperidin-4-yl}-methyl)-N-(2-methoxyethyl)-4-methyl-2H-indazol-5-carboxamide | ¹H-NMR (300 MHz, DMSO-d₆): δ [ppm] = 1.21 (2H), 1.45 (2H), 2.26 (1H), 2.49 (3H), 2.76 (1H), 2.94 (1H), 3.24 (3H), 3.40 (4H), 3.62 (1H), 4.33 (3H), 7.04 (4H), 7.15 (1H), 7.40 (5H), 8.12 (1H), 8.47 (1H). |

| Ex. | Structure | IUPAC name | Analysis |
|---|---|---|---|
| 15 | 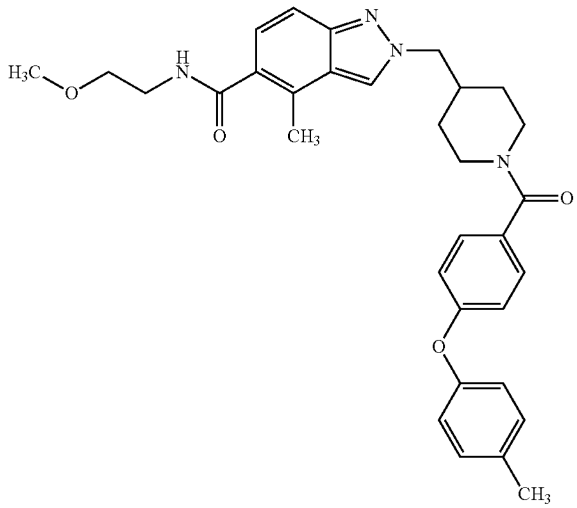 [SMILES: COCCNC(=O)c1ccc2nn(CC3CCN(C(=O)c4ccc(Oc5ccc(C)cc5)cc4)CC3)cc2c1C] | N-(2-methoxyethyl)-4-methyl-2-({1-[4-(4-methylphenoxy)-benzoyl]piperidin-4-yl}methyl)-2H-indazol-5-carboxamide | ¹H-NMR (300 MHz, DMSO-d₆): δ [ppm] = 1.20 (2H), 1.43 (2H), 2.26 (4H), 2.48 (3H), 2.76 (1H), 2.90 (1H), 3.24 (3H), 3.38 (4H), 3.62 (1H), 4.32 (3H), 6.92 (4H), 7.71 (3H), 7.34 (3H), 8.12 (1H), 8.47 (1H). |
| 16 | 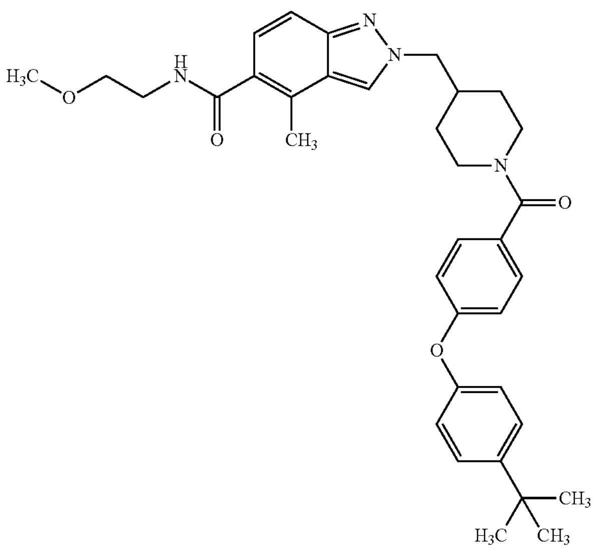 [SMILES: COCCNC(=O)c1ccc2nn(CC3CCN(C(=O)c4ccc(Oc5ccc(C(C)(C)C)cc5)cc4)CC3)cc2c1C] | 2-({1-[4-(4-tert-butylphenoxy)-benzoyl]piperidin-4-yl}methyl)-N-(2-methoxyethyl)-4-methyl-2H-indazol-5-carboxamide | ¹H-NMR (300 MHz, DMSO-d₆): δ [ppm] = 1.21 (2H), 1.25 (9H), 1.44 (2H), 2.26 (1H), 2.48 (3H), 2.77 (1H), 2.291 (1H), 3.24 (3H), 3.39 (4H), 3.64 (1H), 4.32 (3H), 6.95 (4H), 7.14 (1H), 7.36 (5H), 8.12 (1H), 8.47 (1H). |
| 17 | 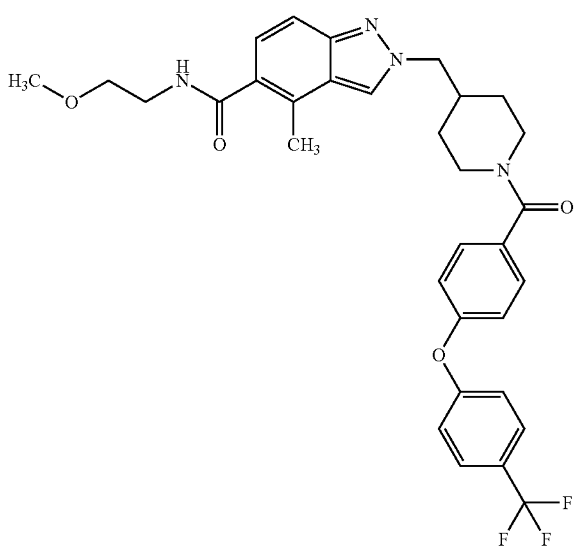 [SMILES: COCCNC(=O)c1ccc2nn(CC3CCN(C(=O)c4ccc(Oc5ccc(C(F)(F)F)cc5)cc4)CC3)cc2c1C] | N-(2-methoxyethyl)-4-methyl-2-[(1-{4-[4-(trifluoromethyl)-phenoxy]benzoyl}-piperidin-4-yl)-methyl]-2H-indazol-5-carboxamide | ¹H-NMR (300 MHz, DMSO-d₆): δ [ppm] = 1.22 (2H), 1.45 (2H), 2.27 (1H), 2.49 (3H), 2.77 (1H), 2.97 (1H), 3.24 (3H), 3.39 (4H), 3.61 (1H), 4.33 (3H), 7.15 (5H), 7.39 (3H), 7.73 (2H), 8.12 (1H), 8.48 (1H). |

-continued

| Ex. | Structure | IUPAC name | Analysis |
|---|---|---|---|
| 18 | 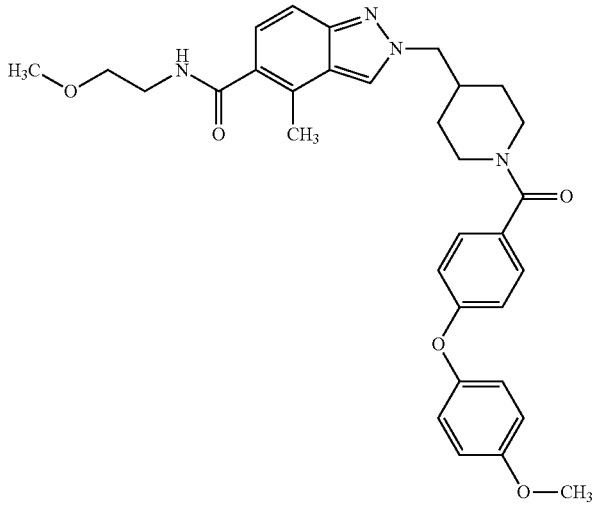 | N-(2-methoxyethyl)-2-({1-[4-(4-methoxy-phenoxy)benzoyl]-piperidin-4-yl}-methyl)-4-methyl-2H-indazol-5-carboxamide | $^1$H-NMR (300 MHz, DMSO-$d_6$): δ [ppm] = 1.19 (2H), 1.44 (2H), 2.25 (1H), 2.48 (3H), 2.86 (2H), 3.24 (3H), 3.40 (4H), 3.64 (1H), 3.72 (3H), 4.32 (3H), 6.88 (2H), 6.95 (2H), 7.02 (2H), 7.14 (1H), 7.31 (2H), 7.38 (1H), 8.12 (1H), 8.47 (1H). |
| 19 | 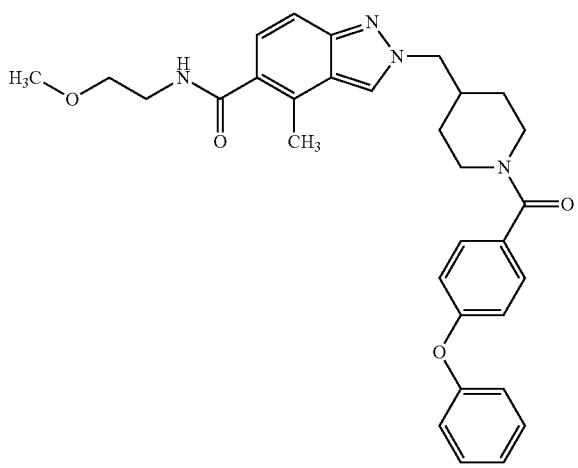 [SMILES: COCCNC(=O)c1ccc2nn(CC3CCN(C(=O)c4ccc(Oc5ccccc5)cc4)CC3)cc2c1C] | N-(2-methoxyethyl)-4-methyl-2-{[1-(4-phenoxybenzoyl)-piperidin-4-yl]-methyl}-2H-indazol-5-carboxamide | $^1$H-NMR (300 MHz, DMSO-$d_6$): δ [ppm] = 1.21 (2H), 1.44 (2H), 2.26 (1H), 2.49 (3H), 2.77 (1H), 2.92 (1H), 3.24 (3H), 3.38 (4H), 3.64 (1H), 4.32 (3H), 6.97 (2H), 7.04 (2H), 7.16 (2H), 7.26 (5H), 8.12 (1H), 8.47 (1H). |
| 20 | 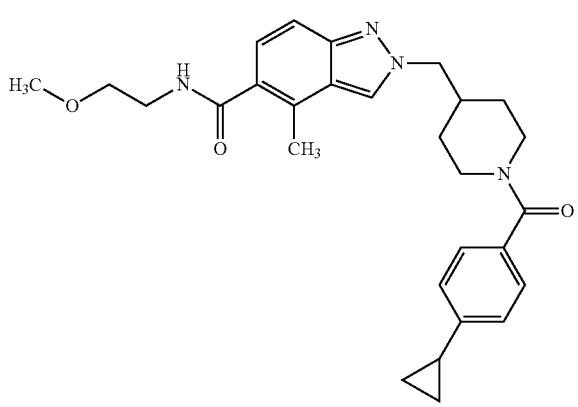 [SMILES: COCCNC(=O)c1ccc2nn(CC3CCN(C(=O)c4ccc(C5CC5)cc4)CC3)cc2c1C] | 2-{[1-(4-cyclopropyl-benzoyl)piperidin-4-yl]methyl}-N-(2-methoxyethyl)-4-methyl-2H-indazol-5-carboxamide | $^1$H-NMR (300 MHz, DMSO-$d_6$): δ [ppm] = 0.65 (2H), 0.93 (2H), 1.19 (2H), 1.43 (2H), 1.90 (1H), 2.25 (1H), 2.48 (3H), 2.73 (1H), 2.92 (1H), 3.24 (3H), 3.39 (4H), 3.59 (1H), 4.32 (3H), 7.14 (5H), 7.38 (1H), 8.12 (1H), 8.47 (1H). |

| Ex. | Structure | IUPAC name | Analysis |
|---|---|---|---|
| 21 | 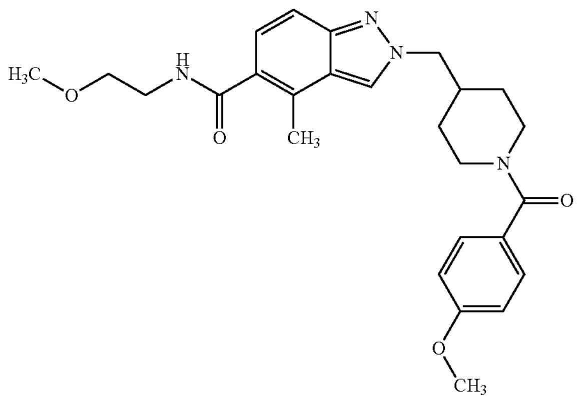 [SMILES: COCCNC(=O)c1ccc2nn(CC3CCN(C(=O)c4ccc(OC)cc4)CC3)cc2c1C] | 2-{[1-(4-methoxy-benzoyl)piperidin-4-yl]methyl}-N-(2-methoxyethyl)-4-methyl-2H-indazol-5-carboxamide | $^1$H-NMR (400 MHz, DMSO-d$_6$): δ [ppm] = 1.19 (2H), 1.44 (2H), 2.26 (1H), 2.49 (3H), 2.82 (2H), 3.24 (3H), 3.36 (2H), 3.42 (2H), 3.50 (1H), 3.74 (3H), 4.31 (3H), 6.93 (2H), 7.14 (1H), 7.29 (2H), 7.38 (1H), 8.12 (1H), 8.47 (1H). |
| 22 | 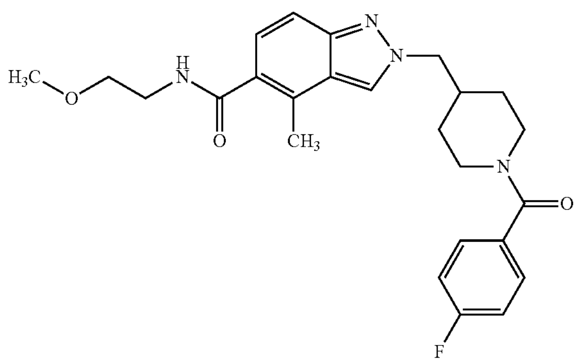 [SMILES: COCCNC(=O)c1ccc2nn(CC3CCN(C(=O)c4ccc(F)cc4)CC3)cc2c1C] | 2-{[1-(4-fluoro-benzoyl)piperidin-4-yl]methyl}-N-(2-methoxyethyl)-4-methyl-2H-indazol-5-carboxamide | $^1$H-NMR (400 MHz, DMSO-d$_6$): δ [ppm] = 1.20 (2H), 1.37 (1H), 1.51 (1H), 2.27 (1H), 2.49 (3H), 2.72 (1H), 2.97 (1H), 3.24 (3H), 3.36 (2H), 3.42 (2H), 3.52 (1H), 4.31 (2H), 4.40 (1H), 7.14 (1H), 7.23 (2H), 7.39 (3H), 8.12 (1H), 8.47 (1H). |
| 23 | 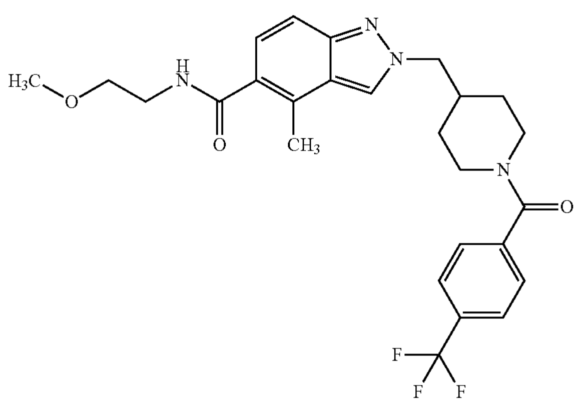 [SMILES: COCCNC(=O)c1ccc2nn(CC3CCN(C(=O)c4ccc(C(F)(F)F)cc4)CC3)cc2c1C] | N-(2-methoxyethyl)-4-methyl-2-({1-[4-(trifluoromethyl)-benzoyl]piperidin-4-yl}methyl)-2H-indazol-5-carboxamide | $^1$H-NMR (400 MHz, DMSO-d$_6$): δ [ppm] = 1.22 (2H), 1.34 (1H), 1.56 (1H), 2.28 (1H), 2.49 (3H), 2.75 (1H), 2.99 (1H), 3.24 (3H), 3.35 (2H), 3.42 (3H), 4.32 (2H), 4.44 (1H), 7.14 (1H), 7.38 (1H), 7.55 (2H), 7.77 (2H), 8.12 (1H), 8.47 (1H). |
| 24 | 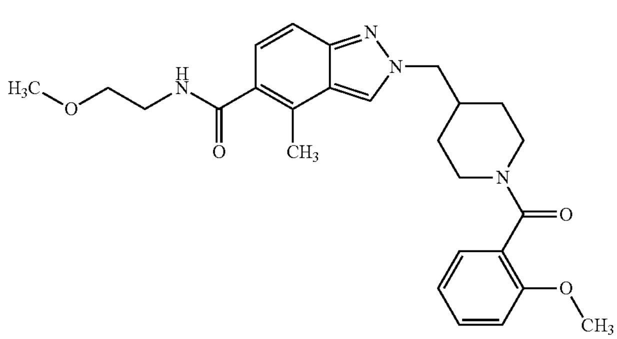 | 2-{[1-(2-methoxy-benzoyl)piperidin-4-yl]methyl}-N-(2-methoxyethyl)-4-methyl-2H-indazol-5-carboxamide | $^1$H-NMR (400 MHz, DMSO-d$_6$): δ [ppm] = 1.11 (2H), 1.35 (1H), 1.52 (1H), 2.23 (1H), 2.49 (3H), 2.66 (1H), 2.87 (1H), 3.22 (1H), 3.24 (3H), 3.35 (2H), 3.42 (2H), 3.71 (3H), 4.29 (1H), 4.33 (1H), 4.45 (1H), 6.94 (1H), 7.07 (3H), 7.33 (1H), 7.39 (1H), 8.12 (1H), 8.48 (1H). |

| Ex. | Structure | IUPAC name | Analysis |
|---|---|---|---|
| 25 | 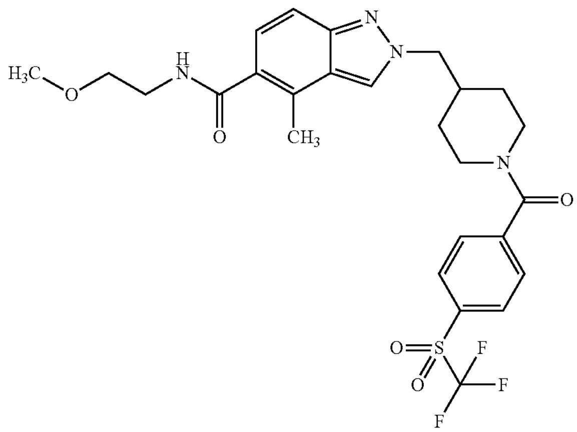 [SMILES: COCCNC(=O)c1ccc2nn(CC3CCN(C(=O)c4ccc(S(=O)(=O)C(F)(F)F)cc4)CC3)cc2c1C] | N-(2-methoxyethyl)-4-methyl-2-[(1-{4-[(trifluoromethyl)-sulphonyl]benzoyl}-piperidin-4-yl)-methyl]-2H-indazol-5-carboxamide | $^1$H-NMR (400 MHz, DMSO-d$_6$): δ [ppm] = 1.23 (2H), 1.36 (1H), 1.57 (1H), 2.29 (1H), 2.49 (3H), 2.77 (1H), 3.01 (1H), 3.24 (3H), 3.35 (1H), 3.42 (2H), 4.32 (2H), 4.44 (1H), 7.14 (1H), 7.38 (1H), 7.77 (2H), 8.15 (3H), 8.47 (1H). |
| 26 | 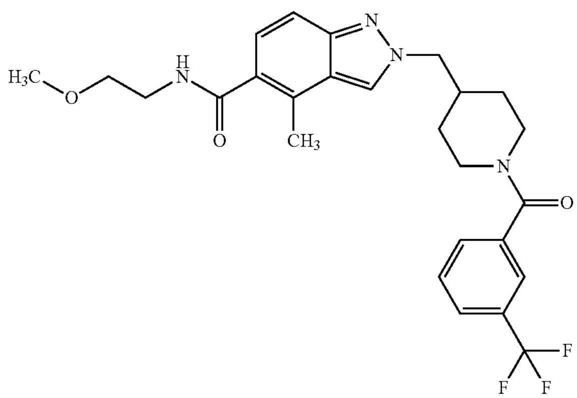 [SMILES: COCCNC(=O)c1ccc2nn(CC3CCN(C(=O)c4cccc(C(F)(F)F)c4)CC3)cc2c1C] | N-(2-methoxyethyl)-4-methyl-2-({1-[3-(trifluoromethyl)-benzoyl]piperidin-4-yl}methyl)-2H-indazol-5-carboxamide | $^1$H-NMR (400 MHz, DMSO-d$_6$): δ [ppm] = 1.24 (2H), 1.37 (1H), 1.55 (1H), 2.28 (1H), 2.49 (3H), 2.75 (1H), 3.01 (1H), 3.24 (3H), 3.36 (2H), 3.42 (3H), 4.32 (2H), 4.43 (1H), 7.14 (1H), 7.38 (1H), 7.65 (3H), 7.78 (1H), 8.12 (1H), 8.47 (1H). |
| 27 | 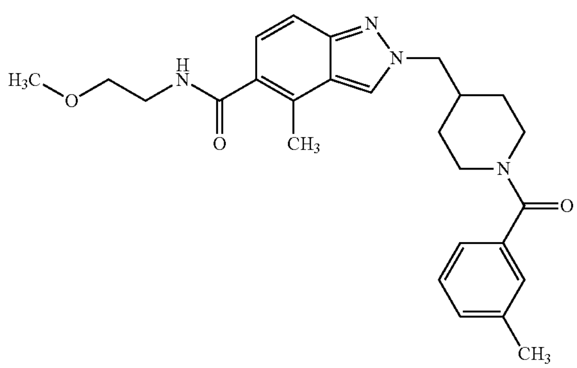 [SMILES: COCCNC(=O)c1ccc2nn(CC3CCN(C(=O)c4cccc(C)c4)CC3)cc2c1C] | N-(2-methoxyethyl)-4-methyl-2-{[1-(3-methylbenzoyl)-piperidin-4-yl]-methyl}-2H-indazol-5-carboxamide | $^1$H-NMR (400 MHz, DMSO-d$_6$): δ [ppm] = 1.20 (2H), 1.36 (1H), 1.52 (1H), 2.29 (4H), 2.49 (3H), 2.69 (1H), 2.95 (1H), 3.24 (3H), 3.36 (2H), 3.42 (2H), 3.53 (1H), 4.31 (2H), 4.41 (1H), 7.12 (3H), 7.21 (1H), 7.27 (1H), 7.38 (1H), 8.12 (1H), 8.47 (1H). |
| 28 | 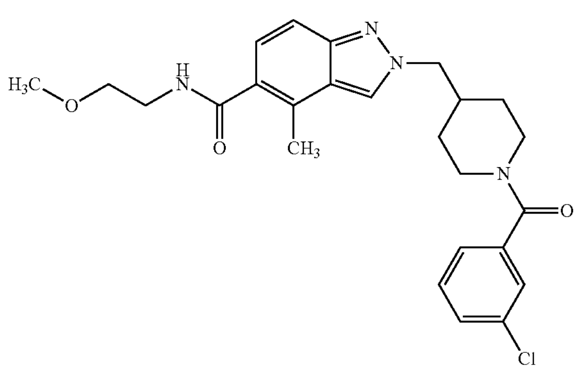 [SMILES: COCCNC(=O)c1ccc2nn(CC3CCN(C(=O)c4cccc(Cl)c4)CC3)cc2c1C] | 2-{[1-(3-chloro-benzoyl)piperidin-4-yl]methyl}-N-(2-methoxyethyl)-4-methyl-2H-indazol-5-carboxamide | $^1$H-NMR (400 MHz, DMSO-d$_6$): δ [ppm] = 1.21 (2H), 1.36 (lH), 1.53 (1H), 2.27 (1H), 2.49 (3H), 2.72 (1H), 2.98 (1H), 3.24 (3H), 3.35 (2H), 3.42 (3H), 4.31 (2H), 4.40 (1H), 7.14 (1H), 7.28 (1H), 7.43 (4H), 8.12 (1H), 8.47 (1H). |

-continued

| Ex. | Structure | IUPAC name | Analysis |
|---|---|---|---|
| 29 | 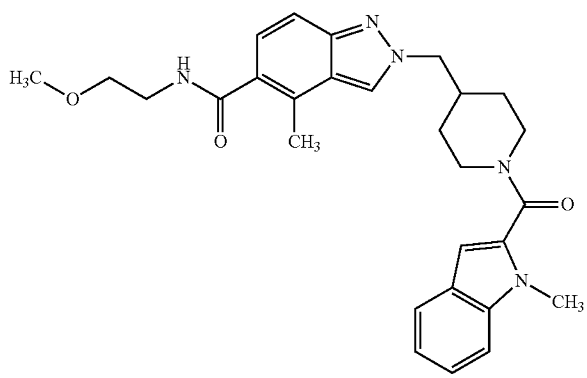 [SMILES: COCCNC(=O)c1ccc2nn(CC3CCN(C(=O)c4cc5ccccc5n4C)CC3)cc2c1C] | N-(2-methoxyethyl)-4-methyl-2-({1-[(1-methyl-1H-indol-2-yl)carbonyl]-piperidin-4-yl}methyl)-2H-indazol-5-carboxamide | $^1$H-NMR (400 MHz, DMSO-d$_6$): δ [ppm] = 1.25 (2H), 1.50 (2H), 2.31 (1H), 2.49 (3H), 2.82 (1H), 3.05 (1H), 3.24 (3H), 3.36 (2H), 3.42 (2H), 3.69 (1H), 3.98 (1H), 4.34 (2H), 4.44 (1H), 6.57 (1H), 7.05 (1H), 7.15 (1H), 7.20 (1H), 7.39 (1H), 7.46 (1H), 7.56 (1H), 8.12 (1H), 8.49 (1H). |
| 30 | 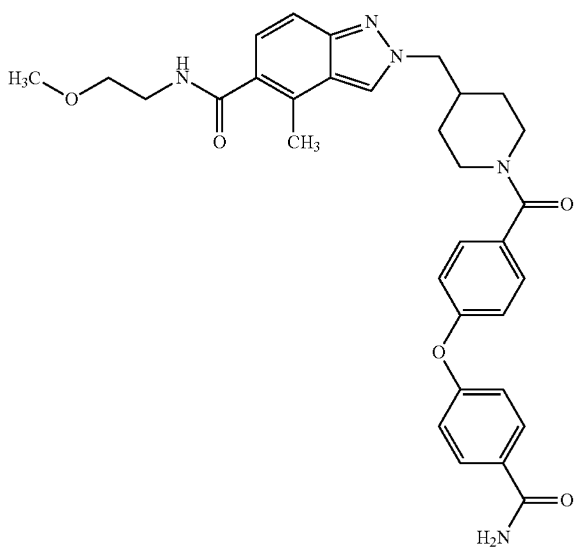 [SMILES: COCCNC(=O)c1ccc2nn(CC3CCN(C(=O)c4ccc(Oc5ccc(C(N)=O)cc5)cc4)CC3)cc2c1C] | 2-({1-[4-(4-carbamoylphenoxy)-benzoyl]piperidin-4-yl}methyl)-N-(2-methoxyethyl)-4-methyl-2H-indazol-5-carboxamide | $^1$H-NMR (400 MHz, DMSO-d$_6$): δ [ppm] = 1.22 (2H), 1.49 (2H), 2.31 (1H), 2.52 (3H), 2.82 (1H), 2.98 (1H), 3.27 (3H), 3.39 (2H), 3.45 (2H), 3.65 (1H), 4.35 (2H), 4.43 (1H), 7.08 (4H), 7.17 (1H), 7.29 (1H), 7.41 (3H), 7.91 (3H), 8.12 (1H), 8.50 (1H). |
| 31 | 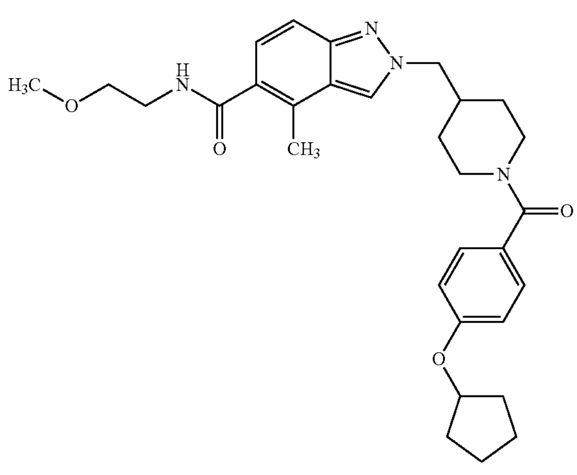 [SMILES: COCCNC(=O)c1ccc2nn(CC3CCN(C(=O)c4ccc(OC5CCCC5)cc4)CC3)cc2c1C] | 2-({1-[4-(cyclo-pentyloxy)benzoyl]-piperidin-4-yl}-methyl)-N-(2-methoxyethyl)-4-methyl-2H-indazol-5-carboxamide | $^1$H-NMR (400 MHz, DMSO-d$_6$): δ [ppm] = 1.23 (2H), 1.47 (2H), 1.57 (2H), 1.68 (4H), 1.90 (2H), 2.28 (1H), 2.52 (3H), 2.86 (2H), 3.27 (3H), 3.39 (2H), 3.45 (2H), 3.85 (2H), 4.34 (2H), 4.83 (1H), 6.91 (2H), 7.17 (1H), 7.28 (2H), 7.41 (1H), 8.12 (1H), 8.49 (1H). |

| Ex. | Structure | IUPAC name | Analysis |
|---|---|---|---|
| 32 | 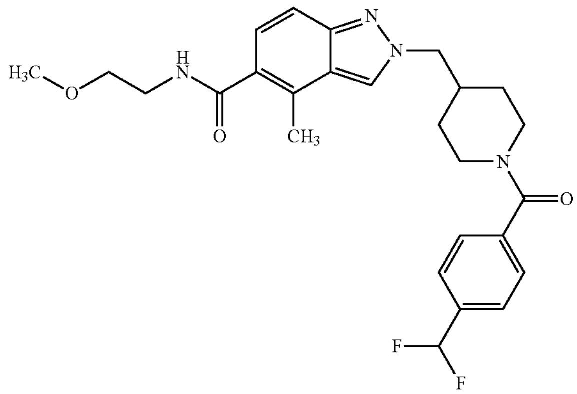 [SMILES: COCCNC(=O)c1ccc2nn(CC3CCN(C(=O)c4ccc(C(F)F)cc4)CC3)cc2c1C] | 2-({1-[4-(difluoromethyl)benzoyl]-piperidin-4-yl}-methyl)-N-(2-methoxyethyl)-4-methyl-2H-indazol-5-carboxamide | $^1$H-NMR (400 MHz, DMSO-d$_6$): δ [ppm] = 1.24 (2H), 1.39 (1H), 1.57 (1H), 2.30 (1H), 2.52 (3H), 2.76 (1H), 3.01 (1H), 3.27 (3H), 3.39 (2H), 3.45 (3H), 4.35 (2H), 4.45 (1H), 7.18 (2H), 7.41 (1H), 7.49 (2H), 7.62 (2H), 8.12 (1H), 8.49 (1H). |
| 33 | 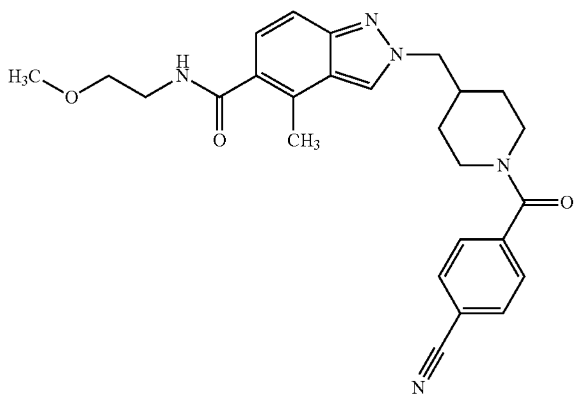 [SMILES: COCCNC(=O)c1ccc2nn(CC3CCN(C(=O)c4ccc(C#N)cc4)CC3)cc2c1C] | 2-{[1-(4-cyanobenzoyl)piperidin-4-yl]methyl}-N-(2-methoxyethyl)-4-methyl-2H-indazol-5-carboxamide | $^1$H-NMR (400 MHz, DMSO-d$_6$): δ [ppm] = 1.24 (2H), 1.39 (1H), 1.58 (1H), 2.30 (1H), 2.52 (3H), 2.77 (1H), 3.01 (1H), 3.27 (3H), 3.39 (3H), 3.45 (2H), 4.34 (2H), 4.44 (1H), 7.17 (1H), 7.41 (1H), 7.54 (2H), 7.90 (2H), 8.12 (1H), 8.49 (1H). |
| 34 | 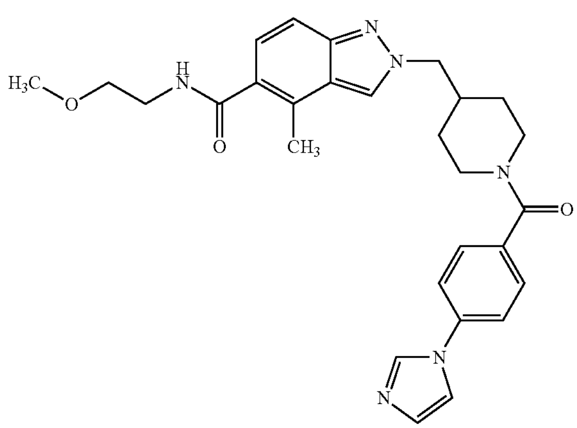 [SMILES: COCCNC(=O)c1ccc2nn(CC3CCN(C(=O)c4ccc(-n5ccnc5)cc4)CC3)cc2c1C] | 2-({1-[4-(1H-imidazol-1-yl)-benzoyl]piperidin-4-yl}methyl)-N-(2-methoxyethyl)-4-methyl-2H-indazol-5-carboxamide | $^1$H-NMR (300 MHz, DMSO-d$_6$): δ [ppm] = 1.24 (2H), 1.39 (1H), 156 (1H), 2.29 (1H), 2.49 (3H), 2.76 (1H), 3.04 (1H), 3.24 (3H), 3.37 (3H), 3.42 (3H), 4.33 (2H), 4.44 (1H), 7.15 (1H), 7.39 (1H), 7.61 (2H), 7.84 (3H), 8.11 (1H), 8.26 (1H), 8.48 (1H). |

-continued

| Ex. | Structure | IUPAC name | Analysis |
|---|---|---|---|
| 35 | 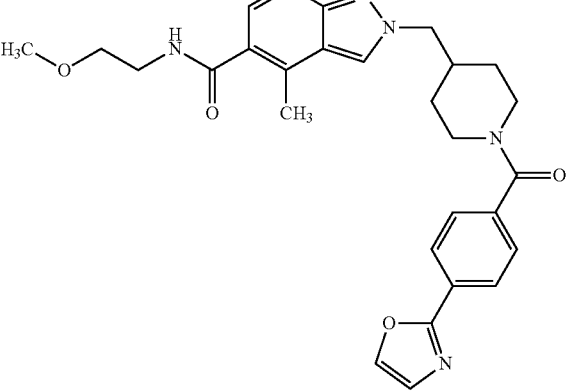 | N-(2-methoxyethyl)-4-methyl-2-({1-[4-(oxazol-2-yl)-benzoyl]piperidin-4-yl}methyl)-2H-indazol-5-carboxamide | $^1$H-NMR (300 MHz, DMSO-d$_6$): δ [ppm] = 1.24 (2H), 1.37 (1H), 1.54 (1H), 2.27 (1H), 2.49 (3H), 2.75 (1H), 3.00 (1H), 3.24 (3H), 3.36 (2H), 3.42 (2H), 3.53 (1H), 4.32 (2H), 4.43 (1H), 7.14 (1H), 7.38 (2H), 7.48 (2H), 8.00 (2H), 8.12 (1H), 8.23 (1H), 8.48 (1H). |
| 36 | 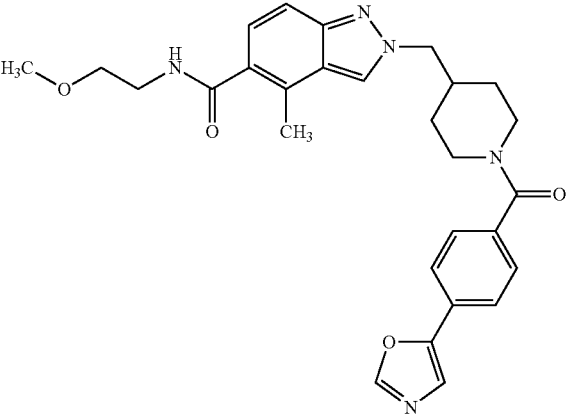 [SMILES: COCCNC(=O)c1ccc2nn(CC3CCN(C(=O)c4ccc(-c5cnco5)cc4)CC3)cc2c1C] | N-(2-methoxyethyl)-4-methyl-2-({1-[4-(oxazol-5-yl)-benzoyl]piperidin-4-yl}methyl)-2H-indazol-5-carboxamide | $^1$H-NMR (300 MHz, DMSO-d$_6$): δ [ppm] = 1.22 (2H), 1.38 (1H), 1.53 (1H), 2.28 (1H), 2.49 (3H), 2.74 (1H), 2.98 (1H), 3.24 (3H), 3.36 (2H), 3.41 (2H), 3.55 (1H), 4.32 (2H), 4.41 (1H), 7.15 (1H), 7.42 (3H), 7.74 (3H), 8.12 (1H), 8.47 (2H). |
| 37 | 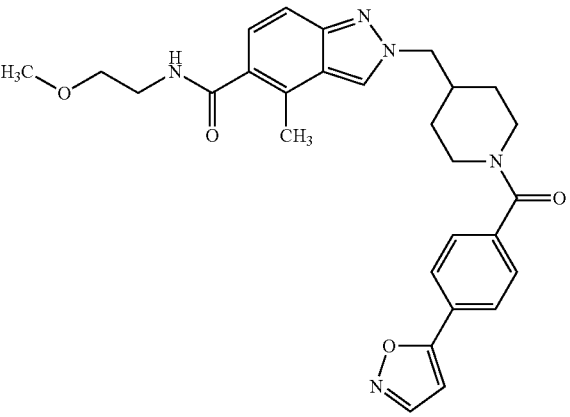 [SMILES: COCCNC(=O)c1ccc2nn(CC3CCN(C(=O)c4ccc(-c5ccno5)cc4)CC3)cc2c1C] | N-(2-methoxyethyl)-4-methyl-2-({1-[4-(isoxazol-5-yl)-benzoyl]piperidin-4-yl}methyl)-2H-indazol-5-carboxamide | $^1$H-NMR (300 MHz, DMSO-d$_6$): δ [ppm] = 1.22 (2H), 1.36 (1H), 1.55 (1H), 2.28 (1H), 2.49 (3H), 2.74 (1H), 2.99 (1H), 3.24 (3H), 3.39 (5H), 4.31 (2H), 4.43 (1H), 4.74 (2H), 7.14 (1H), 7.38 (1H), 7.50 (2H), 7.95 (2H), 8.12 (1H), 8.47 (1H). |

| Ex. | Structure | IUPAC name | Analysis |
|---|---|---|---|
| 38 | 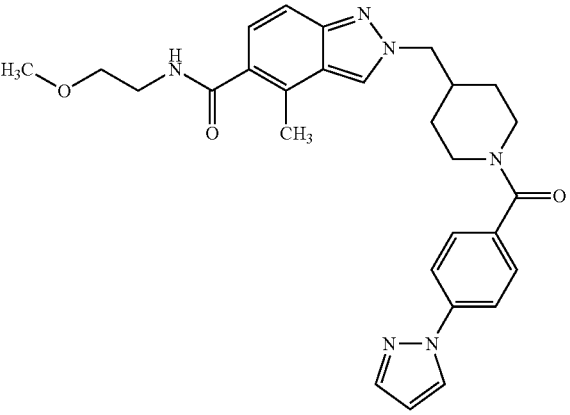 [SMILES: COCCNC(=O)c1ccc2nn(CC3CCN(C(=O)c4ccc(-n5cccn5)cc4)CC3)cc2c1C] | N-(2-methoxyethyl)-4-methyl-2-({1-[4-(1H-pyrazol-1-yl)benzoyl]piperidin-4-yl}methyl)-2H-indazol-5-carboxamide | $^{1}$H-NMR (300 MHz, DMSO-$d_6$): δ [ppm] = 1.22 (2H), 1.46 (2H), 2.28 (1H), 2.49 (3H), 2.76 (1H), 2.99 (1H), 3.24 (3H), 3.39 (4H), 3.61 (1H), 4.32 (2H), 4.41 (1H), 6.54 (1H), 7.15 (1H), 7.39 (1H), 7.46 (2H), 7.74 (1H), 7.87 (2H), 8.12 (1H), 8.50 (2H). |
| 39 | 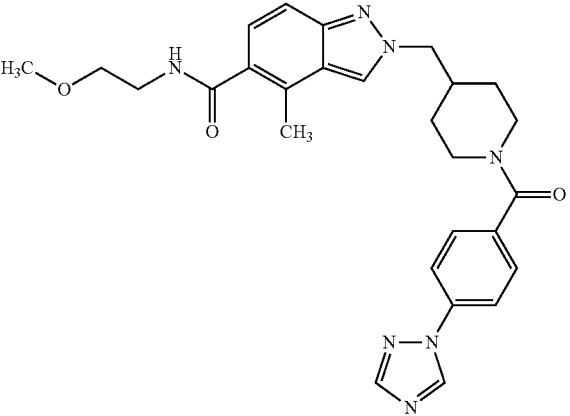 | N-(2-methoxyethyl)-4-methyl-2-({1-[4-(1H-1,2,4-triazol-1-yl)benzoyl]piperidin-4-yl}methyl)-2H-indazol-5-carboxamide | $^{1}$H-NMR (300 MHz, DMSO-$d_6$): δ [ppm] = 1.22 (2H), 1.39 (1H), 1.53 (1H), 2.27 (1H), 2.49 (3H), 2.76 (1H), 3.00 (1H), 3.24 (3H), 3.39 (4H), 3.54 (1H), 4.32 (2H), 4.43 (1H), 7.15 (1H), 7.39 (1H), 7.53 (2H), 7.90 (2H), 8.12 (1H), 8.24 (1H), 8.48 (1H), 9.32 (1H). |
| 40 | 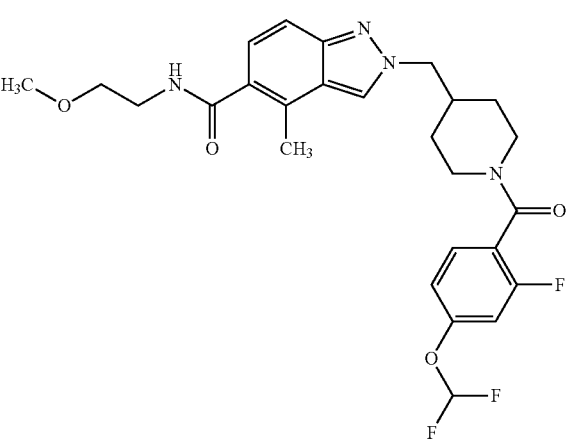 [SMILES: COCCNC(=O)c1ccc2nn(CC3CCN(C(=O)c4ccc(OC(F)F)cc4F)CC3)cc2c1C] | 2-({1-[4-(difluoromethoxy)-2-fluorobenzoyl]piperidin-4-yl}methyl)-N-(2-methoxyethyl)-4-methyl-2H-indazol-5-carboxamide | $^{1}$H-NMR (300 MHz, DMSO-$d_6$): δ [ppm] = 1.16 (2H), 1.38 (1H), 1.55 (1H), 2.26 (1H), 2.48 (3H), 2.73 (1H), 2.98 (1H), 3.24 (3H), 3.38 (5H), 4.31 (2H), 4.44 (1H), 7.12 (3H), 7.31 (1H), 7.40 (2H), 8.12 (1H), 8.47 (1H). |

| Ex. | Structure | IUPAC name | Analysis |
|---|---|---|---|
| 41 | 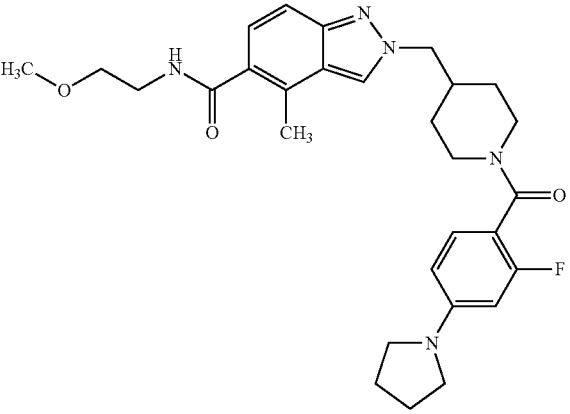 [SMILES: COCCNC(=O)c1ccc2nn(CC3CCN(C(=O)c4ccc(N5CCCC5)cc4F)CC3)cc2c1C] | 2-({1-[2-fluoro-4-(pyrrolidin-1-yl)-benzoyl]piperidin-4-yl}methyl)-N-(2-methoxyethyl)-4-methyl-2H-indazol-5-carboxamide | $^1$H-NMR (300 MHz, DMSO-d$_6$): δ [ppm] = 1.14 (2H), 1.43 (2H), 1.90 (4H), 2.23 (1H), 2.48 (3H), 2.68 (1H), 2.94 (1H), 3.19 (4H), 3.24 (3H), 3.36 (2H), 3.42 (3H), 4.31 (2H), 4.39 (1H), 6.29 (2H), 7.10 (2H), 7.38 (1H), 8.12 (1H), 8.47 (1H). |
| 42 | 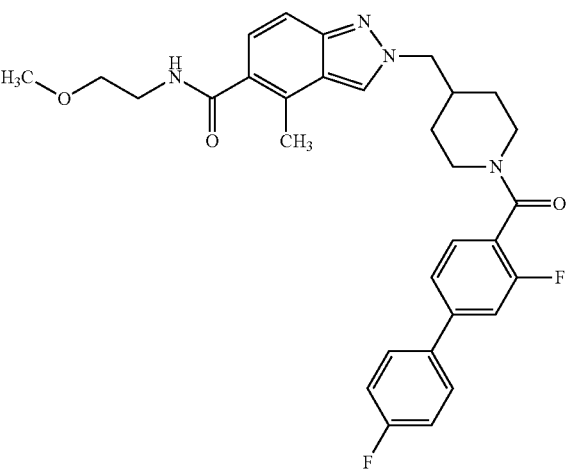 [SMILES: COCCNC(=O)c1ccc2nn(CC3CCN(C(=O)c4ccc(-c5ccc(F)cc5)cc4F)CC3)cc2c1C] | 2-({1-[(3,4'-difluoro-biphenyl-4-yl)-carbonyl]piperidin-4-yl}methyl)-N-(2-methoxyethyl)-4-methyl-2H-indazol-5-carboxamide | $^1$H-NMR (300 MHz, DMSO-d$_6$): δ [ppm] = 1.19 (2H), 1.39 (1H), 1.57 (1H), 2.28 (1H), 2.49 (3H), 2.76 (1H), 3.01 (1H), 3.24 (3H), 3.38 (5H), 4.32 (2H), 4.47 (1H), 7.15 (1H), 7.28 (2H), 7.40 (2H), 7.56 (2H), 7.76 (2H), 8.12 (1H), 8.48 (1H). |
| 43 | 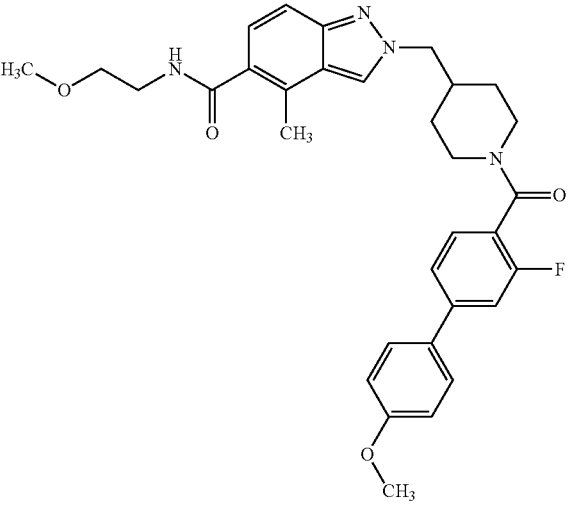 [SMILES: COCCNC(=O)c1ccc2nn(CC3CCN(C(=O)c4ccc(-c5ccc(OC)cc5)cc4F)CC3)cc2c1C] | 2-({1-[(3-fluoro-4'-methoxybiphenyl-4-yl)carbonyl]piperidin-4-yl}methyl)-N-(2-methoxyethyl)-4-methyl-2H-indazol-5-carboxamide | $^1$H-NMR (300 MHz, DMSO-d$_6$): δ [ppm] = 1.19 (2H), 1.39 (1H), 1.57 (1H), 2.28 (1H), 2.49 (3H), 2.76 (1H), 3.01 (1H), 3.24 (3H), 3.38 (5H), 4.32 (2H), 4.47 (1H), 7.15 (1H), 7.28 (2H), 7.40 (2H), 7.56 (2H), 7.76 (2H), 8.12 (1H), 8.48 (1H). |

| Ex. | Structure | IUPAC name | Analysis |
|---|---|---|---|
| 44 | 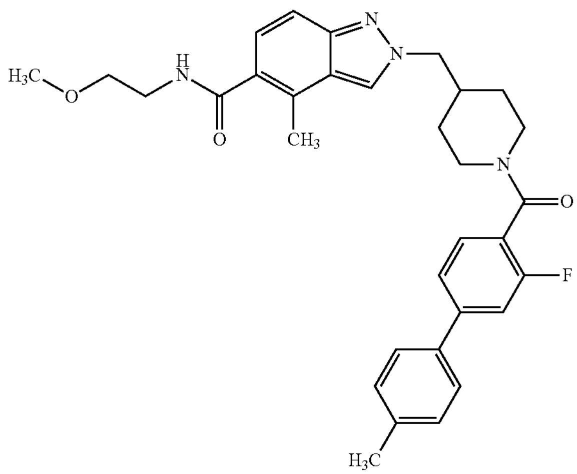 [SMILES: COCCNC(=O)c1ccc2nn(CC3CCN(C(=O)c4ccc(-c5ccc(C)cc5)cc4F)CC3)cc2c1C] | 2-({1-[(3-fluoro-4'-methylbiphenyl-4-yl)carbonyl]piperidin-4-yl}methyl)-N-(2-methoxyethyl)-4-methyl-2H-indazol-5-carboxamide | $^1$H-NMR (400 MHz, DMSO-d$_6$): δ [ppm] = 1.19 (2H), 1.39 (1H), 1.57 (1H), 2.31 (4H), 2.49 (3H), 2.75 (1H), 3.01 (1H), 3.24 (3H), 3.36 (2H), 3.42 (3H), 4.32 (2H), 4.48 (1H), 7.14 (1H), 7.26 (2H), 7.39 (2H), 7.56 (4H), 8.12 (1H), 8.48 (1H). |
| 45 | 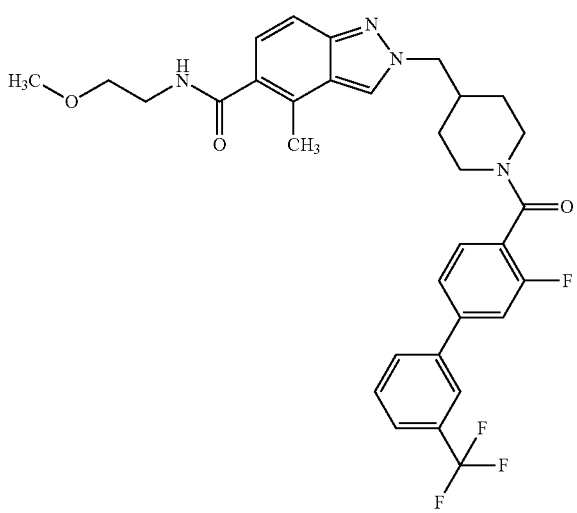 [SMILES: COCCNC(=O)c1ccc2nn(CC3CCN(C(=O)c4ccc(-c5cccc(C(F)(F)F)c5)cc4F)CC3)cc2c1C] | 2-[(1-{[3-fluoro-3'-(trifluoromethyl)biphenyl-4-yl]carbonyl}-piperidin-4-yl)-methyl]-N-(2-methoxyethyl)-4-methyl-2H-indazol-5-carboxamide | $^1$H-NMR (400 MHz, DMSO-d$_6$): δ [ppm] = 1.20 (2H), 1.40 (1H), 1.57 (1H), 2.29 (1H), 2.49 (3H), 2.76 (1H), 3.03 (1H), 3.24 (3H), 3.36 (2H), 3.41 (3H), 4.33 (2H), 4.48 (1H), 7.15 (1H), 7.39 (1H), 7.45 (1H), 7.69 (4H), 8.03 (2H), 8.12 (1H), 8.49 (1H). |
| 46 | 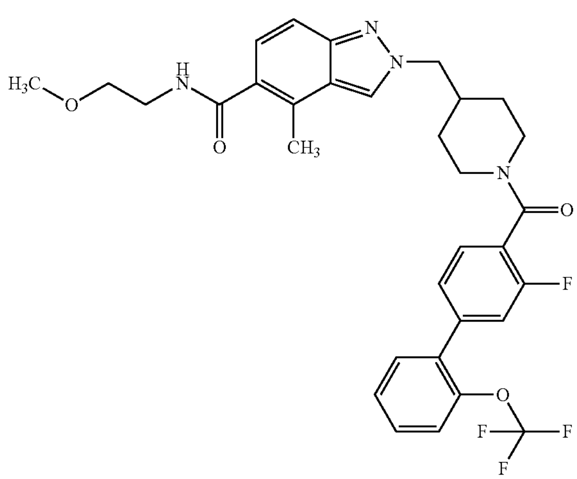 [SMILES: COCCNC(=O)c1ccc2nn(CC3CCN(C(=O)c4ccc(-c5ccccc5OC(F)(F)F)cc4F)CC3)cc2c1C] | 2-[(1-{[3-fluoro-2'-(trifluoromethoxy)-biphenyl-4-yl]carbonyl}piperidin-4-yl)methyl]-N-(2-methoxyethyl)-4-methyl-2H-indazol-5-carboxamide | $^1$H-NMR (300 MHz, DMSO-d$_6$): δ [ppm] = 1.20 (2H), 1.42 (1H), 1.57 (1H), 2.29 (1H), 2.49 (3H), 2.76 (1H), 3.04 (1H), 3.24 (3H), 3.36 (5H), 4.32 (2H), 4.48 (1H), 7.15 (1H), 7.44 (8H), 8.12 (1H), 8.49 (1H). |

| Ex. | Structure | IUPAC name | Analysis |
|---|---|---|---|
| 47 | 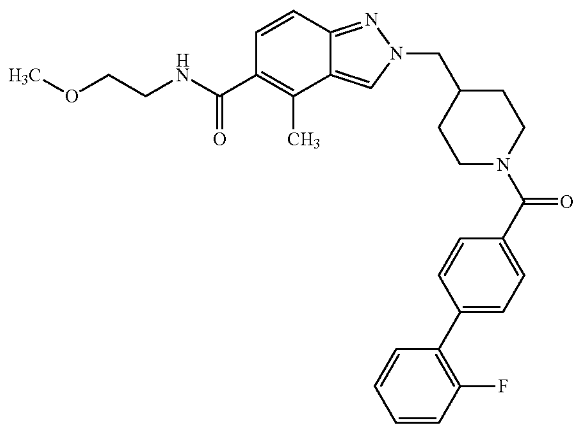 [SMILES: COCCNC(=O)c1ccc2nn(CC3CCN(C(=O)c4ccc(-c5ccccc5F)cc4)CC3)cc2c1C] | 2-({1-[(2'-fluoro-biphenyl-4-yl)-carbonyl]piperidin-4-yl}methyl)-N-(2-methoxyethyl)-4-methyl-2H-indazol-5-carboxamide | $^{1}$H-NMR (300 MHz, DMSO-d$_{6}$): δ [ppm] = 1.23 (2H), 1.41 (1H), 1.53 (1H), 2.29 (1H), 2.49 (3H), 2.74 (1H), 3.01 (1H), 3.24 (3H), 3.36 (4H), 3.60 (1H), 4.33 (2H), 4.44 (1H), 7.15 (1H), 7.29 (2H), 7.40 (4H), 7.55 (3H), 8.12 (1H), 8.48 (1H). |
| 48 | 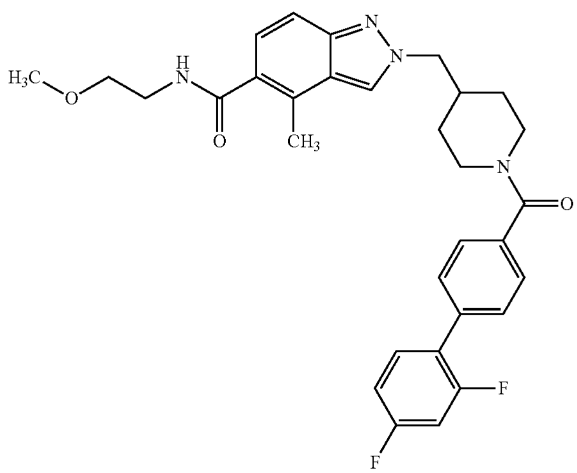 [SMILES: COCCNC(=O)c1ccc2nn(CC3CCN(C(=O)c4ccc(-c5ccc(F)cc5F)cc4)CC3)cc2c1C] | 2-({1-[(2',4'-difluoro-biphenyl-4-yl)-carbonyl]piperidin-4-yl}methyl)-N-(2-methoxyethyl)-4-methyl-2H-indazol-5-carboxamide | $^{1}$H-NMR (300 MHz, DMSO-d$_{6}$): δ [ppm]= 1.23 (2H), 1.39 (1H), 1.53 (1H), 2.28 (1H), 2.49 (3H), 2.75 (1H), 3.01 (1H), 3.24 (3H), 3.39 (4H), 3.60 (1H), 4.33 (2H), 4.43 (1H), 7.16 (2H), 7.40 (4H), 7.56 (3H), 8.12 (1H), 8.48 (1H). |
| 49 | 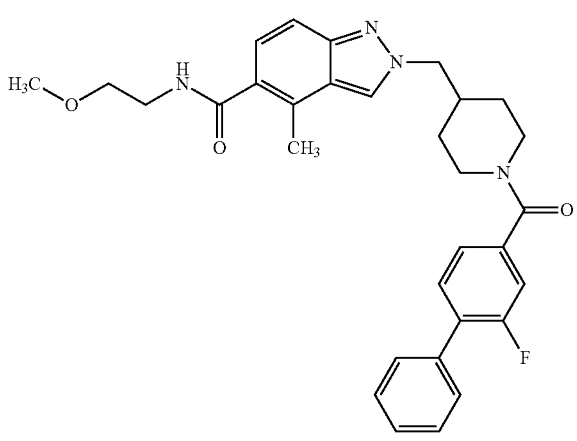 [SMILES: COCCNC(=O)c1ccc2nn(CC3CCN(C(=O)c4ccc(-c5ccccc5)c(F)c4)CC3)cc2c1C] | 2-({1-[(2-fluoro-biphenyl-4-yl)-carbonyl]piperidin-4-yl}methyl)-N-(2-methoxyethyl)-4-methyl-2H-indazol-5-carboxamide | $^{1}$H-NMR (400 MHz, DMSO-d$_{6}$): δ [ppm] = 1.24 (2H), 1.39 (1H), 1.56 (1H), 2.29 (1H), 2.49 (3H), 2.74 (1H), 3.02 (1H), 3.25 (3H), 3.37 (2H), 3.42 (2H), 3.59 (1H), 4.33 (2H), 4.43 (1H), 7.15 (1H), 7.28 (2H), 7.40 (2H), 7.46 (2H), 7.54 (3H), 8.12 (1H), 8.48 (1H). |

-continued

| Ex. | Structure | IUPAC name | Analysis |
|---|---|---|---|
| 50 | 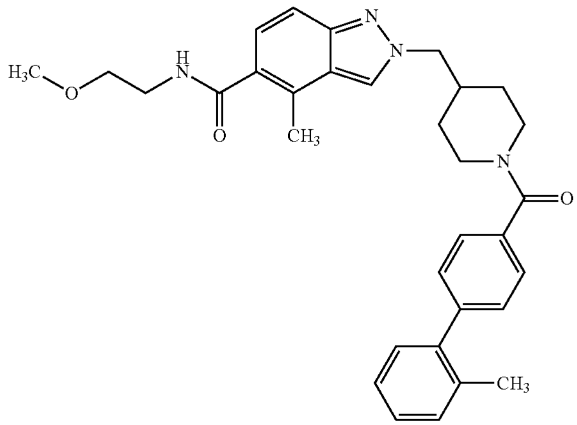 [SMILES: COCCNC(=O)c1ccc2nn(CC3CCN(C(=O)c4ccc(-c5ccccc5C)cc4)CC3)cc2c1C] | N-(2-methoxyethyl)-4-methyl-2-({1-[(2'-methylbiphenyl-4-yl)carbonyl]piperidin-4-yl}methyl)-2H-indazol-5-carboxamide | $^1$H-NMR (400 MHz, DMSO-d$_6$): δ [ppm] = 1.24 (2H), 1.42 (1H), 1.55 (1H), 2.20 (3H), 2.29 (1H), .249 (3H), 2.75 (1H), 3.02 (1H), 3.25 (3H), 3.37 (2H), 3.42 (2H), 3.64 (1H), 4.33 (2H), 4.42 (1H), 7.21 (5H), 7.38 (5H), 8.12 (1H), 8.49 (1H). |
| 51 | 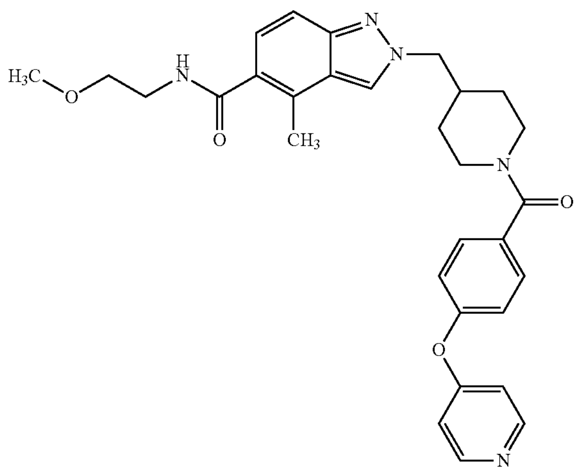 [SMILES: COCCNC(=O)c1ccc2nn(CC3CCN(C(=O)c4ccc(Oc5ccncc5)cc4)CC3)cc2c1C] | N-(2-methoxyethyl)-4-methyl-2-({1-[4-(pyridyloxy)benzoyl]piperidin-4-yl}-methyl)-2H-indazol-5-carboxamide | $^1$H-NMR (400 MHz, DMSO-d$_6$): δ [ppm] = 1.24 (2H), 1.42 (1H), 1.55 (1H), 2.29 (1H), 2.49 (3H), 2.76 (1H), 3.02 (1H), 3.25 (3H), 3.37 (2H), 3.43 (2H), 3.60 (1H), 4.33 (2H), 4.44 (1H), 7.15 (1H), 7.37 (3H), 7.48 (2H), 7.53 (2H), 8.12 (1H), 8.48 (1H), 8.75 (2H). |
| 52 | 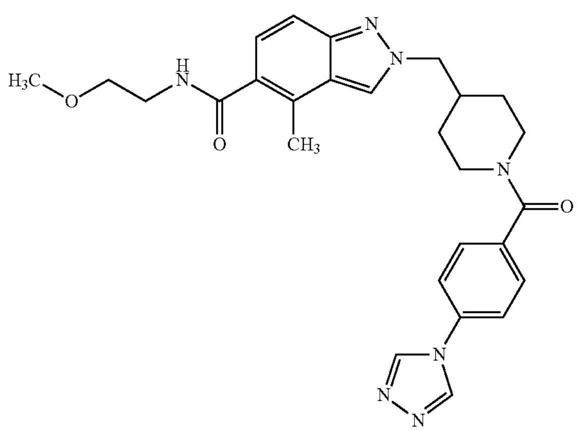 [SMILES: COCCNC(=O)c1ccc2nn(CC3CCN(C(=O)c4ccc(-n5cnnc5)cc4)CC3)cc2c1C] | N-(2-methoxyethyl)-4-methyl-2-((1-[4-(4H-1,2,4-triazol-4-yl)benzoyl]piperidin-4-yl}methyl)-2H-indazol-5-carboxamide | $^1$H-NMR (400 MHz, DMSO-d$_6$): δ [ppm] = 1.23 (2H), 1.38 (1H), 1.54 (1H), 2.28 (1H), 2.49 (3H), 2.74 (1H), 3.02 (1H), 3.24 (3H), 3.36 (2H), 3.42 (2H), 3.53 (1H), 4.32 (2H), 4.42 (1H), 7.14 (1H), 7.38 (1H), 7.55 (2H), 7.75 (2H), 8.14 (1H), 8.48 (1H), 9.15 (2H). |

| Ex. | Structure | IUPAC name | Analysis |
|---|---|---|---|
| 53 | 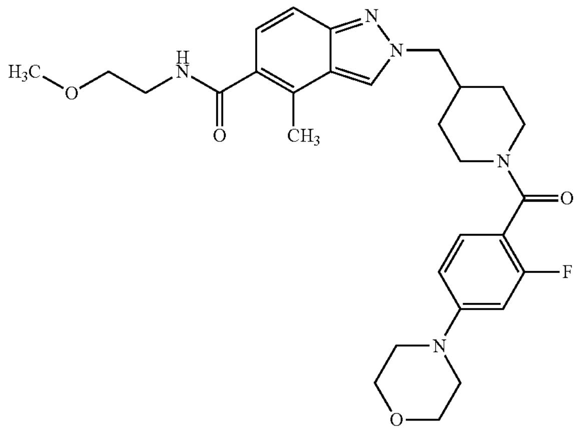 [SMILES: COCCNC(=O)c1ccc2nn(CC3CCN(C(=O)c4ccc(N5CCOCC5)cc4F)CC3)cc2c1C] | 2-{[1-(2-fluoro-4-morpholinobenzoyl)-piperidin-4-yl]-methyl}-N-(2-methoxyethyl)-4-methyl-2H-indazol-5-carboxamide | $^1$H-NMR (600 MHz, DMSO-d$_6$): δ [ppm] = 1.01 (1H), 1.21 (1H), 1.36 (1H), 1.48 (1H), 1.57 (1H), 2.08 (1H), 2.53 (3H), 2.96 (7H), 3.29 (3H), 3.41 (2H), 3.47 (2H), 3.67 (4H), 4.34 (2H), 4.50 (1H), 6.86 (2H), 7.14 (2H), 7.41 (1H), 8.11 (1H), 8.47 (1H), 8.56 (1H). |
| 54 | 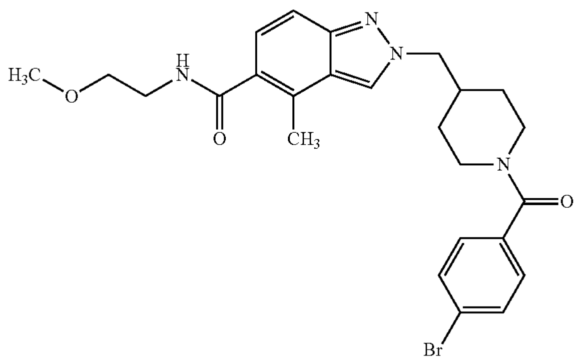 [SMILES: COCCNC(=O)c1ccc2nn(CC3CCN(C(=O)c4ccc(Br)cc4)CC3)cc2c1C] | 2-{[1-(4-bromo-benzoyl)piperidin-4-yl]methyl}-N-(2-methoxyethyl)-4-methyl-2H-indazol-5-carboxamide | $^1$H-NMR (300 MHz, DMSO-d$_6$): δ [ppm] = 1.22 (2H), 1.36 (1H), 1.52 (1H), 2.26 (1H), 2.49 (3H), 2.72 (1H), 2.97 (1H), 3.24 (3H), 3.36 (2H), 3.42 (2H), 3.49 (1H), 4.31 (2H), 4.40 (1H), 7.14 (1H), 7.29 (2H), 7.38 (1H), 7.60 (2H), 8.12 (1H), 8.47 (1H). |

EXAMPLE 55

N-(2-methoxyethyl)-4-methyl-2-({1-[4-(trifluoromethoxy)benzoyl]piperidin-4-yl}methyl)-2H-indazol-5-carboxamide

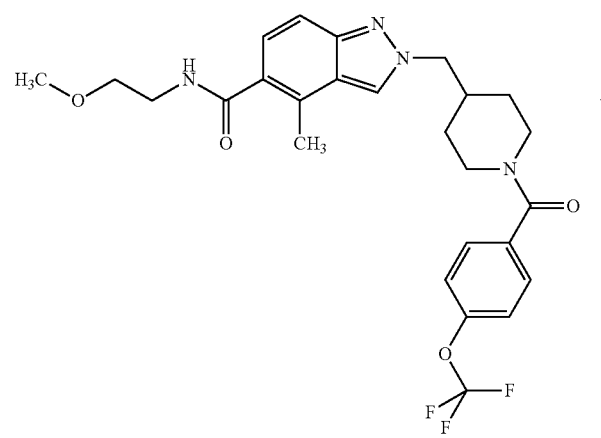

150 mg of the amine prepared in Example 1a were first dissolved in 1.5 ml pyridine. 101 mg of 4-(trifluoromethoxy) benzoyl chloride were then added and the mixture stirred for 30 min at RT. The reaction mixture was then treated with some toluene and concentrated. The residue was taken up in ethyl acetate and washed twice with water, twice with saturated sodium hydrogen carbonate solution (pH 9) and once with saturated sodium chloride solution. The organic phase was dried over sodium sulphate, filtered and concentrated.

The residue was purified chromatographically on the Biotage SP4. Gradient: ethyl acetate/methanol 0-10%. Yield: 118.2 mg of the title compound.

$^1$H-NMR (300 MHz, DMSO-d$_6$): δ [ppm]=1.17-1.30 (2H), 1.30-1.45 (1H), 1.45-1.62 (1H), 2.19-2.35 (1H), 2.49 (3H), 2.64-2.86 (1H), 2.86-3.07 (1H), 3.24 (3H), 3.31-3.56 (5H), 4.31 (2H), 4.36-4.49 (1H), 7.14 (1H), 7.35-7.42 (3H), 7.43-7.50 (2H), 8.11 (1H), 8.47 (1H).

EXAMPLE 56

2-{[1-(4-chlorobenzoyl)piperidin-4-yl]methyl}-N-(2-methoxyethyl)-4-methyl-2H-indazol-5-carboxamide

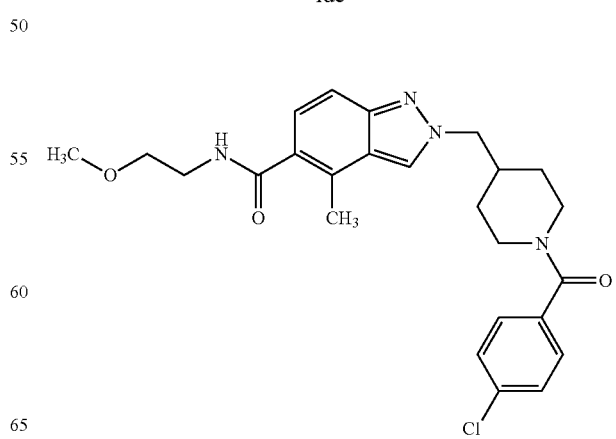

Analogously to Example 55, 183 mg of the title compound was obtained from 300 mg of the amine prepared in Example 1a and 157.4 mg of 4-chlorobenzoyl chloride.

$^1$H-NMR (400 MHz, DMSO-d$_6$): δ [ppm]=1.10-1.29 (2H), 1.29-1.43 (1H), 1.44-1.61 (1H), 2.20-2.34 (1H), 2.49 (3H), 2.66-2.83 (1H), 2.84-3.06 (1H), 3.25 (3H), 3.32-3.39 (2H), 3.40-3.45 (2H), 3.45-3.55 (1H), 4.26-4.35 (2H), 4.35-4.46 (1H), 7.14 (1H), 7.32-7.41 (3H), 7.47 (2H), 8.09-8.15 (1H), 8.47 (1H).

EXAMPLE 57

N-(2-methoxyethyl)-4-methyl-2-[(1-{4-[(trifluoromethyl)sulphanyl]benzoyl}piperidin-4-yl)methyl]-2H-indazol-5-carboxamide

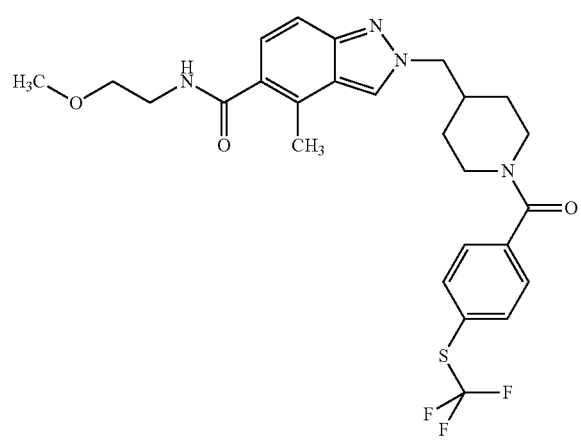 [SMILES: COCCNC(=O)c1ccc2nn(CC3CCN(C(=O)c4ccc(SC(F)(F)F)cc4)CC3)cc2c1C]

60 mg of the amine prepared in Example 1a were first dissolved in 2 ml DCM at 0° C. 0.034 ml of triethylamine and 43.2 mg of 4-[(trifluoromethyl)sulphanyl]benzoyl chloride were then added and the mixture stirred for 2 hrs at 0° C. The reaction mixture was then diluted with DCM and washed with 1-molar hydrochloric acid, saturated sodium hydrogen carbonate solution (pH 9) and saturated sodium chloride solution. The organic phase was dried over sodium sulphate, filtered and concentrated. The residue was purified chromatographically on the Biotage SP4. Gradient: DCM/Methanol 0-10%. The product fraction was taken up in ethyl acetate and extracted twice with saturated sodium hydrogen carbonate solution. The organic phase was concentrated and the residue again purified by HPLC. Yield: 26.5 mg of the title compound.

$^1$H-NMR (400 MHz, DMSO-d$_6$): δ [ppm]=1.14-1.30 (2H), 1.31-1.42 (1H), 1.49-1.61 (1H), 2.21-2.32 (1H), 2.49 (3H), 2.67-2.80 (1H), 2.93-3.05 (1H), 3.25 (3H), 3.36 (2H), 3.42 (3H), 4.27-4.36 (2H), 4.38-4.48 (1H), 7.14 (1H), 7.38 (1H), 7.48 (2H), 7.75 (2H), 8.09-8.14 (1H), 8.47 (1H).

EXAMPLE 58

2-({1-[2-fluoro-4-(trifluoromethyl)benzoyl]piperidin-4-yl}methyl)-4-methyl-N-(2-morpholinoethyl)-2H-indazol-5-carboxamide

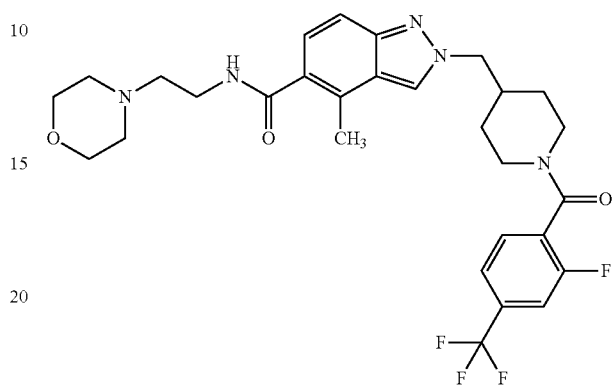

Analogously to Example 1, 34.6 mg of the title compound was obtained from 75 mg of the amine prepared in Example 58a and 37.0 mg of 2-fluoro-4-(trifluoromethyl)benzoic acid.

$^1$H-NMR (400 MHz, methanol-d$_4$): δ [ppm]=1.24-1.43 (2H), 1.50-1.59 (1H), 1.65-1.73 (1H), 2.33-2.45 (1H), 2.65 (3H), 2.80-2.91 (1H), 3.05-3.18 (1H), 3.19-3.26 (2H), 3.39-3.44 (2H), 3.45-3.52 (1H), 3.63-3.70 (2H), 3.71-3.82 (4H), 4.06-4.14 (2H), 4.39 (2H), 4.62-4.70 (1H), 7.39 (1H), 7.47 (1H), 7.54-7.62 (3H), 8.45 (1H).

The starting material was prepared as follows:

EXAMPLE 58a 4-methyl-N-(2-morpholinoethyl)-2-(4-piperidylmethyl)-2H-indazol-5-carboxamide hydrochloride

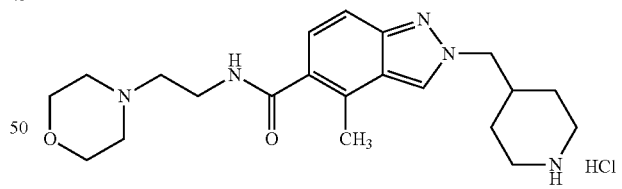

To 624.4 mg of 58b were added 2.9 ml of 4M hydrochloric acid in dioxan and 0.5 ml dioxan. An oily mass was formed, which dissolved on vigorous stirring and gentle warming. The mixture was stirred for 1 hr at ca. 30° C. The reaction mixture was concentrated. Yield: 980 mg of the title compound, which was further reacted without further purification.

$^1$H-NMR (300 MHz, DMSO-d$_6$): δ [ppm]=1.33-1.51 (2H), 1.58-1.64 (1H), 2.17-2.31 (1H), 2.55 (3H), 2.70-2.86 (2H), 3.02-3.31 (7H), 3.43-3.51 (2H), 3.61-3.71 (2H), 3.72-3.88 (3H), 3.89-3.99 (2H), 4.30-4.36 (2H), 7.29 (1H), 7.40 (1H), 8.46-8.52 (1H), 8.54-8.58 (1H), 8.69-8.85 (1H), 8.96-9.10 (1H).

EXAMPLE 58b

Tert-butyl 4-({4-methyl-5-[N-(2-morpholinoethyl) carbamoyl]-1H-indazol-2-yl}-methyl)piperidin-1-carboxylate

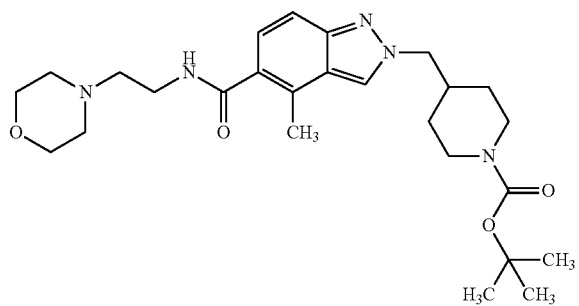 [SMILES: Cc1c(C(=O)NCCN2CCOCC2)ccc2nn(CC3CCN(C(=O)OC(C)(C)C)CC3)cc12]

896 mg of 1c, 857 mg of 2-morpholinoethylamine, 579.3 mg of molybdenum hexacarbonyl, 63.6 mg of tri-tert-butylphosphine tetrafluoroborate and 205.8 mg of trans-bis(acetato)-bis[o-(di-o-tolylphosphino)benzyl]dipalladium(II) were placed in a microwave tube and suspended in 18 ml THF. 1.0 ml of DBU was then added and the mixture was stirred for 20 mins at 125° C. and 200 watts in the microwave. The reaction mixture was diluted with some ethyl acetate and firstly filtered through Celite. The filtrate was diluted with ethyl acetate and the organic phase washed twice with water and once with saturated sodium chloride solution. It was then dried over sodium sulphate, filtered and concentrated. The residue was chromatographed on the Biotage SP4. Gradient: ethyl acetate/methanol 0-10%. Yield: 624.4 mg of the title compound.

$^1$H-NMR (300 MHz, DMSO-$d_6$): δ [ppm]=0.98-1.13 (2H), 1.34 (11H), 2.05-2.27 (2H), 2.33-2.41 (5H), 2.51 (3H), 2.56-2.73 (2H), 3.25-3.37 (2H), 3.51-3.57 (4H), 3.81-3.93 (2H), 4.28 (2H), 7.14 (1H), 7.36-7.41 (1H), 7.95-8.02 (1H), 8.46 (1H).

EXAMPLE 59

4-methyl-N-(2-morpholinoethyl)-2-({1-[4-(trifluoromethoxy)benzoyl]piperidin-4-yl}methyl)-2H-indazol-5-carboxamide

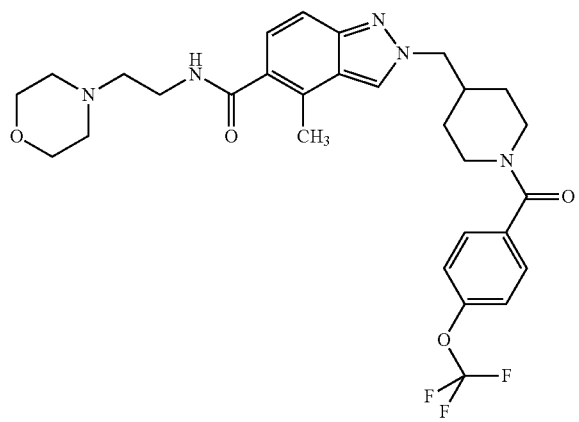 [SMILES: Cc1c(C(=O)NCCN2CCOCC2)ccc2nn(CC3CCN(C(=O)c4ccc(OC(F)(F)F)cc4)CC3)cc12]

Analogously to Example 55, 10.1 mg of the title compound was obtained from 75 mg of the amine prepared in Example 58a and 43.9 mg of 4-(trifluoromethoxy)benzoyl chloride.

$^1$H-NMR (400 MHz, methanol-$d_4$): δ [ppm]=1.24-1.44 (2H), 1.44-1.58 (1H), 1.59-1.74 (1H), 2.32-2.44 (1H), 2.51-2.58 (4H), 2.59-2.65 (5H), 2.77-2.90 (1H), 3.02-3.17 (1H), 3.53 (2H), 3.62-3.72 (5H), 4.35-4.41 (2H), 4.55-4.67 (1H), 7.29 (1H), 7.34 (2H), 7.43 (1H), 7.49 (2H), 8.39 (1H).

EXAMPLE 60

4-methyl-N-(2-morpholinoethyl)-2-({1-[4-(pentafluoro-$\lambda^6$-sulphanyl)benzoyl]-piperidin-4-yl}methyl)-2H-indazol-5-carboxamide

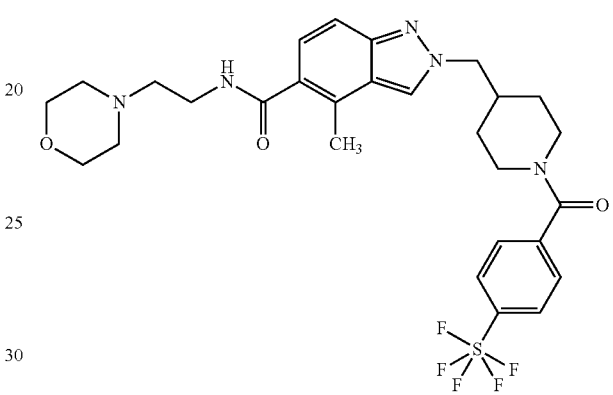

Analogously to Example 1, 14.0 mg of the title compound was obtained from 75 mg of the amine prepared in Example 58a and 44.1 mg of 4-(pentafluoro-$\lambda^6$-sulphanyl)benzoic acid.

$^1$H-NMR (400 MHz, chloroform-d): δ [ppm]=1.16-1.32 (1H), 1.33-1.48 (1H), 1.50-1.63 (1H), 1.71-1.83 (1H), 1.84-2.08 (2H), 2.44 (1H), 2.55 (4H), 2.60-2.71 (5H), 2.72-2.85 (1H), 2.96-3.10 (1H), 3.60 (2H), 3.67-3.78 (4H), 4.33 (2H), 4.71-4.81 (1H), 6.45 (1H), 7.34 (1H), 7.47 (2H), 7.54 (1H), 7.79 (2H), 7.96 (1H).

EXAMPLE 61

4-methyl-N-(2-morpholinoethyl)-2-({1-[3-(trifluoromethoxy)benzoyl]piperidin-4-yl}methyl)-2H-indazol-5-carboxamide

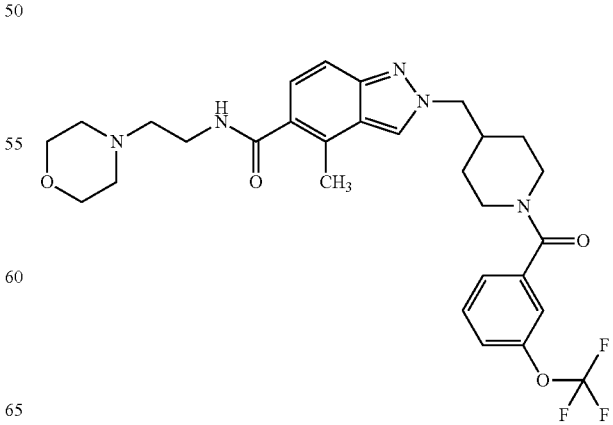

Analogously to Example 55, 18.1 mg of the title compound was obtained from 75 mg of the amine prepared in Example 58a and 43.9 mg of 3-(trifluoromethoxy)benzoyl chloride.

$^1$H-NMR (400 MHz, chloroform-d): δ [ppm]=1.18-1.46 (2H), 1.49-1.63 (1H), 1.66-1.82 (1H), 2.37-2.49 (1H), 2.62 (3H), 2.67 (3H), 2.70-2.78 (4H), 2.79-2.86 (2H), 2.93-3.09 (1H), 3.66-3.74 (2H), 3.83 (4H), 4.32 (2H), 4.66-4.82 (1H), 6.83-6.96 (1H), 7.23-7.29 (2H), 7.29-7.34 (1H), 7.39 (1H), 7.43 (1H), 7.54 (1H), 7.96 (1H).

EXAMPLE 62

2-{[1-(4-chlorobenzoyl)piperidin-4-yl]methyl}-4-methyl-N-(2-morpholinoethyl)-2H-indazol-5-carboxamide

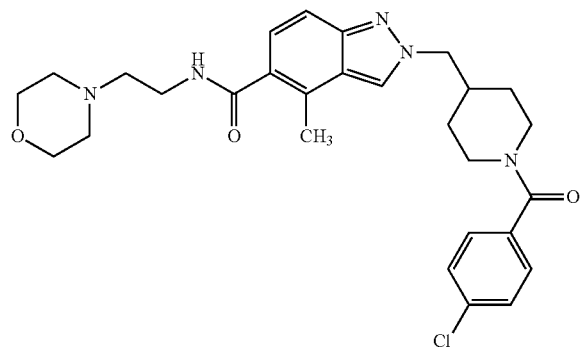 [SMILES: Cc1c(C(=O)NCCN2CCOCC2)ccc2nn(CC3CCN(C(=O)c4ccc(Cl)cc4)CC3)cc12]

Analogously to Example 55, 14.9 mg of the title compound was obtained from 75 mg of the amine prepared in Example 58a and 34.2 mg of 4-chlorobenzoyl chloride.

$^1$H-NMR (400 MHz, methanol-d$_4$): δ [ppm]=1.24-1.42 (2H), 1.46-1.58 (1H), 1.58-1.71 (1H), 2.31-2.43 (1H), 2.63 (5H), 2.65 (3H), 2.73-2.91 (2H), 3.00-3.15 (1H), 3.25-3.33 (2H), 3.63-3.77 (3H), 3.79-4.03 (3H), 4.38 (2H), 4.54-4.67 (1H), 7.38 (3H), 7.42-7.49 (3H), 8.44 (1H).

EXAMPLE 63

4-methyl-N-(2-morpholinoethyl)-2-({1-[4-(trifluoromethyl)benzoyl]piperidin-4-yl}methyl)-2H-indazol-5-carboxamide

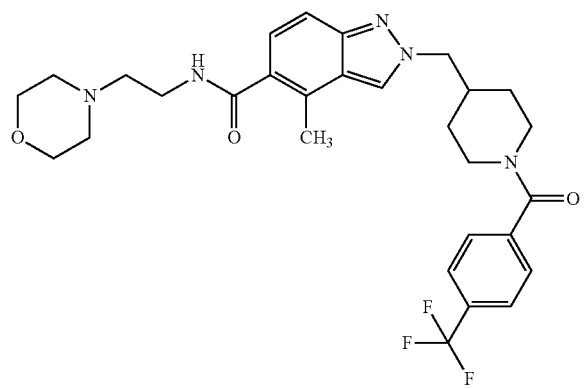 [SMILES: Cc1c(C(=O)NCCN2CCOCC2)ccc2nn(CC3CCN(C(=O)c4ccc(C(F)(F)F)cc4)CC3)cc12]

Analogously to Example 1, 31.7 mg of the title compound was obtained from 75 mg of the amine prepared in Example 58a and 33.8 mg of 4-(trifluoromethyl)benzoic acid.

$^1$H-NMR (400 MHz, methanol-d$_4$): δ [ppm]=1.24-1.43 (2H), 1.45-1.57 (1H), 1.63-1.73 (1H), 2.33-2.45 (1H), 2.66 (3H), 2.79-2.90 (1H), 3.04-3.17 (1H), 3.18-3.27 (2H), 3.39-3.45 (2H), 3.56-3.70 (3H), 3.76 (4H), 4.06-4.14 (2H), 4.36-4.42 (2H), 4.59-4.68 (1H), 7.39 (1H), 7.47 (1H), 7.57 (2H), 7.73 (2H), 8.45 (1H).

EXAMPLE 64

4-methyl-N-(2-morpholinoethyl)-2-({1-[4-(pentafluoro-λ$^6$-sulphanyl)benzoyl]-piperidin-4-yl}methyl)-2H-indazol-5-carboxamide

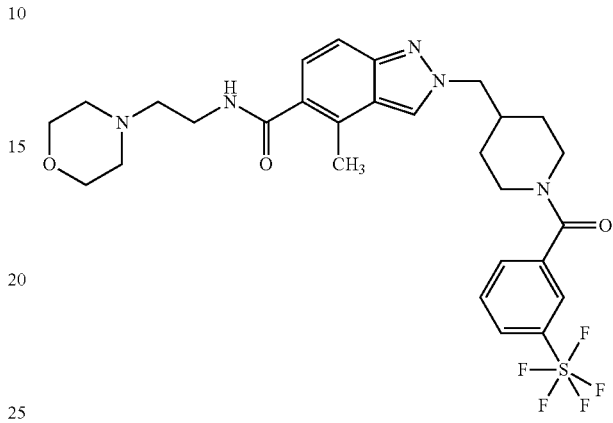

Analogously to Example 1, 24.7 mg of the title compound was obtained from 75 mg of the amine prepared in Example 58a and 44.1 mg of 3-(pentafluoro-λ$^6$-sulphanyl)benzoic acid.

$^1$H-NMR (400 MHz, methanol-d$_4$): δ [ppm]=1.27-1.47 (2H), 1.48-1.60 (1H), 1.60-1.74 (1H), 2.31-2.46 (1H), 2.66 (3H), 2.78-2.93 (1H), 3.04-3.18 (1H), 3.18-3.26 (2H), 3.39-3.43 (2H), 3.57-3.70 (3H), 3.72-3.82 (4H), 4.06-4.14 (2H), 4.39 (2H), 4.55-4.67 (1H), 7.38 (1H), 7.47 (1H), 7.60-7.67 (2H), 7.82-7.86 (1H), 7.89-7.94 (1H), 8.45 (1H).

EXAMPLE 65

4-methyl-N-(2-morpholinoethyl)-2-({1-[3-(trifluoromethyl)benzoyl]piperidin-4-yl}methyl)-2H-indazol-5-carboxamide

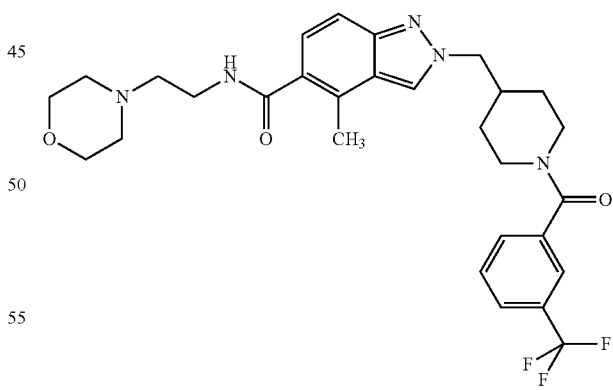

Analogously to Example 1, 14.0 mg of the title compound was obtained from 75 mg of the amine prepared in Example 58a and 33.8 mg of 3-(trifluoromethyl)benzoic acid.

$^1$H-NMR (400 MHz, methanol-d$_4$): δ [ppm]=1.28-1.45 (2H), 1.47-1.59 (1H), 1.59-1.73 (1H), 2.32-2.45 (1H), 2.66 (3H), 2.79-2.93 (1H), 3.05-3.18 (1H), 3.19-3.27 (2H), 3.39-3.45 (2H), 3.58-3.70 (3H), 3.72-3.82 (4H), 4.06-4.14 (2H), 4.39 (2H), 4.57-4.68 (1H), 7.39 (1H), 7.47 (1H), 7.64 (2H), 7.67-7.70 (1H), 7.73-7.78 (1H), 8.45 (1H).

The following compounds were prepared analogously:

| Ex. | Structure | IUPAC name | Analysis |
|---|---|---|---|
| 66 | 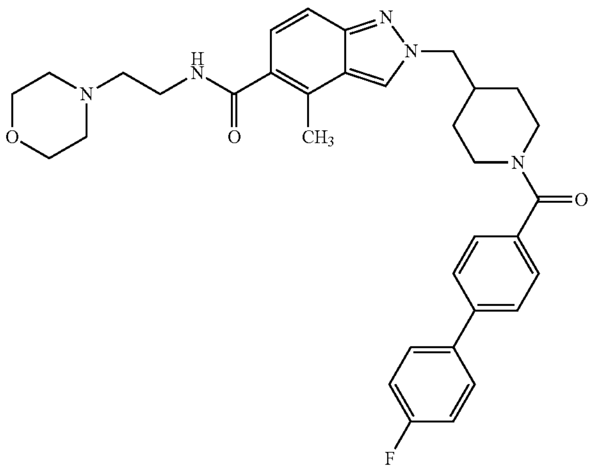 [SMILES: Cc1c(C(=O)NCCN2CCOCC2)ccc2nn(CC3CCN(C(=O)c4ccc(-c5ccc(F)cc5)cc4)CC3)cc12] | 2-({1-[(4'-fluoro-biphenyl-4-yl)-carbonyl]piperidin-4-yl}methyl)-4-methyl-N-(2-morpholino-ethyl)-2H-indazol-5-carboxamide | 1H-NMR (400 MHz, methanol-d$_4$): δ [ppm] = 1.35 (2H), 1.53 (1H), 1.66 (1H), 2.40 (1H), 2.66 (3H), 2.85 (1H), 3.11 (1H), 3.24 (2H), 3.42 (2H), 3.65 (2H), 3.76 (5H), 4.08 (2H), 4.40 (2H), 4.63 (1H), 7.17 (2H), 7.38 (1H), 7.47 (3H), 7.65 (4H), 8.45 (1H). |
| 67 | 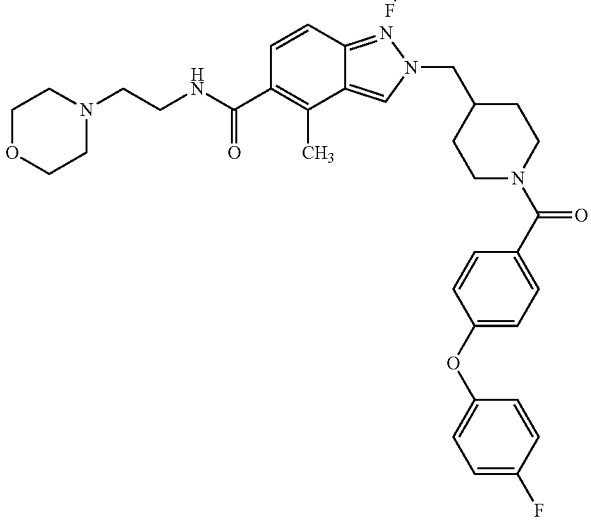 | 2-({1-[4-(4-fluoro-phenoxy)benzoyl]-piperidin-4-yl}-methyl)-4-methyl-N-(2-morpholinoethyl)-2H-indazol-5-carboxamide | 1H-NMR (400 MHz, methanol-d$_4$): δ [ppm] = 1.33 (2H), 1.68 (2H), 2.38 (1H), 2.66 (3H), 2.84 (1H), 3.11 (1H),3.25 (2H),3.42 (2H), 3.65 (2H), 3.76 (5H), 4.11 (2H),4.38(2H), 4.59 (1H), 6.98 (2H), 7.04 (2H), 7.11 (2H), 7.38 (3H), 7.47 (1H), 8.44 (1H). |

EXAMPLE 68

N-[2-(3,3-difluoropyrrolidin-1-yl)ethyl]-4-methyl-2-({1-[4-(pentafluoro-λ$^6$-sulphanyl)benzoyl]piperidin-4-yl}methyl)-2H-indazol-5-carboxamide

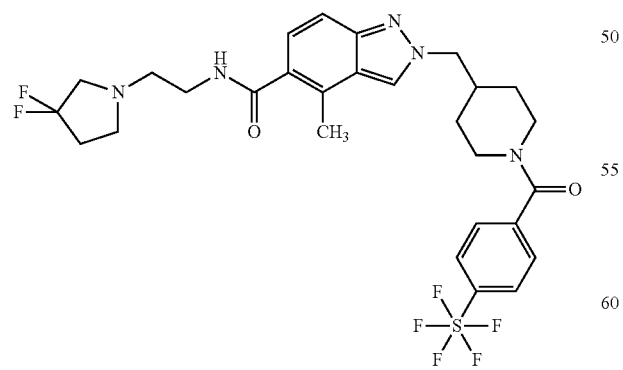

Analogously to Example 57, 61.7 mg of the title compound was obtained from 266.5 mg of the amine prepared in Example 68a and 150.3 mg of 4-(pentafluoro-λ$^6$-sulphanyl) benzoyl chloride.

$^1$H-NMR (300 MHz, chloroform-d): δ [ppm]=1.13-1.46 (2H), 1.48-1.65 (1H), 1.66-1.87 (1H), 2.26-2.50 (3H), 2.66 (3H), 2.71-3.23 (8H), 3.57-3.72 (3H), 4.25-4.42 (2H), 4.67-4.84 (1H), 6.40-6.61 (1H), 7.38 (1H), 7.47 (2H), 7.53 (1H), 7.79 (2H), 7.96 (1H).

The starting material was prepared as follows:

EXAMPLE 68a

N-[2-(3,3-difluoropyrrolidin-1-yl)ethyl]-4-methyl-2-(4-piperidylmethyl)-2H-indazol-5-carboxamide hydrochloride

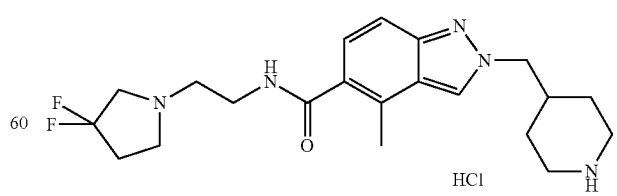

To 416.6 mg of 68b were added 1.85 ml of 4M hydrochloric acid in dioxan and 0.5 ml dioxan. An oily mass was formed, which dissolved on vigorous stirring and gentle warming. The mixture was stirred for 1 hr at ca. 30° C. The reaction mixture was concentrated. Yield: 439.2 mg of the title compound, which was further reacted without further purification.

¹H-NMR (400 MHz, DMSO-d₆): δ [ppm]=1.36-1.48 (2H), 1.54-1.63 (2H), 2.18-2.28 (1H), 2.40-2.45 (2H), 2.55 (3H), 2.72-2.83 (2H), 3.14-3.22 (2H), 3.38-3.44 (2H), 3.56-3.63 (2H), 3.65-3.95 (2H), 4.11-4.21 (2H), 7.32 (1H), 7.40 (1H), 8.43-8.48 (1H), 8.57 (1H), 8.68-8.82 (1H), 8.96-9.07 (1H).

EXAMPLE 68b

Tert-butyl 4-[(5-{N-[2-(3,3-difluoropyrrolidin-1-yl)ethyl]carbamoyl}-4-methyl-2H-indazol-2-yl)methyl]-piperidin-1-carboxylate

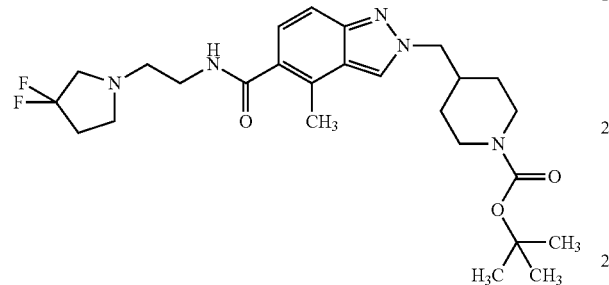

220 mg of 1c, 242.7 mg of 2-(3,3-difluoro-pyrrolidin-1-yl)ethylamine, 142.2 mg of molybdenum hexacarbonyl, 15.6 mg of tri-tert-butylphosphine tetrafluoroborate and 50.5 mg of trans-bis(acetato)-bis-[o-(di-o-tolylphosphino)benzyl]dipalladium(II) were placed in a microwave tube and suspended in 4.4 ml THF. 0.24 ml of DBU were then added and the mixture stirred for 20 mins at 125° C. and 200 watts in the microwave. The reaction mixture was diluted with some ethyl acetate and firstly filtered through Celite. The filtrate was diluted with ethyl acetate and the organic phase washed twice with water and once with saturated sodium chloride solution. It was dried over sodium sulphate, filtered and concentrated. The residue (209.3 mg) was chromatographed on the Biotage SP4. Gradient: DCM/methanol 0-10%. Yield: 53.4 mg of the title compound.

¹H-NMR (400 MHz, DMSO-d₆): δ [ppm]=1.00-1.12 (2H), 1.32-1.42 (2H), 1.34 (9H), 2.07-2.25 (3H), 2.50 (3H), 2.57 (2H), 2.60-2.68 (2H), 2.72 (2H), 2.91 (2H), 3.30-3.35 (2H), 3.83-3.92 (2H), 4.28 (2H), 7.15 (1H), 7.39 (1H), 8.04-8.09 (1H), 8.47 (1H).

EXAMPLE 69

2-{[1-(4-chlorobenzoyl)piperidin-4-yl]methyl}-N-[2-(3,3-difluoropyrrolidin-1-yl)ethyl]-4-methyl-2H-indazol-5-carboxamide

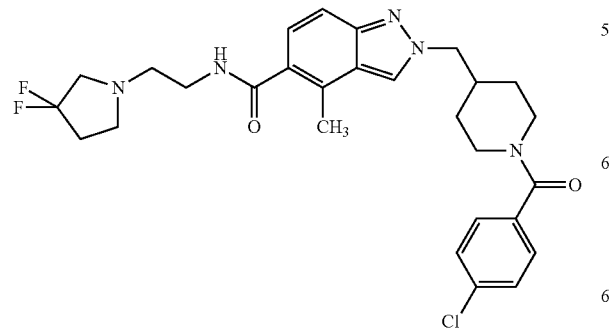

Analogously to Example 57, 79.9 mg of the title compound was obtained from 125.0 mg of the amine prepared in Example 68a and 54.5 mg of 4-chlorobenzoyl chloride.

¹H-NMR (300 MHz, chloroform-d): δ [ppm]=1.13-1.35 (2H), 1.46-1.84 (2H), 2.27-2.50 (3H), 2.66 (3H), 2.80-3.26 (8H), 3.59-3.83 (3H), 4.25-4.39 (2H), 4.62-4.85 (1H), 6.41-6.69 (1H), 7.30-7.40 (6H), 7.55 (1H), 7.96 (1H).

EXAMPLE 70

N-[2-(3,3-difluoropyrrolidin-1-yl)ethyl]-4-methyl-2-[(1-{4-[(trifluoromethyl) sulphanyl]benzoyl}piperidin-4-yl)methyl]-2H-indazol-5-carboxamide

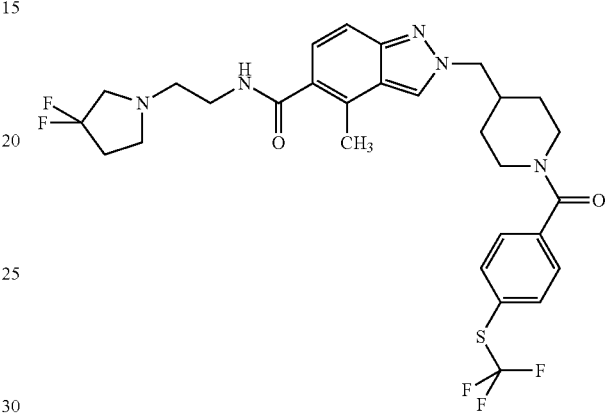

Analogously to Example 55, 15.2 mg of the title compound was obtained from 23.4 mg of the amine prepared in Example 68a and 14.0 mg of 4-[(trifluoromethyl)sulphanyl]benzoyl chloride.

¹H-NMR (400 MHz, chloroform-d): δ [ppm]=1.23-1.26 (1H), 1.33-1.46 (1H), 1.48-1.61 (1H), 1.77 (1H), 2.20-2.35 (2H), 2.36-2.49 (1H), 2.64 (3H), 2.73-2.85 (5H), 2.90-3.10 (3H), 3.56 (2H), 3.63-3.76 (1H), 4.26-4.39 (2H), 4.70-4.82 (1H), 6.28 (1H), 7.33 (1H), 7.42 (2H), 7.53 (1H), 7.68 (2H), 7.96 (1H).

EXAMPLE 71

4-methyl-2-({1-[4-(pentafluoro-λ⁶-sulphanyl)benzoyl]piperidin-4-yl}methyl)-N-(2,2,2-trifluoroethyl)-2H-indazol-5-carboxamide

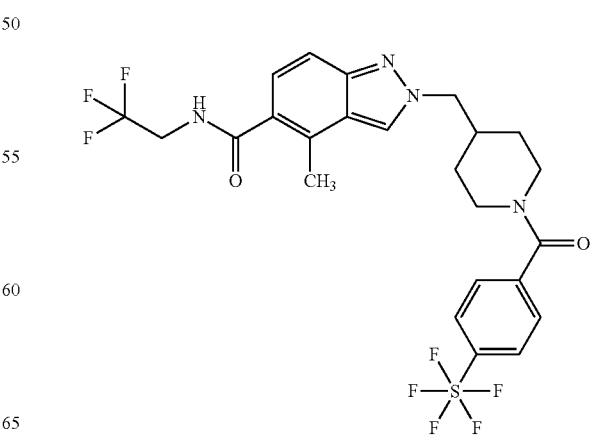

Analogously to Example 1, 124.8 mg of the title compound was obtained from 146.9 mg of the amine prepared in Example 71a and 93.3 mg of 4-(pentafluoro-λ⁶-sulphanyl)benzoic acid.

¹H-NMR (300 MHz, DMSO-d$_6$): δ [ppm]=1.12-1.31 (2H), 1.31-1.45 (1H), 1.47-1.63 (1H), 2.20-2.36 (1H), 2.50 (3H), 2.67-2.83 (1H), 2.91-3.07 (1H), 3.36-3.47 (1H), 3.96-4.10 (2H), 4.29-4.37 (2H), 4.37-4.48 (1H), 7.17 (1H), 7.43 (1H), 7.56 (2H), 7.94 (2H), 8.50-8.54 (1H), 8.75-8.83 (1H).

The starting material was prepared as follows:

EXAMPLE 71a 4-methyl-2-(4-piperidylmethyl)-N-(2,2,2-trifluoroethyl)-2H-indazol-5-carboxamide hydrochloride

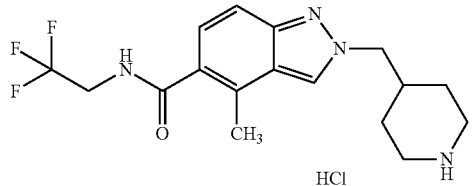 [SMILES: Cc1c(C(=O)NCC(F)(F)F)ccc2nn(CC3CCNCC3)cc12 ; Cl]

To 425.2 mg of 71b were added 2.35 ml of 4M hydrochloric acid in dioxan and 0.5 ml dioxan. An oily mass was formed, which dissolved on vigorous stirring and gentle warming. The mixture was stirred for 1 hr at ca. 30° C. The reaction mixture was concentrated. Yield: 440.6 mg of the title compound, which was further reacted without further purification.

¹H-NMR (400 MHz, DMSO-d$_6$): δ [ppm]=1.35-1.49 (2H), 1.53-1.62 (2H), 2.20-2.32 (1H), 2.51 (3H), 2.72-2.85 (2H), 3.14-3.23 (2H), 3.97-4.09 (2H), 4.34 (2H), 7.18 (1H), 7.43 (1H), 8.58 (1H), 8.64-8.77 (1H), 8.78-8.85 (1H), 8.93-9.08 (1H).

EXAMPLE 71b

Tert-butyl 4-({4-methyl-5-[N-(2,2,2-trifluoroethyl)carbamoyl]-2H-indazol-2-yl}-methyl)piperidin-1-carboxylate

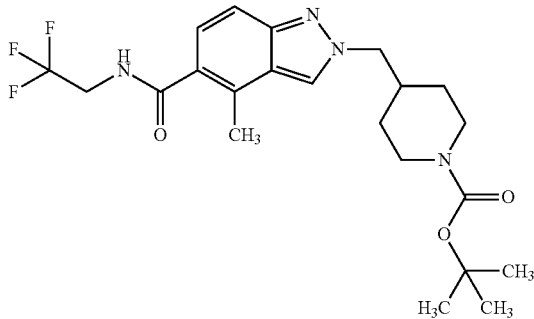 [SMILES: Cc1c(C(=O)NCC(F)(F)F)ccc2nn(CC3CCN(C(=O)OC(C)(C)C)CC3)cc12]

2820 mg of 1c, 2052 mg of 2,2,2-trifluoroethylamine, 1823.2 mg of molybdenum hexacarbonyl, 200.4 mg of tri-tert-butylphosphine tetrafluoroborate and 647.5 mg of trans-bis(acetato)-bis[o-(di-o-tolylphosphino)-benzyl]dipalladium(II) were placed in a microwave tube and suspended in 56 ml THF. 3.1 ml of DBU were then added and the mixture was stirred for 20 mins at 125° C. and 200 watts in the microwave. The reaction mixture was diluted with some ethyl acetate, washed twice with water and once with saturated sodium chloride solution. It was dried over sodium sulphate, filtered and concentrated. The residue was chromatographed on the Biotage SP4. Gradient: hexane/ethyl acetate 0-100%. Yield: 475.2 mg of the title compound.

¹H-NMR (300 MHz, DMSO-d$_6$): δ [ppm]=0.99-1.17 (2H), 1.30-1.44 (11H), 2.05-2.21 (1H), 2.50 (3H), 2.54-2.73 (2H), 3.81-3.94 (2H), 3.95-4.10 (2H), 4.29 (2H), 7.18 (1H), 7.43 (1H), 8.51 (1H), 8.74-8.83 (1H).

EXAMPLE 72

2-{[1-(4-chlorobenzoyl)piperidin-4-yl]methyl}-4-methyl-N-(2,2,2-trifluoroethyl)-2H-indazol-5-carboxamide

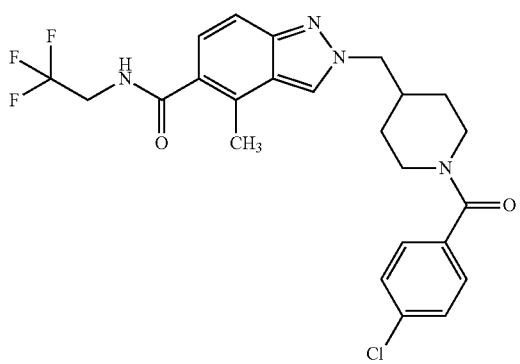 [SMILES: Cc1c(C(=O)NCC(F)(F)F)ccc2nn(CC3CCN(C(=O)c4ccc(Cl)cc4)CC3)cc12]

Analogously to Example 1, 97.8 mg of the title compound was obtained from 146.9 mg of the amine prepared in Example 71a and 58.8 mg of 4-chlorobenzoic acid.

¹H-NMR (300 MHz, DMSO-d$_6$): δ [ppm]=1.11-1.29 (2H), 1.31-1.45 (1H), 1.45-1.61 (1H), 2.20-2.35 (1H), 2.50 (3H), 2.63-2.84 (1H), 2.85-3.08 (1H), 3.42-3.59 (1H), 3.96-4.10 (2H), 4.29-4.47 (3H), 7.17 (1H), 7.36 (2H), 7.40-7.50 (3H), 8.52 (1H), 8.75-8.82 (1H).

EXAMPLE 73

4-methyl-N-(2,2,2-trifluoroethyl)-2-({1-[4-(trifluoromethoxy)benzoyl]piperidin-4-yl}methyl)-2H-indazol-5-carboxamide

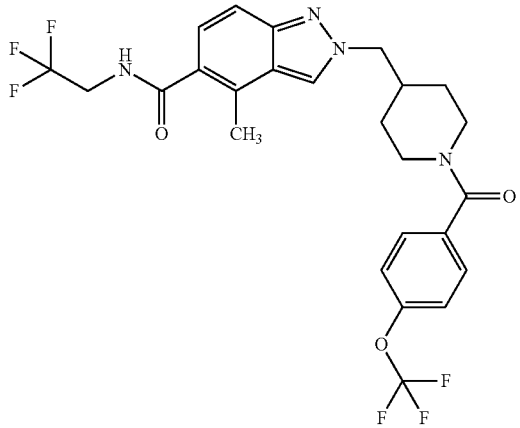 [SMILES: Cc1c(C(=O)NCC(F)(F)F)ccc2nn(CC3CCN(C(=O)c4ccc(OC(F)(F)F)cc4)CC3)cc12]

Analogously to Example 1, 105.4 mg of the title compound was obtained from 146.9 mg of the amine prepared in Example 71a and 77.5 mg of 4-(trifluoromethoxy)benzoic acid.

$^1$H-NMR (300 MHz, DMSO-d$_6$): δ [ppm]=1.12-1.30 (2H), 1.31-1.46 (1H), 1.47-1.64 (1H), 2.20-2.36 (1H), 2.50 (3H), 2.66-2.85 (1H), 2.86-3.09 (1H), 3.40-3.55 (1H), 3.96-4.10 (2H), 4.29-4.48 (3H), 7.17 (1H), 7.36-7.50 (5H), 8.52 (1H), 8.75-8.82 (1H).

EXAMPLE 74

2-{[1-(4-chlorobenzoyl)piperidin-4-yl]methyl}-6-methyl-N-(2-morpholinoethyl)-2H-indazol-5-carboxamide

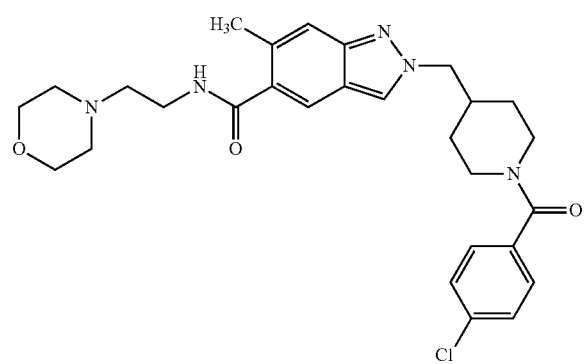 [SMILES: Cc1cc2nn(CC3CCN(C(=O)c4ccc(Cl)cc4)CC3)cc2cc1C(=O)NCCN1CCOCC1]

Analogously to Example 55, 30 mg of the title compound was obtained from 79 mg of the amine prepared in Example 74a and 26 mg of 4-chlorobenzoyl chloride.

$^1$NMR (400 MHz, methanol-d$_4$): δ [ppm]=1.31 (2H), 1.50 (1H), 1.65 (1H), 2.35 (1H), 2.47 (3H), 2.63 (6H), 2.81 (1H), 3.07 (1H), 3.53 (2H), 3.71 (5H), 4.34 (2H), 4.59 (1H), 7.36 (2H), 7.43 (3H), 7.75 (1H), 8.24 (1H).

The starting material was prepared as follows:

EXAMPLE 74a 6-methyl-N-(2-morpholinoethyl)-2-(4-piperidylmethyl)-2H-indazol-5-carboxamide

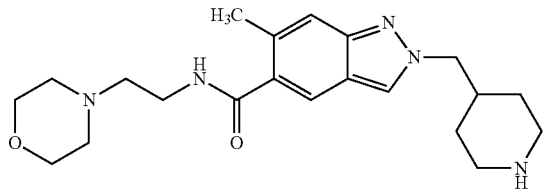 [SMILES: Cc1cc2nn(CC3CCNCC3)cc2cc1C(=O)NCCN1CCOCC1]

768 mg of (1.58 mmol) of tert-butyl carbamate 74b were dissolved in 4.0 ml 4M hydrochloric acid in dioxan and stirred under nitrogen at room temperature. A further 0.8 ml 4M hydrochloric acid in dioxan were added and the mixture stirred at room temperature. The reaction solution was concentrated and yielded 760 mg of the title compound, which was used in the next reaction without further purification.

$^1$H-NMR (400 MHz, DMSO-d$_6$): δ [ppm]=1.34-1.50 (2H), 1.53-1.67 (2H), 2.21-2.30 (1H), 2.41 (3H), 2.74-2.89 (2H), 3.07-3.33 (8H), 3.62-3.71 (2H), 3.77-3.90 (2H), 3.90-4.03 (2H), 4.35 (2H), 7.39 (1H), 7.88 (1H), 8.44 (1H), 8.57 (1H), 8.62-8.79 (1H), 8.87-9.02 (1H), 11.17 (1H).

EXAMPLE 74b

Tert-butyl 4-({6-methyl-5-[N-(2-morpholinoethyl)carbamoyl]-2H-indazol-2-yl}-methyl)piperidin-1-carboxylate

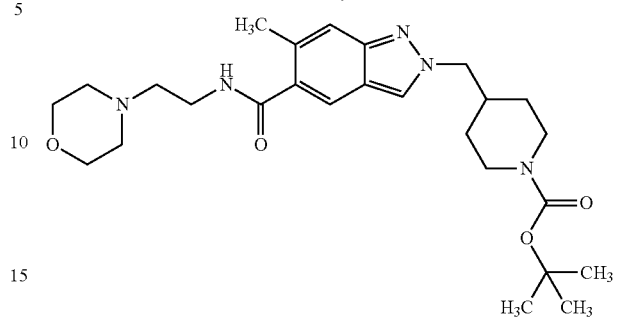

3.00 g (7.35 mmol) of 5-bromoindazole 74c and 2.87 g (22.04 mmol) of 2-morpholinoethylamine were dissolved in 134 ml dioxan and 1.94 g (7.35 mmol) of molybdenum hexacarbonyl, 167 mg (1.47 mmol) of palladium acetate, 213 mg (0.74 mmol) of tributylphosphonium tetrafluoroborate, 2.34 g (22.0 mmol) of sodium carbonate and 2 drops of water were added. The reaction mixture was heated to 125° C. under nitrogen and stirred at this temperature for 2.5 hrs. For the work-up, the suspension was filtered over Celite, rewashed with dioxan, concentrated in vacuo and dried. The crude product was separated by column chromatography. Yield: 518 mg of the title compound.

$^1$H-NMR (300 MHz, DMSO-d$_6$): δ [ppm]=0.93-1.16 (2H), 1.26-1.37 (2H), 1.34 (9H), 1.99-2.17 (1H), 2.32-2.43 (10H), 2.54-2.72 (2H), 3.34 (1H), 3.48-3.59 (4H), 3.86 (2H), 4.26 (2H), 7.35 (1H), 7.63 (1H), 8.09 (1H), 8.32 (1H).

EXAMPLE 74c

Tert-butyl 4-[(5-bromo-6-methyl-2H-indazol-2-yl)methyl]piperidin-1-carboxylate

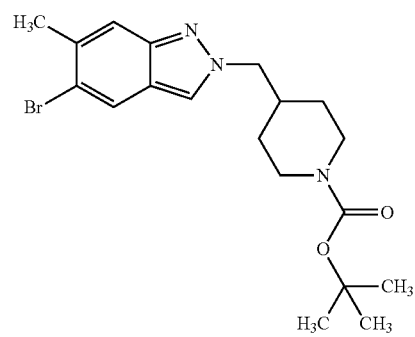 [SMILES: Cc1cc2nn(CC3CCN(C(=O)OC(C)(C)C)CC3)cc2cc1Br]

10.0 g (47.4 mmol) of 5-bromo-4-methyl-1H-indazole and 21.0 g (56.9 mmol) of tert-butyl 4-[(tosyloxy)methyl]piperidin-1-carboxylate were dissolved in 726 ml DMF. To this were added 21.0 g (56.9 mmol) of tetrabutylammonium iodide and 18.5 g (56.9 mmol) of caesium carbonate and the reaction mixture was heated under nitrogen at 80° C. for 1.5 hrs. For the work-up, it was treated with water and ethyl acetate, the organic phase separated and the aqueous phase extracted several times with ethyl acetate. The organic phases were washed with saturated sodium chloride solution, dried over sodium sulphate and concentrated in vacuo. After purification by column chromatography, this yielded the title compound in 5 g yield.

$^1$H-NMR (600 MHz, chloroform-d): δ [ppm]=1.16-1.30 (2H), 1.45 (9H), 1.54 (2H), 2.22-2.33 (1H), 2.51 (3H), 2.67 (2H), 4.03-4.17 (2H), 4.27-4.32 (2H), 7.60 (1H), 7.81 (1H), 7.90 (1H).

The following compounds were prepared analogously:

| Ex. | Structure | IUPAC name | Analysis |
|---|---|---|---|
| 75 | 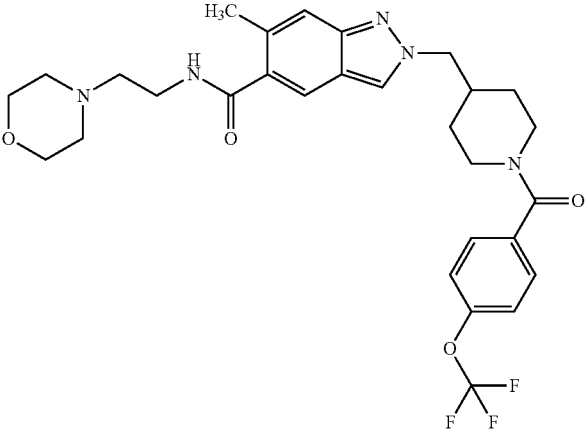 [SMILES: Cc1cc2nn(CC3CCN(C(=O)c4ccc(OC(F)(F)F)cc4)CC3)cc2cc1C(=O)NCCN1CCOCC1] | 6-methyl-N-(2-morpholinoethyl)-2-({1-[4-(trifluoromethoxy)benzoyl]piperidin-4-yl}methyl)-2H-indazol-5-carboxamide | $^{1}$H-NMR (400 MHz, methanol-$d_4$): δ [ppm] = 1.32 (2H), 1.51 (1H), 1.65 (1H), 2.36 (1H), 2.47 (3H), 2.60 (6H), 2.83 (1H), 3.10 (1H), 3.52 (2H), 3.70 (5H), 4.35 (2H), 4.61 (1H), 7.37 (3H), 7.49 (2H), 7.74 (1H), 8.24 (1H). |
| 76 | 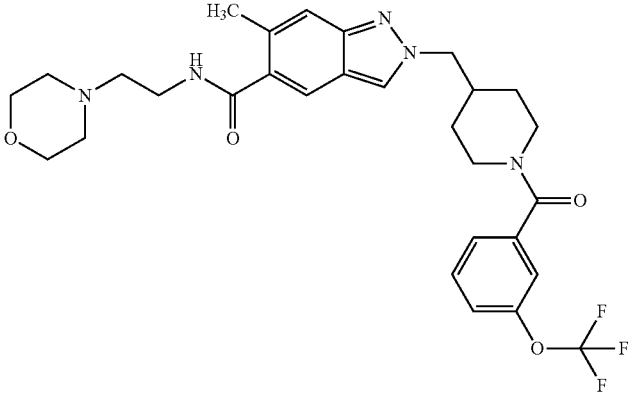 [SMILES: Cc1cc2nn(CC3CCN(C(=O)c4cccc(OC(F)(F)F)c4)CC3)cc2cc1C(=O)NCCN1CCOCC1] | 6-methyl-N-(2-morpholinoethyl)-2-({1-[3-(trifluoromethoxy)benzoyl]piperidin-4-yl}methyl)-2H-indazol-5-carboxamide | $^{1}$H-NMR (400 MHz, methanol-$d_4$): δ [ppm] = 1.32 (2H), 1.49 (1H), 1.65 (1H), 2.36 (1H), 2.46 (3H), 2.59 (6H), 2.83 (1H), 3.10 (1H), 3.51 (2H), 3.69 (5H), 4.35 (2H), 4.60 (1H), 7.33 (2H), 7.40 (2H), 7.54 (1H), 7.74 (1H), 8.24 (1H). |

EXAMPLE 77

6-methyl-N-(2-morpholinoethyl)-2-({1-[4-(pentafluoro-$\lambda^6$-sulphanyl)benzoyl]piperidin-4-yl}methyl)-2H-indazol-5-carboxamide

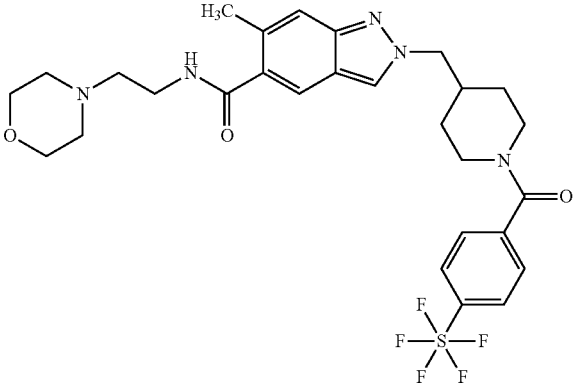 [SMILES: Cc1cc2nn(CC3CCN(C(=O)c4ccc(S(F)(F)(F)(F)F)cc4)CC3)cc2cc1C(=O)NCCN1CCOCC1]

Analogously to Example 1, 23 mg of the title compound was obtained from 79 mg of the amine prepared in Example 74a and 47 mg of the acid.

$^{1}$H-NMR (400 MHz, methanol-$d_4$): δ [ppm]=1.34 (2H), 1.52 (1H), 1.66 (1H), 2.37 (1H), 2.49 (3H), 2.84 (1H), 3.10 (1H), 3.25 (2H), 3.42 (2H), 3.63 (3H), 3.75 (4H), 4.10 (2H), 4.36 (2H), 4.62 (1H), 7.43 (1H), 7.56 (2H), 7.89 (3H), 8.28 (1H).

The following compounds were prepared analogously:

| Ex. | Structure | IUPAC name | Analysis |
|---|---|---|---|
| 78 | 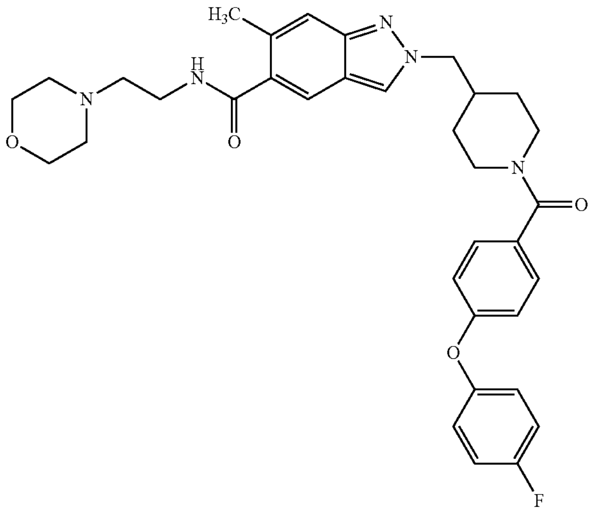 [SMILES: Cc1cc2nn(CC3CCN(C(=O)c4ccc(Oc5ccc(F)cc5)cc4)CC3)cc2cc1C(=O)NCCN1CCOCC1] | 2-({1-[4-(4-fluorophenoxy)benzoyl]-piperidin-4-yl}-methyl)-6-methyl-N-(2-morpholinoethyl)-2H-indazol-5-carboxamide | $^1$H-NMR (400 MHz, methanol-$d_4$): δ [ppm] = 1.31 (2H), 1.58 (2H), 2.35 (1H), 2.49 (3H), 2.40-4.20 (15H), 4.35 (2H), 4.58 (1H), 6.97 (2H), 7.04 (2H), 7.11 (2H), 7.37 (2H), 7.43 (1H), 7.87 (1H), 8.27 (1H). |
| 79 | 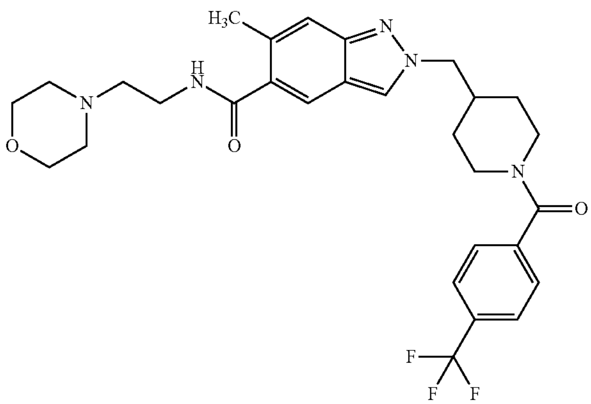 [SMILES: Cc1cc2nn(CC3CCN(C(=O)c4ccc(C(F)(F)F)cc4)CC3)cc2cc1C(=O)NCCN1CCOCC1] | 6-methyl-N-(2-morpholinoethyl)-2-({1-[4-(trifluoromethyl)benzoyl]-piperidin-4-yl}-methyl)-2H-indazol-5-carboxamide | $^1$H-NMR (300 MHz, methanol-$d_4$): δ [ppm] = 1.34 (2H), 1.51 (1H), 1.67 (1H), 2.38 (1H), 2.50 (3H), 2.85 (1H), 3.10 (1H), 3.25 (2H), 3.43 (2H), 3.64 (3H), 3.76 (4H), 4.10 (2H), 4.38 (2H), 4.64 (1H), 7.44 (1H), 7.57 (2H), 7.76 (2H), 7.89 (1H), 8.31 (1H). |
| 80 | 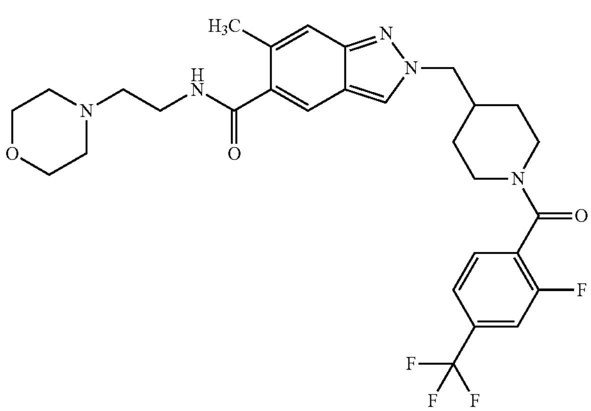 [SMILES: Cc1cc2nn(CC3CCN(C(=O)c4ccc(C(F)(F)F)cc4F)CC3)cc2cc1C(=O)NCCN1CCOCC1] | 2-({1-[2-fluoro-4-(trifluoromethyl)-benzoyl]piperidin-4-yl}-methyl)-6-methyl-N-(2-morpholinoethyl)-2H-indazol-5-carboxamide | $^1$H-NMR (300 MHz, methanol-$d_4$): δ [ppm] = 1.34 (2H), 1.54 (1H), 1.68 (1H), 2.38 (1H), 2.50 (3H), 2.86 (1H), 3.12 (1H), 3.26 (2H), 3.43 (3H), 3.66 (2H), 3.76 (4H), 4.11 (2H), 4.37 (2H), 4.67 (1H), 7.44 (1H), 7.59 (3H), 7.89 (1H), 8.31 (1H). |

-continued

| Ex. | Structure | IUPAC name | Analysis |
|---|---|---|---|
| 81 | 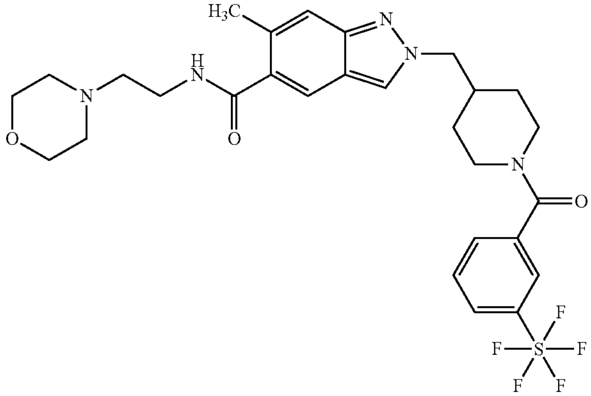 [SMILES: Cc1cc2nn(CC3CCN(C(=O)c4cccc(S(F)(F)(F)(F)F)c4)CC3)cc2cc1C(=O)NCCN1CCOCC1] | 6-methyl-N-(2-morpholinoethyl)-2-({1-[3-(pentafluoro-λ⁶-sulphanyl)benzoyl]-piperidin-4-yl}-methyl)-2H-indazol-5-carboxamide | ¹H-NMR (300 MHz, methanol-d₄): δ [ppm] = 1.35 (2H), 1.53 (1H), 1.65 (1H), 2.38 (1H), 2.50 (3H), 2.86 (1H), 3.14 (1H), 3.26 (2H), 3.43 (2H), 3.66 (3H), 3.76 (4H), 4.11 (2H), 4.37 (2H), 4.62 (1H), 7.44 (1H), 7.63 (2H), 7.89 (3H), 8.30 (1H). |
| 82 | 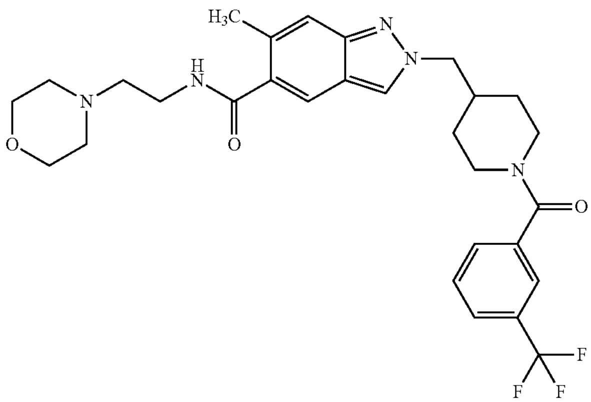 [SMILES: Cc1cc2nn(CC3CCN(C(=O)c4cccc(C(F)(F)F)c4)CC3)cc2cc1C(=O)NCCN1CCOCC1] | 6-methyl-N-(2-morpholinoethyl)-2-({1-[3-(trifluoromethyl)-benzoyl]piperidin-4-yl}methyl)-2H-indazol-5-carboxamide | ¹H-NMR (300 MHz, methanol-d₄): δ [ppm] = 1.35 (2H), 1.53 (1H), 1.65 (1H), 2.38 (1H), 2.50 (3H), 2.85 (1H), 3.12 (1H), 3.26 (2H), 3.43 (2H), 3.66 (3H), 3.76 (4H), 4.11 (2H), 4.38 (2H), 4.63 (1H), 7.45 (1H), 7.66 (3H), 7.77 (1H), 7.90 (1H), 8.33 (1H). |
| 83 | 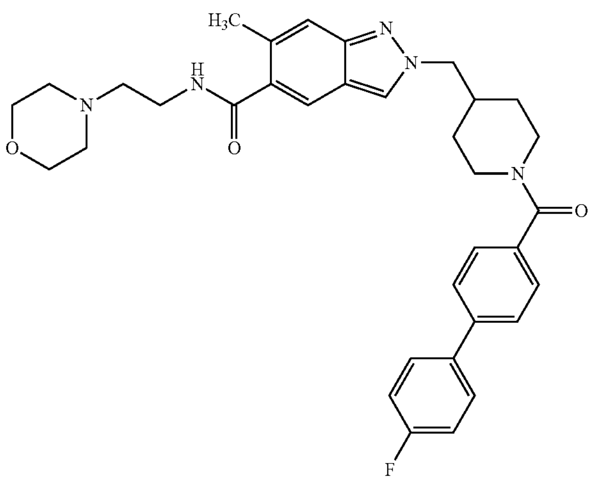 [SMILES: Cc1cc2nn(CC3CCN(C(=O)c4ccc(-c5ccc(F)cc5)cc4)CC3)cc2cc1C(=O)NCCN1CCOCC1] | 2-({1-[(4'-fluoro-biphenyl-4-yl)-carbonyl]piperidin-4-yl}methyl)-6-methyl-N-(2-morpholino-ethyl)-2H-indazol-5-carboxamide | ¹H-NMR (300 MHz, methanol-d₄): δ [ppm] = 1.35 (2H), 1.53 (1H), 1.65 (1H), 2.39 (1H), 2.50 (3H), 2.85 (1H), 3.12 (1H), 3.26 (2H), 3.42 (2H), 3.63 (3H), 3.74 (4H), 4.08 (2H), 4.37 (2H), 4.64 (1H), 7.18 (2H), 7.46 (3H), 7.66 (4H), 7.88 (1H), 8.30 (1H). |

EXAMPLE 84

2-{[1-(4-chlorobenzoyl)piperidin-4-yl]methyl}-N-[2-(cyclopropylmethoxy)ethyl]-4-methyl-2H-indazol-5-carboxamide

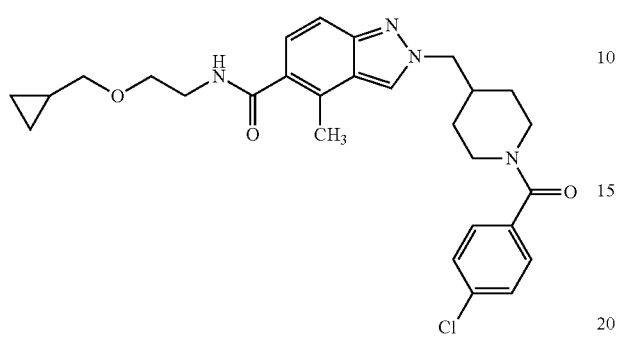

Analogously to Example 1, 38 mg of the title compound was obtained from 75 mg of the amine prepared in Example 84a and 29 mg of 4-chlorobenzoic acid.

$^1$H-NMR (400 MHz, DMSO-d$_6$): δ [ppm]=0.14 (2H), 0.42 (2H), 0.97 (1H), 1.21 (2H), 1.36 (1H), 1.52 (1H), 2.27 (1H), 2.50 (3H), 2.72 (1H), 2.97 (1H), 3.23 (2H), 3.36 (2H), 3.48 (3H), 4.31 (2H), 4.40 (1H), 7.14 (1H), 7.36 (3H), 7.46 (2H), 8.12 (1H), 8.47 (1H).

The starting material was prepared as follows:

EXAMPLE 84a

N-[2-(cyclopropylmethoxy)ethyl]-4-methyl-2-(4-piperidylmethyl)-2H-indazol-5-carboxamide

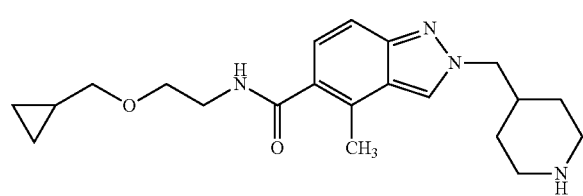 [SMILES: Cc1c(C(=O)NCCOCC2CC2)ccc2nn(CC3CCNCC3)cc12]

500 mg of 1d was reacted with 203 mg of amine analogously to 1b version B. Yield: 781 mg of the title compound.

$^1$H-NMR (300 MHz, DMSO-d$_6$): δ [ppm]=0.98-1.13 (2H), 1.34 (11H), 2.05-2.27 (2H), 2.33-2.41 (5H), 2.51 (3H), 2.56-2.73 (2H), 3.25-3.37 (2H), 3.51-3.57 (4H), 3.81-3.93 (2H), 4.28 (2H), 7.14 (1H), 7.36-7.41 (1H), 7.95-8.02 (1H), 8.46 (1H).

To 781 mg of 84b were added 3.7 ml of 4M hydrochloric acid in dioxan and 0.5 ml dioxan. The mixture was stirred for 30 mins at ca. 30° C. The reaction mixture was concentrated, taken up in some toluene and again concentrated. Yield: 751 mg of the title compound, which was further reacted without further purification.

$^1$H-NMR (400 MHz, DMSO-d$_6$): δ [ppm]=0.14 (2H), 0.42 (2H), 0.97 (1H), 1.43 (2H), 1.58 (2H), 2.26 (1H), 2.50 (3H), 2.65 (1H), 2.78 (2H), 3.18 (2H), 3.22 (2H), 3.36 (2H), 3.49 (2H), 4.33 (2H), 7.16 (2H), 7.38 (1H), 8.11 (1H), 8.53 (1H), 8.80 (1H), 9.06 (1H).

EXAMPLE 84b

Tert-butyl 4-[(5-{N-[2-(cyclopropylmethoxy)ethyl]carbamoyl}-4-methyl-2H-indazol-2-yl)methyl]piperidin-1-carboxylate The following compounds were prepared analogously:

| Ex. | Structure | IUPAC name | Analysis |
|---|---|---|---|
| 85 | 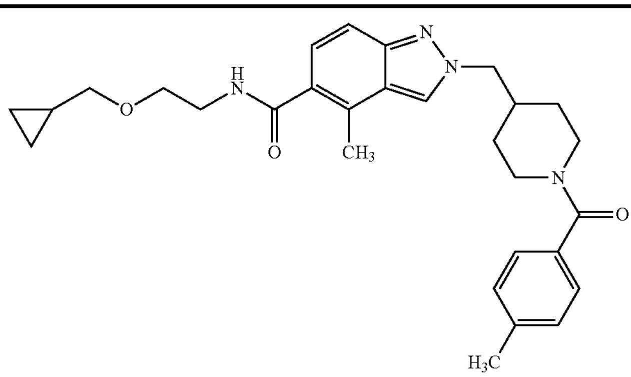 | N-[2-(cyclopropylmethoxy)ethyl]-4-methyl-2-{[1-(4-methylbenzoyl)-piperidin-4-yl]-methyl}-2H-indazol-5-carboxamide | $^1$H-NMR (400 MHz, DMSO-d$_6$): δ [ppm] = 0.14 (2H), 0.42 (2H), 0.97 (1H), 1.19 (2H), 1.37 (1H), 1.50 (1H), 2.26 (1H), 2.29 (3H), 2.50 (3H), 2.72 (1H), 2.94 (1H), 3.23 (2H), 3.36 (2H), 3.48 (2H), 3.57 (1H), 4.30 (2H), 4.39 (1H), 7.14 (1H), 7.21 (4H), 7.38 (1H), 8.12 (1H), 8.47 (1H). |

| Ex. | Structure | IUPAC name | Analysis |
|---|---|---|---|
| 86 | 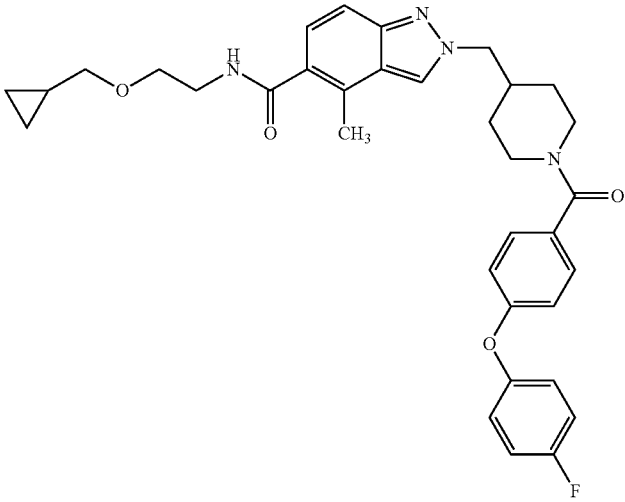 [SMILES: Cc1c(C(=O)NCCOCC2CC2)ccc2nn(CC3CCN(C(=O)c4ccc(Oc5ccc(F)cc5)cc4)CC3)cc12] | N-[2-(cyclopropyl-methoxy)ethyl]-2-({1-[4-(4-fluorophenoxy)-benzoyl]piperidin-4-yl}methyl)-4-methyl-2H-indazol-5-carboxamide | $^1$H-NMR (400 MHz, DMSO-d$_6$): δ [ppm] = 0.14 (2H), 0.42 (2H), 0.97 (1H), 1.19 (2H), 1.45 (2H), 2.26 (1H), 2.50 (3H), 2.75 (1H), 2.96 (1H), 3.23 (2H), 3.36 (2H), 3.48 (2H), 3.62 (1H), 4.31 (2H), 4.39 (1H), 6.95 (2H), 7.12 (3H), 7.23 (2H), 7.36 (3H), 8.12 (1H), 8.47 (1H). |
| 87 | 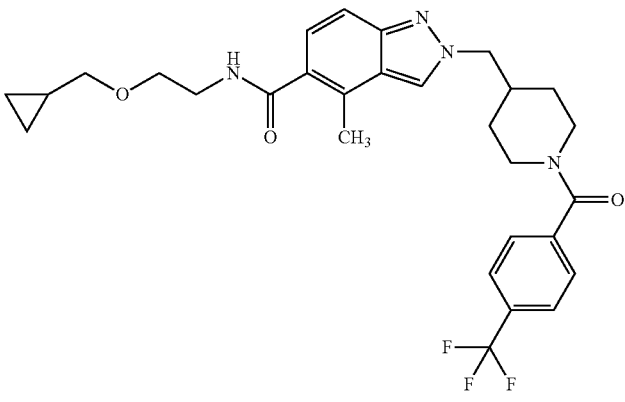 [SMILES: Cc1c(C(=O)NCCOCC2CC2)ccc2nn(CC3CCN(C(=O)c4ccc(C(F)(F)F)cc4)CC3)cc12] | N-[2-(cyclopropyl-methoxy)ethyl]-4-methyl-2-({1-[4-(tri-fluoromethyl)benzoyl]piperidin-4-yl}-methyl)-2H-indazol-5-carboxamide | $^1$H-NMR (400 MHz, DMSO-d$_6$): δ [ppm] = 0.14 (2H), 0.42 (2H), 0.96 (1H), 1.22 (2H), 1.36 (1H), 1.56 (1H), 2.28 (1H), 2.50 (3H), 2.74 (1H), 2.99 (1H), 3.23 (2H), 3.36 (2H), 2.43 (1H), 3.48 (2H), 4.31 (2H), 4.43 (1H), 7.15 (1H), 7.38 (1H), 7.55 (2H), 7.77 (2H), 8.12 (1H), 8.47 (1H). |
| 88 | 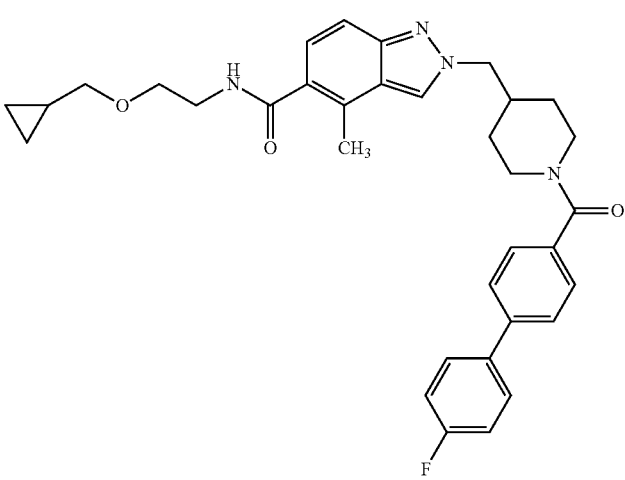 [SMILES: Cc1c(C(=O)NCCOCC2CC2)ccc2nn(CC3CCN(C(=O)c4ccc(-c5ccc(F)cc5)cc4)CC3)cc12] | N-[2-(cyclopropyl-methoxy)ethyl]-2-({1-[(4'-fluorobiphenyl-4-yl)carbonyl]piperidin-4-yl}methyl)-4-methyl-2H-indazol-5-carboxamide | $^1$H-NMR (400 MHz, DMSO-d$_6$): δ [ppm] = 0.14 (2H), 0.42 (2H), 0.96 (1H), 1.23 (2H), 1.39 (1H), 1.55 (1H), 2.28 (1H), 2.50 (3H), 2.74 (1H), 3.01 (1H), 3.23 (2H), 3.36 (2H), 3.48 (2H), 3.61 (1H), 4.33 (2H), 4.44 (1H), 7.15 (1H), 7.28 (2H), 7.40 (3H), 7.69 (4H), 8.12 (1H), 8.48 (1H). |

| Ex. | Structure | IUPAC name | Analysis |
|---|---|---|---|
| 89 | 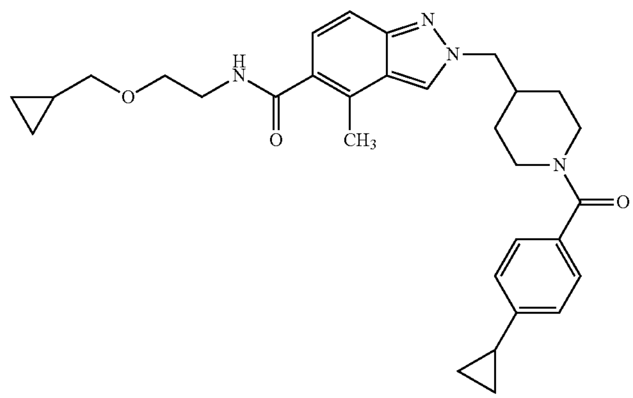 [SMILES: Cc1c(C(=O)NCCOCC2CC2)ccc2nn(CC3CCN(C(=O)c4ccc(C5CC5)cc4)CC3)cc12] | 2-{[1-(4-cyclopropyl-benzoyl)piperidin-4-yl]methyl}-N-[2-(cyclopropylmethoxy)ethyl]-4-methyl-2H-indazol-5-carboxamide | $^1$H-NMR (400 MHz, DMSO-d$_6$): δ [ppm] = 0.17 (2H), 0.45 (2H), 0.69 (2H), 0.97 (3H), 1.21 (2H), 1.47 (2H), 1.93 (1H), 2.27 (1H), 2.52 (3H), 2.78 (1H), 2.93 (1H), 3.26 (2H), 3.37 (2H), 3.51 (2H), 3.62 (1H), 4.34 (2H), 4.41 (1H), 7.10 (2H), 7.17 (1H), 7.22 (2H), 7.41 (1H), 8.11 (1H), 8.49 (1H). |

EXAMPLE 90

2-{[1-(4-chlorobenzoyl)piperidin-4-yl]methyl}-4-methyl-N-[2-(2,2,2-trifluoro-ethoxy)ethyl]-2H-indazol-5-carboxamide

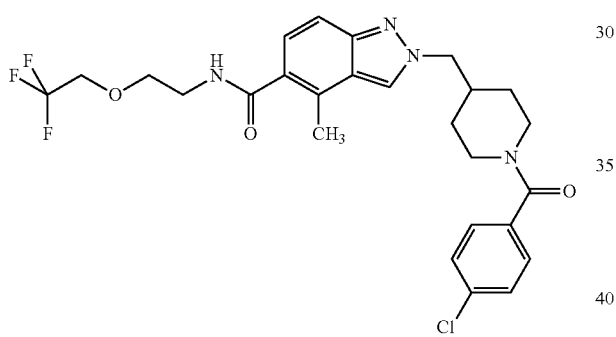

Analogously to Example 1, 40 mg of the title compound was obtained from 75 mg of the amine prepared in Example 90a and 27 mg of 4-chlorobenzoic acid.

$^1$H-NMR (400 MHz, DMSO-d$_6$): δ [ppm]=1.20 (2H), 1.36 (1H), 1.53 (1H), 2.27 (1H), 2.49 (3H), 2.72 (1H), 2.97 (1H), 3.40 (2H), 3.49 (1H), 3.69 (2H), 4.07 (2H), 4.31 (2H), 4.40 (1H), 7.15 (1H), 7.37 (3H), 7.46 (2H), 8.19 (1H), 8.48 (1H).

The starting material was prepared as follows:

EXAMPLE 90a 4-methyl-2-(4-piperidylmethyl)-N-[2-(2,2,2-trifluoroethoxy)ethyl]-2H-indazol-5-carboxamide

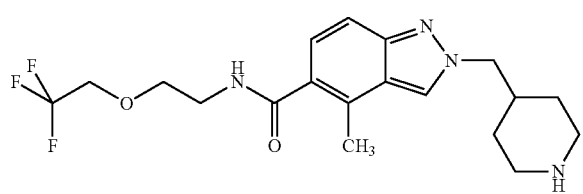 [SMILES: Cc1c(C(=O)NCCOCC(F)(F)F)ccc2nn(CC3CCNCC3)cc12]

To 610 mg of 90b were added 3.0 ml of 4M hydrochloric acid in dioxan and 0.5 ml dioxan. The mixture was stirred for 30 mins at ca. 30° C. The reaction mixture was concentrated, taken up in some toluene and again concentrated. Yield: 619 mg of the title compound, which was further reacted without further purification.

$^1$H-NMR (400 MHz, DMSO-d$_6$): δ [ppm]=1.42 (2H), 1.59 (2H), 2.26 (1H), 2.50 (3H), 2.64 (1H), 2.79 (2H), 3.20 (2H), 3.40 (2H), 3.70 (2H), 4.07 (2H), 4.33 (2H), 5.67 (1H), 7.16 (1H), 7.39 (1H), 8.18 (1H), 8.53 (1H), 8.69 (1H), 8.94 (1H).

EXAMPLE 90b

Tert-butyl 4-[(4-methyl-5-{N-[2-(2,2,2-trifluoroethoxy)ethyl]carbamoyl}-2H-indazol-2-yl)methyl]piperidin-1-carboxylate

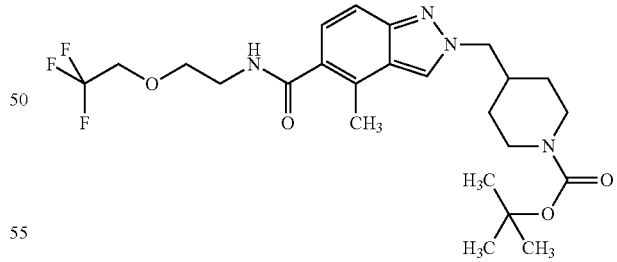

500 mg of 1d was reacted with 240 mg of amine analogously to 1b version B. Yield: 670 mg of the title compound.

$^1$H-NMR (400 MHz, DMSO-d$_6$): δ [ppm]=1.07 (2H), 1.34 (9H), 1.37 (2H), 2.14 (1H), 2.49 (3H), 2.63 (2H), 3.40 (2H), 3.70 (2H), 3.88 (2H), 4.06 (2H), 4.29 (2H), 7.15 (1H), 7.39 (1H), 8.16 (1H), 8.47 (1H).

The following compounds were prepared analogously:

| Ex. | Structure | IUPAC name | Analysis |
|---|---|---|---|
| 91 | 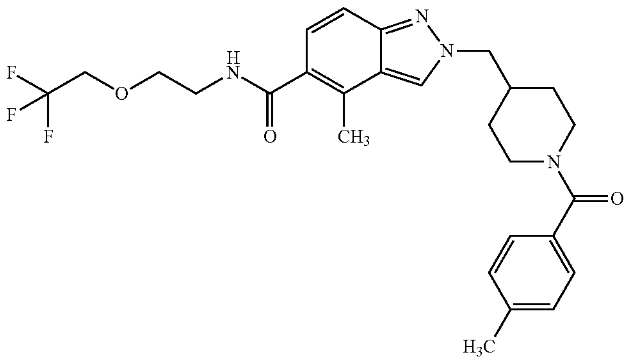 [SMILES: Cc1ccc(C(=O)N2CCC(Cn3cc4c(C)c(C(=O)NCCOCC(F)(F)F)ccc4n3)CC2)cc1] | 4-methyl-2-{[1-(4-methylbenzoyl)-piperidin-4-yl]-methyl}-N-[2-(2,2,2-trifluoro-ethoxy)ethyl]-2H-indazol-5-carboxamide | $^1$H-NMR (400 MHz, DMSO-d$_6$): δ [ppm] = 1.19 (2H), 1.36 (1H), 1.49 (1H), 2.25 (1H), 2.29 (3H), 2.49 (3H), 2.71 (1H), 2.93 (1H), 3.40 (2H), 3.56 (1H), 3.69 (2H), 4.07 (2H), 4.31 (2H), 4.40 (1H), 7.15 (1H), 7.21 (4H), 7.39 (1H), 8.19 (1H), 8.48 (1H). |
| 92 | 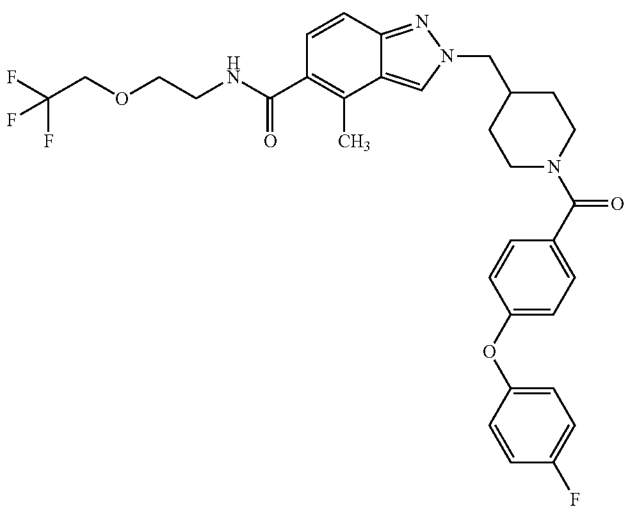 [SMILES: Cc1c(C(=O)NCCOCC(F)(F)F)ccc2nn(CC3CCN(C(=O)c4ccc(Oc5ccc(F)cc5)cc4)CC3)cc12] | 2-({1-[4-(4-fluoro-phenoxy)benzoyl]-piperidin-4-yl}-methyl)-4-methyl-N-[2-(2,2,2-tri-fluoroethoxy)ethyl]-2H-indazol-5-carboxamide | $^1$H-NMR (400 MHz, DMSO-d$_6$): δ [ppm] = 1.19 (2H), 1.44 (2H), 2.26 (1H), 2.49 (3H), 2.73 (1H), 2.95 (1H), 3.40 (2H), 3.60 (1H), 3.69 (2H), 4.07 (2H), 4.31 (2H), 4.38 (1H), 6.95 (2H), 7.12 (3H), 7.22 (2H), 7.37 (3H), 8.19 (1H), 8.48 (1H). |
| 93 | 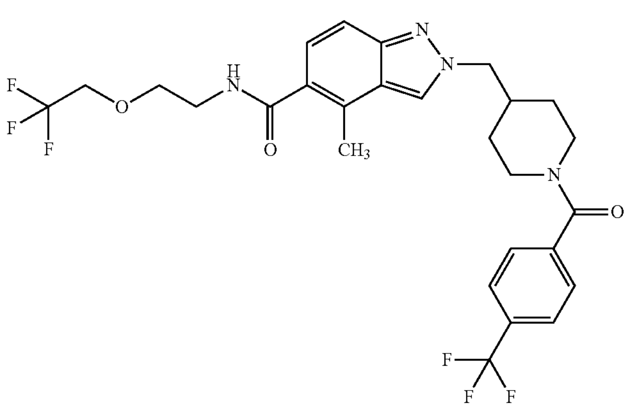 [SMILES: Cc1c(C(=O)NCCOCC(F)(F)F)ccc2nn(CC3CCN(C(=O)c4ccc(C(F)(F)F)cc4)CC3)cc12] | 4-methyl-N-[2-(2,2,2-trifluoro-ethoxy)ethyl]-2-({1-[4-(trifluoro-methyl)benzoyl]-piperidin-4-yl}-methyl)-2H-indazol-5-carboxamide | $^1$H-NMR (400 MHz, DMSO-d$_6$): δ [ppm] = 1.22 (2H), 1.36 (1H), 1.56 (1H), 2.28 (1H), 2.49 (3H), 2.74 (1H), 2.99 (1H), 3.40 (3H), 3.69 (2H), 4.07 (2H), 4.32 (2H), 4.43 (1H), 7.15 (1H), 7.39 (1H), 7.55 (2H), 7.77 (2H), 8.19 (1H), 8.48 (1H). |

| Ex. | Structure | IUPAC name | Analysis |
|---|---|---|---|
| 94 | 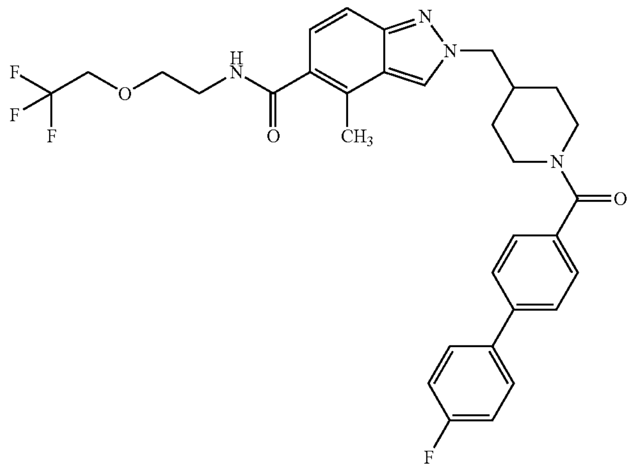 [SMILES: Cc1c(C(=O)NCCOCC(F)(F)F)ccc2nn(CC3CCN(C(=O)c4ccc(-c5ccc(F)cc5)cc4)CC3)cc12] | 2-({1-[(4'-fluoro-biphenyl-4-yl)-carbonyl]piperidin-4-yl}methyl)-4-methyl-N-[2-(2,2,2-trifluoroethoxy)-ethyl]-2H-indazol-5-carboxamide | $^1$H-NMR (300 MHz, DMSO-d$_6$): δ [ppm] = 1.23 (2H), 1.39 (1H), 1.52 (1H), 2.28 (1H), 2.49 (3H), 2.75 (1H), 3.00 (1H), 3.39 (2H), 3.60 (1H), 3.69 (2H), 4.07 (2H), 4.33 (2H), 4.43 (1H), 7.15 (1H), 7.27 (2H), 7.40 (3H), 7.68 (4H), 8.19 (1H), 8.49 (1H). |
| 95 | 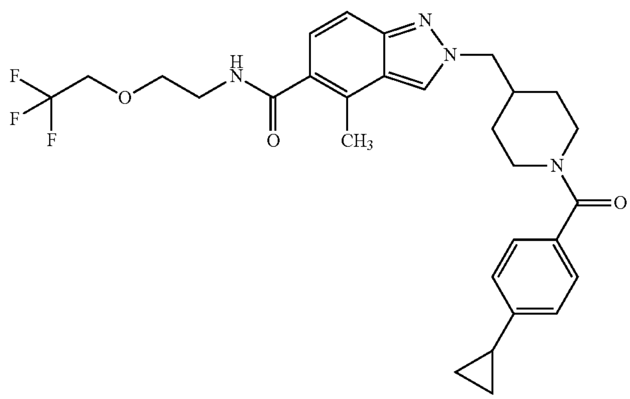 [SMILES: Cc1c(C(=O)NCCOCC(F)(F)F)ccc2nn(CC3CCN(C(=O)c4ccc(C5CC5)cc4)CC3)cc12] | 2-{[1-(4-cyclo-propylbenzoyl)-piperidin-4-yl]-methyl}-4-methyl-N-[2-(2,2,2-tri-fluoroethoxy)ethyl]-2H-indazol-5-carboxamide | $^1$H-NMR (400 MHz, DMSO-d$_6$): δ [ppm] = 0.69 (2H), 0.96 (2H), 1.21 (2H), 1.47 (2H), 1.93 (1H), 2.28 (1H), 2.52 (3H), 2.77 (1H), 2.94 (1H), 3.43 (2H), 3.61 (1H), 3.72 (2H), 4.09 (2H), 4.34 (2H), 4.42 (1H), 7.10 (2H), 7.17 (1H), 7.22 (2H), 7.41 (1H), 8.18 (1H). |

EXAMPLE 96

2-{[1-(4-chlorobenzoyl)piperidin-4-yl]methyl}-N-(2-isopropoxyethyl)-4-methyl-2H-indazol-5-carboxamide

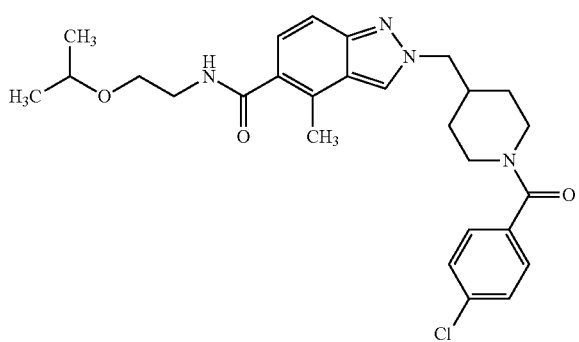 [SMILES: Cc1c(C(=O)NCCOC(C)C)ccc2nn(CC3CCN(C(=O)c4ccc(Cl)cc4)CC3)cc12]

Analogously to Example 1, 36 mg of the title compound was obtained from 75 mg of the amine prepared in Example 96a and 30 mg of 4-chlorobenzoic acid.

$^1$H-NMR (300 MHz, DMSO-d$_6$): δ [ppm]=1.07 (6H), 1.22 (2H), 1.39 (1H), 1.51 (1H), 2.26 (1H), 2.50 (3H), 2.75 (1H), 2.97 (1H), 3.33 (2H), 3.45 (3H), 3.55 (1H), 4.31 (2H), 4.39 (1H), 7.14 (1H), 7.36 (3H), 7.47 (2H), 8.05 (1H), 8.46 (1H).

The starting material was prepared as follows:

EXAMPLE 96a

N-(2-isopropoxyethyl)-4-methyl-2-(4-piperidylmethyl)-2H-indazol-5-carboxamide

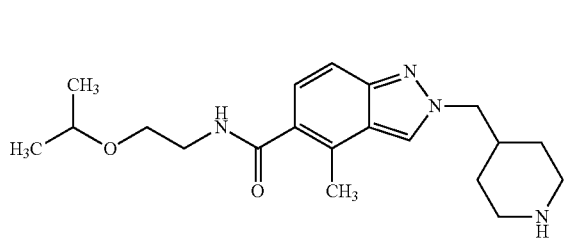 [SMILES: Cc1c(C(=O)NCCOC(C)C)ccc2nn(CC3CCNCC3)cc12]

To 650 mg of 96b were added 3.2 ml of 4M hydrochloric acid in dioxan and 0.5 ml dioxan. The mixture was stirred for 30 mins at ca. 30° C. The reaction mixture was concentrated, taken up in some toluene and again concentrated. Yield: 529 mg of the title compound, which was further reacted without further purification.

$^1$H-NMR (400 MHz, DMSO-d$_6$): δ [ppm]=1.06 (3H), 1.07 (3H), 1.42 (2H), 1.57 (2H), 2.25 (1H), 2.50 (3H), 2.65 (1H), 2.78 (2H), 3.19 (2H), 3.32 (2H), 3.45 (2H), 3.55 (1H), 4.32 (1H), 6.61 (1H), 7.15 (1H), 7.38 (1H), 8.11 (1H), 8.53 (1H), 8.78 (1H), 9.04 (1H).

EXAMPLE 96b

Tert-butyl 4-({5-[N-(2-isopropoxyethyl)carbamoyl]-4-methyl-2H-indazol-2-yl}-methyl)piperidin-1-carboxylate

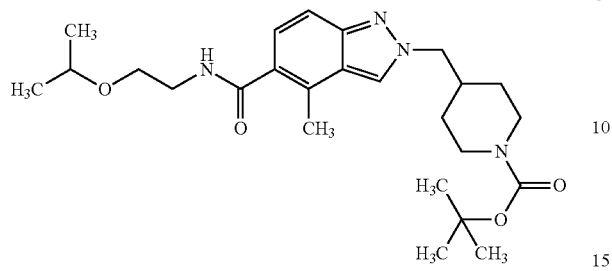

500 mg of 1d was reacted with 138 mg of amine analogously to 1b version B. Yield: 650 mg of the title compound.

$^1$H-NMR (400 MHz, DMSO-d$_6$): δ [ppm]=1.07 (8H), 1.34 (9H), 1.38 (2H), 2.13 (1H), 2.50 (3H), 2.63 (2H), 3.33 (2H), 3.46 (2H), 3.55 (1H), 3.87 (2H), 4.28 (2H), 7.14 (1H), 7.38 (1H), 8.05 (1H), 8.46 (1H).

The following compounds were prepared analogously:

| Ex. | Structure | IUPAC name | Analysis |
|---|---|---|---|
| 97 | 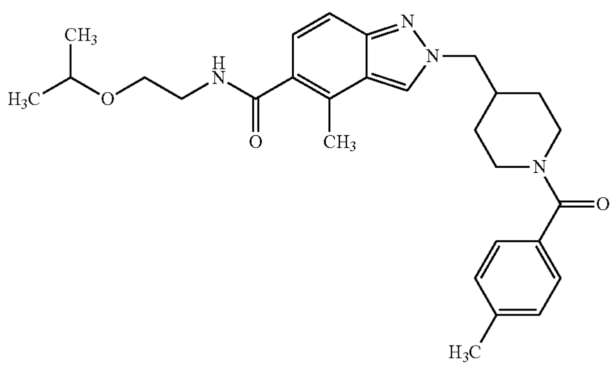 [SMILES: Cc1ccc(C(=O)N2CCC(Cn3cc4c(C)c(C(=O)NCCOC(C)C)ccc4n3)CC2)cc1] | N-(2-isopropoxyethyl)-4-methyl-2-{[1-(4-methylbenzoyl)piperidin-4-yl]methyl}-2H-indazol-5-carboxamide | $^1$H-NMR (300 MHz, DMSO-d$_6$): δ [ppm] = 1.07 (6H), 1.19 (2H), 1.45 (2H), 2.29 (4H), 2.50 (3H), 2.75 (1H), 2.92 (1H), 3.33 (2H), 3.45 (2H), 3.55 (2H), 4.31 (2H), 4.40 (1H), 7.14 (1H), 7.20 (4H), 7.38 (1H), 8.05 (1H), 8.46 (1H). |
| 98 | 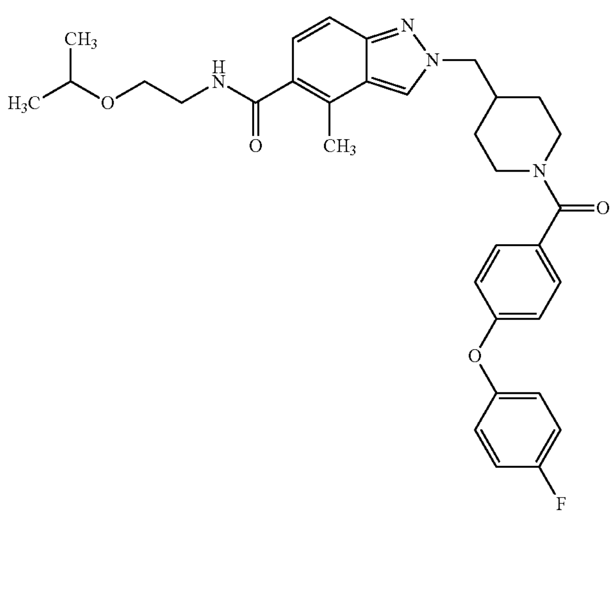 [SMILES: Cc1c(C(=O)NCCOC(C)C)ccc2nn(CC3CCN(C(=O)c4ccc(Oc5ccc(F)cc5)cc4)CC3)cc12] | 2-({1-[4-(4-fluorophenoxy)benzoyl]-piperidin-4-yl}-methyl)-N-(2-isopropoxyethyl)-4-methyl-2H-indazol-5-carboxamide | $^1$H-NMR (300 MHz, DMSO-d$_6$): δ [ppm] = 1.07 (6H), 1.21 (2H), 1.45 (2H), 2.25 (1H), 2.49 (3H), 2.85 (2H), 3.31 (2H), 3.45 (2H), 3.55 (2H), 4.31 (2H), 4.40 (1H), 6.95 (2H), 7.10 (3H), 7.22 (2H), 7.36 (3H), 8.05 (1H), 8.46 (1H). |

| Ex. | Structure | IUPAC name | Analysis |
|---|---|---|---|
| 99 | 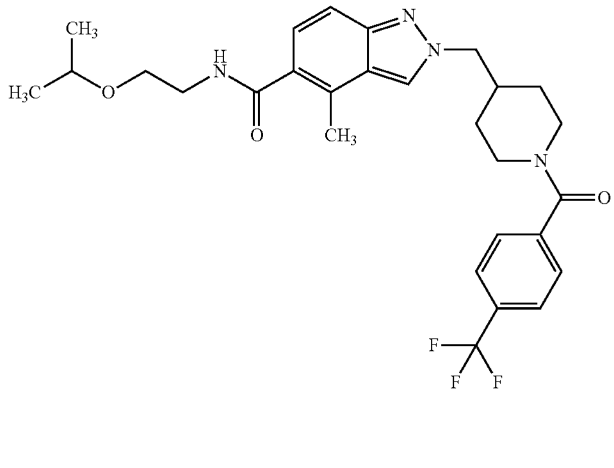 [SMILES: Cc1c(C(=O)NCCOC(C)C)ccc2nn(CC3CCN(C(=O)c4ccc(C(F)(F)F)cc4)CC3)cc12] | N-(2-isopropoxy-ethyl)-4-methyl-2-({1-[4-(trifluoro-methyl)benzoyl]-piperidin-4-yl}-methyl)-2H-indazol-5-carboxamide | $^1$H-NMR (300 MHz, DMSO-d$_6$): δ [ppm] = 1.06 (6H), 1.22 (2H), 1.37 (1H), 1.56 (1H), 2.28 (1H), 2.50 (3H), 2.75 (1H), 2.99 (1H), 3.33 (2H), 3.45 (3H), 3.55 (1H), 4.32 (2H), 4.43 (1H), 7.15 (1H), 7.38 (1H), 7.55 (2H), 7.77 (2H), 8.05 (1H), 8.46 (1H). |
| 100 | 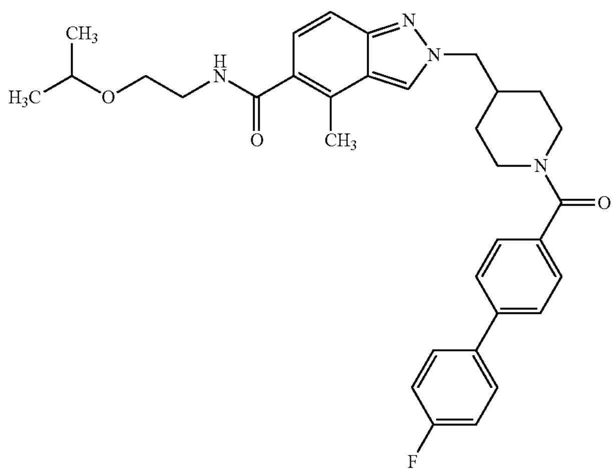 [SMILES: Cc1c(C(=O)NCCOC(C)C)ccc2nn(CC3CCN(C(=O)c4ccc(-c5ccc(F)cc5)cc4)CC3)cc12] | 2-({1-[(4'-fluoro-biphenyl-4-yl)-carbonyl]piperidin-4-yl}methyl)-N-(2-isopropoxyethyl)-4-methyl-2H-indazol-5-carboxamide | $^1$H-NMR (300 MHz, DMSO-d$_6$): δ [ppm] = 1.06 (6H), 1.23 (2H), 1.47 (2H), 2.28 (1H), 2.50 (3H), 2.76 (1H), 2.98 (1H), 3.33 (2H), 3.45 (2H), 3.55 (2H), 4.33 (2H), 4.43 (1H), 7.15 (1H), 7.27 (2H), 7.39 (3H), 7.68 (4H), 8.05 (1H), 8.47 (1H). |
| 101 | 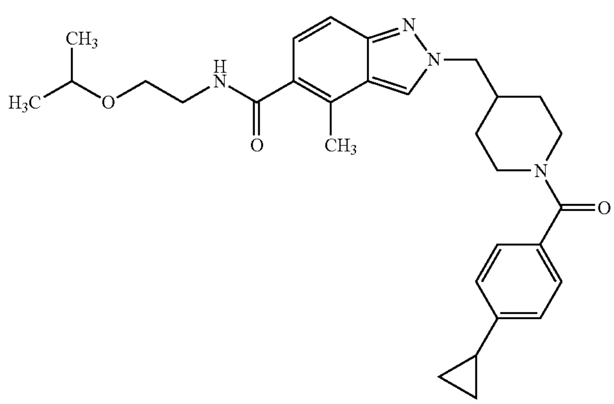 [SMILES: Cc1c(C(=O)NCCOC(C)C)ccc2nn(CC3CCN(C(=O)c4ccc(C5CC5)cc4)CC3)cc12] | 2-{[1-(4-cyclopropyl-benzoyl)piperidin-4-yl]methyl}-N-(2-isopropoxyethyl)-4-methyl-2H-indazol-5-carboxamide | $^1$H-NMR (300 MHz, DMSO-d$_6$): δ [ppm] = 0.66 (2H), 0.94 (2H), 1.06 (6H), 1.20 (2H), 1.44 (2H), 1.90 (1H), 2.24 (1H), 2.49 (3H), 2.82 (2H), 3.32 (2H), 3.45 (2H), 3.55 (2H), 4.31 (2H), 4.39 (1H), 7.12 (5H), 7.38 (1H), 8.05 (1H), 8.46 (1H). |

EXAMPLE 102

(+/−)-2-{[1-(4-chlorobenzoyl)piperidin-4-yl]methyl}-N-[2-(cyclopropylmethoxy) propyl]-4-methyl-2H-indazol-5-carboxamide

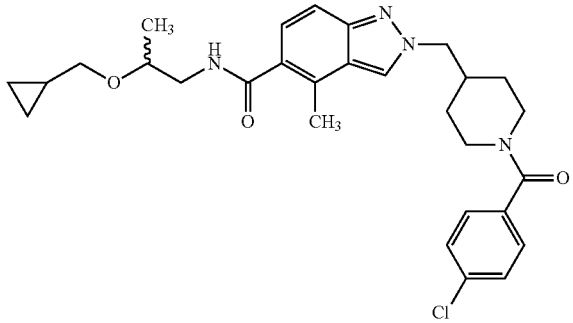 [SMILES: Cc1c(C(=O)NCC(C)OCC2CC2)ccc2nn(CC3CCN(C(=O)c4ccc(Cl)cc4)CC3)cc12]

Analogously to Example 1, 41 mg of the title compound was obtained from 100 mg of the amine prepared in Example 102a and 37 mg of 4-chlorobenzoic acid.

$^1$H-NMR (400 MHz, DMSO-d$_6$): δ [ppm]=0.16 (2H), 0.43 (2H), 0.97 (1H), 1.10 (3H), 1.23 (2H), 1.40 (1H), 1.55 (1H), 2.29 (1H), 2.53 (3H), 2.75 (1H), 2.99 (1H), 3.23 (2H), 3.20 (2H), 3.51 (1H), 3.59 (1H), 4.34 (2H), 4.43 (1H), 7.17 (1H), 7.39 (3H), 7.49 (2H), 8.09 (1H), 8.49 (1H).

The starting material was prepared as follows:

EXAMPLE 102a (+/−)-N-[2-(cyclopropylmethoxy)propyl]-4-methyl-2-(4-piperidylmethyl)-2H-indazol-5-carboxamide

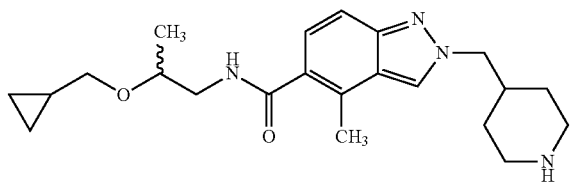 [SMILES: Cc1c(C(=O)NCC(C)OCC2CC2)ccc2nn(CC3CCNCC3)cc12]

To 632 mg of 102b were added 2.9 ml of 4M hydrochloric acid in dioxan and 0.5 ml dioxan. The mixture was stirred for 30 mins at ca. 30° C. The reaction mixture was concentrated, taken up in some toluene and again concentrated. Yield: 561 mg of the title compound, which was further reacted without further purification.

$^1$H-NMR (300 MHz, DMSO-d$_6$): δ [ppm]=0.13 (2H), 0.40 (2H), 0.94 (1H), 1.07 (3H), 1.44 (2H), 1.57 (2H), 2.26 (1H), 2.50 (3H), 2.77 (2H), 3.20 (6H), 3.57 (1H), 4.33 (2H), 6.33 (1H), 7.16 (1H), 7.39 (1H), 8.11 (1H), 8.53 (1H), 8.79 (1H), 9.06 (1H).

EXAMPLE 102b (+/−)-tert-butyl 4-[(5-{N-[2-(cyclopropylmethoxy)propyl]carbamoyl}-4-methyl-2H-indazol-2-yl)methyl]piperidin-1-carboxylate

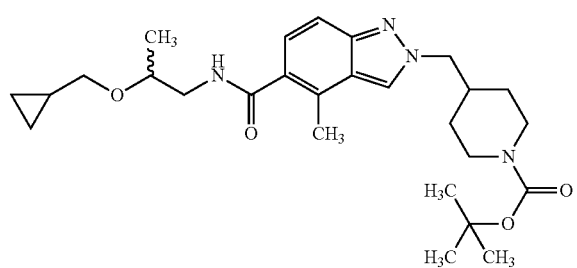

500 mg of 1d was reacted with 222 mg of amine analogously to 1b version B. Yield: 631 mg of the title compound.

$^1$H-NMR (300 MHz, DMSO-d$_6$): δ [ppm]=0.13 (2H), 0.40 (2H), 0-94 (1H), 1.07 (3H), 1.14 (2H), 1.34 (9H), 1.38 (2H), 2.13 (1H), 2.50 (3H), 3.24 (6H), 3.57 (1H), 3.87 (2H), 4.28 (2H), 7.15 (1H), 7.39 (1H), 8.09 (1H), 8.46 (1H).

The following compounds were prepared analogously:

| Ex. | Structure | IUPAC name | Analysis |
|---|---|---|---|
| 103 | (structure shown) | (+/−)-N-[2-(cyclopropylmethoxy)propyl]-2-({1-[4-(4-fluorophenoxy)benzoyl]piperidin-4-yl}-methyl)-4-methyl-2H-indazol-5-carboxamide | $^1$H-NMR (400 MHz, DMSO-d$_6$): δ [ppm] = 0.16 (2H), 0.43 (2H), 0.97 (1H), 1.10 (3H), 1.22 (2H), 1.48 (2H), 2.29 (1H), 2.53 (3H), 2.81 (1H), 2.92 (1H), 3.23 (2H), 3.28 (2H), 3.60 (1H), 3.70 (1H), 4.34 (2H), 4.42 (1H), 6.98 (2H), 7.14 (3H), 7.25 (2H), 7.39 (3H), 8.09 (1H), 8.49 (1H). |

| Ex. | Structure | IUPAC name | Analysis |
|---|---|---|---|
| 104 | 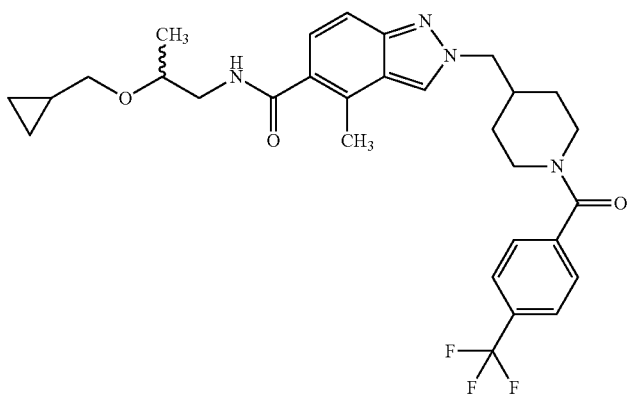 [SMILES: Cc1c(C(=O)NCC(C)OCC2CC2)ccc2nn(CC3CCN(C(=O)c4ccc(C(F)(F)F)cc4)CC3)cc12] | (+/−)-N-[2-(cyclo-propylmethoxy)-propyl]-4-methyl-2-({1-[4-(trifluoro-methyl)benzoyl]-piperidin-4-yl}-methyl)-2H-indazol-5-carboxamide | $^1$H-NMR (400 MHz, DMSO-d$_6$): δ [ppm] = 0.16 (2H), 0.43 (2H), 0.97 (1H), 1.10 (3H), 1.24 (2H), 1.38 (1H), 1.59 (1H), 2.30 (1H), 2.53 (3H), 2.78 (1H), 3.02 (1H), 3.23 (2H), 3.28 (2H), 3.45 (1H), 3.60 (1H), 4.34 (2H), 4.46 (1H), 7.17 (1H), 7.41 (1H), 7.57 (2H), 7.80 (2H), 8.09 (1H), 8.49 (1H). |
| 105 | 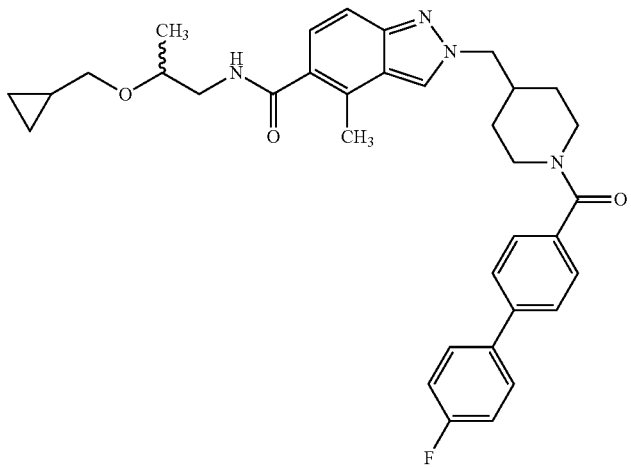 [SMILES: Cc1c(C(=O)NCC(C)OCC2CC2)ccc2nn(CC3CCN(C(=O)c4ccc(-c5ccc(F)cc5)cc4)CC3)cc12] | (+/−)-N-[2-(cyclo-propylmethoxy)-propyl]-2-({1-[(4'-fluorobiphenyl-4-yl)carbonyl]-piperidin-4-yl}-methyl)-4-methyl-2H-indazol-5-carboxamide | $^1$H-NMR (400 MHz, DMSO-d$_6$): δ [ppm] = 0.16 (2H), 0.42 (2H), 0.97 (1H), 1.10 (3H), 1.26 (2H), 1.45 (1H), 1.55 (1H), 2.32 (1H), 2.53 (3H), 2.79 (1H), 3.03 (1H), 3.23 (2H), 3.27 (2H), 3.60 (2H), 4.36 (2H), 4.46 (1H), 7.17 (1H), 7.30 (2H), 7.42 (3H), 7.71 (4H), 8.09 (1H), 8.50 (1H). |
| 106 | 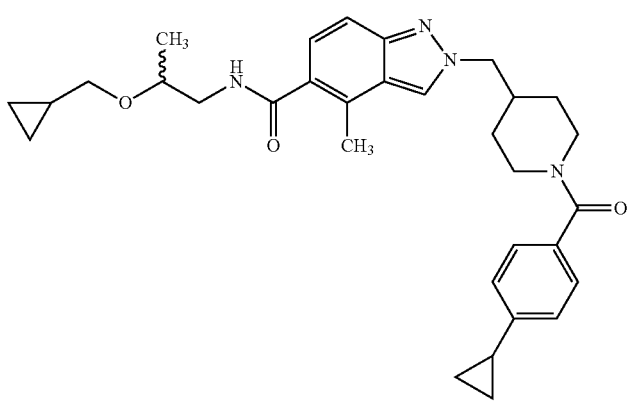 [SMILES: Cc1c(C(=O)NCC(C)OCC2CC2)ccc2nn(CC3CCN(C(=O)c4ccc(C5CC5)cc4)CC3)cc12] | (+/−)-2-{[1-(4-cyclopropylbenzoyl)piperidin-4-yl]-methyl}-N-[2-(cyclopropyl-methoxy)propyl]-4-methyl-2H-indazol-5-carboxamide | $^1$H-NMR (400 MHz, DMSO-d$_6$): δ [ppm] = 0.16 (2H), 0.43 (2H), 0.69 (2H), 0.96 (3H), 1.10 (3H), 1.20 (2H), 1.47 (2H), 1.93 (1H), 2.28 (1H), 2.53 (3H), 2.77 (1H), 2.93 (1H), 3.23 (2H), 3.28 (2H), 3.59 (2H), 4.34 (2H), 4.40 (1H), 7.10 (2H), 7.17 (1H), 7.22 (2H), 7.41 (1H), 8.09 (1H), 8.49 (1H). |

EXAMPLE 107

2-{[1-(4-chlorobenzoyl)piperidin-4-yl]methyl}-4-methyl-N-[2-(trifluoromethoxy)ethyl]-2H-indazol-5-carboxamide

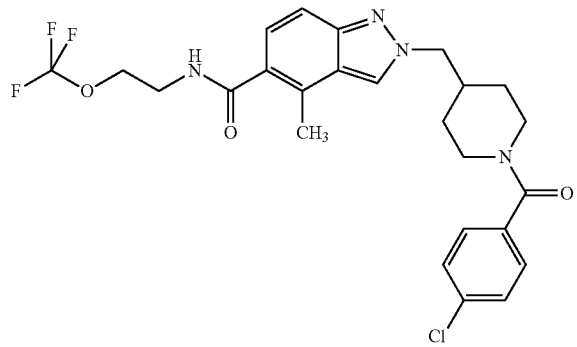 [SMILES: Cc1c(C(=O)NCCOC(F)(F)F)ccc2nn(CC3CCN(C(=O)c4ccc(Cl)cc4)CC3)cc12]

Analogously to Example 1, 26 mg of the title compound was obtained from 75 mg of the amine prepared in Example 107a and 28 mg of 4-chlorobenzoic acid.

$^1$H-NMR (300 MHz, DMSO-d$_6$): δ [ppm]=1.20 (2H), 1.36 (1H), 1.52 (1H), 2.27 (1H), 2.49 (3H), 2.72 (1H), 2.97 (1H), 3.51 (3H), 4.17 (2H), 4.33 (3H), 7.15 (1H), 7.41 (5H), 8.37 (1H), 8.49 (1H).

The starting material was prepared as follows:

EXAMPLE 107a 4-methyl-2-(4-piperidylmethyl)-N-[2-(trifluoromethoxy)ethyl]-2H-indazol-5-carboxamide

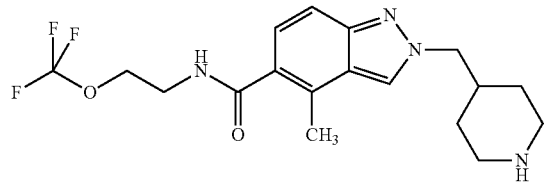 [SMILES: Cc1c(C(=O)NCCOC(F)(F)F)ccc2nn(CC3CCNCC3)cc12]

To 648 mg of 107b were added 3.0 ml of 4M hydrochloric acid in dioxan and 0.5 ml dioxan. The mixture was stirred for 30 mins at ca. 30° C. The reaction mixture was concentrated, taken up in some toluene and again concentrated. Yield: 766 mg of the title compound, which was further reacted without further purification.

$^1$H-NMR (300 MHz, DMSO-d$_6$): δ [ppm]=1.43 (2H), 1.57 (2H), 2.24 (1H), 2.50 (3H), 2.78 (2H), 3.19 (2H), 3.50 (1H), 4.17 (2H), 4.33 (2H), 6.49 (1H), 7.17 (2H), 7.40 (1H), 8.39 (1H), 8.55 (1H), 8.70 (1H), 8.98 (1H).

EXAMPLE 107b

Tert-butyl 4-[(4-methyl-5-{N-[2-(trifluoromethoxy)ethyl]carbamoyl}-2H-indazol-2-yl)methyl]piperidin-1-carboxylate

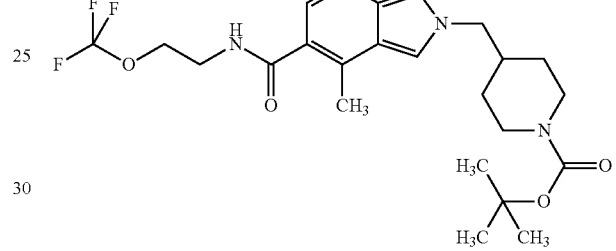

500 mg of 1d was reacted with 293 mg of amine analogously to 1b version B. Yield: 748 mg of the title compound.

$^1$H-NMR (400 MHz, DMSO-d$_6$): δ [ppm]=1.07 (2H), 1.34 (9H), 1.37 (2H), 2.12 (1H), 2.50 (3H), 2.63 (1H), 3.52 (2H), 3.87 (2H), 4.17 (2H), 4.29 (2H), 7.16 (2H), 7.41 (1H), 8.37 (1H), 8.48 (1H).

The following compounds were prepared analogously:

| Ex. | Structure | IUPAC name | Analysis |
|---|---|---|---|
| 108 | 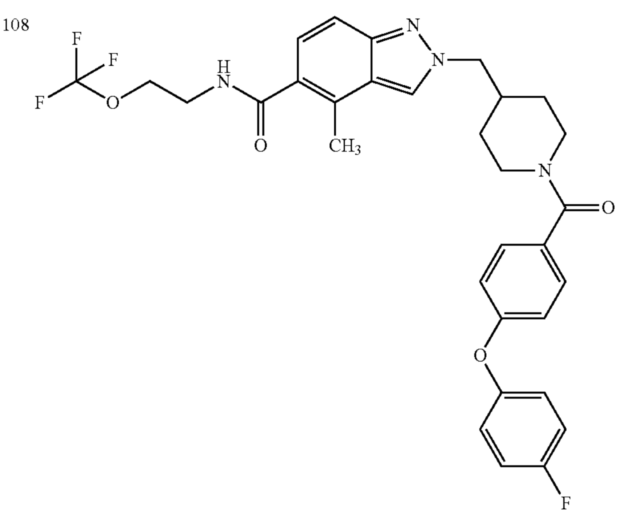 | 2-({1-[4-(4-fluorophenoxy)benzoyl]-piperidin-4-yl}methyl)-4-methyl-N-[2-(trifluoromethoxy)ethyl]-2H-indazol-5-carboxamide | $^1$H-NMR (300 MHz, DMSO-d$_6$): δ [ppm] = 1.19 (2H), 1.46 (2H), 2.26 (1H), 2.49 (3H), 2.87 (2H), 3.51 (3H), 4.17 (2H), 4.33 (3H), 6.95 (2H), 7.16 (5H), 7.38 (3H), 8.36 (1H), 8.49 (1H). |

-continued

| Ex. | Structure | IUPAC name | Analysis |
|---|---|---|---|
| 109 | 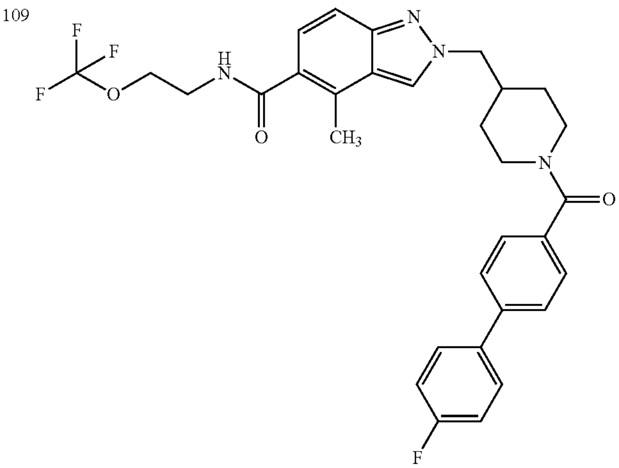 | 2-({1-[(4'-fluoro-biphenyl-4-yl)-carbonyl]piperidin-4-yl}-methyl)-4-methyl-N-[2-(trifluoro-methoxy)ethyl]-2H-indazol-5-carboxamide | ¹H-NMR (300 MHz, DMSO-d₆): δ [ppm] = 1.23 (2H), 1.47 (2H), 2.28 (1H), 2.50 (3H), 2.74 (1H), 2.99 (1H), 3.51 (2H), 3.61 (1H), 4.17 (2H), 4.34 (3H), 7.16 (1H), 7.27 (2H), 7.40 (3H), 7.68 (4H), 8.37 (1H), 8.50 (1H). |
| 110 | 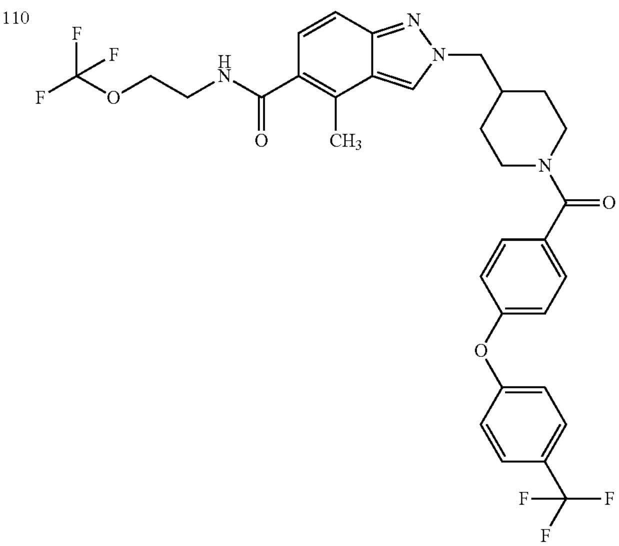 | 4-methyl-N-[2-(trifluoromethoxy)ethyl]-2-[(1-{4-[4-(trifluoro-methyl)phenoxy]-benzoyl}piperidin-4-yl)-methyl]-2H-indazol-5-carboxamide | ¹H-NMR (300 MHz, DMSO-d₆): δ [ppm] = 1.21 (2H), 1.46 (2H), 2.27 (1H), 2.50 (3H), 2.76 (1H), 2.98 (1H), 3.51 (2H), 3.61 (1H), 4.17 (2H), 4.33 (2H), 4.43 (1H), 7.14 (5H), 7.41 (3H), 7.73 (2H), 8.37 (1H), 8.49 (1H). |

EXAMPLE 111

N-(2-tert-butoxyethyl)-2-{[1-(4-chlorobenzoyl)piperidin-4-yl]methyl}-4-methyl-2H-indazol-5-carboxamide Analogously to Example 1, 8 mg of the title compound was obtained from 75 mg of the amine prepared in Example 111a and 28 mg of 4-chlorobenzoic acid.

¹H-NMR (400 MHz, DMSO-d₆): δ [ppm]=1.12 (9H), 1.21 (2H), 1.36 (1H), 1.53 (1H), 2.27 (1H), 2.50 (3H), 2.72 (1H), 2.97 (1H), 3.29 (2H), 3.43 (3H), 4.31 (2H), 4.40 (1H), 7.14 (1H), 7.36 (3H), 7.46 (2H), 8.04 (1H), 8.46 (1H).

EXAMPLE 111a

N-(2-tert-butoxyethyl)-4-methyl-2-(4-piperidylmethyl)-2H-indazol-5-carboxamide

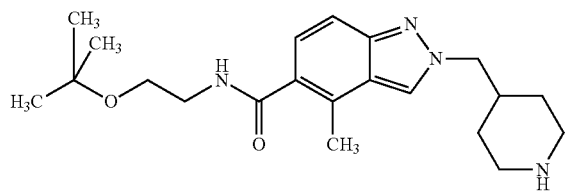 [SMILES: Cc1c(C(=O)NCCOC(C)(C)C)ccc2nn(CC3CCNCC3)cc12]

To 743 mg of 111b were added 3.5 ml of 4M hydrochloric acid in dioxan and 0.5 ml dioxan. The mixture was stirred for 30 mins at ca. 30° C. The reaction mixture was concentrated, taken up in some toluene and again concentrated. Yield: 677 mg of the title compound in a mixture with N-(2-hydroxyethyl)-4-methyl-2-(4-piperidylmethyl)-2H-indazol-5-carboxamide, which was further reacted without further purification.

EXAMPLE 111b

Tert-butyl 4-({5-[N-(2-tert-butoxyethyl)carbamoyl]-4-methyl-2H-indazol-2-yl}methyl)piperidin-1-carboxylate

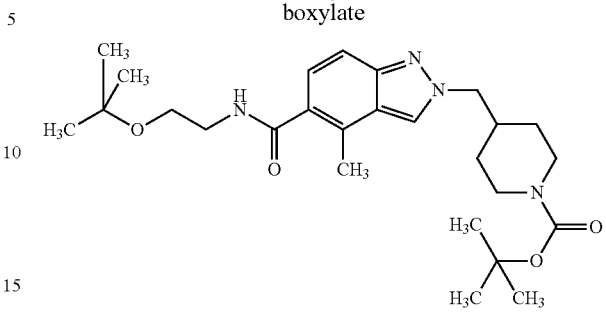

500 mg of 1d was reacted with 206 mg of amine analogously to 1b version B. Yield: 743 mg of the title compound.
$^1$H-NMR (300 MHz, DMSO-$d_6$): δ [ppm]=1.06 (2H), 1.11 (9H), 1.34 (9H), 1.39 (2H), 2.13 (1H), 2.50 (3H), 2.65 (2H), 3.27 (2H), 3.40 (2H), 3.87 (2H), 4.28 (2H), 7.14 (1H), 7.38 (1H), 8.05 (1H), 8.46 (1H).

The following compounds were prepared analogously:

| Ex. | Structure | IUPAC name | Analysis |
|---|---|---|---|
| 112 | 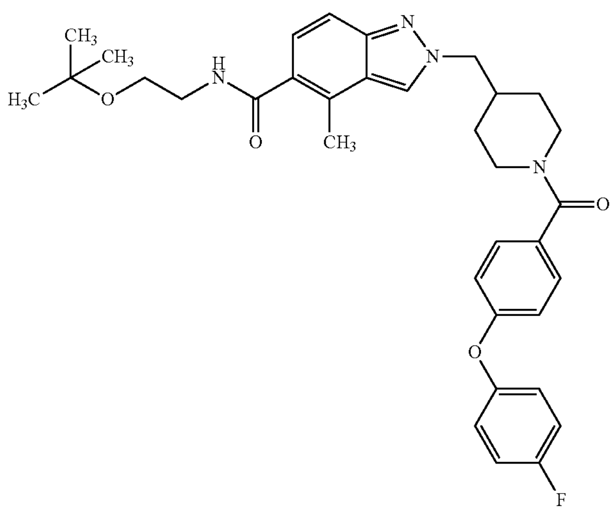 [SMILES: Cc1c(C(=O)NCCOC(C)(C)C)ccc2nn(CC3CCN(C(=O)c4ccc(Oc5ccc(F)cc5)cc4)CC3)cc12] | N-(2-tert-butoxyethyl)-2-({1-[4-(4-fluorophenoxy)benzoyl]-piperidin-4-yl}methyl)-4-methyl-2H-indazol-5-carboxamide | $^1$H-NMR (400 MHz, DMSO-$d_6$): δ [ppm] = 1.12 (9H), 1.20 (2H), 1.44 (2H), 2.26 (1H), 2.50 (3H), 2.76 (1H), 2.93 (1H), 3.30 (2H), 3.40 (2H), 3.57 (1H), 4.31 (2H), 4.39 (1H), 6.95 (2H), 7.12 (3H), 7.23 (2H), 7.36 (3H), 8.04 (1H), 8.46 (1H). |
| 113 | 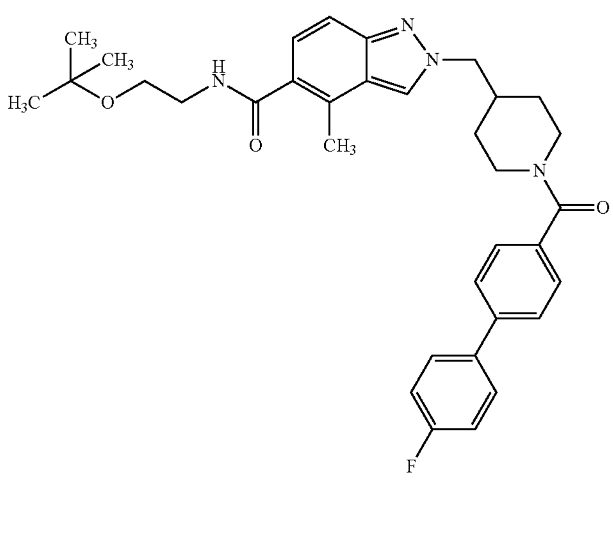 [SMILES: Cc1c(C(=O)NCCOC(C)(C)C)ccc2nn(CC3CCN(C(=O)c4ccc(-c5ccc(F)cc5)cc4)CC3)cc12] | N-(2-tert-butoxyethyl)-2-({1-[(4'-fluorobiphenyl-4-yl)-carbonyl]piperidin-4-yl}methyl)-4-methyl-2H-indazol-5-carboxamide | $^1$H-NMR (400 MHz, DMSO-$d_6$): δ [ppm] = 1.11 (9H), 1.23 (2H), 1.40 (1H), 1.54 (1H), 2.29 (1H), 2.50 (3H), 2.75 (1H), 3.00 (1H), 3.29 (2H), 3.40 (2H), 3.65 (1H), 4.32 (2H), 4.43 (1H), 7.15 (1H), 7.28 (2H), 7.40 (3H), 7.69 (4H), 8.05 (1H), 8.47 (1H). |

| Ex. | Structure | IUPAC name | Analysis |
|---|---|---|---|
| 114 | 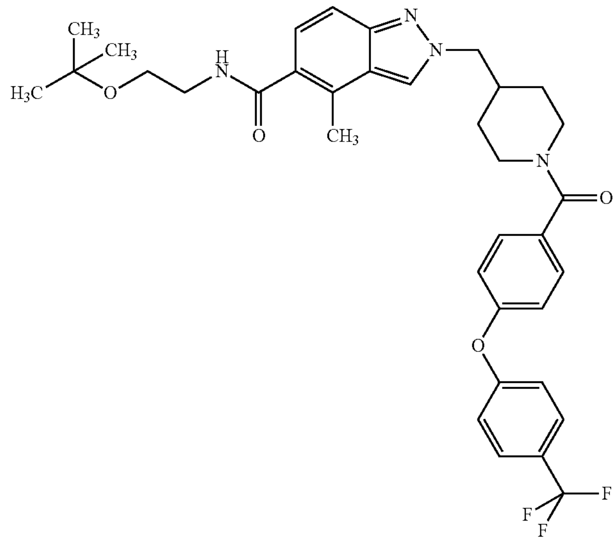 [SMILES: Cc1c(C(=O)NCCOC(C)(C)C)ccc2nn(CC3CCN(C(=O)c4ccc(Oc5ccc(C(F)(F)F)cc5)cc4)CC3)cc12] | N-(2-tert-butoxyethyl)-4-methyl-2-[(1-{4-[4-(trifluoromethyl)-phenoxy]benzoyl}-piperidin-4-yl)methyl]-2H-indazol-5-carboxamide | $^1$H-NMR (400 MHz, DMSO-d$_6$): δ [ppm] = 1.12 (9H), 1.21 (2H), 1.40 (1H), 1.52 (1H), 2.27 (1H), 2.50 (3H), 2.75 (1H), 2.99 (1H), 3.28 (2H), 3.40 (2H), 3.60 (1H), 4.32 (2H), 4.40 (1H), 7.15 (5H), 7.40 (3H), 7.73 (2H), 8.04 (1H), 8.47 (1H). |

EXAMPLE 115

2-{[1-(4-chlorobenzoyl)piperidin-4-yl]methyl}-N-(2-[$^2$H$_3$]methoxy[$^2$H$_4$]ethyl)-4-methyl-2H-indazol-5-carboxamide

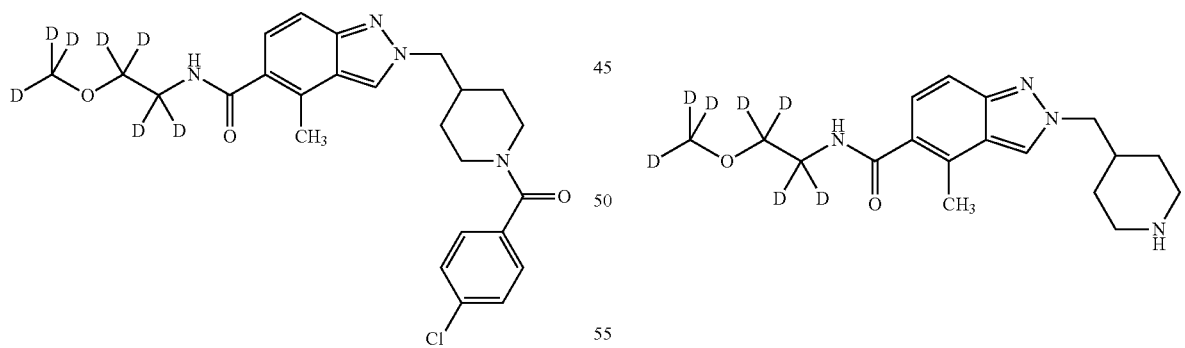

Analogously to Example 1, 1 mg of the title compound was obtained from 54 mg of the amine prepared in Example 115a and 22 mg of 4-chlorobenzoic acid.

$^1$H-NMR (300 MHz, DMSO-d$_6$): δ [ppm]=1.20 (2H), 1.40 (1H), 1.51 (1H), 2.27 (1H), 2.49 (3H), 2.75 (1H), 2.96 (1H), 3.50 (1H), 4.31 (2H), 4.40 (1H), 7.15 (1H), 7.36 (3H), 7.47 (2H), 8.07 (1H), 8.46 (1H).

The starting material was prepared as follows:

EXAMPLE 115a 4-methyl-N-(2-[$^2$H$_3$]methyloxy[$^2$H$_4$]ethyl)-2-(4-piperidylmethyl)-2H-indazol-5-carboxamide To 131 mg of 115b were added 0.7 ml of 4M hydrochloric acid in dioxan and 0.5 ml dioxan. The mixture was stirred for 30 mins at ca. 30° C. The reaction mixture was concentrated, taken up in some toluene and again concentrated. Yield: 108 mg of the title compound, which was further reacted without further purification.

$^1$H-NMR (400 MHz, DMSO-d$_6$): δ [ppm]=1.42 (2H), 1.58 (2H), 2.26 (1H), 2.49 (3H), 2.78 (2H), 3.19 (2H), 4.33 (2H), 5.55 (1H), 7.16 (1H), 7.38 (1H), 8.12 (1H), 8.53 (1H), 8.70 (1H), 8.97 (1H).

EXAMPLE 115b

Tert-butyl 4-({4-methyl-5-[N-(2-[²H₃]methyloxy[²H₄]ethyl)carbamoyl]-2H-indazol-2-yl}methyl)piperidin-1-carboxylate

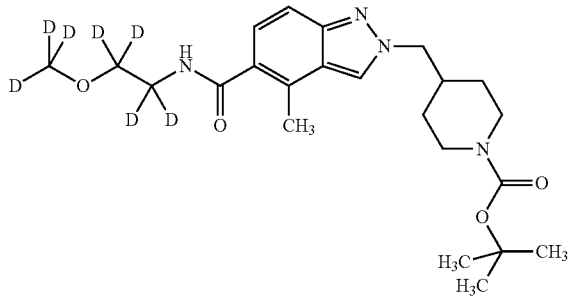 [SMILES: [2H]C([2H])([2H])OC([2H])([2H])C([2H])([2H])NC(=O)c1ccc2nn(CC3CCN(C(=O)OC(C)(C)C)CC3)cc2c1C]

500 mg of 1d was reacted analogously to 1b version B with 110 mg of amine prepared in 115c. Yield: 131 mg of the title compound.

¹H-NMR (300 MHz, DMSO-d₆): δ [ppm]=1.07 (2H), 1.34 (9H), 1.37 (2H), 2.13 (1H), 2.49 (3H), 2.62 (2H), 3.88 (2H), 4.28 (2H), 7.15 (1H), 7.38 (1H), 8.07 (1H), 8.46 (1H).

EXAMPLE 115c

2-[²H₃]methyloxy[²H₄]ethan-1-amine

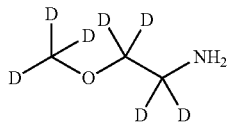

110 mg of (0.51 mmol) of 115d was first placed in 2.2 ml toluene. After addition of 11 mg of palladium/charcoal (10%) and hydrogen under normal pressure, the mixture was stirred for 50 mins at room temperature. The reaction mixture was filtered through Celite and rewashed with toluene. The colourless filtrate was used as solution in the subsequent reaction.

EXAMPLE 115d

Benzyl N-(2-[²H₃]methyloxy[²H₄]ethyl)carbamate

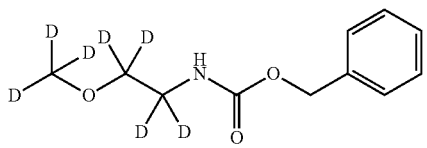 [SMILES: [2H]C([2H])([2H])OC([2H])([2H])C([2H])([2H])NC(=O)OCc1ccccc1]

1.32 g (6.6 mmol) of 115e) was dissolved in 23 ml acetonitrile. 2.3 g (9.9 mmol) of silver oxide and 1.64 ml (3.8 g, 26 mmol) of deuterated iodomethane were then added. The reaction mixture was stirred for 1.5 hrs at 40° C., 7.5 hrs at 72° C. and then overnight at room temperature. A further 2.3 g (9.9 mmol) of silver oxide was added and the mixture stirred for 1.5 hrs at 72° C. For the work-up, the black solid was filtered off at the pump and the clear filtrate concentrated. The residue was purified by column chromatography (hexane/ethyl acetate 0-10%). Yield: 1.13 g of the title compound.

¹H-NMR (300 MHz, DMSO-d₆): δ [ppm]=4.97 (2H), 7.31 (5H).

EXAMPLE 115e

Benzyl N-(2-hydroxy[²H₄]ethyl)carbamate

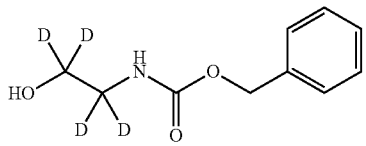 [SMILES: [2H]C([2H])(O)C([2H])([2H])NC(=O)OCc1ccccc1]

1.0 g (15 mmol) of deuterated aminoethanol was first dissolved in 29 ml dichloromethane. Then 2.5 ml (1.8 g, 18 mmol) of triethylamine was added and the reaction mixture cooled to 0° C. At this temperature 2.75 ml (3.34 g, 19.6 mmol) of benzyl chloroformate was now cautiously added dropwise. After completion of the addition, the mixture was stirred for 1 hr more with no ice-bath and in the process warmed up to RT. The reaction mixture was diluted once with some dichloromethane and washed once with saturated sodium chloride solution. The organic phase was dried over sodium sulphate, filtered and concentrated. The crude product was purified twice by column chromatography (dichloromethane/methanol 0-10% and ethyl acetate). Yield: 1.32 g of the title compound.

¹H-NMR (300 MHz, DMSO-d₆): δ [ppm]=4.54 (1H), 4.97 (2H), 7.12 (1H), 7.81 (5H).

The following compound was prepared analogously:

| Ex. | Structure | IUPAC name | Analysis |
|---|---|---|---|
| 116 | 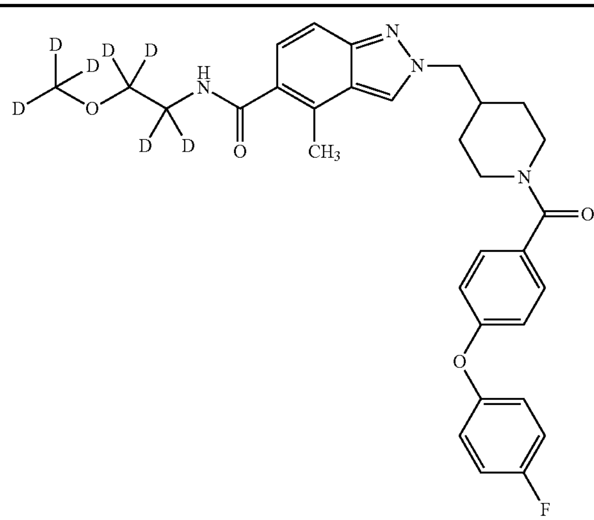 | 2-({1-[4-(4-fluorophenoxy)benzoyl]-piperidin-4-yl}methyl)-4-methyl-N-(2-[²H₃]-methyloxy[²H₄]ethyl)-2H-indazol-5-carboxamide | ¹H-NMR (300 MHz, DMSO-d₆): δ [ppm] = 1.19 (2H), 1.46 (2H), 2.25 (1H), 2.49 (3H), 2.85 (2H), 3.66 (1H), 4.31 (2H), 4.38 (1H), 6.95 (2H), 7.16 (5H), 7.36 (3H), 8.07 (1H), 8.46 (1H). |

EXAMPLE 117

2-{[1-(4-chlorobenzoyl)azetidin-3-yl]methyl}-N-(2-methoxyethyl)-4-methyl-2H-indazol-5-carboxamide

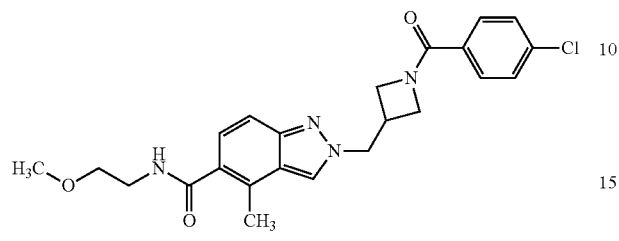

Analogously to Example 55, 471 mg of the title compound was obtained from 500 mg of the compound prepared in Example 117e) and 287 mg of 4-chlorobenzoyl chloride.

$^1$H-NMR (300 MHz, DMSO-d6): δ=2.49 (3H), 3.22 (1H), 3.25 (3H), 3.32-3.46 (4H), 3.89 (1H), 4.09 (1H), 4.19 (1H), 4.37 (1H), 4.67 (2H), 7.15 (1H), 7.38 (1H), 7.48 (2H), 7.59 (2H), 8.12 (1H), 8.54 (1H).

The starting material was prepared as follows:

EXAMPLE 117a

Tert-butyl 3-[(5-bromo-4-methyl-2H-indazol-2-yl)methyl]-azetidin-1-carboxylate

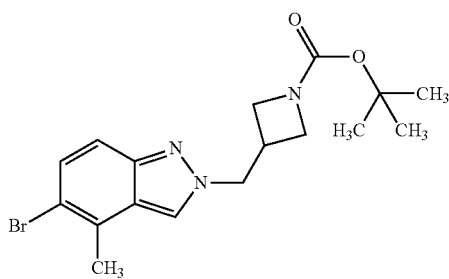 [SMILES: Cc1c(Br)ccc2nn(CC3CN(C(=O)OC(C)(C)C)C3)cc12]

To a solution of 21.1 g of 5-bromo-4-methyl-1H-indazole and 37.6 g of tert-butyl-3-[(tosyloxy)-methyl]azetidin-1-carboxylate in 100 ml dioxan were added 150 ml of a 1M solution of sodium bis(trimethylsilyl)amide in tetrahydrofuran at 25° C. and this was stirred for 6 hrs at 90° C. After cooling, the reaction mixture was treated with ethyl acetate and water, the organic phases separated and the aqueous phase extracted twice with 100 ml portions of ethyl acetate. The combined organic phases were washed with saturated sodium chloride solution, dried over sodium sulphate, and concentrated in vacuo after filtration.

The residue thus obtained was purified by chromatography on the Flashmaster (hexane/ethyl acetate 1:0-0:1). 15.0 g of the title compound was obtained.

$^1$H-NMR (300 MHz, DMSO-d6): δ=1.32 (9H), 2.48 (3H), 3.07 (1H), 3.69 (2H), 3.87 (2H), 4.59 (2H), 7.28 (1H), 7.35 (1H), 8.53 (1H).

EXAMPLE 117b

Methyl 2-{[1-(tert-butoxycarbonyl)azetidin-3-yl]methyl}-4-methyl-2H-indazol-5-carboxylate

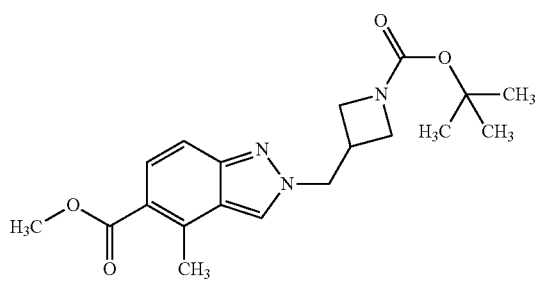 [SMILES: COC(=O)c1ccc2nn(CC3CN(C(=O)OC(C)(C)C)C3)cc2c1C]

To a solution of 8.16 g of the bromide prepared in Example 117a in 65.4 ml methanol, 6.5 g of 1,1 bis(diphenylphosphino)ferrocen-palladium(II) dichloride and 15 g of potassium acetate were added at 25° C. and the mixture was stirred under CO at 10.15 bar and 120° C. for 24 hours in an autoclave. The reaction mixture was then cooled, filtered through Celite at the pump and the filtrate concentrated in vacuo. The residue thus obtained was purified by chromatography on the Flashmaster (hexane/ethyl acetate 1:0-0:1). 6.97 g of the title compound was obtained.

$^1$H-NMR (300 MHz, DMSO-d6): δ=1.32 (9H), 2.73 (3H), 3.09 (1H), 3.71 (2H), 3.79 (3H), 3.87 (2H), 4.62 (2H), 7.42 (1H), 7.63 (1H), 8.74 (1H).

EXAMPLE 117c

2-{[1-(tert-butoxycarbonyl)azetidin-3-yl]methyl}-4-methyl-2H-indazol-5-carboxylic acid

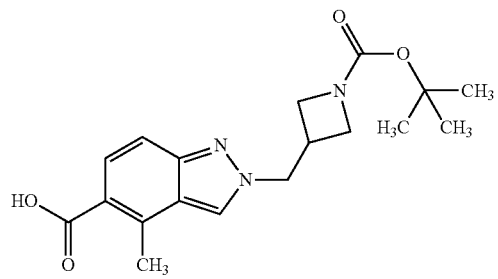 [SMILES: Cc1c(C(=O)O)ccc2nn(CC3CN(C(=O)OC(C)(C)C)C3)cc12]

Analogously to Example 1d, 5.2 g of the title compound was obtained from 15.1 g of the ester prepared in Example 117b.

$^1$H-NMR (300 MHz, DMSO-d6): δ=1.32 (9H), 2.73 (3H), 3.09 (1H), 3.71 (2H), 3.87 (2H), 4.61 (2H), 7.39 (1H), 7.64 (1H), 8.70 (1H), 12.57 (1H).

EXAMPLE 117d

Tert-butyl 3-({5-[N-(2-methoxyethyl)carbamoyl]-4-methyl-2H-indazol-2-yl}-methyl)azetidin-1-carboxylate

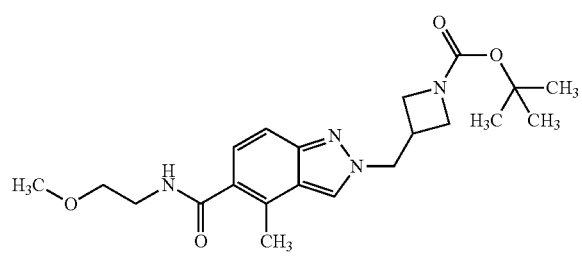 [SMILES: COCCNC(=O)c1ccc2nn(CC3CN(C(=O)OC(C)(C)C)C3)cc2c1C]

Analogously to Example 1, from 2.5 g of the acid prepared in Example 117c and 0.54 g of 2-methoxyethylamine, a crude product was obtained which through purification with a Biotage unit (ethyl acetate: 0 to 30% methanol) yielded 2.69 g of the title compound.

$^1$H-NMR (300 MHz, DMSO-d6): δ=1.32 (9H), 2.49 (3H), 3.08 (1H), 3.25 (3H), 3.32-3.46 (4H), 3.70 (2H), 3.86 (2H), 4.60 (2H), 7.15 (1H), 7.38 (1H), 8.11 (1H), 8.54 (1H).

EXAMPLE 117e 2-(azetidin-3-ylmethyl)-N-(2-methoxyethyl)-4-methyl-2H-indazol-5-carboxamide hydrochloride

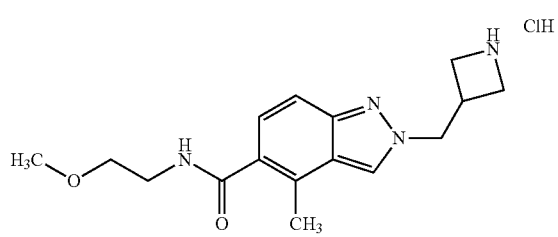 [SMILES: Cl ; COCCNC(=O)c1ccc2nn(CC3CNC3)cc2c1C]

Analogously to Example 1a, from 2.69 g of the amide prepared in Example 117d, 2.59 g of the title compound was obtained, which was reacted without further purification.

EXAMPLE 118

N-(2-methoxyethyl)-4-methyl-2-[(1-{4-[(trifluoromethyl)sulphanyl]benzoyl}azetidin-3-yl)methyl]-2H-indazol-5-carboxamide

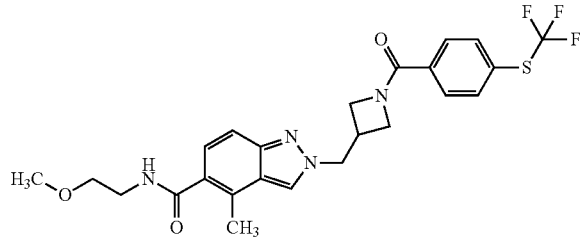 [SMILES: COCCNC(=O)c1ccc2nn(CC3CN(C(=O)c4ccc(SC(F)(F)F)cc4)C3)cc2c1C]

Analogously to Example 55, 29 mg of the title compound was obtained from 55 mg of the compound prepared in Example 117e and 43 mg of 4-[(trifluoromethyl)sulphanyl]benzoyl chloride.

$^1$H-NMR (300 MHz, DMSO-d6): δ=2.49 (3H), 3.22 (1H), 3.25 (3H), 3.36 (2H), 3.42 (2H), 3.92 (1H), 4.11 (1H), 4.20 (1H), 4.39 (1H), 4.67 (2H), 7.15 (1H), 7.38 (1H), 7.69 (2H), 7.76 (2H), 8.12 (1H), 8.54 (1H).

EXAMPLE 119

N-(2-methoxyethyl)-4-methyl-2-({1-[4-(trifluoromethoxy)benzoyl]azetidin-3-yl}methyl)-2H-indazol-5-carboxamide

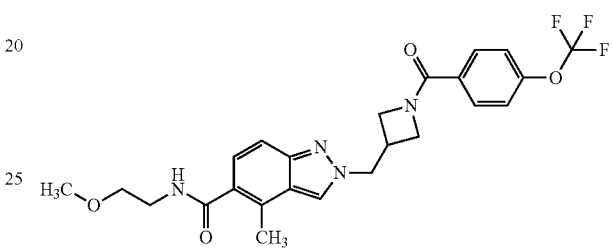

Analogously to Example 55, 27 mg of the title compound was obtained from 55 mg of the compound prepared in Example 117e and 40 mg of 4-(trifluoromethoxy)benzoyl chloride.

$^1$H-NMR (300 MHz, DMSO-d6): δ=2.49 (3H), 3.20 (1H), 3.24 (3H), 3.32-3.46 (4H), 3.91 (1H), 4.10 (1H), 4.20 (1H), 4.39 (1H), 4.67 (2H), 7.15 (1H), 7.35-7.44 (3H), 7.70 (2H), 8.12 (1H), 8.54 (1H).

EXAMPLE 120

2-({1-[2-fluoro-4-(trifluoromethyl)benzoyl]azetidin-3-yl}methyl)-N-(2-methoxy-ethyl)-4-methyl-2H-indazol-5-carboxamide

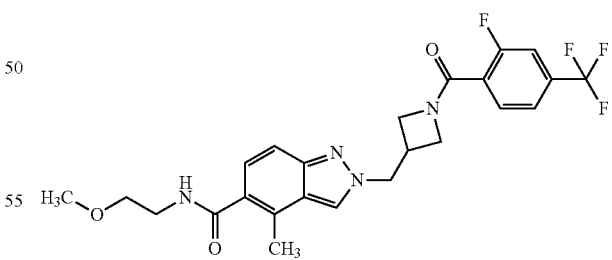

Analogously to Example 55, 17 mg of the title compound was obtained from 55 mg of the compound prepared in Example 117e and 41 mg of 2-fluoro-4-(trifluoromethyl)benzoyl chloride.

$^1$H-NMR (300 MHz, DMSO-d6): δ=2.48 (3H), 3.23 (1H), 3.25 (3H), 3.36 (2H), 3.42 (2H), 3.94 (2H), 4.11 (2H), 4.66 (2H), 7.15 (1H), 7.38 (1H), 7.64 (2H), 7.79 (1H), 8.12 (1H), 8.54 (1H).

EXAMPLE 121

2-{[1-(4-chloro-2-fluorobenzoyl)azetidin-3-yl]methyl}-N-(2-methoxyethyl)-4-methyl-2H-indazol-5-carboxamide

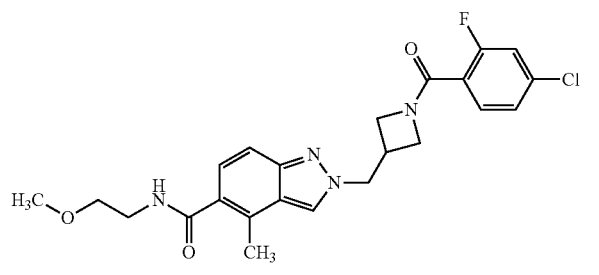 [SMILES: COCCNC(=O)c1ccc2nn(CC3CN(C(=O)c4ccc(Cl)cc4F)C3)cc2c1C]

Analogously to Example 55, 19 mg of the title compound was obtained from 42 mg of the compound prepared in Example 117e and 26 mg of 4-chloro-2-fluorobenzoyl chloride.

$^1$H-NMR (300 MHz, DMSO-d6): δ=2.48 (3H), 3.21 (1H), 3.24 (3H), 3.33-3.46 (4H), 3.86-3.97 (2H), 4.08 (2H), 4.65 (2H), 7.15 (1H), 7.34 (1H), 7.37 (1H), 7.44 (1H), 7.52 (1H), 8.12 (1H), 8.53 (1H).

EXAMPLE 122

2-({1-[3-fluoro-4-(trifluoromethyl)benzoyl]azetidin-3-yl}methyl)-N-(2-methoxy-ethyl)-4-methyl-2H-indazol-5-carboxamide

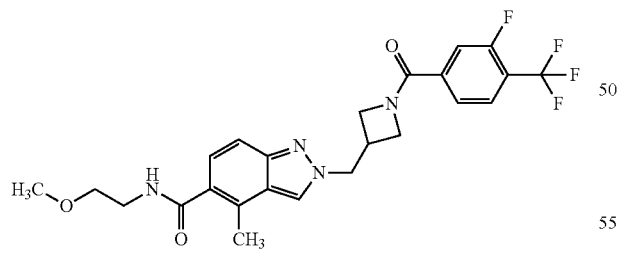

Analogously to Example 55, 15 mg of the title compound was obtained from 42 mg of the compound prepared in Example 117e and 31 mg of 3-fluoro-4-(trifluoromethyl)benzoyl chloride.

$^1$H-NMR (300 MHz, DMSO-d6): δ=2.49 (3H), 3.21 (1H), 3.25 (3H), 3.36 (2H), 3.42 (2H), 3.93 (1H), 4.12 (1H), 4.22 (1H), 4.40 (1H), 4.67 (2H), 7.15 (1H), 7.37 (1H), 7.57 (1H), 7.64 (1H), 7.85 (1H), 8.12 (1H), 8.54 (1H).

EXAMPLE 123

2-({1-[4-chloro-3-(trifluoromethyl)benzoyl]azetidin-3-yl}methyl)-N-(2-methoxy-ethyl)-4-methyl-2H-indazol-5-carboxamide

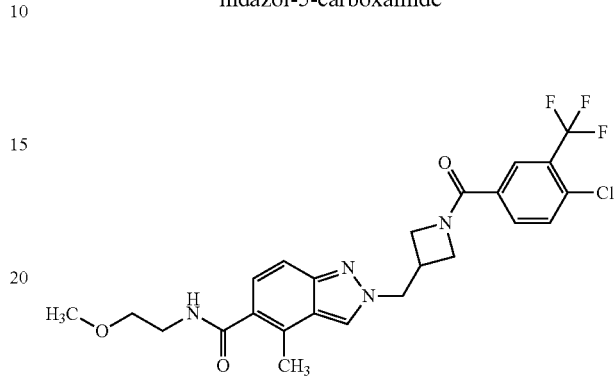

Analogously to Example 55, 6 mg of the title compound was obtained from 42 mg of the compound prepared in Example 117e and 33 mg of 4-chloro-3-(trifluoromethyl)benzoyl chloride.

$^1$H-NMR (300 MHz, DMSO-d6): δ=2.49 (3H), 3.21 (1H), 3.25 (3H), 3.31-3.46 (4H), 3.92 (1H), 4.11 (1H), 4.22 (1H), 4.41 (1H), 4.67 (2H), 7.15 (1H), 7.37 (1H), 7.79 (1H), 7.86 (1H), 7.94 (1H), 8.12 (1H), 8.53 (1H).

EXAMPLE 124

2-{[1-(4-cyclopropylbenzoyl)azetidin-3-yl]methyl}-N-(2-methoxyethyl)-4-methyl-2H-indazol-5-carboxamide

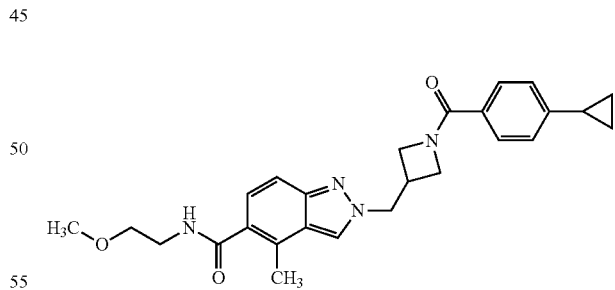

Analogously to Example 1, 76 mg of the title compound was obtained from 163 mg of the compound prepared in Example 117e and 78 mg of 4-cyclopropylbenzoic acid.

$^1$H-NMR (300 MHz, DMSO-d6): δ=0.71 (2H), 0.99 (2H), 1.95 (1H), 2.52 (3H), 3.24 (1H), 3.34-3.41 (5H), 3.45 (2H), 3.90 (1H), 4.09 (1H), 4.20 (1H), 4.38 (1H), 4.68 (2H), 7.12 (2H), 7.18 (1H), 7.41 (1H), 7.48 (2H), 8.12 (1H), 8.57 (1H).

EXAMPLE 125

N-(2-methoxyethyl)-4-methyl-2-[(1-{4-[4-(trifluoromethyl)phenoxy]benzoyl}azetidin-3-yl)methyl]-2H-indazol-5-carboxamide

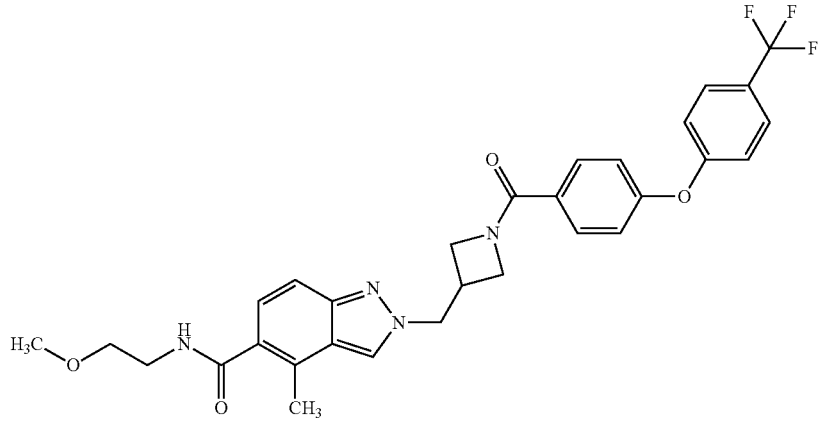

Analogously to Example 1, 478 mg of the title compound was obtained from 1.20 g of the compound prepared in Example 117e and 850 mg of 4-[4-(trifluoromethyl)phenoxy] benzoic acid.

$^1$H-NMR (300 MHz, DMSO-d6): δ=2.52 (3H), 3.25 (1H), 3.27 (3H), 3.39 (2H), 3.45 (2H), 3.94 (1H), 4.12 (1H), 4.24 (1H), 4.42 (1H), 4.70 (2H), 7.14 (2H), 7.18 (1H), 7.22 (2H), 7.41 (1H), 7.69 (2H), 7.77 (2H), 8.12 (1H), 8.57 (1H).

EXAMPLE 126

2-{[1-(4-chlorobenzoyl)azetidin-3-yl]methyl}-N-[2-(3,3-difluoropyrrolidin-1-yl)ethyl]-4-methyl-2H-indazol-5-carboxamide

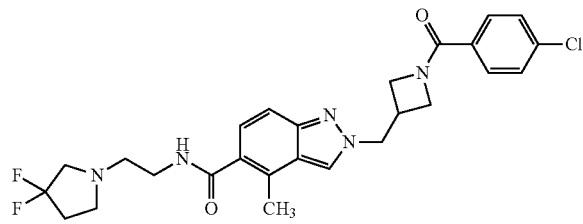 [SMILES: Cc1c(C(=O)NCCN2CCC(F)(F)C2)ccc2nn(CC3CN(C(=O)c4ccc(Cl)cc4)C3)cc12]

Analogously to Example 55, 38 mg of the title compound was obtained from 43 mg of the compound prepared in Example 126a and 20 mg of 4-chlorobenzoyl chloride.

$^1$H-NMR (300 MHz, DMSO-d6): δ=2.10-2.27 (3H), 2.49 (3H), 2.57 (2H), 2.72 (2H), 2.91 (2H), 3.17-3.36 (2H), 3.89 (1H), 4.08 (1H), 4.19 (1H), 4.36 (1H), 4.67 (2H), 7.14 (1H), 7.38 (1H), 7.48 (2H), 7.59 (2H), 8.05 (1H), 8.54 (1H).

EXAMPLE 126a 2-(azetidin-3-ylmethyl)-N-[2-(3,3-difluoropyrrolidin-1-yl)ethyl]-4-methyl-2H-indazol-5-carboxamide hydrochloride

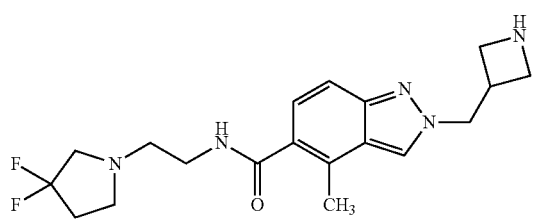

Analogously to Example 1a, from 50 mg of the compound prepared in Example 126b, 43 mg of the title compound was obtained, which was reacted without further purification.

EXAMPLE 126b

Tert-butyl 3-[(5-{N-[2-(3,3-difluoropyrrolidin-1-yl)ethyl]carbamoyl}-4-methyl-2H-indazol-2-yl)methyl]azetidin-1-carboxylate

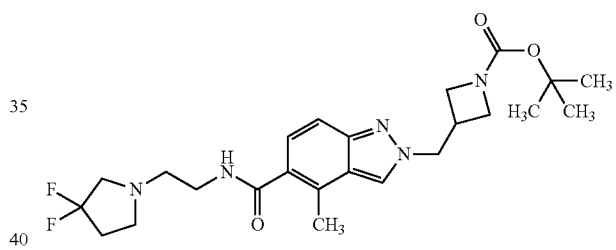

Analogously to Example 1b, 71 mg of the title compound was obtained from 70 mg of the compound prepared in Example 117a and 83 mg of 2-(3,3-difluoropyrrolidin-1-yl) ethylamine.

$^1$H-NMR (300 MHz, DMSO-d6): 1.32 (9H), 2.10-2.28 (2H), 2.50 (3H), 2.57 (2H), 2.66-2.77 (2H), 2.84-2.98 (2H), 3.08 (1H), 3.23-3.36 (2H), 3.69 (2H), 3.86 (2H), 4.60 (2H), 7.14 (1H), 7.39 (1H), 8.05 (1H), 8.55 (1H).

EXAMPLE 127

2-{[1-(4-chlorobenzoyl)azetidin-3-yl]methyl}-4-methyl-N-{2-[(trifluoromethyl) sulphanyl]ethyl}-2H-indazol-5-carboxamide

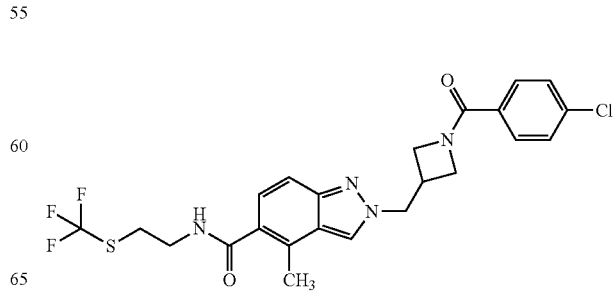

Analogously to Example 55, 143 mg of the title compound was obtained from 130 mg of the compound prepared in Example 127b and 61 mg of 4-chlorobenzoyl chloride.

$^1$H-NMR (300 MHz, DMSO-d6): δ=2.51 (3H), 3.13-3.29 (3H), 3.50 (2H), 3.90 (1H), 4.09 (1H), 4.19 (1H), 4.37 (1H), 4.67 (2H), 7.19 (1H), 7.40 (1H), 7.48 (2H), 7.59 (2H), 8.38 (1H), 8.57 (1H).

The starting material was prepared as follows:

EXAMPLE 127a

Tert-butyl 3-{[4-methyl-5-(N-{2-[(trifluoromethyl)sulphanyl]ethyl}carbamoyl)-indazol-2-yl]methyl}azetidin-1-carboxylate

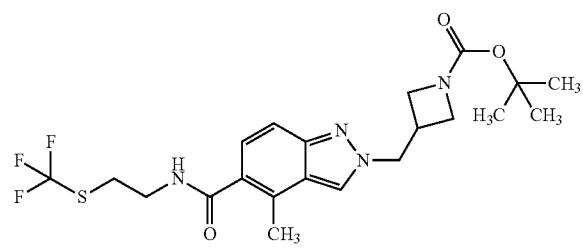

Analogously to Example 1, 674 mg of the title compound was obtained from 500 mg of the compound prepared in Example 117c.

$^1$H-NMR (300 MHz, DMSO-d6): δ=1.32 (9H), 2.52 (3H), 3.08 (1H), 3.17 (2H), 3.50 (2H), 3.69 (2H), 3.86 (2H), 4.61 (2H), 7.19 (1H), 7.41 (1H), 8.38 (1H), 8.57 (1H).

EXAMPLE 127b 2-(azetidin-3-ylmethyl)-4-methyl-N-{2-[(trifluoromethyl)sulphanyl]ethyl}-2H-indazol-5-carboxamide hydrochloride

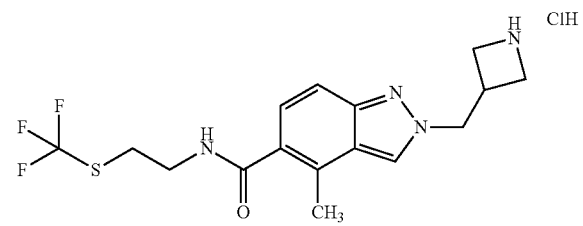 [SMILES: Cl ; Cc1c(C(=O)NCCSC(F)(F)F)ccc2nn(CC3CNC3)cc12]

Analogously to Example 1a, from 150 mg of the compound prepared in Example 127a, 130 mg of the title compound was obtained, which was further reacted without purification.

EXAMPLE 128

2-{[1-(4-chlorobenzoyl)azetidin-3-yl]methyl}-4-methyl-N-(2-morpholinoethyl)-2H-indazol-5-carboxamide

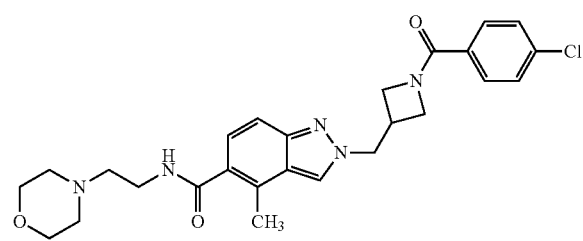 [SMILES: Cc1c(C(=O)NCCN2CCOCC2)ccc2nn(CC3CN(C(=O)c4ccc(Cl)cc4)C3)cc12]

Analogously to Example 55, 30 mg of the title compound was obtained from 50 mg of the compound prepared in Example 128b and 24 mg of 4-chlorobenzoyl chloride.

$^1$H-NMR (300 MHz, DMSO-d6): δ=2.34-2.45 (6H), 2.51 (3H), 3.22 (1H), 3.33 (2H), 3.54 (4H), 3.89 (1H), 4.08 (1H), 4.19 (1H), 4.36 (1H), 4.67 (2H), 7.15 (1H), 7.38 (1H), 7.48 (2H), 7.59 (2H), 7.99 (1H), 8.54 (1H).

The starting material was prepared as follows:

EXAMPLE 128a

Tert-butyl 3-({4-methyl-5-[N-(2-morpholinoethyl)carbamoyl]-2H-indazol-2-yl}methyl)azetidin-1-carboxylate

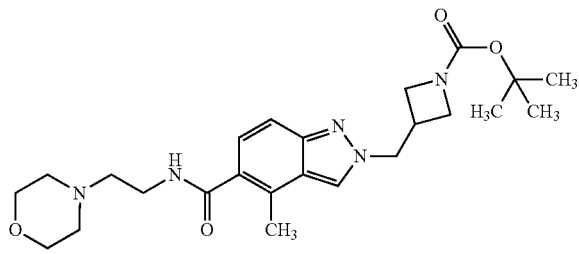 [SMILES: Cc1c(C(=O)NCCN2CCOCC2)ccc2nn(CC3CN(C(=O)OC(C)(C)C)C3)cc12]

Analogously to Example 1b, 59 mg of the title compound was obtained from 200 mg of the compound prepared in Example 117a and 205 mg of 2-morpholinoethylamine.

$^1$H-NMR (300 MHz, DMSO-d6): δ=1.32 (9H), 2.34-2.44 (6H), 2.52 (3H), 3.08 (1H), 3.33 (2H), 3.54 (4H), 3.69 (2H), 3.86 (2H), 4.61 (2H), 7.15 (1H), 7.39 (1H), 7.98 (1H), 8.55 (1H).

EXAMPLE 128b 2-(azetidin-3-ylmethyl)-4-methyl-N-(2-morpholinoethyl)-2H-indazole-5-carboxamide hydrochloride

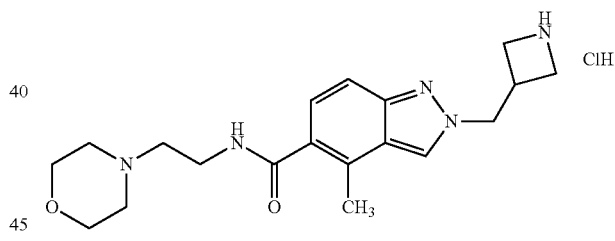

Analogously to Example 1a, from 59 mg of the compound prepared in Example 128a, 63 mg of the title compound was obtained, which was further reacted without purification.

EXAMPLE 129

2-{[1-(4-chlorobenzoyl)azetidin-3-yl]methyl}-4-methyl-N-(2,2,2-trifluoroethyl)-2H-indazol-5-carboxamide

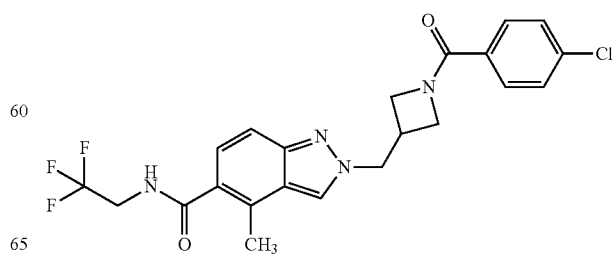

Analogously to Example 55, 127 mg of the title compound was obtained from 128 mg of the compound prepared in Example 129b and 68 mg of 4-chlorobenzoyl chloride.

$^1$H-NMR (300 MHz, DMSO-d6): δ=2.50 (3H), 3.22 (1H), 3.90 (1H), 3.96-4.13 (3H), 4.19 (1H), 4.37 (1H), 4.68 (2H), 7.18 (1H), 7.42 (1H), 7.48 (2H), 7.59 (2H), 8.59 (1H), 8.79 (1H).

The starting material was prepared as follows:

EXAMPLE 129a

Tert-butyl 3-({4-methyl-5-[N-(2,2,2-trifluoroethyl)carbamoyl]-2H-indazol-2-yl}methyl)azetidin-1-carboxylate

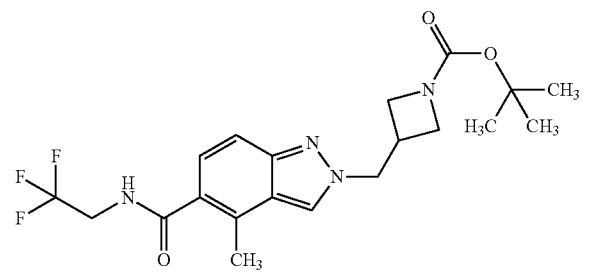 [SMILES: Cc1c(C(=O)NCC(F)(F)F)ccc2nn(CC3CN(C(=O)OC(C)(C)C)C3)cc12]

Analogously to Example 1, 1.02 g of the title compound was obtained from 1.0 g of the compound prepared in Example 117c and 287 mg of 2,2,2-trifluoroethylamine.

$^1$H-NMR (300 MHz, DMSO-d6): δ=1.32 (9H), 2.51 (3H), 3.09 (1H), 3.70 (2H), 3.86 (2H), 4.03 (2H), 4.62 (2H), 7.17 (1H), 7.43 (1H), 8.60 (1H), 8.79 (1H).

EXAMPLE 129b 2-(azetidin-3-ylmethyl)-4-methyl-N-(2,2,2-trifluoroethyl)-2H-indazol-5-carboxamide hydrochloride

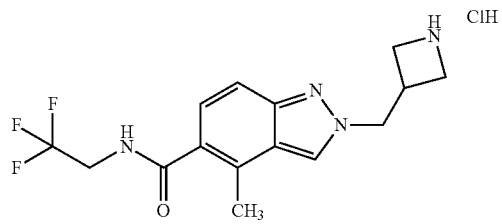 [SMILES: Cl ; Cc1c(C(=O)NCC(F)(F)F)ccc2nn(CC3CNC3)cc12]

Analogously to Example 1a, from 1.0 g of the compound prepared in Example 129a, 852 mg of the title compound was obtained, which was further reacted without purification.

EXAMPLE 130

4-methyl-N-(2,2,2-trifluoroethyl)-2-({1-[4-(trifluoromethoxy)benzoyl]azetidin-3-yl}methyl)-2H-indazol-5-carboxamide

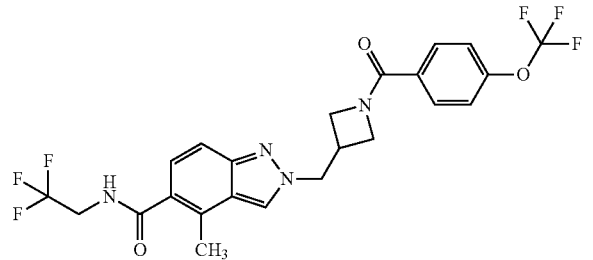 [SMILES: Cc1c(C(=O)NCC(F)(F)F)ccc2nn(CC3CN(C(=O)c4ccc(OC(F)(F)F)cc4)C3)cc12]

Analogously to Example 55, 113 mg of the title compound was obtained from 128 mg of the compound prepared in Example 129b and 87 mg of 4-(trifluoromethoxy)benzoyl chloride.

$^1$H-NMR (300 MHz, DMSO-d6): δ=2.50 (3H), 3.23 (1H), 3.92 (1H), 3.96-4.14 (3H), 4.20 (1H), 4.39 (1H), 4.68 (2H), 7.18 (1H), 7.36-7.46 (3H), 7.70 (2H), 8.59 (1H), 8.79 (1H).

EXAMPLE 131

2-({1-[2-fluoro-4-(trifluoromethyl)benzoyl]azetidin-3-yl}methyl)-4-methyl-N-(2,2,2-trifluoroethyl)-2H-indazol-5-carboxamide

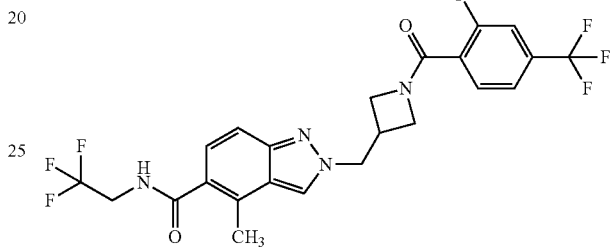

Analogously to Example 55, 128 mg of the title compound was obtained from 128 mg of the compound prepared in Example 129b and 88 mg of 2-fluoro-4-(trifluoromethyl)benzoyl chloride.

$^1$H-NMR (300 MHz, DMSO-d6): δ=2.49 (3H), 3.23 (1H), 3.89-4.16 (6H), 4.67 (2H), 7.17 (1H), 7.42 (1H), 7.60-7.67 (2H), 7.79 (1H), 8.58 (1H), 8.80 (1H).

EXAMPLE 132

4-methyl-2-({1-[4-(pentafluoro-λ$^6$-sulphanyl)benzoyl]azetidin-3-yl}methyl)-N-(2,2,2-trifluoroethyl)-2H-indazol-5-carboxamide

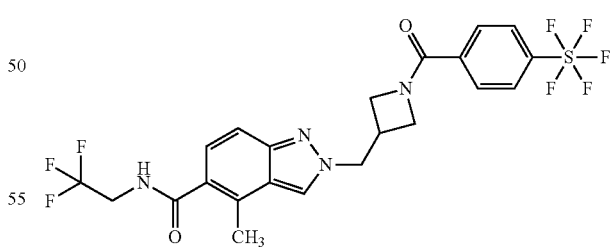

Analogously to Example 1, 121 mg of the title compound was obtained from 128 mg of the compound prepared in Example 129b and 96 mg of 4-(pentafluoro-λ$^6$-sufanyl)benzoic acid.

$^1$H-NMR (300 MHz, DMSO-d6): δ=2.50 (3H), 3.24 (1H), 3.94 (1H), 3.98-4.08 (2H), 4.12 (1H), 4.20 (1H), 4.39 (1H), 4.69 (2H), 7.18 (1H), 7.42 (1H), 7.76 (2H), 7.95 (2H), 8.59 (1H), 8.80 (1H).

EXAMPLE 133

4-methyl-2-({1-[4-(trifluoromethoxy)benzoyl]azetidin-3-yl}methyl)-N-{2-[(trifluoromethyl)sulphanyl]ethyl}-2H-indazol-5-carboxamide

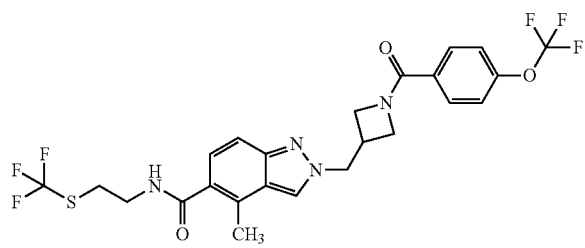 [SMILES: Cc1c(C(=O)NCCSC(F)(F)F)ccc2nn(CC3CN(C(=O)c4ccc(OC(F)(F)F)cc4)C3)cc12]

Analogously to Example 55, 178 mg of the title compound was obtained from 130 mg of the compound prepared in Example 127b and 78 mg of 4-(trifluoromethoxy)benzoyl chloride.

$^1$H-NMR (300 MHz, DMSO-d6): δ=2.51 (3H), 3.13-3.28 (3H), 3.51 (2H), 3.91 (1H), 4.10 (1H), 4.20 (1H), 4.39 (1H), 4.67 (2H), 7.19 (1H), 7.40 (3H), 7.70 (2H), 8.38 (1H), 8.57 (1H).

EXAMPLE 134

2-({1-[2-fluoro-4-(trifluoromethyl)benzoyl]azetidin-3-yl}methyl)-4-methyl-N-{2-[(trifluoromethyl)sulphanyl]ethyl}-2H-indazol-5-carboxamide

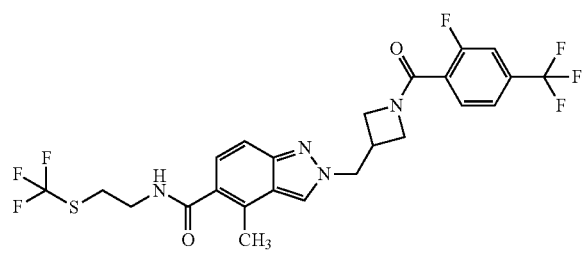 [SMILES: Cc1c(C(=O)NCCSC(F)(F)F)ccc2nn(CC3CN(C(=O)c4ccc(C(F)(F)F)cc4F)C3)cc12]

Analogously to Example 55, 128 mg of the title compound was obtained from 130 mg of the compound prepared in Example 127b and 79 mg of 2-fluoro-4-(trifluoromethyl)benzoyl chloride.

$^1$H-NMR (300 MHz, DMSO-d6): δ=2.51 (3H), 3.12-3.25 (3H), 3.50 (2H), 3.89-3.98 (2H), 4.06-4.16 (2H), 4.67 (2H), 7.19 (1H), 7.40 (1H), 7.64 (2H), 7.79 (1H), 8.39 (1H), 8.56 (1H).

EXAMPLE 135

4-methyl-2-({1-[4-(pentafluoro-$\lambda^6$-sulphanyl)benzoyl]azetidin-3-yl}methyl)-N-{2-[(trifluoromethyl)sulphanyl]ethyl}-2H-indazol-5-carboxamide

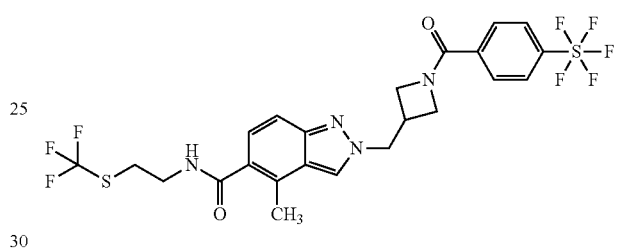

Analogously to Example 1, 84 mg of the title compound was obtained from 130 mg of the compound prepared in Example 127b and 87 mg of 4-(pentafluoro-$\lambda^6$-sulphanyl)benzoic acid.

$^1$H-NMR (300 MHz, DMSO-d6): δ=2.51 (3H), 3.18 (2H), 3.23 (1H), 3.51 (2H), 3.94 (1H), 4.12 (1H), 4.20 (1H), 4.39 (1H), 4.68 (2H), 7.19 (1H), 7.41 (1H), 7.76 (2H), 7.95 (2H), 8.39 (1H), 8.56 (1H).

EXAMPLE 136

N-[2-(cyclopropyloxy)ethyl]-4-methyl-2-({1-[4-(trifluoromethoxy)benzoyl]azetidin-3-yl}methyl)-2H-indazol-5-carboxamide

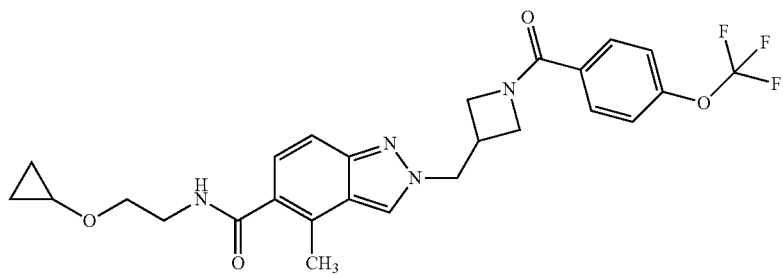 [SMILES: Cc1c(C(=O)NCCOC2CC2)ccc2nn(CC3CN(C(=O)c4ccc(OC(F)(F)F)cc4)C3)cc12]

135

Analogously to Example 55, 172 mg of the title compound was obtained from 161 mg of the compound prepared in Example 136b and 109 mg of 4-(trifluoromethoxy)benzoyl chloride.

$^1$H-NMR (300 MHz, DMSO-d6): δ=0.36-0.48 (4H), 2.48 (3H), 3.22 (1H), 3.27 (1H), 3.35 (2H), 3.53 (2H), 3.91 (1H), 4.10 (1H), 4.20 (1H), 4.39 (1H), 4.67 (2H), 7.14 (1H), 7.35-7.44 (3H), 7.71 (2H), 8.11 (1H), 8.54 (1H).

The starting material was prepared as follows:

EXAMPLE 136a

Tert-butyl 3-[(5-{N-[2-(cyclopropyloxy)ethyl]carbamoyl}-4-methyl-2H-indazol-2-yl)methyl]azetidin-1-carboxylate

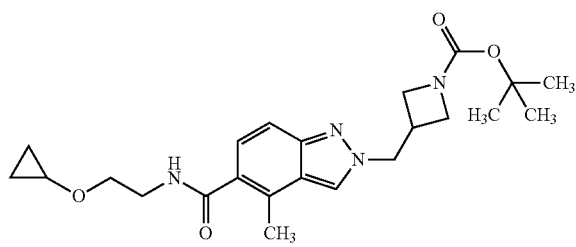 [SMILES: Cc1c(C(=O)NCCOC2CC2)ccc2nn(CC3CN(C(=O)OC(C)(C)C)C3)cc12]

Analogously to Example 1, 189 mg of the title compound was obtained from 150 mg of the compound prepared in Example 118c and 140 mg of 2-cyclopropoxy-ethylammonium trifluoroacetate (preparable according to Example 154a) and 154b) starting from cyclopropanol and bromoacetamide followed by Boc cleavage with trifluoroacetic acid analogously to Example 1a)).

$^1$H-NMR (300 MHz, DMSO-d6): δ=0.36-0.48 (4H), 1.33 (9H), 2.49 (3H), 3.08 (1H), 3.25-3.39 (3H), 3.53 (2H), 3.70 (2H), 3.87 (2H), 4.61 (2H), 7.14 (1H), 7.38 (1H), 8.10 (1H), 8.54 (1H).

136

EXAMPLE 136b 2-(azetidin-3-ylmethyl)-N-[(2-cyclopropyloxy)ethyl]-4-methyl-2H-indazol-5-carboxamide hydrochloride

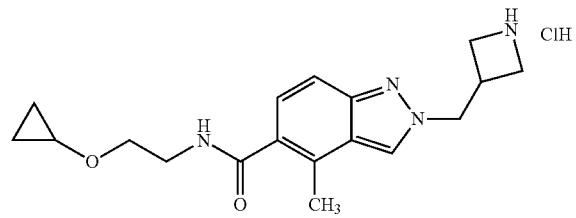

Analogously to Example 1a, from 189 mg of the compound prepared in Example 136a, 161 mg of the title compound was obtained, which was further reacted without purification.

EXAMPLE 137

N-[2-(cyclobutyloxy)ethyl]-4-methyl-2-({1-[4-(trifluoromethoxy)benzoyl]azetidin-3-yl}methyl)-2H-indazol-5-carboxamide

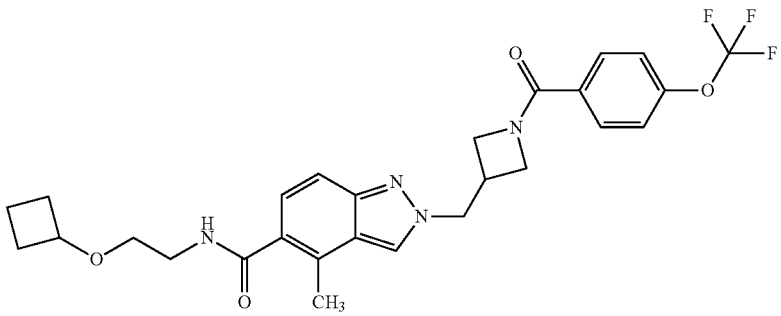 [SMILES: Cc1c(C(=O)NCCOC2CCC2)ccc2nn(CC3CN(C(=O)c4ccc(OC(F)(F)F)cc4)C3)cc12]

Analogously to Example 55, 207 mg of the title compound was obtained from 254 mg of the compound prepared in Example 137b and 166 mg of 4-(trifluoromethoxy)benzoyl chloride.

$^1$H-NMR (300 MHz, DMSO-d6): δ=1.42 (1H), 1.59 (1H), 1.80 (2H), 2.11 (2H), 2.50 (3H), 3.17-3.28 (1H), 3.31-3.41 (4H), 3.85-3.95 (2H), 4.10 (1H), 4.20 (1H), 4.39 (1H), 4.67 (2H), 7.15 (1H), 7.35-7.44 (3H), 7.71 (2H), 8.11 (1H), 8.54 (1H).

The starting material was prepared as follows:

EXAMPLE 137a

Tert-butyl 3-[(5-{N-[2-(cyclobutyloxy)ethyl]carbamoyl}-4-methyl-2H-indazol-2-yl)methyl]azetidin-1-carboxylate

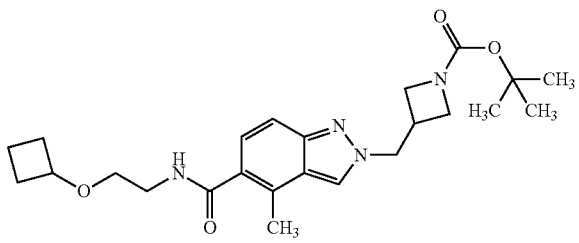 [SMILES: Cc1c(C(=O)NCCOC2CCC2)ccc2nn(CC3CN(C(=O)OC(C)(C)C)C3)cc12]

Analogously to Example 1, 297 mg of the title compound was obtained from 220 mg of the compound prepared in Example 117c and 143 mg of 2-(cyclobutyloxy)ethylammonium trifluoroacetate (preparable according to Example 154a) and 154b) starting from cyclobutanol and bromoacetamide followed by Boc cleavage with trifluoroacetic acid analogously to Example 1a)).

$^1$H-NMR (300 MHz, DMSO-d6): δ=1.33 (9H), 1.35-1.49 (1H), 1.59 (1H), 1.80 (2H), 2.11 (2H), 2.50 (3H), 3.08 (1H), 3.30-3.41 (4H), 3.69 (2H), 3.82-3.95 (3H), 4.61 (2H), 7.15 (1H), 7.38 (1H), 8.10 (1H), 8.54 (1H).

EXAMPLE 137b 2-(azetidin-3-ylmethyl)-N-[(2-(cyclobutyloxy)ethyl]-4-methyl-2H-indazol-5-carboxamide hydrochloride

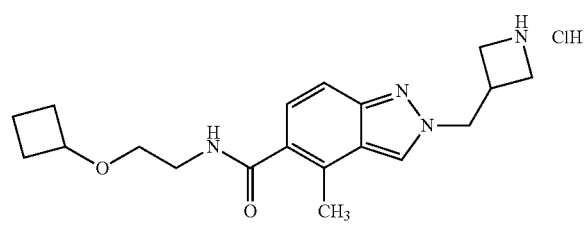 [SMILES: Cc1c(C(=O)NCCOC2CCC2)ccc2nn(CC3CNC3)cc12 ; Cl]

Analogously to Example 1a, from 297 mg of the compound prepared in Example 137a, 254 mg of the title compound was obtained, which was further reacted without purification.

EXAMPLE 138

(+/−)-2-{[1-(4-chlorobenzoyl)azetidin-3-yl]methyl}-N-(2-methoxypropyl)-4-methyl-2H-indazol-5-carboxamide

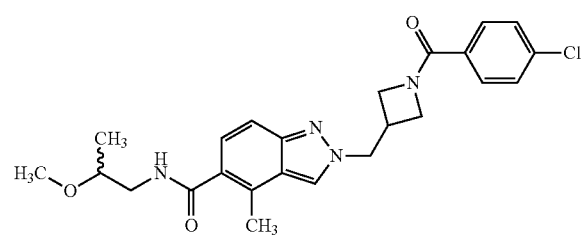 [SMILES: COC(C)CNC(=O)c1ccc2nn(CC3CN(C(=O)c4ccc(Cl)cc4)C3)cc2c1C]

Analogously to Example 55, 166 mg of the title compound was obtained from 237 mg of the compound prepared in Example 138b and 129 mg of 4-chlorobenzoyl chloride.

$^1$H-NMR (300 MHz, DMSO-d6): δ=1.07 (3H), 2.49 (3H), 3.14-3.28 (3H), 3.43 (1H), 3.89 (1H), 4.08 (1H), 4.19 (1H), 4.36 (1H), 4.67 (2H), 7.15 (1H), 7.38 (1H), 7.48 (2H), 7.59 (2H), 8.11 (1H), 8.54 (1H).

The starting material was prepared as follows:

EXAMPLE 138a (+/−)-tert-butyl 3-({5-[N-(2-methoxypropyl)carbamoyl]-4-methyl-2H-indazol-2-yl}methyl)azetidin-1-carboxylate

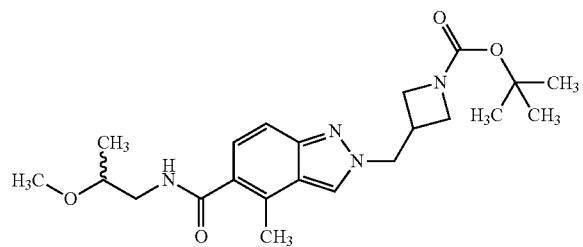 [SMILES: COC(C)CNC(=O)c1ccc2nn(CC3CN(C(=O)OC(C)(C)C)C3)cc2c1C]

Analogously to Example 1, 331 mg of the title compound was obtained from 323 mg of the compound prepared in Example 117c and 117 mg of 2-methoxypropylamine.

$^1$H-NMR (300 MHz, DMSO-d6): δ=1.08 (3H), 1.33 (9H), 2.50 (3H), 3.09 (1H), 3.16-3.31 (2H), 3.44 (1H), 3.69 (2H), 3.85 (2H), 4.61 (2H), 7.15 (1H), 7.39 (1H), 8.08 (1H), 8.54 (1H).

EXAMPLE 138b (+/−)-2-(azetidin-3-ylmethyl)-N-(2-methoxypropyl)-4-methyl-2H-indazol-5-carboxamide hydrochloride

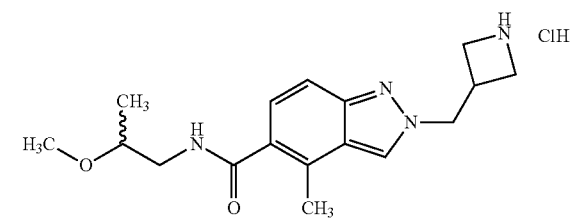 [SMILES: COC(C)CNC(=O)c1ccc2nn(CC3CNC3)cc2c1C ; Cl]

Analogously to Example 1a, from 280 mg of the compound prepared in Example 138a, 247 mg of the title compound was obtained, which was further reacted without purification.

EXAMPLE 139

(R or S)-2-{[1-(4-chlorobenzoyl)azetidin-3-yl]methyl}-N-(2-methoxypropyl)-4-methyl-2H-indazol-5-carboxamide

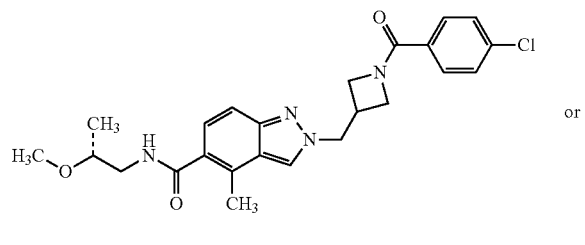

or

139

-continued

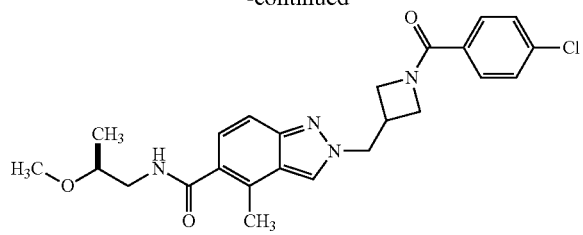

From 158 mg of the racemate prepared in Example 138, 52 mg of the title compound together with 48 mg of the slower-eluting enantiomer (Example 140) were obtained by racemate separation by means of preparative chiral HPLC (Method A).

Analytical chiral HPLC: 14.5 min

EXAMPLE 140

(S or R)-2-{[1-(4-chlorobenzoyl)azetidin-3-yl]methyl}-N-(2-methoxypropyl)-4-methyl-2H-indazol-5-carboxamide

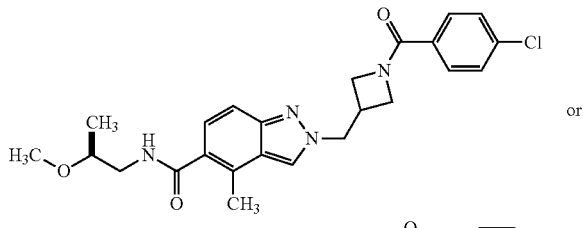

From 158 mg of the racemate prepared in Example 138, 48 mg of the title compound together with 52 mg of the faster-eluting enantiomer (Example 139) were obtained by racemate separation by means of preparative chiral HPLC (Method A).

Analytical chiral HPLC: 17.1 min

EXAMPLE 141

(+/−)-2-{[1-(4-chlorobenzoyl)azetidin-3-yl]methyl}-N-(1,4-dioxan-2-ylmethyl)-4-methyl-2H-indazol-5-carboxamide

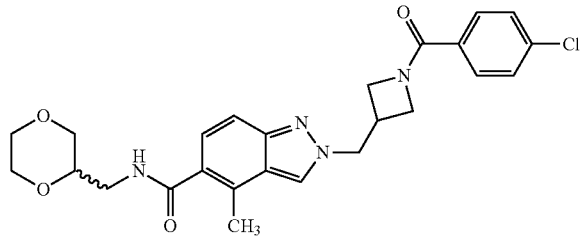

Analogously to Example 55, 177 mg of the title compound was obtained from 269 mg of the compound prepared in Example 141b and 136 mg of 4-chlorobenzoyl chloride.

140

$^1$H-NMR (300 MHz, DMSO-d6): δ=2.49 (3H), 3.13-3.28 (4H), 3.38-3.66 (4H), 3.67-3.77 (2H), 3.89 (1H), 4.08 (1H), 4.19 (1H), 4.37 (1H), 4.67 (2H), 7.15 (1H), 7.38 (1H), 7.48 (2H), 7.59 (2H), 8.17 (1H), 8.55 (1H).

The starting material was prepared as follows:

EXAMPLE 141a (+/−)-tert-butyl 3-({5-[N-(1,4-dioxan-2-ylmethyl) carbamoyl]-4-methyl-2H-indazol-2-yl}methyl)azetidin-1-carboxylate

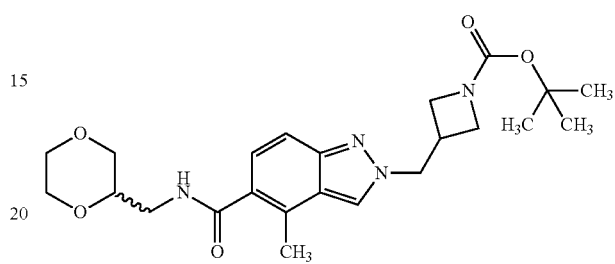

Analogously to Example 1, 364 mg of the title compound was obtained from 323 mg of the compound prepared in Example 117c and 110 mg of 1,4-dioxan-2-ylmethylamine.

$^1$H-NMR (300 MHz, DMSO-d6): δ=1.33 (9H), 2.50 (3H), 3.09 (1H), 3.16-3.29 (3H), 3.40-3.77 (8H), 3.86 (2H), 4.61 (2H), 7.16 (1H), 7.39 (1H), 8.14 (1H), 8.55 (1H).

EXAMPLE 141b (+/−)-2-(azetidin-3-ylmethyl)-N-(1,4-dioxan-2-ylmethyl)-4-methyl-2H-indazol-5-carboxamide hydrochloride

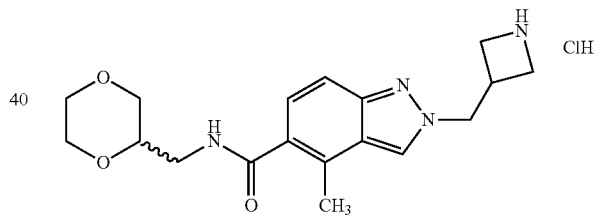

Analogously to Example 1a, from 314 mg of the compound prepared in Example 141a, 274 mg of the title compound was obtained, which was further reacted without purification.

EXAMPLE 142

(R or S)-2-{[1-(4-chlorobenzoyl)azetidin-3-yl]methyl}-N-(1,4-dioxan-2-ylmethyl)-4-methyl-2H-indazol-5-carboxamide

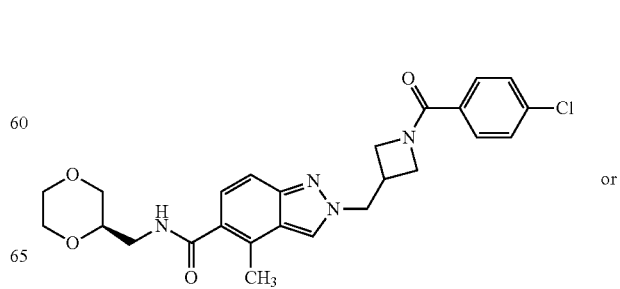

-continued

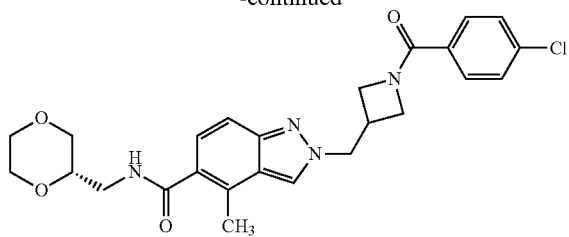

From 172 mg of the racemate prepared in Example 141, 60 mg of the title compound together with 60 mg of the slower-eluting enantiomer (Example 143) were obtained by racemate separation by means of preparative chiral HPLC (Method B).
Analytical chiral HPLC: 5.84 min

EXAMPLE 143

(S or R)-2-{[1-(4-chlorobenzoyl)azetidin-3-yl]methyl}-N-(1,4-dioxan-2-ylmethyl)-4-methyl-2H-indazol-5-carboxamide

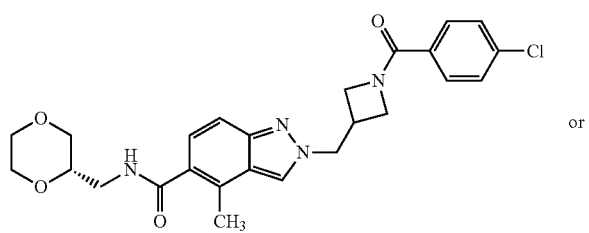

From 172 mg of the racemate prepared in Example 141, 60 mg of the title compound together with 60 mg of the faster-eluting enantiomer (Example 142) were obtained by racemate separation by means of preparative chiral HPLC (Method B).
Analytical chiral HPLC: 6.28 min

EXAMPLE 144

(+/−)-2-{[1-(4-chlorobenzoyl)azetidin-3-yl]methyl}-4-methyl-N-(3,4,5,6-tetrahydro-2H-pyran-2-ylmethyl)-2H-indazol-5-carboxamide

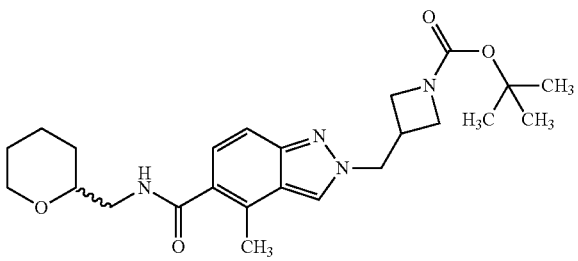

Analogously to Example 55, 144 mg of the title compound was obtained from 255 mg of the compound prepared in Example 144b and 130 mg of 4-chlorobenzoyl chloride.

$^1$H-NMR (300 MHz, DMSO-d6): δ=1.10-1.23 (1H), 1.35-1.47 (3H), 1.61 (1H), 1.71-1.81 (1H), 2.48 (3H), 3.15-3.27 (4H), 3.37 (1H), 3.80-3.93 (2H), 4.08 (1H), 4.19 (1H), 4.36 (1H), 4.66 (2H), 7.14 (1H), 7.37 (1H), 7.48 (2H), 7.59 (2H), 8.09 (1H), 8.54 (1H).

The starting material was prepared as follows:

EXAMPLE 144a (+/−)-tert-butyl 3-({4-methyl-5-[N-(3,4,5,6-tetrahydro-2H-pyran-2-ylmethyl)-carbamoyl]-2H-indazol-2-yl}methyl)azetidin-1-carboxylate Analogously to Example 1, 342 mg of the title compound was obtained from 323 mg of the compound prepared in Example 117c and 141 mg of 3,4,5,6-tetrahydro-2H-pyran-2-ylmethylamine hydrochloride.

$^1$H-NMR (300 MHz, DMSO-d6): δ=1.14-1.21 (1H), 1.33 (9H), 1.37-1.49 (3H), 1.61 (1H), 1.71-1.80 (1H), 2.49 (3H), 3.09 (1H), 3.21 (2H), 3.27-3.43 (2H), 3.69 (2H), 3.81-3.91 (3H), 4.61 (2H), 7.15 (1H), 7.38 (1H), 8.06 (1H), 8.53 (1H).

EXAMPLE 144b (+/−)-2-(azetidin-3-ylmethyl)-4-methyl-N-(3,4,5,6-tetrahydro-2H-pyran-2-ylmethyl)-2H-indazole-5-carboxamide hydrochloride Analogously to Example 1a, from 298 mg of the compound prepared in Example 144a, 261 mg of the title compound was obtained, which was further reacted without purification.

EXAMPLE 145

(R or S)-2-{[1-(4-chlorobenzoyl)azetidin-3-yl]methyl}-4-methyl-N-(3,4,5,6-tetrahydro-2H-pyran-2-ylmethyl)-2H-indazol-5-carboxamide

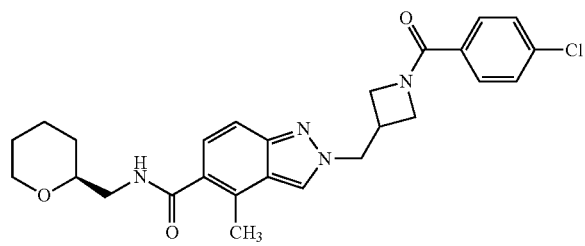

From 140 mg of the racemate prepared in Example 144, 43 mg of the title compound together with 35 mg of the slower-eluting enantiomer (Example 146) were obtained by racemate separation by means of preparative chiral HPLC (Method C).

Analytical chiral HPLC: 4.38 min

From 140 mg of the racemate prepared in Example 144, 35 mg of the title compound together with 43 mg of the faster-eluting enantiomer (Example 145) were obtained by racemate separation by means of preparative chiral HPLC (Method C).

Analytical chiral HPLC: 4.88 min

EXAMPLE 147

(+/−)-2-({1-[4-(4-fluorophenoxy)benzoyl]azetidin-3-yl}methyl)-N-(2-methoxypropyl)-4-methyl-2H-indazol-5-carboxamide

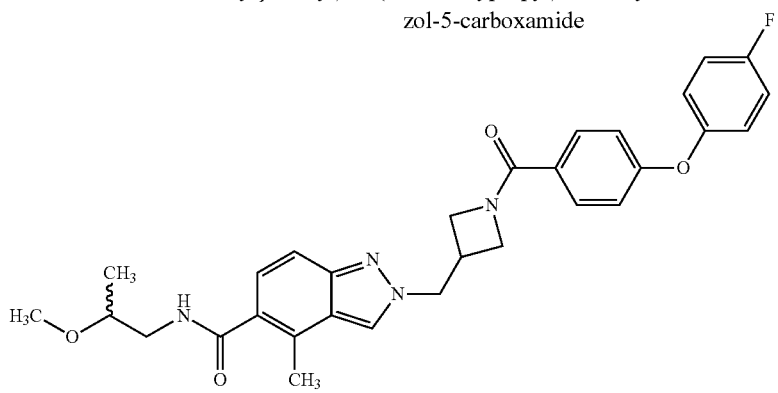

Analogously to Example 1, from 42 mg of the compound prepared in Example 138b and 28 mg of 4-(4-fluorophenoxy)benzoic acid, a material still contaminated after HPLC purification was obtained, which was further purified by an additional preparative thick layer chromatography with ethyl acetate/methanol in the ratio 9:1 as mobile phase. Yield in this manner: 15 mg of the title compound.

$^1$H-NMR (300 MHz, CDCl3): δ=1.22 (3H), 2.64 (3H), 3.28 (1H), 3.36 (3H), 3.40 (1H), 3.57 (1H), 3.76 (1H), 3.97-4.46 (4H), 4.66 (2H), 6.14 (1H), 6.93 (2H), 6.97-7.11 (4H), 7.32 (1H), 7.51 (1H), 7.60 (2H), 8.00 (1H).

EXAMPLE 146

(S or R)-2-{[1-(4-chlorobenzoyl)azetidin-3-yl]methyl}-4-methyl-N-(3,4,5,6-tetrahydro-2H-pyran-2-ylmethyl)-2H-indazol-5-carboxamide

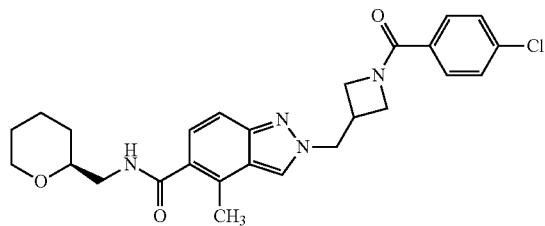

or

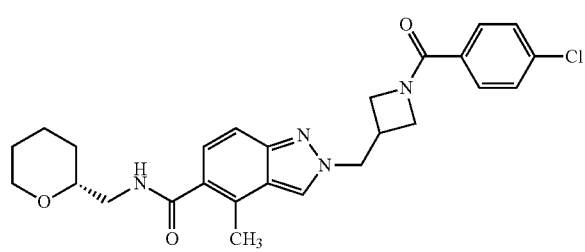 [SMILES: Cc1c(C(=O)NCC2COCCO2)ccc2nn(CC3CN(C(=O)c4ccc(Cl)cc4)C3)cc12]

EXAMPLE 148

(+/−)-N-(1,4-dioxan-2-ylmethyl)-2-({1-[4-(4-fluorophenoxy)benzoyl]azetidin-3-yl}methyl)-4-methyl-2H-indazol-5-carboxamide

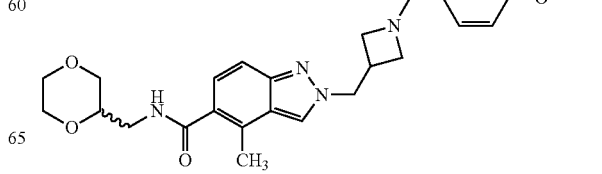

Analogously to Example 1, 18 mg of the title compound was obtained from 43 mg of the compound prepared in Example 141b and 26 mg of 4-(4-fluorophenoxy)benzoic acid.

$^1$H-NMR (300 MHz, DMSO-d6): δ=2.49 (3H), 3.13-3.28 (4H), 3.38-3.66 (4H), 3.67-3.77 (2H), 3.89 (1H), 4.07 (1H), 4.19 (1H), 4.37 (1H), 4.66 (2H), 6.94 (2H), 7.08-7.18 (3H), 7.24 (2H), 7.38 (1H), 7.60 (2H), 8.17 (1H), 8.55 (1H).

EXAMPLE 149

2-{[1-(4-chlorobenzoyl)azetidin-3-yl]methyl}-N-[2-(cyclopropylmethoxy)ethyl]-4-methyl-2H-indazol-5-carboxamide

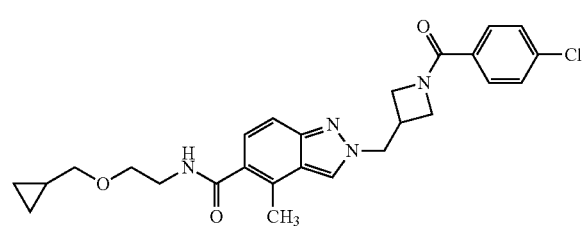 [SMILES: Cc1c(C(=O)NCCOCC2CC2)ccc2nn(CC3CN(C(=O)c4ccc(Cl)cc4)C3)cc12]

Analogously to Example 55, 72 mg of the title compound was obtained from 127 mg of the compound prepared in Example 149b and 65 mg of 4-chlorobenzoyl chloride.

$^1$H-NMR (300 MHz, DMSO-d6): δ=0.17 (2H), 0.45 (2H), 0.99 (1H), 2.51-2.54 (3H), 3.20-3.28 (3H), 3.38 (2H), 3.51 (2H), 3.92 (1H), 4.11 (1H), 4.21 (1H), 4.39 (1H), 4.69 (2H), 7.18 (1H), 7.40 (1H), 7.50 (2H), 7.62 (2H), 8.12 (1H), 8.56 (1H).

The starting material was prepared as follows:

EXAMPLE 149a

Tert-butyl 3-[(5-{N-[2-(cyclopropylmethoxy)ethyl]carbamoyl}-4-methyl-2H-indazol-2-yl)methyl]azetidin-1-carboxylate

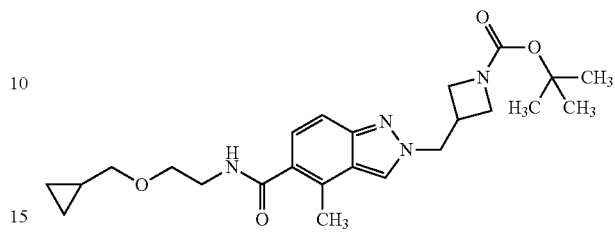

Analogously to Example 1, 448 mg of the title compound was obtained from 400 mg of the compound prepared in Example 117c and 133 mg of 2-(cyclopropylmethoxy)ethylamine hydrochloride.

$^1$H-NMR (300 MHz, DMSO-d6): δ=0.14 (2H), 0.42 (2H), 0.97 (1H), 1.33 (9H), 2.50 (3H), 3.09 (1H), 3.24 (2H), 3.36 (2H), 3.49 (2H), 3.69 (2H), 3.86 (2H), 4.61 (2H), 7.15 (1H), 7.38 (1H), 8.08 (1H), 8.54 (1H).

EXAMPLE 149b 2-(azetidin-3-ylmethyl)-N-[2-(cyclopropylmethoxy)ethyl]-4-methyl-2H-indazol-5-carboxamide hydrochloride

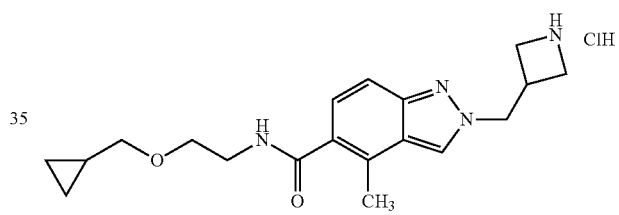

Analogously to Example 1a, from 448 mg of the compound prepared in Example 149a, 390 mg of the title compound was obtained, which was further reacted without purification.

EXAMPLE 150

N-[2-(cyclopropylmethoxy)ethyl]-2-({1-[4-(4-fluorophenoxy)benzoyl]azetidin-3-yl}methyl)-4-methyl-2H-indazol-5-carboxamide

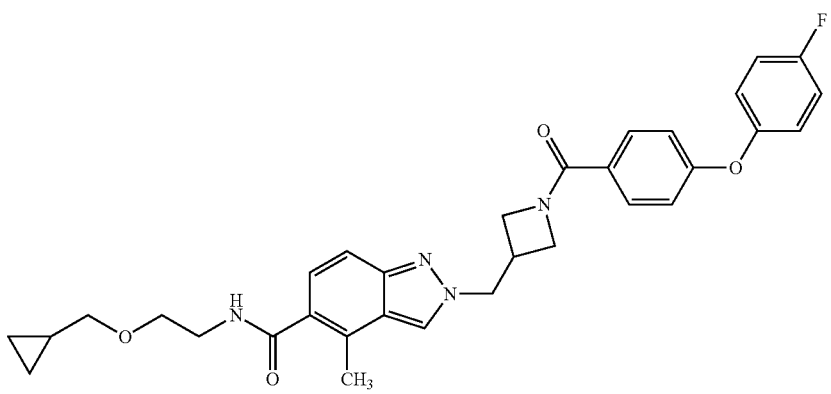 [SMILES: Cc1c(C(=O)NCCOCC2CC2)ccc2nn(CC3CN(C(=O)c4ccc(Oc5ccc(F)cc5)cc4)C3)cc12]

Analogously to Example 1, 48 mg of the title compound was obtained from 102 mg of the compound prepared in Example 149b and 63 mg of 4-(4-fluorophenoxy)benzoic acid.

¹H-NMR (300 MHz, CDCl3): δ=0.20 (2H), 0.54 (2H), 1.05 (1H), 2.65 (3H), 3.32 (2H), 3.35-3.45 (1H), 3.63-3.75 (4H), 3.99-4.50 (4H), 4.66 (2H), 6.22 (1H), 6.93 (2H), 6.97-7.11 (4H), 7.34 (1H), 7.51 (1H), 7.61 (2H), 8.00 (1H).

EXAMPLE 151

N-[2-(cyclopropylmethoxy)ethyl]-4-methyl-2-{[1-(4-methylbenzoyl)azetidin-3-yl]methyl}-2H-indazol-5-carboxamide

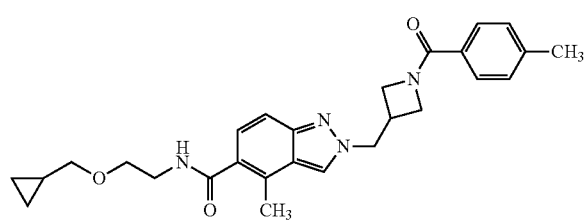 [SMILES: Cc1ccc(C(=O)N2CC(Cn3cc4c(C)c(C(=O)NCCOCC5CC5)ccc4n3)C2)cc1]

Analogously to Example 1, 55 mg of the title compound was obtained from 127 mg of the compound prepared in Example 149b and 46 mg of 4-methylbenzoic acid.

¹H-NMR (300 MHz, DMSO-d6): δ=0.17 (2H), 0.45 (2H), 0.99 (1H), 2.33 (3H), 2.53 (3H), 3.19-3.28 (3H), 3.38 (2H), 3.51 (2H), 3.90 (1H), 4.09 (1H), 4.20 (1H), 4.38 (1H), 4.69 (2H), 7.18 (1H), 7.24 (2H), 7.41 (1H), 7.50 (2H), 8.11 (1H), 8.57 (1H).

EXAMPLE 152

2-{[1-(4-chlorobenzoyl)azetidin-3-yl]methyl}-4-methyl-N-[2-(trifluoromethoxy)ethyl]-2H-indazol-5-carboxamide

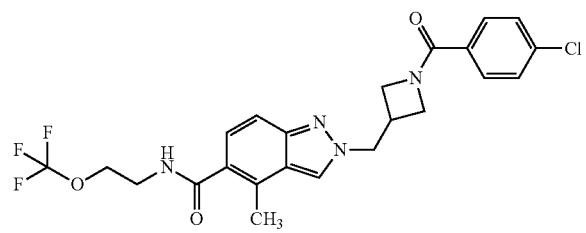 [SMILES: Cc1c(C(=O)NCCOC(F)(F)F)ccc2nn(CC3CN(C(=O)c4ccc(Cl)cc4)C3)cc12]

Analogously to Example 55, 122 mg of the title compound was obtained from 234 mg of the compound prepared in Example 152b and 115 mg of 4-chlorobenzoyl chloride.

¹H-NMR (300 MHz, DMSO-d6): δ=2.52 (3H), 3.25 (1H), 3.54 (2H), 3.93 (1H), 4.11 (1H), 4.17-4.25 (3H), 4.40 (1H), 4.70 (2H), 7.19 (1H), 7.43 (1H), 7.50 (2H), 7.61 (2H), 8.38 (1H), 8.58 (1H).

The starting material was prepared as follows:

EXAMPLE 152a

Tert-butyl 3-[(4-methyl-5-{N-[2-(trifluoromethoxy)ethyl]carbamoyl}-2H-indazol-2-yl)methyl]azetidin-1-carboxylate

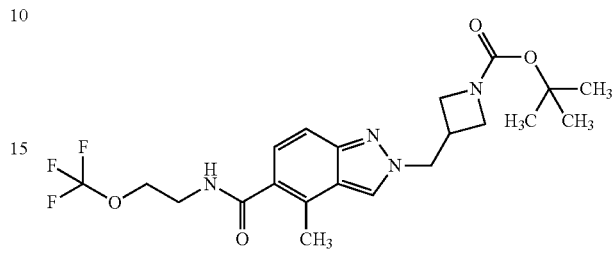

Analogously to Example 1, 272 mg of the title compound was obtained from 250 mg of the compound prepared in Example 117c and 120 mg of 2-(trifluoromethoxy)ethylamine hydrochloride.

¹H-NMR (300 MHz, DMSO-d6): δ=1.32 (9H), 2.50 (3H), 3.08 (1H), 3.51 (2H), 3.70 (2H), 3.86 (2H), 4.17 (2H), 4.61 (2H), 7.16 (1H), 7.41 (1H), 8.36 (1H), 8.56 (1H).

EXAMPLE 152b 2-(azetidin-3-ylmethyl)-4-methyl-N-[2-(trifluoromethoxy)ethyl]-2H-indazol-5-carboxamide hydrochloride

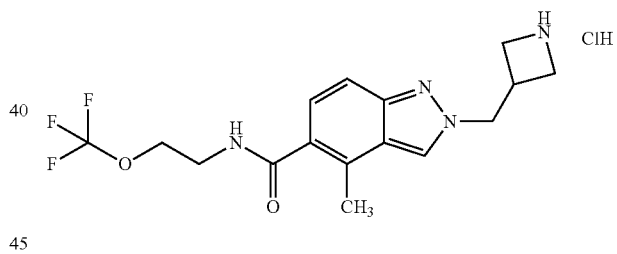

Analogously to Example 1a, from 272 mg of the compound prepared in Example 152a, 240 mg of the title compound was obtained, which was further reacted without purification.

EXAMPLE 153

N-(2-tert-butoxyethyl)-2-{[1-(4-chlorobenzoyl)azetidin-3-yl]methyl}-4-methyl-2H-indazol-5-carboxamide

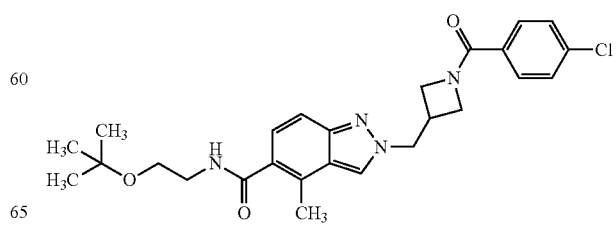

Analogously to Example 55) 12 mg of the title compound was obtained from 160 mg of the compound prepared in Example 153b) and 81 mg of 4-chlorobenzoyl chloride.

¹H-NMR (300 MHz, DMSO-d6): δ=1.14 (9H), 2.53 (3H), 3.19-3.34 (3H), 3.43 (2H), 3.92 (1H), 4.11 (1H), 4.21 (1H), 4.39 (1H), 4.69 (2H), 7.18 (1H), 7.40 (1H), 7.50 (2H), 7.62 (2H), 8.05 (1H), 8.56 (1H).

The starting material was prepared as follows:

EXAMPLE 153a

Tert-butyl 3-({5-[N-(2-tert-butoxyethyl)carbamoyl]-4-methyl-2H-indazol-2-yl}-methyl)azetidin-1-carboxylate

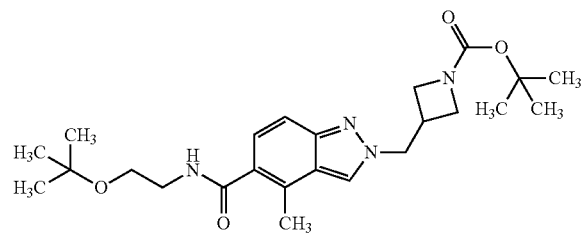 [SMILES: Cc1c(C(=O)NCCOC(C)(C)C)ccc2nn(CC3CN(C(=O)OC(C)(C)C)C3)cc12]

Analogously to Example 1, 284 mg of the title compound was obtained from 250 mg of the compound prepared in Example 117c and 111 mg of 2-tert-butoxyethylamine hydrochloride.

¹H-NMR (300 MHz, DMSO-d6): δ=1.11 (9H), 1.32 (9H), 2.50 (3H), 3.08 (1H), 3.27 (2H), 3.40 (2H), 3.69 (2H), 3.86 (2H), 4.60 (2H), 7.15 (1H), 7.38 (1H), 8.04 (1H), 8.54 (1H).

EXAMPLE 153b 2-(azetidin-3-ylmethyl)-N-(2-tert-butoxyethyl)-4-methyl-2H-indazol-5-carboxamide hydrochloride

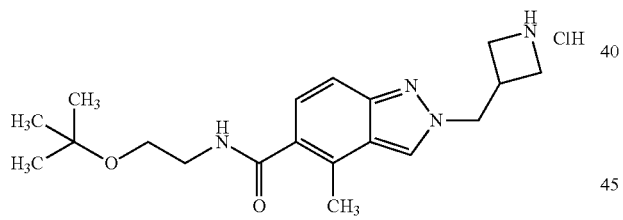

Analogously to Example 1a, from 284 mg of the compound prepared in Example 153a, 240 mg of the title compound was obtained, which was further reacted without purification.

EXAMPLE 154

(+/−)-2-{[1-(4-chlorobenzoyl)azetidin-3-yl]methyl}-N-[2-(cyclobutyloxy)propyl]-4-methyl-2H-indazol-5-carboxamide

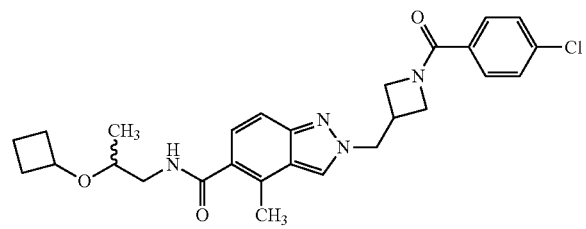 [SMILES: Cc1c(C(=O)NCC(C)OC2CCC2)ccc2nn(CC3CN(C(=O)c4ccc(Cl)cc4)C3)cc12]

Analogously to Example 55, 135 mg of the title compound was obtained from 222 mg of the compound prepared in Example 154d and 109 mg of 4-chlorobenzoyl chloride.

¹H-NMR (300 MHz, DMSO-d6): δ=1.05 (3H), 1.39 (1H), 1.55 (1H), 1.80 (2H), 2.11 (2H), 2.50 (3H), 3.08-3.23 (3H), 3.55 (1H), 3.89 (1H), 4.03-4.13 (1H), 4.19 (1H), 4.37 (1H), 4.67 (2H), 7.15 (1H), 7.38 (1H), 7.48 (2H), 7.59 (2H), 8.07 (1H), 8.53 (1H).

The starting material was prepared as follows:

EXAMPLE 154a (+/−)-2-(cyclobutyloxy)-propanamide

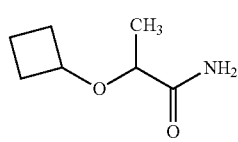

To a suspension of 732 mg of sodium hydride in 15 ml THF, 2.0 g of cyclobutanol in 0.5 ml THF were added dropwise and stirred for 30 minutes at 25° C. The reaction mixture was then cooled to 0° C. and 2.11 g of (+/−) 2-bromopropanamide in 0.5 ml tetrahydrofuran were added dropwise and then stirred for 18 hours at 25° C. The reaction mixture was poured onto ice-water and extracted once with 75 ml dichloromethane. The organic phase was washed with saturated sodium chloride solution, dried over sodium sulphate and concentrated in vacuo after filtration. The crude product thus obtained was purified by column chromatography on silica gel with hexane/0-50% ethyl acetate. Yield: 0.79 g of the title compound.

¹H-NMR (300 MHz, DMSO-d6): δ=1.14 (3H), 1.38 (1H), 1.56 (1H), 1.83 (2H), 2.08 (2H), 3.62 (1H), 3.90 (1H), 7.07 (2H).

EXAMPLE 154b (+/−)-tert-butyl N-[2-(cyclobutyloxy)propyl]carbamate

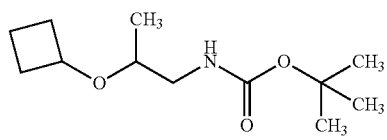

To a suspension of 6.9 g of lithium aluminium hydride in 250 ml THF, 6.5 g of the amide prepared in Example 154a in 81 ml THF were cautiously added dropwise at 0° C. The mixture was then first stirred for 30 minutes at 0° C. and then heated for 5 hours under reflux. After cooling, the mixture was cautiously treated with 20 g of sodium sulphate decahydrate and 20 g of potassium fluoride and solid matter removed by filtration shortly afterwards. The filtrate was concentrated in vacuo. The residue thus obtained (5.8 g) was dissolved without further purification in 174 ml dichloromethane and treated with 11.9 g of di-tert-butyl dicarbonate. After 16 hours' stirring at 25° C., this was concentrated in vacuo and the residue thus obtained purified by two-fold column chromatography on silica gel with hexane/0-40% ethyl acetate.

Yield: 8.54 g of the title compound.

¹H-NMR (300 MHz, DMSO-d6): δ=0.94 (3H), 1.28-1.42 (10H), 1.53 (1H), 1.76 (2H), 2.07 (2H), 2.76 (1H), 2.90 (1H), 3.34 (1H), 3.92 (1H), 6.72 (1H).

EXAMPLE 154c (+/−)-tert-butyl 3-[(5-{N-[2-(cyclobutyloxy)propyl]carbamoyl}-4-methyl-2H-indazol-2-yl)methyl]azetidin-1-carboxylate

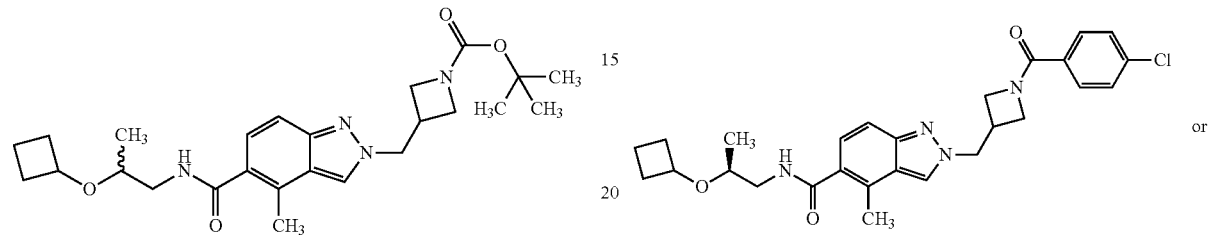

Analogously to Example 1a, from 200 mg of the compound prepared in Example 154b), 2-(cyclobutyloxy)propylamine was obtained as the hydrochloride, which without further purification together with 250 mg of the compound prepared in Example 117c analogously to Example 1, yielded 259 mg of the title compound.

¹H-NMR (300 MHz, DMSO-d6): δ=1.05 (3H), 1.32 (9H), 1.39 (1H), 1.55 (1H), 1.80 (2H), 2.11 (2H), 2.50 (3H), 3.02-3.17 (2H), 3.22 (1H), 3.54 (1H), 3.69 (2H), 3.86 (2H), 3.99 (1H), 4.61 (2H), 7.15 (1H), 7.39 (1H), 8.09 (1H), 8.55 (1H).

EXAMPLE 154d (+/−)-2-(azetidin-3-ylmethyl)-N-[2-(cyclobutyloxy)propyl]-4-methyl-2H-indazol-5-carboxamide hydrochloride

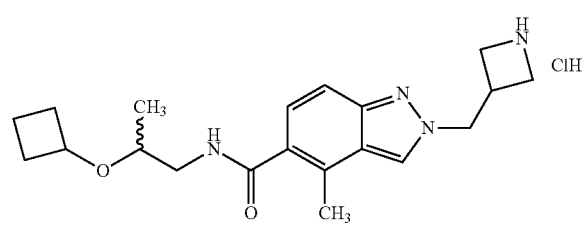 [SMILES: Cc1c(C(=O)NCC(C)OC2CCC2)ccc2nn(CC3CNC3)cc12 ; Cl]

Analogously to Example 1a, from 259 mg of the compound prepared in Example 154c, 225 mg of the title compound was obtained, which was further reacted without purification.

EXAMPLE 155

(S or R)-2-{[1-(4-chlorobenzoyl)azetidin-3-yl]methyl}-N-[2-(cyclobutyloxy)-propyl]-4-methyl-2H-indazol-5-carboxamide

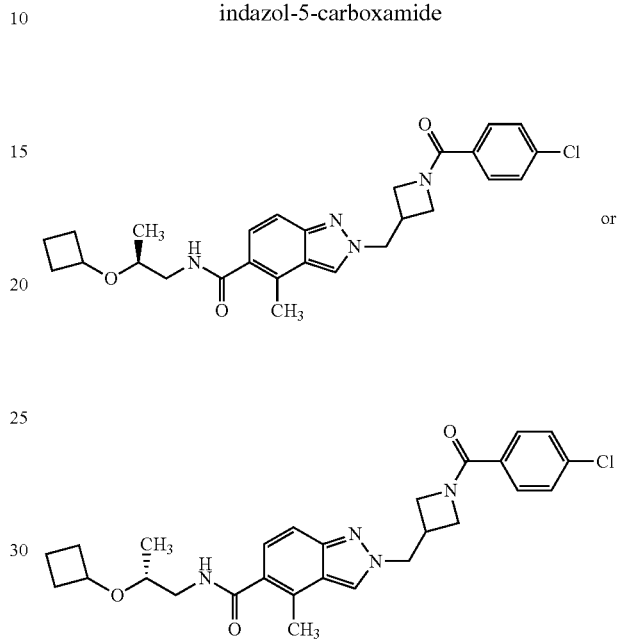

From 135 mg of the racemate prepared in Example 154, 41 mg of the title compound together with 21 mg of the slower-eluting enantiomer (Example 156) were obtained by racemate separation by means of preparative chiral HPLC (Method A).

Analytical chiral HPLC: 10.05 min

EXAMPLE 156

(R or S)-2-{[1-(4-chlorobenzoyl)azetidin-3-yl]methyl}-N-[2-(cyclobutyloxy)-propyl]-4-methyl-2H-indazol-5-carboxamide

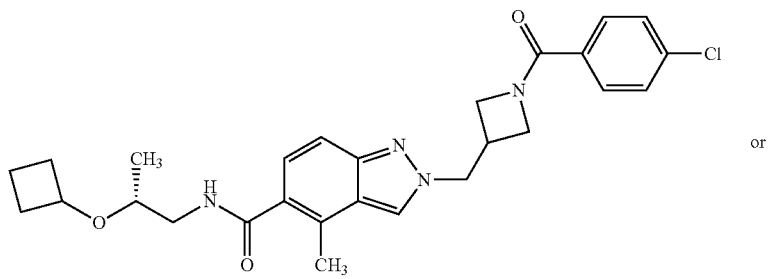

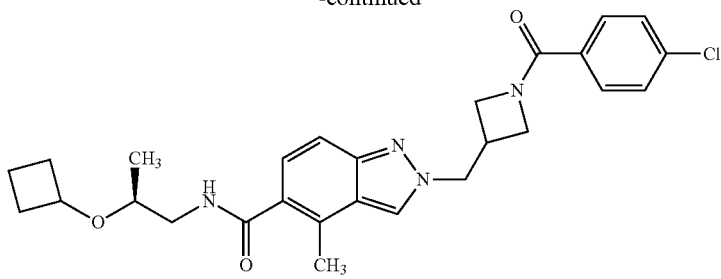

From 135 mg of the racemate prepared in Example 154, 21 mg of the title compound together with 41 mg of the faster-eluting enantiomer (Example 155) were obtained by racemate separation by means of preparative chiral HPLC (Method A).

Analytical chiral HPLC: 13.14 min

EXAMPLE 157

N-[2-(cyclopropylmethoxy)ethyl]-2-({1-[(4'-fluoro-biphenyl-4-yl)carbonyl]azetidin-3-yl}methyl)-4-methyl-2H-indazol-5-carboxamide

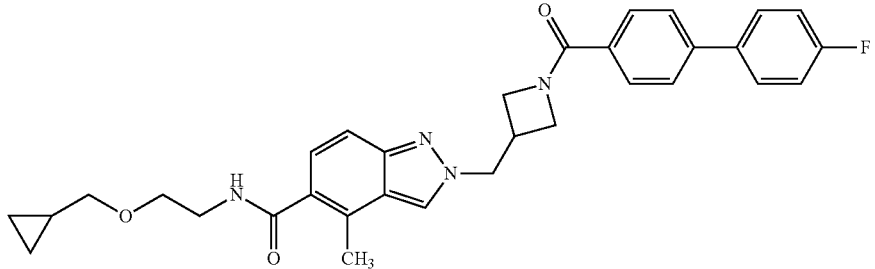 [SMILES: Cc1c(C(=O)NCCOCC2CC2)ccc2nn(CC3CN(C(=O)c4ccc(-c5ccc(F)cc5)cc4)C3)cc12]

Analogously to Example 1, 54 mg of the title compound was obtained from 102 mg of the compound prepared in Example 149b and 58 mg of 4'-fluorobiphenyl-4-carboxylic acid.

$^1$H-NMR (300 MHz, CDCl3): δ=0.20 (2H), 0.54 (2H), 1.05 (1H), 2.66 (3H), 3.32 (2H), 3.42 (1H), 3.61-3.73 (4H), 4.09 (1H), 4.28 (1H), 4.38 (1H), 4.49 (1H), 4.69 (2H), 6.22 (1H), 7.10-7.18 (2H), 7.26 (2H), 7.35 (1H), 7.50-7.59 (3H), 7.70 (2H), 8.01 (1H).

EXAMPLE 158

2-({1-[(4'-fluorobiphenyl-4-yl)carbonyl]azetidin-3-yl}methyl)-N-(2-methoxy-ethyl)-4-methyl-2H-indazol-5-carboxamide

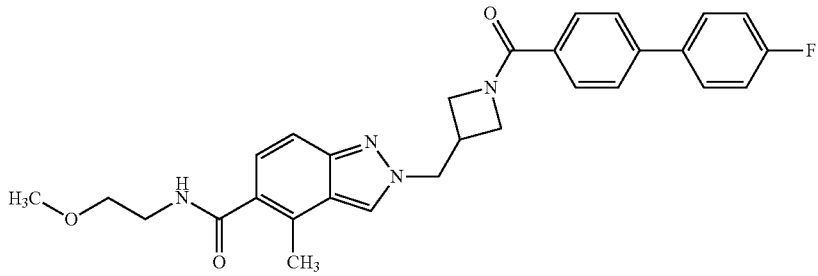 [SMILES: COCCNC(=O)c1ccc2nn(CC3CN(C(=O)c4ccc(-c5ccc(F)cc5)cc4)C3)cc2c1C]

Analogously to Example 1, 54 mg of the title compound was obtained from 108 mg of the compound prepared in Example 117e and 69 mg of 4'-fluorobiphenyl-4-carboxylic acid.

$^1$H-NMR (300 MHz, DMSO-d6): δ=2.49 (3H), 3.17-3.29 (4H), 3.36 (2H), 3.43 (2H), 3.92 (1H), 4.11 (1H), 4.24 (1H), 4.42 (1H), 4.68 (2H), 7.15 (1H), 7.29 (2H), 7.39 (1H), 7.63-7.78 (6H), 8.12 (1H), 8.56 (1H).

EXAMPLE 159

2-({1-[4-(4-fluorophenoxy)benzoyl]azetidin-3-yl}methyl)-N-(2-methoxyethyl)-4-methyl-2H-indazol-5-carboxamide

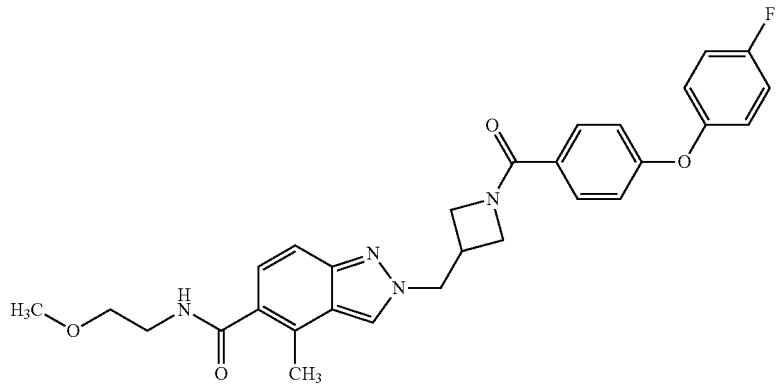 [SMILES: COCCNC(=O)c1ccc2nn(CC3CN(C(=O)c4ccc(Oc5ccc(F)cc5)cc4)C3)cc2c1C]

Analogously to Example 1, 28 mg of the title compound was obtained from 108 mg of the compound prepared in Example 117e and 74 mg of 4-(4-fluorophenoxy)benzoic acid.

$^1$H-NMR (300 MHz, CDCl3): δ=2.65 (3H), 3.31-3.46 (4H), 3.58 (2H), 3.67 (2H), 4.06 (1H), 4.24 (1H), 4.40 (2H), 4.66 (2H), 6.15 (1H), 6.89-7.13 (6H), 7.33 (1H), 7.51 (1H), 7.61 (2H), 8.00 (1H).

EXAMPLE 160

2-({1-[4-(4-fluorophenoxy)benzoyl]azetidin-3-yl}methyl)-4-methyl-N-(2,2,2-trifluoroethyl)-2H-indazol-5-carboxamide

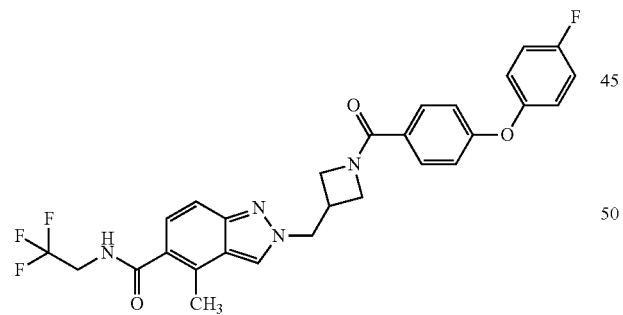

Analogously to Example 1, 47 mg of the title compound was obtained from 115 mg of the compound prepared in Example 129b and 74 mg of 4-(4-fluorophenoxy)benzoic acid.

$^1$H-NMR (300 MHz, CDCl3): δ=2.65 (3H), 3.39 (1H), 3.97-4.52 (6H), 4.67 (2H), 6.04 (1H), 6.89-7.12 (6H), 7.31 (1H), 7.53 (1H), 7.60 (2H), 8.03 (1H).

EXAMPLE 161

2-({1-[(4'-fluorobiphenyl-4-yl)carbonyl]azetidin-3-yl}methyl)-4-methyl-N-(2,2,2-trifluoroethyl)-2H-indazol-5-carboxamide

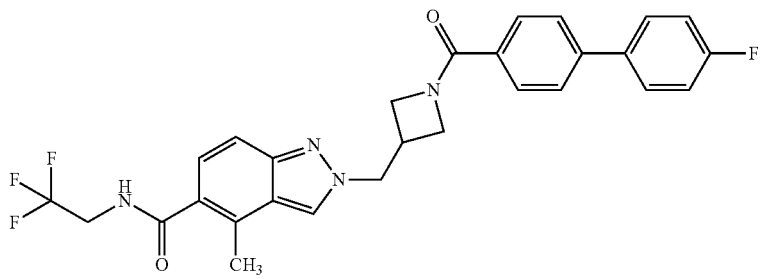 [SMILES: Cc1c(C(=O)NCC(F)(F)F)ccc2nn(CC3CN(C(=O)c4ccc(-c5ccc(F)cc5)cc4)C3)cc12]

Analogously to Example 1, 28 mg of the title compound was obtained from 115 mg of the compound prepared in Example 129b and 69 mg of 4'-fluorobiphenyl-4-carboxylic acid.

¹H-NMR (300 MHz, DMSO-d6): δ=2.65 (3H), 3.42 (1H), 4.01-4.54 (6H), 4.69 (2H), 6.02 (1H), 7.15 (2H), 7.32 (1H), 7.51-7.62 (5H), 7.69 (2H), 8.04 (1H).

EXAMPLE 162

2-{[1-(4-chlorobenzoyl)azetidin-3-yl]methyl}-4-methyl-N-[2-(2,2,2-trifluoro-ethoxy)ethyl]-2H-indazol-5-carboxamide

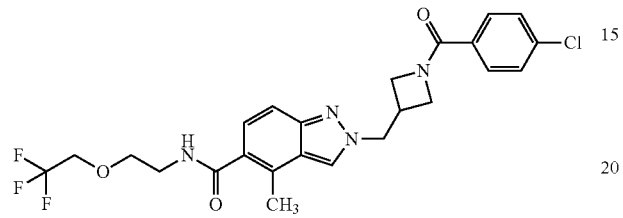

Analogously to Example 55, 197 mg of the title compound was obtained from 252 mg of the compound prepared in Example 162a and 108 mg of 4-chlorobenzoyl chloride.

¹H-NMR (300 MHz, DMSO-d6): δ=2.49 (3H), 3.22 (1H), 3.40 (2H), 3.69 (2H), 3.90 (1H), 4.03-4.13 (3H), 4.19 (1H), 4.37 (1H), 4.67 (2H), 7.15 (1H), 7.38 (1H), 7.48 (2H), 7.59 (2H), 8.19 (1H), 8.55 (1H).

The starting material was prepared as follows:

EXAMPLE 162a 2-(azetidin-3-ylmethyl)-4-methyl-N-[2-(2,2,2-trifluoroethoxy)ethyl]-2H-indazol-5-carboxamide hydrochloride

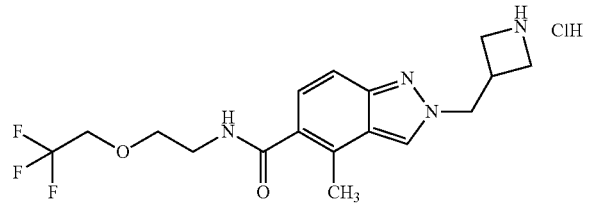 [SMILES: Cc1c(C(=O)NCCOCC(F)(F)F)ccc2nn(CC3CNC3)cc12 ; Cl]

Analogously to Example 1a, from 583 mg of the compound prepared in Example 162b, 505 mg of the title compound was obtained, which was further reacted without purification.

EXAMPLE 162b

Tert-butyl 3-[(4-methyl-5-{N-[2-(2,2,2-trifluoroethoxy)ethyl]carbamoyl}-2H-indazol-2-yl)methyl]azetidin-1-carboxylate

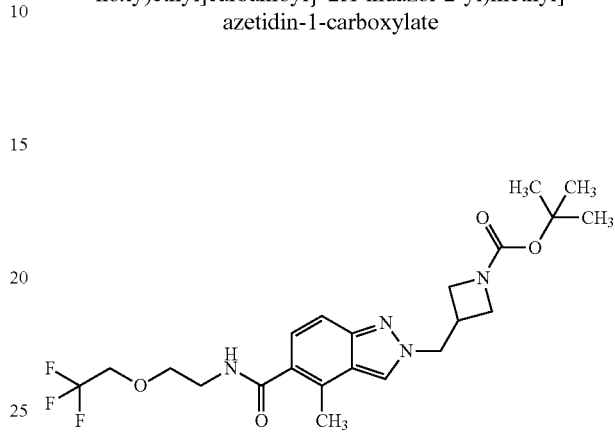

Analogously to Example 1, 580 mg of the title compound was obtained from 500 mg of the compound prepared in Example 117c and 260 mg of 2-(2,2,2-trifluoroethoxy)ethylamine hydrochloride.

¹H-NMR (300 MHz, DMSO-d6): δ=1.32 (9H), 2.50 (3H), 3.08 (1H), 3.40 (2H), 3.61-3.76 (4H), 3.86 (2H), 4.07 (2H), 4.61 (2H), 7.15 (1H), 7.39 (1H), 8.18 (1H), 8.55 (1H).

EXAMPLE 163

4-methyl-N-[2-(2,2,2-trifluoroethoxy)ethyl]-2-[(1-{4-[4-(trifluoromethyl)phenoxy]benzoyl}azetidin-3-yl)methyl]-2H-indazol-5-carboxamide

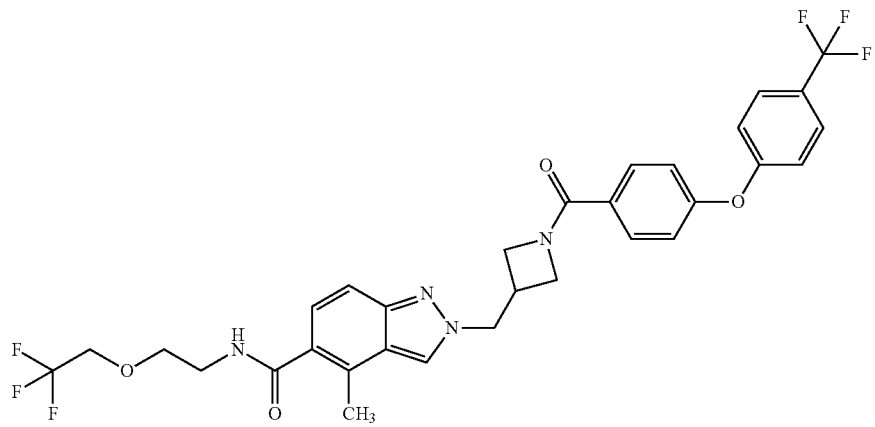 [SMILES: Cc1c(C(=O)NCCOCC(F)(F)F)ccc2nn(CC3CN(C(=O)c4ccc(Oc5ccc(C(F)(F)F)cc5)cc4)C3)cc12]

Analogously to Example 1, 89 mg of the title compound was obtained from 252 mg of the compound prepared in Example 162a and 175 mg of 4-[4-(trifluoromethyl)phenoxy]benzoic acid.

$^1$H-NMR (300 MHz, DMSO-d6): δ=2.49 (3H), 3.23 (1H), 3.40 (2H), 3.69 (2H), 3.90 (1H), 4.01-4.14 (3H), 4.21 (1H), 4.40 (1H), 4.68 (2H), 7.11 (2H), 7.15 (1H), 7.20 (2H), 7.39 (1H), 7.66 (2H), 7.75 (2H), 8.19 (1H), 8.56 (1H).

EXAMPLE 164

4-methyl-N-(2,2,2-trifluoroethyl)-2-[(1-{4-[4-(trifluoromethyl)phenoxy]benzoyl}azetidin-3-yl)methyl]-2H-indazol-5-carboxamide

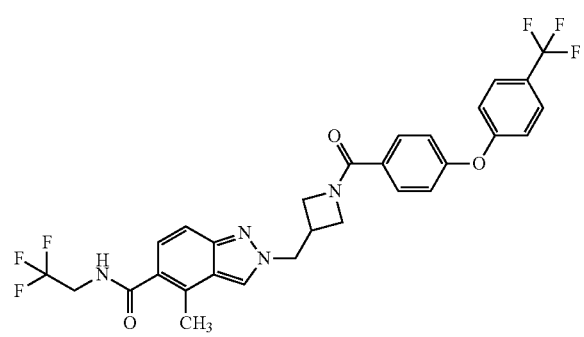 [SMILES: Cc1c(C(=O)NCC(F)(F)F)ccc2nn(CC3CN(C(=O)c4ccc(Oc5ccc(C(F)(F)F)cc5)cc4)C3)cc12]

Analogously to Example 1, 64 mg of the title compound was obtained from 225 mg of the compound prepared in Example 129b and 149 mg of 4-[4-(trifluoromethyl)phenoxy]benzoic acid.

$^1$H-NMR (300 MHz, DMSO-d6): δ=2.50 (3H), 3.24 (1H), 3.91 (1H), 3.95-4.15 (3H), 4.22 (1H), 4.40 (1H), 4.69 (2H), 7.11 (2H), 7.15-7.23 (3H), 7.43 (1H), 7.66 (2H), 7.75 (2H), 8.60 (1H), 8.79 (1H).

EXAMPLE 165

2-({1-[4-(4-chlorophenoxy)benzoyl]azetidin-3-yl}methyl)-4-methyl-N-(2,2,2-trifluoroethyl)-2H-indazol-5-carboxamide

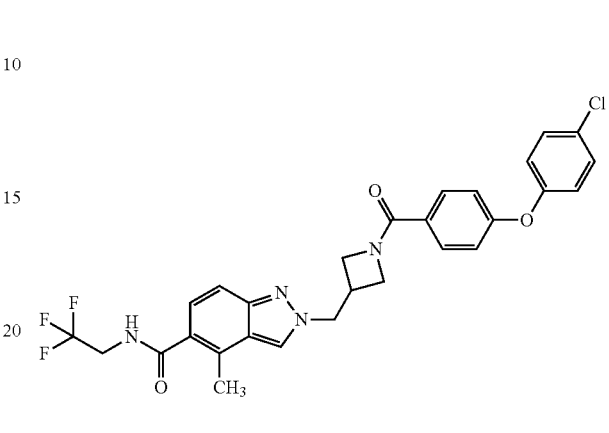

Analogously to Example 1, 97 mg of the title compound was obtained from 225 mg of the compound prepared in Example 129b and 131 mg of 4-(4-chlorophenoxy)benzoic acid.

$^1$H-NMR (300 MHz, DMSO-d6): δ=2.50 (3H), 3.23 (1H), 3.90 (1H), 3.96-4.12 (3H), 4.20 (1H), 4.38 (1H), 4.68 (2H), 7.00 (2H), 7.09 (2H), 7.18 (1H), 7.40-7.48 (3H), 7.62 (2H), 8.60 (1H), 8.79 (1H)

EXAMPLE 166

2-({1-[4-(4-chlorophenoxy)benzoyl]azetidin-3-yl}methyl)-N-(2-methoxyethyl)-4-methyl-2H-indazol-5-carboxamide

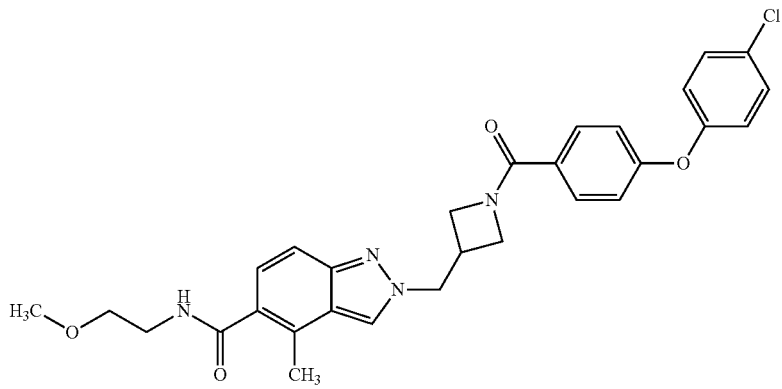 [SMILES: COCCNC(=O)c1ccc2nn(CC3CN(C(=O)c4ccc(Oc5ccc(Cl)cc5)cc4)C3)cc2c1C]

Analogously to Example 1, 99 mg of the title compound was obtained from 225 mg of the compound prepared in Example 117e and 140 mg of 4-(4-chlorophenoxy)benzoic acid.

$^1$H-NMR (300 MHz, DMSO-d6): δ=2.49 (3H), 3.16-3.27 (4H), 3.36 (2H), 3.42 (2H), 3.89 (1H), 4.08 (1H), 4.19 (1H), 4.38 (1H), 4.67 (2H), 7.00 (2H), 7.09 (2H), 7.15 (1H), 7.38 (1H), 7.45 (2H), 7.62 (2H), 8.12 (1H), 8.55 (1H).

EXAMPLE 167

2-({1-[(5-fluoro-1-methyl-1H-indol-2-yl)carbonyl]azetidin-3-yl}methyl)-4-methyl-N-(2,2,2-trifluoroethyl)-2H-indazol-5-carboxamide

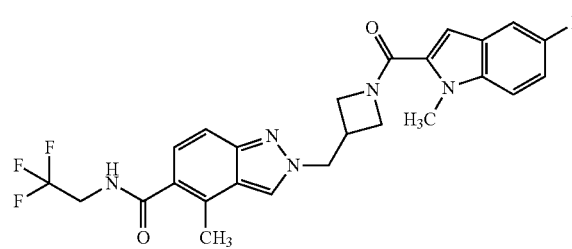

Analogously to Example 1, 48 mg of the title compound was obtained from 180 mg of the compound prepared in Example 129b and 82 mg of 5-fluoro-1-methyl-1H-indol-2-carboxylic acid.

$^1$H-NMR (300 MHz, CDCl3): δ=2.66 (3H), 2.80 (3H), 3.36-3.51 (1H), 4.01 (3H), 4.04-4.63 (6H), 4.70 (2H), 6.03 (1H), 6.68 (1H), 7.08 (1H), 7.22-7.36 (3H), 7.55 (1H), 8.05 (1H).

EXAMPLE 168

2-({1-[(5-methoxy-1-methyl-1H-indol-2-yl)carbonyl]azetidin-3-yl}methyl)-4-methyl-N-(2,2,2-trifluoroethyl)-2H-indazol-5-carboxamide

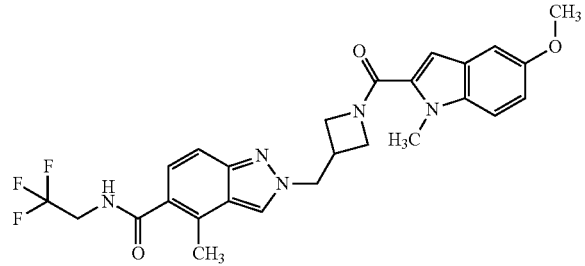 [SMILES: COc1ccc2c(c1)cc(C(=O)N1CC(Cn3cc4c(C)c(C(=O)NCC(F)(F)F)ccc4n3)C1)n2C]

Analogously to Example 1, 15 mg of the title compound was obtained from 180 mg of the compound prepared in Example 129b and 87 mg of 5-methoxy-1-methyl-1H-indol-2-carboxylic acid.

$^1$H-NMR (300 MHz, CDCl3): δ=2.66 (3H), 3.43 (1H), 3.84 (3H), 4.00 (3H), 4.03-4.59 (6H), 4.70 (2H), 6.02 (1H), 6.66 (1H), 7.02 (1H), 7.27-7.35 (3H), 7.56 (1H), 8.06 (1H).

EXAMPLE 169

2-({1-[(6-methoxy-1-methyl-1H-indol-2-yl)carbonyl]azetidin-3-yl}methyl)-4-methyl-N-(2,2,2-trifluoroethyl)-2H-indazol-5-carboxamide Analogously to Example 1, 57 mg of the title compound was obtained from 180 mg of the compound prepared in Example 129b and 87 mg of 6-methoxy-1-methyl-1H-indol-2-carboxylic acid.

$^1$H-NMR (300 MHz, CDCl3): δ=2.66 (3H), 3.43 (1H), 3.89 (3H), 3.99 (3H), 4.05-4.60 (6H), 4.70 (2H), 6.01 (1H), 6.69 (1H), 6.77 (1H), 6.81 (1H), 7.32 (1H), 7.48 (1H), 7.56 (1H), 8.05 (1H).

EXAMPLE 170

2-({1-[(5-fluoro-1-methyl-1H-indol-2-yl)carbonyl]azetidin-3-yl}methyl)-N-(2-methoxyethyl)-4-methyl-2H-indazol-5-carboxamide Analogously to Example 1, 95 mg of the title compound was obtained from 180 mg of the compound prepared in Example 117e and 87 mg of 5-fluoro-1-methyl-1H-indol-2-carboxylic acid.

vNMR (300 MHz, CDCl3): δ=2.65 (3H), 3.35-3.51 (4H), 3.58 (2H), 3.67 (2H), 4.01 (3H), 4.02-4.62 (4H), 4.69 (2H), 6.15 (1H), 6.68 (1H), 7.08 (1H), 7.21-7.38 (3H), 7.53 (1H), 8.02 (1H).

EXAMPLE 171

2-({1-[(5-chloro-1-methyl-1H-indol-2-yl)carbonyl]azetidin-3-yl}methyl)-N-(2-methoxyethyl)-4-methyl-2H-indazol-5-carboxamide

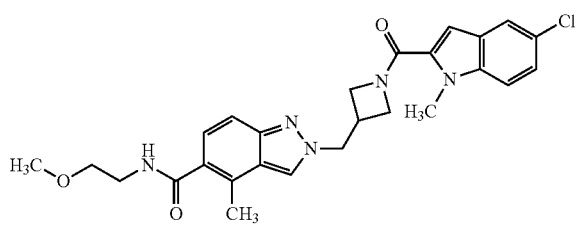 [SMILES: COCCNC(=O)c1ccc2nn(CC3CN(C(=O)c4cc5cc(Cl)ccc5n4C)C3)cc2c1C]

Analogously to Example 1, 90 mg of the title compound was obtained from 180 mg of the compound prepared in Example 117e and 95 mg of 5-chloro-1-methyl-1H-indol-2-carboxylic acid.

$^1$H-NMR (300 MHz, CDCl3): δ=2.66 (3H), 3.37-3.49 (4H), 3.58 (2H), 3.67 (2H), 4.00 (3H), 4.08 (1H), 4.37 (2H), 4.56 (1H), 4.70 (2H), 6.15 (1H), 6.66 (1H), 7.27-7.38 (3H), 7.53 (1H), 7.58 (1H), 8.02 (1H).

EXAMPLE 172

N-(2-methoxyethyl)-2-({1-[(5-methoxy-1-methyl-1H-indol-2-yl)carbonyl]azetidin-3-yl}methyl)-4-methyl-2H-indazol-5-carboxamide

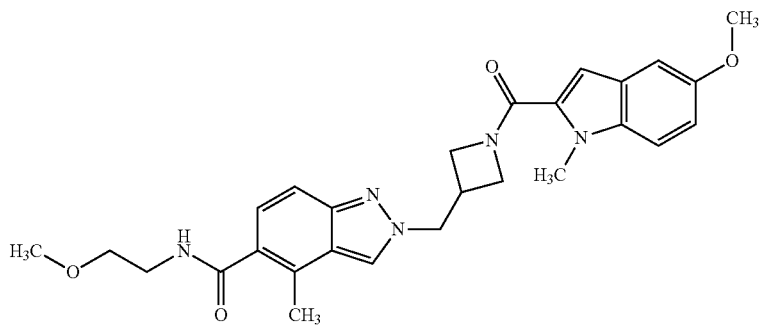

Analogously to Example 1, 86 mg of the title compound was obtained from 180 mg of the compound prepared in Example 117e and 93 mg of 5-methoxy-1-methyl-1H-indol-2-carboxylic acid.

$^1$H-NMR (300 MHz, CDCl3): δ=2.65 (3H), 3.36-3.50 (4H), 3.58 (2H), 3.67 (2H), 3.84 (3H), 4.00 (3H), 4.07 (1H), 4.35 (2H), 4.55 (1H), 4.69 (2H), 6.15 (1H), 6.66 (1H), 6.97-7.06 (2H), 7.28 (1H), 7.34 (1H), 7.53 (1H), 8.02 (1H).

EXAMPLE 173

N-(2-methoxyethyl)-2-({1-[(6-methoxy-1-methyl-1H-indol-2-yl)carbonyl]azetidin-3-yl}methyl)-4-methyl-2H-indazol-5-carboxamide

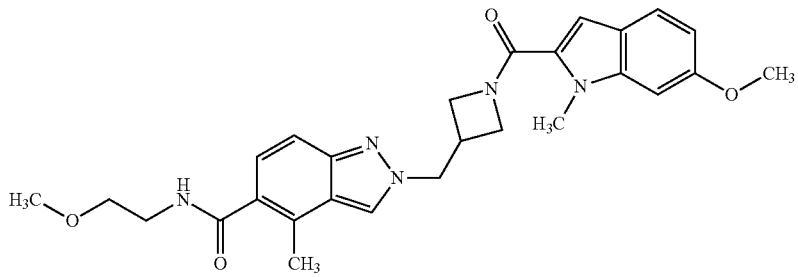

Analogously to Example 1, 97 mg of the title compound was obtained from 180 mg of the compound prepared in Example 117e and 93 mg of 6-methoxy-1-methyl-1H-indol-2-carboxylic acid.

$^1$H-NMR (300 MHz, CDCl3): δ=2.66 (3H), 3.37-3.47 (4H), 3.58 (2H), 3.67 (2H), 3.89 (3H), 3.99 (3H), 4.02-4.60 (4H), 4.69 (2H), 6.15 (1H), 6.69 (1H), 6.77 (1H), 6.81 (1H), 7.34 (1H), 7.48 (1H), 7.53 (1H), 8.02 (1H).

EXAMPLE 174

N-(2-methoxyethyl)-4-methyl-2-{[1-(4-{[5-(trifluoromethyl)pyridin-2-yl]oxy}benzoyl)azetidin-3-yl]methyl}-2H-indazol-5-carboxamide

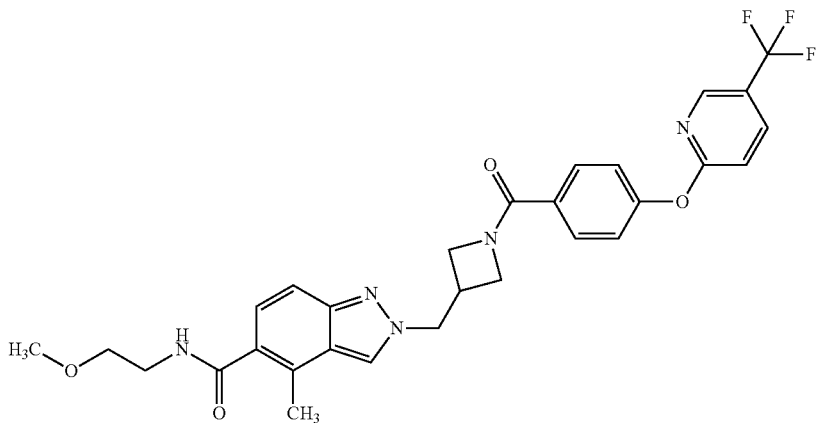 [SMILES: COCCNC(=O)c1ccc2nn(CC3CN(C(=O)c4ccc(Oc5ccc(C(F)(F)F)cn5)cc4)C3)cc2c1C]

Analogously to Example 1, 66 mg of the title compound was obtained from 135 mg of the compound prepared in Example 117e and 96 mg of 4-{[5-(trifluoromethyl)pyridin-2-yl]oxy}-benzoic acid.

$^1$H-NMR (300 MHz, DMSO-d6): δ=2.50 (3H), 3.18-3.27 (4H), 3.36 (2H), 3.42 (2H), 3.91 (1H), 4.10 (1H), 4.24 (1H), 4.42 (1H), 4.68 (2H), 7.15 (1H), 7.24 (2H), 7.28 (1H), 7.39 (1H), 7.67 (2H), 8.12 (1H), 8.24 (1H), 8.56 (2H).

EXAMPLE 175

N-(2-methoxyethyl)-2-{[1-(7-methoxy-2-naphthoyl)azetidin-3-yl]methyl}-4-methyl-2H-indazol-5-carboxamide

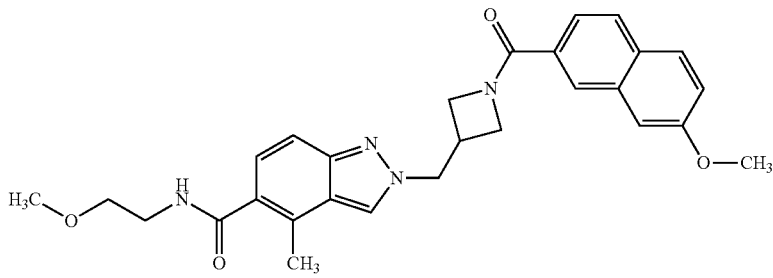

Analogously to Example 1, 72 mg of the title compound was obtained from 135 mg of the compound prepared in Example 117e and 69 mg of 7-methoxy-naphthalen-2-carboxylic acid.

$^1$H-NMR (300 MHz, DMSO-d6): δ=2.50 (3H), 3.21-3.28 (4H), 3.36 (2H), 3.42 (2H), 3.85 (3H), 3.93-3.99 (1H), 4.14 (1H), 4.26 (1H), 4.47 (1H), 4.69 (2H), 7.15 (1H), 7.22 (1H), 7.38 (1H), 7.43 (1H), 7.50 (1H), 7.81-7.88 (2H), 8.05 (1H), 8.12 (1H), 8.56 (1H).

EXAMPLE 176

N-(2-methoxyethyl)-2-{[1-(6-methoxy-2-naphthoyl)azetidin-3-yl]methyl}-4-methyl-2H-indazol-5-carboxamide

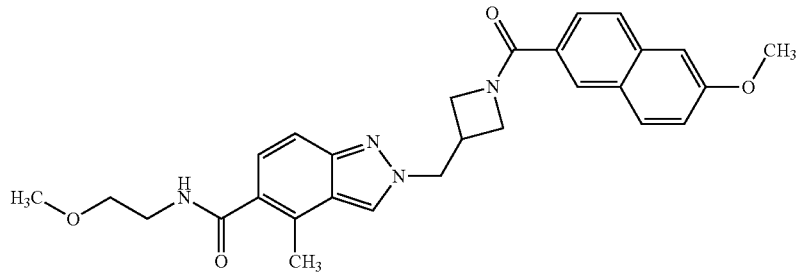

Analogously to Example 1, 72 mg of the title compound was obtained from 135 mg of the compound prepared in Example 117e and 69 mg of 6-methoxynaphthalen-2-carboxylic acid.

¹H-NMR (300 MHz, DMSO-d6): δ=2.49 (3H), 3.21-3.28 (4H), 3.33-3.39 (2H), 3.42 (2H), 3.86 (3H), 3.91-3.98 (1H), 4.13 (1H), 4.27 (1H), 4.48 (1H), 4.69 (2H), 7.15 (1H), 7.19 (1H), 7.34 (1H), 7.38 (1H), 7.63 (1H), 7.82 (1H), 7.92 (1H), 8.08-8.14 (2H), 8.56 (1H).

EXAMPLE 177

4-methyl-N-(2,2,2-trifluoroethyl)-2-{[1-(4-{[5-(trifluoromethyl)pyridin-2-yl]oxy}benzoyl)azetidin-3-yl]methyl}-2H-indazol-5-carboxamide

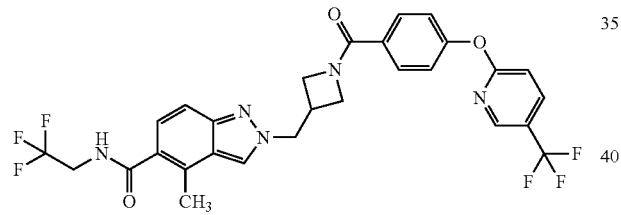

Analogously to Example 1, 68 mg of the title compound was obtained from 170 mg of the compound prepared in Example 129b and 113 mg of 4-{[5-(trifluoromethyl)pyridin-2-yl]oxy}benzoic acid.

¹H-NMR (300 MHz, DMSO-d6): δ=2.35 (3H), 3.21 (1H), 3.89 (1H), 3.96-4.13 (3H), 4.21 (1H), 4.40 (1H), 4.68 (2H), 7.24 (2H), 7.28 (1H), 7.40 (1H), 7.66 (2H), 7.72 (1H), 8.24 (1H), 8.48 (1H), 8.56 (1H), 8.89 (1H).

EXAMPLE 178

2-{[1-(4-chlorobenzoyl)azetidin-3-yl]methyl}-N-(2-methoxyethyl)-6-methyl-2H-indazol-5-carboxamide

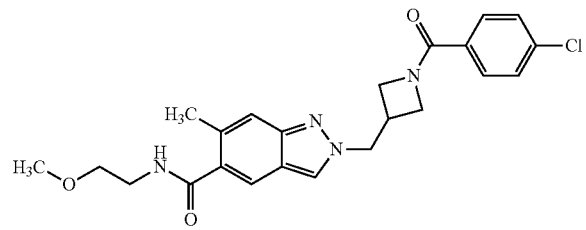 [SMILES: COCCNC(=O)c1cc2cn(CC3CN(C(=O)c4ccc(Cl)cc4)C3)nc2cc1C]

Analogously to Example 55, 154 mg of the title compound was obtained from 210 mg of the compound prepared in Example 178e and 119 mg of 4-chlorobenzoyl chloride.

¹H-NMR (300 MHz, DMSO-d6): δ=2.34 (3H), 3.19 (1H), 3.24 (3H), 3.34 (2H), 3.42 (2H), 3.87 (1H), 4.07 (1H), 4.16 (1H), 4.34 (1H), 4.65 (2H), 7.35 (1H), 7.48 (2H), 7.59 (2H), 7.63 (1H), 8.21 (1H), 8.41 (1H).

The starting material was prepared as follows:

EXAMPLE 178a

Tert-butyl 3-[(5-bromo-6-methyl-2H-indazol-2-yl)methyl]azetidin-1-carboxylate

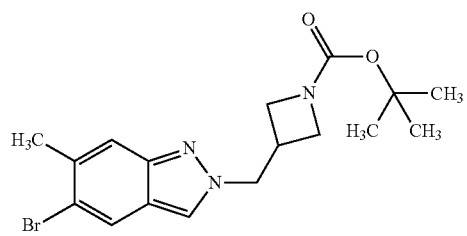 [SMILES: Cc1cc2nn(CC3CN(C(=O)OC(C)(C)C)C3)cc2cc1Br]

To a solution of 6.18 g of 5-bromo-6-methyl-1H-indazole and 15 g of tert-butyl-3-[(tosyl-oxy)methyl]azetidin-1-carboxylate in 200 ml DMF were added 9.54 g of caesium carbonate and 10.8 g of tetrabutylammonium iodide at 25° C., and this was then heated under reflux for 1.5 hrs. After cooling, the reaction mixture was treated with 1:1 hexane/ether and water, the phases separated and the aqueous phase extracted twice with 250 ml portions of 1:1 hexane/ether. The combined organic phases were washed with saturated sodium chloride solution, dried over sodium sulphate, and concentrated in vacuo after filtration.

The residue thus obtained was purified by twofold column chromatography on silica gel with hexane/0-20% ethyl acetate. 2.88 g of the title compound was obtained.

¹H-NMR (300 MHz, DMSO-d6): δ=1.32 (9H), 2.37 (3H), 3.05 (1H), 3.67 (2H), 3.85 (2H), 4.59 (2H), 7.56 (1H), 7.97 (1H), 8.33 (1H).

EXAMPLE 178b

Methyl 2-{[1-(tert-butoxycarbonyl)azetidin-3-yl]methyl}-6-methyl-2H-indazol-5-carboxylate

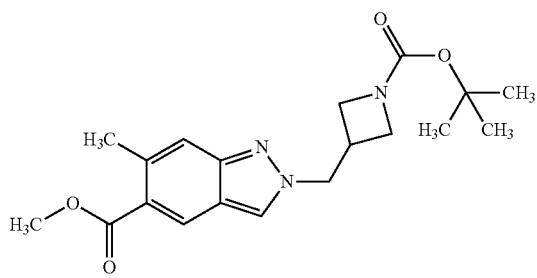 [SMILES: COC(=O)c1cc2cn(CC3CN(C(=O)OC(C)(C)C)C3)nc2cc1C]

To a solution of 730 mg of the bromide prepared in Example 178a in 17.5 ml tetrahydrofuran were added 0.23 ml of methanol, 145 mg of trans-bis(acetato)-bis[o-(di-o-tolylphosphino)-benzyl]dipalladium(II), 877 mg of DBU and 760 mg of molybdenum hexacarbonyl This reaction mixture was then heated in the microwave (120 watts) for 20 minutes at 125° C. Seven further preparations were performed in the same manner and all worked up together. For this, they were concentrated in vacuo and the residue taken up in water and ethyl acetate. After phase separation, the aqueous phase was extracted three times with 75 ml portions of ethyl acetate and the combined organic phases washed with saturated sodium chloride solution, dried over sodium sulphate and concentrated in vacuo after filtration. The residue thus obtained was purified by twofold column chromatography on silica gel with hexane/0-30% ethyl acetate. Yield: 4.0 g of the title compound.

$^1$H-NMR (300 MHz, DMSO-d6): δ=1.32 (9H), 2.52 (3H), 3.07 (1H), 3.69 (2H), 3.86 (2H), 3.78 (3H), 4.62 (2H), 7.43 (1H), 8.33 (1H), 8.53 (1H).

EXAMPLE 178c

2-{[1-(tert-butoxycarbonyl)azetidin-3-yl]methyl}-6-methyl-2H-indazol-5-carboxylic acid

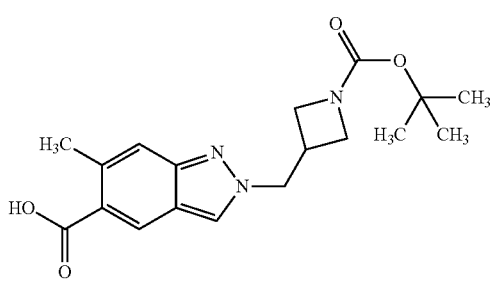 [SMILES: Cc1cc2nn(CC3CN(C(=O)OC(C)(C)C)C3)cc2cc1C(=O)O]

Analogously to Example 1d, 3.2 g of the title compound was obtained from 4.0 g of the ester prepared in Example 178b.

$^1$H-NMR (300 MHz, DMSO-d6): δ=1.32 (9H), 2.53 (3H), 3.07 (1H), 3.69 (2H), 3.86 (2H), 4.61 (2H), 7.39 (1H), 8.31 (1H), 8.50 (1H), 12.48 (1H).

EXAMPLE 178d

Tert-butyl 3-({5-[N-(2-methoxyethyl)carbamoyl]-6-methyl-2H-indazol-2-yl}-methyl)azetidin-1-carboxylate

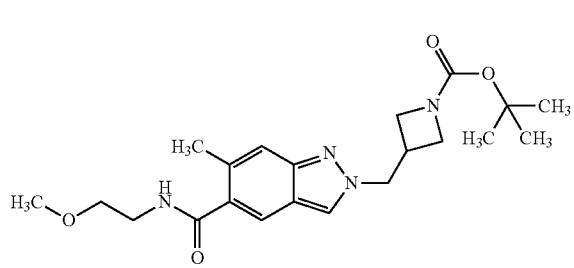 [SMILES: COCCNC(=O)c1cc2cn(CC3CN(C(=O)OC(C)(C)C)C3)nc2cc1C]

Analogously to Example 1, 603 mg of the title compound was obtained from 500 mg of the acid prepared in Example 178c and 109 mg of 2-methoxyethylamine.

$^1$H-NMR (300 MHz, DMSO-d6): δ=1.32 (9H), 2.34 (3H), 3.06 (1H), 3.25 (3H), 3.32-3.45 (4H), 3.67 (2H), 3.84 (2H), 4.59 (2H), 7.35 (1H), 7.64 (1H), 8.21 (1H), 8.41 (1H).

EXAMPLE 178e 2-(azetidin-3-ylmethyl)-N-(2-methoxyethyl)-6-methyl-2H-indazol-5-carboxamide hydrochloride

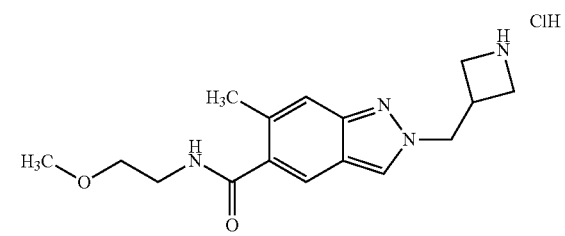 [SMILES: Cl ; COCCNC(=O)c1cc2cn(CC3CNC3)nc2cc1C]

Analogously to Example 1a, from 250 mg of the amide prepared in Example 178d, 275 mg of the title compound was obtained, which was reacted without further purification.

EXAMPLE 179

2-{[1-(3,5-Difluorobenzoyl)azetidin-3-yl]methyl}-N-(2-methoxyethyl)-6-methyl-2H-indazol-5-carboxamide

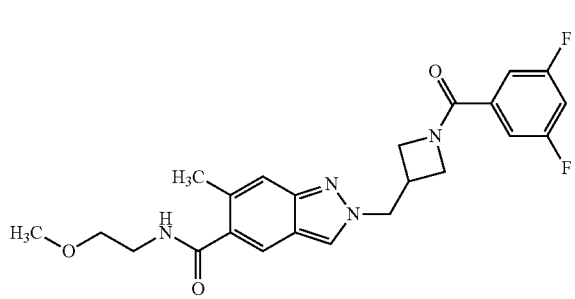 [SMILES: COCCNC(=O)c1cc2cn(CC3CN(C(=O)c4cc(F)cc(F)c4)C3)nc2cc1C]

Analogously to Example 55, 51 mg of the title compound was obtained from 77 mg of the compound prepared in Example 178e and 44 mg of 3,5-difluorobenzoyl chloride.

$^1$H-NMR (300 MHz, DMSO-d6): δ=2.33 (3H), 3.18 (1H), 3.24 (3H), 3.34 (2H), 3.42 (2H), 3.87 (1H), 4.03-4.11 (1H), 4.20 (1H), 4.38 (1H), 4.65 (2H), 7.20-7.28 (2H), 7.34 (1H), 7.36-7.45 (2H), 7.64 (1H), 8.22 (1H), 8.42 (1H).

EXAMPLE 180

N-(2-methoxyethyl)-6-methyl-2-[(1-{4-[(trifluoromethyl)sulphanyl]benzoyl}azetidin-3-yl)methyl]-2H-indazol-5-carboxamide

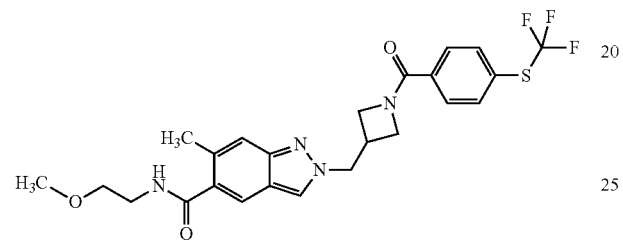

Analogously to Example 55, 30 mg of the title compound was obtained from 43 mg of the compound prepared in Example 178e and 34 mg of 4-[(trifluoromethyl)sulphanyl]benzoyl chloride.

$^1$H-NMR (300 MHz, DMSO-d6): δ=2.34 (3H), 3.20 (1H), 3.24 (3H), 3.34 (2H), 3.42 (2H), 3.89 (1H), 4.09 (1H), 4.17 (1H), 4.36 (1H), 4.65 (2H), 7.34 (1H), 7.63 (1H), 7.69 (2H), 7.76 (2H), 8.21 (1H), 8.41 (1H).

EXAMPLE 181

N-(2-methoxyethyl)-6-methyl-2-({1-[4-(trifluoromethoxy)benzoyl]azetidin-3-yl}methyl)-2H-indazol-5-carboxamide

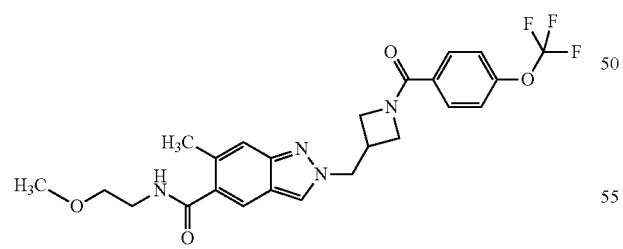

Analogously to Example 55, 221 mg of the title compound was obtained from 294 mg of the compound prepared in Example 178e and 214 mg of 4-(trifluoromethoxy)benzoyl chloride.

$^1$H-NMR (300 MHz, DMSO-d6): δ=2.34 (3H), 3.20 (1H), 3.25 (3H), 3.34 (2H), 3.42 (2H), 3.89 (1H), 4.08 (1H), 4.18 (1H), 4.36 (1H), 4.65 (2H), 7.35 (1H), 7.40 (2H), 7.64 (1H), 7.70 (2H), 8.21 (1H), 8.42 (1H).

EXAMPLE 182

2-({1-[2-fluoro-4-(trifluoromethyl)benzoyl]azetidin-3-yl}methyl)-N-(2-methoxy-ethyl)-6-methyl-2H-indazol-5-carboxamide

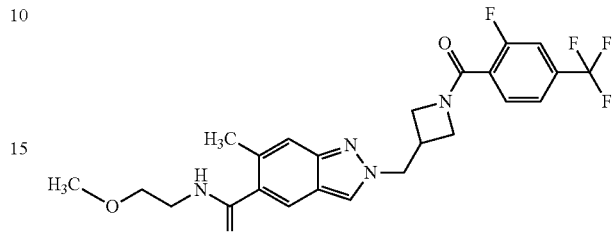

Analogously to Example 55, 11 mg of the title compound was obtained from 43 mg of the compound prepared in Example 178e and 32 mg of 2-fluoro-4-(trifluoromethyl)benzoyl chloride.

$^1$H-NMR (300 MHz, DMSO-d6): δ=2.33 (3H), 3.20 (1H), 3.24 (3H), 3.35 (2H), 3.42 (2H), 3.86-3.95 (2H), 4.02-4.16 (2H), 4.65 (2H), 7.34 (1H), 7.61-7.69 (3H), 7.79 (1H), 8.21 (1H), 8.41 (1H).

EXAMPLE 183

2-{[1-(4-chloro-2-fluorobenzoyl)azetidin-3-yl]methyl}-N-(2-methoxyethyl)-6-methyl-2H-indazol-5-carboxamide

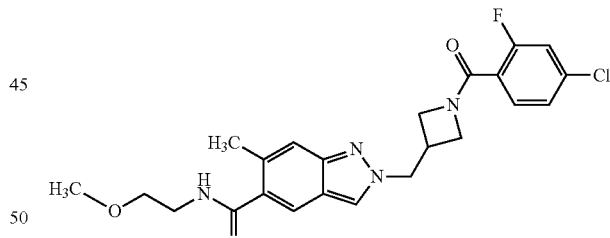

Analogously to Example 55, from 70 mg of the compound prepared in Example 178e and 44 mg of 4-chloro-2-fluorobenzoyl chloride, a material still contaminated after HPLC purification was obtained, which was further purified by additional preparative thick layer chromatography with ethyl acetate/methanol in the ratio 9:1 as mobile phase. This yielded 12 mg of the title compound.

$^1$H-NMR (300 MHz, DMSO-d6): δ=2.34 (3H), 3.19 (1H), 3.25 (3H), 3.34 (2H), 3.42 (2H), 3.84-3.93 (2H), 4.02-4.10 (2H), 4.64 (2H), 7.32-7.36 (2H), 7.46 (1H), 7.53 (1H), 7.63 (1H), 8.22 (1H), 8.41 (1H).

EXAMPLE 184

2-({1-[3-fluoro-4-(trifluoromethyl)benzoyl]azetidin-3-yl}methyl)-N-(2-methoxy-ethyl)-6-methyl-2H-indazol-5-carboxamide

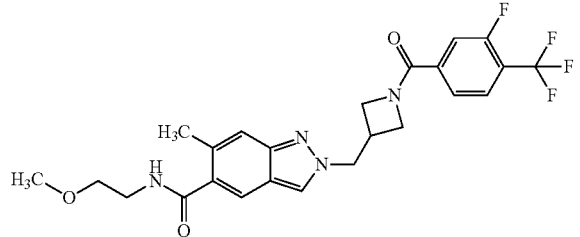 [SMILES: COCCNC(=O)c1cc2cn(CC3CN(C(=O)c4ccc(C(F)(F)F)c(F)c4)C3)nc2cc1C]

Analogously to Example 55, 32 mg of the title compound was obtained from 70 mg of the compound prepared in Example 178e and 52 mg of 3-fluoro-4-(trifluoromethyl)benzoyl chloride.

$^1$H-NMR (300 MHz, DMSO-d6): δ=2.34 (3H), 3.20 (1H), 3.24 (3H), 3.30-3.38 (2H), 3.42 (2H), 3.90 (1H), 4.10 (1H), 4.19 (1H), 4.38 (1H), 4.66 (2H), 7.34 (1H), 7.57 (1H), 7.60-7.67 (2H), 7.85 (1H), 8.21 (1H), 8.41 (1H).

EXAMPLE 185

2-({1-[4-chloro-3-(trifluoromethyl)benzoyl]azetidin-3-yl}methyl)-N-(2-methoxy-ethyl)-6-methyl-2H-indazol-5-carboxamide

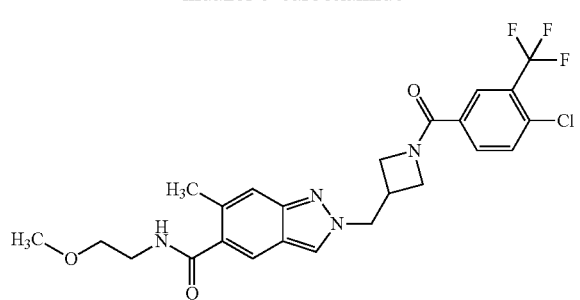 [SMILES: COCCNC(=O)c1cc2cn(CC3CN(C(=O)c4ccc(Cl)c(C(F)(F)F)c4)C3)nc2cc1C]

Analogously to Example 55, 30 mg of the title compound was obtained from 70 mg of the compound prepared in Example 178e and 55 mg of 4-chloro-3-(trifluoromethyl)benzoyl chloride.

$^1$H-NMR (300 MHz, DMSO-d6): δ=2.34 (3H), 3.19 (1H), 3.24 (3H), 3.34 (2H), 3.42 (2H), 3.89 (1H), 4.10 (1H), 4.20 (1H), 4.35-4.43 (1H), 4.65 (2H), 7.33 (1H), 7.64 (1H), 7.78 (1H), 7.85 (1H), 7.93 (1H), 8.21 (1H), 8.40 (1H).

EXAMPLE 186

N-(2-methoxyethyl)-6-methyl-2-({1-[4-(trifluoromethyl)benzoyl]azetidin-3-yl}methyl)-2H-indazol-5-carboxamide

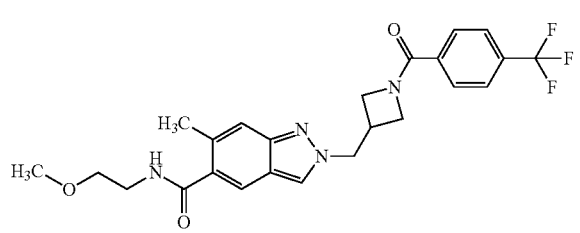 [SMILES: COCCNC(=O)c1cc2cn(CC3CN(C(=O)c4ccc(C(F)(F)F)cc4)C3)nc2cc1C]

Analogously to Example 55, 31 mg of the title compound was obtained from 70 mg of the compound prepared in Example 178e and 47 mg of 4-(trifluoromethyl)benzoyl chloride.

$^1$H-NMR (300 MHz, DMSO-d6): δ=2.34 (3H), 3.20 (1H), 3.24 (3H), 3.35 (2H), 3.42 (2H), 3.90 (1H), 4.06-4.21 (2H), 4.35 (1H), 4.66 (2H), 7.34 (1H), 7.63 (1H), 7.73-7.82 (4H), 8.21 (1H), 8.41 (1H).

EXAMPLE 187

6-methyl-2-({1-[4-(pentafluoro-λ$^6$-sulphanyl)benzoyl]azetidin-3-yl}methyl)-N-{2-[(trifluoromethyl)sulphanyl]ethyl}-2H-indazol-5-carboxamide

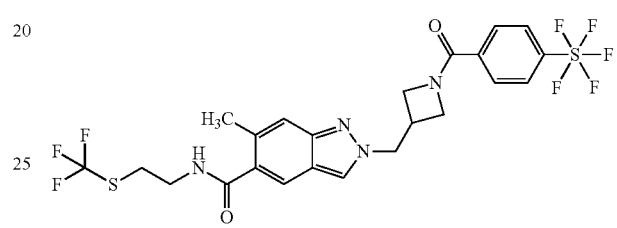

Analogously to Example 1, 35 mg of the title compound was obtained from 170 mg of the compound prepared in Example 187b and 103 mg of 4-(pentafluoro-λ$^6$-sulphanyl)benzoic acid.

$^1$H-NMR (300 MHz, DMSO-d6): δ=2.36 (3H), 3.12-3.23 (3H), 3.49 (2H), 3.91 (1H), 4.06-4.21 (2H), 4.36 (1H), 4.66 (2H), 7.36 (1H), 7.69 (1H), 7.76 (2H), 7.95 (2H), 8.44 (1H), 8.46 (1H).

The starting material was prepared as follows:

EXAMPLE 187a

Tert-butyl 3-{[6-methyl-5-(N-{2-[(trifluoromethyl)sulphanyl]ethyl}carbamoyl)-2H-indazol-2-yl]methyl}azetidin-1-carboxylate

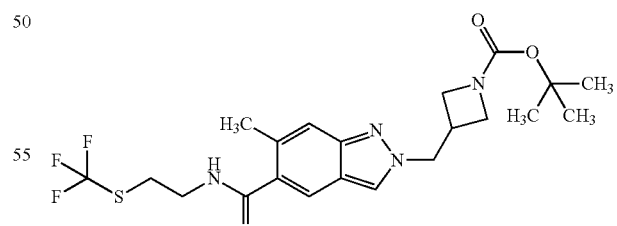

Analogously to Example 1, 998 mg of the title compound was obtained from 800 mg of the acid prepared in Example 178c and 336 mg of 2-[(trifluoromethyl)sulphanyl]ethylamine.

$^1$H-NMR (300 MHz, DMSO-d6): δ=1.32 (9H), 2.36 (3H), 3.06 (1H), 3.13-3.21 (2H), 3.49 (2H), 3.67 (2H), 3.84 (2H), 4.59 (2H), 7.37 (1H), 7.70 (1H), 8.44 (1H), 8.47 (1H).

EXAMPLE 187b 2-(azetidin-3-ylmethyl)-6-methyl-N-{2-[(trifluoromethyl)sulphanyl]ethyl}-2H-indazol-5-carboxamide hydrochloride

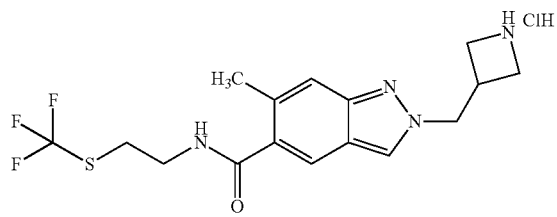 [SMILES: Cl ; Cc1cc2nn(CC3CNC3)cc2cc1C(=O)NCCSC(F)(F)F]

Analogously to Example 1a), from 395 mg of the amide prepared in Example 187a), 402 mg of the title compound was obtained, which was reacted without further purification.

EXAMPLE 188

6-methyl-2-({1-[4-(pentafluoro-λ⁶-sulphanyl)benzoyl]azetidin-3-yl}methyl)-N-(2,2,2-trifluoroethyl)-2H-indazol-5-carboxamide

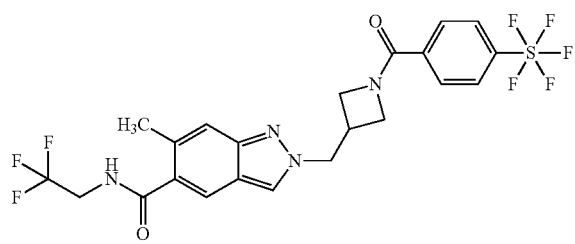 [SMILES: Cc1cc2nn(CC3CN(C(=O)c4ccc(S(F)(F)(F)(F)F)cc4)C3)cc2cc1C(=O)NCC(F)(F)F]

Analogously to Example 1, 25 mg of the title compound was obtained from 136 mg of the compound prepared in Example 188b and 93 mg of 4-(pentafluoro-λ⁶-sulphanyl)benzoic acid.

¹H-NMR (300 MHz, DMSO-d6): δ=2.34 (3H), 3.20 (1H), 3.91 (1H), 3.95-4.21 (4H), 4.36 (1H), 4.67 (2H), 7.38 (1H), 7.71 (1H), 7.76 (2H), 7.95 (2H), 8.45 (1H), 8.86 (1H).

The starting material was prepared as follows:

EXAMPLE 188a

Tert-butyl 3-({6-methyl-5-[N-(2,2,2-trifluoroethyl)carbamoyl]-2H-indazol-2-yl}methyl)azetidin-1-carboxylate

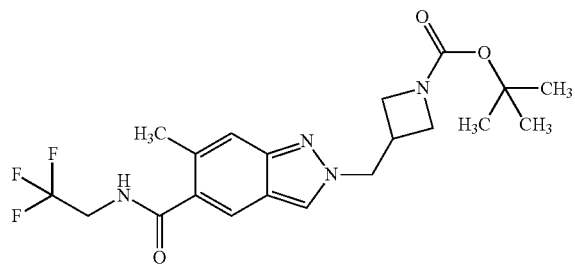 [SMILES: Cc1cc2nn(CC3CN(C(=O)OC(C)(C)C)C3)cc2cc1C(=O)NCC(F)(F)F]

Analogously to Example 1, 550 mg of the title compound was obtained from 560 mg of the acid prepared in Example 178c and 160 mg of 2,2,2-trifluoroethylamine ¹H-NMR (300 MHz, DMSO-d6): δ=1.32 (9H), 2.34 (3H), 3.06 (1H), 3.67 (2H), 3.84 (2H), 3.93-4.10 (2H), 4.60 (2H), 7.40 (1H), 7.71 (1H), 8.46 (1H), 8.88 (1H).

EXAMPLE 188b 2-(azetidin-3-ylmethyl)-6-methyl-N-(2,2,2-trifluoroethyl)-2H-indazol-5-carboxamide hydrochloride

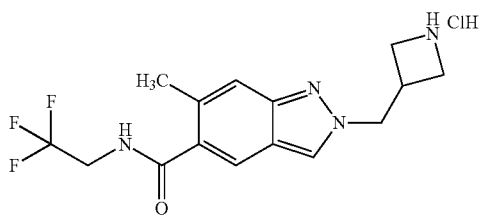 [SMILES: Cl ; Cc1cc2nn(CC3CNC3)cc2cc1C(=O)NCC(F)(F)F]

Analogously to Example 1a, from 550 mg of the amide prepared in Example 188a, 530 mg of the title compound was obtained, which was reacted without further purification.

EXAMPLE 189

2-{[1-(4-chlorobenzoyl)azetidin-3-yl]methyl}-6-methyl-N-{2-[(trifluoromethyl) sulphanyl]ethyl}-2H-indazol-5-carboxamide

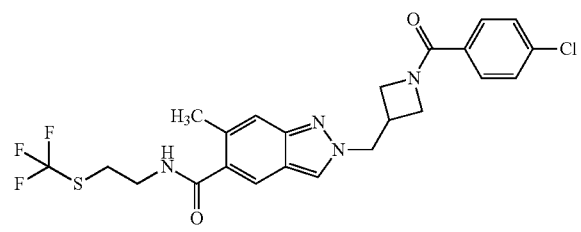

Analogously to Example 55, 45 mg of the title compound was obtained from 170 mg of the compound prepared in Example 187b and 80 mg of 4-chlorobenzoyl chloride.

¹H-NMR (300 MHz, DMSO-d6): δ=2.39 (3H), 3.17-3.27 (3H), 3.52 (2H), 3.90 (1H), 4.10 (1H), 4.19 (1H), 4.37 (1H), 4.68 (2H), 7.39 (1H), 7.50 (2H), 7.61 (2H), 7.72 (1H), 8.47 (1H), 8.49 (1H).

EXAMPLE 190

2-{[1-(4-chlorobenzoyl)azetidin-3-yl]methyl}-6-methyl-N-(2,2,2-trifluoroethyl)-2H-indazol-5-carboxamide

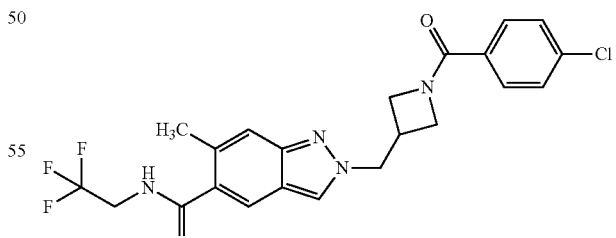

Analogously to Example 55, 60 mg of the title compound was obtained from 136 mg of the compound prepared in Example 188b and 72 mg of 4-chlorobenzoyl chloride.

¹H-NMR (300 MHz, DMSO-d6): δ=2.34 (3H), 3.20 (1H), 3.87 (1H), 3.94-4.11 (3H), 4.16 (1H), 4.35 (1H), 4.66 (2H), 7.39 (1H), 7.48 (2H), 7.59 (2H), 7.71 (1H), 8.46 (1H), 8.89 (1H).

EXAMPLE 191

(+/−)-2-{[1-(4-chlorobenzoyl)azetidin-3-yl]methyl}-6-methyl-N-(3,4,5,6-tetrahydro-2H-pyran-2-ylmethyl)-2H-indazol-5-carboxamide

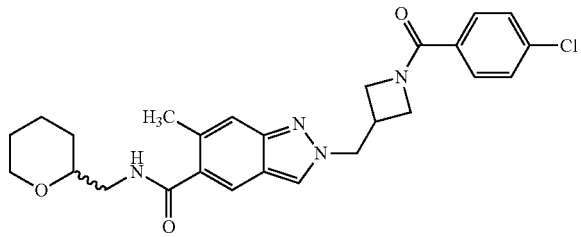 [SMILES: Cc1cc2nn(CC3CN(C(=O)c4ccc(Cl)cc4)C3)cc2cc1C(=O)NCC1CCCCO1]

Analogously to Example 55, 49 mg of the title compound was obtained from 120 mg of the compound prepared in Example 191b and 61 mg of 4-chlorobenzoyl chloride.

$^1$H-NMR (300 MHz, DMSO-d6): δ=1.08-1.23 (1H), 1.36-1.49 (3H), 1.62 (1H), 1.72-1.80 (1H), 2.34 (3H), 3.10-3.43 (5H), 3.80-3.92 (2H), 4.07 (1H), 4.16 (1H), 4.34 (1H), 4.65 (2H), 7.34 (1H), 7.47 (2H), 7.59 (2H), 7.63 (1H), 8.16 (1H), 8.40 (1H).

The starting material was prepared as follows:

EXAMPLE 191a (+/−)-tert-butyl 3-({6-methyl-5-[N-(3,4,5,6-tetrahydro-2H-pyran-2-ylmethyl)-carbamoyl]-2H-indazol-2-yl}methyl)azetidin-1-carboxylate

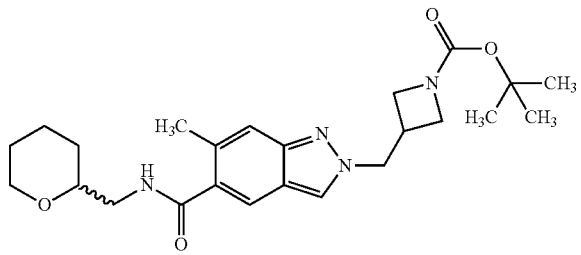 [SMILES: Cc1cc2nn(CC3CN(C(=O)OC(C)(C)C)C3)cc2cc1C(=O)NCC1CCCCO1]

Analogously to Example 1, 140 mg of the title compound was obtained from 300 mg of the acid prepared in Example 178c and 105 mg of 3,4,5,6-tetrahydro-2H-pyran-2-ylmethylamine.

$^1$H-NMR (300 MHz, DMSO-d6): δ=1.07-1.24 (1H), 1.27-1.49 (12H), 1.62 (1H), 1.76 (1H), 2.33 (3H), 3.06 (1H), 3.20 (2H), 3.29-3.45 (2H), 3.67 (2H), 3.78-3.90 (3H), 4.59 (2H), 7.35 (1H), 7.63 (1H), 8.16 (1H), 8.40 (1H).

EXAMPLE 191b (+/−)-2-(azetidin-3-ylmethyl)-6-methyl-N-(3,4,5,6-tetrahydro-2H-pyran-2-ylmethyl)-2H-indazol-5-carboxamide hydrochloride

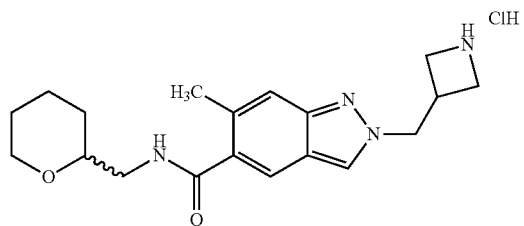 [SMILES: Cl ; Cc1cc2nn(CC3CNC3)cc2cc1C(=O)NCC1CCCCO1]

Analogously to Example 1a, from 140 mg of the amide prepared in Example 191a, 132 mg of the title compound was obtained, which was reacted without further purification.

EXAMPLE 192

(+/−)-2-{[1-(4-chlorobenzoyl)azetidin-3-yl]methyl}-N-(2-methoxypropyl)-6-methyl-2H-indazol-5-carboxamide

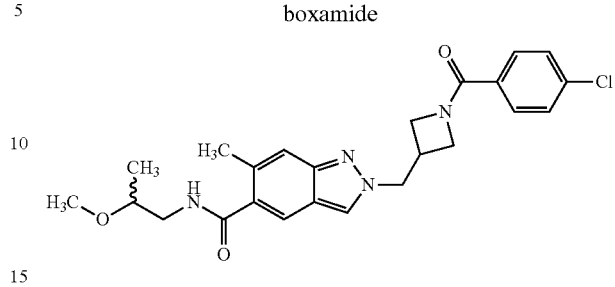

Analogously to Example 55, 89 mg of the title compound was obtained from 151 mg of the compound prepared in Example 192b and 82 mg of 4-chlorobenzoyl chloride.

$^1$H-NMR (300 MHz, DMSO-d6): δ=1.08 (3H), 2.34 (3H), 3.13-3.32 (6H), 3.43 (1H), 3.87 (1H), 4.07 (1H), 4.16 (1H), 4.34 (1H), 4.65 (2H), 7.35 (1H), 7.48 (2H), 7.59 (2H), 7.63 (1H), 8.18 (1H), 8.41 (1H).

The starting material was prepared as follows:

EXAMPLE 192a (+/−)-tert-butyl 3-({5-[N-(2-methoxypropyl)carbamoyl]-6-methyl-2H-indazol-2-yl}methyl)azetidin-1-carboxylate

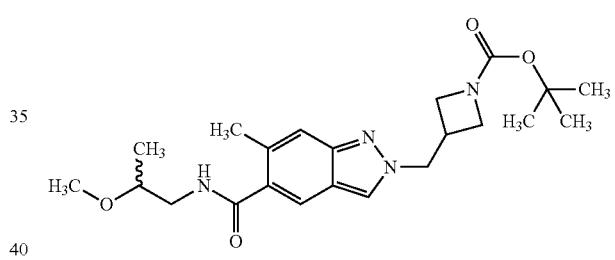

Analogously to Example 1, 358 mg of the title compound was obtained from 300 mg of the acid prepared in Example 178c and 77 mg of 2-methoxypropan-1-amine.

$^1$H-NMR (300 MHz, DMSO-d6): δ=1.08 (3H), 1.32 (9H), 2.34 (3H), 3.06 (1H), 3.13-3.31 (5H), 3.43 (1H), 3.67 (2H), 3.84 (2H), 4.59 (2H), 7.35 (1H), 7.64 (1H), 8.18 (1H), 8.40 (1H).

EXAMPLE 192b (+/−)-2-(azetidin-3-ylmethyl)-N-(2-methoxypropyl)-6-methyl-2H-indazol-5-carboxamide hydrochloride

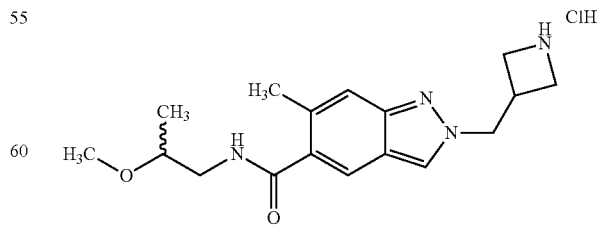

Analogously to Example 1a), from 358 mg of the amide prepared in Example 192a), 319 mg of the title compound was obtained, which was reacted without further purification.

EXAMPLE 193

(+/−)-N-(2-methoxypropyl)-6-methyl-2-({1-[4-(trifluoromethoxy)benzoyl]-azetidin-3-yl}methyl)-2H-indazol-5-carboxamide

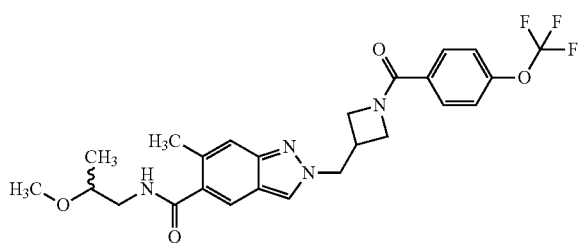 [SMILES: COC(C)CNC(=O)c1cc2cn(CC3CN(C(=O)c4ccc(OC(F)(F)F)cc4)C3)nc2cc1C]

Analogously to Example 55, 87 mg of the title compound was obtained from 151 mg of the compound prepared in Example 192b and 106 mg of 4-(trifluoromethoxy)benzoyl chloride.

$^1$H-NMR (300 MHz, DMSO-d6): δ=1.08 (3H), 2.34 (3H), 3.13-3.31 (6H), 3.43 (1H), 3.88 (1H), 4.08 (1H), 4.17 (1H), 4.36 (1H), 4.65 (2H), 7.35 (1H), 7.40 (2H), 7.64 (1H), 7.70 (2H), 8.18 (1H), 8.41 (1H).

EXAMPLE 194

6-methyl-2-({1-[4-(trifluoromethoxy)benzoyl]azetidin-3-yl}methyl)-N-{2-[(trifluoromethyl)sulphanyl]ethyl}-2H-indazol-5-carboxamide

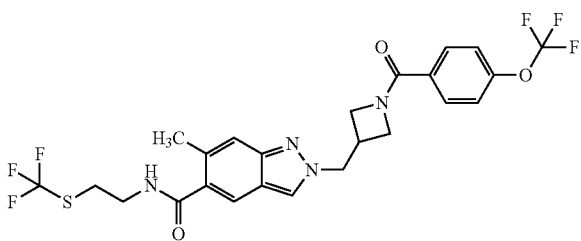 [SMILES: Cc1cc2nn(CC3CN(C(=O)c4ccc(OC(F)(F)F)cc4)C3)cc2cc1C(=O)NCCSC(F)(F)F]

Analogously to Example 55, 87 mg of the title compound was obtained from 173 mg of the compound prepared in Example 187b and 105 mg of 4-(trifluoromethoxy)benzoyl chloride.

$^1$H-NMR (300 MHz, DMSO-d6): δ=2.36 (3H), 3.11-3.24 (3H), 3.49 (2H), 3.89 (1H), 4.09 (1H), 4.17 (1H), 4.36 (1H), 4.66 (2H), 7.36 (1H), 7.40 (2H), 7.66-7.74 (3H), 8.44 (1H), 8.46 (1H).

EXAMPLE 195

6-methyl-N-(2,2,2-trifluoroethyl)-2-({1-[4-(trifluoromethoxy)benzoyl]azetidin-3-yl}methyl)-2H-indazol-5-carboxamide

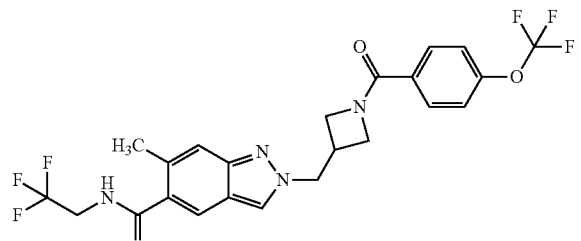

Analogously to Example 55, 70 mg of the title compound was obtained from 170 mg of the compound prepared in Example 188b and 116 mg of 4-(trifluoromethoxy)benzoyl chloride.

$^1$H-NMR (300 MHz, DMSO-d6): δ=2.35 (3H), 3.21 (1H), 3.89 (1H), 3.95-4.13 (3H), 4.18 (1H), 4.36 (1H), 4.67 (2H), 7.40 (3H), 7.66-7.75 (3H), 8.45 (1H), 8.86 (1H).

EXAMPLE 196

6-methyl-2-({1-[4-(trifluoromethoxy)benzoyl]azetidin-3-yl}methyl)-N-[2-(trifluoromethoxy)ethyl]-2H-indazol-5-carboxamide

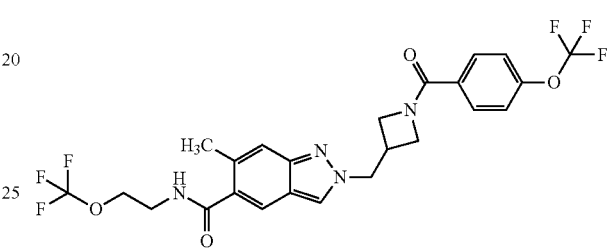

Analogously to Example 55, 22 mg of the title compound was obtained from 179 mg of the compound prepared in Example 196b and 113 mg of 4-(trifluoromethoxy)benzoyl chloride.

$^1$H-NMR (300 MHz, DMSO-d6): δ=2.34 (3H), 3.20 (1H), 3.50 (2H), 3.89 (1H), 4.08 (1H), 4.14-4.21 (3H), 4.36 (1H), 4.66 (2H), 7.36 (1H), 7.40 (2H), 7.66 (1H), 7.70 (2H), 8.44 (1H), 8.46 (1H).

The starting material was prepared as follows:

EXAMPLE 196a

Tert-butyl 3-[(6-methyl-5-{N-[2-(trifluoromethoxy)ethyl]carbamoyl}-2H-indazol-2-yl)methyl]azetidin-1-carboxylate

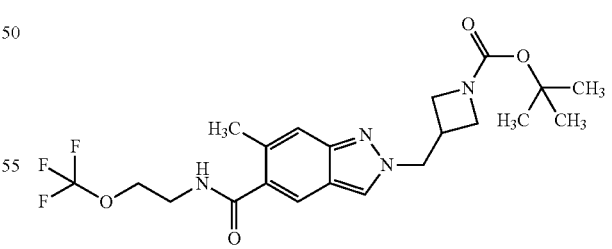

Analogously to Example 1, 417 mg of the title compound was obtained from 300 mg of the acid prepared in Example 178c and 144 mg of 2-(trifluoromethoxy)ethylamine hydrochloride.

$^1$H-NMR (300 MHz, DMSO-d6): δ=1.32 (9H), 2.34 (3H), 3.06 (1H), 3.50 (2H), 3.68 (2H), 3.84 (2H), 4.16 (2H), 4.59 (2H), 7.37 (1H), 7.66 (1H), 8.44 (1H), 8.46 (1H).

EXAMPLE 196b 2-(azetidin-3-ylmethyl)-6-methyl-N-[2-(trifluoromethoxy)ethyl]-2H-indazol-5-carboxamide hydrochloride

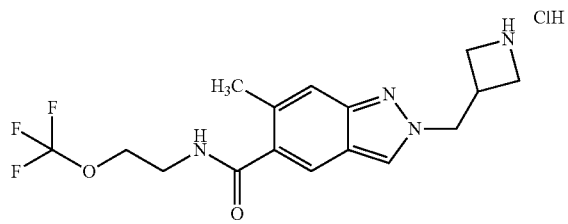 [SMILES: Cl ; Cc1cc2nn(CC3CNC3)cc2cc1C(=O)NCCOC(F)(F)F]

Analogously to Example 1a, from 417 mg of the amide prepared in Example 196a, 369 mg of the title compound was obtained, which was reacted without further purification.

EXAMPLE 197

2-{[1-(4-chlorobenzoyl)azetidin-3-yl]methyl}-6-methyl-N-[2-(trifluoromethoxy)ethyl]-2H-indazol-5-carboxamide

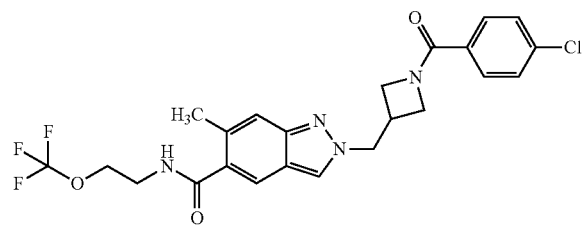 [SMILES: Cc1cc2nn(CC3CN(C(=O)c4ccc(Cl)cc4)C3)cc2cc1C(=O)NCCOC(F)(F)F]

Analogously to Example 55, 41 mg of the title compound was obtained from 179 mg of the compound prepared in Example 196b and 88 mg of 4-chlorobenzoyl chloride.

$^1$H-NMR (300 MHz, DMSO-d6): δ=2.34 (3H), 3.19 (1H), 3.50 (2H), 3.87 (1H), 4.07 (1H), 4.13-4.21 (3H), 4.34 (1H), 4.65 (2H), 7.36 (1H), 7.48 (2H), 7.59 (2H), 7.66 (1H), 8.44 (1H), 8.46 (1H).

EXAMPLE 198

2-{[1-(4-chlorobenzoyl)azetidin-3-yl]methyl}-N-[2-(cyclopropylmethoxy)ethyl]-6-methyl-2H-indazol-5-carboxamide

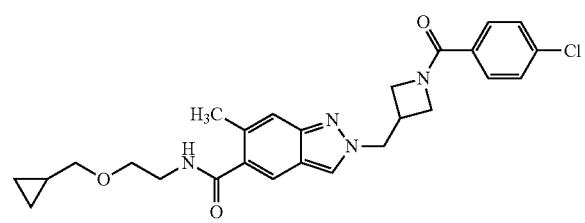 [SMILES: Cc1cc2nn(CC3CN(C(=O)c4ccc(Cl)cc4)C3)cc2cc1C(=O)NCCOCC1CC1]

Analogously to Example 55, 107 mg of the title compound was obtained from 214 mg of the compound prepared in Example 198b and 109 mg of 4-chlorobenzoyl chloride.

$^1$H-NMR (300 MHz, DMSO-d6): δ=0.14 (2H), 0.42 (2H), 0.97 (1H), 2.34 (3H), 3.12-3.26 (3H), 3.34 (2H), 3.47 (2H), 3.87 (1H), 4.07 (1H), 4.16 (1H), 4.34 (1H), 4.65 (2H), 7.35 (1H), 7.48 (2H), 7.59 (2H), 7.63 (1H), 8.21 (1H), 8.42 (1H).

The starting material was prepared as follows:

EXAMPLE 198a

Tert-butyl 3-[(5-{N-[2-(cyclopropylmethoxy)ethyl]carbamoyl}-6-methyl-2H-indazol-2-yl)methyl]azetidin-1-carboxylate

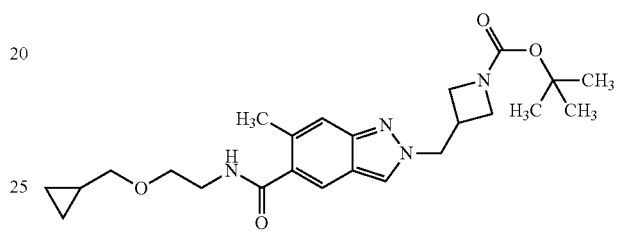

Analogously to Example 1, 247 mg of the title compound was obtained from 245 mg of the acid prepared in Example 178c and 82 mg of 2-(cyclopropylmethoxy)ethylamine hydrochloride.

$^1$H-NMR (300 MHz, DMSO-d6): δ=0.14 (2H), 0.43 (2H), 0.97 (1H), 1.32 (9H), 2.35 (3H), 3.06 (1H), 3.23 (2H), 3.34 (2H), 3.48 (2H), 3.67 (2H), 3.85 (2H), 4.59 (2H), 7.35 (1H), 7.64 (1H), 8.18 (1H), 8.41 (1H).

EXAMPLE 198b 2-(azetidin-3-ylmethyl)-N-[2-(cyclopropylmethoxy)ethyl]-6-methyl-2H-indazol-5-carboxamide hydrochloride

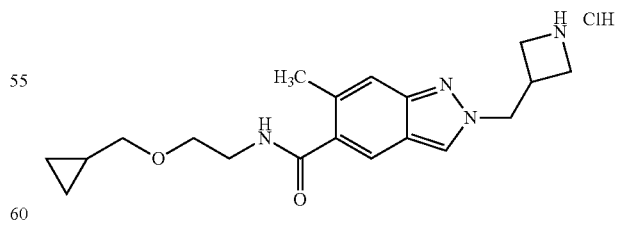

Analogously to Example 1a, from 247 mg of the amide prepared in Example 198a, 214 mg of the title compound was obtained, which was reacted without further purification.

EXAMPLE 199

2-({1-[4-(4-fluorophenoxy)benzoyl]azetidin-3-yl}methyl)-6-methyl-N-{2-[(trifluoromethyl)sulphanyl]ethyl}-2H-indazol-5-carboxamide

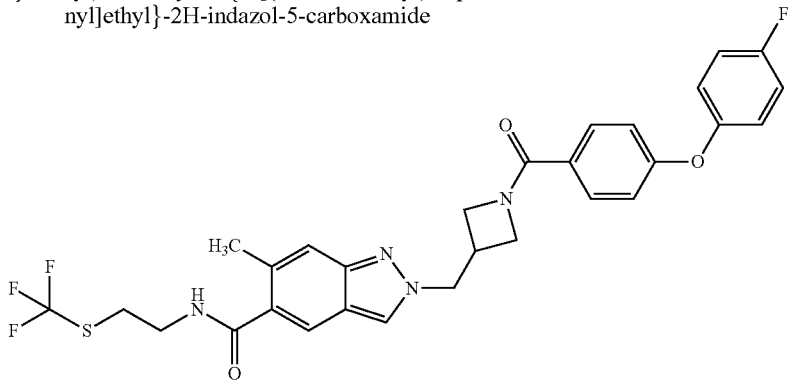

Analogously to Example 1, 56 mg of the title compound was obtained from 173 mg of the compound prepared in Example 187b and 98 mg of 4-(4-fluorophenoxy)benzoic acid.

$^1$H-NMR (300 MHz, DMSO-d6): δ=2.38 (3H), 3.16-3.27 (3H), 3.52 (2H), 3.90 (1H), 4.08 (1H), 4.19 (1H), 4.38 (1H), 4.68 (2H), 6.97 (2H), 7.14 (2H), 7.27 (2H), 7.39 (1H), 7.62 (2H), 7.72 (1H), 8.47 (1H), 8.49 (1H).

EXAMPLE 200

2-{[1-(4-cyclopropylbenzoyl)azetidin-3-yl]methyl}-N-(2-methoxyethyl)-6-methyl-2H-indazol-5-carboxamide

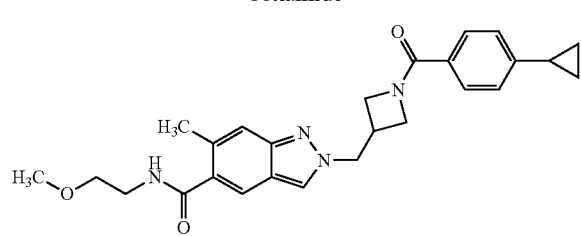

Analogously to Example 1, 86 mg of the title compound was obtained from 168 mg of the compound prepared in Example 178e and 80 mg of 4-cyclopropylbenzoic acid.

$^1$H-NMR (300 MHz, DMSO-d6): δ=0.71 (2H), 0.99 (2H), 1.95 (1H), 2.37 (3H), 3.21 (1H), 3.27 (3H), 3.37 (2H), 3.45 (2H), 3.88 (1H), 4.07 (1H), 4.17 (1H), 4.35 (1H), 4.67 (2H), 7.12 (2H), 7.38 (1H), 7.47 (2H), 7.66 (1H), 8.22 (1H), 8.44 (1H).

EXAMPLE 201

6-methyl-N-(2,2,2-trifluoroethyl)-2-[(1-{4-[4-(trifluoromethyl)phenoxy]benzoyl}azetidin-3-yl)methyl]-2H-indazol-5-carboxamide

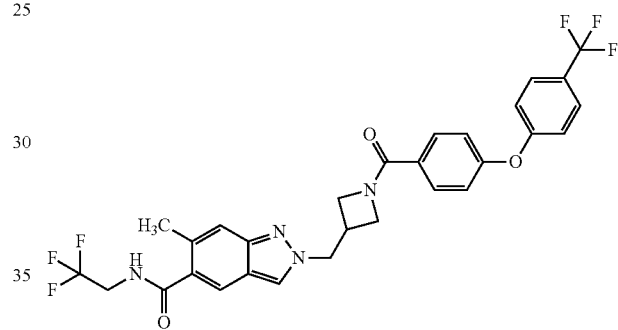

Analogously to Example 1, 71 mg of the title compound was obtained from 180 mg of the compound prepared in Example 188b and 95 mg of 4-[4-(trifluoromethyl)phenoxy]benzoic acid.

$^1$H-NMR (300 MHz, DMSO-d6): δ=2.34 (3H), 3.21 (1H), 3.88 (1H), 3.95-4.13 (3H), 4.19 (1H), 4.37 (1H), 4.67 (2H), 7.11 (2H), 7.19 (2H), 7.39 (1H), 7.65 (2H), 7.69-7.79 (3H), 8.47 (1H), 8.88 (1H).

EXAMPLE 202

N-(2-methoxyethyl)-6-methyl-2-[(1-{4-[4-(trifluoromethyl)phenoxy]benzoyl}-azetidin-3-yl)methyl]-2H-indazol-5-carboxamide

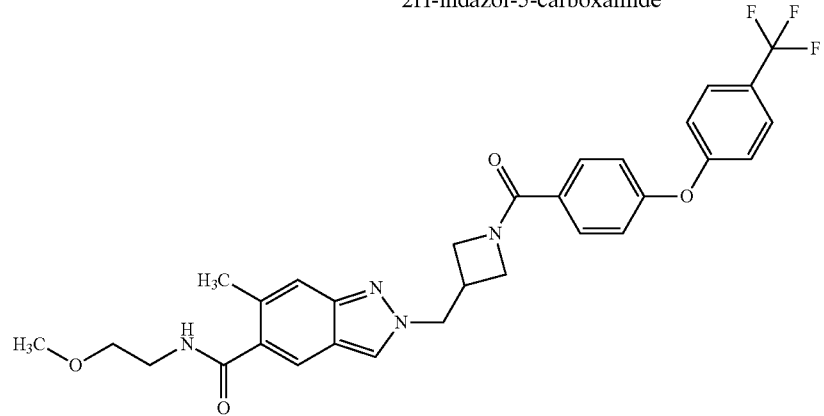

Analogously to Example 1, 108 mg of the title compound was obtained from 180 mg of the compound prepared in Example 178e and 102 mg of 4-[4-(trifluoromethyl)phenoxy]benzoic acid.

$^1$H-NMR (300 MHz, DMSO-d6): δ=2.34 (3H), 3.14-3.26 (4H), 3.34 (2H), 3.42 (2H), 3.88 (1H), 4.07 (1H), 4.19 (1H), 4.37 (1H), 4.66 (2H), 7.11 (2H), 7.19 (2H), 7.35 (1H), 7.61-7.68 (3H), 7.75 (2H), 8.21 (1H), 8.42 (1H).

EXAMPLE 203

2-({1-[(4'-fluorobiphenyl-4-yl)carbonyl]azetidin-3-yl}methyl)-6-methyl-N-(2,2,2-trifluoroethyl)-2H-indazol-5-carboxamide

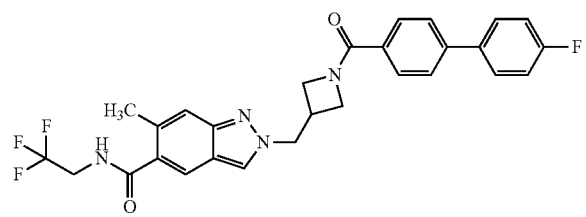 [SMILES: Cc1cc2nn(CC3CN(C(=O)c4ccc(-c5ccc(F)cc5)cc4)C3)cc2cc1C(=O)NCC(F)(F)F]

Analogously to Example 1, 104 mg of the title compound was obtained from 180 mg of the compound prepared in Example 188b and 73 mg of 4'-fluorobiphenyl-4-carboxylic acid.

$^1$H-NMR (300 MHz, DMSO-d6): δ=2.34 (3H), 3.22 (1H), 3.90 (1H), 3.95-4.14 (3H), 4.21 (1H), 4.40 (1H), 4.68 (2H), 7.28 (2H), 7.40 (1H), 7.60-7.77 (7H), 8.48 (1H), 8.89 (1H).

EXAMPLE 204

2-({1-[(4'-fluorobiphenyl-4-yl)carbonyl]azetidin-3-yl}methyl)-N-(2-methoxy-ethyl)-6-methyl-2H-indazol-5-carboxamide

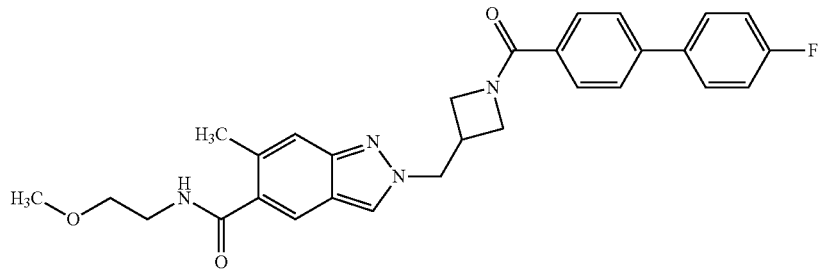 [SMILES: COCCNC(=O)c1cc2cn(CC3CN(C(=O)c4ccc(-c5ccc(F)cc5)cc4)C3)nc2cc1C]

Analogously to Example 1, 73 mg of the title compound was obtained from 180 mg of the compound prepared in Example 178e and 78 mg of 4'-fluorobiphenyl-4-carboxylic acid.

$^1$H-NMR (300 MHz, DMSO-d6): δ=2.34 (3H), 3.14-3.26 (4H), 3.34 (2H), 3.41 (2H), 3.89 (1H), 4.09 (1H), 4.21 (1H), 4.39 (1H), 4.66 (2H), 7.28 (2H), 7.35 (1H), 7.61-7.77 (7H), 8.21 (1H), 8.43 (1H).

EXAMPLE 205

2-{[1-(4-chlorobenzoyl)piperidin-4-yl]methyl}-N-(2-methoxyethyl)-6-methyl-2H-indazol-5-carboxamide

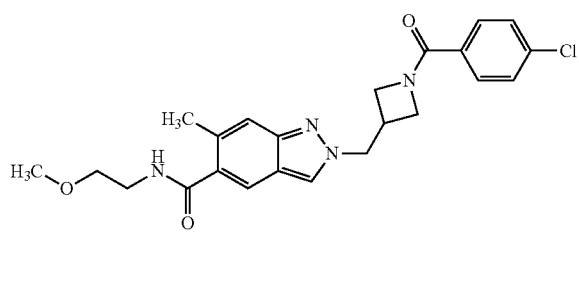 [SMILES: COCCNC(=O)c1cc2cn(CC3CN(C(=O)c4ccc(Cl)cc4)C3)nc2cc1C]

Analogously to Example 55, from 85 mg of the compound prepared in Example 205c and 45 mg of 4-chlorobenzoyl chloride, a material still contaminated after column chromatography was obtained which was further purified by additional preparative thick layer chromatography with dichloromethane/methanol in the ratio 95:5 as mobile phase. Yield: 48 mg of the title compound.

$^1$H-NMR (300 MHz, DMSO-d6): δ=1.09-1.53 (4H), 2.24 (1H), 2.34 (3H), 2.71 (1H), 2.97 (1H), 3.24 (3H), 3.34 (2H), 3.38-3.54 (3H), 7.31-7.37 (3H), 7.46 (2H), 7.63 (1H), 8.21 (1H), 8.33 (H).

The starting material was prepared as follows:

EXAMPLE 205a

Tert-butyl 4-[(5-bromo-6-methyl-2H-indazol-2-yl)methyl]piperidin-1-carboxylate

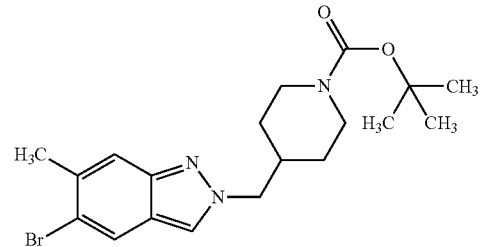 [SMILES: Cc1cc2nn(CC3CCN(C(=O)OC(C)(C)C)CC3)cc2cc1Br]

Analogously to Example 1c, 2.99 g of the title compound was obtained from 5.7 g of 5-bromo-6-methyl-1H-indazole and 15.0 g of tert-butyl-4-[(tosyloxy)methyl]piperidin-1-carboxylate.

$^1$H-NMR (300 MHz, CDCl3): δ=1.14-1.30 (2H), 1.44 (9H), 1.53 (2H), 2.24 (1H), 2.50 (3H), 2.66 (2H), 4.11 (2H), 4.23 (2H), 7.55 (1H), 7.77 (1H), 7.87 (1H).

EXAMPLE 205b

Tert-butyl 4-({5-[N-(2-methoxyethyl)carbamoyl]-6-methyl-2H-indazol-2-yl}-methyl)piperidin-1-carboxylate

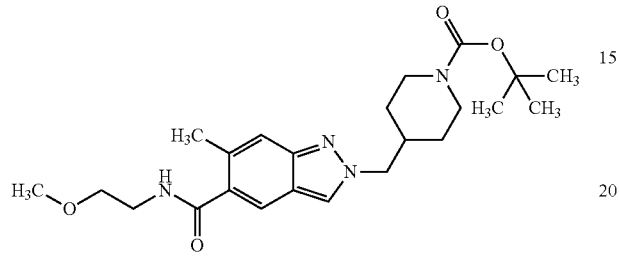

Analogously to Example 1b, 3.56 g of the title compound was obtained from 600 mg of the bromide prepared in Example 205a and 331 mg of 2-methoxyethylamine after four runs and twofold purification by chromatography.

$^1$H-NMR (300 MHz, DMSO-d6): δ=0.96-1.15 (2H), 1.29-1.42 (10H), 2.03-2.18 (1H), 2.34 (3H), 2.51-2.73 (3H), 3.25 (3H), 3.31-3.45 (4H), 3.86 (2H), 4.26 (2H), 7.35 (1H), 7.63 (1H), 8.21 (1H), 8.32 (1H).

EXAMPLE 205c

N-(2-methoxyethyl)-6-methyl-2-(4-piperidylmethyl)-2H-indazol-5-carboxamide hydrochloride

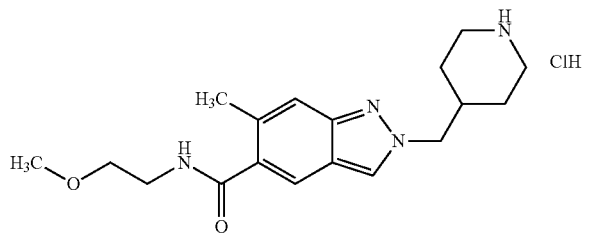 [SMILES: COCCNC(=O)c1cc2cn(CC3CCNCC3)nc2cc1C ; Cl]

Analogously to Example 1a, from 100 mg of the amide prepared in Example 205b, 85 mg of the title compound was obtained, which was reacted without further purification.

EXAMPLE 206

2-({1-[2-fluoro-4-(trifluoromethyl)benzoyl]piperidin-4-yl}methyl)-N-(2-methoxy-ethyl)-6-methyl-2H-indazol-5-carboxamide

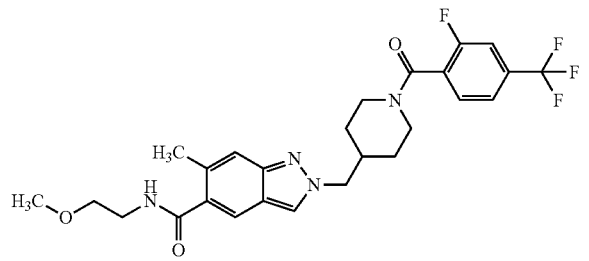 [SMILES: COCCNC(=O)c1cc2cn(CC3CCN(C(=O)c4ccc(C(F)(F)F)cc4F)CC3)nc2cc1C]

Analogously to Example 55, from 85 mg of the compound prepared in Example 205c and 58 mg of 2-fluoro-4-(trifluoromethyl)benzoyl chloride, a material still contaminated after column chromatography was obtained which was further purified by additional preparative thick layer chromatography with dichloromethane/methanol in the ratio 95:5 as mobile phase. Yield: 40 mg of the title compound.

$^1$H-NMR (300 MHz, DMSO-d6): δ=1.03-1.28 (2H), 1.37 (1H), 1.53 (1H), 2.23 (1H), 2.34 (3H), 2.77 (1H), 3.00 (1H), 3.26-3.49 (11H), 4.30 (2H), 4.44 (1H), 7.35 (1H), 7.54-7.67 (3H), 7.78 (1H), 8.21 (1H), 8.34 (1H).

EXAMPLE 207

2-{[1-(4-chloro-2-fluorobenzoyl)piperidin-4-yl]methyl}-N-(2-methoxyethyl)-6-methyl-2H-indazol-5-carboxamide

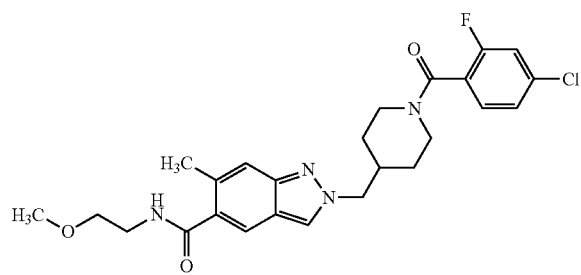 [SMILES: COCCNC(=O)c1cc2cn(CC3CCN(C(=O)c4ccc(Cl)cc4F)CC3)nc2cc1C]

Analogously to Example 55, 68 mg of the title compound was obtained from 85 mg of the compound prepared in Example 205c and 49 mg of 4-chloro-2-fluorobenzoyl chloride.

$^1$H-NMR (300 MHz, DMSO-d6): δ=1.04-1.25 (2H), 1.37 (1H), 1.51 (1H), 2.23 (1H), 2.34 (3H), 2.73 (1H), 2.98 (1H), 3.21-3.48 (3H), 3.30-3.38 (3H), 3.42 (2H), 4.29 (2H), 4.42 (1H), 7.29-7.42 (3H), 7.51 (1H), 7.63 (1H), 8.21 (1H), 8.33 (1H).

EXAMPLE 208

2-({1-[3-fluoro-4-(trifluoromethyl)benzoyl]piperidin-4-yl}methyl)-N-(2-methoxyethyl)-6-methyl-2H-indazol-5-carboxamide

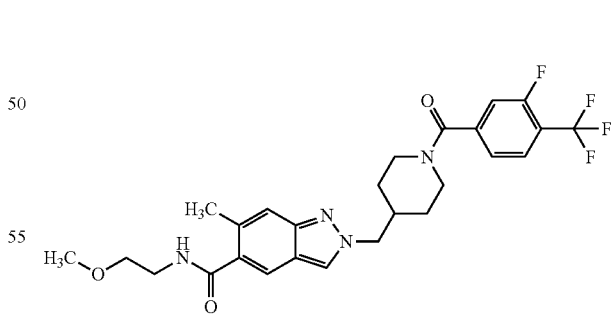

Analogously to Example 55, 70 mg of the title compound was obtained from 85 mg of the compound prepared in Example 205c and 58 mg of 3-fluoro-4-(trifluoromethyl)benzoyl chloride.

$^1$H-NMR (300 MHz, DMSO-d6): δ=1.13-1.27 (2H), 1.35 (1H), 1.51 (1H), 2.23 (1H), 2.34 (3H), 2.74 (1H), 2.98 (1H), 3.22-3.45 (8H), 4.29 (2H), 4.40 (1H), 7.32-7.38 (2H), 7.52 (1H), 7.63 (1H), 7.82 (1H), 8.21 (1H), 8.33 (1H).

EXAMPLE 209

2-({1-[4-chloro-3-(trifluoromethyl)benzoyl]piperidin-4-yl}methyl)-N-(2-methoxyethyl)-6-methyl-2H-indazol-5-carboxamide

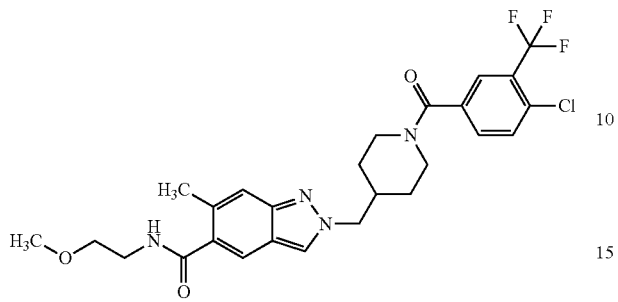

Analogously to Example 55, 92 mg of the title compound was obtained from 85 mg of the compound prepared in Example 205c and 62 mg of 4-chloro-3-(trifluoromethyl)benzoyl chloride.

$^1$H-NMR (300 MHz, DMSO-d6): δ=1.14-1.28 (2H), 1.35 (1H), 1.44-1.53 (1H), 2.25 (1H), 2.34 (3H), 2.74 (1H), 3.01 (1H), 3.24 (3H), 3.34 (2H), 3.39-3.50 (3H), 4.29 (2H), 4.39 (1H), 7.35 (1H), 7.61-7.68 (2H), 7.74-7.80 (2H), 8.21 (1H), 8.33 (1H).

EXAMPLE 210

N-(2-methoxyethyl)-6-methyl-2-({1-[4-(pentafluoro-λ$^6$-sulphanyl)benzoyl]-piperidin-4-yl}methyl)-2H-indazol-5-carboxamide

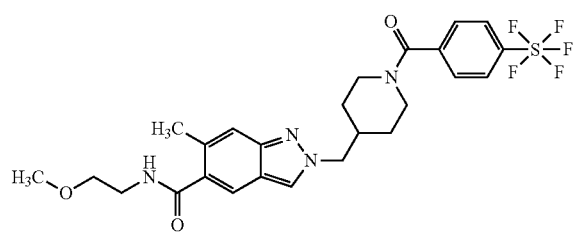 [SMILES: COCCNC(=O)c1cc2cn(CC3CCN(C(=O)c4ccc(S(F)(F)(F)(F)F)cc4)CC3)nc2cc1C]

Analogously to Example 1, 126 mg of the title compound was obtained from 85 mg of the compound prepared in Example 205c and 58 mg of 4-(pentafluoro-λ$^6$-sulphanyl)benzoic acid.

$^1$H-NMR (300 MHz, DMSO-d6): δ=1.12-1.27 (2H), 1.35 (1H), 1.51 (1H), 2.24 (1H), 2.34 (3H), 2.74 (1H), 2.99 (1H), 3.24 (3H), 3.34-3.46 (5H), 4.30 (2H), 4.41 (1H), 7.35 (1H), 7.55 (2H), 7.63 (1H), 7.94 (2H), 8.21 (1H), 8.33 (1H).

EXAMPLE 211

N-(2-methoxyethyl)-6-methyl-2-({1-[4-(trifluoromethyl)benzoyl]piperidin-4-yl}-methyl)-2H-indazol-5-carboxamide

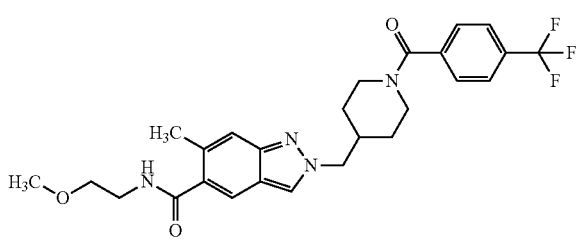 [SMILES: COCCNC(=O)c1cc2cn(CC3CCN(C(=O)c4ccc(C(F)(F)F)cc4)CC3)nc2cc1C]

Analogously to Example 55, 69 mg of the title compound was obtained from 85 mg of the compound prepared in Example 205c and 53 mg of 4-(trifluoromethyl)benzoyl chloride.

$^1$H-NMR (300 MHz, DMSO-d6): δ=1.10-1.26 (2H), 1.35 (1H), 1.51 (1H), 2.19-2.30 (1H), 2.34 (3H), 2.74 (1H), 2.98 (1H), 3.21-3.47 (8H), 4.30 (2H), 4.42 (1H), 7.35 (1H), 7.54 (2H), 7.63 (1H), 7.77 (2H), 8.21 (1H), 8.33 (1H).

EXAMPLE 212

2-{[1-(4-chlorobenzoyl)piperidin-4-yl]methyl}-4-ethyl-N-(2-methoxyethyl)-2H-indazol-5-carboxamide

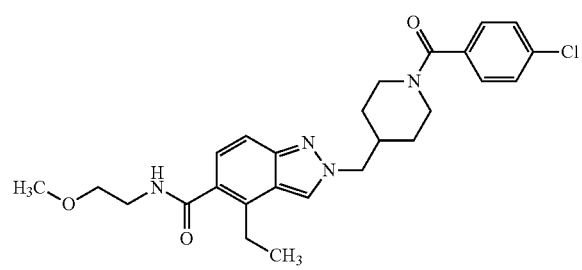 [SMILES: CCc1c(C(=O)NCCOC)ccc2nn(CC3CCN(C(=O)c4ccc(Cl)cc4)CC3)cc12]

Analogously to Example 55, 61 mg of the title compound was obtained from 91 mg of the compound prepared in Example 212i and 46 mg of 4-chlorobenzoyl chloride.

$^1$H-NMR (300 MHz, DMSO-d6): δ=1.14-1.28 (5H), 1.31-1.60 (2H), 2.27 (1H), 2.63-3.04 (4H), 3.24 (3H), 3.31-3.56 (5H), 4.31 (2H), 4.39 (1H), 7.10 (1H), 7.32-7.41 (3H), 7.46 (2H), 8.11 (1H), 8.50 (1H).

The starting material was prepared as follows:

EXAMPLE 212a 4-bromo-3-ethyl-2-methylaniline

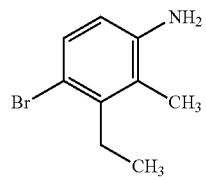

A suspension of 3 g of 3-ethyl-2-methylaniline hydrochloride in 200 ml ethyl acetate was washed twice with 30 ml portions of saturated sodium carbonate solution and twice with 20 ml portions of saturated sodium chloride solution, dried over sodium sulphate and concentrated in vacuo after filtration. This yielded 2.69 g of ethyl-2-methylaniline, which was further reacted without purification.

To a solution of 2.36 g of the amine prepared above in 29 ml DMF, a solution of 3.1 g of N-bromosuccinimide in 14.5 ml DMF was added dropwise at 0° C. and stirred for 30 minutes at 0° C. Then the reaction mixture was diluted with 400 ml ethyl acetate and washed once with 30 ml of a 10% aqueous sodium carbonate solution and once with 30 ml water. After drying over sodium sulphate and filtration, this was concentrated in vacuo. The crude product thus obtained (3.86 g) was used in the next step without purification.

EXAMPLE 212b

N-(4-bromo-3-ethyl-2-methylphenyl)acetamide

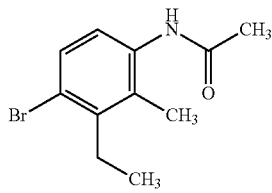

To a solution of 3.86 g of the bromide prepared in Example 212a in 48 ml pyridine, 2.04 ml of acetic anhydride was added dropwise at 0° C. and stirred for 20 hours at 25° C. The reaction mixture was concentrated in vacuo and the crude product thus obtained was purified by column chromatography on silica gel with hexane/0-100% ethyl acetate. In this manner, 3.73 g of the title compound was obtained.

$^1$H-NMR (300 MHz, CDCl3): δ=1.13 (3H), 2.20 (3H), 2.25 (3H), 2.86 (2H), 6.91 (1H), 7.33 (1H), 7.40 (1H).

EXAMPLE 212c 1-(5-bromo-4-ethyl-1H-indazol-1-yl)ethan-1-one

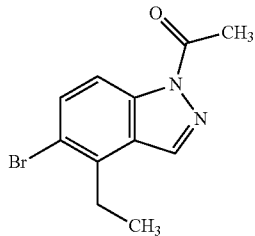

To a solution of 3.72 g of the acetamide prepared in Example 212b in 31.5 ml chloroform were added 4.1 ml of acetic anhydride and 2.85 g of potassium acetate, and 192 mg of 18-crown-6 and 3.4 g of isopentyl nitrite were then added dropwise. The reaction mixture was heated for 20 hours under reflux and after cooling diluted with 200 ml ethyl acetate. The organic phase was washed with 20 ml sodium carbonate solution and once with saturated sodium chloride solution. After drying over sodium sulphate and filtration, this was concentrated in vacuo and the crude product thus obtained purified by column chromatography on silica gel with hexane/0-50% ethyl acetate. Yield: 3.78 g of the title compound.

$^1$H-NMR (300 MHz, DMSO-d6): δ=1.18 (3H), 2.68 (3H), 3.04 (2H), 7.73 (1H), 8.03 (1H), 8.64 (1H).

EXAMPLE 212d 5-bromo-4-ethyl-1H-indazole

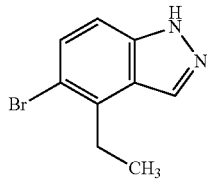

A mixture of 3.78 g of the compound prepared in Example 212c in 7.3 ml methanol and 26.3 ml of 37% hydrochloric acid was heated under reflux for 2 hours. This was then diluted with 400 ml ethyl acetate. The organic phase was washed three times with 50 ml portions of sodium hydrogen carbonate solution and once with 50 ml saturated sodium chloride solution, dried over sodium sulphate and concentrated in vacuo. The crude product thus obtained was purified by column chromatography on silica gel with hexane/0-50% ethyl acetate. Yield: 2.97 g of the title compound.

$^1$H-NMR (300 MHz, DMSO-d6): δ=1.17 (3H), 2.98 (2H), 7.30 (1H), 7.41 (1H), 8.16 (1H), 13.17 (1H).

EXAMPLE 212e

Tert-butyl 4-[(5-bromo-4-ethyl-2H-indazol-2-yl)methyl]piperidin-1-carboxylate

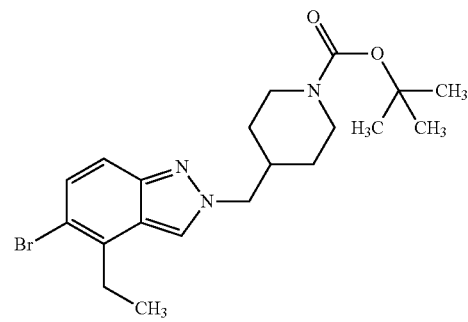 [SMILES: CCc1c(Br)ccc2nn(CC3CCN(C(=O)OC(C)(C)C)CC3)cc12]

Analogously to Example 1c, 961 mg of the title compound was obtained from 2.97 g of the indazole prepared in Example 212d and 7.3 g of tert-butyl-4-[(tosyloxy)methyl]piperidin-1-carboxylate.

$^1$H-NMR (300 MHz, DMSO-d6): δ=1.01-1.13 (2H), 1.16 (3H), 1.34 (9H), 1.41 (2H), 2.12 (1H), 2.63 (2H), 2.90 (2H), 3.87 (2H), 4.27 (2H), 7.27 (1H), 7.35 (1H), 8.49 (1H).

EXAMPLE 212f

Methyl 2-{[1-(tert-butoxycarbonyl)piperidin-4-yl]methyl}-4-ethyl-2H-indazol-5-carboxylate

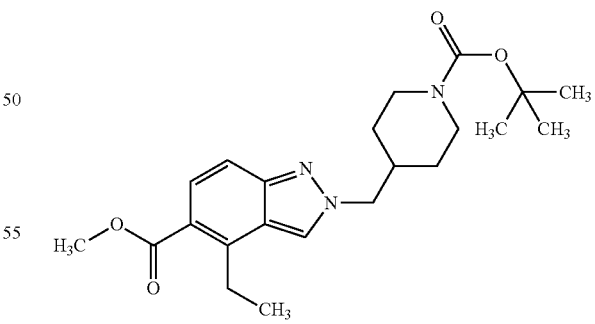

Analogously to Example 1e, after two runs 571 mg of the title compound was obtained from 347 mg of the bromide prepared in Example 212e and 0.1 ml of methanol.

$^1$H-NMR (300 MHz, DMSO-d6): δ=1.02-1.15 (2H), 1.17-1.24 (3H), 1.34 (9H), 1.42 (2H), 2.14 (1H), 2.63 (2H), 3.17 (2H), 3.79 (3H), 3.88 (2H), 4.30 (2H), 7.43 (1H), 7.60 (1H), 8.68 (1H).

EXAMPLE 212g

2-{[1-(tert-butoxycarbonyl)piperidin-4-yl]methyl}-4-ethyl-2H-indazol-5-carboxylic acid

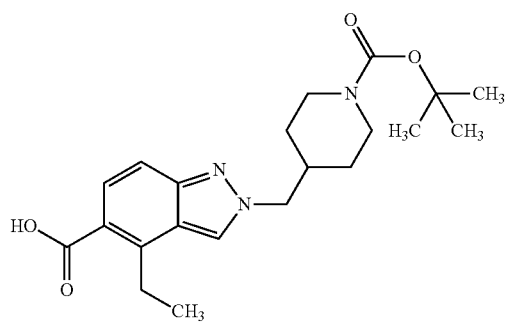 [SMILES: CCc1c(C(=O)O)ccc2nn(CC3CCN(C(=O)OC(C)(C)C)CC3)cc12]

Analogously to Example 1d, 427 mg of the title compound was obtained from 371 mg of the ester in Example 212f.

¹H-NMR (300 MHz, DMSO-d6): δ=1.00-1.15 (2H), 1.20 (3H), 1.34 (9H), 1.42 (2H), 2.14 (1H), 2.64 (2H), 3.19 (2H), 3.88 (2H), 4.29 (2H), 7.39 (1H), 7.61 (1H), 8.63 (1H), 12.33 (1H).

EXAMPLE 212h

Tert-butyl 4-({4-ethyl-5-[N-(2-methoxyethyl)carbamoyl]-2H-indazol-2-yl}-methyl)piperidin-1-carboxylate

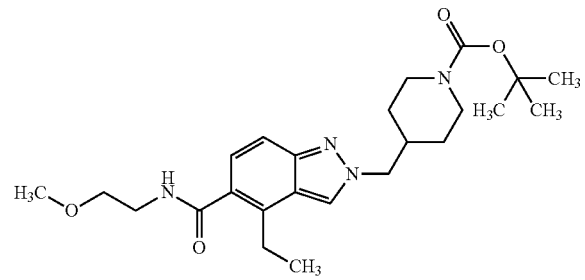 [SMILES: CCc1c(C(=O)NCCOC)ccc2nn(CC3CCN(C(=O)OC(C)(C)C)CC3)cc12]

Analogously to Example 1, 215 mg of the title compound was obtained from 427 mg of the acid prepared in Example 212g and 83 mg of 2-methoxy-ethylamine.

¹H-NMR (300 MHz, DMSO-d6): δ=0.98-1.14 (2H), 1.19 (3H), 1.30-1.47 (11H), 2.13 (1H), 2.65 (2H), 2.90 (2H), 3.24 (3H), 3.32-3.45 (4H), 3.87 (2H), 4.28 (2H), 7.10 (1H), 7.38 (1H), 8.12 (1H), 8.50 (1H).

EXAMPLE 212i 4-ethyl-N-(2-methoxyethyl)-2-(4-piperidylmethyl)-2H-indazol-5-carboxamide hydrochloride

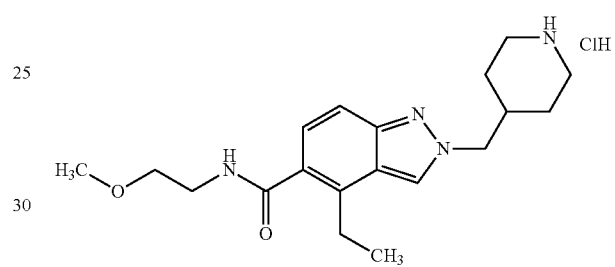

Analogously to Example 1a, from 215 mg of the amide prepared in Example 212h, 258 mg of the title compound was obtained, which was reacted without further purification.

EXAMPLE 213

4-Ethyl-N-(2-methoxyethyl)-2-({1-[4-(trifluoromethoxy)benzoyl]piperidin-4-yl}methyl)-2H-indazol-5-carboxamide

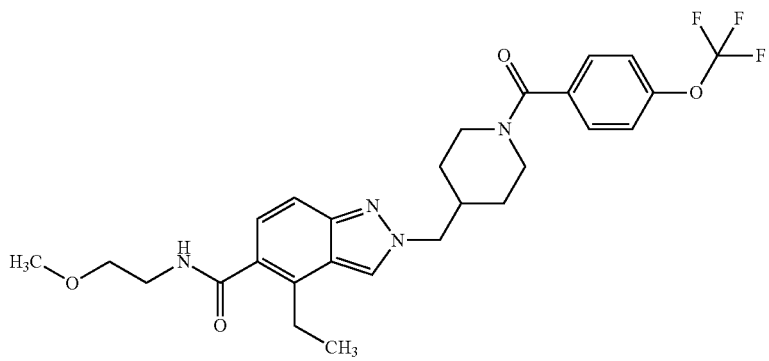 [SMILES: CCc1c(C(=O)NCCOC)ccc2nn(CC3CCN(C(=O)c4ccc(OC(F)(F)F)cc4)CC3)cc12]

Analogously to Example 55, 32 mg of the title compound was obtained from 91 mg of the compound prepared in Example 212i and 59 mg of 4-(trifluoromethoxy)benzoyl chloride.

¹H-NMR (300 MHz, DMSO-d6): δ=1.14-1.29 (5H), 1.31-1.61 (2H), 2.20-2.35 (1H), 2.66-3.06 (4H), 3.24 (3H), 3.30-3.56 (5H), 4.31 (2H), 4.41 (1H), 7.10 (1H), 7.34-7.43 (3H), 7.47 (2H), 8.11 (1H), 8.50 (1H).

EXAMPLE 214

2-{[1-(4-chlorobenzoyl)azetidin-3-yl]methyl}-4-methoxy-N-(2-methoxyethyl)-2H-indazol-5-carboxamide

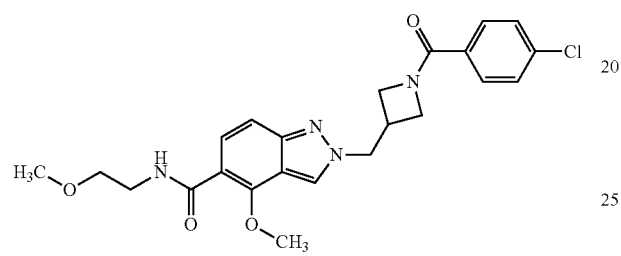

Analogously to Example 55, 691 mg of the title compound was obtained from 68 mg of the compound prepared in Example 214c and 37 mg of 4-chlorobenzoyl chloride.

¹H-NMR (300 MHz, DMSO-d6): δ=3.22 (1H), 3.27 (3H), 3.40-3.47 (4H), 3.92 (1H), 4.10 (1H), 4.16 (3H), 4.19 (1H), 4.38 (1H), 4.66 (2H), 7.21 (1H), 7.48 (2H), 7.55-7.67 (3H), 8.18 (1H), 8.87 (1H).

The starting material was prepared as follows:

EXAMPLE 214a

Tert-butyl 3-[(5-bromo-4-methoxy-2H-indazol-2-yl)methyl]azetidin-1-carboxylate

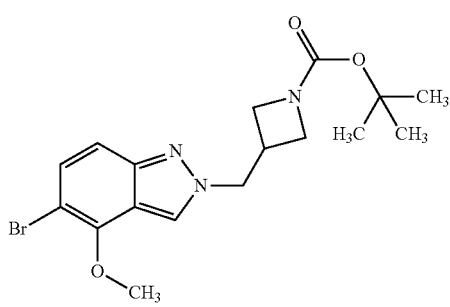 [SMILES: COc1c(Br)ccc2nn(CC3CN(C(=O)OC(C)(C)C)C3)cc12]

To a solution of 1.94 g of tert-butyl 3-[(tosyloxy)methyl]azetidin-1-carboxylate in 15.5 ml acetone were added 837 mg of lithium iodide and the reaction mixture was stirred for 16 hours at 35° C. After cooling, it was diluted with 200 ml ethyl acetate and the organic phase washed twice with 30 ml portions of water and once with 20 ml saturated sodium chloride solution. After drying over sodium sulphate and filtration, this was concentrated in vacuo. In this manner, 1.6 g of tert-butyl-3-(iodomethyl)azetidin-1-carboxylate were obtained, which was further reacted without purification.

To a solution of 620 mg of 5-bromo-7-methoxy-1H-indazole in 24 ml DMF were added 1.11 g of potassium carbonate and the mixture stirred at 25° C. for 30 minutes. Then 1.25 g of the iodide prepared above was added and the reaction mixture stirred for 3 hours at 60° C. After cooling, it was diluted with 200 ml 1:1 tert-butyl methyl ether/hexane, washed once each with 20 ml portions of water and saturated sodium chloride solution, dried over sodium sulphate and concentrated in vacuo and the crude product thus obtained purified by column chromatography on silica gel with a hexane/ethyl acetate gradient. Yield: 263 mg of the title compound.

¹H-NMR (300 MHz, CDCl3): δ=1.43 (9H), 3.23 (1H), 3.78 (2H), 4.07 (2H), 4.10 (3H), 4.59 (2H), 7.28 (1H), 7.36 (1H), 8.03 (1H).

EXAMPLE 214b

Tert-butyl 3-({4-methoxy-5-[N-(2-methoxyethyl)carbamoyl]-2H-indazol-2-yl}methyl)azetidin-1-carboxylate

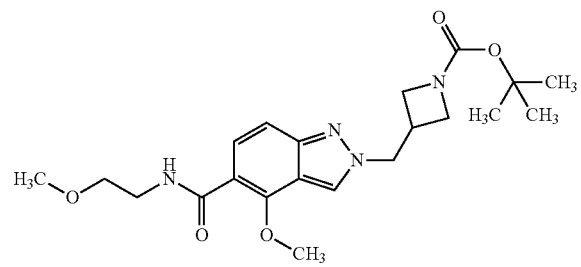 [SMILES: COCCNC(=O)c1ccc2nn(CC3CN(C(=O)OC(C)(C)C)C3)cc2c1OC]

Analogously to Example 1b, a total of 193 mg of the title compound was obtained from 110 and 252 mg respectively of the compound prepared in Example 214a and 63 and 143 mg respectively of 2-methoxyethylamine.

¹H-NMR (300 MHz, DMSO-d6): δ=1.32 (9H), 3.10 (1H), 3.27 (3H), 3.38-3.48 (4H), 3.72 (2H), 3.82-3.94 (2H), 4.17 (3H), 4.60 (2H), 7.21 (1H), 7.63 (1H), 8.18 (1H), 8.87 (1H).

EXAMPLE 214c 2-(azetidin-3-ylmethyl)-4-methoxy-N-(2-methoxyethyl)-2H-indazol-5-carboxamide hydrochloride

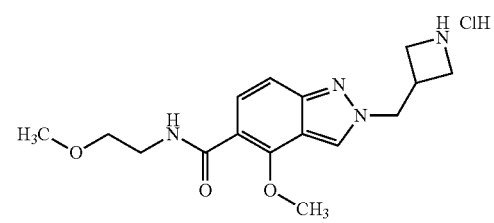 [SMILES: Cl ; COCCNC(=O)c1ccc2nn(CC3CNC3)cc2c1OC]

Analogously to Example 1a, from 50 mg of the compound prepared in Example 214b, 42 mg of the title compound was obtained, which was further reacted without purification.

EXAMPLE 215

4-methoxy-N-(2-methoxyethyl)-2-[(1-{4-[(trifluoromethyl)sulphanyl]benzoyl}azetidin-3-yl)methyl]-2H-indazol-5-carboxamide

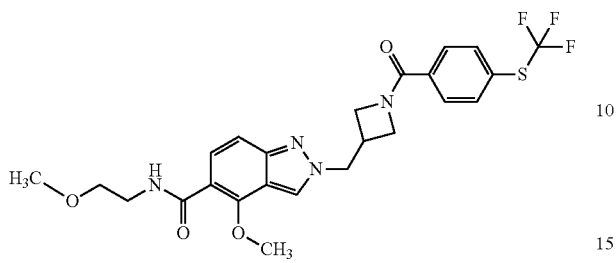

Analogously to Example 55, 56 mg of the title compound was obtained from 42 mg of the compound prepared in Example 214c and 32 mg of 4-[(trifluoromethyl)sulphany]benzoyl chloride.

$^1$H-NMR (300 MHz, DMSO-d6): δ=3.21 (1H), 3.27 (3H), 3.38-3.49 (4H), 3.95 (1H), 4.12 (1H), 4.16 (3H), 4.21 (1H), 4.40 (1H), 4.67 (2H), 7.20 (1H), 7.63 (1H), 7.69 (2H), 7.76 (2H), 8.18 (1H), 8.87 (1H).

EXAMPLE 216

2-{[1-(4-bromobenzoyl)azetidin-3-yl]methyl}-4-methoxy-N-(2-methoxyethyl)-2H-indazol-5-carboxamide

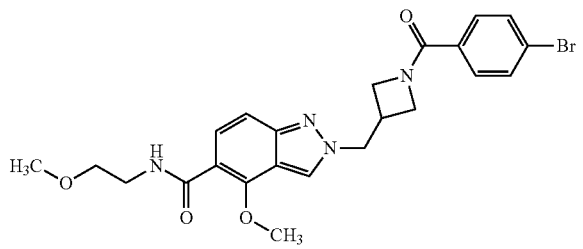 [SMILES: COCCNC(=O)c1ccc2nn(CC3CN(C(=O)c4ccc(Br)cc4)C3)cc2c1OC]

Analogously to Example 55, 48 mg of the title compound was obtained from 42 mg of the compound prepared in Example 214c and 29 mg of 4-bromobenzoyl chloride.

$^1$H-NMR (300 MHz, DMSO-d6): δ=3.23 (1H), 3.26 (3H), 3.38-3.48 (4H), 3.92 (1H), 4.09 (1H), 4.16 (3H), 4.19 (1H), 4.38 (1H), 4.66 (2H), 7.20 (1H), 7.51 (2H), 7.58-7.68 (3H), 8.18 (1H), 8.86 (1H).

EXAMPLE 217

2-{[(R)-1-(4-chlorobenzoyl)pyrrolidin-3-yl]methyl}-N-(2-methoxyethyl)-4-methyl-2H-indazol-5-carboxamide

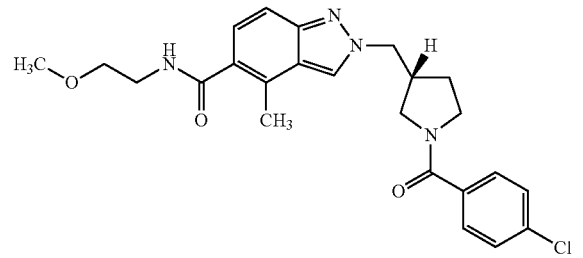 [SMILES: COCCNC(=O)c1ccc2nn(C[C@@H]3CCN(C(=O)c4ccc(Cl)cc4)C3)cc2c1C]

Analogously to Example 55, 50 mg of the title compound was obtained from 106 mg of the compound prepared in Example 217e and 58 mg of 4-chlorobenzoyl chloride.

$^1$H-NMR (300 MHz, DMSO-d6): δ=1.57-1.73 (1H), 1.81-1.97 (1H), 2.47/2.51 (3H), 2.78-2.93 (1H), 3.25 (3H), 3.19-3.61 (8H), 4.39/4.51 (2H), 7.11-7.18 (1H), 7.33-7.43 (1H), 7.45 (2H), 7.50 (2H), 8.09-8.16 (1H), 8.47/8.55 (1H).

The starting material was prepared as follows:

EXAMPLE 217a (R)-tert-butyl-3-[(5-bromo-4-methyl-2H-indazol-2-yl)methyl]pyrrolidine-1-carboxylate

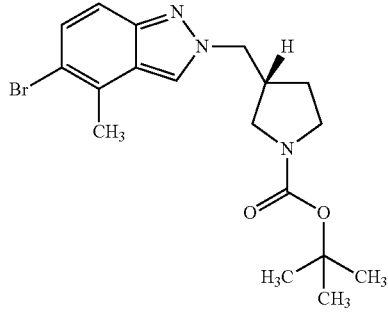 [SMILES: Cc1c(Br)ccc2nn(C[C@@H]3CCN(C(=O)OC(C)(C)C)C3)cc12]

To a solution of 9.0 g of (R)-tert-butyl 3-(hydroxymethyl)pyrrolidin-1-carboxylate in 100 ml pyridine was added 12.8 g of p-toluenesulphonyl chloride at 0° C. under nitrogen and stirred for 3 hours at 25° C. The reaction mixture was diluted with ethyl acetate and stirred for 30 minutes with sodium hydrogen carbonate. The phases were then separated and the organic phase washed with saturated sodium chloride solution, dried over sodium sulphate and concentrated in vacuo after filtration. The residue thus obtained was purified by column chromatography on silica gel with hexane/0-100% ethyl acetate. Yield: 11.4 g of (R)-tert-butyl-3-[(tosyloxy)methyl]pyrrolidin-1-carboxylate.

Analogously to Example 1c, 1.97 g of the title compound was obtained from 4.53 g of 5-bromo-4-methyl-1H-indazole and 11.4 g of the (R)-tert-butyl-3-[(tosyloxy)methyl]pyrrolidin-1-carboxylate prepared above with addition of 7.9 g of tetrabutylammonium iodide.

$^1$H-NMR (300 MHz, DMSO-d6): δ=1.34 (9H), 1.50-1.66 (1H), 1.81 (1H), 2.48 (3H), 2.78 (1H), 3.01 (1H), 3.16 (1H), 3.25-3.37 (2H), 4.41 (2H), 7.29 (1H), 7.36 (1H), 8.51 (1H).

EXAMPLE 217b

Methyl 2-{[(R)-1-(tert-butoxycarbonyl)pyrrolidin-3-yl]methyl}-4-methyl-2H-indazol-5-carboxylate

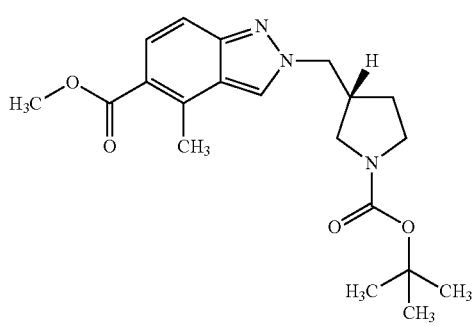 [SMILES: COC(=O)c1ccc2nn(C[C@@H]3CCN(C(=O)OC(C)(C)C)C3)cc2c1C]

Analogously to Example 1e, after two runs 820 mg of the title compound was obtained from 563 mg of the bromide prepared in Example 217a and 0.17 ml of methanol.

¹H-NMR (300 MHz, DMSO-d6): δ=1.34 (9H), 1.58 (1H), 1.83 (1H), 2.73 (3H), 2.80 (1H), 3.03 (1H), 3.17 (1H), 3.25-3.37 (2H), 3.79 (3H), 4.37-4.49 (2H), 7.44 (1H), 7.64 (1H), 8.72 (1H).

EXAMPLE 217c

2-{[(R)-1-(tert-butoxycarbonyl)pyrrolidin-3-yl]methyl}-4-methyl-2H-indazol-5-carboxylic acid

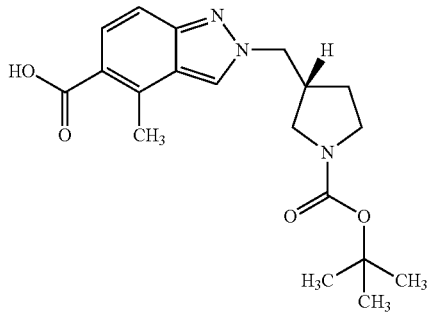 [SMILES: Cc1c(C(=O)O)ccc2nn(C[C@@H]3CCN(C(=O)OC(C)(C)C)C3)cc12]

Analogously to Example 1d, 701 mg of the title compound was obtained from 620 mg of the ester prepared in Example 217b.

¹H-NMR (300 MHz, DMSO-d6): δ=1.34 (9H), 1.50-1.69 (1H), 1.82 (1H), 1.75-1.86 (1H), 2.69-2.88 (4H), 3.03 (1H), 3.17 (1H), 3.24-3.38 (1H), 4.42 (2H), 7.40 (1H), 7.65 (1H), 8.68 (1H), 12.28 (1H).

EXAMPLE 217d (R)-tert-butyl 3-({5-[N-(2-methoxyethyl)carbamoyl]-4-methyl-2H-indazol-2-yl}methyl)pyrrolidin-1-carboxylate

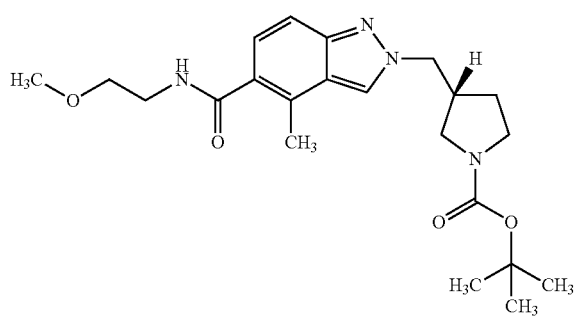 [SMILES: COCCNC(=O)c1ccc2nn(C[C@@H]3CCN(C(=O)OC(C)(C)C)C3)cc2c1C]

Analogously to Example 1, 376 mg of the title compound was obtained from 350 mg of the acid prepared in Example 217c and 73 mg of 2-methoxyethylamine.

¹H-NMR (300 MHz, DMSO-d6): δ=1.35 (9H), 1.57 (1H), 1.80 (1H), 2.50 (3H), 2.73-2.86 (1H), 3.01 (1H), 3.11-3.22 (1H), 3.25 (3H), 3.26-3.39 (3H), 3.39-3.46 (2H), 4.42 (2H), 7.15 (1H), 7.39 (1H), 8.13 (1H), 8.52 (1H).

EXAMPLE 217e

N-(2-methoxyethyl)-4-methyl-2-[(R)-pyrrolidin-3-ylmethyl]-2H-indazol-5-carboxamide hydrochloride

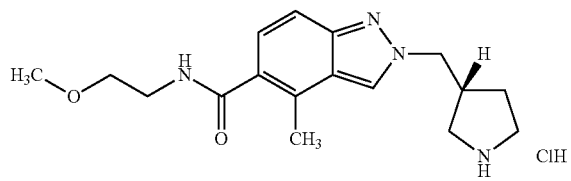 [SMILES: COCCNC(=O)c1ccc2nn(C[C@@H]3CCNC3)cc2c1C ; Cl]

Analogously to Example 1a, from 376 mg of the amide prepared in Example 217d, 465 mg of the title compound was obtained, which was reacted without further purification.

EXAMPLE 218

N-(2-methoxyethyl)-4-methyl-2-({(R)-1-[4-(trifluoromethoxy)benzoyl]-pyrrolidin-3-yl}methyl)-2H-indazol-5-carboxamide

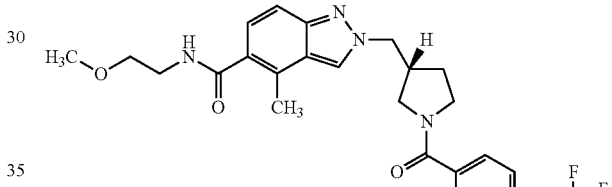

Analogously to Example 55, 61 mg of the title compound was obtained from 106 mg of the compound prepared in Example 217e and 74 mg of 4-(trifluoromethoxy)benzoyl chloride.

¹H-NMR (300 MHz, DMSO-d6): δ=1.57-1.74 (1H), 1.81-1.97 (1H), 2.47/2.51 (3H), 2.77-2.94 (1H), 3.25-3.62 (11H), 4.40/4.51 (2H), 7.09-7.19 (1H), 7.31-7.44 (3H), 7.61 (2H), 8.08-8.16 (1H), 8.47/8.55 (1H).

EXAMPLE 219

N-(2-methoxyethyl)-4-methyl-2-({(3R)-1-[4-(pentafluoro-λ⁶-sulphanyl)benzoyl]-pyrrolidin-3-yl}methyl)-2H-indazol-5-carboxamide

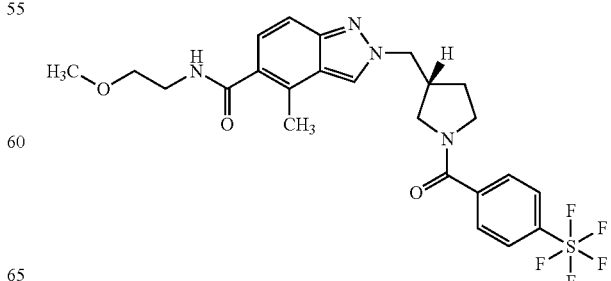

Analogously to Example 1, 29 mg of the title compound was obtained from 106 mg of the compound prepared in Example 217e and 75 mg of 4-(pentafluoro-λ⁶-sulphanyl)benzoic acid.

¹H-NMR (300 MHz, DMSO-d6): δ=1.57-1.76 (1H), 1.81-1.99 (1H), 2.50 (3H), 2.77-2.94 (1H), 3.16-3.62 (11H), 4.39/4.52 (2H), 7.09-7.19 (1H), 7.32-7.44 (1H), 7.68 (2H), 7.90-7.97 (2H), 8.10-8.17 (1H), 8.46/8.55 (1H).

EXAMPLE 220

2-{[(R)-1-(4-chlorobenzoyl)pyrrolidin-3-yl]methyl}-4-methyl-N-{2-[(trifluoromethyl)sulphanyl]ethyl}-2H-indazol-5-carboxamide

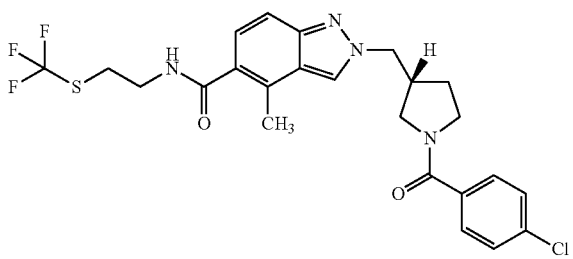 [SMILES: Cc1c(C(=O)NCCSC(F)(F)F)ccc2nn(C[C@@H]3CCN(C(=O)c4ccc(Cl)cc4)C3)cc12]

Analogously to Example 55, 29 mg of the title compound was obtained from 106 mg of the compound prepared in Example 220b and 48 mg of 4-chlorobenzoyl chloride.

¹H-NMR (300 MHz, DMSO-d6): δ=1.57-1.73 (1H), 1.81-1.96 (1H), 2.48/2.53 (3H), 2.79-2.93 (1H), 3.13-3.60 (8H), 4.40/4.51 (2H), 7.14-7.23 (1H), 7.33-7.53 (5H), 8.35-8.42 (1H), 8.49/8.58 (1H).

The starting material was prepared as follows:

EXAMPLE 220a (R)-tert-butyl 3-{[4-methyl-5-(N-{2-[(trifluoromethyl)sulphanyl]ethyl}-carbamoyl)-2H-indazol-2-yl]methyl}pyrrolidin-1-carboxylate

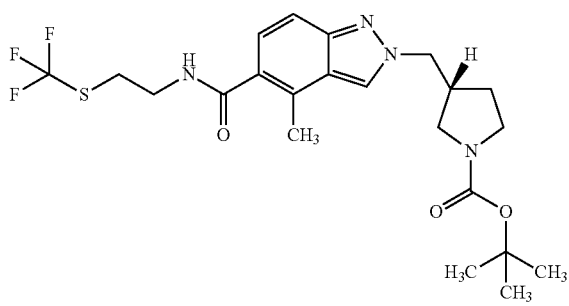 [SMILES: Cc1c(C(=O)NCCSC(F)(F)F)ccc2nn(C[C@@H]3CCN(C(=O)OC(C)(C)C)C3)cc12]

Analogously to Example 1, 245 mg of the title compound was obtained from 350 mg of the acid prepared in Example 217c and 141 mg of 2-[(trifluoromethyl)sulphanyl]ethylamine.

¹H-NMR (300 MHz, DMSO-d6): δ=1.35 (9H), 1.52-1.64 (1H), 1.81 (1H), 2.52 (3H), 2.71-2.96 (2H), 2.97-3.05 (12H), 3.18 (2H), 3.23-3.28 (1H), 3.51 (2H), 4.42 (2H), 7.19 (1H), 7.42 (1H), 8.39 (1H), 8.54 (1H).

EXAMPLE 220b 4-methyl-2-[(R)-pyrrolidin-3-ylmethyl]-N-{2-[(trifluoromethyl)sulphanyl]-ethyl}-2H-indazol-5-carboxamide hydrochloride

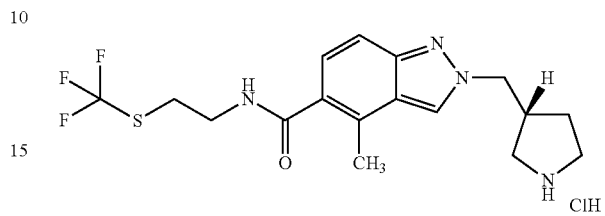

Analogously to Example 1a, from 245 mg of the amide prepared in Example 220a, 410 mg of the title compound was obtained, which was reacted without further purification.

EXAMPLE 221

4-methyl-2-({(R)-1-[4-(trifluoromethoxy)benzoyl]pyrrolidin-3-yl}methyl)-N-{2-[(trifluoromethyl)sulphanyl]ethyl}-2H-indazol-5-carboxamide

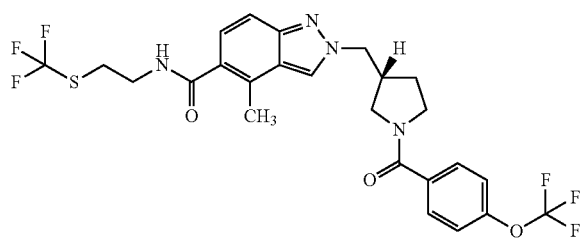 [SMILES: Cc1c(C(=O)NCCSC(F)(F)F)ccc2nn(C[C@@H]3CCN(C(=O)c4ccc(OC(F)(F)F)cc4)C3)cc12]

Analogously to Example 55, 49 mg of the title compound was obtained from 106 mg of the compound prepared in Example 220b and 62 mg of 4-(trifluoromethoxy)benzoyl chloride.

¹H-NMR (300 MHz, DMSO-d6): δ=1.58-1.74 (1H), 1.81-1.98 (1H), 2.48/2.53 (3H), 2.78-2.94 (1H), 3.12-3.62 (8H), 4.40/4.52 (2H), 7.14-7.23 (1H), 7.32-7.49 (3H), 7.61 (2H), 8.35-8.43 (1H), 8.49/8.58 (1H).

EXAMPLE 222

2-{[(S)-1-(4-chlorobenzoyl)pyrrolidin-3-yl]methyl}-N-(2-methoxyethyl)-4-methyl-2H-indazol-5-carboxamide

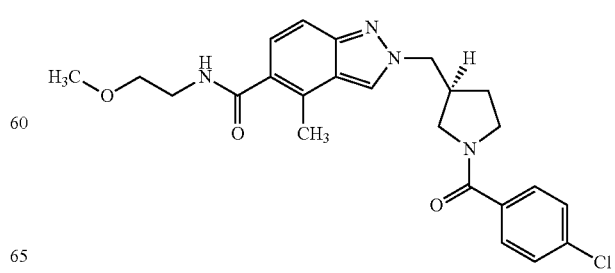

Analogously to Example 55, 67 mg of the title compound was obtained from 134 mg of the compound prepared in Example 222a and 73 mg of 4-chlorobenzoyl chloride.

¹H-NMR (300 MHz, CDCl3): δ=1.72-1.86 (1H), 1.99-2.20 (1H), 2.64 (3H), 2.93-3.13 (1H), 3.29-3.36 (1H), 3.39 (3H), 3.45-3.71 (6H), 3.76-3.86 (1H), 4.31-4.57 (2H), 6.12-6.20 (1H), 7.30-7.42 (3H), 7.43-7.56 (3H), 7.90/8.02 (1H).

The starting material was prepared as follows:

EXAMPLE 222a (S)-tert-butyl 3-({5-[N-(2-methoxyethyl)carbamoyl]-4-methyl-2H-indazol-2-yl}methyl)pyrrolidin-1-carboxylate

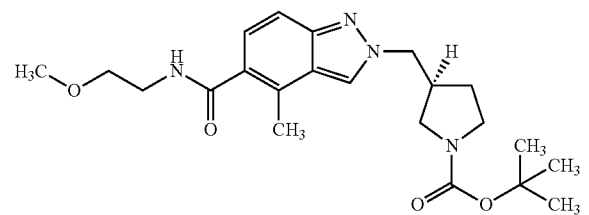 [SMILES: COCCNC(=O)c1ccc2nn(C[C@H]3CCN(C(=O)OC(C)(C)C)C3)cc2c1C]

Analogously to Example 217a to 217d, this title compound was prepared in a quantity of 760 mg starting from (S)-tert-butyl-3-(hydroxymethyl)pyrrolidin-1-carboxylate.

¹H-NMR (300 MHz, DMSO-d6): δ=1.35 (9H), 1.52-1.64 (1H), 1.77-1.87 (1H), 1.76-1.82 (1H), 2.50 (3H), 2.74-2.86 (1H), 3.02 (1H), 3.12-3.20 (1H), 3.25 (3H), 3.31 (1H), 3.36 (2H), 3.43 (2H), 4.42 (2H), 7.16 (1H), 7.39 (1H), 8.10 (1H), 8.51 (1H).

EXAMPLE 222b

N-(2-methoxyethyl)-4-methyl-2-[(S)-pyrrolidin-3-ylmethyl]-2H-indazol-5-carboxamide hydrochloride

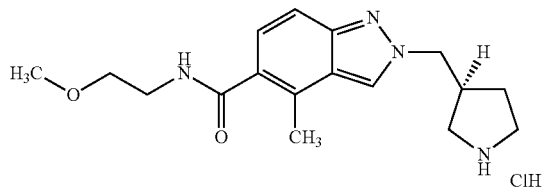 [SMILES: COCCNC(=O)c1ccc2nn(C[C@H]3CCNC3)cc2c1C ; Cl]

Analogously to Example 1a, from 159 mg of the amide prepared in Example 222a, 134 mg of the title compound was obtained, which was reacted without further purification.

EXAMPLE 223

2-({(S)-1-[(4'-fluorobiphenyl-4-yl)carbonyl]pyrrolidin-3-yl}methyl)-N-(2-methoxyethyl)-4-methyl-2H-indazol-5-carboxamide

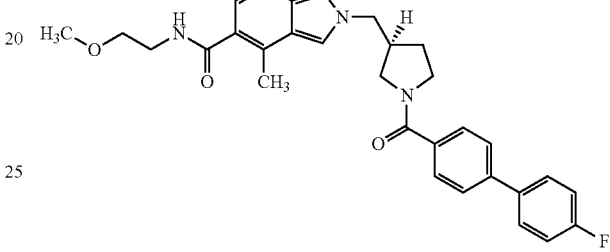

Analogously to Example 1, 128 mg of the title compound was obtained from 230 mg of the compound prepared in Example 222b and 141 mg of 4'-fluorobiphenyl-4-carboxylic acid.

¹H-NMR (300 MHz, CDCl3): δ=1.73-1.89 (1H), 1.98-2.24 (1H), 2.60/2.67 (3H), 2.94-3.18 (1H), 3.37/3.39 (3H), 3.49-3.76 (6H), 3.79-3.91 (2H), 4.32-4.61 (2H), 6.08-6.21 (1H), 7.09-7.20 (2H), 7.28-7.38 (1H), 7.46-7.62 (7H), 7.91/8.04 (1H).

EXAMPLE 224

N-(2-methoxyethyl)-4-methyl-2-{[(S)-1-{4-[4-(trifluoromethyl)phenoxy]benzoyl}pyrrolidin-3-yl]methyl}-2H-indazol-5-carboxamide

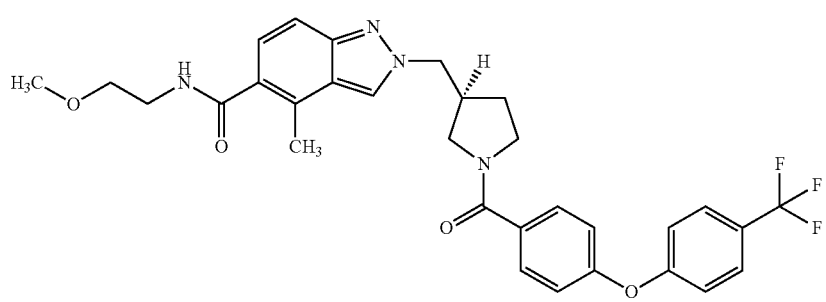 [SMILES: COCCNC(=O)c1ccc2nn(C[C@H]3CCN(C(=O)c4ccc(Oc5ccc(C(F)(F)F)cc5)cc4)C3)cc2c1C]

Analogously to Example 1, 102 mg of the title compound was obtained from 230 mg of the compound prepared in Example 222b and 184 mg of 4-[4-(trifluoromethyl)phenoxy]benzoic acid.

$^1$H-NMR (300 MHz, CDCl3): δ=1.70-2.25 (2H), 2.63/2.66 (3H), 2.94-3.17 (1H), 3.39 (3H), 3.47-3.92 (8H), 4.33-4.59 (2H), 6.15 (1H), 7.00-7.11 (4H), 7.30-7.40 (1H), 7.47-7.65 (5H), 7.91/8.03 (1H).

EXAMPLE 225

2-{[1-(4-chlorobenzoyl)piperidin-4-yl]methyl}-4-(difluoromethoxy)-N-(2-methoxyethyl)-2H-indazol-5-carboxamide

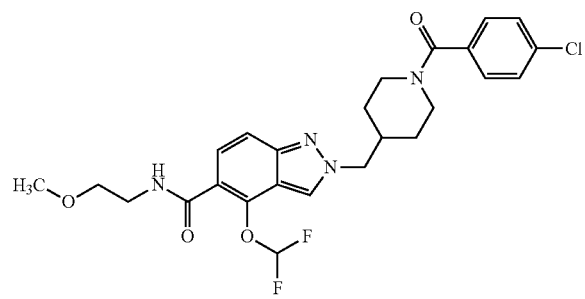 [SMILES: COCCNC(=O)c1ccc2nn(CC3CCN(C(=O)c4ccc(Cl)cc4)CC3)cc2c1OC(F)F]

Analogously to Example 55, 90 mg of the title compound was obtained from 106 mg of the compound prepared in Example 225h and 49 mg of 4-chlorobenzoyl chloride.

$^1$H-NMR (300 MHz, DMSO-d6): δ=1.14-1.58 (4H), 2.19-2.34 (1H), 2.67-2.81 (1H), 2.97 (1H), 3.22-3.53 (9H), 4.37 (2H), 7.13 (1H), 7.31-7.39 (3H), 7.47 (2H), 7.54 (1H), 8.21 (1H), 8.50 (1H).

The starting material was prepared as follows:

EXAMPLE 225a

N-[4-bromo-3-(difluoromethoxy)-2-methylphenyl]acetamide

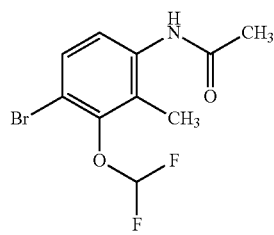 [SMILES: CC(=O)Nc1ccc(Br)c(OC(F)F)c1C]

To a solution of 5.0 g of 3-difluoromethoxy-2-methylaniline in 48 ml DMF, a solution of 5.1 g of N-bromosuccinimide in 24 ml DMF was added dropwise at 0° C. and stirred for 1 hour at 0° C. Then the reaction mixture was diluted with 400 ml hexane/ethyl acetate, and washed once with 50 ml of a 10% aqueous sodium carbonate solution and three times with 50 ml portions of water. After drying over sodium sulphate and filtration, this was concentrated in vacuo. The crude product thus obtained (6.68 g) was used in the next step without purification.

To a solution of 6.39 g of the bromide prepared above in 70 ml pyridine, 3.0 ml of acetic anhydride were added dropwise at 0° C. and stirred for 20 hours at 25° C. The reaction mixture was concentrated in vacuo and the crude product thus obtained purified by column chromatography on silica gel with hexane/0-100% ethyl acetate. The substance was then recrystallized from hexane. In this manner, 6.39 g of the title compound was obtained.

$^1$H-NMR (300 MHz, CDCl3): δ=2.22 (3H), 2.27 (3H), 6.51 (1H), 6.95 (1H), 7.46 (1H), 7.71 (1H).

EXAMPLE 225b

1-[5-bromo-4-(difluoromethoxy)-1H-indazol-1-yl]ethan-1-one

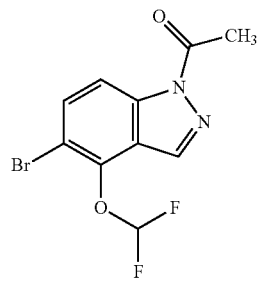 [SMILES: CC(=O)n1ncc2c(OC(F)F)c(Br)ccc21]

Analogously to Example 212c, 5.32 g of the title compound was obtained from 6.38 g of the amide prepared in Example 225a.

$^1$H-NMR (300 MHz, DMSO-d6): δ=2.70 (3H), 7.34 (1H), 7.90 (1H), 8.16 (1H), 8.46 (1H).

EXAMPLE 225c 5-bromo-4-(difluoromethoxy)-1H-indazole

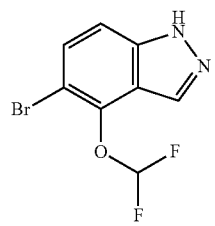 [SMILES: FC(F)Oc1c(Br)ccc2[nH]ncc12]

Analogously to Example 212d, 4.12 g of the title compound was obtained from 5.32 g of the indazole prepared in Example 225b.

$^1$H-NMR (300 MHz, DMSO-d6): δ=7.30 (1H), 7.44 (1H), 7.56 (1H), 8.06 (1H), 13.54 (1H).

EXAMPLE 225d

Tert-butyl 4-{[5-bromo-4-(difluoromethoxy)-2H-indazol-2-yl]methyl}-piperidin-1-carboxylate

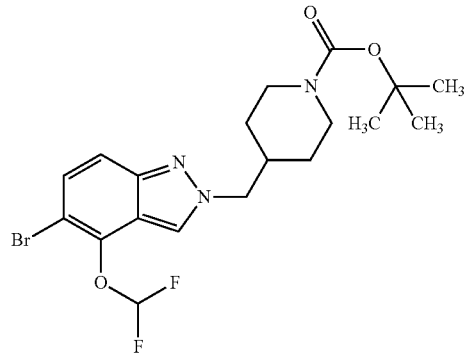 [SMILES: CC(C)(C)OC(=O)N1CCC(Cn2cc3c(OC(F)F)c(Br)ccc3n2)CC1]

Analogously to Example 212e, 2.06 g of the title compound was obtained from 4.1 g of the indazole prepared in Example 225c and 8.7 g of tert-butyl 4-[(tosyloxy)methyl]piperidin-1-carboxylate.

$^1$H-NMR (300 MHz, CDCl3): δ=1.19-1.28 (2H), 1.45 (9H), 1.51-1.59 (2H), 2.25 (1H), 2.68 (2H), 4.12 (2H), 4.27 (2H), 6.61 (1H), 7.41 (1H), 7.50 (1H), 7.95 (1H).

EXAMPLE 225e

Methyl 2-{[1-(tert-butoxycarbonyl)piperidin-4-yl]methyl}-4-(difluoromethoxy)-2H-indazol-5-carboxylate

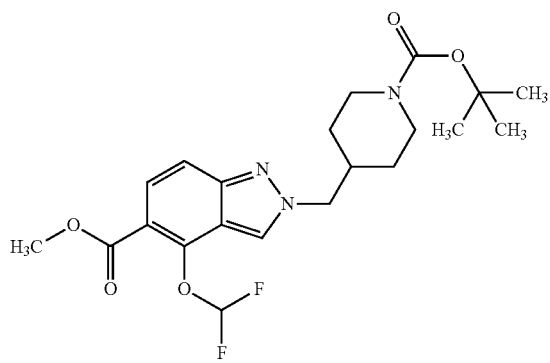 [SMILES: COC(=O)c1ccc2nn(CC3CCN(C(=O)OC(C)(C)C)CC3)cc2c1OC(F)F]

Analogously to Example 1e, after three runs 1.28 g of the title compound was obtained from 683 mg of the bromide prepared in Example 225d and 0.18 ml of methanol.

$^1$H-NMR (300 MHz, DMSO-d6): δ=0.96-1.22 (2H), 1.28-1.47 (11H), 2.14 (1H), 2.54-2.74 (2H), 3.81 (3H), 3.87 (2H), 4.36 (2H), 7.17 (1H), 7.58 (1H), 7.65 (1H), 8.62 (1H).

EXAMPLE 225f

2-{[1-(tert-butoxycarbonyl)piperidin-4-yl]methyl}-4-(difluoromethoxy)-2H-indazol-5-carboxylic acid

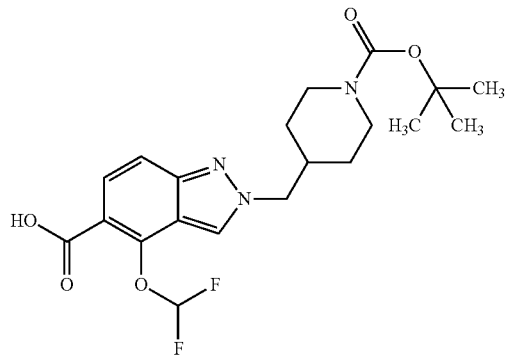 [SMILES: CC(C)(C)OC(=O)N1CCC(Cn2cc3c(OC(F)F)c(C(=O)O)ccc3n2)CC1]

Analogously to Example 1d, 1.05 g of the title compound was obtained from 1.28 g of the ester prepared in Example 225e.

$^1$H-NMR (300 MHz, DMSO-d6): δ=0.97-1.16 (2H), 1.28-1.47 (11H), 2.13 (1H), 2.63 (2H), 3.87 (2H), 4.35 (2H), 7.14 (1H), 7.54 (1H), 7.65 (1H), 8.58 (1H), 13.05 (1H).

EXAMPLE 225g

Tert-butyl 4-({4-(difluoromethoxy)-5-[N-(2-methoxyethyl)carbamoyl]-2H-indazol-2-yl}methyl)piperidin-1-carboxylate

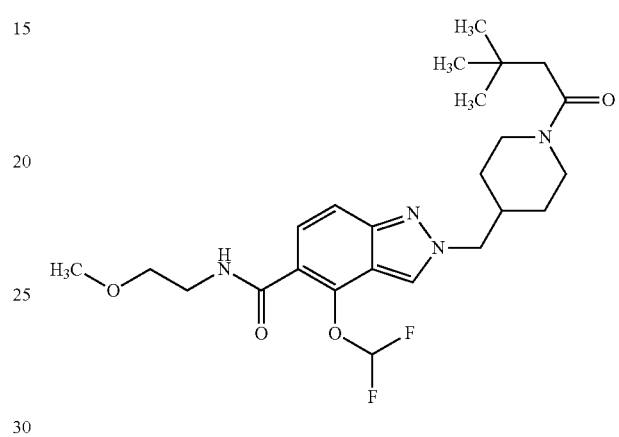

Analogously to Example 1, 503 mg of the title compound was obtained from 520 mg of the compound prepared in Example 225f and 92 mg of 2-methoxyethylamine.

$^1$H-NMR (300 MHz, DMSO-d6): δ=1.01-1.13 (2H), 1.34 (9H), 1.38 (2H), 2.13 (1H), 2.59-2.71 (6H), 3.24 (3H), 3.34-3.44 (2H), 3.87 (2H), 4.34 (2H), 7.14 (1H), 7.33 (1H), 7.54 (1H), 8.21 (1H), 8.50 (1H).

EXAMPLE 225h 4-(difluoromethoxy)-N-(2-methoxyethyl)-2-(4-piperidylmethyl)-2H-indazol-5-carboxamide hydrochloride

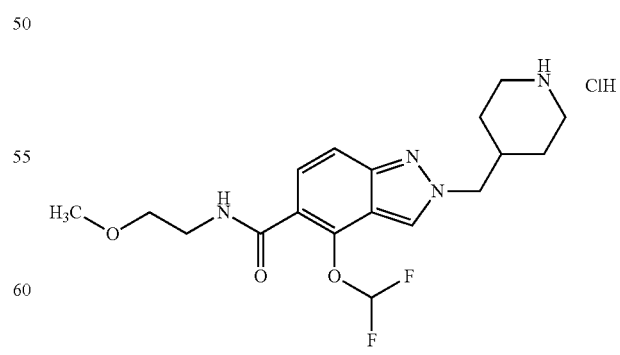

Analogously to Example 1a, from 122 mg of the amide prepared in Example 225g, 106 mg of the title compound was obtained, which was reacted without further purification.

EXAMPLE 226

4-(difluoromethoxy)-2-({1-[4-(4-fluorophenoxy)benzoyl]piperidin-4-yl}methyl)-N-(2-methoxyethyl)-2H-indazol-5-carboxamide

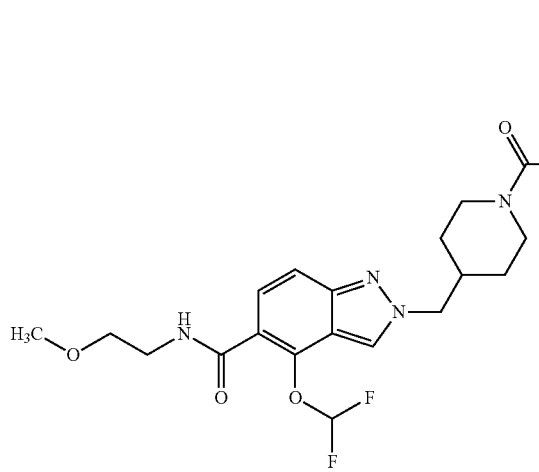

Analogously to Example 1, 11 mg of the title compound was obtained from 106 mg of the compound prepared in Example 225h and 59 mg of 4-(4-fluorophenoxy)benzoic acid.

$^1$H-NMR (300 MHz, DMSO-d6): δ=1.10-1.59 (4H), 2.23-2.33 (1H), 2.75-3.01 (2H), 3.24 (3H), 3.33-3.51 (5H), 3.51-3.72 (1H), 4.37 (2H), 6.95 (2H), 7.07-7.12 (2H), 7.13 (1H), 7.17-7.26 (2H), 7.28-7.39 (3H), 7.54 (1H), 8.21 (1H), 8.50 (1H).

EXAMPLE 227

4-(difluoromethoxy)-2-({1-[(4'-fluorobiphenyl-4-yl)carbonyl]piperidin-4-yl}methyl)-N-(2-methoxyethyl)-2H-indazol-5-carboxamide

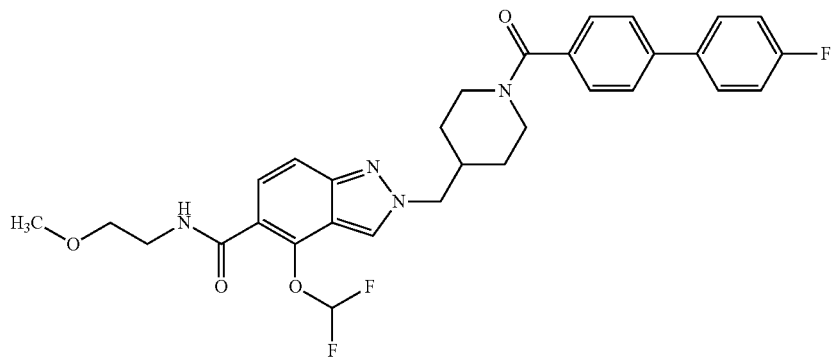 [SMILES: COCCNC(=O)c1ccc2nn(CC3CCN(C(=O)c4ccc(-c5ccc(F)cc5)cc4)CC3)cc2c1OC(F)F]

Analogously to Example 1, 38 mg of the title compound was obtained from 106 mg of the compound prepared in Example 225h and 55 mg of 4'-fluorobiphenyl-4-carboxylic acid.

$^1$H-NMR (300 MHz, DMSO-d6): δ=1.14-1.62 (4H), 2.23-2.35 (1H), 2.68-2.85 (1H), 2.91-3.09 (1H), 3.24 (3H), 3.32-3.48 (5H), 3.50-3.70 (1H), 4.38 (2H), 7.14 (1H), 7.28 (2H), 7.33 (1H), 7.40 (2H), 7.55 (1H), 7.64-7.75 (4H), 8.21 (1H), 8.51 (1H).

EXAMPLE 228

2-{[1-(4-cyclopropylbenzoyl)piperidin-4-yl]methyl}-4-(difluoromethoxy)-N-(2-methoxyethyl)-2H-indazol-5-carboxamide

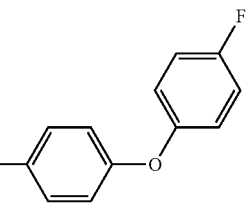

Analogously to Example 1, 75 mg of the title compound was obtained from 106 mg of the compound prepared in Example 225h and 41 mg of 4-cyclopropylbenzoic acid.

$^1$H-NMR (300 MHz, DMSO-d6): δ=0.66 (2H), 0.94 (2H), 1.10-1.54 (4H), 1.90 (1H), 2.14-2.31 (1H), 2.72-3.02 (2H), 3.03-3.18 (1H), 3.24 (3H), 3.33-3.47 (4H), 3.49-3.68 (1H), 4.37 (2H), 7.07 (2H), 7.13 (1H), 7.19 (2H), 7.33 (1H), 7.54 (1H), 8.21 (1H), 8.50 (1H).

EXAMPLE 229

2-{[1-(4-chlorobenzoyl)piperidin-4-yl]methyl}-N-[2-(cyclopropylmethoxy)-ethyl]-4-(difluoromethoxy)-2H-indazol-5-carboxamide

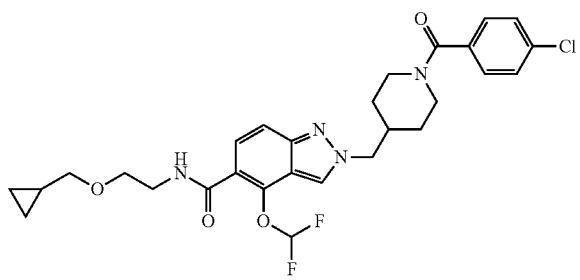 [SMILES: O=C(NCCOCC1CC1)c1ccc2nn(CC3CCN(C(=O)c4ccc(Cl)cc4)CC3)cc2c1OC(F)F]

Analogously to Example 55, 170 mg of the title compound was obtained from 127 mg of the compound prepared in Example 229b and 53 mg of 4-chlorobenzoyl chloride.

¹H-NMR (300 MHz, DMSO-d6): δ=0.14 (2H), 0.42 (2H), 0.96 (1H), 1.10-1.27 (2H), 1.37 (1H), 1.51 (1H), 2.26 (1H), 2.71 (1H), 2.97 (1H), 3.20-3.55 (8H), 4.37 (2H), 7.14 (1H), 7.31-7.38 (3H), 7.47 (2H), 7.55 (1H), 8.21 (1H), 8.51 (1H).

The starting material was prepared as follows:

EXAMPLE 229a

Tert-butyl 4-{[5-{N-[2-(cyclopropylmethoxy)ethyl]carbamoyl}-4-(difluoromethoxy)-2H-indazol-2-yl]methyl}piperidin-1-carboxylate

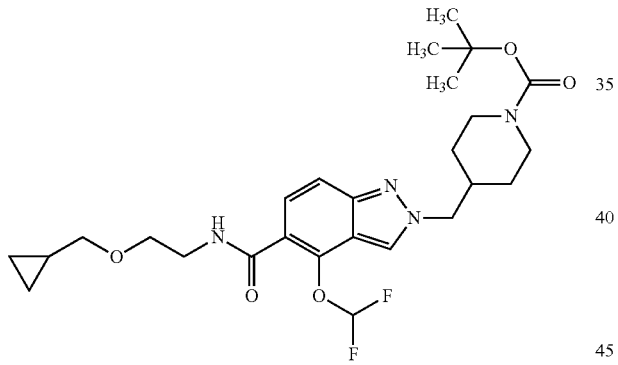

Analogously to Example 1, 453 mg of the title compound was obtained from 520 mg of the compound prepared in Example 225f and 185 mg of 2-(cyclopropylmethoxy)ethylamine.

¹H-NMR (300 MHz, DMSO-d6): δ=0.14 (2H), 0.42 (2H), 0.97 (1H), 1.07 (2H), 1.34 (9H), 1.39 (2H), 2.13 (1H), 2.56-2.72 (2H), 3.23 (2H), 3.37 (2H), 3.48 (2H), 3.87 (2H), 4.34 (2H), 7.15 (1H), 7.34 (1H), 7.55 (1H), 8.21 (1H), 8.50 (1H).

EXAMPLE 229b

N-[(2-cyclopropylmethoxy)ethyl]-4-(difluoromethoxy)-2-(4-piperidylmethyl)-2H-indazol-5-carboxamide hydrochloride

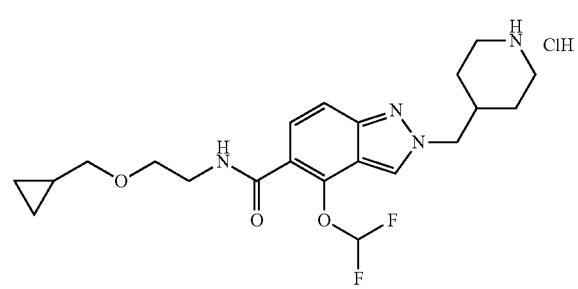 [SMILES: O=C(NCCOCC1CC1)c1ccc2nn(CC3CCNCC3)cc2c1OC(F)F ; Cl]

Analogously to Example 1a, from 145 mg of the amide prepared in Example 229a, 127 mg of the title compound was obtained, which was reacted without further purification.

EXAMPLE 230

N-[2-(cyclopropylmethoxy)ethyl]-4-(difluoromethoxy)-2-({1-[4-(4-fluoro-phenoxy)benzoyl]piperidin-4-yl}methyl)-2H-indazol-5-carboxamide

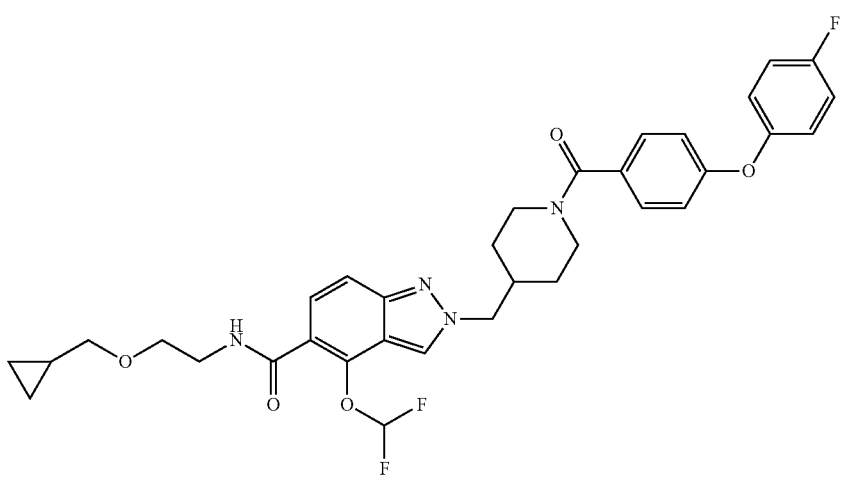 [SMILES: O=C(NCCOCC1CC1)c1ccc2nn(CC3CCN(C(=O)c4ccc(Oc5ccc(F)cc5)cc4)CC3)cc2c1OC(F)F]

Analogously to Example 1, 156 mg of the title compound was obtained from 127 mg of the compound prepared in Example 229b and 64 mg of 4-(4-fluorophenoxy)benzoic acid.

$^1$H-NMR (300 MHz, DMSO-d6): δ=0.14 (2H), 0.42 (2H), 0.96 (1H), 1.10-1.54 (4H), 2.18-2.33 (1H), 2.71-3.02 (2H), 3.03-3.16 (1H), 3.22 (2H), 3.37 (2H), 3.47 (2H), 3.55-3.68 (1H), 4.37 (2H), 6.95 (2H), 7.10 (2H), 7.14 (1H), 7.22 (2H), 7.34 (3H), 7.55 (1H), 8.21 (1H), 8.51 (1H).

EXAMPLE 231

N-[2-(cyclopropylmethoxy)ethyl]-4-(difluoromethoxy)-2-({1-[(4'-fluorobiphenyl-4-yl)carbonyl]piperidin-4-yl}methyl)-2H-indazol-5-carboxamide

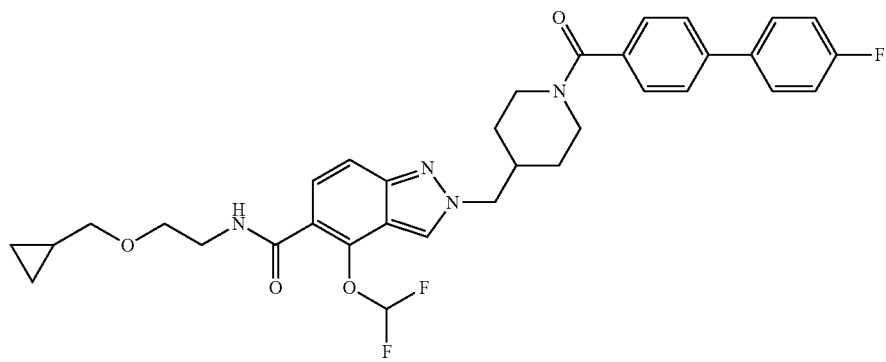 [SMILES: O=C(NCCOCC1CC1)c1ccc2nn(CC3CCN(C(=O)c4ccc(-c5ccc(F)cc5)cc4)CC3)cc2c1OC(F)F]

Analogously to Example 1, 164 mg of the title compound was obtained from 127 mg of the compound prepared in Example 229b and 60 mg of 4'-fluorobiphenyl-4-carboxylic acid.

$^1$H-NMR (300 MHz, DMSO-d6): δ=0.14 (2H), 0.42 (2H), 0.96 (1H), 1.14-1.60 (4H), 2.27 (1H), 2.70-3.04 (2H), 2.87 (1H), 3.03-3.15 (1H), 3.22 (2H), 3.37 (2H), 3.47 (2H), 3.60 (1H), 4.38 (2H), 7.14 (1H), 7.28 (2H), 7.34 (1H), 7.41 (2H), 7.55 (1H), 7.64-7.75 (4H), 8.21 (1H), 8.52 (1H).

EXAMPLE 232

2-{[1-(4-chlorobenzoyl)piperidin-4-yl]methyl}-N-(2-methoxyethyl)-4-(2,2,2-trifluoroethoxy)-2H-indazol-5-carboxamide

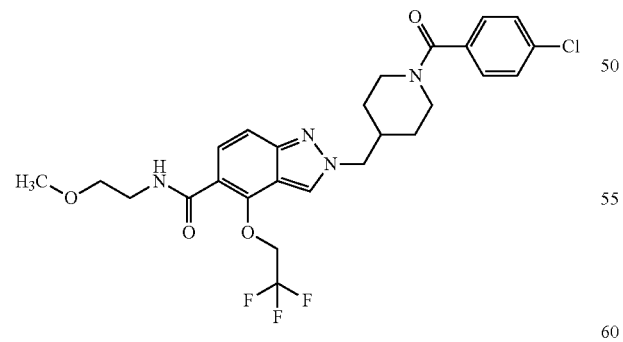

Analogously to Example 55, 113 mg of the title compound was obtained from 109 mg of the compound prepared in Example 232h and 46 mg of 4-chlorobenzoyl chloride.

$^1$H-NMR (300 MHz, DMSO-d6): δ=1.12-1.61 (3H), 2.19-2.34 (1H), 2.67-3.07 (2H), 3.23 (3H), 3.33-3.56 (4H), 4.28-4.47 (3H), 4.95 (2H), 7.31-7.39 (3H), 7.40-7.50 (3H), 7.99 (1H), 8.65 (1H).

The starting material was prepared as follows:

EXAMPLE 232a

N-[4-bromo-2-methyl-3-(2,2,2-trifluoroethoxy)phenyl]acetamide

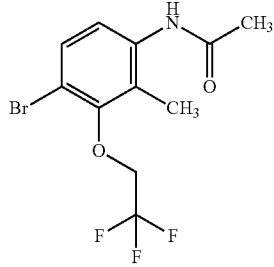 [SMILES: CC(=O)Nc1ccc(Br)c(OCC(F)(F)F)c1C]

Analogously to Example 225a, 6.13 g of the title compound was obtained from 5.0 g of 2-methyl-3-(2,2,2-trifluoroethoxy)aniline.

$^1$H-NMR (300 MHz, DMSO-d6): δ=2.07 (3H), 2.18 (3H), 4.55 (2H), 7.29 (1H), 7.45 (1H), 9.42 (1H).

EXAMPLE 232b

1-[5-bromo-4-(2,2,2-trifluoroethoxy)-1H-indazol-1-yl]ethan-1-one

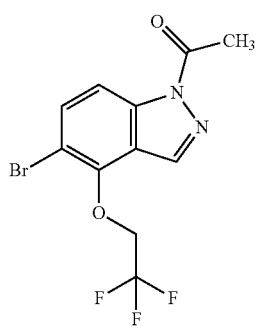 [SMILES: CC(=O)n1ncc2c(OCC(F)(F)F)c(Br)ccc21]

Analogously to Example 212c, 5.08 g of the title compound was obtained from 6.13 g of the amide prepared in Example 232a.

$^1$H-NMR (300 MHz, DMSO-d6): δ=2.69 (3H), 5.14 (2H), 7.80 (1H), 7.99 (1H), 8.64 (1H).

EXAMPLE 232c 5-bromo-4-(2,2,2-trifluoroethoxy)-1H-indazole

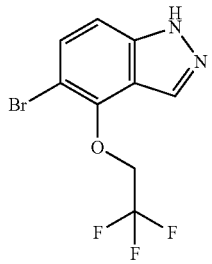 [SMILES: FC(F)(F)COc1c(Br)ccc2[nH]ncc12]

Analogously to Example 212d, 3.57 g of the title compound was obtained from 5.08 g of the indazole prepared in Example 232b.

¹H-NMR (300 MHz, DMSO-d6): δ=5.05 (2H), 7.24 (1H), 7.45 (1H), 8.26 (1H), 13.38 (1H).

EXAMPLE 232d

Tert-butyl 4-{[5-bromo-4-(2,2,2-trifluoroethoxy)-2H-indazol-2-yl]methyl}-piperidin-1-carboxylate

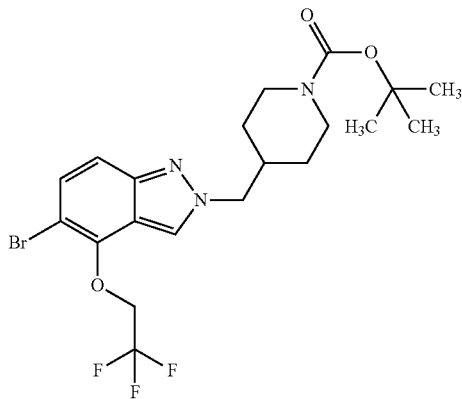 [SMILES: CC(C)(C)OC(=O)N1CCC(Cn2cc3c(OCC(F)(F)F)c(Br)ccc3n2)CC1]

Analogously to Example 212e, 1.77 g of the title compound was obtained from 3.57 g of the indazole prepared in Example 232c and 6.7 g of tert-butyl 4-[(tosyloxy)methyl]piperidin-1-carboxylate.

¹H-NMR (300 MHz, CDCl3): δ=1.16-1.31 (2H), 1.45 (9H), 1.54 (2H), 2.25 (1H), 2.68 (2H), 4.05-4.21 (2H), 4.27 (2H), 4.54 (2H), 7.35 (1H), 7.41 (1H), 7.91 (1H).

EXAMPLE 232e

Methyl 2-{[1-(tert-butoxycarbonyl)piperidin-4-yl]methyl}-4-(2,2,2-trifluoro-ethoxy)-2H-indazole-5-carboxylate

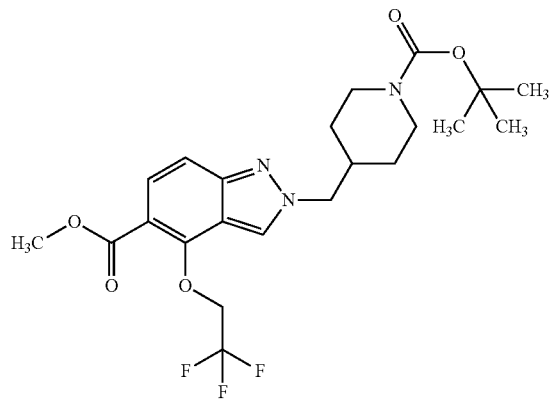 [SMILES: COC(=O)c1ccc2nn(CC3CCN(C(=O)OC(C)(C)C)CC3)cc2c1OCC(F)(F)F]

Analogously to Example 1e, after three runs 857 mg of the title compound was obtained from 590 mg of the bromide prepared in Example 232d and 0.15 ml of methanol.

¹H-NMR (300 MHz, DMSO-d6): δ=1.00-1.17 (2H), 1.34 (9H), 1.37-1.47 (2H), 2.13 (1H), 2.55-2.74 (2H), 3.79 (3H), 3.87 (2H), 4.32 (2H), 4.89 (2H), 7.39 (1H), 7.56 (1H), 8.67 (1H).

EXAMPLE 232f

2-{[1-(tert-butoxycarbonyl)piperidin-4-yl]methyl}-4-(2,2,2-trifluoroethoxy)-2H-indazole-5-carboxylic acid

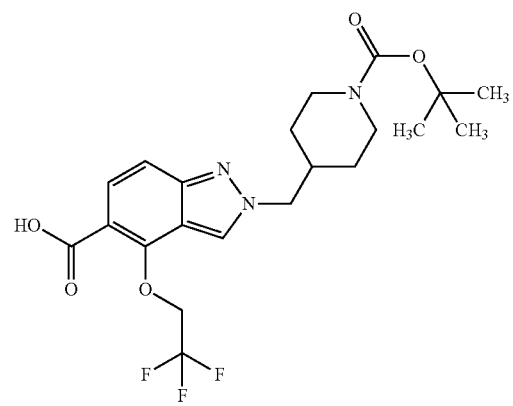 [SMILES: CC(C)(C)OC(=O)N1CCC(Cn2cc3c(OCC(F)(F)F)c(C(=O)O)ccc3n2)CC1]

Analogously to Example 1d, 724 mg of the title compound was obtained from 854 mg of the ester prepared in Example 232e.

¹H-NMR (300 MHz, DMSO-d6): δ=1.01-1.17 (2H), 1.34 (9H), 1.40 (2H), 2.13 (1H), 2.53-2.75 (2H), 3.87 (2H), 4.32 (2H), 4.84 (2H), 7.37 (1H), 7.58 (1H), 8.60 (1H), 12.74 (1H).

EXAMPLE 232g

Tert-butyl 4-({5-[N-(2-methoxyethyl)carbamoyl]-4-(2,2,2-trifluoroethoxy)-2H-indazol-2-yl}methyl)piperidin-1-carboxylate

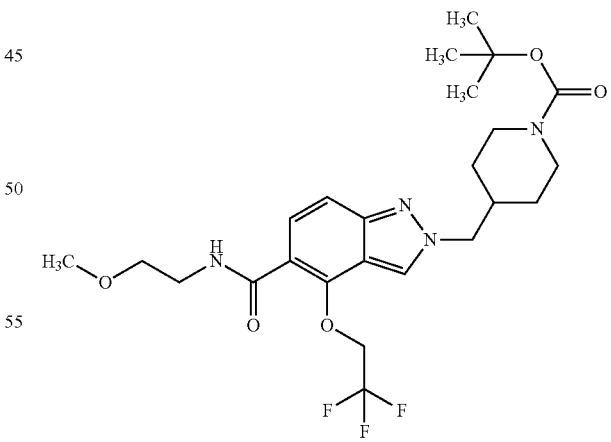

Analogously to Example 1, 386 mg of the title compound was obtained from 360 mg of the compound prepared in Example 232f and 59 mg of 2-methoxyethylamine.

¹H-NMR (300 MHz, DMSO-d6): δ=0.98-1.18 (2H), 1.34 (9H), 1.43 (2H), 2.14 (1H), 2.65 (2H), 3.23 (3H), 3.35-3.47 (4H), 3.88 (2H), 4.30 (2H), 4.96 (2H), 7.35 (1H), 7.43 (1H), 7.99 (1H), 8.65 (1H).

EXAMPLE 232h
N-(2-methoxyethyl)-2-(4-piperidylmethyl)-4-(2,2,2-trifluoroethoxy)-2H-indazol-5-carboxamide hydrochloride

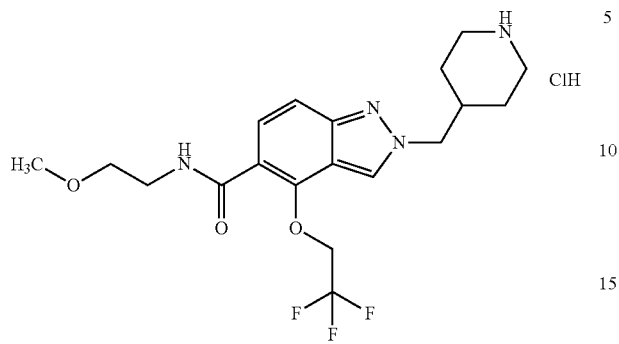

Analogously to Example 1a, from 109 mg of the amide prepared in Example 232g, 113 mg of the title compound was obtained, which was reacted without further purification.

EXAMPLE 233
2-({1-[4-(4-fluorophenoxy)benzoyl]piperidin-4-yl}methyl)-N-(2-methoxyethyl)-4-(2,2,2-trifluoroethoxy)-2H-indazol-5-carboxamide

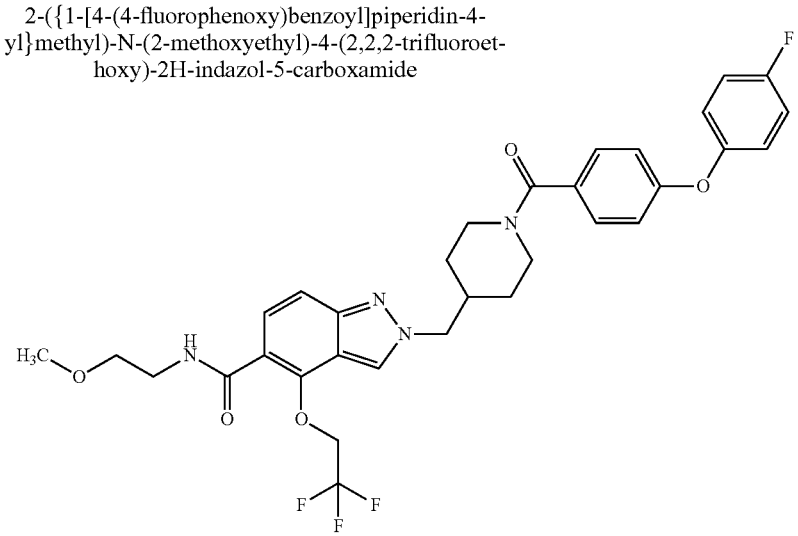

Analogously to Example 1, 51 mg of the title compound was obtained from 109 mg of the compound prepared in Example 232h and 56 mg of 4-(4-fluorophenoxy)benzoic acid.

$^1$H-NMR (300 MHz, DMSO-d6): δ=1.10-1.31 (1H), 1.48 (2H), 2.18-2.37 (1H), 2.69-3.04 (2H), 3.23 (3H), 3.37-3.48 (4H), 3.56-3.71 (1H), 4.33 (2H), 4.95 (2H), 6.95 (2H), 7.06-7.15 (2H), 7.18-7.27 (2H), 7.31-7.38 (3H), 7.40-7.47 (1H), 7.99 (1H), 8.66 (1H).

EXAMPLE 234
2-({1-[(4'-fluorobiphenyl-4-yl)carbonyl]piperidin-4-yl}methyl)-N-(2-methoxy-ethyl)-4-(2,2,2-trifluoroethoxy)-2H-indazol-5-carboxamide

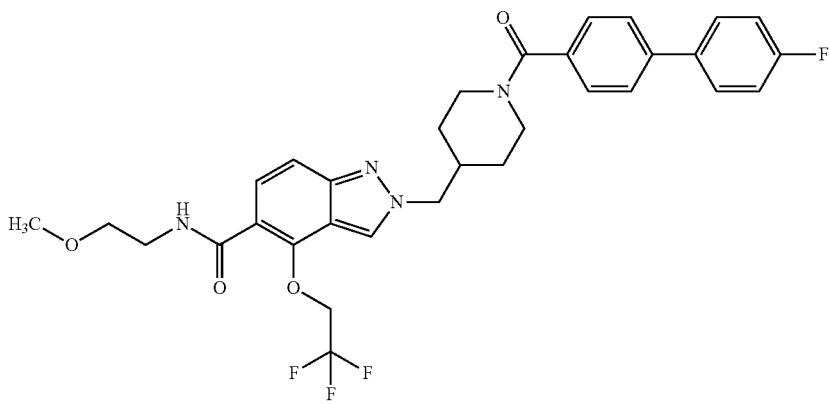 [SMILES: COCCNC(=O)c1ccc2nn(CC3CCN(C(=O)c4ccc(-c5ccc(F)cc5)cc4)CC3)cc2c1OCC(F)(F)F]

Analogously to Example 1, 61 mg of the title compound was obtained from 109 mg of the compound prepared in Example 232h and 52 mg of 4-(4-fluorophenyl)benzoic acid.

$^1$H-NMR (300 MHz, DMSO-d6): δ=1.14-1.63 (3H), 2.19-2.37 (1H), 2.68-3.09 (2H), 3.23 (3H), 3.34-3.48 (4H), 3.62 (1H), 4.28-4.42 (2H), 4.96 (2H), 7.22-7.47 (6H), 7.64-7.76 (4H), 7.99 (1H), 8.66 (1H).

EXAMPLE 235

2-{[1-(4-chlorobenzoyl)piperidin-4-yl]methyl}-N-[2-(cyclopropylmethoxy)-ethyl]-4-(2,2,2-trifluoroethoxy)-2H-indazol-5-carboxamide

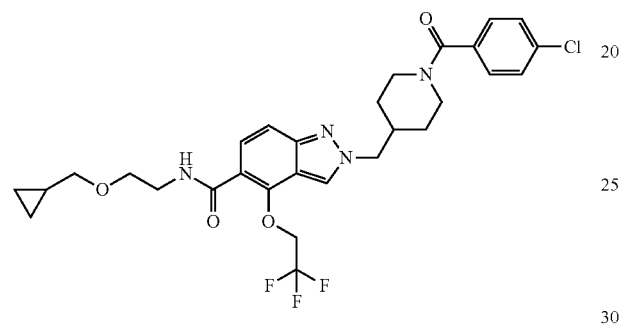

Analogously to Example 55, 122 mg of the title compound was obtained from 122 mg of the compound prepared in Example 235b and 48 mg of 4-chlorobenzoyl chloride.

$^1$H-NMR (300 MHz, DMSO-d6): δ=0.13 (2H), 0.41 (2H), 0.95 (1H), 1.11-1.62 (3H), 2.19-2.34 (1H), 2.73 (1H), 2.98 (1H), 3.21 (2H), 3.33-3.57 (5H), 4.33 (2H), 4.95 (2H), 7.31-7.51 (6H), 8.00 (1H), 8.65 (1H).

The starting material was prepared as follows:

EXAMPLE 235a

Tert-butyl 4-{[5-{N-[2-(cyclopropylmethoxy)ethyl]carbamoyl}-4-(2,2,2-trifluoroethoxy)-2H-indazol-2-yl]methyl}piperidin-1-carboxylate

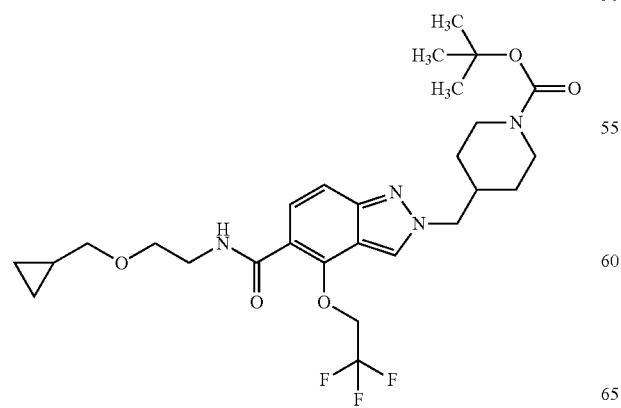

Analogously to Example 1, 429 mg of the title compound was obtained from 360 mg of the compound prepared in Example 232f and 119 mg of 2-(cyclopropylmethoxy)ethylamine.

$^1$H-NMR (300 MHz, DMSO-d6): δ=0.13 (2H), 0.42 (2H), 0.95 (1H), 1.08 (2H), 1.34 (9H), 1.41 (2H), 2.14 (1H), 3.22 (2H), 3.41 (2H), 3.48 (2H), 3.88 (2H), 4.30 (2H), 4.95 (2H), 7.35 (1H), 7.42 (1H), 8.00 (1H), 8.65 (1H).

EXAMPLE 235b

N-[2-(cyclopropylmethoxy)ethyl]-2-(4-piperidylmethyl)-4-(2,2,2-trifluoro-ethoxy)-2H-indazol-5-carboxamide hydrochloride

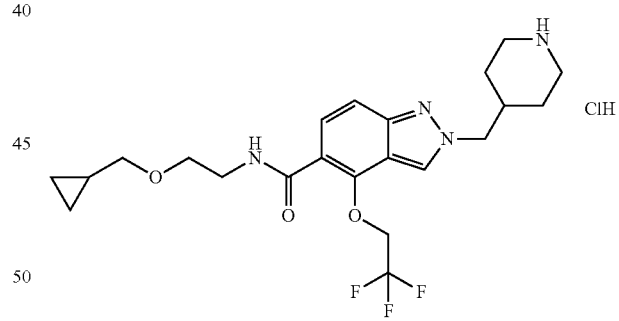

Analogously to Example 1a, from 138 mg of the amide prepared in Example 235a, 122 mg of the title compound was obtained, which was reacted without further purification.

EXAMPLE 236

N-[2-(cyclopropylmethoxy)ethyl]-2-({1-[4-(4-fluorophenoxy)benzoyl]piperidin-4-yl}methyl)-4-(2,2,2-trifluoroethoxy)-2H-indazol-5-carboxamide

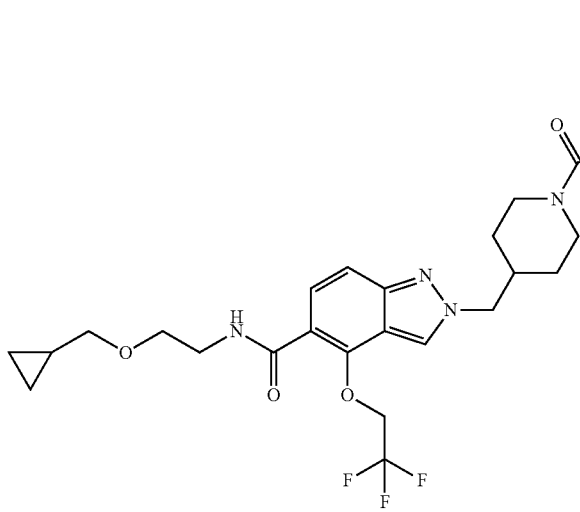

Analogously to Example 1, 95 mg of the title compound was obtained from 122 mg of the compound prepared in Example 235b and 58 mg of 4-(4-fluorophenoxy)benzoic acid.

$^1$H-NMR (300 MHz, DMSO-d6): δ=0.13 (2H), 0.41 (2H), 0.95 (1H), 1.09-1.60 (3H), 2.17-2.36 (1H), 2.68-3.06 (2H), 3.22 (2H), 3.34-3.76 (5H), 4.33 (2H), 4.95 (2H), 6.95 (2H), 7.06-7.14 (2H), 7.17-7.27 (2H), 7.30-7.38 (3H), 7.42 (1H), 7.99 (1H), 8.65 (1H).

EXAMPLE 237

N-[2-(cyclopropylmethoxy)ethyl]-2-({1-[(4'-fluorobiphenyl-4-yl)carbonyl]piperidin-4-yl}methyl)-4-(2,2,2-trifluoroethoxy)-2H-indazol-5-carboxamide

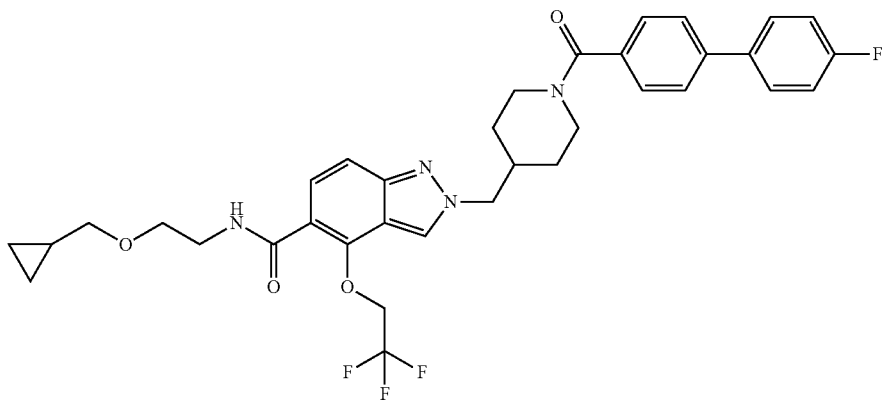 [SMILES: O=C(NCCOCC1CC1)c1ccc2nn(CC3CCN(C(=O)c4ccc(-c5ccc(F)cc5)cc4)CC3)cc2c1OCC(F)(F)F]

Analogously to Example 1, 98 mg of the title compound was obtained from 122 mg of the compound prepared in Example 235b and 54 mg of 4-(4-fluorophenoxy)benzoic acid.

$^1$H-NMR (300 MHz, DMSO-d6): δ=0.12 (2H), 0.41 (2H), 0.95 (1H), 1.15-1.64 (3H), 2.21-2.36 (1H), 2.70-3.10 (2H), 3.21 (2H), 3.35-3.69 (5H), 4.35 (2H), 4.95 (2H), 7.22-7.46 (6H), 7.63-7.77 (4H), 7.99 (1H), 8.66 (1H).

EXAMPLE 238

2-{[1-(4-chlorobenzoyl)piperidin-4-yl]methyl}-N-[2-(3-methoxyazetidin-1-yl)ethyl]-4-methyl-2H-indazol-5-carboxamide

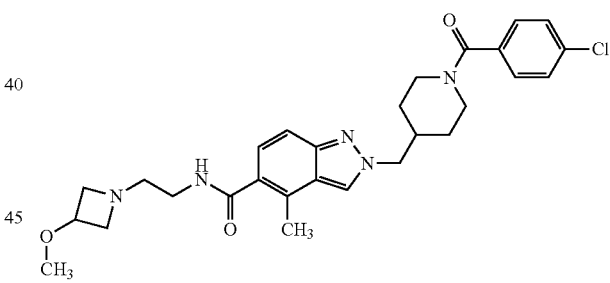

223

Analogously to Example 1, 33 mg of the title compound was obtained from 120 mg of the compound prepared in Example 238c and 40 mg of 2-(3-methoxyazetidin-1-yl)ethylamine (prepared analogously to WO2006/104406).

¹H-NMR (300 MHz, CDCl3): δ=0.83 (1H), 1.20-2.01 (4H), 2.38 (1H), 2.66 (3H), 2.69-3.09 (2H), 3.31 (3H), 3.43 (2H), 3.56-3.90 (5H), 4.18-4.32 (3H), 4.43 (2H), 6.91 (1H), 7.30-7.41 (5H), 7.52 (1H), 7.95 (1H).

The starting material was prepared as follows:

EXAMPLE 238a methyl 4-methyl-2-(4-piperidylmethyl)-2H-indazol-5-carboxylate hydrochloride

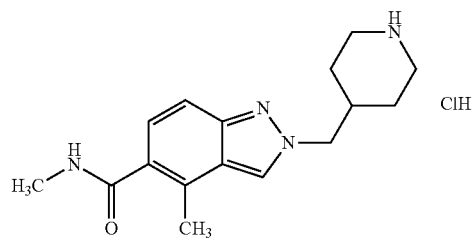 [SMILES: CNC(=O)c1ccc2nn(CC3CCNCC3)cc2c1C ; Cl]

Analogously to Example 1a, from 3.0 g of the ester prepared in Example 1e, 2.51 g of the title compound was obtained, which was reacted without further purification.

EXAMPLE 238b

Methyl 2-{[1-(4-chlorobenzoyl)piperidin-4-yl]methyl}-4-methyl-2H-indazol-5-carboxylate

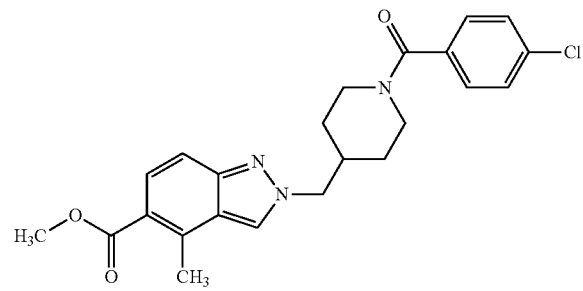 [SMILES: COC(=O)c1ccc2nn(CC3CCN(C(=O)c4ccc(Cl)cc4)CC3)cc2c1C]

Analogously to Example 55, 3.27 g of the title compound was obtained from 2.5 g of the compound prepared in Example 238a and 1.5 g of 4-chlorobenzoyl chloride.

¹H-NMR (300 MHz, DMSO-d6): δ=1.16-1.63 (4H), 2.21-2.33 (1H), 2.73 (4H), 2.90-3.05 (1H), 3.44-3.55 (1H), 3.79 (3H), 4.32 (2H), 4.36-4.47 (1H), 7.36 (2H), 7.42 (1H), 7.46 (2H), 7.63 (1H), 8.67 (1H).

EXAMPLE 238c

2-{[1-(4-chlorobenzoyl)piperidin-4-yl]methyl}-4-methyl-2H-indazol-5-carboxylic acid

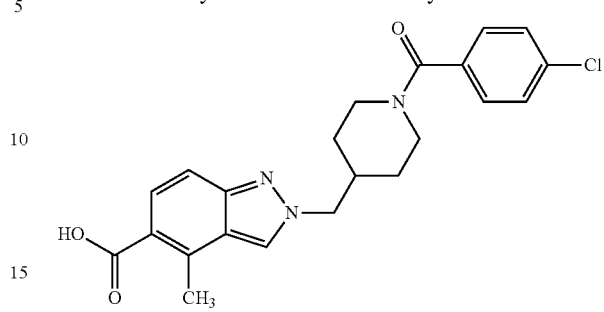

Analogously to Example 1d, 470 mg of the title compound was obtained from 485 mg of the ester prepared in Example 238b.

EXAMPLE 239

(+/−)-2-{[1-(4-chlorobenzoyl)piperidin-4-yl]methyl}-4-methyl-N-(3,4,5,6-tetrahydro-2H-pyran-2-ylmethyl)-2H-indazol-5-carboxamide

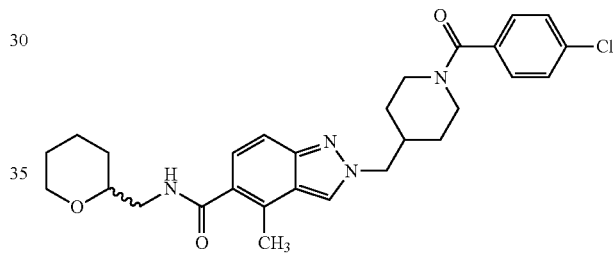

Analogously to Example 1, 188 mg of the title compound was obtained from 300 mg of the compound prepared in Example 238c and 92 mg of 3,4,5,6-tetrahydro-2H-pyran-2-ylmethylamine hydrochloride.

¹H-NMR (300 MHz, DMSO-d6): δ=1.01-1.27 (3H), 1.29-1.64 (7H), 2.19-2.32 (1H), 2.48 (3H), 2.66-2.80 (1H), 2.89-3.00 (1H), 3.00-3.08 (1H), 3.16-3.25 (2H), 3.34-3.42 (1H), 3.43-3.55 (1H), 3.77-3.88 (1H), 4.31 (2H), 4.39 (1H), 7.14 (1H), 7.32-7.40 (2H), 7.46 (2H), 7.83 (1H), 8.09 (1H), 8.46 (1H).

EXAMPLE 240

(R or S)-2-{[1-(4-chlorobenzoyl)piperidin-4-yl]methyl}-4-methyl-N-(3,4,5,6-tetrahydro-2H-pyran-2-ylmethyl)-2H-indazol-5-carboxamide

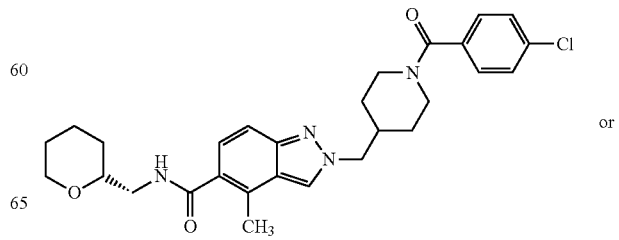

or

-continued

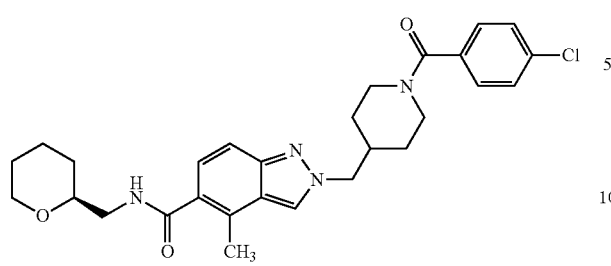

From 185 mg of the racemate prepared in Example 239, 51 mg of the title compound together with 53 mg of the slower-eluting enantiomer (Example 241) were obtained by racemate separation by means of preparative chiral HPLC (Method B).

Analytical chiral HPLC: 7.02 min

EXAMPLE 241

(S or R)-2-{[1-(4-chlorobenzoyl)piperidin-4-yl]methyl}-4-methyl-N-(3,4,5,6-tetrahydro-2H-pyran-2-ylmethyl)-2H-indazol-5-carboxamide

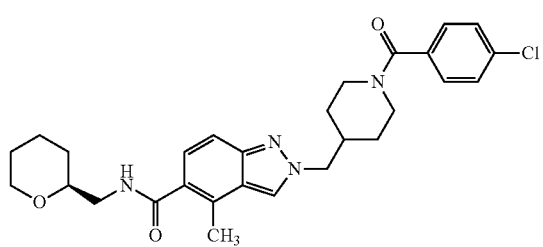

or

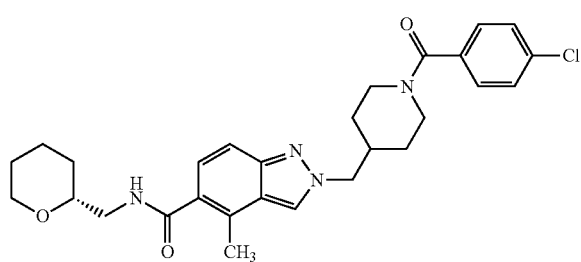 [SMILES: Cc1c(C(=O)NCC2CCCCO2)ccc2nn(CC3CCN(C(=O)c4ccc(Cl)cc4)CC3)cc12]

From 185 mg of the racemate prepared in Example 239, 53 mg of the title compound together with 51 mg of the faster-eluting enantiomer (Example 240) were obtained by racemate separation by means of preparative chiral HPLC (Method B).

Analytical chiral HPLC: 8.24 min

EXAMPLE 242

2-{[1-(4-chlorobenzoyl)piperidin-4-yl]methyl}-N-ethyl-4-methyl-2H-indazol-5-carboxamide

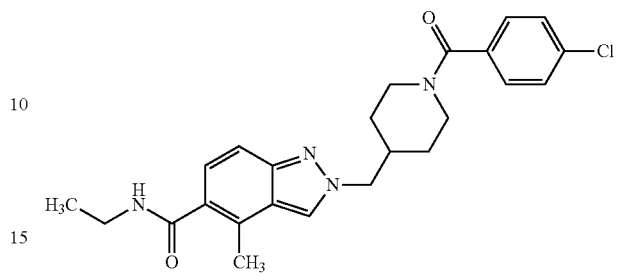

Analogously to Example 1, 85 mg of the title compound was obtained from 300 mg of the compound prepared in Example 238c and 43 mg of ethylamine 2M in THF.

$^1$H-NMR (300 MHz, DMSO-d6): δ=1.08 (3H), 1.16-1.60 (4H), 2.20-2.33 (1H), 2.48 (3H), 2.63-3.07 (2H), 3.22 (2H), 3.48 (1H), 4.24-4.46 (3H), 7.14 (1H), 7.31-7.42 (3H), 7.46 (2H), 8.08 (1H), 8.46 (1H).

EXAMPLE 243

2-{[1-(4-chlorobenzoyl)piperidin-4-yl]methyl}-N-isobutyl-4-methyl-2H-indazol-5-carboxamide

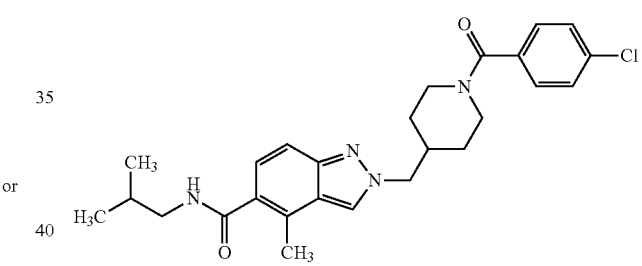

Analogously to Example 1, 92 mg of the title compound was obtained from 300 mg of the compound prepared in Example 238c and 69 mg of isobutylamine.

$^1$H-NMR (300 MHz, DMSO-d6): δ=0.85-0.90 (6H), 1.13-1.57 (4H), 1.75-1.83 (1H), 2.21-2.34 (1H), 2.49 (3H), 3.03 (4H), 3.48 (1H), 4.27-4.45 (3H), 7.14 (1H), 7.31-7.41 (3H), 7.46 (2H), 8.11 (1H), 8.47 (1H).

EXAMPLE 244

2-{[1-(4-chlorobenzoyl)piperidin-4-yl]methyl}-N-(2-mesylethyl)-4-methyl-2H-indazol-5-carboxamide

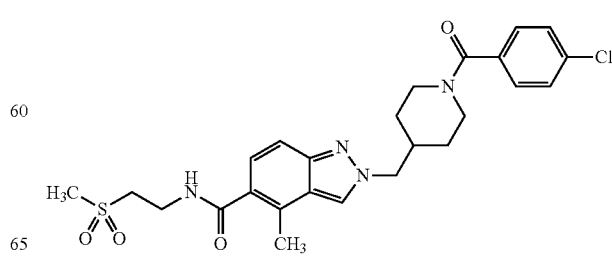

Analogously to Example 1, 132 mg of the title compound was obtained from 300 mg of the compound prepared in Example 238c and 151 mg of 2-mesylethylamine hydrochloride.

¹H-NMR (300 MHz, DMSO-d6): δ=1.19-1.62 (4H), 2.24-2.36 (1H), 2.54 (3H), 2.70-3.05 (2H), 3.05 (3H), 3.38 (2H), 3.52 (1H), 3.65 (2H), 4.30-4.49 (3H), 7.22 (1H), 7.38 (2H), 7.42 (1H), 7.49 (2H), 8.33 (1H), 8.52 (1H).

EXAMPLE 245

N-(2-mesylethyl)-4-methyl-2-[(1-{4-[4-(trifluoromethyl)phenoxy]benzoyl}-piperidin-4-yl)methyl]-2H-indazol-5-carboxamide Analogously to Example 1, 2.73 g of the title compound was obtained from 3.76 g of the compound prepared in Example 238a and 3.28 g of 4-[4-(trifluoromethyl)phenoxy]benzoic acid.

¹H-NMR (300 MHz, DMSO-d6): δ=1.25 (2H), 1.35-1.70 (2H), 2.20-2.37 (1H), 2.65-2.70 (3H), 2.75-3.10 (2H), 3.52-3.72 (1H), 3.82 (4H), 4.36 (2H), 7.14 (2H), 7.20 (2H), 7.39-7.48 (3H), 7.66 (1H), 7.75 (2H), 8.70 (1H).

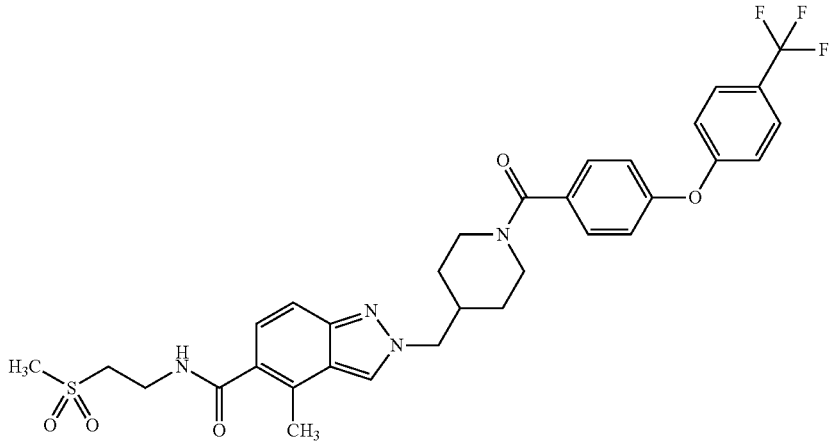 [SMILES: Cc1c(C(=O)NCCS(C)(=O)=O)ccc2nn(CC3CCN(C(=O)c4ccc(Oc5ccc(C(F)(F)F)cc5)cc4)CC3)cc12]

Analogously to Example 1, 67 mg of the title compound was obtained from 137 mg of the compound prepared in Example 245b and 41 mg of 2-mesylethylamine hydrochloride.

¹H-NMR (300 MHz, DMSO-d6): δ=1.15-1.62 (4H), 2.22-2.33 (1H), 2.50 (3H), 2.68-3.01 (2H), 3.02 (2H), 3.35 (1H), 3.52-3.69 (3H), 4.28-4.47 (2H), 7.12 (1H), 7.15-7.22 (2H), 7.37-7.44 (2H), 7.73 (1H), 8.32 (1H), 8.50 (1H).

The starting material was prepared as follows:

EXAMPLE 245a

Methyl 4-methyl-2-[(1-{4-[4-(trifluoromethyl)phenoxy]benzoyl}piperidin-4-yl)methyl]-2H-indazol-5-carboxylate

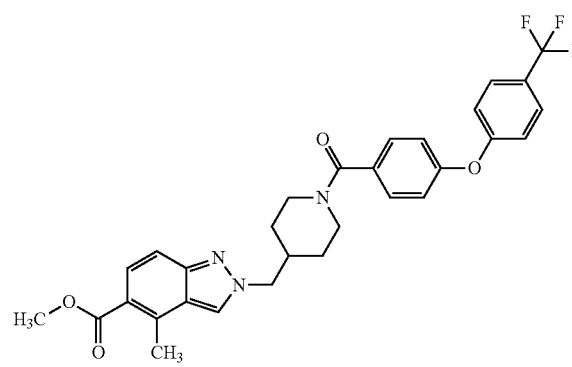

EXAMPLE 245b 4-methyl-2-[(1-{4-[4-(trifluoromethyl)phenoxy]benzoyl}piperidin-4-yl)-methyl]-2H-indazol-5-carboxylic acid

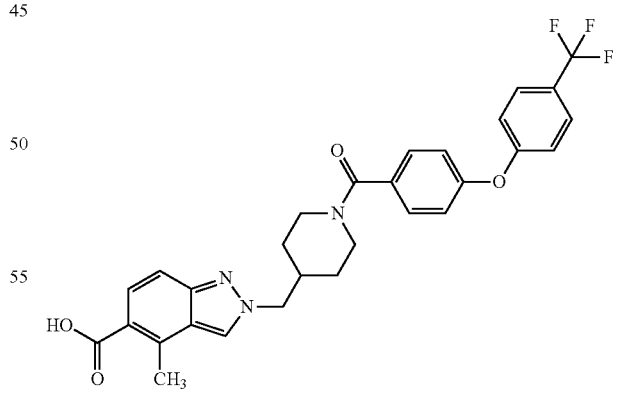

Analogously to Example 1d, 1.1 g of the title compound was obtained from 2.73 g of the ester prepared in Example 245a.

EXAMPLE 246

N-(2-cyanoethyl)-4-methyl-2-[(1-{4-[4-(trifluoromethyl)phenoxy]benzoyl}piperidin-4-yl)methyl]-2H-indazol-5-carboxamide

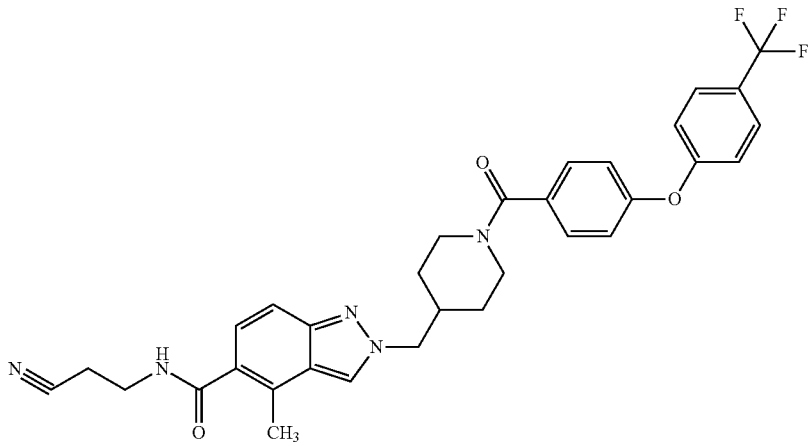 [SMILES: Cc1c(C(=O)NCCC#N)ccc2nn(CC3CCN(C(=O)c4ccc(Oc5ccc(C(F)(F)F)cc5)cc4)CC3)cc12]

Analogously to Example 1, 144 mg of the title compound was obtained from 137 mg of the compound prepared in Example 245b and 18 mg of 3-aminopropanenitrile.

$^1$H-NMR (300 MHz, DMSO-d6): δ=1.13-1.58 (4H), 2.21-2.33 (1H), 2.52 (3H), 2.75 (2H), 2.80-3.16 (2H), 3.44 (2H), 3.59 (1H), 4.27-4.50 (3H), 7.12 (2H), 7.15-7.21 (3H), 7.37-7.44 (3H), 7.73 (2H), 8.46 (1H), 8.51 (1H)

EXAMPLE 247

N-(cyanomethyl)-4-methyl-2-[(1-{4-[4-(trifluoromethyl)phenoxy]benzoyl}piperidin-4-yl)methyl]-2H-indazol-5-carboxamide

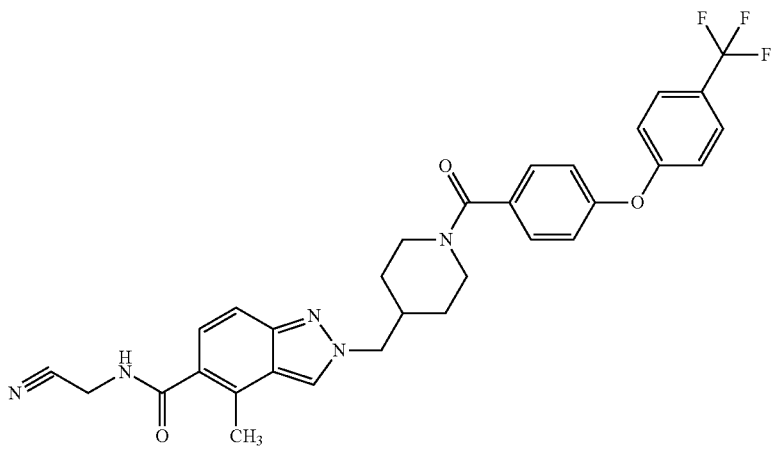 [SMILES: Cc1c(C(=O)NCC#N)ccc2nn(CC3CCN(C(=O)c4ccc(Oc5ccc(C(F)(F)F)cc5)cc4)CC3)cc12]

Analogously to Example 1, 125 mg of the title compound was obtained from 137 mg of the compound prepared in Example 245b and 24 mg of 2-aminoacetonitrile hydrochloride.

$^1$H-NMR (300 MHz, DMSO-d6): δ=1.16-1.60 (4H), 2.23-2.34 (1H), 2.53 (3H), 2.69-3.06 (2H), 3.59 (1H), 4.26 (2H), 4.29-4.50 (3H), 7.08-7.23 (5H), 7.38-7.46 (3H), 7.73 (2H), 8.54 (1H), 8.83 (1H).

EXAMPLE 248

(+/−)-4-methyl-N-(3,4,5,6-tetrahydro-2H-pyran-2-ylmethyl)-2-[(1-{4-[4-(trifluoromethyl)phenoxy]benzoyl}piperidin-4-yl)methyl]-2H-indazol-5-carboxamide

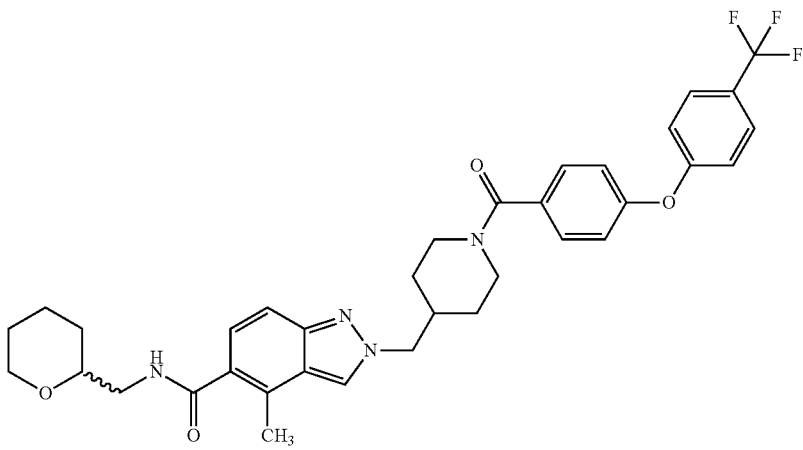 [SMILES: Cc1c(C(=O)NCC2CCCCO2)ccc2nn(CC3CCN(C(=O)c4ccc(Oc5ccc(C(F)(F)F)cc5)cc4)CC3)cc12]

Analogously to Example 1, 231 mg of the title compound was obtained from 254 mg of the compound prepared in Example 245b and 72 mg of 3,4,5,6-tetrahydro-2H-pyran-2-ylmethylamine.

$^1$H-NMR (300 MHz, DMSO-d6): δ=1.01-1.66 (10H), 2.24-2.32 (1H), 2.70-3.15 (4H), 3.21 (3H), 3.34-3.43 (1H), 3.54-3.64 (1H), 3.76-3.89 (2H), 4.32 (3H), 7.09-7.21 (5H), 7.35-7.44 (3H), 7.73 (2H), 8.09 (1H), 8.47 (1H).

EXAMPLE 249

(+/−)-N-(1,4-dioxan-2-ylmethyl)-4-methyl-2-[(1-{4-[4-(trifluoromethyl)phenoxy]benzoyl}piperidin-4-yl)methyl]-2H-indazol-5-carboxamide

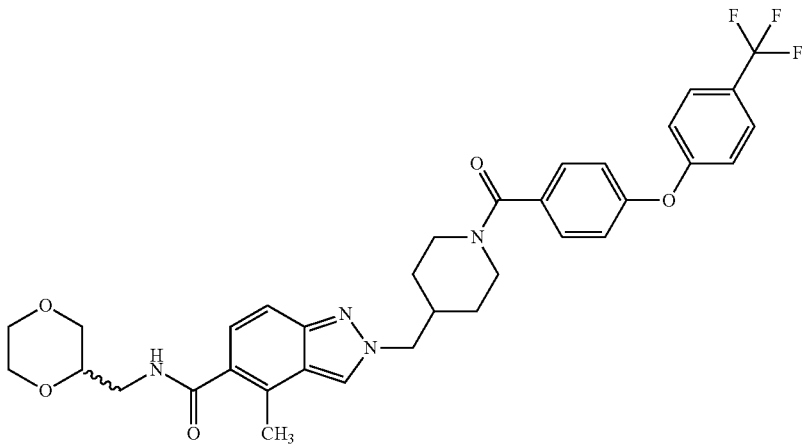 [SMILES: Cc1c(C(=O)NCC2COCCO2)ccc2nn(CC3CCN(C(=O)c4ccc(Oc5ccc(C(F)(F)F)cc5)cc4)CC3)cc12]

Analogously to Example 1, 280 mg of the title compound was obtained from 254 mg of the compound prepared in Example 245b and 73 mg of 1,4-dioxan-2-ylmethylamine.

$^1$H-NMR (300 MHz, DMSO-d6): δ=1.13-1.61 (4H), 2.23-2.32 (1H), 2.49 (3H), 2.75 (1H), 2.94-3.27 (4H), 3.38-3.77 (8H), 4.32 (2H), 7.09-7.21 (5H), 7.36-7.44 (3H), 7.73 (2H), 8.16 (1H), 8.48 (1H).

EXAMPLE 250

2-{[1-(4-chlorobenzoyl)piperidin-4-yl]methyl}-N-(cyclobutylmethyl)-4-methyl-2H-indazol-5-carboxamide

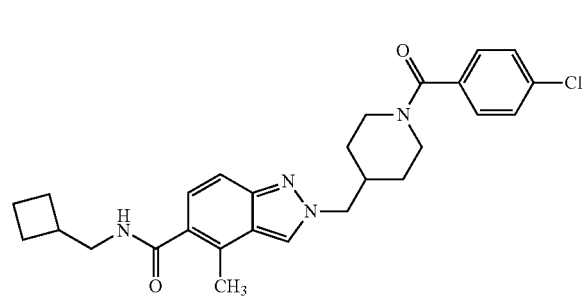

Analogously to Example 1, 79 mg of the title compound was obtained from 300 mg of the compound prepared in Example 238c and 115 mg of cyclobutylmethylamine hydrochloride.

$^1$H-NMR (300 MHz, DMSO-d6): δ=1.16-1.58 (4H), 1.64-1.86 (4H), 1.90-2.01 (2H), 2.19-2.32 (1H), 2.48 (3H), 2.50 (1H), 2.66-3.05 (2H), 3.19-3.25 (2H), 3.48 (1H), 4.27-4.47 (3H), 7.12 (1H), 7.31-7.40 (3H), 7.46 (2H), 8.09 (1H), 8.46 (1H).

EXAMPLE 251

2-{[1-(4-chlorobenzoyl)piperidin-4-yl]methyl}-N-(2,2-dimethylpropyl)-4-methyl-2H-indazol-5-carboxamide

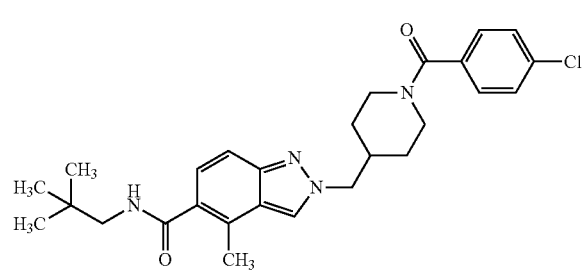

Analogously to Example 1, 108 mg of the title compound was obtained from 300 mg of the compound prepared in Example 238c and 83 mg of 2,2-dimethylpropan-1-amine.

$^1$H-NMR (300 MHz, DMSO-d6): δ=0.91 (9H), 1.17-1.63 (4H), 2.24-2.36 (1H), 2.52 (3H), 2.70-3.04 (2H), 3.07 (2H), 3.52 (1H), 4.30-4.50 (3H), 7.17 (1H), 7.38 (2H), 7.42 (1H), 7.49 (2H), 8.07 (1H), 8.49 (1H).

EXAMPLE 252

2-{[1-(4-chlorobenzoyl)piperidin-4-yl]methyl}-N-(2-hydroxyethyl)-4-methyl-2H-indazol-5-carboxamide

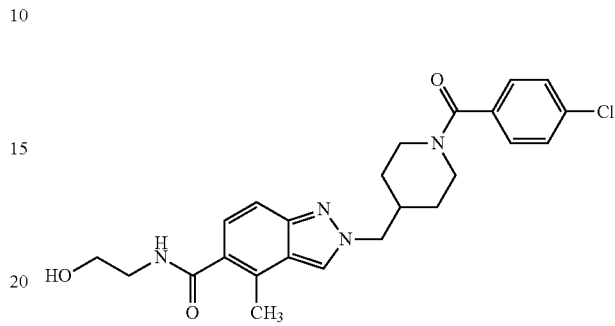

Analogously to Example 1, 84 mg of the title compound was obtained from 370 mg of the compound prepared in Example 238c and 54 mg of 2-aminoethanol.

$^1$H-NMR (300 MHz, DMSO-d6): δ=1.14-1.64 (4H), 2.24-2.35 (1H), 2.53 (3H), 2.69-3.09 (2H), 3.30 (2H), 3.43-3.58 (3H), 4.27-4.50 (3H), 4.67 (1H), 7.20 (1H), 7.35-7.43 (3H), 7.49 (2H), 8.02 (1H), 8.49 (1H).

EXAMPLE 253

2-{[1-(4-chlorobenzoyl)piperidin-4-yl]methyl}-N-(3-hydroxypropyl)-4-methyl-2H-indazol-5-carboxamide

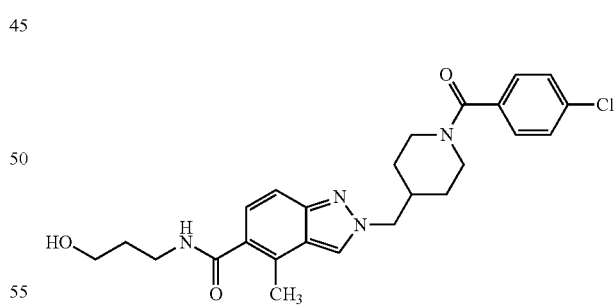

Analogously to Example 1, 95 mg of the title compound was obtained from 370 mg of the compound prepared in Example 238c and 66 mg of 3-aminopropan-1-ol.

$^1$H-NMR (300 MHz, DMSO-d6): δ=1.17-1.60 (4H), 1.66 (2H), 2.22-2.35 (1H), 2.53 (3H), 2.70-3.09 (2H), 3.27 (2H), 3.47 (2H), 3.47-3.67 (1H), 4.34 (2H), 4.41 (1H), 4.45 (1H), 7.17 (1H), 7.35-7.43 (3H), 7.49 (2H), 8.07 (1H), 8.49 (1H).

EXAMPLE 254

4-methoxy-N-(2-methoxyethyl)-2-({1-[4-(trifluoromethoxy)benzoyl]azetidin-3-yl}methyl)-2H-indazol-5-carboxamide

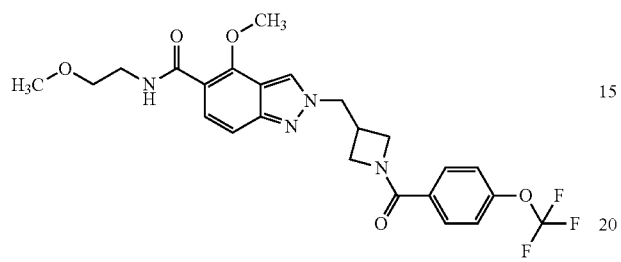

Analogously to Example 1, 90 mg of the title compound was obtained from 100 mg of the compound prepared in Example 214c and 97 mg of 4-(trifluoromethoxy)benzoic acid in DMF.

$^1$H-NMR (400 MHz, DMSO-$d_6$): δ [ppm]=3.24-3.29 (1H), 3.29-3.32 (3H), 3.43-3.51 (4H), 3.91-4.04 (1H), 4.10-4.18 (1H), 4.20 (3H), 4.22-4.29 (1H), 4.44 (1H), 4.70 (2H), 7.24 (1H), 7.37-7.51 (2H), 7.66 (1H), 7.70-7.80 (2H), 8.22 (1H), 8.91 (1H).

EXAMPLE 255

2-({1-[2-fluoro-4-(trifluoromethyl)benzoyl]azetidin-3-yl}methyl)-4-methoxy-N-(2-methoxyethyl)-2H-indazol-5-carboxamide

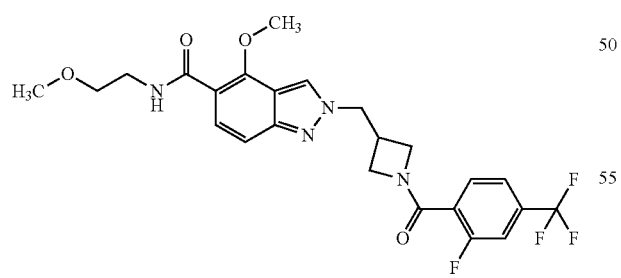

Analogously to Example 1, 40 mg of the title compound was obtained from 100 mg of the compound prepared in Example 214c and 98 mg of 2-fluoro-4-(trifluoromethyl)benzoic acid in DMF.

$^1$H-NMR (400 MHz, DMSO-$d_6$): δ [ppm]=3.30 (4H), 3.44-3.50 (4H), 3.94-4.04 (2H), 4.15 (2H), 4.20 (3H), 4.70 (2H), 7.24 (1H), 7.60-7.75 (3H), 7.78-7.89 (1H), 8.16-8.27 (1H), 8.90 (1H).

EXAMPLE 256

2-({1-[4-chloro-3-(trifluoromethyl)benzoyl]azetidin-3-yl}methyl)-4-methoxy-N-(2-methoxyethyl)-2H-indazol-5-carboxamide

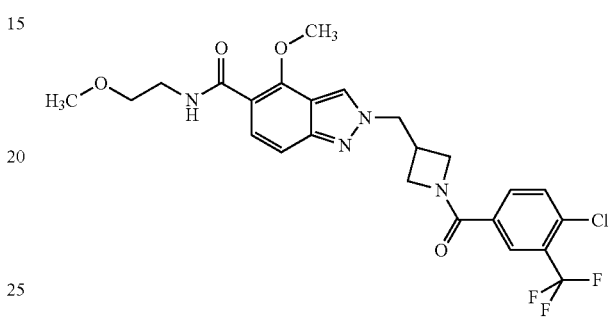

Analogously to Example 1, 40 mg of the title compound was obtained from 100 mg of the compound prepared in Example 214c and 106 mg of 4-chloro-3-(trifluoromethyl)benzoic acid in DMF.

$^1$H-NMR (400 MHz, DMSO-$d_6$): δ [ppm]=3.30 (4H), 3.43-3.53 (4H), 3.95-4.05 (1H), 4.20 (4H), 4.23-4.31 (1H), 4.47 (1H), 4.71 (2H), 7.23 (1H), 7.67 (1H), 7.78-7.85 (1H), 7.86-7.93 (1H), 7.96 (1H), 8.22 (1H), 8.90 (1H).

EXAMPLE 257

2-{[1-(4-chloro-2-fluorobenzoyl)azetidin-3-yl]methyl}-4-methoxy-N-(2-methoxyethyl)-2H-indazol-5-carboxamide

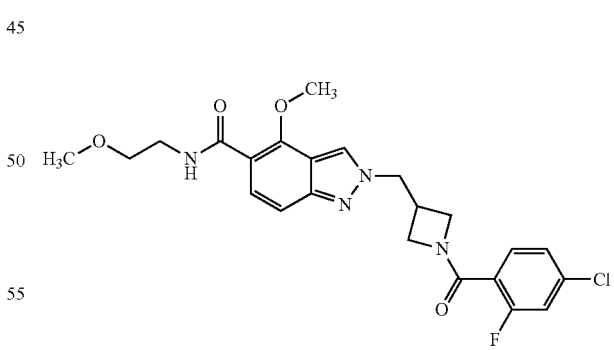

Analogously to Example 1, 20 mg of the title compound was obtained from 100 mg of the compound prepared in Example 214c and 82 mg of 4-chloro-2-fluorobenzoic acid in DMF.

$^1$H-NMR (400 MHz, DMSO-$d_6$): δ [ppm]=3.30 (4H), 3.42-3.51 (4H), 3.98 (2H), 4.14 (2H), 4.20 (3H), 4.69 (2H), 7.24 (1H), 7.38 (1H), 7.48 (1H), 7.56 (1H), 7.66 (1H), 8.15-8.30 (1H), 8.90 (1H).

EXAMPLE 258

2-{[1-(4-chlorobenzoyl)azetidin-3-yl]methyl}-4-methoxy-N-(2-morpholinoethyl)-2H-indazol-5-carboxamide

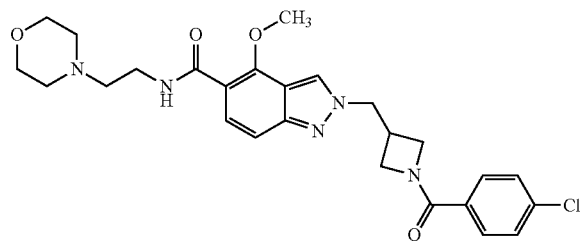 [SMILES: COc1c(C(=O)NCCN2CCOCC2)ccc2nn(CC3CN(C(=O)c4ccc(Cl)cc4)C3)cc12]

Analogously to Example 1b Version B, 67 mg of the title compound was obtained from 66 mg of the compound prepared in Example 258d and 32 mg of 2-morpholinoethylamine in DMF.

$^{1}$H-NMR (400 MHz, DMSO-d$_{6}$): δ [ppm]=2.44 (4H), 3.21-3.36 (3H), 3.42 (2H), 3.61 (4H), 3.88-4.04 (1H), 4.07-4.18 (1H), 4.23 (4H), 4.35-4.50 (1H), 4.70 (2H), 7.25 (1H), 7.41-7.56 (2H), 7.59-7.66 (2H), 7.70 (1H), 8.32 (1H), 8.91 (1H).

The starting material was prepared as follows:

EXAMPLE 258a

Methyl 2-{[1-(tert-butoxycarbonyl)azetidin-3-yl]methyl}-4-methoxy-2H-indazol-5-carboxylate

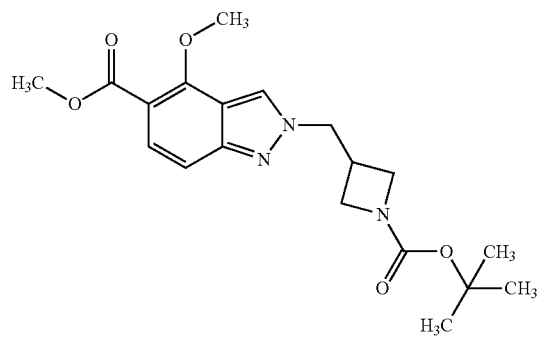 [SMILES: COC(=O)c1ccc2nn(CC3CN(C(=O)OC(C)(C)C)C3)cc2c1OC]

Analogously to Example 1e, 448 mg of the title compound was obtained from 750 mg of the compound prepared in Example 214a and 546 mg of methanol.

$^{1}$H-NMR (400 MHz, DMSO-d$_{6}$): δ [ppm]=1.27-1.44 (9H), 3.01-3.22 (1H), 3.78 (5H), 3.85-3.99 (2H), 4.14 (3H), 4.64 (2H), 7.24 (1H), 7.51 (1H), 8.94 (1H).

EXAMPLE 258b

Methyl 2-(azetidin-3-ylmethyl)-4-methoxy-2H-indazol-5-carboxylate

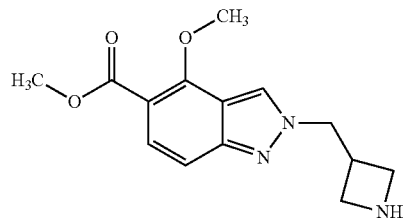 [SMILES: COC(=O)c1ccc2nn(CC3CNC3)cc2c1OC]

800 mg of 258a were first placed in 40 ml acetone, treated with 40 ml of semiconcentrated hydrochloric acid, stirred until complete conversion and concentrated to dryness. Yield: 414 mg of the title compound.

$^{1}$H-NMR (400 MHz, DMSO-d$_{6}$): δ [ppm]=3.39 (1H), 3.79 (3H), 3.84-3.95 (2H), 3.96-4.07 (2H), 4.15 (3H), 4.72 (2H), 7.25 (1H), 7.52 (1H), 8.92 (1H).

EXAMPLE 258c

Methyl 2-{[1-(4-chlorobenzoyl)azetidin-3-yl]methyl}-4-methoxy-2H-indazol-5-carboxylate

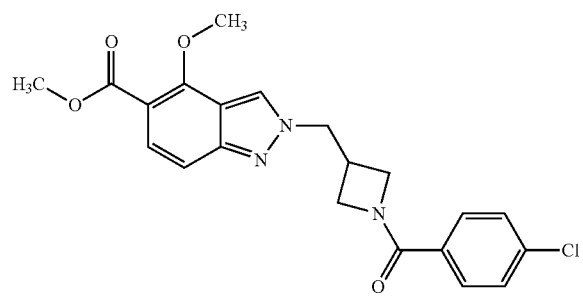 [SMILES: COC(=O)c1ccc2nn(CC3CN(C(=O)c4ccc(Cl)cc4)C3)cc2c1OC]

404 mg of 258b were first placed in 30 ml DCM at 0° C., treated with 0.21 ml of 4-chlorobenzoyl chloride and 0.75 ml of N-ethyldiisopropylamine and stirred at room temperature until complete conversion. For the work-up, the reaction solution was treated with saturated sodium hydrogen carbonate solution, extracted with DCM and the combined organic phases dried with sodium sulphate and concentrated to dryness. This yielded 608 mg of the title compound, which was used in the next step without further purification.

EXAMPLE 258d

2-{[1-(4-chlorobenzoyl)azetidin-3-yl]methyl}-4-methoxy-2H-indazol-5-carboxylic acid

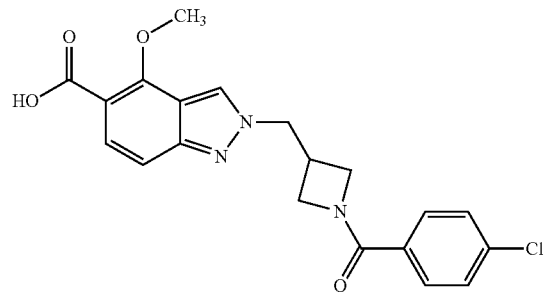 [SMILES: COc1c(C(=O)O)ccc2nn(CC3CN(C(=O)c4ccc(Cl)cc4)C3)cc12]

550 mg of 258c were first placed in 20 ml ethanol, treated with 20 ml of 2N sodium hydroxide and stirred until complete conversion. For the work-up, the reaction solution was adjusted to a pH of 3 with 1N hydrochloric acid, extracted with ethyl acetate, and the combined organic phases dried with sodium sulphate and concentrated to dryness. Yield after purification by column chromatography on silica gel with a hexane/ethyl acetate gradient: 213 mg of the title compound.

$^1$H-NMR (400 MHz, DMSO-$d_6$): δ [ppm]=3.27 (1H), 3.97 (1H), 4.07-4.17 (4H), 4.24 (1H), 4.42 (1H), 4.70 (2H), 7.22 (1H), 7.46-7.57 (3H), 7.59-7.68 (2H), 8.88 (1H), 12.61 (m, 1H).

EXAMPLE 259

2-{[1-(4-chlorobenzoyl)azetidin-3-yl]methyl}-N-(2-ethoxyethyl)-4-methoxy-2H-indazol-5-carboxamide

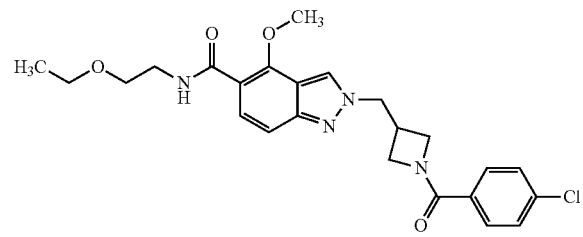 [SMILES: CCOCCNC(=O)c1ccc2nn(CC3CN(C(=O)c4ccc(Cl)cc4)C3)cc2c1OC]

Analogously to Example 1b Version B, 30 mg of the title compound was obtained from 66 mg of the compound prepared in Example 258d and 22 mg of 2-ethoxyethylamine in DMF.

$^1$H-NMR (400 MHz, DMSO-$d_6$): δ [ppm]=1.07-1.21 (3H), 3.30 (1H), 3.40-3.57 (6H), 3.90-4.02 (1H), 4.08-4.17 (1H), 4.21 (4H), 4.34-4.48 (1H), 4.70 (2H), 7.24 (1H), 7.45-7.57 (2H), 7.60-7.74 (3H), 8.24 (1H), 8.91 (1H).

EXAMPLE 260

2-{[1-(4-chlorobenzoyl)azetidin-3-yl]methyl}-N-[2-(3,3-difluoropyrrolidin-1-yl)ethyl]-4-methoxy-2H-indazol-5-carboxamide

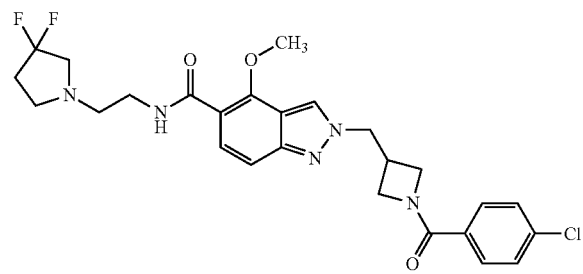 [SMILES: COc1c(C(=O)NCCN2CCC(F)(F)C2)ccc2nn(CC3CN(C(=O)c4ccc(Cl)cc4)C3)cc12]

Analogously to Example 1b Version B, 58 mg of the title compound was obtained from 66 mg of the compound prepared in Example 258d and 37 mg of 2-(3,3-difluoropyrrolidin-1-yl)ethylamine in DMF.

$^1$H-NMR (400 MHz, DMSO-$d_6$): δ [ppm]=2.27 (2H), 2.64 (2H), 2.77 (2H), 2.96 (2H), 3.22-3.30 (1H), 3.41 (2H), 3.92-4.01 (1H), 4.11 (1H), 4.19 (4H), 4.35-4.48 (1H), 4.70 (2H), 7.24 (1H), 7.51 (2H), 7.57-7.75 (3H), 8.32 (1H), 8.90 (1H).

EXAMPLE 261

2-{[1-(4-chlorobenzoyl)piperidin-4-yl]methyl}-4-methoxy-N-(2-morpholinoethyl)-2H-indazol-5-carboxamide

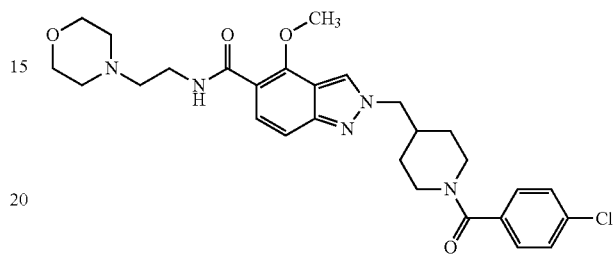

Analogously to Example 1b, Version B, 77 mg of the title compound was obtained from 100 mg of the compound prepared in Example 261e and 46 mg of 2-morpholinoethylamine in DMF.

$^1$H-NMR (400 MHz, DMSO-$d_6$): δ [ppm]=1.11-1.33 (2H), 1.35-1.75 (2H), 2.18-2.39 (1H), 2.65-2.88 (2H), 2.90-3.23 (3H), 3.41-3.82 (8H), 3.84-4.12 (2H), 4.24 (3H), 4.35 (3H), 7.26 (1H), 7.33-7.44 (2H), 7.46-7.58 (2H), 7.69 (1H), 8.27-8.52 (1H), 8.87 (1H).

The starting material was prepared as follows:

EXAMPLE 261a

Tert-butyl 4-[(5-bromo-4-methoxy-2H-indazol-2-yl)methyl]piperidin-1-carboxylate

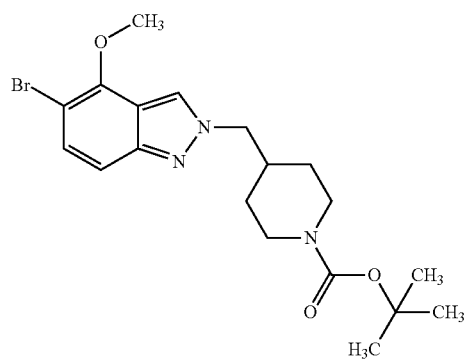 [SMILES: COc1c(Br)ccc2nn(CC3CCN(C(=O)OC(C)(C)C)CC3)cc12]

Analogously to Example 1c, 5.57 g of the title compound was obtained from 9.65 g of 5-bromo-4-methoxy-1H-indazole and 23.55 g of tert-butyl-4-[(tosyloxy)methyl]piperidin-1-carboxylate.

$^1$H-NMR (400 MHz, chloroform-d): δ [ppm]=1.16-1.31 (2H), 1.39-1.49 (9H), 1.52-1.64 (2H), 2.16-2.36 (1H), 2.56-2.80 (2H), 4.11 (5H), 4.26 (2H), 7.28-7.33 (1H), 7.34-7.39 (1H), 7.99 (1H).

EXAMPLE 261b

Methyl 2-{[1-(tert-butoxycarbonyl)piperidin-4-yl]methyl}-4-methoxy-2H-indazol-5-carboxylate

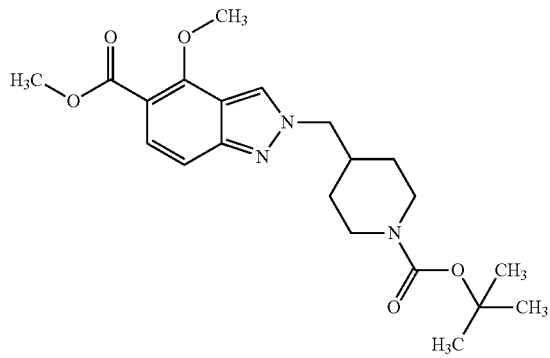 [SMILES: COC(=O)c1ccc2nn(CC3CCN(C(=O)OC(C)(C)C)CC3)cc2c1OC]

Analogously to Example 1e, 1.1 g of the title compound was obtained from 2.4 g of the compound prepared in Example 261a and 1.63 g of methanol.

EXAMPLE 261c

Methyl 4-methoxy-2-(4-piperidylmethyl)-2H-indazol-5-carboxylate

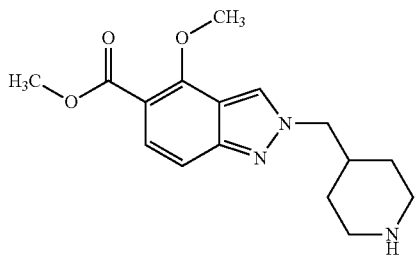 [SMILES: COC(=O)c1ccc2nn(CC3CCNCC3)cc2c1OC]

Analogously to Example 258b, from 1.1 g of the compound prepared in Example 261b 1.1 g of the title compound was obtained, which was reacted in the next step without further purification.

EXAMPLE 261d

Methyl 2-{[1-(4-chlorobenzoyl)piperidin-4-yl]methyl}-4-methoxy-2H-indazol-5-carboxylate

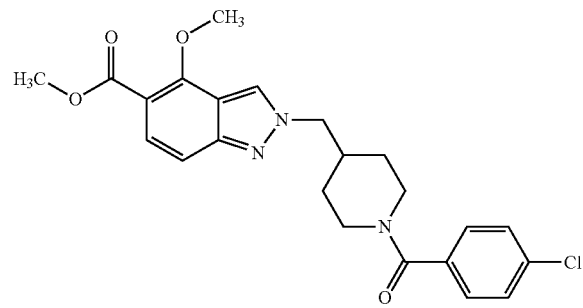 [SMILES: COC(=O)c1ccc2nn(CC3CCN(C(=O)c4ccc(Cl)cc4)CC3)cc2c1OC]

Analogously to Example 258c, from 1.1 g of the compound prepared in Example 261c and 762 mg of 4-chlorobenzoyl chloride, 980 mg of the title compound was obtained after purification by column chromatography on silica gel with a hexane/ethyl acetate gradient.

$^1$H-NMR (300 MHz, DMSO-$d_6$): δ [ppm]=1.24 (2H), 1.36-1.76 (2H), 2.18-2.40 (1H), 2.65-2.88 (1H), 2.91-3.12 (1H), 3.42-3.67 (1H), 3.78 (3H), 4.05-4.21 (3H), 4.35 (3H), 7.24 (1H), 7.34-7.43 (2H), 7.45-7.56 (3H), 8.86 (1H).

EXAMPLE 261e

2-{[1-(4-chlorobenzoyl)piperidin-4-yl]methyl}-4-methoxy-2H-indazol-5-carboxylic acid

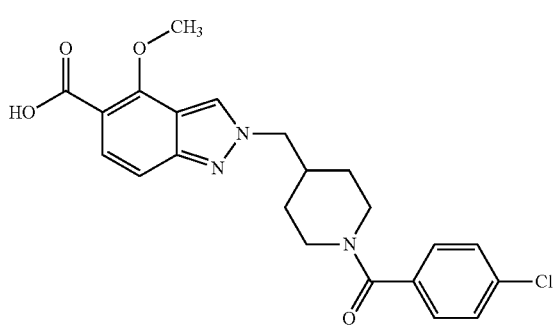 [SMILES: COc1c(C(=O)O)ccc2nn(CC3CCN(C(=O)c4ccc(Cl)cc4)CC3)cc12]

Analogously to Example 258d, 547 mg of the title compound was obtained from 980 mg of the compound prepared in Example 261d.

$^1$H-NMR (400 MHz, DMSO-$d_6$): δ [ppm]=1.12-1.35 (2H), 1.35-1.73 (2H), 2.21-2.40 (1H), 2.63-3.12 (2H), 3.14-3.70 (3H), 4.34 (3H), 5.76 (s, 1H), 7.21 (1H), 7.32-7.45 (2H), 7.46-7.58 (3H), 8.76 (1H).

EXAMPLE 262

2-{[1-(4-chlorobenzoyl)piperidin-4-yl]methyl}-4-methoxy-N-(2-methoxyethyl)-2H-indazol-5-carboxamide

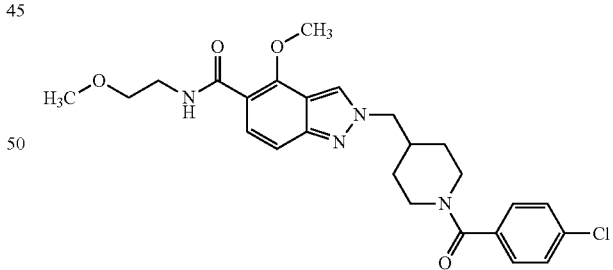

Analogously to Example 1b, Version B, 50 mg of the title compound was obtained from 100 mg of the compound prepared in Example 261e and 26 mg of 2-methoxyethylamine in DMF.

$^1$H-NMR (400 MHz, DMSO-$d_6$): δ [ppm]=1.11-1.35 (2H), 1.35-1.72 (2H), 2.21-2.39 (1H), 2.69-2.88 (1H), 2.92-3.11 (1H), 3.30 (s, 3H), 3.38-3.64 (5H), 4.20 (3H), 4.34 (3H), 7.25 (1H), 7.34-7.43 (2H), 7.45-7.57 (2H), 7.66 (1H), 8.22 (1H), 8.83 (1H).

EXAMPLE 263

2-{[1-(4-chlorobenzoyl)piperidin-4-yl]methyl}-4-methoxy-N-(2,2,2-trifluoro-ethyl)-2H-indazol-5-carboxamide

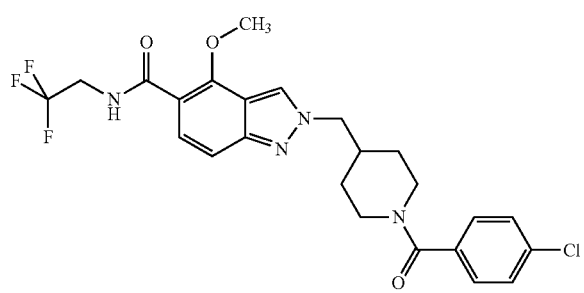 [SMILES: COc1c(C(=O)NCC(F)(F)F)ccc2nn(CC3CCN(C(=O)c4ccc(Cl)cc4)CC3)cc12]

Analogously to Example 1b, Version B, 68 mg of the title compound was obtained from 100 mg of the compound prepared in Example 261e and 35 mg of 2,2,2-trifluoroethylamine in DMF.

$^1$H-NMR (400 MHz, DMSO-d$_6$): δ [ppm]=1.09-1.35 (2H), 1.37-1.75 (2H), 2.21-2.41 (1H), 2.69-2.88 (1H), 2.92-3.19 (1H), 3.42-3.69 (1H), 4.13 (2H), 4.23 (3H), 4.35 (3H), 7.26 (1H), 7.34-7.45 (2H), 7.46-7.55 (2H), 7.61 (1H), 8.59 (1H), 8.88 (1H).

EXAMPLE 264

2-{[1-(4-chlorobenzoyl)piperidin-4-yl]methyl}-N-(2-ethoxyethyl)-4-methoxy-2H-indazol-5-carboxamide

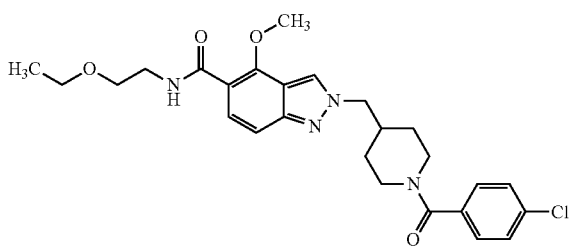 [SMILES: CCOCCNC(=O)c1ccc2nn(CC3CCN(C(=O)c4ccc(Cl)cc4)CC3)cc2c1OC]

Analogously to Example 1b, Version B, 60 mg of the title compound was obtained from 100 mg of the compound prepared in Example 261e and 31 mg of 2-ethoxyethylamine in DMF.

$^1$H-NMR (400 MHz, DMSO-d$_6$): δ [ppm]=1.14 (3H), 1.19-1.35 (2H), 1.37-1.72 (2H), 2.23-2.43 (1H), 2.68-2.88 (1H), 2.91-3.15 (1H), 3.41-3.56 (m, 7H), 4.20 (3H), 4.34 (3H), 7.25 (1H), 7.33-7.45 (2H), 7.46-7.55 (2H), 7.67 (1H), 8.23 (1H), 8.83 (1H).

EXAMPLE 265

2-{[1-(4-chlorobenzoyl)piperidin-4-yl]methyl}-4-methoxy-N-{2-[(trifluoromethyl)sulphanyl]ethyl}-2H-indazol-5-carboxamide

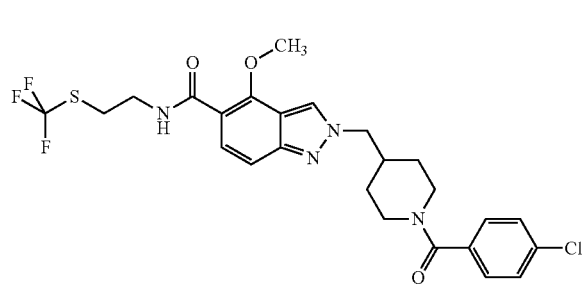 [SMILES: COc1c(C(=O)NCCSC(F)(F)F)ccc2nn(CC3CCN(C(=O)c4ccc(Cl)cc4)CC3)cc12]

Analogously to Example 1b, Version B, 68 mg of the title compound was obtained from 100 mg of the compound prepared in Example 261e and 51 mg of 2-[(trifluoromethyl)sulphanyl]-ethylamine in DMF.

$^1$H-NMR (400 MHz, DMSO-d$_6$): δ [ppm]=1.14-1.35 (2H), 1.36-1.72 (2H), 2.18-2.40 (1H), 2.66-2.87 (1H), 2.91-3.11 (1H), 3.21 (2H), 3.42-3.70 (3H), 4.22 (3H), 4.34 (3H), 7.24 (1H), 7.32-7.45 (2H), 7.46-7.55 (2H), 7.64 (1H), 8.45 (1H), 8.85 (1H).

EXAMPLE 266

4-methoxy-N-(2-methoxyethyl)-2-({1-[4-(trifluoromethoxy)benzoyl]piperidin-4-yl}methyl)-2H-indazol-5-carboxamide

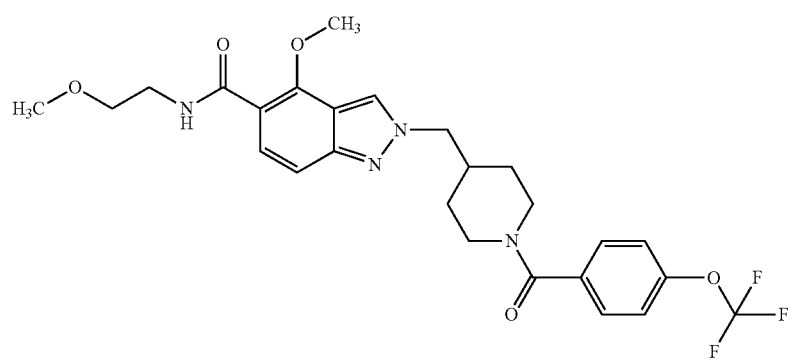 [SMILES: COCCNC(=O)c1ccc2nn(CC3CCN(C(=O)c4ccc(OC(F)(F)F)cc4)CC3)cc2c1OC]

Analogously to Example 1b, Version B, 84 mg of the title compound was obtained from 100 mg of the compound prepared in Example 266b and 89 mg of 4-(trifluoromethoxy)benzoic acid in DMF.

LC-MS: $R_t$=1.16 min, MS (ES+): m/z=435 (M+H)$^+$.

The starting material was prepared as follows:

EXAMPLE 266a

Tert-butyl 4-({4-methoxy-5-[N-(2-methoxyethyl)carbamoyl]-2H-indazol-2-yl}methyl)piperidin-1-carboxylate

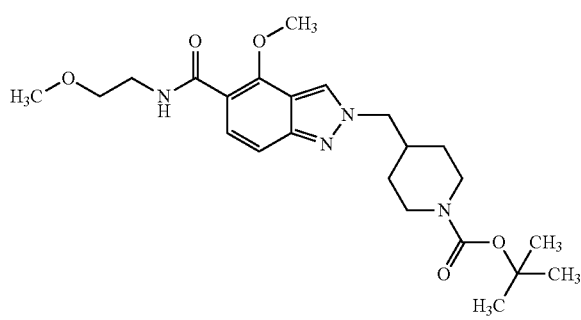 [SMILES: COCCNC(=O)c1ccc2nn(CC3CCN(C(=O)OC(C)(C)C)CC3)cc2c1OC]

3 g of compound 261a, 1.59 g of 2-methoxyethylamine, 1.87 g of molybdenum hexacarbonyl, 204 mg of tri-tert-butylphosphine tetrafluoroborate and 316 mg of palladium (II) acetate were first suspended in 100 ml 1,4-dioxan. Then 2.25 g of sodium carbonate and a few drops of water were added, and the mixture stirred for 25 mins at 140° C. and 150 watts in the microwave. The reaction mixture was concentrated and the residue was purified by column chromatography on silica gel using a hexane/ethyl acetate/methanol gradient. Yield: 1.3 g of the title compound.

$^1$H-NMR (300 MHz, DMSO-d$_6$): δ [ppm]=0.99-1.22 (2H), 1.29-1.55 (11H), 2.03-2.33 (1H), 2.60-2.83 (2H), 3.28-3.31 (3H), 3.43-3.52 (4H), 3.82-4.03 (2H), 4.20 (3H), 4.31 (2H), 7.25 (1H), 7.66 (1H), 8.21 (1H), 8.82 (1H).

EXAMPLE 266b 4-methoxy-N-(2-methoxyethyl)-2-(4-piperidylmethyl)-2H-indazol-5-carboxamide

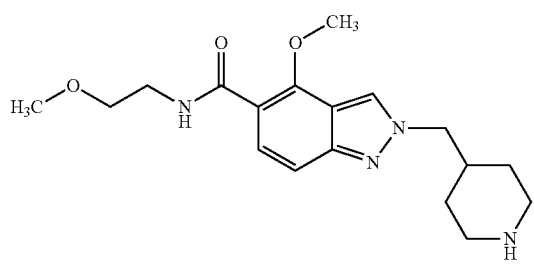 [SMILES: COCCNC(=O)c1ccc2nn(CC3CCNCC3)cc2c1OC]

Analogously to Example 258b, from 1.3 g of the compound prepared in Example 266a, 1.48 g of the title compound was obtained, which was used in the subsequent reactions without further purification.

EXAMPLE 267

2-({1-[2-fluoro-4-(trifluoromethyl)benzoyl]piperidin-4-yl}methyl)-4-methoxy-N-(2-methoxyethyl)-2H-indazol-5-carboxamide

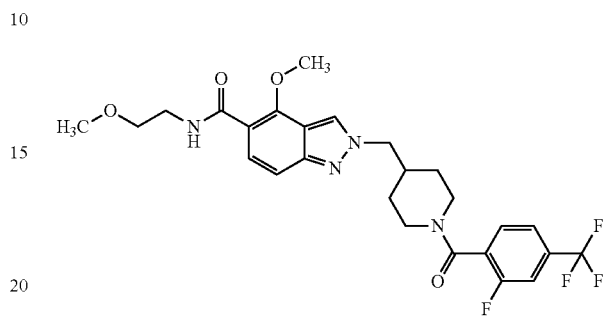

Analogously to Example 1b, Version B, 20 mg of the title compound was obtained from 100 mg of the compound prepared in Example 266b and 90 mg of 2-fluoro-4-(trifluoromethyl)benzoic acid in DMF.

$^1$H-NMR (400 MHz, DMSO-d$_6$): δ [ppm]=1.05-1.36 (2H), 1.39-1.53 (1H), 1.56-1.72 (1H), 2.21-2.40 (1H), 2.75-2.90 (1H), 2.92-3.15 (1H), 3.27-3.35 (4H), 3.44-3.53 (4H), 4.20 (3H), 4.27-4.43 (2H), 4.44-4.58 (1H), 7.25 (1H), 7.54-7.74 (3H), 7.81 (1H), 8.20 (1H), 8.83 (1H).

EXAMPLE 268

4-methoxy-N-(2-methoxyethyl)-2-({1-[4-(pentafluoro-λ$^6$-sulphanyl)benzoyl]-piperidin-4-yl}methyl)-2H-indazol-5-carboxamide

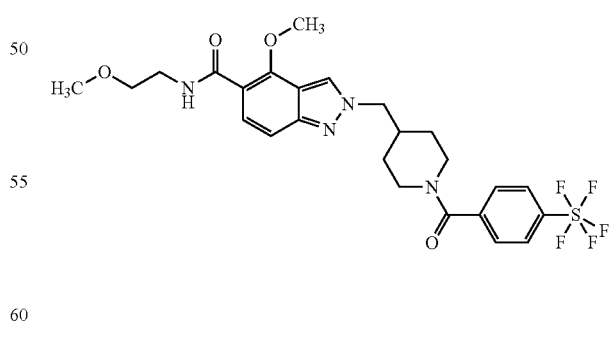

Analogously to Example 1b, Version B, 39 mg of the title compound was obtained from 100 mg of the compound prepared in Example 266b and 107 mg of 4-(pentafluoro-λ$^6$-sulphanyl)benzoic acid in DMF.

LC-MS: $R_t$=1.18 min, MS (ES+): m/z=577 (M+H)$^+$.

EXAMPLE 269

4-methoxy-N-(2-methoxyethyl)-2-[(1-{4-[(trifluoromethyl)sulphanyl]benzoyl}-piperidin-4-yl)methyl]-2H-indazol-5-carboxamide

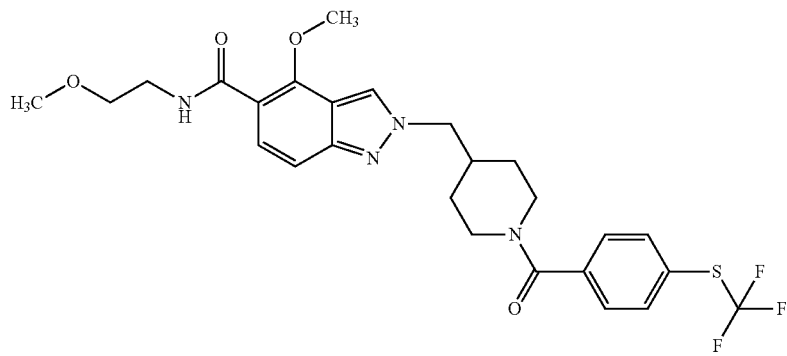 [SMILES: COCCNC(=O)c1ccc2nn(CC3CCN(C(=O)c4ccc(SC(F)(F)F)cc4)CC3)cc2c1OC]

Analogously to Example 1b, Version B, 25 mg of the title compound was obtained from 100 mg of the compound prepared in Example 266b and 96 mg of 4-[(trifluoromethyl)sulphanyl]benzoic acid in DMF.

$^1$H-NMR (400 MHz, DMSO-d$_6$): δ [ppm]=1.09-1.37 (2H), 1.38-1.72 (2H), 2.23-2.39 (1H), 2.70-2.93 (1H), 2.95-3.16 (1H), 3.30 (3H), 3.40-3.55 (5H), 4.20 (3H), 4.35 (d, 3H), 7.25 (1H), 7.46-7.58 (2H), 7.66 (1H), 7.78 (2H), 8.20 (1H), 8.82 (1H).

EXAMPLE 270

2-({1-[4-chloro-3-(trifluoromethyl)benzoyl]piperidin-4-yl}methyl)-4-methoxy-N-(2-methoxyethyl)-2H-indazol-5-carboxamide

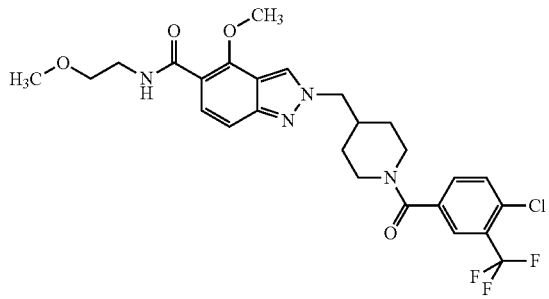 [SMILES: COCCNC(=O)c1ccc2nn(CC3CCN(C(=O)c4ccc(Cl)c(C(F)(F)F)c4)CC3)cc2c1OC]

Analogously to Example 1b, Version B, 27 mg of the title compound was obtained from 100 mg of the compound prepared in Example 266b and 97 mg of 4-chloro-3-(trifluoromethyl)benzoic acid in DMF.

$^1$H-NMR (400 MHz, DMSO-d$_6$): δ [ppm]=1.15-1.37 (2H), 1.38-1.73 (2H), 2.14-2.41 (1H), 2.70-2.88 (1H), 2.95-3.18 (1H), 3.30 (3H), 3.39-3.62 (5H), 4.20 (3H), 4.35 (3H), 7.25 (1H), 7.59-7.73 (2H), 7.75-7.86 (2H), 8.20 (1H), 8.82 (1H).

EXAMPLE 271

2-{[1-(4-chloro-2-fluorobenzoyl)piperidin-4-yl]methyl}-4-methoxy-N-(2-methoxyethyl)-2H-indazol-5-carboxamide

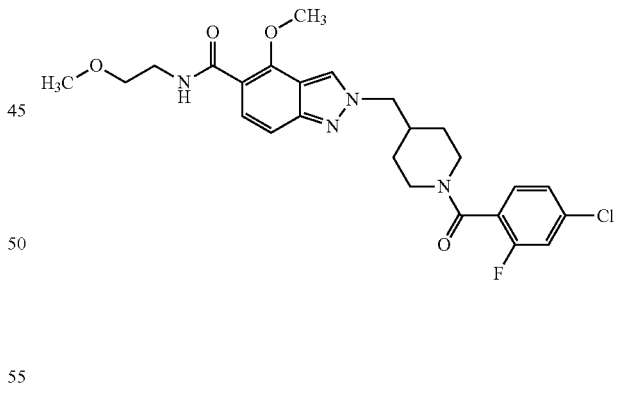

Analogously to Example 1b, Version B, 17 mg of the title compound was obtained from 100 mg of the compound prepared in Example 266b and 75 mg of 4-chloro-2-fluorobenzoic acid in DMF.

$^1$H-NMR (400 MHz, DMSO-d$_6$): δ [ppm]=1.08-1.33 (2H), 1.37-1.52 (1H), 1.53-1.70 (1H), 2.20-2.42 (1H), 2.72-2.88 (1H), 2.94-3.12 (1H), 3.30 (3H), 3.37 (1H), 3.43-3.51 (4H), 4.20 (3H), 4.34 (2H), 4.42-4.55 (1H), 7.25 (1H), 7.31-7.48 (2H), 7.55 (1H), 7.66 (1H), 8.20 (1H), 8.83 (1H).

EXAMPLE 272

2-({1-[3-fluoro-4-(trifluoromethoxy)benzoyl]piperidin-4-yl}methyl)-4-methoxy-N-(2-methoxyethyl)-2H-indazol-5-carboxamide

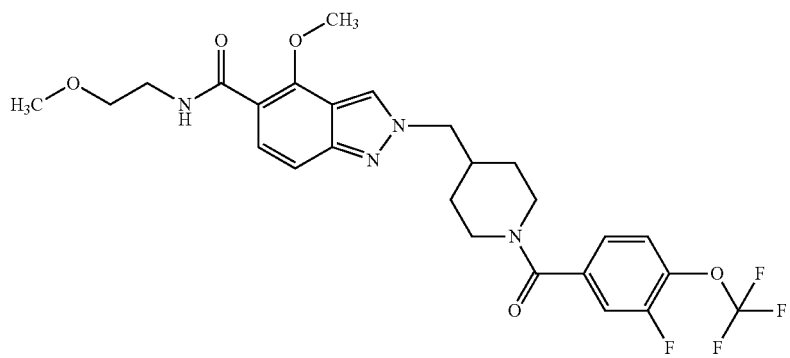 [SMILES: COCCNC(=O)c1ccc2nn(CC3CCN(C(=O)c4ccc(OC(F)(F)F)c(F)c4)CC3)cc2c1OC]

Analogously to Example 1b, Version B, 12 mg of the title compound was obtained from 100 mg of the compound prepared in Example 266b and 97 mg of 3-fluoro-4-(trifluoromethoxy)benzoic acid in DMF.

LC-MS: $R_t$=1.18 min, MS (ES+): m/z=553 (M+H)$^+$.

EXAMPLE 273

4-methoxy-N-(2-methoxyethyl)-2-({1-[(1-methyl-1H-indol-3-yl)carbonyl]-piperidin-4-yl}methyl)-2H-indazol-5-carboxamide

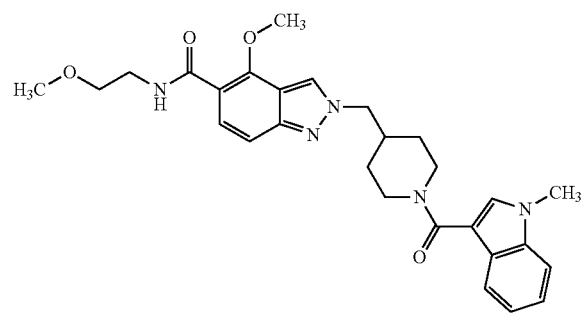

Analogously to Example 1b, Version B, 19 mg of the title compound was obtained from 100 mg of the compound prepared in Example 266b and 76 mg of 1-methyl-1H-indol-3-carboxylic acid in DMF.

$^1$H-NMR (300 MHz, DMSO-d$_6$): δ [ppm]=1.11-1.40 (2H), 1.54 (2H), 2.18-2.42 (1H), 2.93 (2H), 3.30 (3H), 3.40-3.45 (4H), 3.70-3.91 (3H), 4.12-4.48 (7H), 7.00-7.34 (3H), 7.48 (1H), 7.66 (3H), 8.22 (1H), 8.84 (1H).

EXAMPLE 274

2-{[1-(4-chlorobenzoyl)piperidin-4-yl]methyl}-4-ethoxy-N-(2-methoxyethyl)-2H-indazol-5-carboxamide

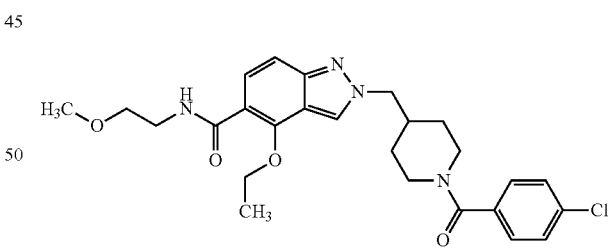

Analogously to Example 1b, Version B, 47 mg of the title compound was obtained from 110 mg of the compound prepared in Example 274c and 72 mg of 4-chlorobenzoic acid in DMF.

$^1$H-NMR (400 MHz, DMSO-d$_6$): δ [ppm]=1.10-1.33 (2H), 1.44 (5H), 2.20-2.39 (1H), 2.68-2.85 (1H), 2.92-3.12 (1H), 3.32 (7H), 3.51-3.62 (1H), 4.20-4.59 (5H), 7.26 (1H), 7.33-7.44 (2H), 7.47-7.55 (2H), 7.70 (1H), 8.30 (1H), 8.79 (1H).

The starting material was prepared as follows:

EXAMPLE 274a

Tert-butyl 4-[(5-bromo-4-ethoxy-2H-indazol-2-yl)methyl]piperidin-1-carboxylate

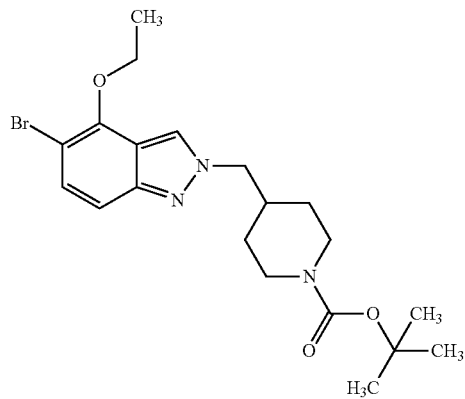 [SMILES: CCOc1c(Br)ccc2nn(CC3CCN(C(=O)OC(C)(C)C)CC3)cc12]

Analogously to Example 74c, 285 mg of the title compound was obtained from 484 mg of 5-bromo-4-ethoxy-1H-indazole and 1.11 g of tert-butyl-4-[(5-bromo-4-ethoxy-2H-indazol-2-yl)-methyl]piperidin-1-carboxylate.

$^1$H-NMR (400 MHz, chloroform-d): δ [ppm]=1.13-1.34 (2H), 1.46 (9H), 1.49 (3H), 1.56-1.63 (2H), 2.16-2.37 (1H), 2.54-2.80 (2H), 4.02-4.21 (2H), 4.26 (2H), 4.33 (2H), 7.28-7.43 (2H), 7.93 (1H).

EXAMPLE 274b

Tert-butyl 4-({4-ethoxy-5-[N-(2-methoxyethyl)carbamoyl]-2H-indazol-2-yl}-methyl)piperidin-1-carboxylate

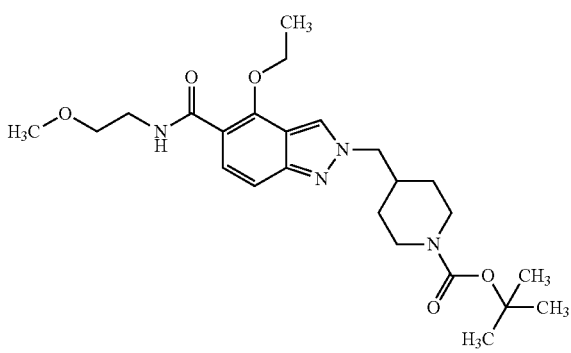 [SMILES: CCOc1c(C(=O)NCCOC)ccc2nn(CC3CCN(C(=O)OC(C)(C)C)CC3)cc12]

Analogously to Example 266a, 235 mg of the title compound was obtained from 285 mg of the compound prepared in Example 274a and 146 mg of 2-methoxyethylamine.

$^1$H-NMR (300 MHz, DMSO-$d_6$): δ [ppm]=0.97-1.22 (2H), 1.29-1.56 (14H), 2.06-2.31 (1H), 2.59-2.86 (2H), 3.33 (3H), 3.49 (4H), 3.80-4.02 (2H), 4.30 (2H), 4.51 (2H), 7.26 (1H), 7.71 (1H), 8.31 (1H), 8.79 (1H).

EXAMPLE 274c 4-ethoxy-N-(2-methoxyethyl)-2-(4-piperidylmethyl)-2H-indazol-5-carboxamide

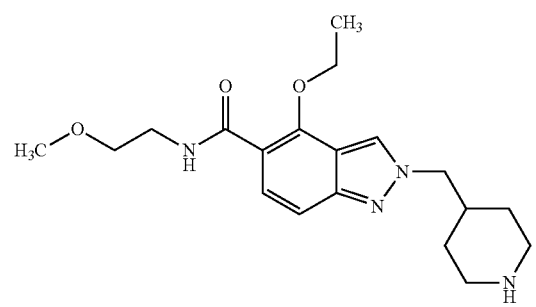 [SMILES: CCOc1c(C(=O)NCCOC)ccc2nn(CC3CCNCC3)cc12]

Analogously to Example 258b, from 235 mg of the compound prepared in Example 274b, 237 mg of the title compound was obtained, which was reacted in the next step without further purification.

EXAMPLE 275

4-ethoxy-N-(2-methoxyethyl)-2-({1-[4-(pentafluoro-$\lambda^6$-sulphanyl)benzoyl]-piperidin-4-yl}methyl)-2H-indazol-5-carboxamide Analogously to Example 1b, Version B, 30 mg of the title compound was obtained from 110 mg of the compound prepared in Example 274c and 113 mg of 4-(pentafluoro-$\lambda^6$-sulphanyl)benzoic acid in DMF.

$^1$H-NMR (400 MHz, DMSO-$d_6$): δ [ppm]=1.10-1.36 (2H), 1.44 (4H), 1.54-1.69 (1H), 2.22-2.40 (1H), 2.70-2.87 (1H), 2.93-3.13 (1H), 3.30 (3H), 3.48 (5H), 4.34 (2H), 4.41-4.63 (3H), 7.26 (1H), 7.59 (2H), 7.70 (1H), 7.98 (2H), 8.30 (1H), 8.79 (1H).

EXAMPLE 276

2-{[1-(4-chlorobenzoyl)azetidin-3-yl]methyl}-4-ethoxy-N-(2-methoxyethyl)-2H-indazol-5-carboxamide

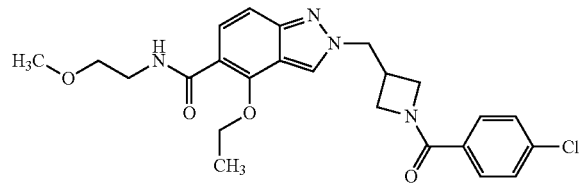 [SMILES: CCOc1c(C(=O)NCCOC)ccc2nn(CC3CN(C(=O)c4ccc(Cl)cc4)C3)cc12]

Analogously to Example 1b, Version B, 25 mg of the title compound was obtained from 50 mg of the compound prepared in Example 276c and 35 mg of 4-chlorobenzoic acid in DMF.

$^1$H-NMR (400 MHz, DMSO-$d_6$): δ [ppm]=1.44 (3H), 3.21-3.29 (1H), 3.31 (3H), 3.49 (4H), 3.96 (1H), 4.06-4.30 (2H), 4.34-4.59 (3H), 4.69 (2H), 7.25 (1H), 7.51 (2H), 7.62 (2H), 7.71 (1H), 8.30 (1H), 8.86 (1H).

The starting material was prepared as follows:

EXAMPLE 276a

Tert-butyl 3-[(5-bromo-4-ethoxy-2H-indazol-2-yl)methyl]azetidin-1-carboxylate

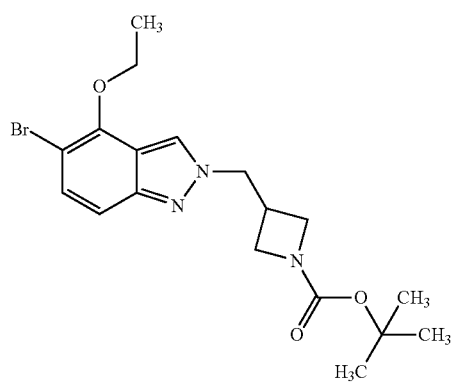 [SMILES: CCOc1c(Br)ccc2nn(CC3CN(C(=O)OC(C)(C)C)C3)cc12]

Analogously to Example 74c, 204 mg of the title compound was obtained from 500 mg of 5-bromo-4-ethoxy-1H-indazole and 1.06 g of tert-butyl-3-[(tosyloxy)methyl]azetidin-1-carboxylate.

$^1$H-NMR (600 MHz, chloroform-d): δ [ppm]=1.44 (9H), 1.49 (3H), 3.14-3.30 (1H), 3.72-3.83 (2H), 4.07 (2H), 4.33 (2H), 4.59 (2H), 7.29 (1H), 7.37 (1H), 7.98 (1H).

EXAMPLE 276b

Tert-butyl 3-({4-ethoxy-5-[N-(2-methoxyethyl)carbamoyl]-2H-indazol-2-yl}-methyl)azetidin-1-carboxylate

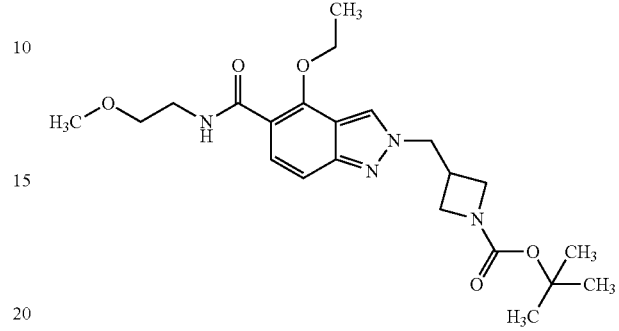

Analogously to Example 266a, from 191 mg of the compound prepared in Example 276a and 105 mg of 2-methoxyethylamine, 121 mg of the title compound was obtained, which was reacted in the next step without further purification.

EXAMPLE 276c 2-(azetidin-3-ylmethyl)-4-ethoxy-N-(2-methoxyethyl)-2H-indazol-5-carboxamide

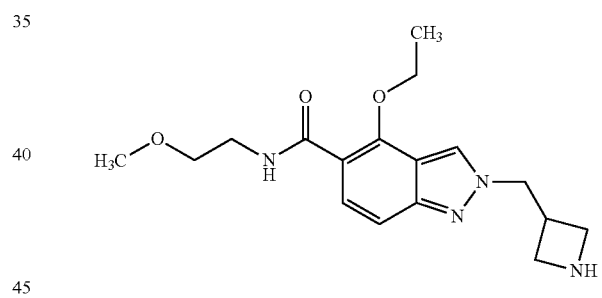

Analogously to Example 258b, from 121 mg of the compound prepared in Example 276b, 93 mg of the title compound was obtained, which was reacted in the next step without further purification.

EXAMPLE 277

4-ethoxy-N-(2-methoxyethyl)-2-({1-[4-(pentafluoro-λ$^6$-sulphanyl)benzoyl]-azetidin-3-yl}methyl)-2H-indazol-5-carboxamide

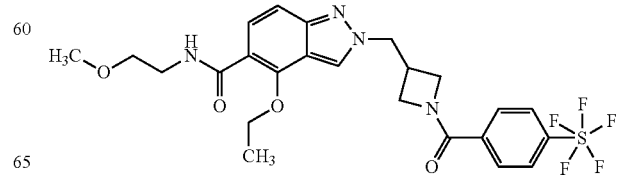

Analogously to Example 1b, Version B, 35 mg of the title compound was obtained from 50 mg of 276c and 56 mg of 4-(pentafluoro-λ⁶-sulphanyl)benzoic acid in DMF.

¹H-NMR (400 MHz, DMSO-d₆): δ [ppm]=1.37-1.50 (3H), 3.26 (1H), 3.31 (3H), 3.43-3.57 (4H), 3.92-4.05 (1H), 4.10-4.31 (2H), 4.38-4.57 (3H), 4.70 (2H), 7.25 (1H), 7.66-7.87 (3H), 7.98 (2H), 8.30 (1H), 8.86 (1H).

EXAMPLE 278

2-{[1-(4-chlorobenzoyl)azetidin-3-yl]methyl}-6-methyl-N-(2-morpholinoethyl)-2H-indazol-5-carboxamide

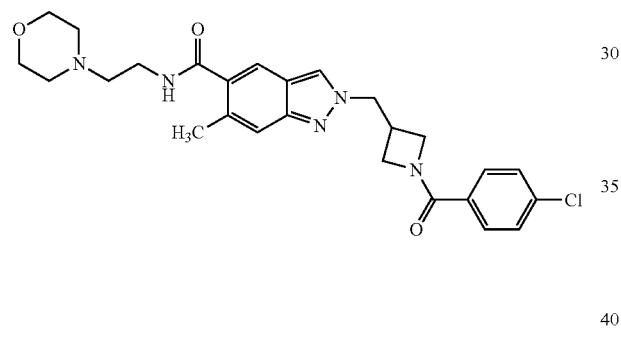

Analogously to Example 1b, Version B, 23 mg of the title compound was obtained from 100 mg of 278b and 66 mg of 4-chlorobenzoic acid in DMF.

¹H-NMR (400 MHz, DMSO-d₆): δ [ppm]=2.42 (s, 3H), 3.09-3.27 (m, 3H), 3.29-3.33 (2H), 3.49-3.73 (m, 6H), 3.84-3.96 (m, 1H), 3.97-4.15 (m, 3H), 4.16-4.27 (m, 1H), 4.31-4.45 (m, 1H), 4.62-4.80 (m, 2H), 7.36-7.47 (1H), 7.48-7.57 (2H), 7.58-7.70 (2H), 7.77-7.89 (1H), 8.41-8.58 (2H).

The starting material was prepared as follows:

EXAMPLE 278a

Tert-butyl 3-({6-methyl-5-[N-(2-morpholinoethyl)carbamoyl]-2H-indazol-2-yl}methyl)azetidin-1-carboxylate

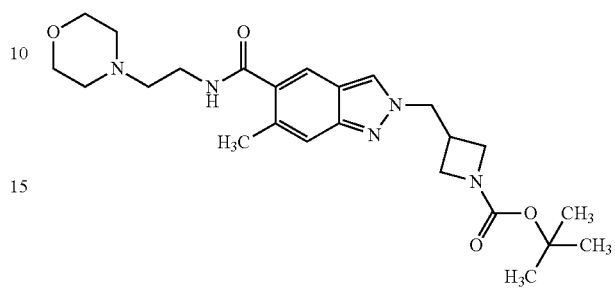

Analogously to Example 1b, Version B, 418 mg of the title compound was obtained from 410 mg of 178c and 232 mg of 2-morpholinoethylamine in DMF.

¹H-NMR (400 MHz, DMSO-d₆): δ [ppm]=1.36 (9H), 2.39 (3H), 2.44 (4H), 2.95-3.17 (1H), 3.24-3.43 (4H), 3.58 (4H), 3.64-3.79 (2H), 3.88 (2H), 4.62 (2H), 7.39 (1H), 7.68 (1H), 8.04-8.22 (1H), 8.45 (1H).

EXAMPLE 278b 2-(azetidin-3-ylmethyl)-6-methyl-N-(2-morpholinoethyl)-2H-indazol-5-carboxamide

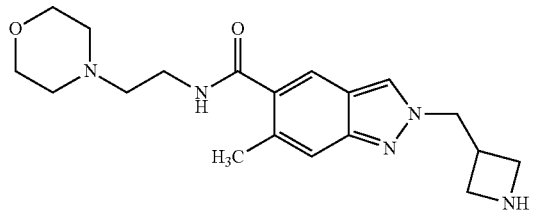 [SMILES: Cc1cc2nn(CC3CNC3)cc2cc1C(=O)NCCN1CCOCC1]

Analogously to Example 258b, from 400 mg of the compound prepared in Example 278a, 372 mg of the title compound was obtained, which was reacted in the next step without further purification.

EXAMPLE 279

6-methyl-N-(2-morpholinoethyl)-2-({1-[4-(trifluoromethoxy)benzoyl]azetidin-3-yl}methyl)-2H-indazol-5-carboxamide

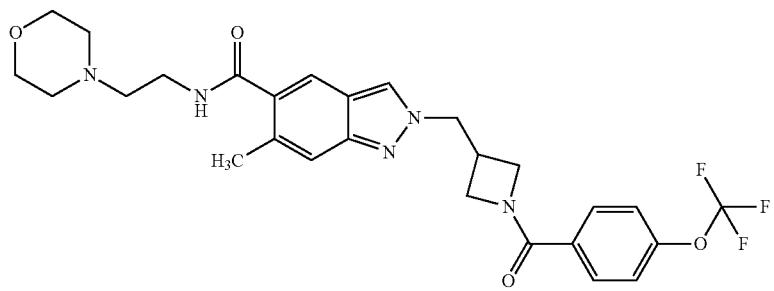 [SMILES: Cc1cc2nn(CC3CN(C(=O)c4ccc(OC(F)(F)F)cc4)C3)cc2cc1C(=O)NCCN1CCOCC1]

Analogously to Example 1b, Version B, 44 mg of the title compound was obtained from 100 mg of 278b and 86 mg of 4-(trifluoromethoxy)benzoic acid in DMF.

$^1$H-NMR (300 MHz, DMSO-$d_6$): δ [ppm]=2.42 (3H), 3.07-3.27 (5H), 3.48-3.74 (6H), 3.85-4.17 (4H), 4.18-4.29 (1H), 4.33-4.48 (1H), 4.61-4.82 (2H), 7.30-7.54 (3H), 7.68-7.78 (2H), 7.79-7.88 (1H), 8.43-8.60 (2H).

EXAMPLE 280

6-methyl-N-(2-morpholinoethyl)-2-({1-[4-(pentafluoro-λ$^6$-sulphanyl)benzoyl]-azetidin-3-yl}methyl)-2H-indazol-5-carboxamide

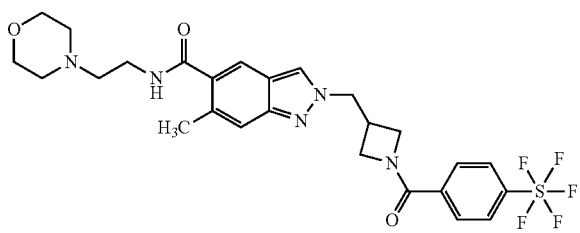 [SMILES: Cc1cc2nn(CC3CN(C(=O)c4ccc(S(F)(F)(F)(F)F)cc4)C3)cc2cc1C(=O)NCCN1CCOCC1]

Analogously to Example 1b, Version B, 37 mg of the title compound was obtained from 100 mg of 278b and 104 mg of 4-(pentafluoro-λ$^6$-sulphanyl)benzoic acid in DMF.

$^1$H-NMR (300 MHz, DMSO-$d_6$): δ [ppm]=2.42 (3H), 3.06-3.27 (5H), 3.47-3.75 (6H), 3.87-4.08 (3H), 4.09-4.29 (2H), 4.33-4.49 (1H), 4.61-4.80 (2H), 7.34-7.52 (1H), 7.71-7.88 (3H), 7.92-8.07 (2H), 8.39-8.59 (2H).

EXAMPLE 281

N-(2-methoxyethyl)-6-methyl-2-({1-[(1-methyl-1H-indol-3-yl)carbonyl]-piperidin-4-yl}methyl)-2H-indazol-5-carboxamide

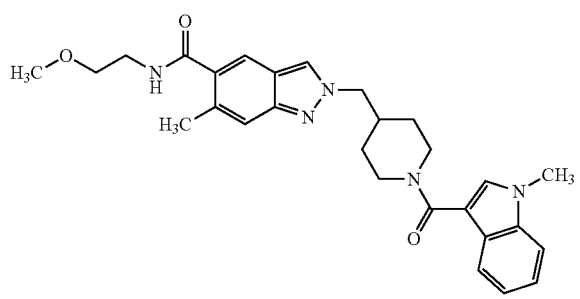

Analogously to Example 1b, Version B, 4.2 mg of the title compound was obtained from 150 mg of 205c and 119 mg of 1-methyl-1H-indol-3-carboxylic acid in DMF.

LC-MS: $R_t$=1.01 min, MS (ES+): m/z=489 (M+H)$^+$.

EXAMPLE 282

N-(2-methoxyethyl)-4-methyl-2-({1-[(1-methyl-1H-indol-3-yl)carbonyl]azetidin-3-yl}methyl)-2H-indazol-5-carboxamide

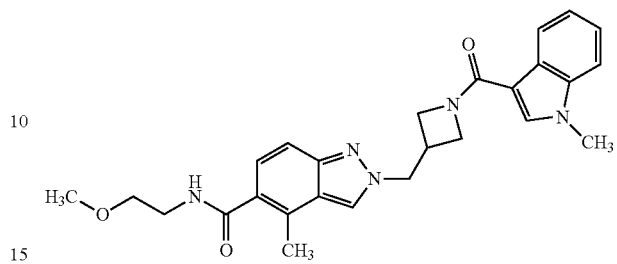

Analogously to Example 1b, Version B, 35 mg of the title compound was obtained from 175 mg of 117e and 122 mg of 1-methyl-1H-indol-3-carboxylic acid in DMF.

LC-MS: $R_t$=0.95 min, MS (ES+): m/z=460 (M+H)$^+$.

EXAMPLE 283

2-({1-[4-(4-fluorophenoxy)benzoyl]piperidin-4-yl}methyl)-4-methyl-N-(2,2,2-trifluoroethyl)-2H-indazol-5-carboxamide

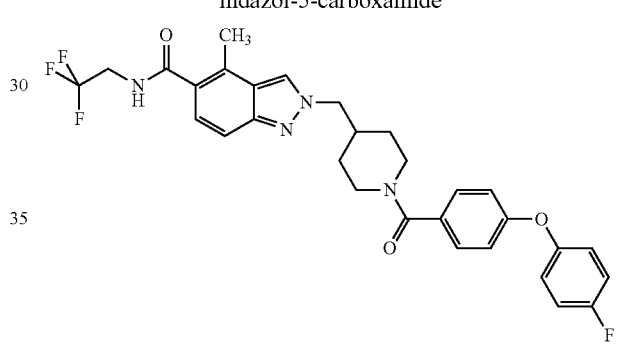

Analogously to Example 1b, Version B, 267 mg of the title compound was obtained from 250 mg of 71a and 246 mg of 4-(4-fluorophenoxy)benzoic acid in DMF.

$^1$H-NMR (400 MHz, DMSO-$d_6$): δ [ppm]=1.16-1.32 (2H), 1.35-1.69 (2H), 2.20-2.39 (1H), 2.54 (3H), 2.70-3.15 (2H), 3.50-3.83 (1H), 4.07 (2H), 4.36 (3H), 6.91-7.05 (2H), 7.08-7.31 (5H), 7.34-7.42 (2H), 7.46 (1H), 8.56 (1H), 8.83 (1H).

EXAMPLE 284

2-({1-[4-(4-chlorophenoxy)benzoyl]piperidin-4-yl}methyl)-4-methyl-N-(2,2,2-trifluoroethyl)-2H-indazol-5-carboxamide

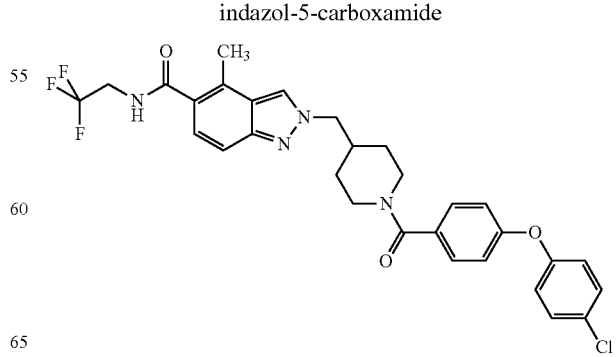

Analogously to Example 1b, Version B, 55 mg of the title compound was obtained from 100 mg of 71a and 105 mg of 4-(4-chlorophenoxy)benzoic acid in DMF.

$^1$H-NMR (400 MHz, DMSO-d$_6$): δ [ppm]=1.23 (2H), 1.34-1.72 (2H), 2.21-2.41 (1H), 2.54 (3H), 2.67-3.20 (2H), 3.51-3.83 (1H), 4.07 (2H), 4.36 (3H), 6.92-7.15 (4H), 7.20 (1H), 7.35-7.53 (5H), 8.56 (1H), 8.84 (1H).

EXAMPLE 285

4-methyl-2-({1-[4-(4-methylphenoxy)benzoyl]piperidin-4-yl}methyl)-N-(2,2,2-trifluoroethyl)-2H-indazol-5-carboxamide

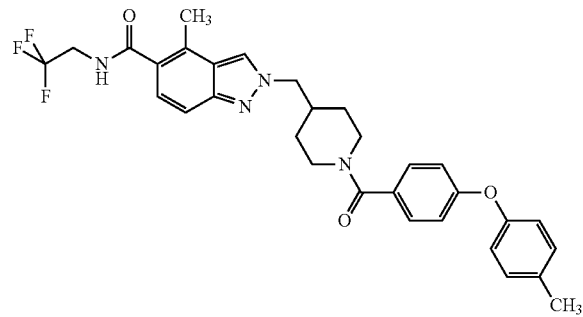 [SMILES: Cc1ccc(Oc2ccc(C(=O)N3CCC(Cn4cc5c(C)c(C(=O)NCC(F)(F)F)ccc5n4)CC3)cc2)cc1]

Analogously to Example 1b, Version B, 60 mg of the title compound was obtained from 100 mg of 71a and 97 mg of 4-(4-methylphenoxy)benzoic acid in DMF.

$^1$H-NMR (400 MHz, DMSO-d$_6$): δ [ppm]=1.23 (2H), 1.36-1.71 (2H), 2.30 (4H), 2.54 (3H), 2.64-3.17 (2H), 3.49-3.82 (1H), 4.07 (2H), 4.36 (3H), 6.85-7.04 (4H), 7.21 (3H), 7.29-7.41 (2H), 7.46 (1H), 8.56 (1H), 8.84 (s1H).

EXAMPLE 286

2-({1-[(4'-fluorobiphenyl-4-yl)carbonyl]piperidin-4-yl}methyl)-4-methyl-N-(2,2,2-trifluoroethyl)-2H-indazol-5-carboxamide

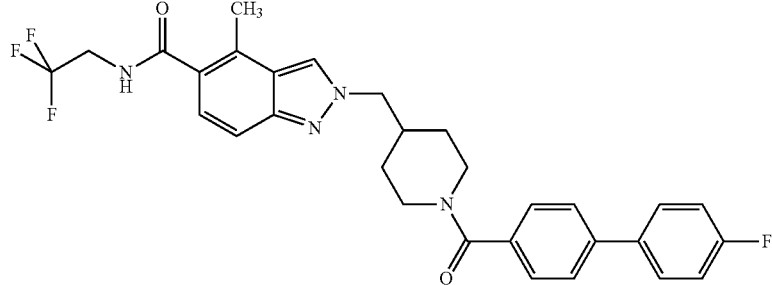 [SMILES: Cc1c(C(=O)NCC(F)(F)F)ccc2nn(CC3CCN(C(=O)c4ccc(-c5ccc(F)cc5)cc4)CC3)cc12]

Analogously to Example 1b, Version B, 39 mg of the title compound was obtained from 100 mg of 71a and 92 mg of 4-(4-fluorophenyl)benzoic acid in DMF.

$^1$H-NMR (400 MHz, DMSO-d$_6$): δ [ppm]=1.14-1.36 (2H), 1.36-1.73 (2H), 2.18-2.41 (1H), 2.54 (3H), 2.70-3.16 (2H), 3.51-3.82 (1H), 4.07 (2H), 4.38 (3H), 7.21 (1H), 7.31 (2H), 7.40-7.53 (3H), 7.64-7.85 (4H), 8.56 (1H), 8.81 (1H).

EXAMPLE 287

4-methyl-2-{[1-(4-morpholinobenzoyl)piperidin-4-yl]methyl}-N-(2,2,2-trifluoro-ethyl)-2H-indazol-5-carboxamide

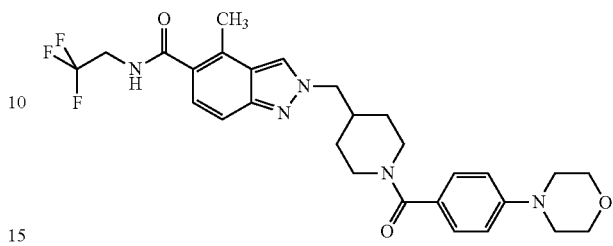

Analogously to Example 1b, Version B, 45 mg of the title compound was obtained from 100 mg of 71a and 88 mg of 4-morpholinobenzoic acid in DMF.

$^1$H-NMR (400 MHz, DMSO-d$_6$): δ [ppm]=1.24 (2H), 1.40-1.60 (2H), 2.20-2.40 (1H), 2.54 (3H), 2.73-3.01 (2H), 3.38 (4H), 3.64-3.81 (5H), 4.07 (3H), 4.36 (2H), 6.94 (2H), 7.16-7.30 (3H), 7.46 (1H), 8.55 (1H), 8.81 (1H).

EXAMPLE 288

4-methyl-N-(2,2,2-trifluoroethyl)-2-[(1-{4-[(trifluoromethyl)sulphanyl]benzoyl}-piperidin-4-yl)methyl]-2H-indazol-5-carboxamide

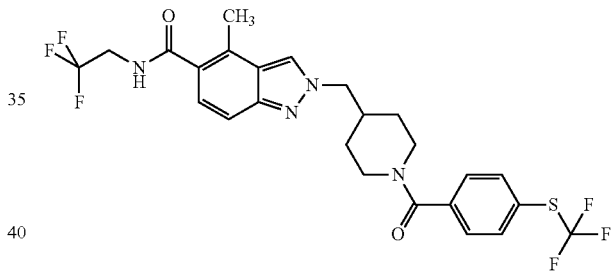

Analogously to Example 1b, Version B, 67 mg of the title compound was obtained from 100 mg of 71a and 94 mg of 4-[(trifluoromethyl)sulphanyl]benzoic acid in DMF.

$^1$H-NMR (400 MHz, DMSO-d$_6$): δ [ppm]=1.12-1.35 (2H), 1.35-1.70 (2H), 2.21-2.40 (1H), 2.54 (3H), 2.70-2.88 (1H), 2.94-3.12 (1H), 3.38-3.61 (1H), 4.07 (2H), 4.36 (3H), 7.21 (1H), 7.37-7.60 (3H), 7.78 (2H), 8.55 (1H), 8.81 (1H).

EXAMPLE 289

4-methyl-2-({1-[(1-methyl-1H-indol-3-yl)carbonyl]piperidin-4-yl}methyl)-N-(2,2,2-trifluoroethyl)-2H-indazol-5-carboxamide

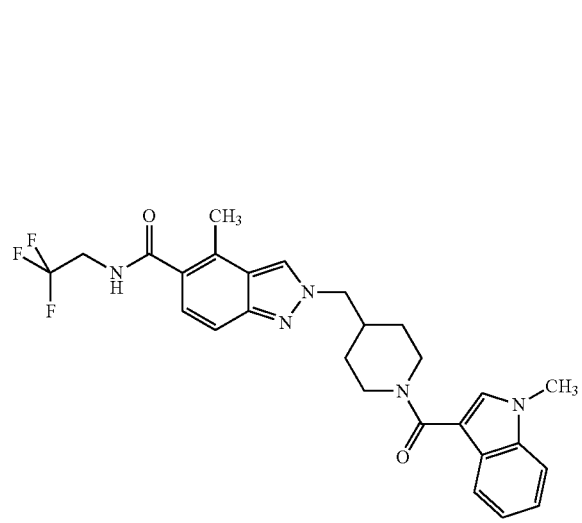 [SMILES: Cc1c(C(=O)NCC(F)(F)F)ccc2nn(CC3CCN(C(=O)c4cn(C)c5ccccc45)CC3)cc12]

Analogously to Example 1b, Version B, 43 mg of the title compound was obtained from 100 mg of 71a and 74 mg of 1-methyl-1H-indol-3-carboxylic acid in DMF.

$^1$H-NMR (400 MHz, DMSO-d$_6$): δ [ppm]=1.27 (2H), 1.52 (2H), 2.20-2.40 (1H), 2.54 (3H), 2.92 (2H), 3.82 (3H), 4.07 (2H), 4.27 (2H), 4.38 (2H), 6.92-7.33 (3H), 7.47 (2H), 7.61-7.76 (2H), 8.56 (1H), 8.81 (1H).

EXAMPLE 290

4-methyl-2-({1-[(1-methyl-1H-indol-2-yl)carbonyl]piperidin-4-yl}methyl)-N-(2,2,2-trifluoroethyl)-2H-indazol-5-carboxamide

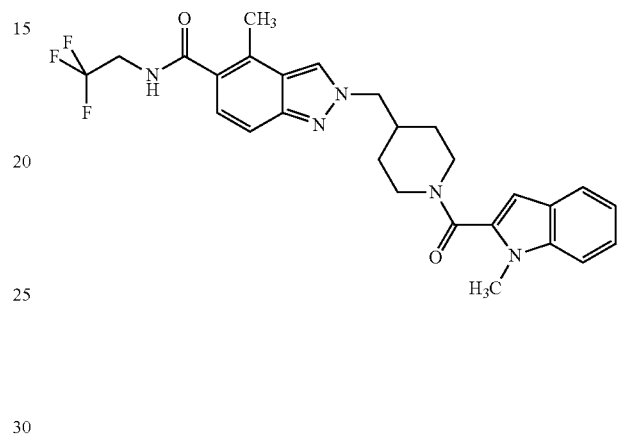

Analogously to Example 1b, Version B, 51 mg of the title compound was obtained from 100 mg of 71a and 74 mg of 1-methyl-1H-indol-2-carboxylic acid in DMF.

$^1$H-NMR (400 MHz, DMSO-d$_6$): δ [ppm]=1.17-1.41 (2H), 1.43-1.73 (2H), 2.19-2.43 (1H), 2.54 (3H), 2.74-3.23 (2H), 3.73 (3H), 4.07 (3H), 4.39 (3H), 6.60 (s, 1H), 7.03-7.14 (1H), 7.16-7.30 (2H), 7.48 (2H), 7.59 (1H), 8.57 (1H), 8.81 (1H).

EXAMPLE 291

4-methyl-N-(2,2,2-trifluoroethyl)-2-[(1-{4-[4-(trifluoromethyl)phenoxy]-benzoyl}piperidin-4-yl)methyl]-2H-indazol-5-carboxamide

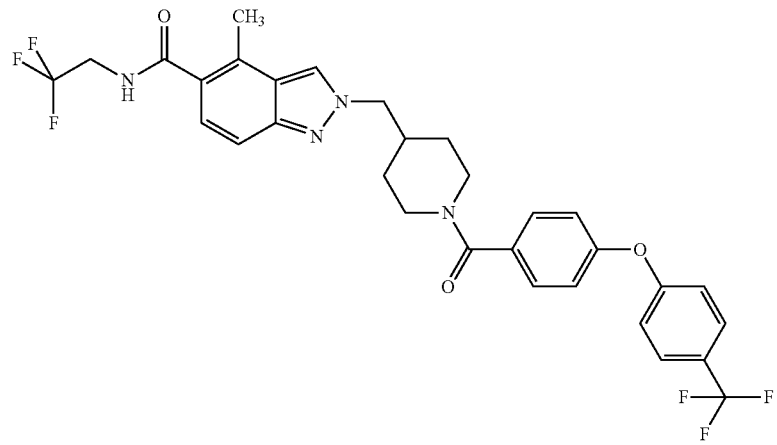 [SMILES: Cc1c(C(=O)NCC(F)(F)F)ccc2nn(CC3CCN(C(=O)c4ccc(Oc5ccc(C(F)(F)F)cc5)cc4)CC3)cc12]

Analogously to Example 1b, Version B, 156 mg of the title compound was obtained from 150 mg of 71a and 179 mg of 4-[4-(trifluoromethyl)phenoxy]benzoic acid in DMF.

$^1$H-NMR (400 MHz, DMSO-d$_6$): δ [ppm]=1.23 (2H), 1.36-1.68 (2H), 2.20-2.43 (1H), 2.54 (3H), 2.68-3.17 (2H), 3.50-3.79 (1H), 4.07 (2H), 4.37 (3H), 7.09-7.28 (5H), 7.35-7.51 (3H), 7.76 (2H), 8.56 (1H), 8.83 (1H).

EXAMPLE 292

2-({1-[(5-fluoro-1-methyl-1H-indol-2-yl)carbonyl]piperidin-4-yl}methyl)-4-methyl-N-(2,2,2-trifluoroethyl)-2H-indazol-5-carboxamide

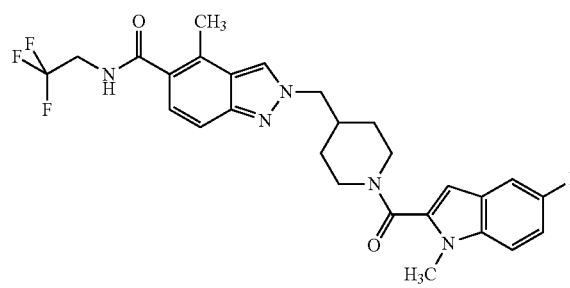

Analogously to Example 1b, Version B, 28 mg of the title compound was obtained from 100 mg of 71a and 82 mg of 5-fluoro-1-methyl-1H-indol-2-carboxylic acid in DMF.

$^1$H-NMR (400 MHz, DMSO-d$_6$): δ [ppm]=1.18-1.38 (2H), 1.39-1.72 (2H), 2.25-2.42 (1H), 2.54 (3H), 2.74-3.25 (2H), 3.73 (3H), 4.07 (3H), 4.38 (3H), 6.58 (1H), 7.09 (1H), 7.21 (1H), 7.36 (1H), 7.47 (2H), 8.57 (1H), 8.83 (1H).

EXAMPLE 293

2-({1-[(5-methoxy-1-methyl-1H-indol-2-yl)carbonyl]piperidin-4-yl}methyl)-4-methyl-N-(2,2,2-trifluoroethyl)-2H-indazol-5-carboxamide

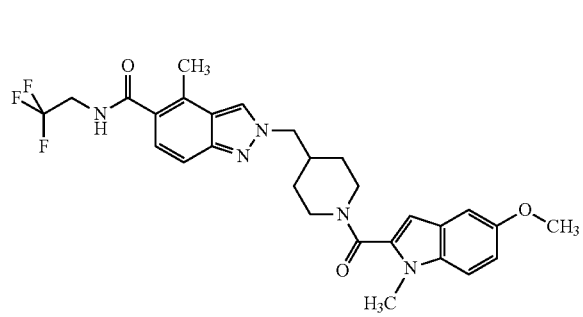 [SMILES: COc1ccc2c(c1)cc(C(=O)N1CCC(Cn3cc4c(C)c(C(=O)NCC(F)(F)F)ccc4n3)CC1)n2C]

Analogously to Example 1b, Version B, 37 mg of the title compound was obtained from 100 mg of 71a and 87 mg of 5-methoxy-1-methyl-1H-indol-2-carboxylic acid in DMF.

$^1$H-NMR (400 MHz, DMSO-d$_6$): δ [ppm]=1.30 (2H), 1.41-1.71 (2H), 2.25-2.43 (1H), 2.54 (3H), 2.71-3.22 (2H), 3.69 (3H), 3.75 (3H), 4.07 (3H), 4.39 (3H), 6.51 (1H), 6.88 (1H), 7.07 (1H), 7.21 (1H), 7.34-7.54 (2H), 8.57 (1H), 8.83 (1H).

EXAMPLE 294

2-({1-[(5-chloro-1-methyl-1H-indol-2-yl)carbonyl]piperidin-4-yl}methyl)-4-methyl-N-(2,2,2-trifluoroethyl)-2H-indazol-5-carboxamide

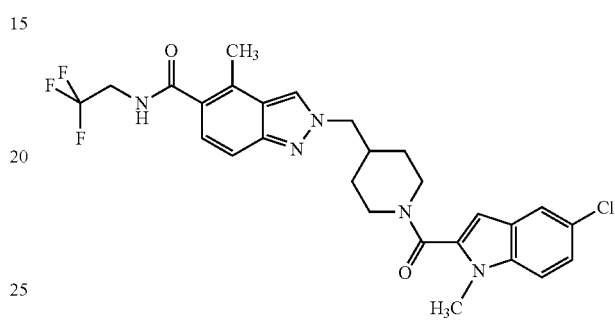

Analogously to Example 1b, Version B, 43 mg of the title compound was obtained from 100 mg of 71a and 89 mg of 5-chloro-1-methyl-1H-indol-2-carboxylic acid in DMF.

$^1$H-NMR (400 MHz, DMSO-d$_6$): δ [ppm]=1.29 (2H), 1.38-1.72 (2H), 2.26-2.43 (1H), 2.54 (3H), 2.71-3.21 (2H), 3.73 (3H), 3.84-4.18 (3H), 4.38 (3H), 6.59 (1H), 7.15-7.28 (2H), 7.47 (1H), 7.55 (1H), 7.65 (1H), 8.57 (1H), 8.83 (1H).

EXAMPLE 295

2-({1-[(6-methoxy-1-methyl-1H-indol-2-yl)carbonyl]piperidin-4-yl}methyl)-4-methyl-N-(2,2,2-trifluoroethyl)-2H-indazol-5-carboxamide

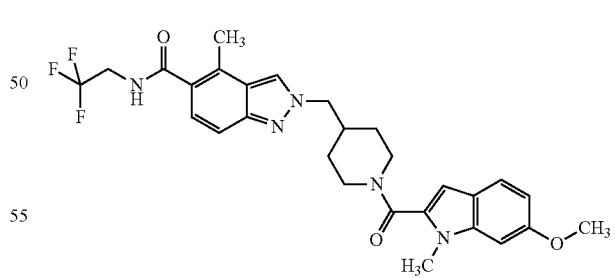

Analogously to Example 1b, Version B, 36 mg of the title compound was obtained from 100 mg of 71a and 87 mg of 6-methoxy-1-methyl-1H-indol-2-carboxylic acid in DMF.

$^1$H-NMR (400 MHz, DMSO-d$_6$): δ [ppm]=1.28 (2H), 1.52 (2H), 2.25-2.43 (1H), 2.54 (3H), 2.78-3.16 (2H), 3.70 (3H), 3.82 (3H), 3.97-4.63 (6H), 6.54 (1H), 6.73 (1H), 7.01 (1H), 7.21 (1H), 7.39-7.53 (2H), 8.57 (1H), 8.83 (t1H).

EXAMPLE 296

2-{[1-(1H-Indol-2-ylcarbonyl)piperidin-4-yl]methyl}-4-methyl-N-(2,2,2-trifluoroethyl)-2H-indazol-5-carboxamide

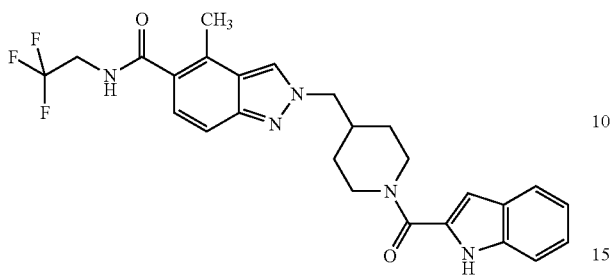

Analogously to Example 1b, Version B, 43 mg of the title compound was obtained from 100 mg of 71a and 68 mg of indol-2-carboxylic acid in DMF.

$^1$H-NMR (400 MHz, DMSO-d$_6$): δ [ppm]=1.16-1.40 (2H), 1.58 (2H), 2.27-2.44 (1H), 2.55 (3H), 2.77-3.24 (2H), 4.07 (2H), 4.30-4.59 (4H), 6.74 (1H), 6.95-7.08 (1H), 7.10-7.26 (2H), 7.40 (1H), 7.48 (1H), 7.59 (1H), 8.58 (1H), 8.84 (1H), 11.54 (1H).

EXAMPLE 297

4-methyl-2-({1-[(1-methyl-1H-benzimidazol-2-yl)carbonyl]piperidin-4-yl}-methyl)-N-(2,2,2-trifluoroethyl)-2H-indazol-5-carboxamide

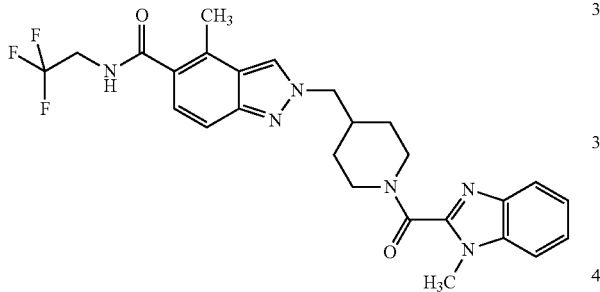

Analogously to Example 1b, Version B, 26 mg of the title compound was obtained from 100 mg of 71a and 75 mg of 1-methyl-1H-benzimidazol-2-carboxylic acid in DMF.

$^1$H-NMR (400 MHz, DMSO-d$_6$): δ [ppm]=1.17-1.42 (2H), 1.46 (1H), 1.57-1.75 (1H), 2.27-2.44 (1H), 2.54 (3H), 2.87 (1H), 3.11 (1H), 3.83 (3H), 4.07 (3H), 4.40 (2H), 4.48-4.62 (1H), 7.13-7.41 (3H), 7.47 (1H), 7.58-7.76 (2H), 8.58 (1H), 8.83 (1H).

EXAMPLE 298

4-methyl-2-({1-[(2-phenylthiazol-5-yl)carbonyl]piperidin-4-yl}methyl)-N-(2,2,2-trifluoroethyl)-2H-indazol-5-carboxamide

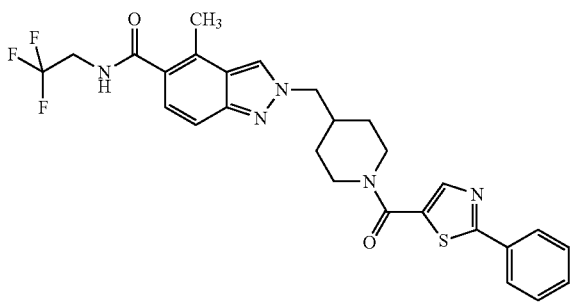 [SMILES: Cc1c(C(=O)NCC(F)(F)F)ccc2nn(CC3CCN(C(=O)c4cnc(-c5ccccc5)s4)CC3)cc12]

Analogously to Example 1b, Version B, 53 mg of the title compound was obtained from 100 mg of 71a and 87 mg of 2-phenylthiazol-5-carboxylic acid in DMF.

$^1$H-NMR (400 MHz, DMSO-d$_6$): δ [ppm]=1.18-1.41 (2H), 1.56 (2H), 2.27-2.44 (1H), 2.54 (3H), 2.73-3.29 (2H), 3.93-4.53 (6H), 7.21 (1H), 7.42-7.61 (4H), 7.93-8.03 (2H), 8.14 (1H), 8.57 (1H), 8.83 (1H).

EXAMPLE 299

2-{[1-(benzoxazol-2-ylcarbonyl)piperidin-4-yl]methyl}-4-methyl-N-(2,2,2-trifluoroethyl)-2H-indazol-5-carboxamide

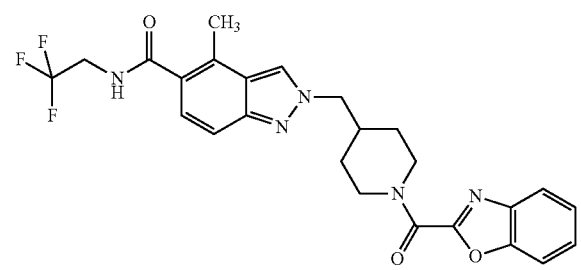 [SMILES: Cc1c(C(=O)NCC(F)(F)F)ccc2nn(CC3CCN(C(=O)c4nc5ccccc5o4)CC3)cc12]

Analogously to Example 1b, Version B, 20 mg of the title compound was obtained from 100 mg of 71a and 69 mg of benzoxazol-2-carboxylic acid in DMF.

$^1$H-NMR (400 MHz, DMSO-d$_6$): δ [ppm]=1.19-1.44 (2H), 1.48-1.72 (2H), 2.29-2.46 (1H), 2.54 (3H), 2.82-3.01 (1H), 3.12-3.31 (1H), 4.07 (2H), 4.40 (4H), 7.21 (1H), 7.42-7.61 (3H), 7.78-7.95 (2H), 8.58 (1H), 8.83 (1H).

EXAMPLE 300

4-methyl-2-({1-[(2-phenyloxazol-5-yl)carbonyl]piperidin-4-yl}methyl)-N-(2,2,2-trifluoroethyl)-2H-indazol-5-carboxamide

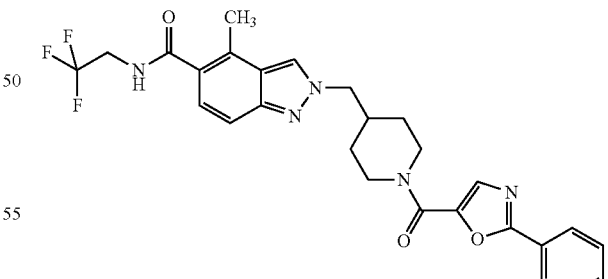

Analogously to Example 1b, Version B, 20 mg of the title compound was obtained from 100 mg of 71a and 80 mg of 2-phenyloxazol-5-carboxylic acid in DMF.

$^1$H-NMR (400 MHz, DMSO-d$_6$): δ [ppm]=1.15-1.43 (2H), 1.59 (2H), 2.31-2.45 (1H), 2.55 (3H), 2.70-3.35 (2H), 4.07 (2H), 4.39 (4H), 7.21 (1H), 7.48 (1H), 7.53-7.67 (3H), 7.80 (1H), 7.94-8.07 (2H), 8.58 (1H), 8.83 (1H).

EXAMPLE 301

4-methyl-N-(2,2,2-trifluoroethyl)-2-{[1-(4-{[5-(trifluoromethyl)pyridin-2-yl]-oxy}benzoyl)piperidin-4-yl]methyl}-2H-indazol-5-carboxamide

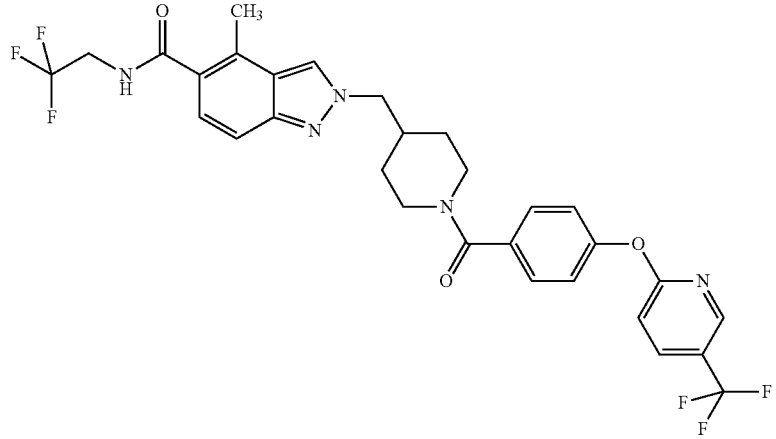 [SMILES: Cc1c(C(=O)NCC(F)(F)F)ccc2nn(CC3CCN(C(=O)c4ccc(Oc5ccc(C(F)(F)F)cn5)cc4)CC3)cc12]

Analogously to Example 1b, Version B, 23 mg of the title compound was obtained from 75 mg of 71a and 90 mg of 4-{[5-(trifluoromethyl)pyridin-2-yl]oxy}benzoic acid in DMF.

$^1$H-NMR (300 MHz, DMSO-d$_6$): δ [ppm]=1.13-1.35 (2H), 1.37-1.72 (2H), 2.19-2.42 (1H), 2.54 (3H), 2.69-3.17 (2H), 3.55-3.82 (1H), 3.91-4.18 (2H), 4.26-4.60 (3H), 7.28 (4H), 7.38-7.56 (3H), 8.16-8.33 (1H), 8.49-8.63 (2H), 8.75-8.91 (1H).

EXAMPLE 302

2-{[1-(benzothiazol-2-ylcarbonyl)piperidin-4-yl]methyl}-4-methyl-N-(2,2,2-trifluoroethyl)-2H-indazol-5-carboxamide

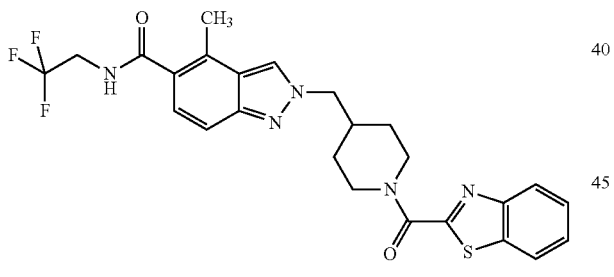

Analogously to Example 1b, Version B, 35 mg of the title compound was obtained from 75 mg of 71a and 57 mg of benzothiazol-2-carboxylic acid in DMF.

$^1$H-NMR (300 MHz, DMSO-d$_6$): δ [ppm]=1.36 (2H), 1.59 (2H), 2.31-2.46 (1H), 2.55 (3H), 2.91 (1H), 3.26 (1H), 4.07 (2H), 4.31-4.61 (3H), 4.95-5.23 (1H), 7.21 (1H), 7.41-7.69 (3H), 8.05-8.28 (2H), 8.58 (1H), 8.83 (1H).

EXAMPLE 303

4-methyl-N-(2,2,2-trifluoroethyl)-2-{[1-(4-{[6-(trifluoromethyl)pyridin-3-yl]-oxy}benzoyl)piperidin-4-yl]methyl}-2H-indazol-5-carboxamide

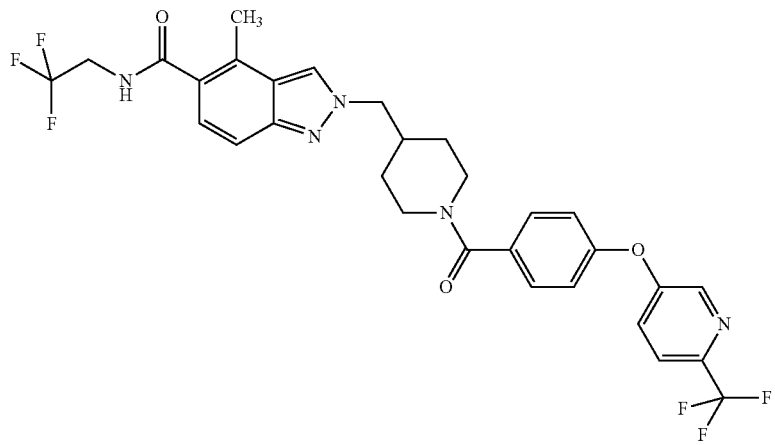 [SMILES: Cc1c(C(=O)NCC(F)(F)F)ccc2nn(CC3CCN(C(=O)c4ccc(Oc5ccc(C(F)(F)F)nc5)cc4)CC3)cc12]

Analogously to Example 1b, Version B, 42 mg of the title compound was obtained from 75 mg of 71a and 90 mg of the carboxylic acid prepared in Example 303b) in DMF.

$^1$H-NMR (400 MHz, DMSO-$d_6$): δ [ppm]=1.16-1.33 (2H), 1.34-1.67 (2H), 2.21-2.39 (1H), 2.54 (3H), 2.68-3.16 (2H), 3.52-3.76 (1H), 3.95-4.16 (2H), 4.28-4.61 (3H), 7.13-7.31 (3H), 7.46 (3H), 7.59-7.71 (1H), 7.92 (1H), 8.52-8.65 (2H), 8.84 (1H).

The starting material was prepared as follows:

EXAMPLE 303a

4-{[6-(trifluoromethyl)pyridin-3-yl]oxy}benzonitrile

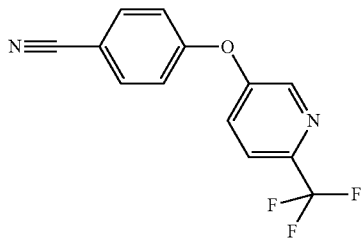 [SMILES: N#Cc1ccc(Oc2ccc(C(F)(F)F)nc2)cc1]

2.5 g of 5-bromo-2-(trifluoromethyl)pyridine, 5.8 g of 4-hydroxybenzonitrile, 10.8 g of caesium carbonate and 1.87 g of molybdenum hexacarbonyl in 100 ml 1,4-dioxan were heated under reflux until complete conversion. The reaction mixture was diluted with water, extracted several times with ethyl acetate, and the combined organic phases washed with saturated sodium chloride solution, dried over sodium sulphate and concentrated. The residue was purified by column chromatography on silica gel using a hexane/ethyl acetate gradient. Yield: 1.35 g of the title compound.

$^1$H-NMR (300 MHz, DMSO-$d_6$): δ [ppm]=7.35 (2H), 7.75-7.84 (1H), 7.89-8.03 (3H), 8.66 (1H).

EXAMPLE 303b

4-{[6-(trifluoromethyl)pyridin-2-yl]oxy}benzoic acid

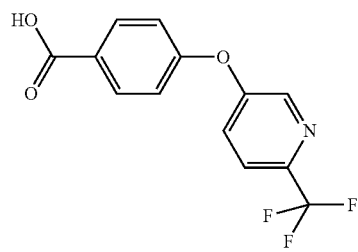 [SMILES: O=C(O)c1ccc(Oc2ccc(C(F)(F)F)nc2)cc1]

1.33 g of the compound prepared in Example 303a in 64 ml ethanol was treated with 32 ml of 40% potassium hydroxide solution and heated under reflux until complete conversion. The reaction mixture was diluted with water and extracted with ethyl acetate. The organic phase was washed with saturated sodium chloride solution, dried over sodium sulphate and concentrated. Yield: 1.32 g of the title compound.

$^1$H-NMR (400 MHz, DMSO-$d_6$): δ [ppm]=7.19-7.33 (2H), 7.68-7.81 (1H), 7.90-8.08 (3H), 8.64 (1H), 12.71-13.28 (1H).

EXAMPLE 304

4-methyl-N-(2,2,2-trifluoroethyl)-2-{[1-(4-{[6-(trifluoromethyl)pyridin-2-yl]-oxy}benzoyl)piperidin-4-yl]methyl}-2H-indazol-5-carboxamide

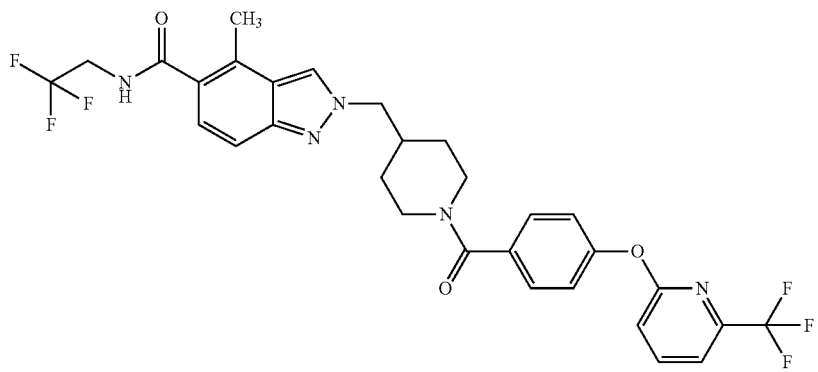 [SMILES: Cc1c(C(=O)NCC(F)(F)F)ccc2nn(CC3CCN(C(=O)c4ccc(Oc5cccc(C(F)(F)F)n5)cc4)CC3)cc12]

Analogously to Example 1b, Version B, 48 mg of the title compound was obtained from 75 mg of 71a and 90 mg of 4-{[6-(trifluoromethyl)pyridin-2-yl]oxy}benzoic acid in DMF.

$^1$H-NMR (400 MHz, DMSO-$d_6$): δ [ppm]=1.15-1.34 (2H), 1.35-1.71 (2H), 2.23-2.41 (1H), 2.54 (3H), 2.67-3.17 (2H), 3.51-3.77 (1H), 3.97-4.18 (2H), 4.22-4.65 (3H), 7.13-7.31 (3H), 7.37 (1H), 7.41-7.53 (3H), 7.67 (1H), 8.07-8.20 (1H), 8.57 (1H), 8.75-8.92 (1H).

EXAMPLE 305

4-methyl-2-({1-[(3-phenyl-1,2,4-oxadiazol-5-yl)carbonyl]piperidin-4-yl}methyl)-N-(2,2,2-trifluoroethyl)-2H-indazol-5-carboxamide

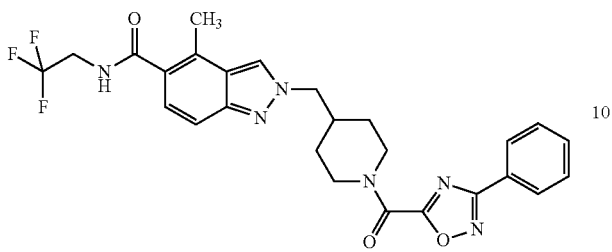

Analogously to Example 1b, Version B, 40 mg of the title compound was obtained from 90 mg of 71a and 73 mg of 3-phenyl-1,2,4-oxadiazol-5-carboxylic acid in DMF.

$^1$H-NMR (400 MHz, DMSO-d$_6$): δ [ppm]=1.18-1.43 (2H), 1.48-1.72 (2H), 2.33-2.47 (1H), 2.54 (3H), 2.95 (1H), 3.24 (1H), 3.94-4.17 (3H), 4.33-4.53 (3H), 7.21 (1H), 7.47 (1H), 7.55-7.70 (3H), 7.96-8.12 (2H), 8.57 (1H), 8.83 (1H).

EXAMPLE 306

2-({1-[4-(4-cyanophenoxy)benzoyl]piperidin-4-yl}methyl)-4-methyl-N-(2,2,2-trifluoroethyl)-2H-indazol-5-carboxamide

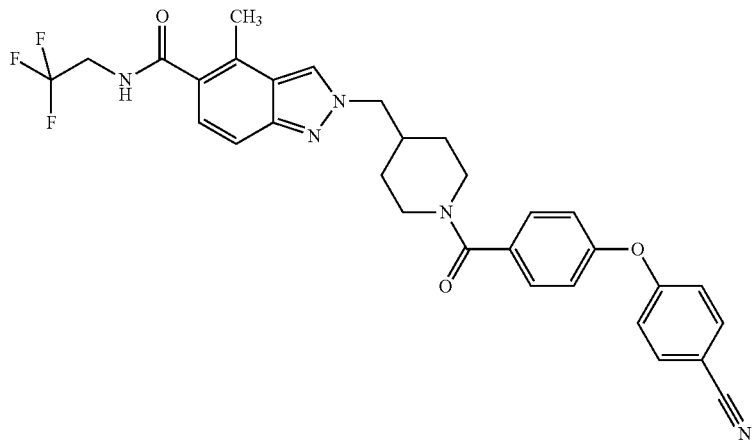

Analogously to Example 1b, Version B, 59 mg of the title compound was obtained from 110 mg of 71a and 101 mg of 4-(4-cyanophenoxy)benzoic acid in DMF.

$^1$H-NMR (400 MHz, DMSO-d$_6$): δ [ppm]=1.17-1.34 (2H), 1.35-1.70 (2H), 2.18-2.41 (1H), 2.54 (3H), 2.70-3.18 (2H), 3.54-3.79 (1H), 4.07 (2H), 4.37 (3H), 7.10-7.28 (5H), 7.41-7.52 (3H), 7.79-7.94 (2H), 8.56 (s1H), 8.81 (s1H).

EXAMPLE 307

2-({1-[4-(3-fluorophenoxy)benzoyl]piperidin-4-yl}methyl)-4-methyl-N-(2,2,2-trifluoroethyl)-2H-indazol-5-carboxamide

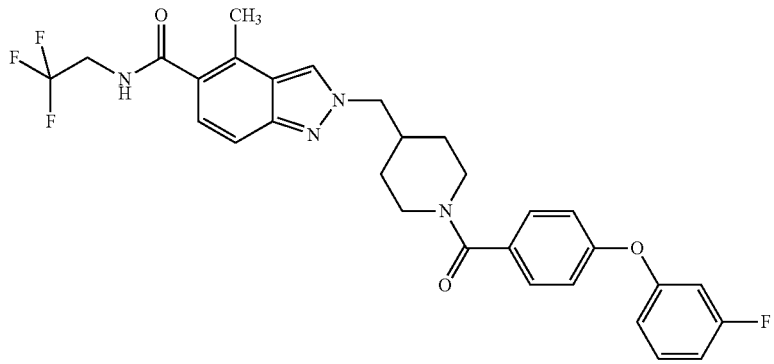 [SMILES: Cc1c(C(=O)NCC(F)(F)F)ccc2nn(CC3CCN(C(=O)c4ccc(Oc5cccc(F)c5)cc4)CC3)cc12]

Analogously to Example 1b, Version B, 40 mg of the title compound was obtained from 100 mg of 71a and 89 mg of 4-(3-fluorophenoxy)benzoic acid in DMF.

$^1$H-NMR (400 MHz, DMSO-$d_6$): δ [ppm]=1.14-1.34 (2H), 1.36-1.70 (2H), 2.22-2.44 (1H), 2.54 (3H), 2.70-3.13 (2H), 3.52-3.86 (1H), 4.07 (2H), 4.37 (3H), 6.79-7.12 (5H), 7.21 (1H), 7.35-7.52 (4H), 8.55 (1H), 8.81 (1H).

EXAMPLE 308

4-methyl-N-(2,2,2-trifluoroethyl)-2-[(1-{4-[3-(trifluoromethyl)phenoxy]-benzoyl}piperidin-4-yl)methyl]-2H-indazol-5-carboxamide

EXAMPLE 309

4-methyl-2-({1-[(5-phenyloxazol-2-yl)carbonyl]piperidin-4-yl}methyl)-N-(2,2,2-trifluoroethyl)-2H-indazol-5-carboxamide

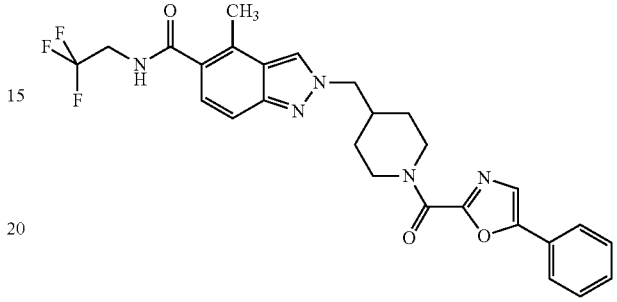

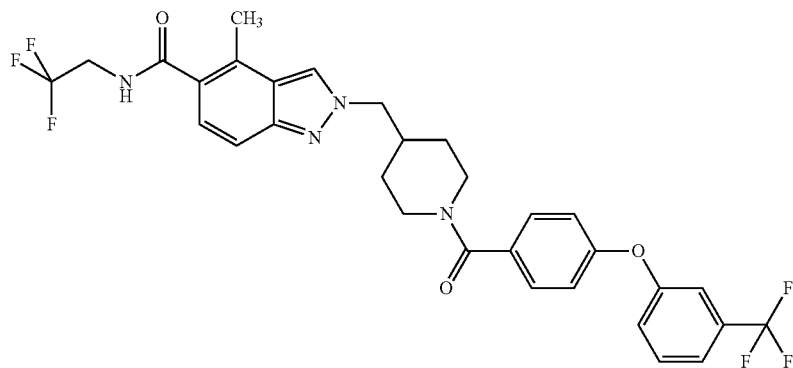 [SMILES: Cc1c(C(=O)NCC(F)(F)F)ccc2nn(CC3CCN(C(=O)c4ccc(Oc5cccc(C(F)(F)F)c5)cc4)CC3)cc12]

Analogously to Example 1b, Version B, 47 mg of the title compound was obtained from 100 mg of 71a and 119 mg of 4-[3-(trifluoromethyl)phenoxy]benzoic acid in DMF.

$^1$H-NMR (400 MHz, DMSO-$d_6$): δ [ppm]=1.16-1.34 (2H), 1.37-1.66 (2H), 2.22-2.38 (1H), 2.54 (3H), 2.69-3.14 (2H), 3.50-3.83 (1H), 4.07 (2H), 4.37 (3H), 7.10 (2H), 7.21 (1H), 7.36 (1H), 7.39-7.50 (4H), 7.54 (1H), 7.61-7.75 (1H), 8.55 (1H), 8.81 (1H).

Analogously to Example 1b, Version B, 10 mg of the title compound was obtained from 100 mg of 71a and 73 mg of 5-phenyloxazol-2-carboxylic acid in DMF.

$^1$H-NMR (400 MHz, DMSO-$d_6$): δ [ppm]=1.24 (2H), 1.58 (2H), 2.29-2.45 (1H), 2.55 (3H), 2.86 (1H), 3.21 (1H), 4.07 (2H), 4.31-4.52 (3H), 4.62 (1H), 7.21 (1H), 7.39-7.57 (4H), 7.74-7.83 (2H), 7.88 (1H), 8.57 (1H), 8.81 (1H).

EXAMPLE 310

2-[(1-{4-[(5-cyanopyridin-2-yl)oxy]benzoyl}piperidin-4-yl)methyl]-4-methyl-N-(2,2,2-trifluoroethyl)-2H-indazol-5-carboxamide

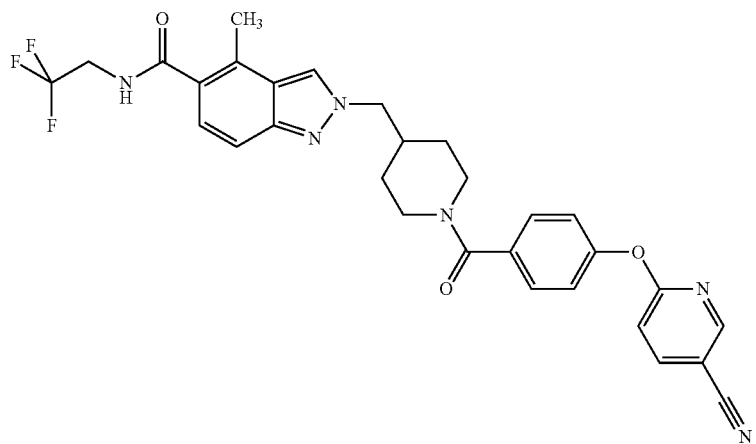 [SMILES: Cc1c(C(=O)NCC(F)(F)F)ccc2nn(CC3CCN(C(=O)c4ccc(Oc5ccc(C#N)cn5)cc4)CC3)cc12]

Analogously to Example 1b, Version B, 47 mg of the title compound was obtained from 100 mg of 71a and 119 mg of 4-[3-(trifluoromethyl)phenoxy]benzoic acid in DMF.

$^1$H-NMR (400 MHz, DMSO-d$_6$): δ [ppm]=1.16-1.34 (2H), 1.37-1.66 (2H), 2.22-2.38 (1H), 2.54 (3H), 2.69-3.14 (2H), 3.50-3.83 (1H), 4.07 (2H), 4.37 (3H), 7.10 (2H), 7.21 (1H), 7.36 (1H), 7.39-7.50 (4H), 7.54 (1H), 7.61-7.75 (1H), 8.55 (1H), 8.81 (1H).

EXAMPLE 311

2-[(1-{4-[(5-chloropyridin-2-yl)oxy]benzoyl}piperidin-4-yl)methyl]-4-methyl-N-(2,2,2-trifluoroethyl)-2H-indazol-5-carboxamide

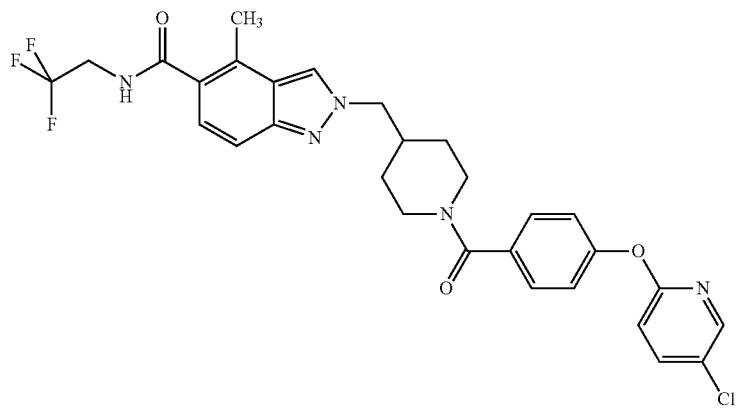 [SMILES: Cc1c(C(=O)NCC(F)(F)F)ccc2nn(CC3CCN(C(=O)c4ccc(Oc5ccc(Cl)cn5)cc4)CC3)cc12]

Analogously to Example 1b, Version B, 72 mg of the title compound was obtained from 100 mg of 71a and 96 mg of 4-[(5-chloropyridin-2-yl)oxy]benzoic acid in DMF.

$^1$H-NMR (400 MHz, DMSO-d$_6$): δ [ppm]=1.17-1.34 (2H), 1.36-1.73 (2H), 2.22-2.41 (1H), 2.54 (3H), 2.69-3.18 (2H), 3.47-3.88 (1H), 4.07 (2H), 4.37 (3H), 7.06-7.28 (4H), 7.34-7.52 (3H), 7.99 (1H), 8.22 (1H), 8.56 (1H), 8.81 (1H).

EXAMPLE 312

4-methyl-N-(2,2,2-trifluoroethyl)-2-[(1-{4-[5-(trifluoromethyl)pyridin-2-yl]-benzoyl}piperidin-4-yl)methyl]-2H-indazol-5-carboxamide

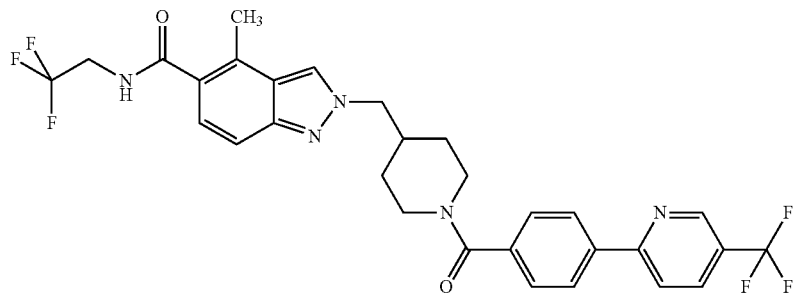 [SMILES: Cc1c(C(=O)NCC(F)(F)F)ccc2nn(CC3CCN(C(=O)c4ccc(-c5ccc(C(F)(F)F)cn5)cc4)CC3)cc12]

Analogously to Example 1b, Version B, 83 mg of the title compound was obtained from 100 mg of 71a and 103 mg of 4-[5-(trifluoromethyl)pyridin-2-yl]benzoic acid in DMF.

$^1$H-NMR (400 MHz, DMSO-d$_6$): δ [ppm]=1.28 (2H), 1.36-1.73 (2H), 2.33 (1H), 2.54 (3H), 2.70-3.18 (2H), 3.47-3.76 (1H), 3.96-4.16 (2H), 4.38 (3H), 7.21 (1H), 7.41-7.60 (3H), 8.17-8.40 (4H), 8.56 (1H), 8.81 (1H), 9.07 (1H).

EXAMPLE 313

2-({1-[4-(2,4-difluorophenoxy)benzoyl]piperidin-4-yl}methyl)-4-methyl-N-(2,2,2-trifluoroethyl)-2H-indazol-5-carboxamide

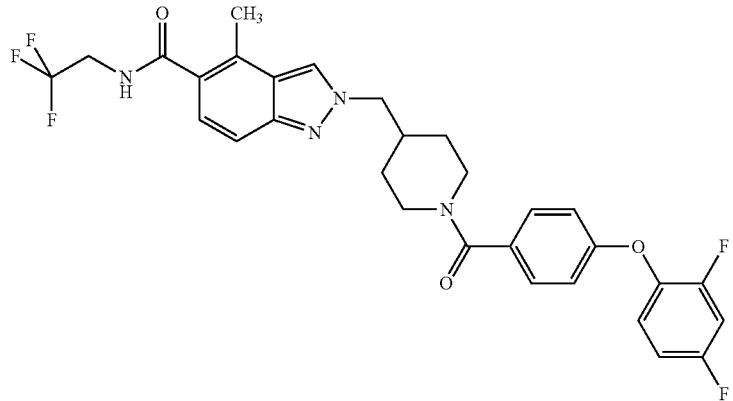 [SMILES: Cc1c(C(=O)NCC(F)(F)F)ccc2nn(CC3CCN(C(=O)c4ccc(Oc5ccc(F)cc5F)cc4)CC3)cc12]

Analogously to Example 1b, Version B, 87 mg of the title compound was obtained from 100 mg of 71a and 96 mg of 4-(2,4-difluorophenoxy)benzoic acid in DMF.

$^1$H-NMR (400 MHz, DMSO-d$_6$): δ [ppm]=1.23 (2H), 1.34-1.72 (2H), 2.18-2.42 (1H), 2.52-2.58 (3H), 2.69-3.20 (2H), 3.43-3.84 (1H), 4.07 (2H), 4.36 (3H), 6.92-7.06 (2H), 7.09-7.25 (2H), 7.28-7.42 (3H), 7.43-7.61 (2H), 8.55 (1H), 8.81 (1H).

EXAMPLE 314

2-({1-[4-(3,4-difluorophenoxy)benzoyl]piperidin-4-yl}methyl)-4-methyl-N-(2,2,2-trifluoroethyl)-2H-indazol-5-carboxamide

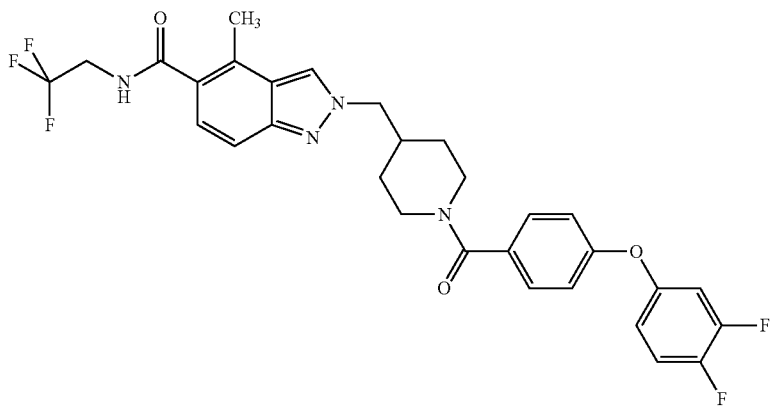 [SMILES: Cc1c(C(=O)NCC(F)(F)F)ccc2nn(CC3CCN(C(=O)c4ccc(Oc5ccc(F)c(F)c5)cc4)CC3)cc12]

Analogously to Example 1b, Version B, 48 mg of the title compound was obtained from 100 mg of 71a and 96 mg of 4-(3,4-difluorophenoxy)benzoic acid in DMF.

$^1$H-NMR (400 MHz, DMSO-d$_6$): δ [ppm]=1.24 (2H), 1.36-1.72 (2H), 2.19-2.42 (1H), 2.54 (3H), 2.70-3.17 (2H), 3.44-3.86 (1H), 3.99-4.17 (2H), 4.36 (3H), 6.86-6.97 (1H), 7.01-7.11 (2H), 7.21 (1H), 7.29 (1H), 7.35-7.55 (4H), 8.55 (1H), 8.81 (1H).

EXAMPLE 315

4-methyl-N-(2,2,2-trifluoroethyl)-2-[(1-{[4'-(trifluoromethyl)biphenyl-4-yl]-carbonyl}piperidin-4-yl)methyl]-2H-indazol-5-carboxamide

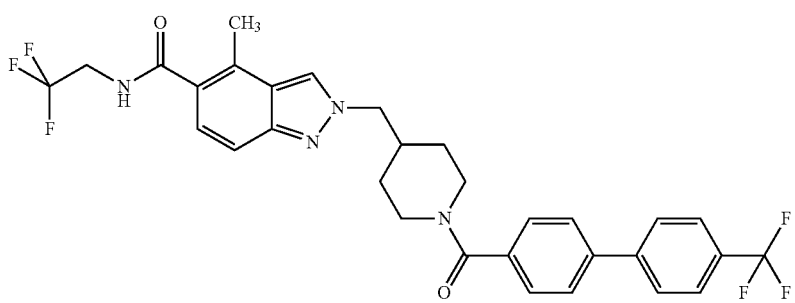 [SMILES: Cc1c(C(=O)NCC(F)(F)F)ccc2nn(CC3CCN(C(=O)c4ccc(-c5ccc(C(F)(F)F)cc5)cc4)CC3)cc12]

Analogously to Example 1b, Version B, 32 mg of the title compound was obtained from 100 mg of 71a and 102 mg of 4'-(trifluoromethyl)biphenyl-4-carboxylic acid in DMF.

$^1$H-NMR (400 MHz, DMSO-$d_6$): δ [ppm]=1.27 (2H), 1.37-1.71 (2H), 2.24-2.39 (1H), 2.53 (3H), 2.70-3.18 (2H), 3.43-3.51 (2H), 3.54-3.86 (1H), 4.37 (3H), 7.18 (1H), 7.38-7.57 (3H), 7.72-7.88 (4H), 7.89-7.98 (2H), 8.13 (1H), 8.51 (1H).

Analogously to Example 1b, Version B, 6.96 g of the title compound was obtained from 5.61 g 71a and 2.89 g of 4-bromobenzoic acid.

$^1$H-NMR (300 MHz, DMSO-$d_6$): δ [ppm]=1.17-1.32 (2H), 1.34-1.74 (2H), 2.19-2.41 (1H), 2.54 (3H), 2.88-3.22 (2H), 3.42-3.74 (1H), 3.94-4.18 (2H), 4.36 (3H), 7.20 (1H), 7.32 (2H), 7.46 (1H), 7.64 (2H), 8.55 (1H), 8.83 (1H).

EXAMPLE 317

2-({1-[4-(5-chloropyridin-2-yl)benzoyl]piperidin-4-yl}methyl)-4-methyl-N-(2,2,2-trifluoroethyl)-2H-indazol-5-carboxamide

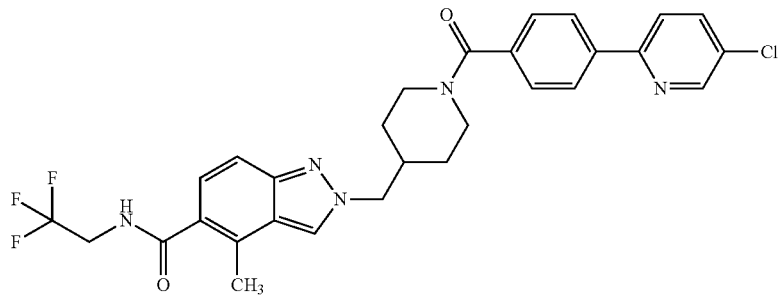

EXAMPLE 316

2-{[1-(4-bromobenzoyl)piperidin-4-yl]methyl}-4-methyl-N-(2,2,2-trifluoro-ethyl)-2H-indazol-5-carboxamide

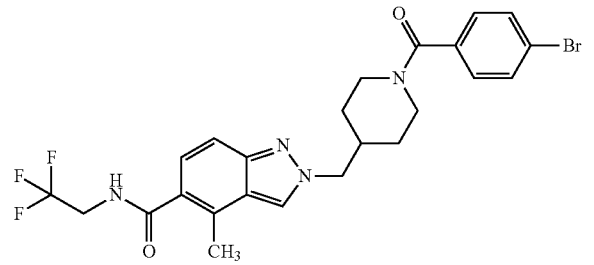 [SMILES: Cc1c(C(=O)NCC(F)(F)F)ccc2nn(CC3CCN(C(=O)c4ccc(Br)cc4)CC3)cc12]

80 mg of the aryl bromide prepared in Example 316 together with 32 mg of (5-chloropyridin-2-yl)boronic acid was first placed in 1 ml tetrahydrofuran, treated with 17.3 mg of 1,1'-bis(diphenylphosphino)ferrocenodichloropalladium (II) and 0.17 ml of 1M potassium carbonate solution and heated in the microwave for 10 minutes at 120° C. (100 watts). After fresh addition of 11 mg of (5-chloropyridin-2-yl)boronic acid and 17.3 mg of the palladium(II) catalyst, the reaction mixture was again heated in the microwave for 10 minutes at 120° C. (100 watts) until complete conversion. The reaction mixture was concentrated. After HPLC purification, this yielded 15 mg of the title compound.

$^1$H-NMR (300 MHz, DMSO-$d_6$): δ [ppm]=1.18-1.36 (2H), 1.37-1.75 (2H), 2.28-2.38 (1H), 2.54 (3H), 2.73-3.18 (2H), 3.49-3.74 (1H), 3.95-4.16 (2H), 4.28-4.62 (3H), 7.22 (1H), 7.33-7.65 (5H), 7.98-8.22 (3H), 8.56 (1H), 8.77-8.91 (1H).

EXAMPLE 318

2-({1-[(4'-methoxy-2'-methylbiphenyl-4-yl)carbonyl]piperidin-4-yl}methyl)-4-methyl-N-(2,2,2-trifluoroethyl)-2H-indazol-5-carboxamide

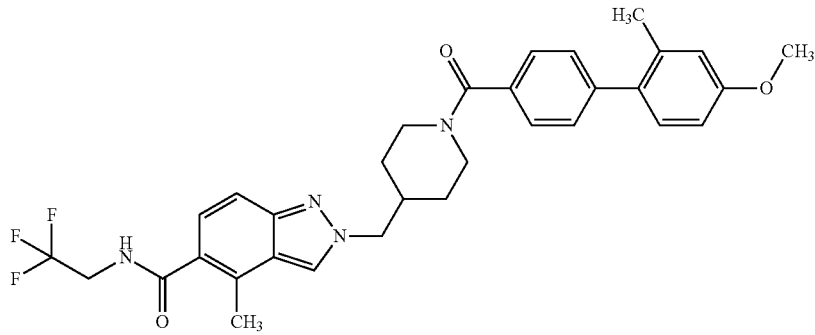 [SMILES: COc1ccc(-c2ccc(C(=O)N3CCC(Cn4cc5c(C)c(C(=O)NCC(F)(F)F)ccc5n4)CC3)cc2)c(C)c1]

Analogously to Example 317, 50 mg of the title compound was obtained from 125 mg of 316 and 53 mg of (4-methoxy-2-methyl-phenyl)boronic acid.

$^1$H-NMR (300 MHz, DMSO-d$_6$): δ [ppm]=1.16-1.36 (2H), 1.37-1.74 (2H), 2.23 (3H), 2.29-2.38 (1H), 2.54 (3H), 2.72-3.12 (2H), 3.77 (4H), 3.97-4.17 (2H), 4.38 (3H), 6.75-6.94 (2H), 7.07-7.26 (2H), 7.29-7.56 (5H), 8.56 (1H), 8.81 (1H).

EXAMPLE 319

4-methyl-2-({1-[4-(6-methylpyridin-3-yl)benzoyl]piperidin-4-yl}methyl)-N-(2,2,2-trifluoroethyl)-2H-indazol-5-carboxamide

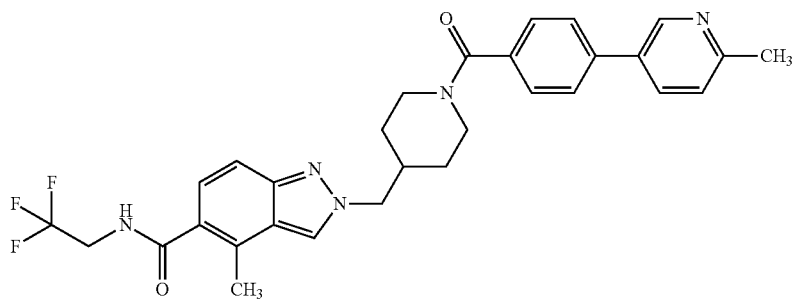 [SMILES: Cc1ccc(-c2ccc(C(=O)N3CCC(Cn4cc5c(C)c(C(=O)NCC(F)(F)F)ccc5n4)CC3)cc2)cn1]

Analogously to Example 317, 37 mg of the title compound was obtained from 125 mg of 316 and 44 mg of (6-methylpyridin-3-yl)boronic acid under reflux.

$^1$H-NMR (300 MHz, DMSO-d$_6$): δ [ppm]=1.15-1.35 (2H), 1.37-1.71 (2H), 2.20-2.40 (1H), 2.52 (3H), 2.54 (3H), 2.74-3.15 (2H), 3.52-3.82 (1H), 4.07 (2H), 4.38 (3H), 7.20 (1H), 7.37 (1H), 7.47 (3H), 7.77 (2H), 8.01 (1H), 8.57 (1H), 8.72-8.92 (2H).

EXAMPLE 320

2-({1-[(4'-fluoro-2'-methoxybiphenyl-4-yl)carbonyl]piperidin-4-yl}methyl)-4-methyl-N-(2,2,2-trifluoroethyl)-2H-indazol-5-carboxamide

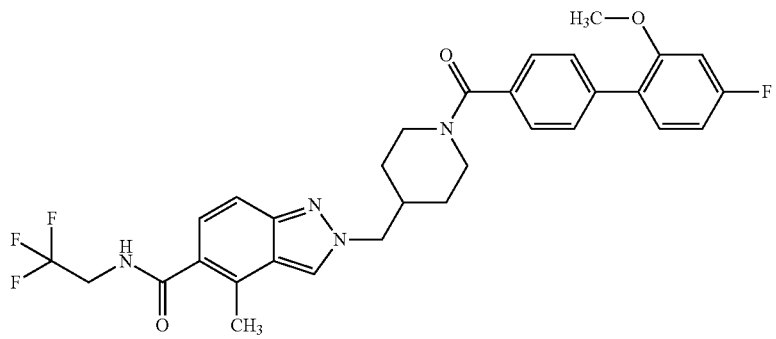 [SMILES: COc1cc(F)ccc1-c1ccc(C(=O)N2CCC(Cn3cc4c(C)c(C(=O)NCC(F)(F)F)ccc4n3)CC2)cc1]

Analogously to Example 317, 60 mg of the title compound was obtained from 125 mg of 316 and 75 g of (4-fluoro-2-methoxyphenyl)boronic acid under reflux.

$^1$H-NMR (300 MHz, DMSO-d$_6$): δ [ppm]=1.16-1.37 (2H), 1.38-1.75 (2H), 2.25-2.37 (1H), 2.54 (3H), 2.72-3.17 (2H), 3.79 (4H), 4.07 (2H), 4.38 (3H), 6.87 (1H), 7.04 (1H), 7.21 (1H), 7.27-7.58 (6H), 8.56 (1H), 8.81 (1H).

EXAMPLE 321

4-methyl-N-(2,2,2-trifluoroethyl)-2-[(1-{4-[6-(trifluoromethyl)pyridin-3-yl]-benzoyl}piperidin-4-yl)methyl]-2H-indazol-5-carboxamide

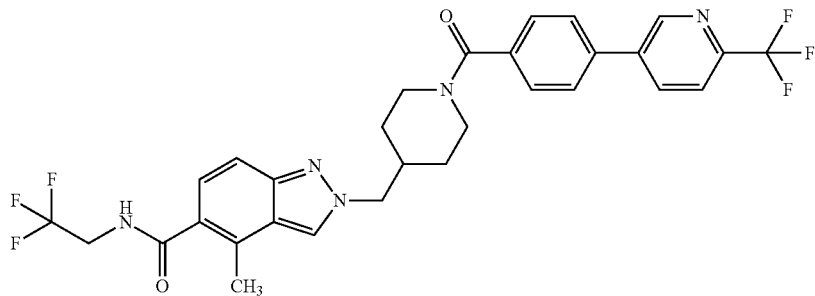 [SMILES: Cc1c(C(=O)NCC(F)(F)F)ccc2nn(CC3CCN(C(=O)c4ccc(-c5ccc(C(F)(F)F)nc5)cc4)CC3)cc12]

Analogously to Example 317, 45 mg of the title compound was obtained from 125 mg of 316 and 84 mg of [6-(trifluoromethyl)pyridin-3-yl]boronic acid under reflux.

$^1$H-NMR (300 MHz, DMSO-d$_6$): δ [ppm]=1.15-1.37 (2H), 1.37-1.71 (2H), 2.22-2.41 (1H), 2.54 (3H), 2.73-3.20 (2H), 3.45-3.74 (1H), 3.93-4.17 (2H), 4.29-4.62 (3H), 7.21 (1H), 7.39-7.62 (4H), 7.89 (2H), 8.01 (1H), 8.57 (1H), 8.73-8.92 (1H), 9.13 (1H).

EXAMPLE 322

2-({1-[4-(6-methoxypyridin-3-yl)benzoyl]piperidin-4-yl}methyl)-4-methyl-N-(2,2,2-trifluoroethyl)-2H-indazol-5-carboxamide

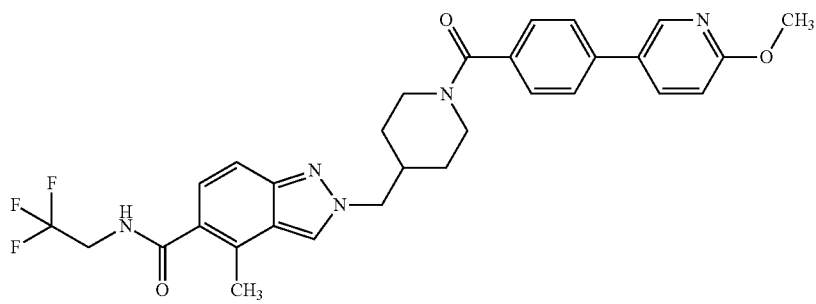 [SMILES: COc1ccc(-c2ccc(C(=O)N3CCC(Cn4cc5c(C)c(C(=O)NCC(F)(F)F)ccc5n4)CC3)cc2)cn1]

Analogously to Example 317, 54 mg of the title compound was obtained from 125 mg of 316 and 68 mg of (6-methoxypyridin-3-yl)boronic acid under reflux.

$^1$H-NMR (300 MHz, DMSO-d$_6$): δ [ppm]=1.13-1.35 (2H), 1.36-1.71 (2H), 2.20-2.40 (1H), 2.54 (3H), 2.73-3.16 (2H), 3.51-3.77 (1H), 3.90 (3H), 3.96-4.19 (2H), 4.37 (3H), 6.93 (1H), 7.20 (1H), 7.39-7.52 (3H), 7.73 (2H), 8.05 (1H), 8.47-8.63 (2H), 8.83 (1H).

EXAMPLE 323

2-({1-[4-(6-methoxypyridin-2-yl)benzoyl]piperidin-4-yl}methyl)-4-methyl-N-(2,2,2-trifluoroethyl)-2H-indazol-5-carboxamide

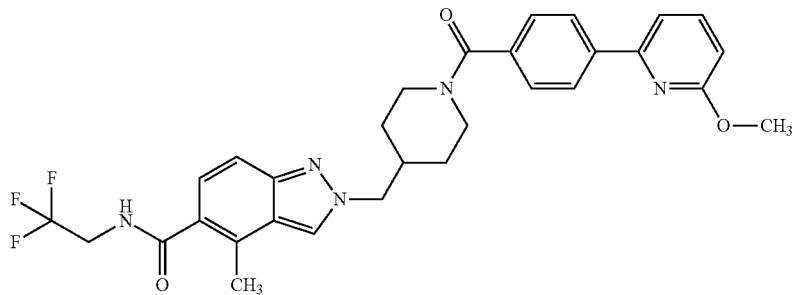 [SMILES: COc1cccc(-c2ccc(C(=O)N3CCC(Cn4cc5c(C)c(C(=O)NCC(F)(F)F)ccc5n4)CC3)cc2)n1]

Analogously to Example 317, 55 mg of the title compound was obtained from 125 mg of 316 and 49 mg of (6-methoxypyridin-2-yl)boronic acid under reflux.

$^1$H-NMR (300 MHz, DMSO-d$_6$): δ [ppm]=1.16-1.36 (2H), 1.37-1.69 (2H), 2.20-2.41 (1H), 2.54 (3H), 2.74-3.16 (2H), 3.47-3.81 (1H), 3.96 (3H), 4.06 (2H), 4.38 (3H), 6.81 (1H), 7.21 (1H), 7.47 (3H), 7.60 (1H), 7.74-7.90 (1H), 8.15 (2H), 8.56 (1H), 8.81 (1H).

EXAMPLE 324

4-methyl-2-({1-[4-(5-methylpyridin-2-yl)benzoyl]piperidin-4-yl}methyl)-N-(2,2,2-trifluoroethyl)-2H-indazol-5-carboxamide

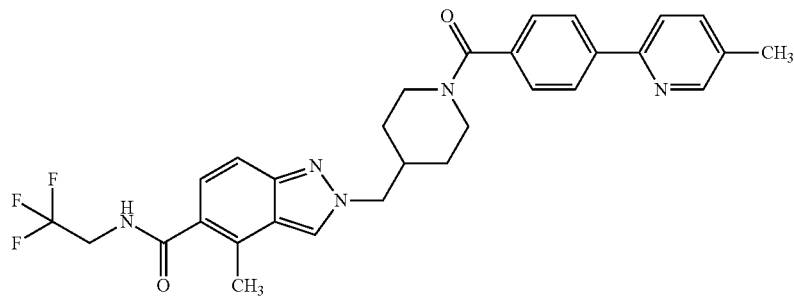

Analogously to Example 317, 9 mg of the title compound was obtained from 125 mg of 316 and 44 mg of (5-methylpyridin-2-yl)boronic acid under reflux.

$^1$H-NMR (300 MHz, DMSO-d$_6$): δ [ppm]=1.16-1.36 (2H), 1.37-1.71 (2H), 2.24-2.30 (1H), 2.34 (3H), 2.54 (3H), 2.74-3.16 (2H), 3.52-3.79 (1H), 3.93-4.17 (2H), 4.38 (3H), 7.20 (1H), 7.37-7.54 (3H), 7.66-7.78 (1H), 7.89 (1H), 8.11 (2H), 8.45-8.61 (2H), 8.74-8.88 (1H).

EXAMPLE 325

2-({1-[4-(5-fluoropyridin-2-yl)benzoyl]piperidin-4-yl}methyl)-4-methyl-N-(2,2,2-trifluoroethyl)-2H-indazol-5-carboxamide

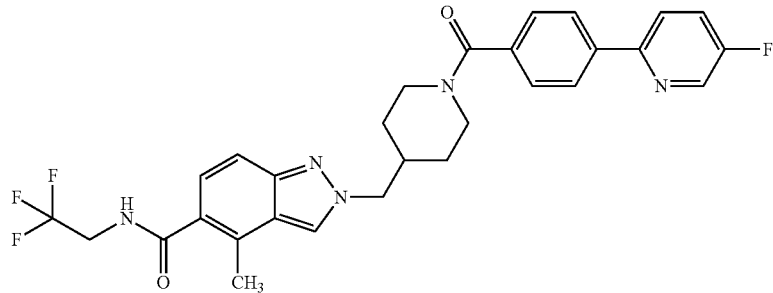 [SMILES: Cc1c(C(=O)NCC(F)(F)F)ccc2nn(CC3CCN(C(=O)c4ccc(-c5ccc(F)cn5)cc4)CC3)cc12]

Analogously to Example 317, 35 mg of the title compound was obtained from 125 mg of 316 and 45 mg of (5-fluoropyridin-2-yl)boronic acid under reflux.

$^1$H-NMR (400 MHz, DMSO-d$_6$): δ [ppm]=1.17-1.34 (2H), 1.35-1.69 (2H), 2.22-2.41 (1H), 2.54 (3H), 2.69-3.19 (2H), 3.51-3.78 (1H), 4.07 (2H), 4.38 (3H), 7.20 (1H), 7.40-7.53 (3H), 7.85 (1H), 8.04-8.17 (3H), 8.57 (1H), 8.68 (1H), 8.83 (1H).

EXAMPLE 326

2-({1-[4-(5-methoxypyridin-2-yl)benzoyl]piperidin-4-yl}methyl)-4-methyl-N-(2,2,2-trifluoroethyl)-2H-indazol-5-carboxamide

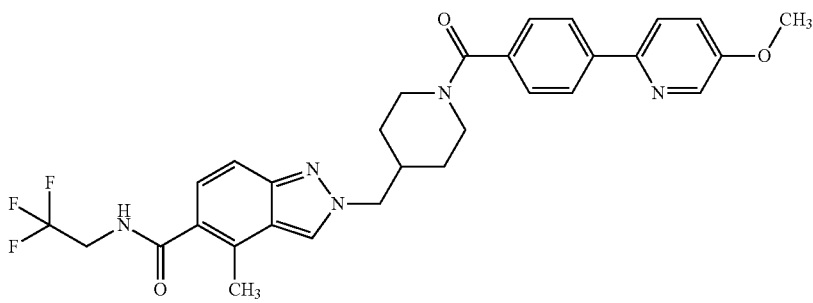

Analogously to Example 317, 94 mg of the title compound was obtained from 125 mg of 316 and 49 mg of (5-methoxypyridin-2-yl)boronic acid under reflux.

$^1$H-NMR (300 MHz, DMSO-$d_6$): δ [ppm]=1.19-1.36 (2H), 1.37-1.69 (2H), 2.28-2.40 (1H), 2.54 (3H), 2.73-3.19 (2H), 3.48-3.79 (1H), 3.88 (3H), 4.07 (2H), 4.38 (3H), 7.20 (1H), 7.38-7.55 (4H), 7.96 (1H), 8.07 (2H), 8.39 (1H), 8.57 (1H), 8.82 (1H).

EXAMPLE 327

4-methyl-2-({1-[4-(2-methylpyrimidin-5-yl)benzoyl]piperidin-4-yl}methyl)-N-(2,2,2-trifluoroethyl)-2H-indazol-5-carboxamide

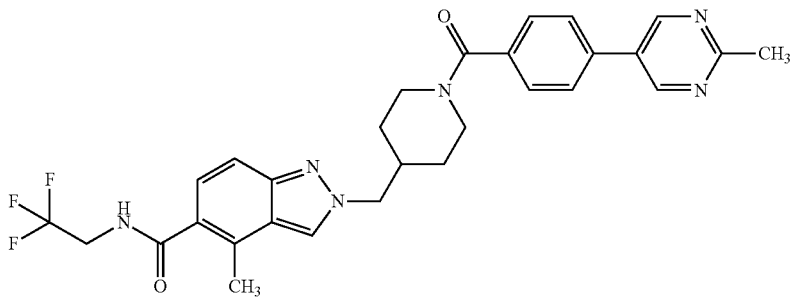

Analogously to Example 317, 46 mg of the title compound was obtained from 125 mg of 316 and 102 mg of (2-methylpyrimidin-5-yl)boronic acid pinacol ester under reflux.

$^1$H-NMR (400 MHz, DMSO-$d_6$): δ [ppm]=1.16-1.35 (2H), 1.35-1.67 (2H), 2.21-2.42 (1H), 2.54 (3H), 2.67 (3H), 2.71-2.89 (1H), 2.93-3.20 (1H), 3.50-3.73 (1H), 4.07 (2H), 4.37 (3H), 7.20 (1H), 7.40-7.57 (3H), 7.85 (2H), 8.57 (1H), 8.84 (1H), 9.05 (2H).

EXAMPLE 328

4-methyl-N-(2,2,2-trifluoroethyl)-2-[(1-{4-[2-(trifluoromethyl)pyrimidin-5-yl]-benzoyl}piperidin-4-yl)methyl]-2H-indazol-5-carboxamide

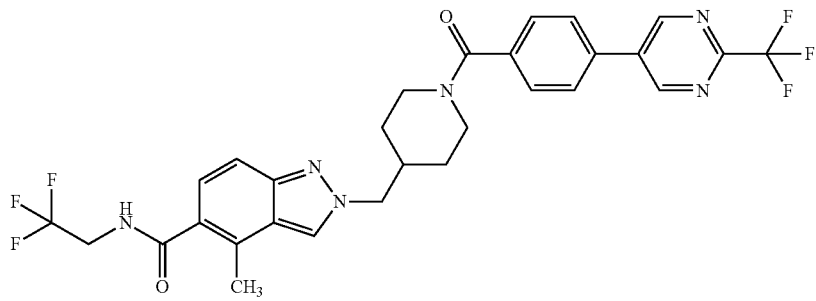

Analogously to Example 317, 34 mg of the title compound was obtained from 125 mg of 316 and 89 mg of [2-(trifluoromethyl)pyrimidin-5-yl]boronic acid under reflux.

$^1$H-NMR (400 MHz, DMSO-d$_6$): δ [ppm]=1.21-1.35 (2H), 1.36-1.71 (2H), 2.23-2.41 (1H), 2.54 (3H), 2.71-2.89 (1H), 2.94-3.17 (1H), 3.48-3.72 (1H), 4.05 (2H), 4.28-4.61 (3H), 7.21 (1H), 7.47 (1H), 7.57 (2H), 7.98 (2H), 8.57 (1H), 8.84 (1H), 9.44 (2H).

EXAMPLE 329

4-methyl-N-(2,2,2-trifluoroethyl)-2-[(1-{4-[6-(trifluoromethyl)pyridin-2-yl]-benzoyl}piperidin-4-yl)methyl]-2H-indazol-5-carboxamide

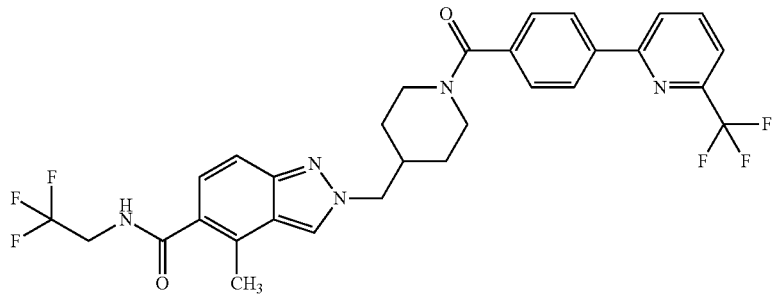 [SMILES: Cc1c(C(=O)NCC(F)(F)F)ccc2nn(CC3CCN(C(=O)c4ccc(-c5cccc(C(F)(F)F)n5)cc4)CC3)cc12]

Analogously to Example 317, 70 mg of the title compound was obtained from 125 mg of 316 and 121 mg of [6-(trifluoromethyl)pyridin-2-yl]boronic acid pinacol ester under reflux.

$^1$H-NMR (400 MHz, DMSO-d$_6$): δ [ppm]=1.19-1.36 (2H), 1.37-1.72 (2H), 2.23-2.39 (1H), 2.54 (3H), 2.68-2.90 (1H), 2.92-3.16 (1H), 3.50-3.73 (1H), 4.06 (2H), 4.38 (3H), 7.20 (1H), 7.41-7.60 (3H), 7.89 (1H), 8.11-8.27 (3H), 8.33 (1H), 8.56 (1H), 8.81 (1H).

EXAMPLE 330

2-({1-[4-(4-cyanophenoxy)benzoyl]piperidin-4-yl}methyl)-N-(2-methoxyethyl)-4-methyl-2H-indazol-5-carboxamide

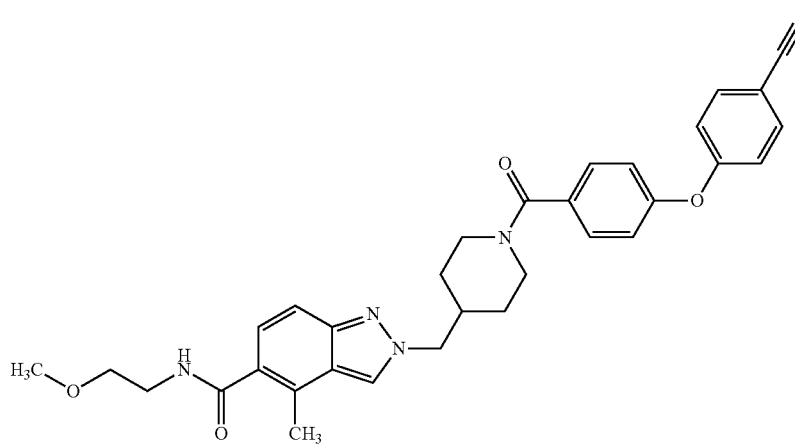

Analogously to Example 1b, Version B, 151 mg of the title compound was obtained from 213 mg of 71a and 153 mg of 4-(4-cyanophenoxy)benzoic acid in DMF.

$^1$H-NMR (300 MHz, DMSO-d$_6$): δ [ppm]=1.22 (2H), 1.31-1.66 (2H), 2.15-2.36 (1H), 2.49 (3H), 2.70-3.12 (2H), 3.24 (3H), 3.36 (2H), 3.39-3.46 (2H), 3.50-3.79 (1H), 4.32 (3H), 7.00-7.23 (5H), 7.30-7.49 (3H), 7.75-7.91 (2H), 8.12 (1H), 8.48 (1H).

EXAMPLE 331

N-(2-methoxyethyl)-4-methyl-2-({1-[(1-methyl-1H-indol-3-yl)carbonyl]-piperidin-4-yl}methyl)-2H-indazol-5-carboxamide

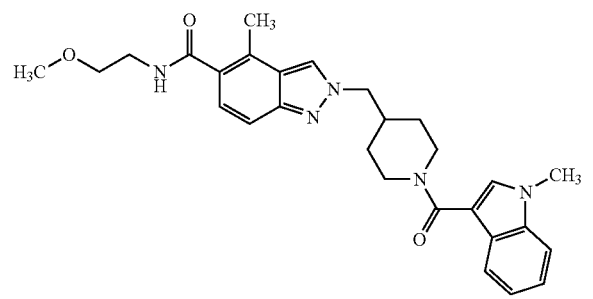

Analogously to Example 1b, Version B, 26 mg of the title compound was obtained from 38 mg of 71a and 36 mg of 1-methyl-1H-indol-3-carboxylic acid in DMF.

$^1$H-NMR (300 MHz, DMSO-d$_6$): δ [ppm]=1.23 (2H), 1.43-1.64 (2H), 2.20-2.39 (1H), 2.53 (3H), 2.80-3.03 (2H), 3.28 (3H), 3.37-3.50 (4H), 3.81 (3H), 4.37 (4H), 7.18 (3H), 7.36-7.53 (2H), 7.67 (2H), 8.04-8.25 (1H), 8.52 (1H).

EXAMPLE 332

2-{[1-(4-bromo-3-methylbenzoyl)piperidin-4-yl]methyl}-N-(2-methoxyethyl)-4-methyl-2H-indazol-5-carboxamide

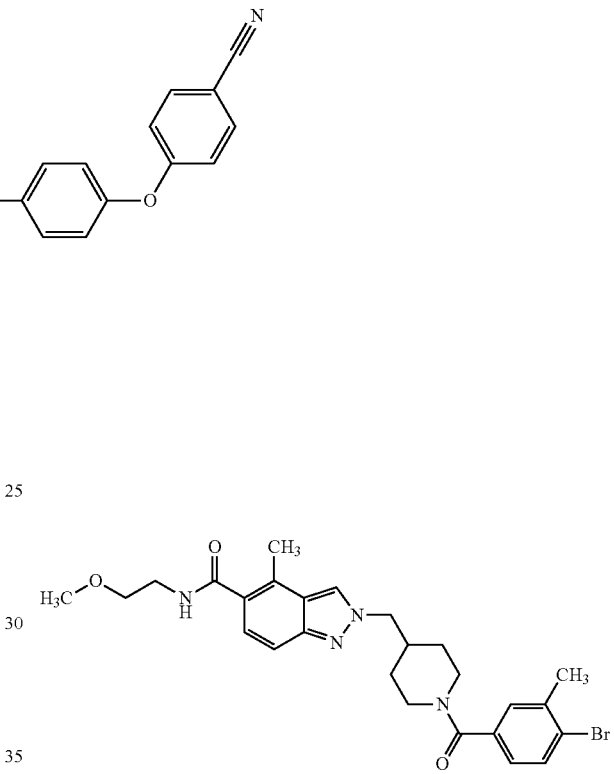

Analogously to Example 1b, Version B, 498 mg of the title compound was obtained from 807 mg of 71a and 788 mg of 4-bromo-3-methylbenzoic acid in DMF.

$^1$H-NMR (300 MHz, DMSO-d$_6$): δ [ppm]=1.20-1.32 (2H), 1.33-1.67 (2H), 2.24-2.33 (1H), 2.36 (3H), 2.52 (3H), 2.73 (1H), 2.91-3.13 (1H), 3.28 (3H), 3.35-3.63 (5H), 4.34 (3H), 7.03-7.23 (2H), 7.30-7.49 (2H), 7.63 (1H), 8.15 (1H), 8.51 (1H).

EXAMPLE 333

2-{[1-(4-tert-butylbenzoyl)piperidin-4-yl]methyl}-N-(2-methoxyethyl)-4-methyl-2H-indazol-5-carboxamide

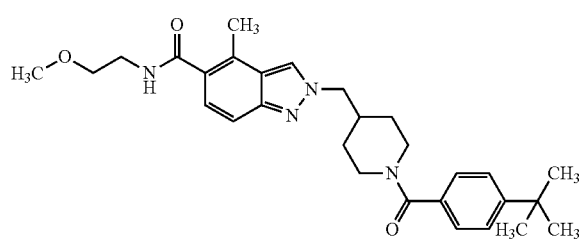 [SMILES: COCCNC(=O)c1ccc2nn(CC3CCN(C(=O)c4ccc(C(C)(C)O)cc4)CC3)cc2c1C]

Analogously to Example 1b, Version B, 50 mg of the title compound was obtained from 100 mg of 71a and 81 mg of 4-tert-butylbenzoic acid in DMF.

$^1$H-NMR (400 MHz, DMSO-$d_6$): δ [ppm]=1.20-1.33 (11H), 1.33-1.67 (2H), 2.21-2.37 (1H), 2.52 (3H), 2.68-3.10 (2H), 3.28 (3H), 3.36-3.43 (2H), 3.45 (2H), 3.52-3.74 (1H), 4.35 (3H), 7.18 (1H), 7.25-7.35 (2H), 7.36-7.52 (3H), 8.15 (1H), 8.50 (1H).

EXAMPLE 334

2-({1-[4-(1-hydroxy-1-methylethyl)benzoyl]piperidin-4-yl}methyl)-N-(2-methoxyethyl)-4-methyl-2H-indazol-5-carboxamide

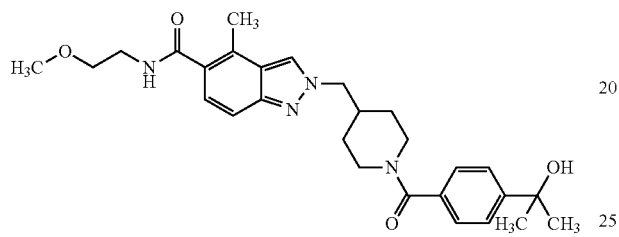

Analogously to Example 1b, Version B, 28 mg of the title compound was obtained from 100 mg of 71a and 82 mg of 4-(1-hydroxy-1-methylethyl)benzoic acid in DMF.

$^1$H-NMR (400 MHz, DMSO-$d_6$): δ [ppm]=1.24 (2H), 1.42 (8H), 2.20-2.40 (1H), 2.52 (3H), 2.64-3.11 (2H), 3.28 (3H), 3.34-3.43 (2H), 3.43-3.51 (2H), 3.53-3.71 (1H), 4.35 (3H), 4.76-5.43 (1H), 7.18 (1H), 7.28 (2H), 7.42 (1H), 7.46-7.56 (2H), 8.15 (1H), 8.51 (1H).

EXAMPLE 335

2-{[1-(4-cyclohexylbenzoyl)piperidin-4-yl]methyl}-N-(2-methoxyethyl)-4-methyl-2H-indazol-5-carboxamide

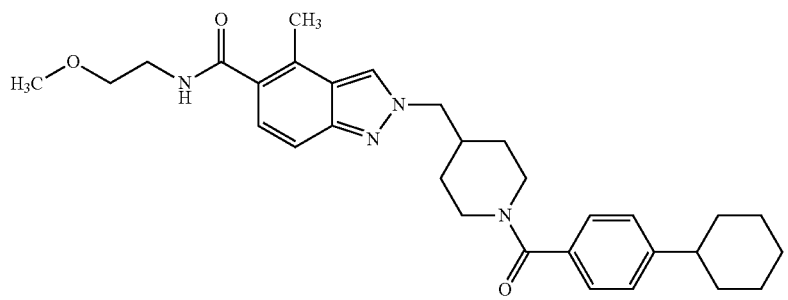 [SMILES: COCCNC(=O)c1ccc2nn(CC3CCN(C(=O)c4ccc(C5CCCCC5)cc4)CC3)cc2c1C]

Analogously to Example 1b, Version B, 75 mg of the title compound was obtained from 100 mg of 71a and 93 mg of 4-cyclohexylbenzoic acid in DMF.

$^1$H-NMR (400 MHz, DMSO-$d_6$): δ [ppm]=1.10-1.63 (9H), 1.64-1.89 (5H), 2.17-2.40 (1H), 2.52 (3H), 2.69-3.08 (2H), 3.28 (3H), 3.38-3.43 (2H), 3.43-3.49 (2H), 3.53-3.73 (1H), 4.35 (3H), 7.18 (1H), 7.27 (4H), 7.42 (1H), 8.15 (1H), 8.50 (1H).

EXAMPLE 336

N-(2-methoxyethyl)-2-{[1-(6-methoxy-2-naphthoyl)piperidin-4-yl]methyl}-4-methyl-2H-indazol-5-carboxamide

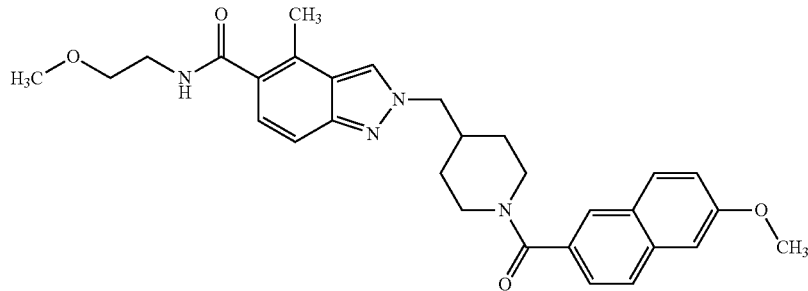

Analogously to Example 1b, Version B, 23 mg of the title compound was obtained from 100 mg of 71a) and 92 mg of 6-methoxy-naphthalen-2-carboxylic acid in DMF.

$^1$H-NMR (400 MHz, DMSO-$d_6$): δ [ppm]=1.23 (2H), 1.37-1.72 (2H), 2.23-2.39 (1H), 2.52 (3H), 2.72-3.12 (2H), 3.28 (3H), 3.36-3.42 (2H), 3.43-3.49 (2H), 3.59-3.81 (1H), 3.89 (3H), 4.36 (3H), 7.09-7.27 (2H), 7.33-7.49 (3H), 7.79-7.95 (3H), 8.15 (1H), 8.51 (1H).

EXAMPLE 337

N-(2-methoxyethyl)-4-methyl-2-({1-[(2-phenylthiazol-5-yl)carbonyl]piperidin-4-yl}methyl)-2H-indazol-5-carboxamide

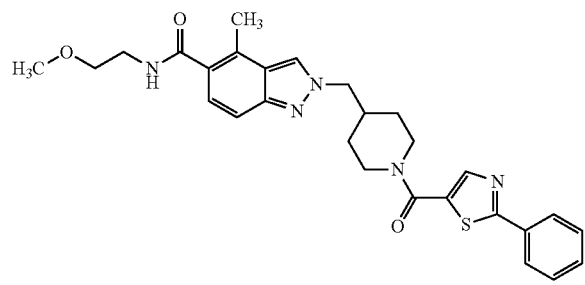 [SMILES: COCCNC(=O)c1ccc2nn(CC3CCN(C(=O)c4cnc(-c5ccccc5)s4)CC3)cc2c1C]

Analogously to Example 1b, Version B, 36 mg of the title compound was obtained from 100 mg of 71a and 93 mg of 2-phenylthiazol-5-carboxylic acid in DMF.

$^1$H-NMR (400 MHz, DMSO-$d_6$): δ [ppm]=1.23 (2H), 1.55 (2H), 2.19-2.45 (1H), 2.52-2.56 (3H), 2.70-3.24 (2H), 3.28 (3H), 3.36-3.43 (2H), 3.44-3.49 (2H), 4.37 (4H), 7.19 (1H), 7.43 (1H), 7.49-7.62 (3H), 7.90-8.03 (2H), 8.08-8.25 (2H), 8.52 (1H).

EXAMPLE 338

N-(2-methoxyethyl)-4-methyl-2-({1-[(1-methyl-1H-benzimidazol-2-yl)carbonyl]-piperidin-4-yl}methyl)-2H-indazol-5-carboxamide Analogously to Example 1b, Version B, 39 mg of the title compound was obtained from 100 mg of 71a and 80 mg of 1-methyl-1H-benzimidazol-2-carboxylic acid in DMF.

$^1$H-NMR (400 MHz, DMSO-$d_6$): δ [ppm]=1.22-1.43 (2H), 1.43-1.53 (1H), 1.59-1.70 (1H), 2.27-2.44 (1H), 2.53 (3H), 2.87 (1H), 3.11 (1H), 3.28 (3H), 3.36-3.42 (2H), 3.43-3.48 (2H), 3.83 (3H), 4.00-4.14 (1H), 4.39 (2H), 4.48-4.61 (1H), 7.18 (1H), 7.23-7.46 (3H), 7.58-7.74 (2H), 8.10-8.20 (1H), 8.53 (1H).

EXAMPLE 339

N-(2-methoxyethyl)-4-methyl-2-({1-[(2-phenyloxazol-5-yl)carbonyl]piperidin-4-yl}methyl)-2H-indazol-5-carboxamide Analogously to Example 1b, Version B, 30 mg of the title compound was obtained from 100 mg of 71a and 86 mg of 2-phenyloxazol-5-carboxylic acid in DMF.

$^1$H-NMR (400 MHz, DMSO-$d_6$): δ [ppm]=1.14-1.48 (2H), 1.59 (2H), 2.24-2.46 (1H), 2.52-2.56 (3H), 2.71-3.01 (1H), 3.11-3.26 (1H), 3.28 (3H), 3.36-3.43 (2H), 3.43-3.50 (2H), 4.38 (4H), 7.19 (1H), 7.43 (1H), 7.52-7.67 (3H), 7.80 (1H), 7.97-8.05 (2H), 8.16 (1H), 8.53 (1H).

EXAMPLE 340

2-{[1-(benzoxazol-2-ylcarbonyl)piperidin-4-yl]methyl}-N-(2-methoxyethyl)-4-methyl-2H-indazol-5-carboxamide

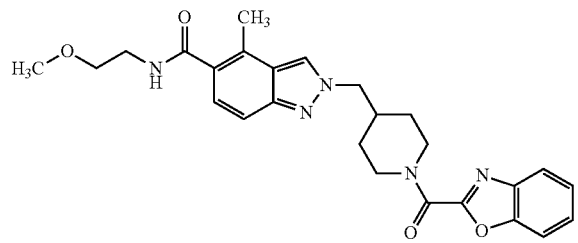 [SMILES: COCCNC(=O)c1ccc2nn(CC3CCN(C(=O)c4nc5ccccc5o4)CC3)cc2c1C]

Analogously to Example 1b, Version B, 37 mg of the title compound was obtained from 100 mg of 71a and 84 mg of benzoxazol-2-carboxylic acid in DMF.

$^1$H-NMR (400 MHz, DMSO-$d_6$): δ [ppm]=1.19-1.43 (2H), 1.48-1.73 (2H), 2.28-2.45 (1H), 2.53 (3H), 2.91 (1H), 3.22 (1H), 3.33-3.57 (m, 7H), 4.25-4.60 (4H), 7.18 (1H), 7.36-7.62 (3H), 7.78-7.95 (2H), 8.16 (1H), 8.53 (1H).

EXAMPLE 341

2-({1-[4-(1-cyano-1-methylethyl)benzoyl]piperidin-4-yl}methyl)-N-(2-methoxy-ethyl)-4-methyl-2H-indazol-5-carboxamide

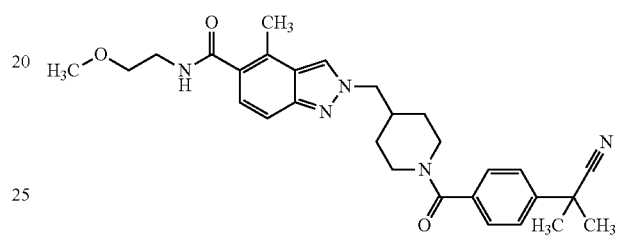

Analogously to Example 1b, Version B, 20 mg of the title compound was obtained from 100 mg of 71a and 86 mg of 4-(1-cyano-1-methylethyl)benzoic acid in DMF.

$^1$H-NMR (300 MHz, DMSO-$d_6$): δ [ppm]=1.17-1.34 (2H), 1.35-1.64 (2H), 1.70 (6H), 2.16-2.40 (1H), 2.52 (3H), 2.64-3.13 (2H), 3.28 (3H), 3.40 (2H), 3.43-3.49 (2H), 3.49-3.67 (1H), 4.35 (3H), 7.18 (1H), 7.42 (3H), 7.58 (2H), 8.15 (1H), 8.50 (1H).

EXAMPLE 342

N-(2-methoxyethyl)-4-methyl-2-({1-[4-(pyrimidin-2-yloxy)benzoyl]piperidin-4-yl}methyl)-2H-indazol-5-carboxamide

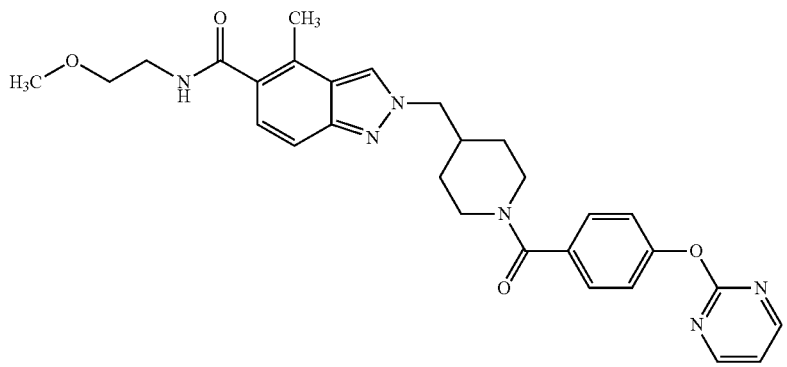 [SMILES: COCCNC(=O)c1ccc2nn(CC3CCN(C(=O)c4ccc(Oc5ncccn5)cc4)CC3)cc2c1C]

Analogously to Example 1b, Version B, 37 mg of the title compound was obtained from 100 mg of 71a and 98 mg of 4-(2-pyrimidinyloxy)benzoic acid in DMF.

$^{1}$H-NMR (400 MHz, DMSO-d$_{6}$): δ [ppm]=1.26 (2H), 1.38-1.66 (2H), 2.20-2.40 (1H), 2.52-2.56 (3H), 2.70-3.16 (2H), 3.28 (3H), 3.36-3.43 (2H), 3.43-3.49 (2H), 3.64-3.77 (m, 1H), 4.36 (3H), 7.18 (1H), 7.22-7.33 (3H), 7.39-7.49 (3H), 8.15 (1H), 8.43-8.57 (1H), 8.66 (2H).

EXAMPLE 343

N-(2-methoxyethyl)-4-methyl-2-({1-[4-(3-pyridyloxy)benzoyl]piperidin-4-yl}methyl)-2H-indazol-5-carboxamide

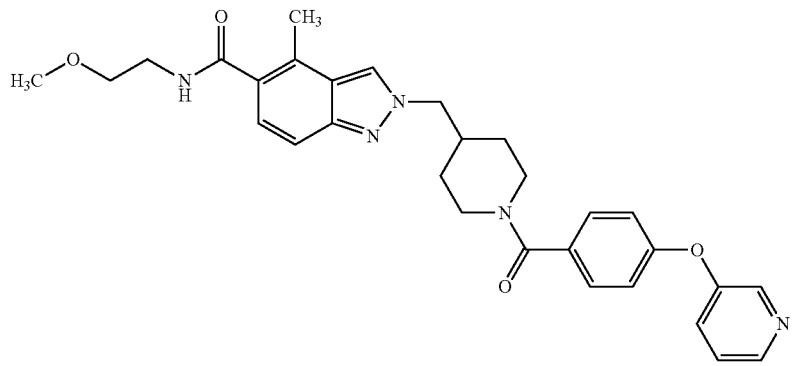 [SMILES: COCCNC(=O)c1ccc2nn(CC3CCN(C(=O)c4ccc(Oc5cccnc5)cc4)CC3)cc2c1C]

Analogously to Example 1b, Version B, 7 mg of the title compound was obtained from 75 mg of 71a and 73 mg of 4-(3-pyridyloxy)benzoic acid in DMF.

$^{1}$H-NMR (400 MHz, DMSO-d$_{6}$): δ [ppm]=1.17-1.32 (2H), 1.35-1.69 (2H), 2.19-2.38 (1H), 2.52 (3H), 2.70-3.14 (2H), 3.28 (3H), 3.34-3.43 (2H), 3.43-3.51 (2H), 3.55-3.70 (1H), 4.35 (3H), 7.04-7.13 (2H), 7.18 (1H), 7.37-7.46 (3H), 7.47-7.54 (1H), 7.58 (1H), 8.15 (1H), 8.38-8.55 (3H).

EXAMPLE 344

N-(2-methoxyethyl)-2-{[1-(7-methoxy-2-naphthoyl)piperidin-4-yl]methyl}-4-methyl-2H-indazol-5-carboxamide

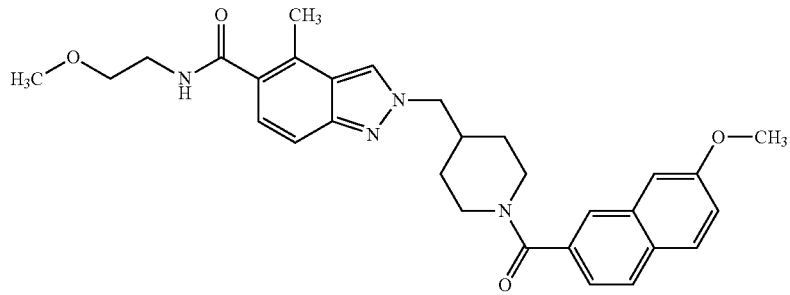

Analogously to Example 1b, Version B, 28 mg of the title compound was obtained from 75 mg of 71a and 69 mg of the carboxylic acid prepared in Example 344c) in DMF.

$^1$H-NMR (400 MHz, DMSO-d$_6$): δ [ppm]=1.21-1.35 (2H), 1.37-1.75 (2H), 2.23-2.39 (1H), 2.52 (3H), 2.73-3.13 (2H), 3.28 (3H), 3.35-3.42 (2H), 3.45 (2H), 3.53-3.74 (1H), 3.88 (3H), 4.37 (3H), 7.13-7.25 (2H), 7.29 (1H), 7.36-7.48 (2H), 7.77-7.93 (3H), 8.15 (1H), 8.52 (1H).

The starting material was prepared as follows:

EXAMPLE 344a 7-methoxynaphthalen-2-yl-1,1,2,2,3,3,4,4,4-nonafluorobutan-1-sulphonate

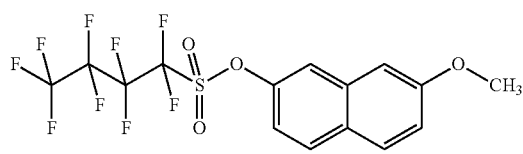 [SMILES: COc1ccc2ccc(OS(=O)(=O)C(F)(F)C(F)(F)C(F)(F)C(F)(F)F)cc2c1]

5.12 g of 7-methoxy-2-naphthol were dissolved in 50 ml toluene and cooled to 0° C. 30.7 ml of N,N-diisopropylethylamine and 17.6 ml of nonafluorobutanesulphonyl fluoride were successively added dropwise to this and the reaction mixture was then stirred at room temperature until complete conversion. The reaction mixture was poured into 600 ml of saturated ammonium chloride solution, the deposited brown oil separated and the aqueous phase extracted several times with ethyl acetate. The combined organic phases were washed with water and saturated sodium chloride solution, dried and concentrated. The residue was purified by column chromatography on silica gel using a hexane/ethyl acetate gradient. Yield: 11.45 g of the title compound.

$^1$H-NMR (400 MHz, DMSO-d$_6$): δ [ppm]=3.89 (3H), 7.28 (1H), 7.41 (1H), 7.52 (1H), 7.90-8.00 (2H), 8.05 (1H).

EXAMPLE 344b

Methyl 7-methoxynaphthalen-2-carboxylate

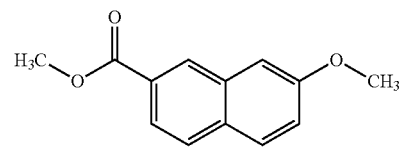

Analogously to Example 1e, 2.34 g of the title compound was obtained from 11.0 g of 344a and 8.8 ml of methanol.

$^1$H-NMR (400 MHz, DMSO-d$_6$): δ [ppm]=3.89 (3H), 3.91 (3H), 7.31 (1H), 7.57 (1H), 7.82 (1H), 7.94 (2H), 8.54 (1H).

EXAMPLE 344c 7-methoxynaphthalen-2-carboxylic acid

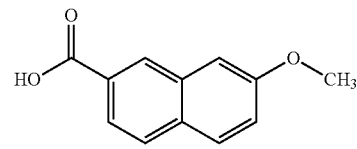

Analogously to Example 258d, 1.27 g of the title compound was obtained from 2.0 g of 344b.

$^1$H-NMR (300 MHz, DMSO-d$_6$): δ [ppm]=3.89 (3H), 7.30 (1H), 7.53 (1H), 7.78-7.86 (1H), 7.87-8.01 (2H), 8.50 (1H), 12.99 (1H).

EXAMPLE 345

N-(2-methoxyethyl)-4-methyl-2-{[1-(4-{[5-(trifluoromethyl)pyridin-2-yl]oxy}-benzoyl)piperidin-4-yl]methyl}-2H-indazol-5-carboxamide

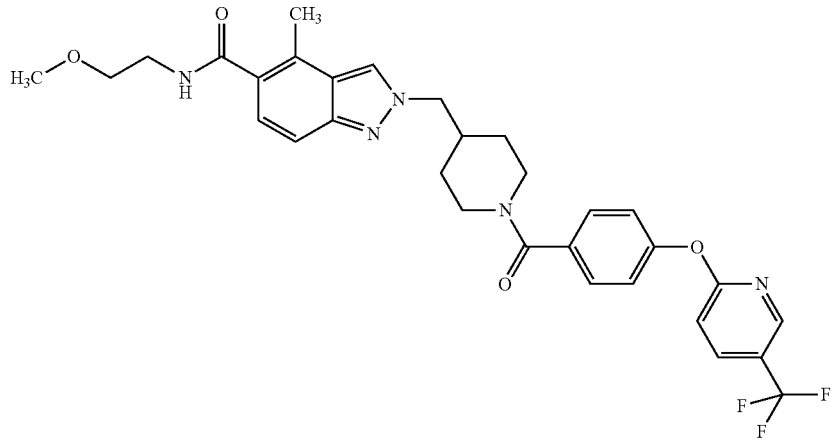 [SMILES: COCCNC(=O)c1ccc2nn(CC3CCN(C(=O)c4ccc(Oc5ccc(C(F)(F)F)cn5)cc4)CC3)cc2c1C]

Analogously to Example 1b, Version B, 221 mg of the title compound was obtained from 200 mg of 71a and 232 mg of 4-{[5-(trifluoromethyl)pyridin-2-yl]oxy}benzoic acid in DMF.

$^1$H-NMR (400 MHz, DMSO-d$_6$): δ [ppm]=1.21-1.34 (2H), 1.36-1.72 (2H), 2.23-2.39 (1H), 2.53 (3H), 2.89 (2H), 3.31 (3H), 3.36-3.43 (2H), 3.43-3.50 (2H), 3.53-3.86 (1H), 4.36 (3H), 7.18 (1H), 7.23-7.33 (3H), 7.37-7.50 (3H), 8.13 (1H), 8.25 (1H), 8.51 (1H), 8.55-8.63 (1H).

EXAMPLE 346

N-(2-methoxyethyl)-4-methyl-2-({1-[4-(2-pyridyloxy)benzoyl]piperidin-4-yl}-methyl)-2H-indazol-5-carboxamide

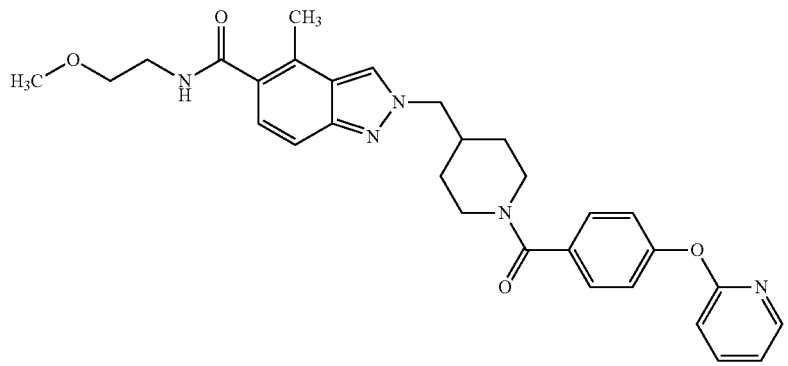

Analogously to Example 1b, Version B, 29 mg of the title compound was obtained from 100 mg of 71a and 98 mg of 4-(2-pyridyloxy)benzoic acid in DMF.

$^1$H-NMR (400 MHz, DMSO-d$_6$): δ [ppm]=1.23 (2H), 1.39-1.68 (2H), 2.24-2.39 (1H), 2.52-2.56 (3H), 2.71-3.13 (2H), 3.28 (3H), 3.36-3.43 (2H), 3.45 (2H), 3.53-3.87 (1H), 4.36 (3H), 7.08 (1H), 7.13-7.26 (4H), 7.34-7.52 (3H), 7.88 (1H), 8.07-8.23 (2H), 8.51 (1H).

EXAMPLE 347

N-(2-methoxyethyl)-4-methyl-2-{[1-(4-{[4-(trifluoromethyl)pyrimidin-2-yl]-oxy}benzoyl)piperidin-4-yl]methyl}-2H-indazol-5-carboxamide

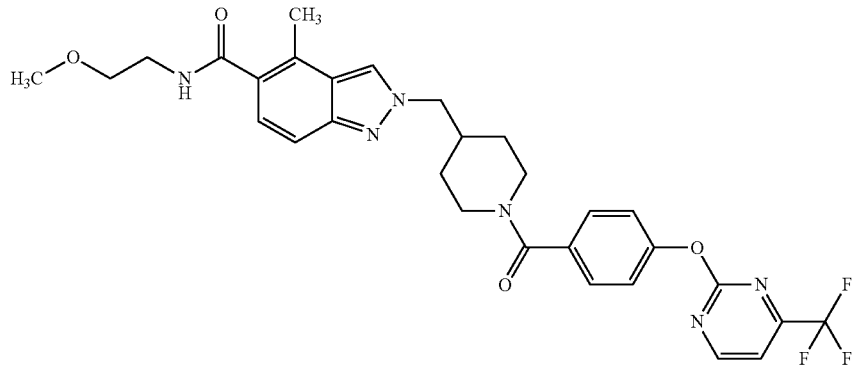 [SMILES: COCCNC(=O)c1ccc2nn(CC3CCN(C(=O)c4ccc(Oc5nccc(C(F)(F)F)n5)cc4)CC3)cc2c1C]

Analogously to Example 1b, Version B, 11 mg of the title compound was obtained from 75 mg of 71a and 97 mg of 4-{[4-(trifluoromethyl)pyrimidin-2-yl]oxy}benzoic acid in DMF.

$^1$H-NMR (400 MHz, DMSO-d$_6$): δ [ppm]=1.23 (2H), 1.37-1.69 (2H), 2.19-2.39 (1H), 2.53 (3H), 2.68-3.18 (2H), 3.28 (3H), 3.36-3.43 (2H), 3.45 (2H), 3.51-3.79 (1H), 4.36 (3H), 7.18 (1H), 7.31-7.39 (2H), 7.39-7.53 (3H), 7.81 (1H), 8.15 (1H), 8.51 (1H), 9.00 (1H).

EXAMPLE 348

2-{[1-(benzothiazol-2-ylcarbonyl)piperidin-4-yl]methyl}-N-(2-methoxyethyl)-4-methyl-2H-indazol-5-carboxamide

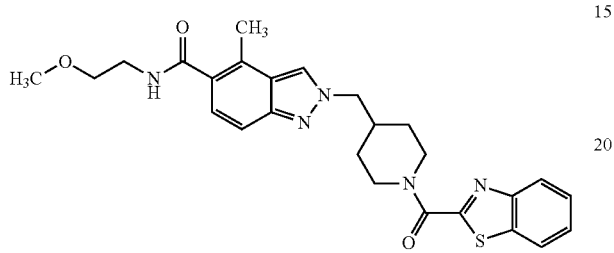

Analogously to Example 1b, Version B, 28 mg of the title compound was obtained from 75 mg of 71a and 61 mg of benzothiazol-2-carboxylic acid in DMF.

$^1$H-NMR (300 MHz, DMSO-d$_6$): δ [ppm]=1.34 (2H), 1.62 (2H), 2.32-2.45 (1H), 2.53 (3H), 2.82-3.00 (1H), 3.26 (1H), 3.28 (3H), 3.40 (2H), 3.43-3.50 (2H), 4.38 (3H), 4.98-5.23 (1H), 7.19 (1H), 7.43 (1H), 7.59 (2H), 8.01-8.30 (3H), 8.53 (1H).

EXAMPLE 349

N-(2-methoxyethyl)-4-methyl-2-{[1-(4-{[6-(trifluoromethyl)pyridin-3-yl]oxy}-benzoyl)piperidin-4-yl]methyl}-2H-indazol-5-carboxamide

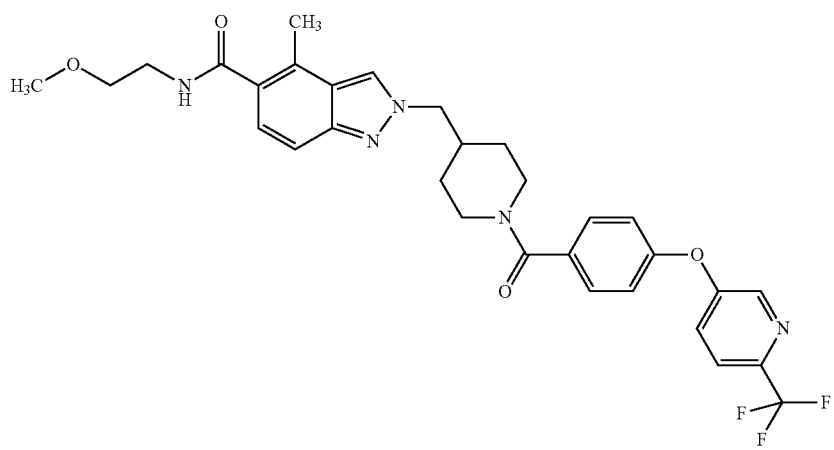

Analogously to Example 1b, Version B, 34 mg of the title compound was obtained from 75 mg of 71a and 96 mg of 303b in DMF.

$^1$H-NMR (400 MHz, DMSO-d$_6$): δ [ppm]=1.24 (2H), 1.37-1.68 (2H), 2.22-2.38 (1H), 2.53 (3H), 2.71-3.14 (2H), 3.28 (3H), 3.36-3.43 (2H), 3.44-3.49 (2H), 3.52-3.84 (1H), 4.36 (3H), 7.09-7.29 (3H), 7.35-7.53 (3H), 7.65 (1H), 7.92 (1H), 8.13 (1H), 8.51 (1H), 8.60 (1H).

EXAMPLE 350

N-(2-methoxyethyl)-4-methyl-2-{[1-(4-{[6-(trifluoromethyl)pyridin-2-yl]oxy}-benzoyl)piperidin-4-yl]methyl}-2H-indazol-5-carboxamide

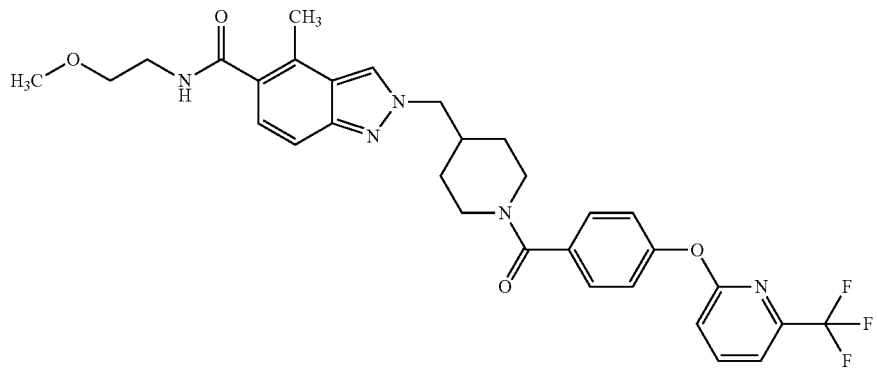 [SMILES: COCCNC(=O)c1ccc2nn(CC3CCN(C(=O)c4ccc(Oc5cccc(C(F)(F)F)n5)cc4)CC3)cc2c1C]

Analogously to Example 1b, Version B, 36 mg of the title compound was obtained from 100 mg of 71a and 129 mg of 4-{[6-(trifluoromethyl)pyridin-2-yl]oxy}benzoic acid in DMF.

$^1$H-NMR (400 MHz, DMSO-d$_6$): δ [ppm]=1.20-1.34 (2H), 1.36-1.66 (2H), 2.24-2.39 (1H), 2.53 (3H), 2.70-3.16 (2H), 3.28 (3H), 3.36-3.43 (2H), 3.44-3.49 (2H), 3.53-3.82 (1H), 4.36 (3H), 7.18 (1H), 7.22-7.30 (2H), 7.32-7.50 (4H), 7.67 (1H), 8.06-8.21 (2H), 8.51 (1H).

EXAMPLE 351

2-({1-[(4'-methoxybiphenyl-4-yl)carbonyl]piperidin-4-yl}methyl)-N-(2-methoxy-ethyl)-4-methyl-2H-indazol-5-carboxamide

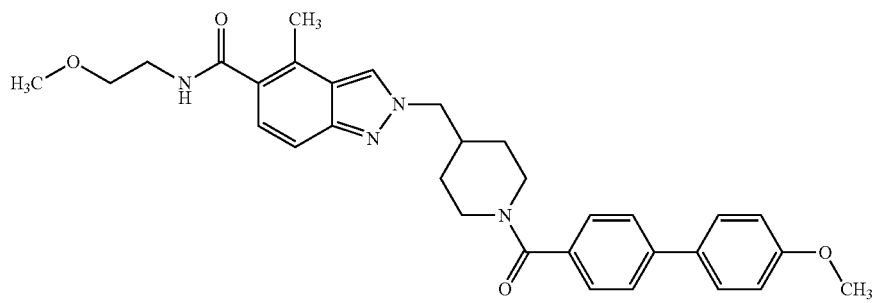

Analogously to Example 1b, Version B, 15 mg of the title compound was obtained from 100 mg of 71a and 104 mg of 4'-methoxy-biphenyl-4-carboxylic acid in DMF.

$^1$H-NMR (300 MHz, DMSO-d$_6$): δ [ppm]=1.24 (2H), 1.37-1.64 (2H), 2.19-2.32 (1H), 2.53 (3H), 2.74-3.10 (2H), 3.28 (3H), 3.40 (2H), 3.45 (2H), 3.67-3.91 (4H), 4.21-4.64 (3H), 7.04 (2H), 7.19 (1H), 7.41 (2H), 7.66 (5H), 8.04-8.22 (1H), 8.51 (1H).

EXAMPLE 352

N-(2-methoxyethyl)-4-methyl-2-({1-[(3-phenyl-1,2,4-oxadiazol-5-yl)carbonyl]-piperidin-4-yl}methyl)-2H-indazol-5-carboxamide

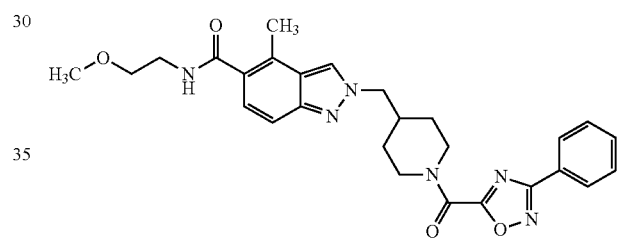

Analogously to Example 1b, Version B, 12 mg of the title compound was obtained from 100 mg of 71a and 78 mg of 3-phenyl-1,2,4-oxadiazol-5-carboxylic acid in DMF.

$^1$H-NMR (300 MHz, DMSO-d$_6$): δ [ppm]=1.33 (2H), 1.50-1.72 (2H), 2.31-2.45 (1H), 2.53 (3H), 2.86-3.04 (1H), 3.16-3.26 (1H), 3.28 (3H), 3.41 (2H), 3.43-3.51 (2H), 3.94-4.13 (1H), 4.28-4.55 (3H), 7.19 (1H), 7.43 (1H), 7.52-7.72 (3H), 7.96-8.09 (2H), 8.13 (1H), 8.52 (1H).

EXAMPLE 353

N-(2-methoxyethyl)-4-methyl-2-({1-[4-(3,4,5,6-tetrahydro-2H-pyran-4-yloxy)-benzoyl]piperidin-4-yl}methyl)-2H-indazol-5-carboxamide

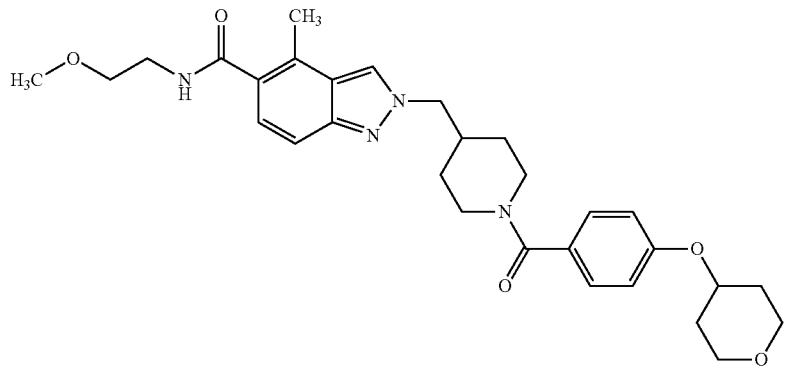 [SMILES: COCCNC(=O)c1ccc2nn(CC3CCN(C(=O)c4ccc(OC5CCOCC5)cc4)CC3)cc2c1C]

Analogously to Example 1b, Version B, 21 mg of the title compound was obtained from 100 mg of 71a and 91 mg of 4-(3,4,5,6-tetrahydro-2H-pyran-4-yloxy)benzoic acid in DMF.

$^1$H-NMR (300 MHz, DMSO-d$_6$): δ [ppm]=1.23 (2H), 1.38-1.70 (4H), 1.97 (2H), 2.18-2.41 (1H), 2.53 (3H), 2.75-3.02 (2H), 3.28 (3H), 3.35-3.54 (8H), 3.84 (2H), 4.35 (2H), 4.52-4.77 (1H), 7.00 (2H), 7.18 (1H), 7.30 (2H), 7.42 (1H), 8.13 (1H), 8.50 (1H).

EXAMPLE 354

N-(2-methoxyethyl)-4-methyl-2-({1-[(5-phenyloxazol-2-yl)carbonyl]piperidin-4-yl}methyl)-2H-indazol-5-carboxamide

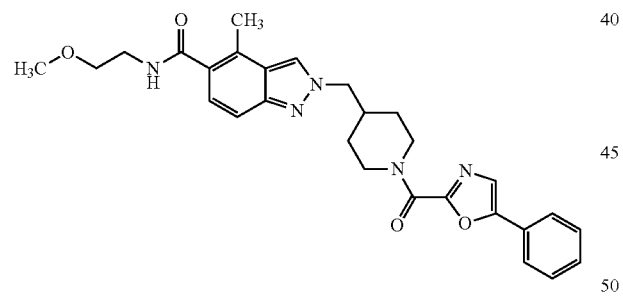

Analogously to Example 1b, Version B, 10 mg of the title compound was obtained from 100 mg of 71a and 77 mg of 5-phenyl-oxazol-2-carboxylic acid in DMF.

$^1$H-NMR (400 MHz, DMSO-d$_6$): δ [ppm]=1.17-1.41 (2H), 1.59 (2H), 2.28-2.45 (1H), 2.52-2.56 (3H), 2.85 (1H), 3.20 (1H), 3.28 (3H), 3.36-3.43 (2H), 3.44-3.50 (2H), 4.38 (3H), 4.57-4.74 (1H), 7.19 (1H), 7.39-7.57 (4H), 7.74-7.82 (2H), 7.88 (1H), 8.13 (1H), 8.52 (1H).

EXAMPLE 355

N-(2-methoxyethyl)-4-methyl-2-[(1-{4-[3-(trifluoromethyl)phenoxy]benzoyl}-piperidin-4-yl)methyl]-2H-indazol-5-carboxamide

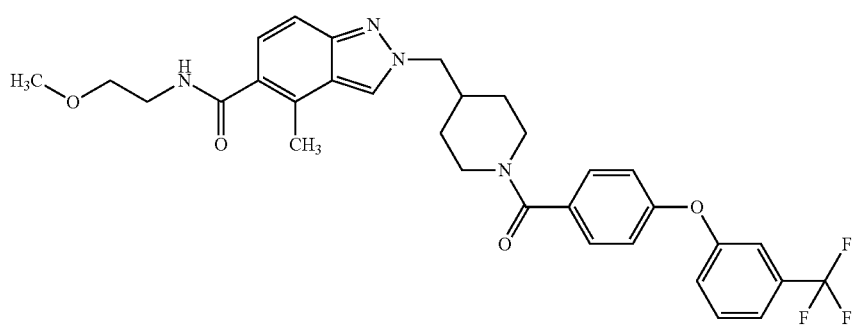 [SMILES: COCCNC(=O)c1ccc2nn(CC3CCN(C(=O)c4ccc(Oc5cccc(C(F)(F)F)c5)cc4)CC3)cc2c1C]

Analogously to Example 1b, Version B, 40 mg of the title compound was obtained from 100 mg of 71a and 115 mg of 4-[(3-(trifluoromethyl)phenoxy]benzoic acid in DMF.

$^1$H-NMR (400 MHz, DMSO-$d_6$): δ [ppm]=1.23 (2H), 1.35-1.65 (2H), 2.19-2.38 (1H), 2.52-2.56 (3H), 2.71-3.12 (2H), 3.28 (3H), 3.36-3.43 (2H), 3.43-3.50 (2H), 3.53-3.87 (1H), 4.35 (3H), 7.07-7.15 (2H), 7.18 (1H), 7.30-7.48 (5H), 7.54 (1H), 7.64 (1H), 8.13 (1H), 8.50 (1H).

EXAMPLE 356

2-[(1-{4-[(5-cyanopyridin-2-yl)oxy]benzoyl}piperidin-4-yl)methyl]-N-(2-methoxyethyl)-4-methyl-2H-indazol-5-carboxamide

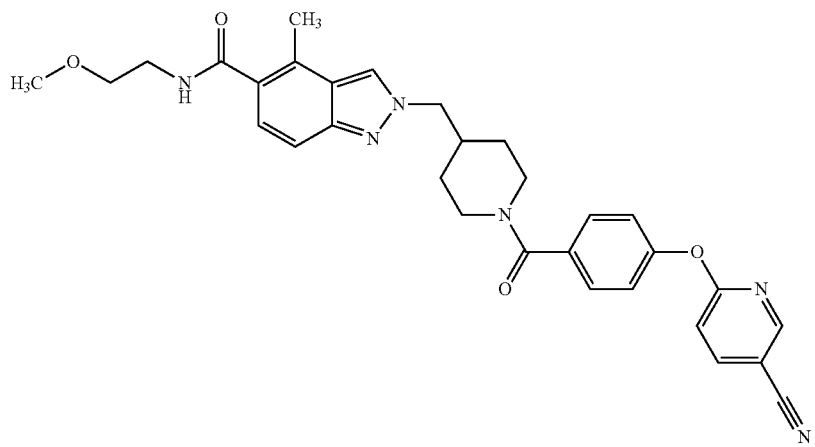 [SMILES: COCCNC(=O)c1ccc2nn(CC3CCN(C(=O)c4ccc(Oc5ccc(C#N)cn5)cc4)CC3)cc2c1C]

Analogously to Example 1b, Version B, 15 mg of the title compound was obtained from 100 mg of 71a and 98 mg of 4-[(5-cyanopyridin-2-yl)oxy]benzoic acid in DMF.

$^1$H-NMR (400 MHz, DMSO-$d_6$): δ [ppm]=1.21-1.35 (2H), 1.36-1.75 (2H), 2.23-2.39 (1H), 2.53 (3H), 2.69-3.19 (2H), 3.28 (3H), 3.36-3.43 (2H), 3.46 (2H), 3.53-3.85 (1H), 4.36 (3H), 7.18 (1H), 7.23-7.33 (3H), 7.36-7.53 (3H), 8.13 (1H), 8.34 (1H), 8.51 (1H), 8.66 (1H).

EXAMPLE 357

2-[(1-{4-[(5-chloropyridin-2-yl)oxy]benzoyl}piperidin-4-yl)methyl]-N-(2-methoxyethyl)-4-methyl-2H-indazol-5-carboxamide

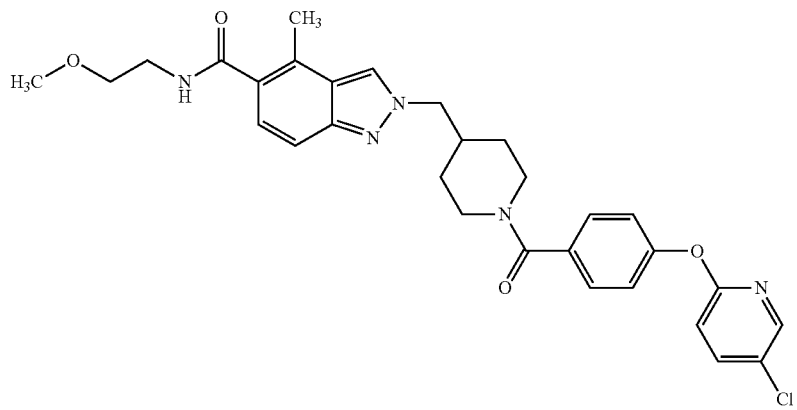 [SMILES: COCCNC(=O)c1ccc2nn(CC3CCN(C(=O)c4ccc(Oc5ccc(Cl)cn5)cc4)CC3)cc2c1C]

Analogously to Example 1b, Version B, 40 mg of the title compound was obtained from 100 mg of 71a and 102 mg of 4-[(5-chloropyridin-2-yl)oxy]benzoic acid in DMF.

$^1$H-NMR (300 MHz, DMSO-$d_6$): δ [ppm]=1.25 (2H), 1.36-1.70 (2H), 2.20-2.39 (1H), 2.53 (3H), 2.66-3.15 (2H), 3.28 (3H), 3.40 (2H), 3.43-3.50 (2H), 3.55-3.90 (1H), 4.36 (3H), 7.08-7.28 (4H), 7.42 (3H), 7.99 (1H), 8.10-8.30 (2H), 8.51 (1H).

EXAMPLE 358

2-({1-[4-(2,4-difluorophenoxy)benzoyl]piperidin-4-yl}methyl)-N-(2-methoxy-ethyl)-4-methyl-2H-indazol-5-carboxamide

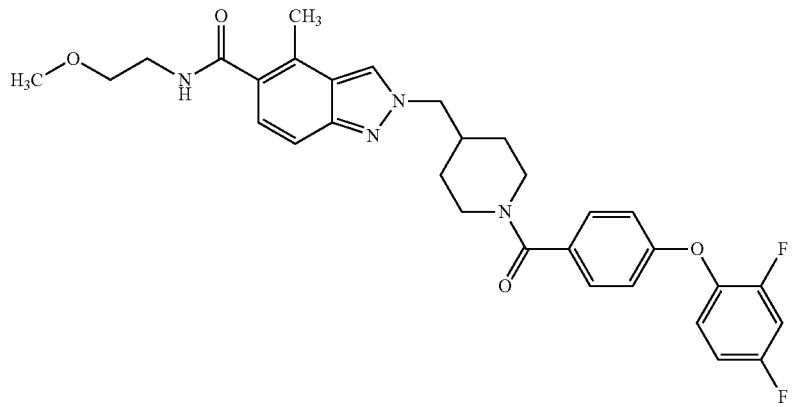 [SMILES: COCCNC(=O)c1ccc2nn(CC3CCN(C(=O)c4ccc(Oc5ccc(F)cc5F)cc4)CC3)cc2c1C]

Analogously to Example 1b, Version B, 22 mg of the title compound was obtained from 100 mg of 71a and 102 mg of 4-(2,4-difluorophenoxy)benzoic acid in DMF.

$^1$H-NMR (400 MHz, DMSO-$d_6$): δ [ppm]=1.21 (2H), 1.33-1.76 (2H), 2.20-2.39 (1H), 2.52 (3H), 2.69-3.13 (2H), 3.28 (3H), 3.36-3.43 (2H), 3.43-3.50 (2H), 3.53-3.90 (1H), 4.35 (3H), 6.91-7.04 (2H), 7.11-7.22 (2H), 7.30-7.46 (4H), 7.51 (1H), 8.13 (1H), 8.50 (1H).

EXAMPLE 359

2-({1-[4-(3,4-difluorophenoxy)benzoyl]piperidin-4-yl}methyl)-N-(2-methoxy-ethyl)-4-methyl-2H-indazol-5-carboxamide

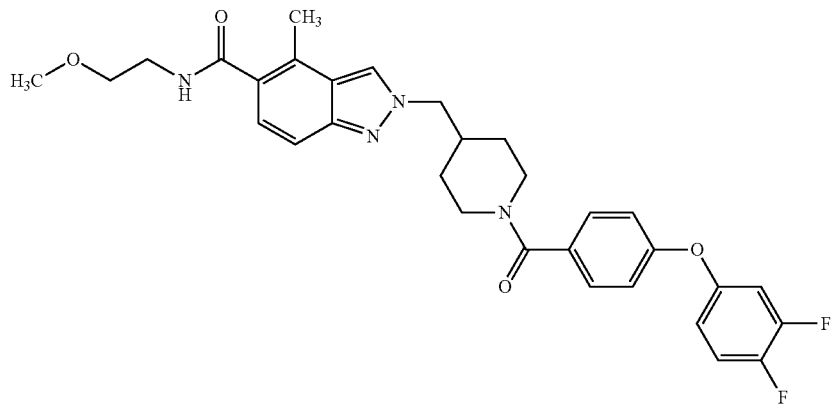 [SMILES: COCCNC(=O)c1ccc2nn(CC3CCN(C(=O)c4ccc(Oc5ccc(F)c(F)c5)cc4)CC3)cc2c1C]

Analogously to Example 1b, Version B, 23 mg of the title compound was obtained from 100 mg of 71a and 102 mg of 4-(3,4-difluorophenoxy)benzoic acid in DMF.

$^1$H-NMR (300 MHz, DMSO-$d_6$): δ [ppm]=1.17-1.30 (2H), 1.35-1.70 (2H), 2.20-2.40 (1H), 2.52 (3H), 2.74-3.14 (2H), 3.28 (3H), 3.40 (2H), 3.43-3.51 (2H), 3.52-3.89 (1H), 4.35 (3H), 6.94 (1H), 7.05 (2H), 7.18 (1H), 7.30 (1H), 7.36-7.59 (4H), 8.15 (1H), 8.51 (1H).

EXAMPLE 360

N-(2-methoxyethyl)-4-methyl-2-[(1-{[4'-(trifluoromethyl)biphenyl-4-yl]-carbonyl}piperidin-4-yl)methyl]-2H-indazol-5-carboxamide

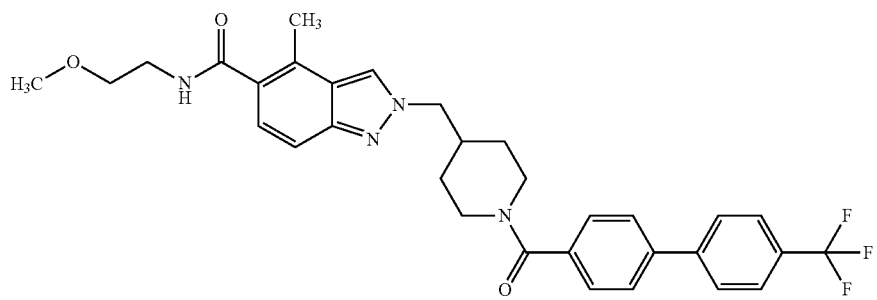 [SMILES: COCCNC(=O)c1ccc2nn(CC3CCN(C(=O)c4ccc(-c5ccc(C(F)(F)F)cc5)cc4)CC3)cc2c1C]

Analogously to Example 1b, Version B, 44 mg of the title compound was obtained from 100 mg of 71a and 109 mg of 4'-(trifluoromethyl)biphenyl-4-carboxylic acid in DMF LC-MS: $R_t$=1.28 min, MS (ES+): m/z=579 (M+H)$^+$.

EXAMPLE 361

2-({1-[4-(3-fluorophenoxy)benzoyl]piperidin-4-yl}methyl)-N-(2-methoxyethyl)-4-methyl-2H-indazol-5-carboxamide

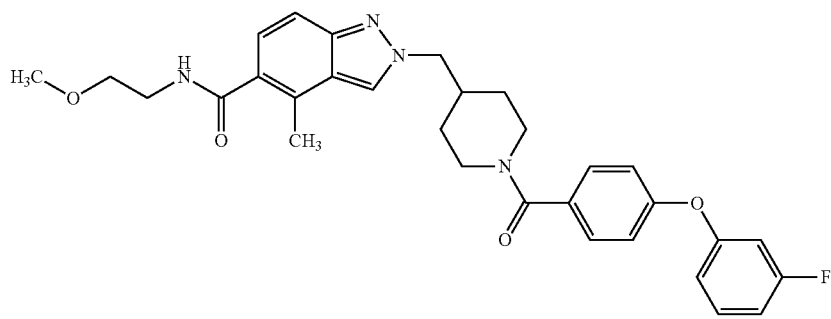 [SMILES: COCCNC(=O)c1ccc2nn(CC3CCN(C(=O)c4ccc(Oc5cccc(F)c5)cc4)CC3)cc2c1C]

Analogously to Example 1b, Version B, 43 mg of the title compound was obtained from 100 mg of 71a and 95 mg of 4-(3-fluorophenoxy)benzoic acid in DMF.

$^1$H-NMR (400 MHz, DMSO-$d_6$): δ [ppm]=1.17-1.31 (2H), 1.33-1.69 (2H), 2.19-2.38 (1H), 2.52 (3H), 2.70-3.11 (2H), 3.28 (3H), 3.36-3.43 (2H), 3.43-3.49 (2H), 3.54-3.85 (1H), 4.35 (3H), 6.85-7.13 (5H), 7.18 (1H), 7.35-7.55 (4H), 8.15 (1H), 8.51 (1H).

EXAMPLE 362

2-{[1-(2-fluoro-4-isopropoxybenzoyl)piperidin-4-yl]methyl}-N-(2-methoxy-ethyl)-4-methyl-2H-indazol-5-carboxamide

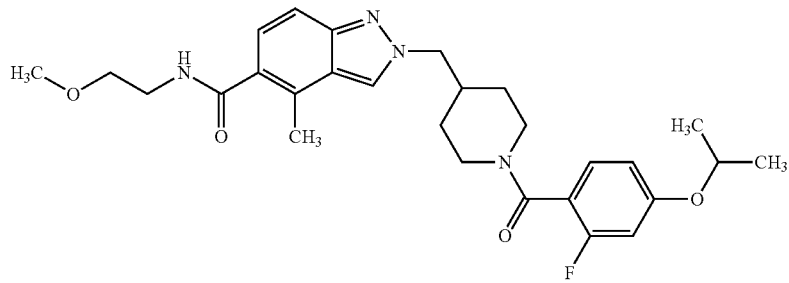 [SMILES: COCCNC(=O)c1ccc2nn(CC3CCN(C(=O)c4ccc(OC(C)C)cc4F)CC3)cc2c1C]

Analogously to Example 1b, Version B, 31 mg of the title compound was obtained from 75 mg of 71a and 41 mg of 2-fluoro-4-isopropoxybenzoic acid.

$^1$H-NMR (300 MHz, chloroform-d): δ [ppm]=1.21-1.42 (8H), 1.51 (1H), 1.69 (1H), 2.38 (1H), 2.56-2.80 (4H), 2.87-3.08 (1H), 3.36 (3H), 3.48-3.73 (4H), 4.28 (2H), 4.51 (1H), 4.74 (1H), 5.28 (1H), 6.19 (1H), 6.54 (1H), 6.67 (1H), 7.13-7.38 (2H), 7.50 (1H), 7.94 (1H).

EXAMPLE 363

2-({1-[(3-fluoro-3',4'-dimethylbiphenyl-4-yl)carbonyl]piperidin-4-yl}methyl)-N-(2-methoxyethyl)-4-methyl-2H-indazol-5-carboxamide

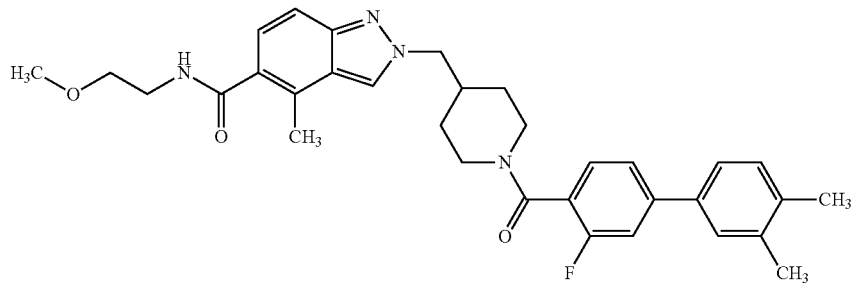

Analogously to Example 1b, Version B, 35 mg of the title compound was obtained from 75 mg of 71a and 50 mg of 3-fluoro-3',4'-dimethylbiphenyl-4-carboxylic acid.

$^1$H-NMR (300 MHz, chloroform-d): δ [ppm]=1.25-1.51 (2H), 1.57 (1H), 1.76 (1H), 2.25-2.37 (6H), 2.45 (1H), 2.61-2.71 (3H), 2.79 (1H), 3.06 (1H), 3.40 (3H), 3.53-3.77 (5H), 4.34 (2H), 4.83 (1H), 6.04-6.30 (1H), 7.15-7.47 (7H), 7.55 (1H), 7.98 (1H).

EXAMPLE 364

2-({1-[(2',3-difluoro-4'-methoxybiphenyl-4-yl)carbonyl]piperidin-4-yl}methyl)-N-(2-methoxyethyl)-4-methyl-2H-indazol-5-carboxamide

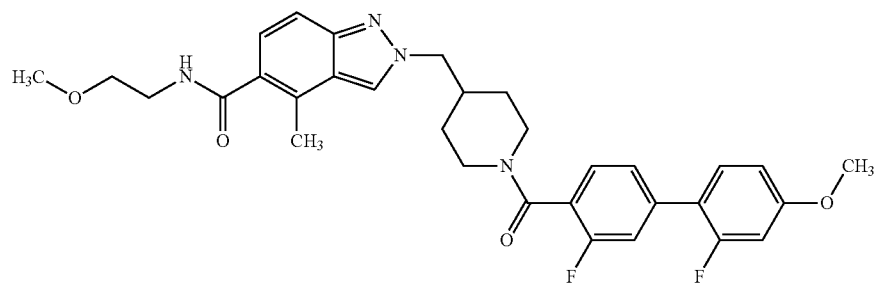

Analogously to Example 1b, Version B, 28 mg of the title compound was obtained from 90 mg of 71a and 65 mg of 3,2'-difluoro-4'-methoxybiphenyl-4-carboxylic acid.

$^1$H-NMR (300 MHz, chloroform-d): δ [ppm]=1.25-1.50 (2H), 1.50-1.84 (2H), 2.44 (1H), 2.66 (3H), 2.78 (1H), 3.03 (1H), 3.39 (3H), 3.53-3.76 (5H), 3.85 (3H), 4.23-4.45 (2H), 4.83 (1H), 6.17 (1H), 6.64-6.92 (2H), 7.18-7.48 (5H), 7.54 (1H), 7.97 (1H).

EXAMPLE 365

2-({1-[4-(difluoromethoxy)benzoyl]piperidin-4-yl}methyl)-N-(2-methoxyethyl)-4-methyl-2H-indazol-5-carboxamide

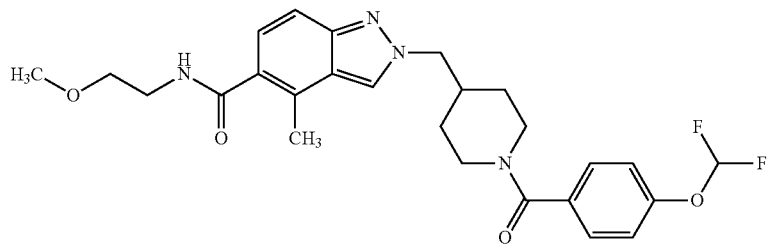 [SMILES: COCCNC(=O)c1ccc2nn(CC3CCN(C(=O)c4ccc(OC(F)F)cc4)CC3)cc2c1C]

Analogously to Example 1b, Version B, 23 mg of the title compound was obtained from 75 mg of 71a and 38 mg of 4-(difluoromethoxy)benzoic acid.

$^1$H-NMR (300 MHz, chloroform-d): δ [ppm]=1.26 (2H), 1.59 (2H), 2.26-2.49 (1H), 2.62 (3H), 2.84 (2H), 3.36 (3H), 3.43 (1H), 3.50-3.96 (4H), 4.29 (2H), 4.46-5.02 (1H), 6.13-6.25 (1H), 6.26-6.82 (1H), 7.11 (2H), 7.22-7.43 (3H), 7.50 (1H), 7.93 (1H).

EXAMPLE 366

2-({1-[4-(2-fluorophenoxy)benzoyl]piperidin-4-yl}methyl)-N-(2-methoxyethyl)-4-methyl-2H-indazol-5-carboxamide

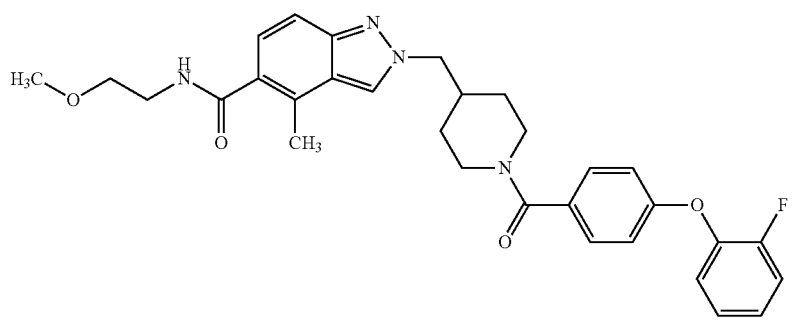 [SMILES: COCCNC(=O)c1ccc2nn(CC3CCN(C(=O)c4ccc(Oc5ccccc5F)cc4)CC3)cc2c1C]

120 mg of compound 54, 26 mg of o-fluorophenol, 152 mg of caesium carbonate, 6.7 mg of copper(I) bromide and 3.2 mg of (2-pyridyl)acetone were suspended in 6 ml dimethyl sulphoxide and stirred for 3 days at 80° C. The reaction mixture was filtered, the filter cake washed with water and ethyl acetate, and the aqueous phase extracted several times with ethyl acetate. The combined organic phases were dried with sodium sulphate and concentrated. The residue was purified by HPLC and 12 mg of the title compound was obtained.

$^1$H-NMR (300 MHz, chloroform-d): δ [ppm]=1.16-1.47 (2H), 1.62 (2H), 2.43 (1H), 2.66 (3H), 2.85 (2H), 3.39 (3H), 3.53-3.74 (4H), 3.79-4.19 (1H), 4.33 (2H), 4.47-5.02 (1H), 6.15 (1H), 6.96 (2H), 7.07-7.23 (3H), 7.30-7.45 (3H), 7.54 (1H), 7.96 (1H).

EXAMPLE 367

2-({1-[(4'-cyano-2'-methylbiphenyl-4-yl)carbonyl]piperidin-4-yl}methyl)-N-(2-methoxyethyl)-4-methyl-2H-indazol-5-carboxamide

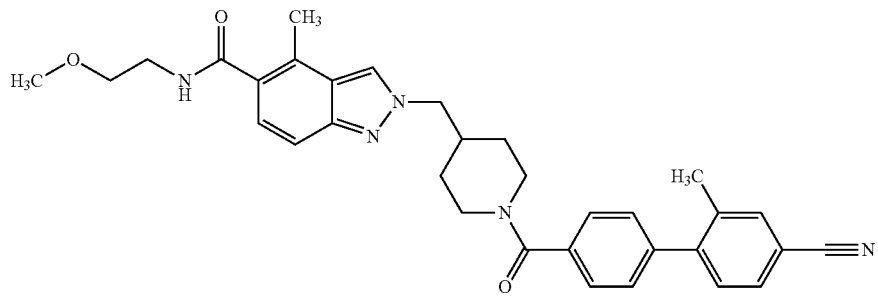 [SMILES: COCCNC(=O)c1ccc2nn(CC3CCN(C(=O)c4ccc(-c5ccc(C#N)cc5C)cc4)CC3)cc2c1C]

Analogously to Example 317, 40 mg of the title compound was obtained from 80 mg of 54 and 38 mg of (2-methyl-4-cyanophenyl)boronic acid under reflux.

$^1$H-NMR (400 MHz, DMSO-d$_6$): δ [ppm]=1.20-1.34 (2H), 1.36-1.69 (2H), 2.28 (4H), 2.53 (3H), 2.69-3.19 (2H), 3.28 (3H), 3.36-3.43 (2H), 3.43-3.50 (2H), 3.54-3.77 (1H), 4.37 (3H), 7.18 (1H), 7.37-7.50 (6H), 7.74 (1H), 7.83 (1H), 8.15 (1H), 8.52 (1H).

EXAMPLE 368

2-({1-[4-(5-chloropyridin-2-yl)benzoyl]piperidin-4-yl}methyl)-N-(2-methoxy-ethyl)-4-methyl-2H-indazol-5-carboxamide

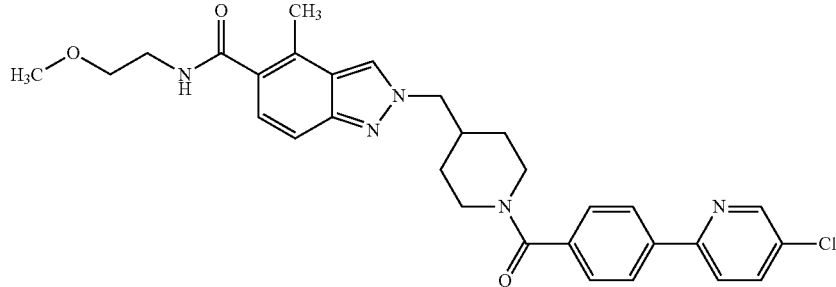 [SMILES: COCCNC(=O)c1ccc2nn(CC3CCN(C(=O)c4ccc(-c5ccc(Cl)cn5)cc4)CC3)cc2c1C]

200 mg of the aryl bromide prepared in Example 54 together with 187 mg of (5-chloropyridin-2-yl)-2-boronic acid pinacol ester were first placed in 3 ml DMF, treated with 48 mg of 1,1'-bis(diphenylphosphino)ferrocenodichloropalladium(II), 39 mg of copper(I)chloride 254 mg of caesium carbonate and 22 mg of 1,1'-bis(diphenylphosphino)ferrocene and heated for ca. 1 day at 70° C., until further progress of the reaction could no longer be observed. The reaction mixture was treated with water and saturated sodium hydrogen carbonate solution, treated several times with ethyl acetate, and the combined organic phases dried with sodium sulphate and concentrated. After HPLC purification, this yielded 92 mg of the title compound.

$^1$H-NMR (400 MHz, DMSO-d$_6$): δ [ppm]=1.19-1.36 (2H), 1.37-1.72 (2H), 2.23-2.41 (1H), 2.52-2.57 (3H), 2.70-3.13 (2H), 3.28 (3H), 3.39 (2H), 3.45 (2H), 3.51-3.80 (1H), 4.36 (3H), 7.18 (1H), 7.36-7.52 (3H), 8.05 (2H), 8.09-8.22 (3H), 8.51 (1H), 8.73 (1H).

EXAMPLE 369

N-(2-methoxyethyl)-4-methyl-2-[(1-{4-[6-(trifluoromethyl)pyridin-2-yl]-benzoyl}piperidin-4-yl)methyl]-2H-indazol-5-carboxamide

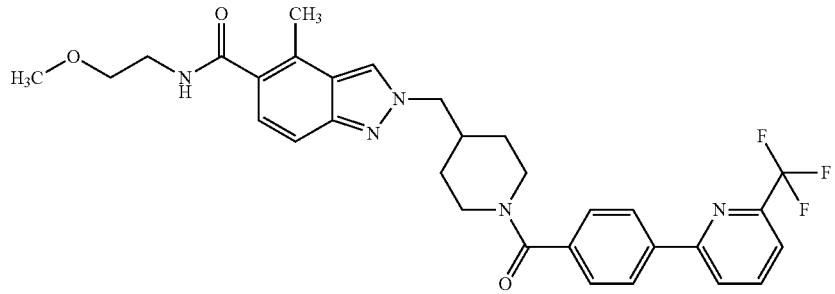 [SMILES: COCCNC(=O)c1ccc2nn(CC3CCN(C(=O)c4ccc(-c5cccc(C(F)(F)F)n5)cc4)CC3)cc2c1C]

Analogously to Example 317, 33 mg of the title compound was obtained from 100 mg of 54 and 80 mg of [6-(trifluoromethyl)pyridin-2-yl]boronic acid pinacol ester under reflux.

$^1$H-NMR (400 MHz, DMSO-d$_6$): δ [ppm]=1.18-1.35 (2H), 1.36-1.67 (2H), 2.25-2.41 (1H), 2.53 (3H), 2.70-3.15 (2H), 3.28 (3H), 3.35-3.43 (2H), 3.43-3.51 (2H), 3.53-3.73 (1H), 4.37 (3H), 7.18 (1H), 7.42 (1H), 7.53 (2H), 7.89 (1H), 8.06-8.26 (4H), 8.33 (1H), 8.51 (1H).

EXAMPLE 370

N-(2-methoxyethyl)-2-({1-[(4'-methoxy-2'-methylbiphenyl-4-yl)carbonyl]-piperidin-4-yl}methyl)-4-methyl-2H-indazol-5-carboxamide

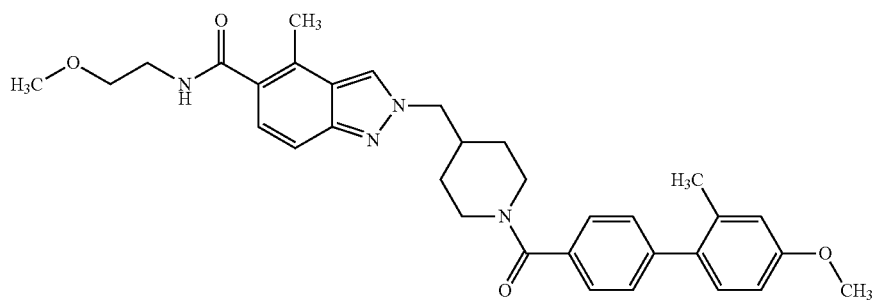

Analogously to Example 317, 52 mg of the title compound was obtained from 100 mg of 54 and 48 mg of (4-methoxy-2-methylphenyl)boronic acid under reflux.

$^1$H-NMR (400 MHz, DMSO-d$_6$): δ [ppm]=1.16-1.35 (2H), 1.37-1.67 (2H), 2.23 (3H), 2.26-2.42 (1H), 2.53 (3H), 2.70-3.12 (2H), 3.28 (3H), 3.36-3.43 (2H), 3.43-3.50 (2H), 3.77 (4H), 4.36 (3H), 6.77-6.92 (2H), 7.10-7.22 (2H), 7.39 (5H), 8.15 (1H), 8.52 (1H).

EXAMPLE 371

2-({1-[(4'-chloro-2'-methylbiphenyl-4-yl)carbonyl]piperidin-4-yl}methyl)-N-(2-methoxyethyl)-4-methyl-2H-indazol-5-carboxamide

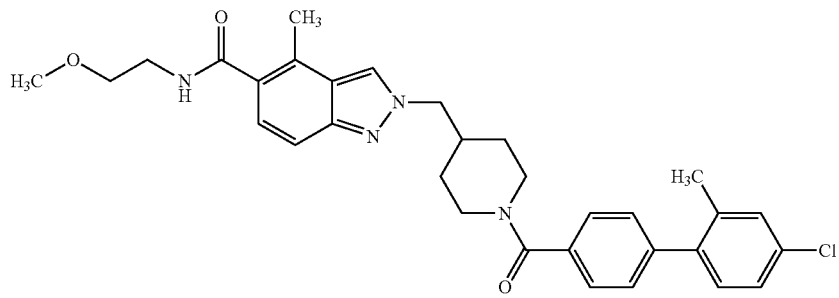 [SMILES: COCCNC(=O)c1ccc2nn(CC3CCN(C(=O)c4ccc(-c5ccc(Cl)cc5C)cc4)CC3)cc2c1C]

Analogously to Example 317, 43 mg of the title compound was obtained from 100 mg of 54 and 50 mg of (4-chloro-2-methylphenyl)boronic acid under reflux.

$^1$H-NMR (400 MHz, DMSO-d$_6$): δ [ppm]=1.27 (2H), 1.38-1.70 (2H), 2.23 (4H), 2.53 (3H), 2.70-3.15 (2H), 3.28 (3H), 3.36-3.43 (2H), 3.43-3.49 (2H), 3.55-3.84 (1H), 4.36 (3H), 7.12-7.27 (2H), 7.28-7.35 (1H), 7.36-7.47 (6H), 8.15 (1H), 8.52 (1H).

EXAMPLE 372

2-[(1-{[4'-(1-cyano-1-methylethyl)biphenyl-4-yl]
carbonyl}piperidin-4-yl)-methyl]-N-(2-methoxy-
ethyl)-4-methyl-2H-indazol-5-carboxamide

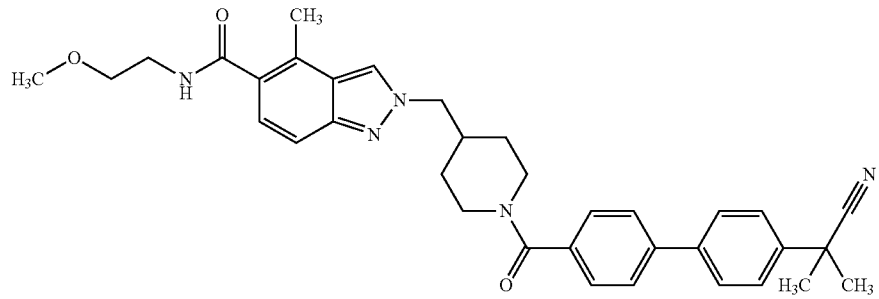 [SMILES: COCCNC(=O)c1ccc2nn(CC3CCN(C(=O)c4ccc(-c5ccc(C(C)(C)C#N)cc5)cc4)CC3)cc2c1C]

Analogously to Example 317, 67 mg of the title compound was obtained from 100 mg of 54 and 55 mg of [4-(1-cyano-1-methylethyl)phenyl]boronic acid under reflux.

$^1$H-NMR (400 MHz, DMSO-d$_6$): δ [ppm]=1.28 (2H), 1.36-1.65 (2H), 1.72 (6H), 2.24-2.40 (1H), 2.53 (3H), 2.70-3.14 (2H), 3.28 (3H), 3.36-3.43 (2H), 3.43-3.49 (2H), 3.54-3.77 (1H), 4.36 (3H), 7.18 (1H), 7.38-7.50 (3H), 7.62 (2H), 7.75 (4H), 8.15 (1H), 8.52 (1H).

EXAMPLE 373

N-(2-methoxyethyl)-2-({1-[4-(5-methoxypyridin-2-
yl)benzoyl]piperidin-4-yl}-methyl)-4-methyl-2H-
indazol-5-carboxamide

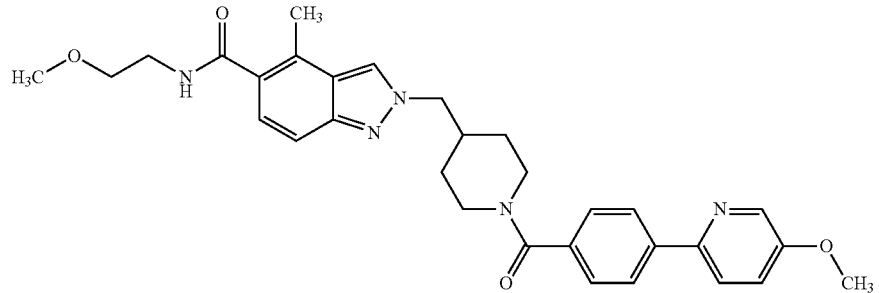

Analogously to Example 368, 12 mg of the title compound was obtained from 200 mg of 54 and 183 mg of (5-methoxy-pyridin-2-yl)boronic acid pinacol ester under reflux.

$^1$H-NMR (400 MHz, DMSO-d$_6$): δ [ppm]=1.22-1.33 (2H), 1.36-1.66 (2H), 2.23-2.38 (1H), 2.53 (3H), 2.68-3.12 (2H), 3.28 (3H), 3.35-3.42 (2H), 3.43-3.50 (2H), 3.54-3.78 (1H), 3.88 (3H), 4.36 (3H), 7.18 (1H), 7.36-7.55 (4H), 7.96 (1H), 8.07 (2H), 8.13 (1H), 8.39 (1H), 8.51 (1H).

EXAMPLE 374

N-(2-methoxyethyl)-4-methyl-2-[(1-{4-[6-(trifluoromethyl)pyridin-3-yl]-benzoyl}piperidin-4-yl)methyl]-2H-indazol-5-carboxamide

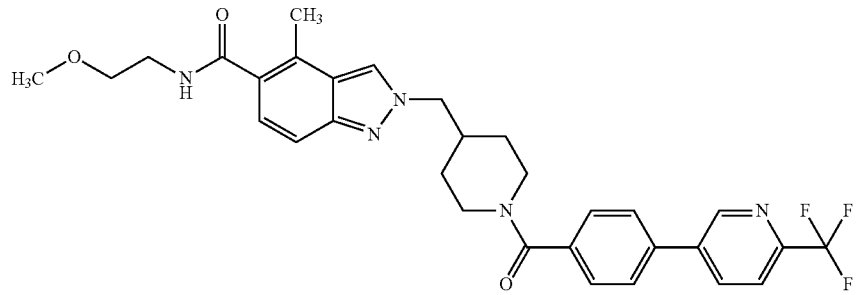 [SMILES: COCCNC(=O)c1ccc2nn(CC3CCN(C(=O)c4ccc(-c5ccc(C(F)(F)F)nc5)cc4)CC3)cc2c1C]

Analogously to Example 317, 37 mg of the title compound was obtained from 100 mg of 54 and 56 mg of [2-(trifluoromethyl)pyridin-5-yl]boronic acid under reflux.

$^1$H-NMR (400 MHz, DMSO-$d_6$): δ [ppm]=1.19-1.36 (2H), 1.36-1.69 (2H), 2.21-2.42 (1H), 2.53 (3H), 2.70-3.14 (2H), 3.28 (3H), 3.36-3.43 (2H), 3.43-3.50 (2H), 3.53-3.72 (1H), 4.36 (3H), 7.18 (1H), 7.42 (1H), 7.53 (2H), 7.89 (2H), 8.01 (1H), 8.15 (1H), 8.41 (1H), 8.52 (1H), 9.13 (1H).

EXAMPLE 375

N-(2-methoxyethyl)-2-({1-[4-(6-methoxypyridin-3-yl)benzoyl]piperidin-4-yl}-methyl)-4-methyl-2H-indazol-5-carboxamide

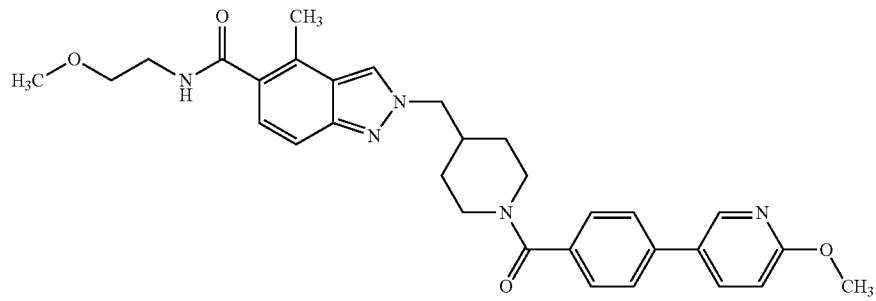

Analogously to Example 317, 50 mg of the title compound was obtained from 100 mg of 54 and 47 mg of (2-methoxypyridin-5-yl)boronic acid under reflux.

$^1$H-NMR (400 MHz, DMSO-$d_6$): δ [ppm]=1.26 (2H), 1.34-1.70 (2H), 2.21-2.40 (1H), 2.53 (3H), 2.69-3.15 (2H), 3.28 (3H), 3.36-3.43 (2H), 3.43-3.49 (2H), 3.51-3.79 (1H), 3.90 (3H), 4.36 (3H), 6.93 (1H), 7.18 (1H), 7.36-7.52 (3H), 7.72 (2H), 8.05 (1H), 8.15 (1H), 8.46-8.57 (2H).

EXAMPLE 376

2-({1-[(4'-fluoro-2'-methylbiphenyl-4-yl)carbonyl]piperidin-4-yl}methyl)-N-(2-methoxyethyl)-4-methyl-2H-indazol-5-carboxamide

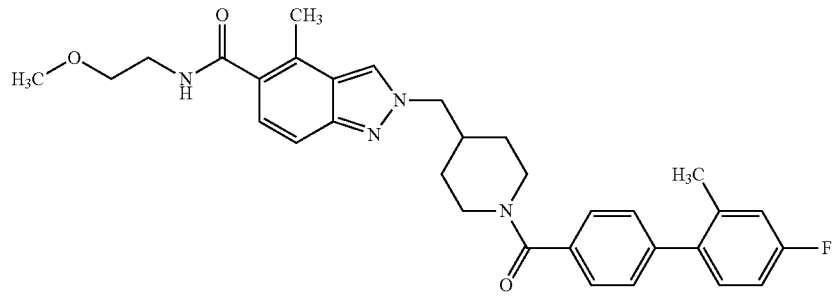 [SMILES: COCCNC(=O)c1ccc2nn(CC3CCN(C(=O)c4ccc(-c5ccc(F)cc5C)cc4)CC3)cc2c1C]

Analogously to Example 317, 261 mg of the title compound was obtained from 300 mg of 54 and 135 mg of (4-fluoro-2-methylphenyl)boronic acid under reflux.

$^1$H-NMR (400 MHz, DMSO-$d_6$): δ [ppm]=1.27 (2H), 1.37-1.70 (2H), 2.24 (4H), 2.53 (3H), 2.71-3.14 (2H), 3.28 (3H), 3.36-3.43 (2H), 3.43-3.50 (2H), 3.55-3.83 (1H), 4.37 (3H), 7.05-7.12 (1H), 7.18 (2H), 7.22-7.30 (1H), 7.40 (5H), 8.14 (1H), 8.52 (1H).

EXAMPLE 377

N-(2-methoxyethyl)-4-methyl-2-({1-[4-(6-methylpyridin-3-yl)benzoyl]piperidin-4-yl}methyl)-2H-indazol-5-carboxamide

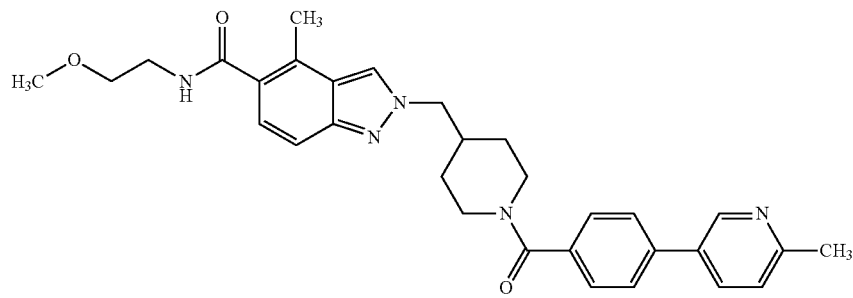

Analogously to Example 317, 45 mg of the title compound was obtained from 80 mg of 54 and 32 mg of (2-methylpyridin-5-yl)boronic acid under reflux.

$^1$H-NMR (300 MHz, DMSO-$d_6$): δ [ppm]=1.26 (2H), 1.37-1.71 (2H), 2.18-2.39 (1H), 2.52-2.58 (3H), 2.73-3.16 (2H), 3.28 (3H), 3.36-3.43 (2H), 3.45 (2H), 3.54-3.79 (1H), 4.36 (3H), 7.18 (1H), 7.30-7.54 (4H), 7.76 (2H), 8.00 (1H), 8.15 (1H), 8.51 (1H), 8.78 (1H).

EXAMPLE 378

N-(2-methoxyethyl)-2-({1-[4-(6-methoxypyridin-2-yl)benzoyl]piperidin-4-yl}methyl)-4-methyl-2H-indazol-5-carboxamide

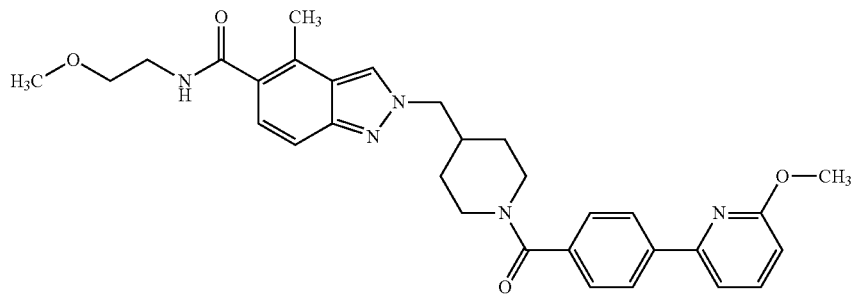

Analogously to Example 317, 30 mg of the title compound was obtained from 100 mg of 54 and 45 mg of (6-methoxy-pyridin-2-yl)boronic acid under reflux.

$^1$H-NMR (400 MHz, DMSO-d$_6$): δ [ppm]=1.26 (2H), 1.35-1.68 (2H), 2.32 (1H), 2.52 (3H), 2.70-3.13 (2H), 3.28 (3H), 3.36-3.43 (2H), 3.43-3.50 (2H), 3.53-3.74 (1H), 3.96 (3H), 4.36 (3H), 6.81 (1H), 7.18 (1H), 7.37-7.67 (4H), 7.81 (1H), 8.15 (3H), 8.51 (1H).

EXAMPLE 379

N-(2-methoxyethyl)-4-methyl-2-({1-[4-(2-methylpyrimidin-5-yl)benzoyl]-piperidin-4-yl}methyl)-2H-indazol-5-carboxamide

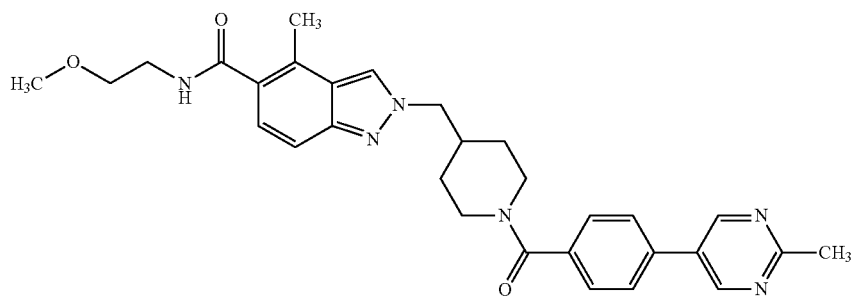

Analogously to Example 317, 36 mg of the title compound was obtained from 100 mg of 54 and 64 mg of (2-methylpyrimidin-5-yl)boronic acid pinacol ester under reflux.

$^1$H-NMR (300 MHz, DMSO-d$_6$): δ [ppm]=1.27 (2H), 1.38-1.70 (2H), 2.21-2.40 (1H), 2.53 (3H), 2.67 (3H), 2.73-3.16 (2H), 3.28 (3H), 3.40 (2H), 3.43-3.50 (2H), 3.53-3.76 (1H), 4.36 (3H), 7.18 (1H), 7.42 (1H), 7.51 (2H), 7.84 (2H), 8.13 (1H), 8.51 (1H), 9.05 (2H).

EXAMPLE 380

2-({1-[(4'-fluoro-2'-methoxybiphenyl-4-yl)carbonyl]
piperidin-4-yl}methyl)-N-(2-methoxyethyl)-4-methyl-2H-indazol-5-carboxamide

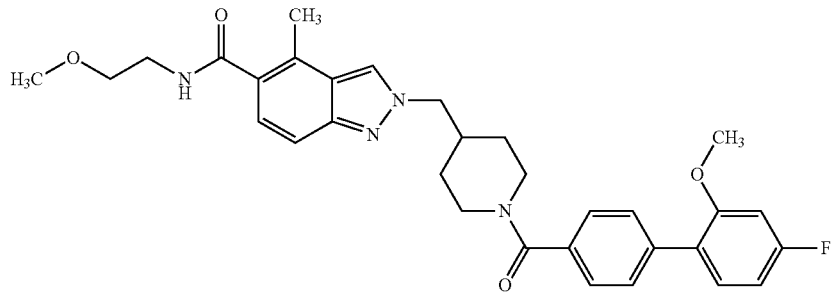 [SMILES: COCCNC(=O)c1ccc2nn(CC3CCN(C(=O)c4ccc(-c5ccc(F)cc5OC)cc4)CC3)cc2c1C]

Analogously to Example 317, 47 mg of the title compound was obtained from 100 mg of 54 and 50 mg of (4-fluoro-2-methoxyphenyl)boronic acid under reflux.

$^1$H-NMR (400 MHz, DMSO-d$_6$): δ [ppm]=1.19-1.34 (2H), 1.37-1.71 (2H), 2.22-2.40 (1H), 2.53 (3H), 2.70-3.15 (2H), 3.28 (3H), 3.36-3.43 (2H), 3.43-3.50 (2H), 3.56-3.75 (1H), 3.79 (3H), 4.36 (3H), 6.87 (1H), 6.99-7.10 (1H), 7.18 (1H), 7.30-7.46 (4H), 7.50 (2H), 8.13 (1H), 8.51 (1H).

EXAMPLE 381

2-({1-[(4'-chloro-2'-methoxybiphenyl-4-yl)carbonyl]
piperidin-4-yl}methyl)-N-(2-methoxyethyl)-4-methyl-2H-indazol-5-carboxamide

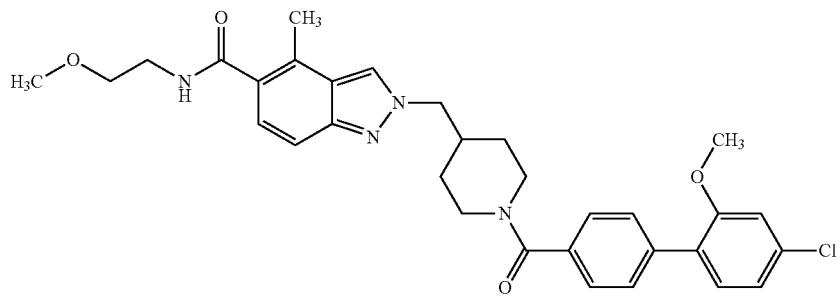 [SMILES: COCCNC(=O)c1ccc2nn(CC3CCN(C(=O)c4ccc(-c5ccc(Cl)cc5OC)cc4)CC3)cc2c1C]

Analogously to Example 317, 87 mg of the title compound was obtained from 100 mg of 54 and 54 mg of (4-fluoro-2-methoxyphenyl)boronic acid under reflux.

$^1$H-NMR (300 MHz, DMSO-d$_6$): δ [ppm]=1.26 (2H), 1.39-1.69 (2H), 2.19-2.39 (1H), 2.53 (3H), 2.75-3.14 (2H), 3.28 (3H), 3.40 (2H), 3.45 (2H), 3.57-3.74 (1H), 3.81 (3H), 4.36 (3H), 7.04-7.25 (3H), 7.28-7.62 (6H), 8.13 (1H), 8.51 (1H).

EXAMPLE 382

N-(2-methoxyethyl)-4-methyl-2-[(1-{4-[2-(trifluoromethyl)pyrimidin-5-yl]-benzoyl}piperidin-4-yl)methyl]-2H-indazol-5-carboxamide

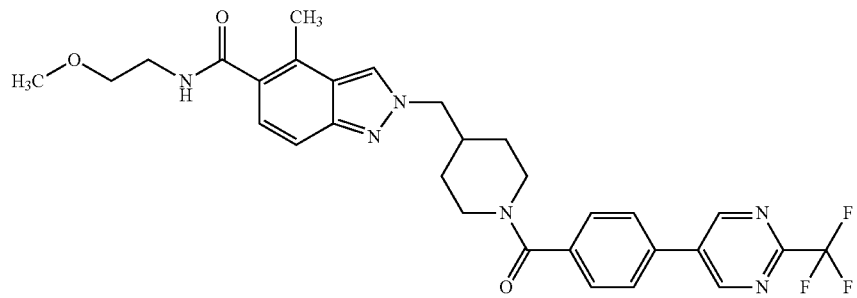 [SMILES: COCCNC(=O)c1ccc2nn(CC3CCN(C(=O)c4ccc(-c5cnc(C(F)(F)F)nc5)cc4)CC3)cc2c1C]

Analogously to Example 317, 14 mg of the title compound was obtained from 100 mg of 54 and 56 mg of [2-(trifluoromethyl)pyrimidin-5-yl]boronic acid under reflux.

$^1$H-NMR (400 MHz, DMSO-d$_6$): δ [ppm]=1.24 (2H), 1.38-1.73 (2H), 2.22-2.41 (1H), 2.53 (3H), 2.70-2.89 (1H), 2.94-3.18 (1H), 3.28 (3H), 3.36-3.43 (2H), 3.44-3.49 (2H), 3.51-3.70 (1H), 4.37 (3H), 7.18 (1H), 7.42 (1H), 7.57 (2H), 7.97 (2H), 8.13 (1H), 8.51 (1H), 9.43 (2H).

EXAMPLE 383

2-({1-[(4'-chloro-2'-fluorobiphenyl-4-yl)carbonyl]piperidin-4-yl}methyl)-N-(2-methoxyethyl)-4-methyl-2H-indazol-5-carboxamide

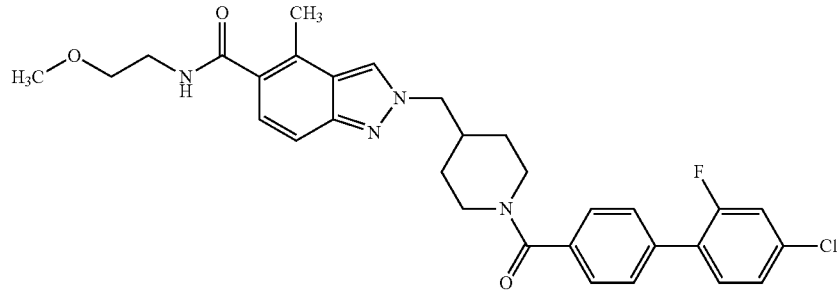 [SMILES: COCCNC(=O)c1ccc2nn(CC3CCN(C(=O)c4ccc(-c5ccc(Cl)cc5F)cc4)CC3)cc2c1C]

Analogously to Example 317, 51 mg of the title compound was obtained from 100 mg of 54 and 51 mg of (4-chloro-2-fluorophenyl)boronic acid under reflux.

$^1$H-NMR (400 MHz, DMSO-d$_6$): δ [ppm]=1.27 (2H), 1.38-1.68 (2H), 2.32 (1H), 2.53 (3H), 2.71-2.91 (1H), 2.93-3.16 (1H), 3.28 (3H), 3.40 (2H), 3.45 (2H), 3.53-3.78 (m, 1H), 4.37 (3H), 7.18 (1H), 7.33-7.52 (4H), 7.53-7.74 (4H), 8.13 (1H), 8.51 (1H).

EXAMPLE 384

2-({1-[(2'-chloro-4'-fluorobiphenyl-4-yl)carbonyl]piperidin-4-yl}methyl)-N-(2-methoxyethyl)-4-methyl-2H-indazol-5-carboxamide

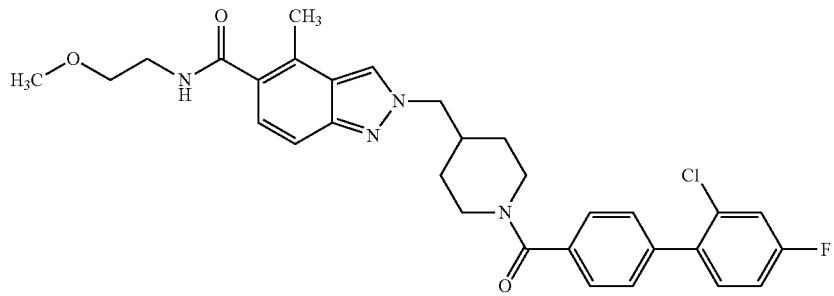 [SMILES: COCCNC(=O)c1ccc2nn(CC3CCN(C(=O)c4ccc(-c5ccc(F)cc5Cl)cc4)CC3)cc2c1C]

Analogously to Example 317, 26 mg of the title compound was obtained from 100 mg of 54 and 51 mg of (2-chloro-4-fluorophenyl)boronic acid under reflux.

$^1$H-NMR (400 MHz, DMSO-$d_6$): δ [ppm]=1.28 (2H), 1.38-1.67 (2H), 2.23-2.39 (1H), 2.53 (3H), 2.71-2.91 (1H), 2.94-3.15 (1H), 3.28 (3H), 3.36-3.43 (2H), 3.43-3.50 (2H), 3.54-3.74 (1H), 4.37 (3H), 7.18 (1H), 7.33 (1H), 7.39-7.63 (7H), 8.13 (1H), 8.51 (1H).

EXAMPLE 385

2-({1-[4-(5-chloropyridin-3-yl)benzoyl]piperidin-4-yl}methyl)-N-(2-methoxy-ethyl)-4-methyl-2H-indazol-5-carboxamide

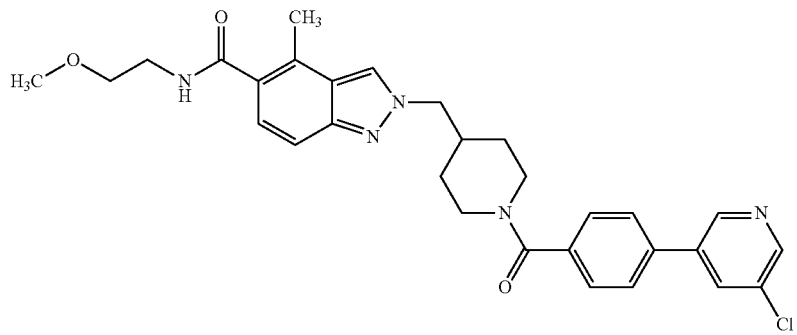 [SMILES: COCCNC(=O)c1ccc2nn(CC3CCN(C(=O)c4ccc(-c5cncc(Cl)c5)cc4)CC3)cc2c1C]

Analogously to Example 317, 22 mg of the title compound was obtained from 100 mg of 54 and 46 mg of (5-chloropyridin-3-yl)boronic acid under reflux.

$^1$H-NMR (300 MHz, DMSO-$d_6$): δ [ppm]=1.21-1.35 (2H), 1.36-1.69 (2H), 2.23-2.40 (1H), 2.53 (3H), 2.69-2.90 (1H), 2.92-3.16 (1H), 3.28 (3H), 3.40 (2H), 3.45 (2H), 3.53-3.73 (1H), 4.36 (3H), 7.18 (1H), 7.35-7.57 (3H), 7.86 (2H), 8.15 (1H), 8.30 (1H), 8.52 (1H), 8.65 (1H), 8.90 (1H).

EXAMPLE 386

2-({1-[4-(5-fluoropyridin-3-yl)benzoyl]piperidin-4-yl}methyl)-N-(2-methoxy-ethyl)-4-methyl-2H-indazol-5-carboxamide

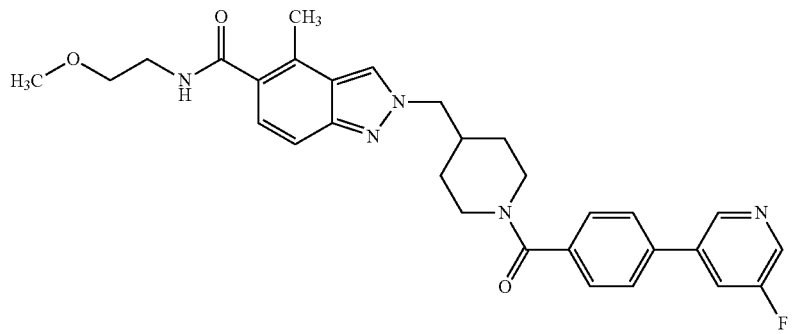 [SMILES: COCCNC(=O)c1ccc2nn(CC3CCN(C(=O)c4ccc(-c5cncc(F)c5)cc4)CC3)cc2c1C]

Analogously to Example 317, 57 mg of the title compound was obtained from 100 mg of 54 and 41 mg of (5-fluoropyridin-3-yl)boronic acid under reflux.

$^1$H-NMR (400 MHz, DMSO-$d_6$): δ [ppm]=1.27 (2H), 1.37-1.70 (2H), 2.24-2.40 (1H), 2.52-2.55 (3H), 2.70-2.89 (1H), 2.93-3.15 (1H), 3.28 (3H), 3.36-3.43 (2H), 3.43-3.50 (2H), 3.53-3.73 (1H), 4.36 (3H), 7.18 (1H), 7.42 (1H), 7.50 (2H), 7.86 (2H), 8.07-8.18 (2H), 8.51 (1H), 8.61 (1H), 8.84 (1H).

EXAMPLE 387

N-(2-methoxyethyl)-4-methyl-2-[(1-{4-[5-(trifluoromethyl)pyridin-3-yl]-benzoyl}piperidin-4-yl)methyl]-2H-indazol-5-carboxamide

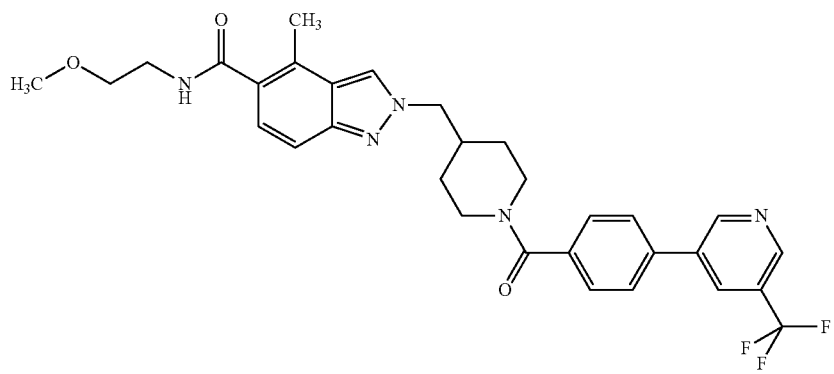 [SMILES: COCCNC(=O)c1ccc2nn(CC3CCN(C(=O)c4ccc(-c5cncc(C(F)(F)F)c5)cc4)CC3)cc2c1C]

Analogously to Example 317, 73 mg of the title compound was obtained from 100 mg of 54 and 56 mg of [5-(trifluoromethyl)pyridin-3-yl]boronic acid under reflux.

$^1$H-NMR (400 MHz, DMSO-$d_6$): δ [ppm]=1.20-1.35 (2H), 1.36-1.67 (2H), 2.23-2.40 (1H), 2.53 (3H), 2.69-2.92 (1H), 2.93-3.17 (1H), 3.28 (3H), 3.35-3.43 (2H), 3.43-3.49 (2H), 3.53-3.75 (1H), 4.37 (3H), 7.18 (1H), 7.42 (1H), 7.52 (2H), 7.93 (2H), 8.07-8.20 (1H), 8.45-8.58 (2H), 9.00 (1H), 9.24 (1H).

EXAMPLE 388

2-[(1-{[4'-(1-hydroxy-1-methylethyl)biphenyl-4-yl]
carbonyl}piperidin-4-yl)-methyl]-N-(2-methoxy-
ethyl)-4-methyl-2H-indazol-5-carboxamide

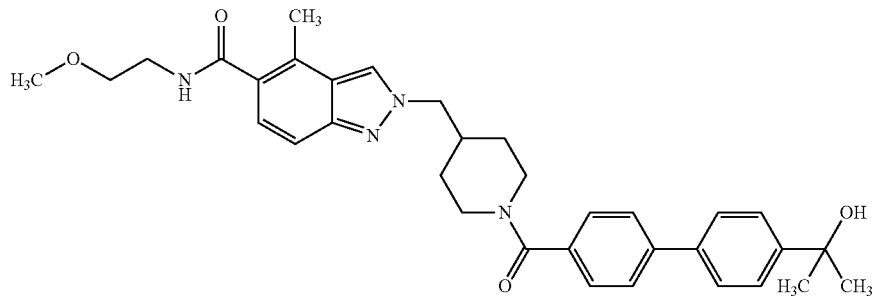 [SMILES: COCCNC(=O)c1ccc2nn(CC3CCN(C(=O)c4ccc(-c5ccc(C(C)(C)O)cc5)cc4)CC3)cc2c1C]

Analogously to Example 317, 46 mg of the title compound was obtained from 100 mg of 54 and 77 mg of (4-hydroxy-tert-butylphenyl)boronic acid pinacol ester under reflux.

$^1$H-NMR (300 MHz, DMSO-d$_6$): δ [ppm]=1.26 (2H), 1.45 (8H), 2.22-2.42 (1H), 2.53 (3H), 2.71-2.90 (1H), 2.91-3.14 (1H), 3.28 (3H), 3.40 (2H), 3.43-3.50 (2H), 3.56-3.80 (1H), 4.36 (3H), 5.06 (1H), 7.18 (d, 1H), 7.37-7.50 (3H), 7.50-7.67 (4H), 7.71 (2H), 8.15 (1H), 8.52 (1H).

EXAMPLE 389

2-({1-[(3',5'-difluorobiphenyl-4-yl)carbonyl]piperi-
din-4-yl}methyl)-N-(2-methoxyethyl)-4-methyl-2H-
indazol-5-carboxamide

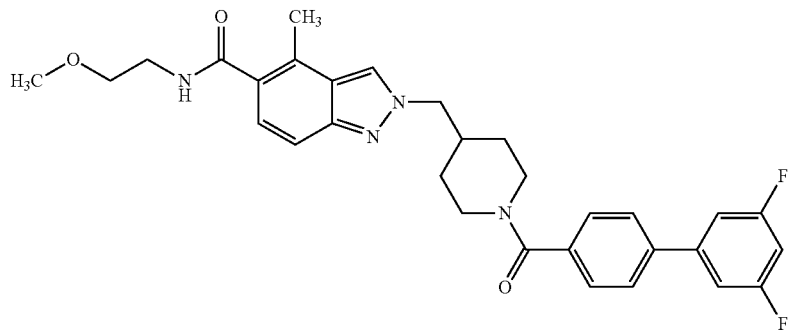 [SMILES: COCCNC(=O)c1ccc2nn(CC3CCN(C(=O)c4ccc(-c5cc(F)cc(F)c5)cc4)CC3)cc2c1C]

Analogously to Example 317, 22 mg of the title compound was obtained from 100 mg of 54 and 46 mg of (3,5-difluorophenyl)boronic acid under reflux.

$^1$H-NMR (400 MHz, DMSO-d$_6$): δ [ppm]=1.18-1.35 (2H), 1.36-1.70 (2H), 2.19-2.39 (1H), 2.52-2.56 (3H), 2.71-2.92 (1H), 2.93-3.17 (1H), 3.28 (3H), 3.36-3.43 (2H), 3.43-3.49 (2H), 3.52-3.71 (1H), 4.36 (3H), 7.11-7.33 (2H), 7.37-7.54 (5H), 7.81 (2H), 8.13 (1H), 8.51 (1H).

EXAMPLE 390

2-({1-[(4'-fluoro-2-methylbiphenyl-4-yl)carbonyl]piperidin-4-yl}methyl)-N-(2-methoxyethyl)-4-methyl-2H-indazol-5-carboxamide

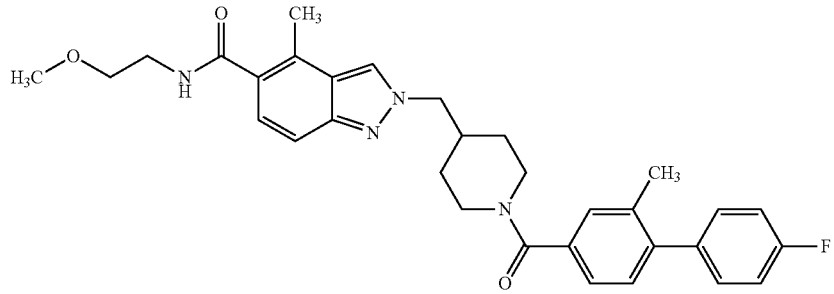

Analogously to Example 317, 25 mg of the title compound was obtained from 60 mg of 332 and 19 mg of (4-fluorophenyl)boronic acid under reflux.

$^1$H-NMR (400 MHz, DMSO-$d_6$): δ [ppm]=1.25 (2H), 1.37-1.67 (2H), 2.24 (4H), 2.53 (3H), 2.69-2.87 (1H), 2.92-3.14 (1H), 3.28 (3H), 3.36-3.43 (2H), 3.43-3.50 (2H), 3.56-3.81 (1H), 4.36 (3H), 7.11-7.34 (6H), 7.36-7.46 (3H), 8.15 (1H), 8.52 (1H).

EXAMPLE 391

2-({1-[(3',5'-difluoro-2-methylbiphenyl-4-yl)carbonyl]piperidin-4-yl}methyl)-N-(2-methoxyethyl)-4-methyl-2H-indazol-5-carboxamide

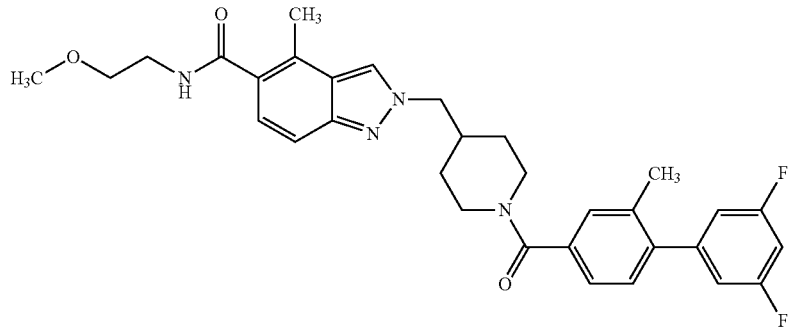 [SMILES: COCCNC(=O)c1ccc2nn(CC3CCN(C(=O)c4ccc(-c5cc(F)cc(F)c5)c(C)c4)CC3)cc2c1C]

Analogously to Example 317, 30 mg of the title compound was obtained from 60 mg of 332 and 27 mg of (3,5-difluorophenyl)boronic acid under reflux.

$^1$H-NMR (400 MHz, DMSO-$d_6$): δ [ppm]=1.23 (2H), 1.36-1.69 (2H), 2.27 (4H), 2.53 (3H), 2.69-2.90 (1H), 2.92-3.15 (1H), 3.28 (3H), 3.36-3.43 (2H), 3.45 (2H), 3.53-3.76 (1H), 4.36 (3H), 7.08-7.21 (3H), 7.22-7.34 (4H), 7.42 (1H), 8.15 (1H), 8.52 (1H).

EXAMPLE 392

N-(2-methoxyethyl)-4-methyl-2-({1-[3-methyl-4-(3-pyridyl)benzoyl]piperidin-4-yl}methyl)-2H-indazol-5-carboxamide

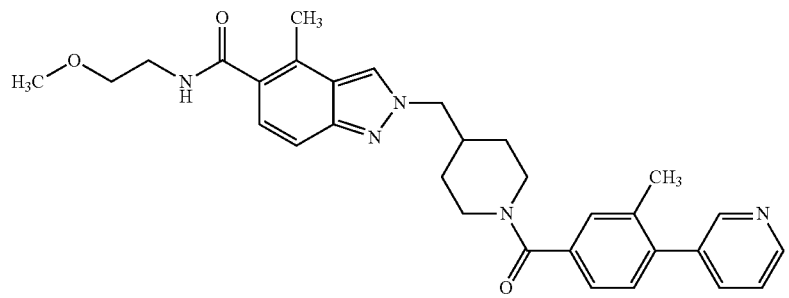 [SMILES: COCCNC(=O)c1ccc2nn(CC3CCN(C(=O)c4ccc(-c5cccnc5)c(C)c4)CC3)cc2c1C]

Analogously to Example 317, 19 mg of the title compound was obtained from 60 mg of 332 and 21 mg of pyridine-3-ylboronic acid under reflux.

$^1$H-NMR (400 MHz, DMSO-d$_6$): δ [ppm]=1.20-1.33 (2H), 1.37-1.71 (2H), 2.26 (4H), 2.53 (3H), 2.70-2.88 (1H), 2.94-3.17 (1H), 3.28 (3H), 3.36-3.43 (2H), 3.43-3.49 (2H), 3.56-3.82 (1H), 4.36 (3H), 7.18 (1H), 7.23-7.37 (3H), 7.39-7.56 (2H), 7.83 (1H), 8.15 (1H), 8.52 (1H), 8.56-8.65 (2H).

EXAMPLE 393

N-(2-methoxyethyl)-4-methyl-2-({1-[3-methyl-4-(4-pyridyl)benzoyl]piperidin-4-yl}methyl)-2H-indazol-5-carboxamide

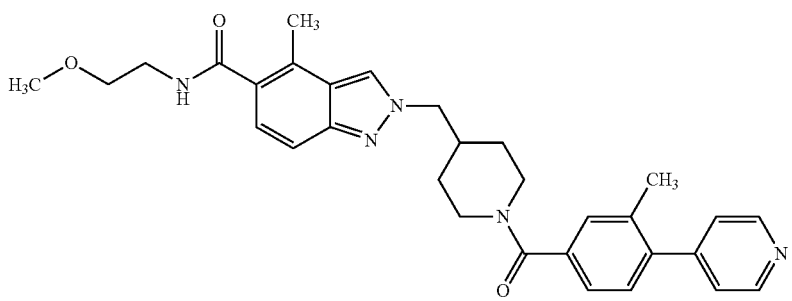 [SMILES: COCCNC(=O)c1ccc2nn(CC3CCN(C(=O)c4ccc(-c5ccncc5)c(C)c4)CC3)cc2c1C]

Analogously to Example 317, 19 mg of the title compound was obtained from 60 mg of 332 and 21 mg of pyridine-4-ylboronic acid under reflux.

$^1$H-NMR (400 MHz, DMSO-d$_6$): δ [ppm]=1.18-1.33 (2H), 1.37-1.67 (2H), 2.27 (4H), 2.52-2.56 (3H), 2.70-2.86 (1H), 2.93-3.13 (1H), 3.28 (3H), 3.36-3.43 (2H), 3.43-3.49 (2H), 3.55-3.75 (1H), 4.36 (3H), 7.18 (1H), 7.23-7.36 (3H), 7.38-7.48 (3H), 8.15 (1H), 8.52 (1H), 8.60-8.69 (2H).

EXAMPLE 394

N-(2-methoxyethyl)-4-methyl-2-({1-[(2-methylbiphenyl-4-yl)carbonyl]piperidin-4-yl}methyl)-2H-indazol-5-carboxamide

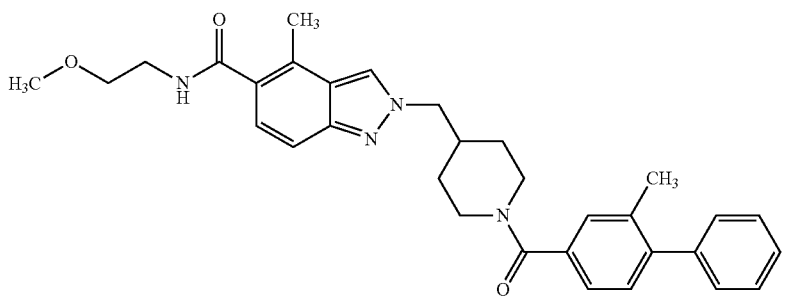

Analogously to Example 317, 57 mg of the title compound was obtained from 60 mg of 332 and 21 mg of phenylboronic acid under reflux.

$^1$H-NMR (400 MHz, DMSO-d$_6$): δ [ppm]=1.19-1.34 (2H), 1.37-1.67 (2H), 2.25 (4H), 2.53 (3H), 2.68-2.88 (1H), 2.92-3.17 (1H), 3.28 (3H), 3.36-3.43 (2H), 3.45 (2H), 3.59-3.81 (1H), 4.36 (3H), 7.13-7.32 (4H), 7.33-7.50 (6H), 8.15 (1H), 8.52 (1H).

EXAMPLE 395

2-{[1-(4-bromobenzoyl)piperidin-4-yl]methyl}-N-(2-mesylethyl)-4-methyl-2H-indazol-5-carboxamide

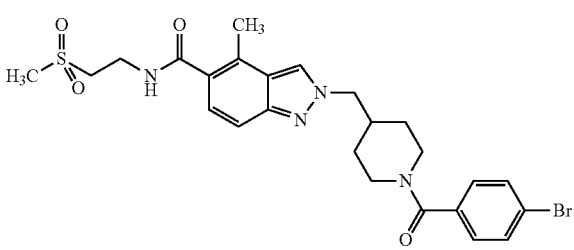 [SMILES: Cc1c(C(=O)NCCS(C)(=O)=O)ccc2nn(CC3CCN(C(=O)c4ccc(Br)cc4)CC3)cc12]

Analogously to Example 1b, Version B, 383 mg of the title compound was obtained from 1 g of 395b and 797 mg of 4-bromobenzoic acid in DMF.

$^1$H-NMR (400 MHz, DMSO-d$_6$): δ [ppm]=1.21-1.32 (2H), 1.34-1.67 (2H), 2.21-2.38 (1H), 2.55 (3H), 2.68-2.87 (1H), 3.05 (4H), 3.39 (2H), 3.45-3.59 (1H), 3.66 (2H), 4.35 (3H), 7.23 (1H), 7.28-7.37 (2H), 7.43 (1H), 7.59-7.70 (2H), 8.34 (1H), 8.52 (1H).

The starting material was prepared as follows:

EXAMPLE 395a

Tert-butyl 4-({5-[N-(2-mesylethyl)carbamoyl]-4-methyl-2H-indazol-2-yl}-methyl)piperidin-1-carboxylate

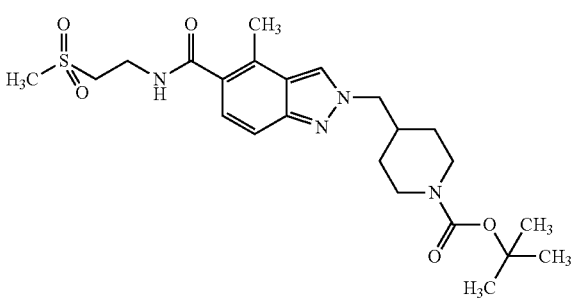 [SMILES: Cc1c(C(=O)NCCS(C)(=O)=O)ccc2nn(CC3CCN(C(=O)OC(C)(C)C)CC3)cc12]

Analogously to Example 266a, 1.26 g of the title compound was obtained from 2.506 g of 1c and 3.022 g of 2-mesylethylamine hydrochloride.

$^1$H-NMR (300 MHz, DMSO-d$_6$): δ [ppm]=1.02-1.17 (2H), 1.34-1.54 (11H), 2.08-2.24 (1H), 2.55 (3H), 2.73 (2H), 3.06 (3H), 3.34-3.47 (2H), 3.57-3.76 (2H), 3.91 (2H), 4.32 (2H), 7.23 (1H), 7.43 (1H), 8.33 (1H), 8.52 (1H).

EXAMPLE 395b

N-(2-mesylethyl)-4-methyl-2-(4-piperidylmethyl)-2H-indazol-5-carboxamide hydrochloride

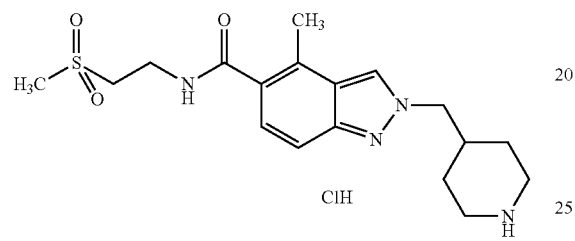

Analogously to Example 258b from 1.26 g of compound 395a, 1.29 g of the title compound was obtained, which was reacted without further purification.

EXAMPLE 396

N-(2-mesylethyl)-4-methyl-2-{[1-(4-{[5-(trifluoromethyl)pyridin-2-yl]oxy}-benzoyl)piperidin-4-yl]methyl}-2H-indazol-5-carboxamide

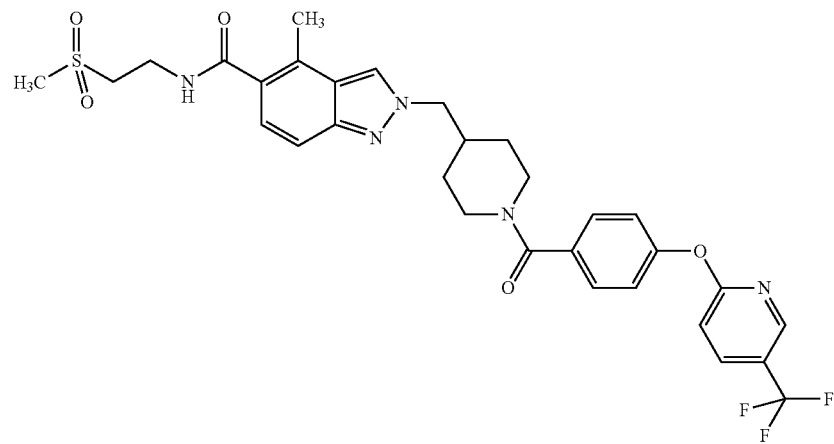 [SMILES: Cc1c(C(=O)NCCS(C)(=O)=O)ccc2nn(CC3CCN(C(=O)c4ccc(Oc5ccc(C(F)(F)F)cn5)cc4)CC3)cc12]

Analogously to Example 1b, Version B, 30 mg of the title compound was obtained from 80 mg of 395b and 90 mg of 4-{[5-(trifluoromethyl)pyridin-2-yl]oxy}benzoic acid in DMF.

$^1$H-NMR (400 MHz, DMSO-d$_6$): δ [ppm]=1.19-1.35 (2H), 1.36-1.72 (2H), 2.22-2.41 (1H), 2.55 (3H), 3.06 (5H), 3.39 (2H), 3.49-3.89 (3H), 4.37 (3H), 7.20-7.32 (4H), 7.40-7.49 (3H), 8.25 (1H), 8.34 (1H), 8.53 (1H), 8.58 (1H).

EXAMPLE 397

N-(2-mesylethyl)-4-methyl-2-{[1-(4-{[6-(trifluoromethyl)pyridin-3-yl]oxy}-benzoyl)piperidin-4-yl]methyl}-2H-indazol-5-carboxamide

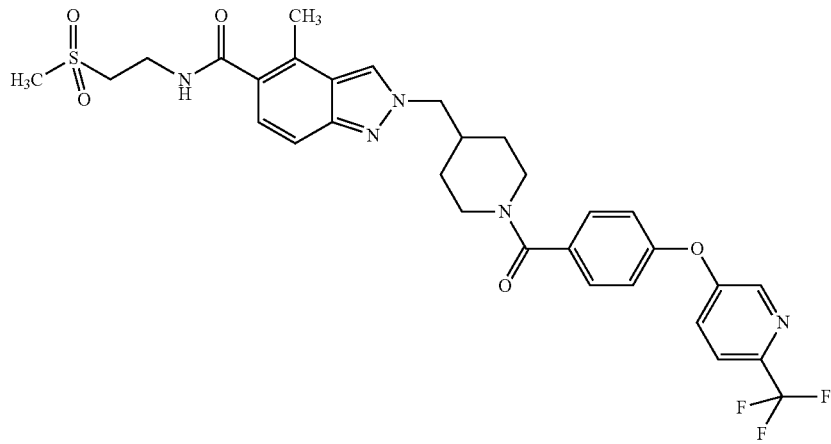 [SMILES: Cc1c(C(=O)NCCS(C)(=O)=O)ccc2nn(CC3CCN(C(=O)c4ccc(Oc5ccc(C(F)(F)F)nc5)cc4)CC3)cc12]

Analogously to Example 1b, Version B, 30 mg of the title compound was obtained from 80 mg of 395b and 90 mg of 303b in DMF.

$^1$H-NMR (400 MHz, DMSO-d$_6$): δ [ppm]=1.24 (2H), 1.35-1.70 (2H), 2.22-2.40 (1H), 2.55 (3H), 3.06 (5H), 3.39 (2H), 3.55-3.75 (3H), 4.36 (3H), 7.20-7.28 (3H), 7.40-7.49 (3H), 7.65 (1H), 7.92 (1H), 8.34 (1H), 8.53 (1H), 8.60 (1H).

EXAMPLE 398

2-({1-[(2',4'-difluorobiphenyl-4-yl)carbonyl]piperidin-4-yl}methyl)-N-(2-mesylethyl)-4-methyl-2H-indazol-5-carboxamide

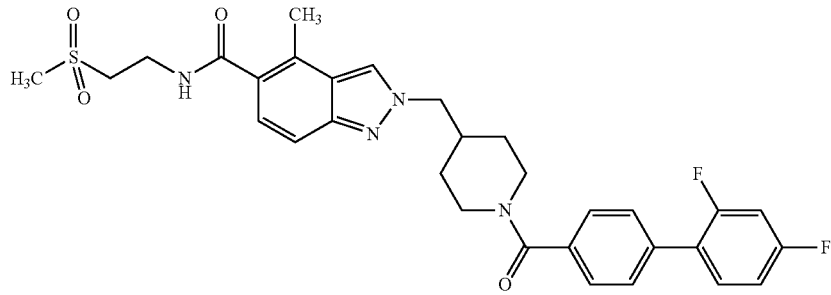 [SMILES: Cc1c(C(=O)NCCS(C)(=O)=O)ccc2nn(CC3CCN(C(=O)c4ccc(-c5ccc(F)cc5F)cc4)CC3)cc12]

Analogously to Example 1b, Version B, 25 mg of the title compound was obtained from 80 mg of 395b and 74 mg of 2',4'-difluorobiphenyl-4-carboxylic acid in DMF.

$^1$H-NMR (400 MHz, DMSO-d$_6$): δ [ppm]=1.21-1.35 (2H), 1.37-1.70 (2H), 2.22-2.41 (1H), 2.55 (3H), 3.05 (5H), 3.38 (2H), 3.50-3.83 (3H), 4.37 (3H), 7.15-7.29 (2H), 7.31-7.52 (4H), 7.55-7.73 (3H), 8.34 (1H), 8.53 (1H).

EXAMPLE 399

2-{[1-(4-chlorobenzoyl)piperidin-4-yl]methyl}-N-(3-hydroxy-3-methylbutyl)-4-methyl-2H-indazol-5-carboxamide

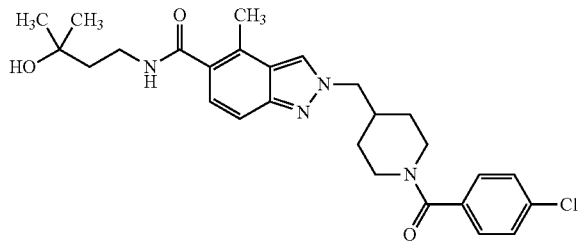 [SMILES: Cc1c(C(=O)NCCC(C)(C)O)ccc2nn(CC3CCN(C(=O)c4ccc(Cl)cc4)CC3)cc12]

Analogously to Example 1b, Version B, 37 mg of the title compound was obtained from 160 mg of 399b and 105 mg of 4-chlorobenzoic acid in DMF.

$^1$H-NMR (400 MHz, DMSO-$d_6$): δ [ppm]=1.14 (6H), 1.17-1.32 (2H), 1.33-1.71 (4H), 2.23-2.37 (1H), 2.51 (3H), 2.68-2.87 (1H), 2.87-3.13 (1H), 3.31 (2H), 3.47-3.55 (1H), 4.34 (s, 4H), 7.17 (1H), 7.33-7.45 (3H), 7.50 (2H), 7.97-8.09 (1H), 8.50 (1H).

The starting material was prepared as follows:

EXAMPLE 399a

Tert-butyl 4-({5-[N-(3-hydroxy-3-methylbutyl)carbamoyl]-4-methyl-2H-indazol-2-yl}methyl)piperidin-1-carboxylate

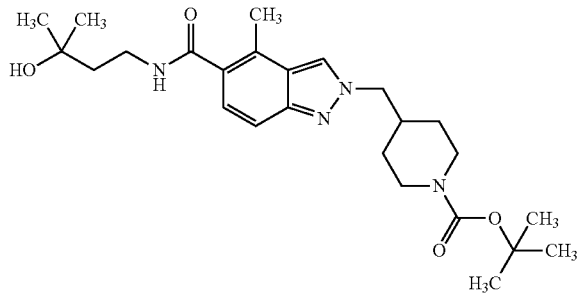 [SMILES: Cc1c(C(=O)NCCC(C)(C)O)ccc2nn(CC3CCN(C(=O)OC(C)(C)C)CC3)cc12]

Analogously to Example 1b, Version B, 150 mg of 1d and 69 mg of 4-amino-2-methylbutan-2-ol in DMF were reacted at 60° C. After phase separation and extraction, the combined organic phases were additionally washed with 0.1 N hydrochloric acid and saturated sodium hydrogen carbonate solution. This yielded 132 mg of the title compound, which was used in the next step without further purification.

EXAMPLE 399b

N-(3-hydroxy-3-methylbutyl)-4-methyl-2-(4-piperidylmethyl)-2H-indazol-5-carboxamide

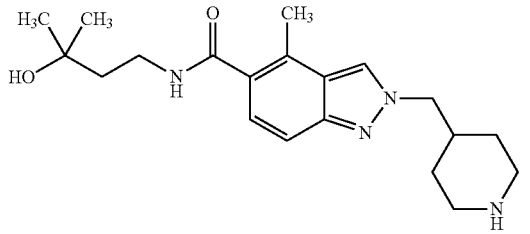 [SMILES: Cc1c(C(=O)NCCC(C)(C)O)ccc2nn(CC3CCNCC3)cc12]

Analogously to Example 258b, from 132 mg of 399a, 162 mg of the title compound was obtained, which was used in the next step without further purification.

EXAMPLE 400

2-{[1-(4-chlorobenzoyl)piperidin-4-yl]methyl}-N-(2-cyanoethyl)-4-methyl-2H-indazol-5-carboxamide

Analogously to Example 1b, Version B, 55 mg of the title compound was obtained from 177 mg of 400b and 128 mg of 4-chlorobenzoic acid in DMF.

$^1$H-NMR (400 MHz, DMSO-$d_6$): δ [ppm]=1.23 (2H), 1.33-1.70 (2H), 2.20-2.38 (1H), 2.56 (3H), 2.78 (3H), 2.90-3.11 (1H), 3.47 (3H), 4.35 (3H), 7.22 (1H), 7.34-7.56 (5H), 8.44-8.57 (2H).

The starting material was prepared as follows:

EXAMPLE 400a

Tert-butyl 4-({5-[N-(2-cyanoethyl)carbamoyl]-4-methyl-2H-indazol-2-yl}-methyl)-piperidin-1-carboxylate

Analogously to Example 1b, Version B, 150 mg of 1d and 42 mg of 3-aminopropannitrile in DMF were reacted at 60° C. After phase separation and extraction, the combined organic phases were additionally washed with 0.1 N hydrochloric acid and saturated sodium hydrogen carbonate solution. This yielded 137 mg of the title compound, which was used in the next step without further purification.

EXAMPLE 400b

N-(2-cyanoethyl)-4-methyl-2-(4-piperidylmethyl)-2H-indazol-5-carboxamide

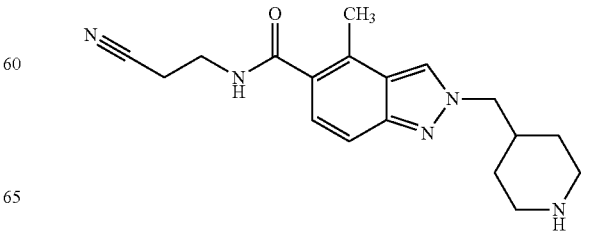

Analogously to Example 258b, from 137 mg of 400a 177 mg of the title compound was obtained, which was used in the next step without further purification.

EXAMPLE 401

2-{[1-(4-chlorobenzoyl)piperidin-4-yl]methyl}-N-(cyanomethyl)-4-methyl-2H-indazol-5-carboxamide

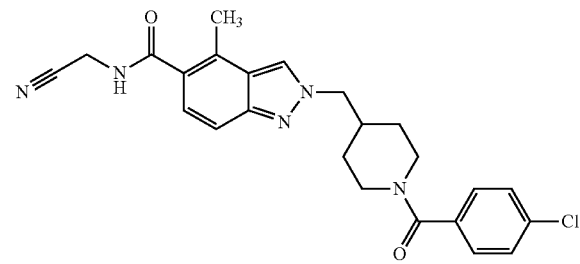 [SMILES: Cc1c(C(=O)NCC#N)ccc2nn(CC3CCN(C(=O)c4ccc(Cl)cc4)CC3)cc12]

Analogously to Example 1b, Version B, 75 mg of the title compound was obtained from 90 mg of 238c and 29 mg of aminoacetonitrile in DMF.

$^1$H-NMR (400 MHz, DMSO-d$_6$): δ [ppm]=1.21-1.33 (23H), 1.34-1.69 (2H), 2.15-2.41 (1H), 2.57 (3H), 2.75-2.86 (1H), 2.93-3.14 (1H), 3.39-3.69 (1H), 4.29 (2H), 4.33-4.55 (3H), 7.18-7.28 (1H), 7.39 (2H), 7.43-7.55 (3H), 8.57 (1H), 8.77-8.90 (1H).

EXAMPLE 402

2-{[1-(4-chlorobenzoyl)piperidin-4-yl]methyl}-N-(cyclopropylmethyl)-4-methyl-2H-indazol-5-carboxamide

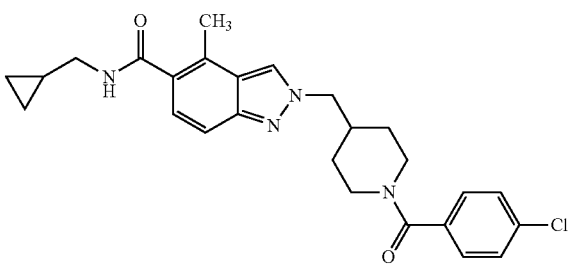 [SMILES: Cc1c(C(=O)NCC2CC2)ccc2nn(CC3CCN(C(=O)c4ccc(Cl)cc4)CC3)cc12]

Analogously to Example 1b, Version B, 44 mg of the title compound was obtained from 90 mg of 238c) and 19 mg of cyclopropylmethylamine in DMF.

$^1$H-NMR (300 MHz, DMSO-d$_6$): δ [ppm]=0.23 (2H), 0.33-0.53 (2H), 0.94-1.11 (1H), 1.20-1.33 (2H), 1.34-1.68 (2H), 2.21-2.41 (1H), 2.54 (3H), 2.69-2.85 (1H), 2.93-3.08 (1H), 3.13 (2H), 3.44-3.68 (1H), 4.35 (3H), 7.18 (1H), 7.33-7.46 (3H), 7.47-7.60 (2H), 8.07-8.30 (1H), 8.51 (1H).

EXAMPLE 403

N-(cyclobutylmethyl)-4-methyl-2-[(1-{4-[4-(trifluoromethyl)phenoxy]benzoyl}-piperidin-4-yl)methyl]-2H-indazol-5-carboxamide

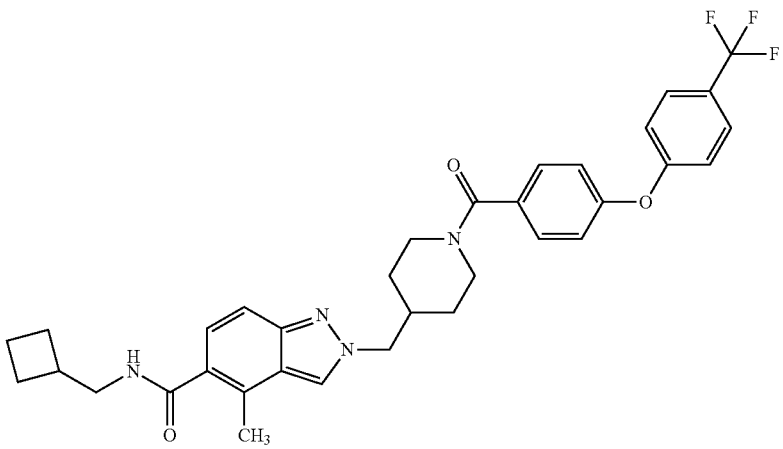 [SMILES: Cc1c(C(=O)NCC2CCC2)ccc2nn(CC3CCN(C(=O)c4ccc(Oc5ccc(C(F)(F)F)cc5)cc4)CC3)cc12]

Analogously to Example 1b, Version B, 48 mg of the title compound was obtained from 137 mg of 403b and 31 mg of (cyclobutylamino)methylamine hydrochloride.

¹H-NMR (400 MHz, DMSO-d₆): δ [ppm]=1.17-1.32 (2H), 1.35-1.64 (2H), 1.67-1.90 (4H), 1.93-2.08 (2H), 2.22-2.38 (1H), 2.51-2.52 (3H), 2.69-2.88 (1H), 2.90-3.13 (1H), 3.20-3.30 (2H), 3.51-3.83 (1H), 4.36 (3H), 7.09-7.27 (5H), 7.35-7.52 (3H), 7.76 (2H), 8.13 (1H), 8.51 (1H).

The starting material was prepared as follows:

EXAMPLE 403a

Methyl 4-methyl-2-[(1-{4-[4-(trifluoromethyl)phenoxy]benzoyl}piperidin-4-yl)methyl]-2H-indazol-5-carboxylate

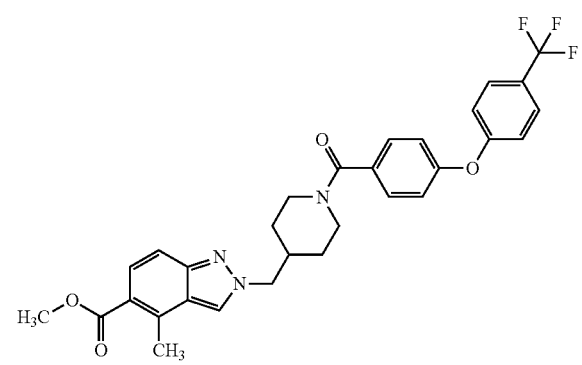 [SMILES: COC(=O)c1ccc2nn(CC3CCN(C(=O)c4ccc(Oc5ccc(C(F)(F)F)cc5)cc4)CC3)cc2c1C]

Analogously to Example 1b, Version B, 2.73 g of the title compound was obtained from 3.76 g of 238a and 3.28 g of 4-[4-(trifluoromethyl)phenoxy]benzoic acid.

¹H-NMR (400 MHz, DMSO-d₆): δ [ppm]=1.19-1.35 (2H), 1.38-1.74 (2H), 2.17-2.41 (1H), 2.76 (3H), 2.78-3.14 (2H), 3.44-3.76 (1H), 3.82 (3H), 4.37 (3H), 7.06-7.28 (4H), 7.38-7.50 (3H), 7.67 (1H), 7.76 (2H), 8.71 (1H).

EXAMPLE 403b 4-methyl-2-[(1-{4-[4-(trifluoromethyl)phenoxy]benzoyl}piperidin-4-yl)-methyl]-2H-indazol-5-carboxylic acid

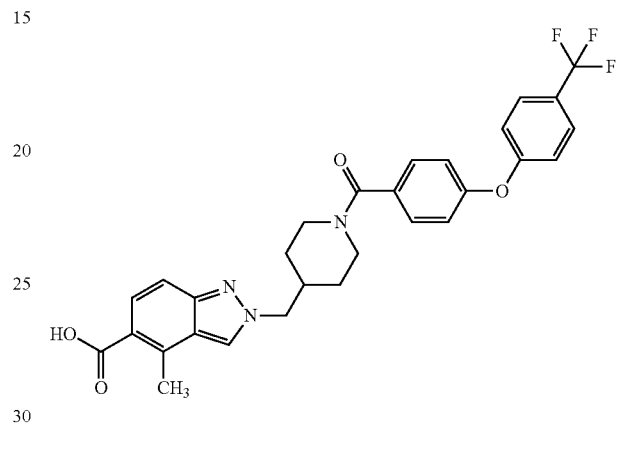

Analogously to Example 1d, from 1.05 g of 403a, 970 mg of the title compound was obtained, which was used in the next step without further purification.

EXAMPLE 404

N-isobutyl-4-methyl-2-[(1-{4-[4-(trifluoromethyl)phenoxy]benzoyl}piperidin-4-yl)methyl]-2H-indazol-5-carboxamide

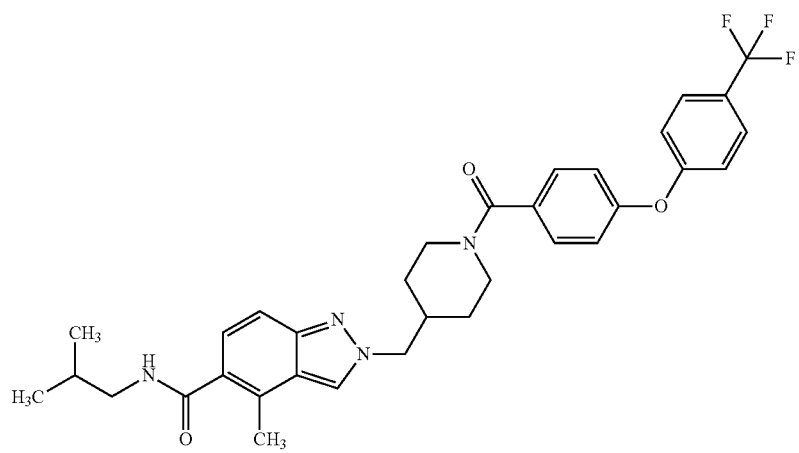 [SMILES: Cc1c(C(=O)NCC(C)C)ccc2nn(CC3CCN(C(=O)c4ccc(Oc5ccc(C(F)(F)F)cc5)cc4)CC3)cc12]

Analogously to Example 1b, Version B, 35 mg of the title compound was obtained from 100 mg of 403b and 14 mg of isobutylamine.

¹H-NMR (300 MHz, DMSO-d₆): δ [ppm]=0.91 (6H), 1.24 (2H), 1.34-1.69 (2H), 1.82 (1H), 2.19-2.42 (1H), 2.52 (3H), 2.71-2.90 (1H), 3.06 (3H), 3.51-3.85 (1H), 4.36 (3H), 7.05-7.27 (5H), 7.37-7.52 (3H), 7.76 (2H), 8.16 (1H), 8.51 (1H).

EXAMPLE 405

4-methyl-N-neopentyl-2-[(1-{4-[4-(trifluoromethyl)phenoxy]benzoyl}piperidin-4-yl)methyl]-2H-indazol-5-carboxamide

EXAMPLE 406

N-(cyclopropylmethyl)-4-methyl-2-[(1-{4-[4-(trifluoromethyl)phenoxy]-benzoyl}piperidin-4-yl)methyl]-2H-indazol-5-carboxamide

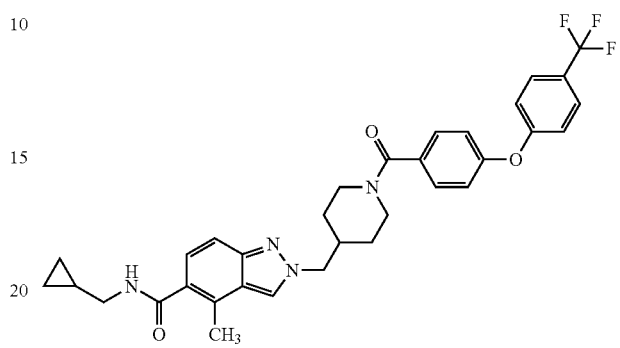

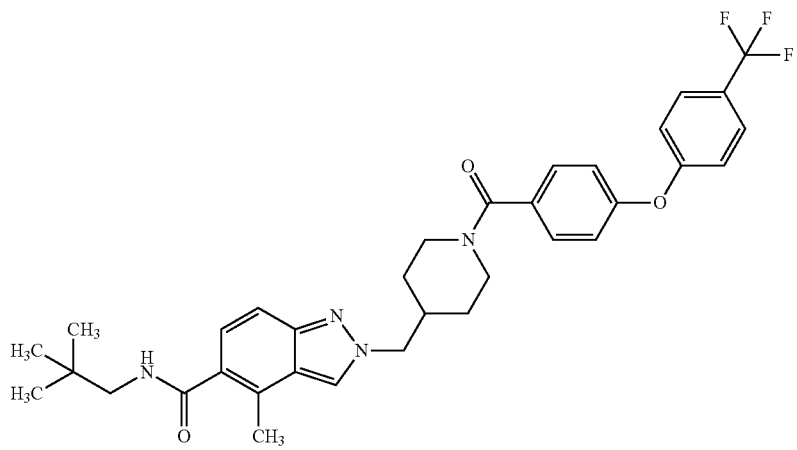 [SMILES: Cc1c(C(=O)NCC(C)(C)C)ccc2nn(CC3CCN(C(=O)c4ccc(Oc5ccc(C(F)(F)F)cc5)cc4)CC3)cc12]

Analogously to Example 1b, Version B, 36 mg of the title compound was obtained from 100 mg of 403b and 16 mg of neopentylamine.

¹H-NMR (400 MHz, DMSO-d₆): δ [ppm]=0.92 (9H), 1.17-1.32 (2H), 1.34-1.69 (2H), 2.21-2.38 (1H), 2.52-2.57 (3H), 2.70-2.88 (1H), 3.08 (3H), 3.53-3.85 (1H), 4.36 (3H), 7.04-7.28 (5H), 7.35-7.52 (3H), 7.76 (2H), 8.12 (1H), 8.51 (1H).

Analogously to Example 1b, Version B, 33 mg of the title compound was obtained from 100 mg of 403b and 26 mg of cyclopropylmethylamine.

¹H-NMR (300 MHz, DMSO-d₆): δ [ppm]=0.23 (2H), 0.35-0.54 (2H), 0.93-1.11 (1H), 1.23 (2H), 1.36-1.67 (2H), 2.18-2.41 (1H), 2.54 (3H), 2.66-3.22 (4H), 3.47-3.85 (1H), 4.36 (3H), 7.03-7.29 (5H), 7.35-7.53 (3H), 7.76 (2H), 8.22 (1H), 8.52 (1H).

EXAMPLE 407

N-(2-cyanoethyl)-2-({1-[(4'-fluorobiphenyl-4-yl)carbonyl]piperidin-4-yl}-methyl)-4-methyl-2H-indazol-5-carboxamide

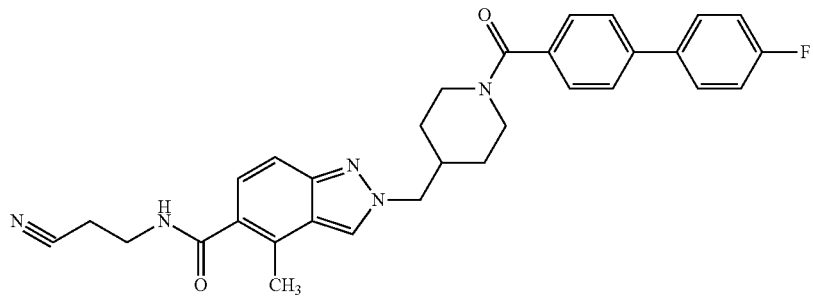 [SMILES: Cc1c(C(=O)NCCC#N)ccc2nn(CC3CCN(C(=O)c4ccc(-c5ccc(F)cc5)cc4)CC3)cc12]

Analogously to Example 1b, Version B, 37 mg of the title compound was obtained from 140 mg of 407a and 84 mg of 4'-fluorobiphenyl-4-carboxylic acid.

$^1$H-NMR (300 MHz, DMSO-d$_6$): δ [ppm]=1.18-1.37 (2H), 1.37-1.68 (2H), 2.22-2.41 (1H), 2.56 (3H), 2.78 (4H), 3.39-3.53 (2H), 3.56-3.82 (1H), 4.37 (3H), 7.14-7.37 (3H), 7.39-7.53 (3H), 7.63-7.83 (4H), 8.36-8.60 (2H).

The starting material was prepared as follows:

EXAMPLE 407a

N-(2-cyanoethyl)-4-methyl-2-(4-piperidylmethyl)-2H-indazol-5-carboxamide hydrochloride

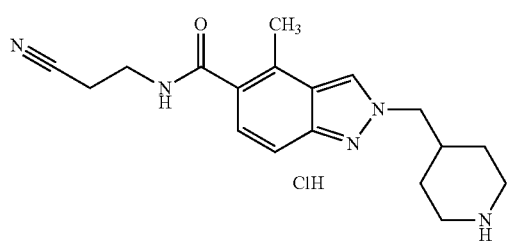 [SMILES: Cc1c(C(=O)NCCC#N)ccc2nn(CC3CCNCC3)cc12 ; Cl]

Analogously to Example 1a, from 165 mg of 400a, 140 mg of the title compound was obtained, which was used in the next step without further purification.

EXAMPLE 408

2-({1-[(4'-fluorobiphenyl-4-yl)carbonyl]piperidin-4-yl}methyl)-N-(2-mesylethyl)-4-methyl-2H-indazol-5-carboxamide

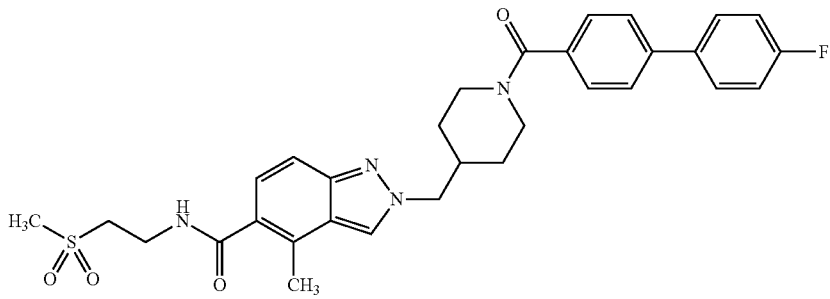 [SMILES: Cc1c(C(=O)NCCS(C)(=O)=O)ccc2nn(CC3CCN(C(=O)c4ccc(-c5ccc(F)cc5)cc4)CC3)cc12]

Analogously to Example 1b), Version B, 126 mg of the title compound was obtained from 300 mg of 408a) and 156 mg of 4'-fluorobiphenyl-4-carboxylic acid.

LC-MS: $R_t$=1.20 min, MS (ES+): m/z=577 (M+H)$^+$.

The starting material was prepared as follows:

EXAMPLE 408a

N-(2-mesylethyl)-4-methyl-2-(4-piperidylmethyl)-2H-indazol-5-carboxamide hydrochloride

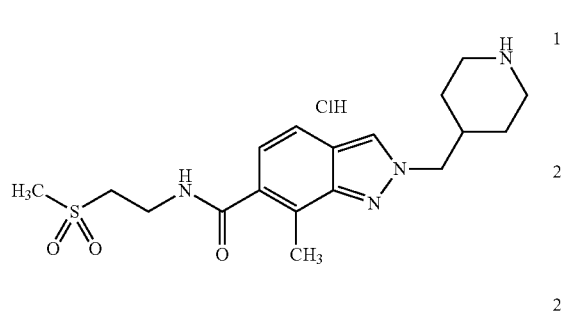

Analogously to Example 1a, from 346 mg of 395a, 300 mg of the title compound was obtained, which was used in the next step without further purification.

EXAMPLE 409

2-({1-[(4'-fluorobiphenyl-4-yl)carbonyl]piperidin-4-yl}methyl)-N-(3-hydroxypropyl)-4-methyl-2H-indazol-5-carboxamide

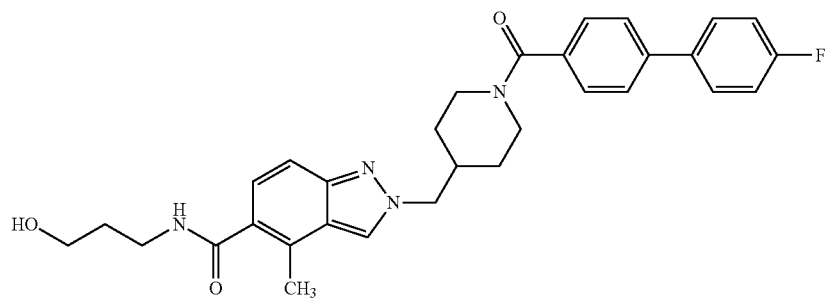 [SMILES: Cc1c(C(=O)NCCCO)ccc2nn(CC3CCN(C(=O)c4ccc(-c5ccc(F)cc5)cc4)CC3)cc12]

Analogously to Example 1b, Version B, 20 mg of the title compound was obtained from 124 mg of 409b) and 73 mg of 4'-fluorobiphenyl-4-carboxylic acid.

$^1$H-NMR (300 MHz, DMSO-d$_6$): δ [ppm]=1.26 (2H), 1.38-1.59 (2H), 1.67 (2H), 2.23-2.42 (1H), 2.52-2.57 (3H), 2.69-3.17 (2H), 3.19-3.94 (6H), 4.36 (3H), 7.18 (1H), 7.31 (2H), 7.38-7.51 (3H), 7.63-7.86 (4H), 8.08 (1H), 8.51 (1H).

The starting material was prepared as follows:

EXAMPLE 409a

Tert-butyl 4-({5-[N-(3-hydroxypropyl)carbamoyl]-4-methyl-2H-indazol-2-yl}-methyl)piperidin-1-carboxylate

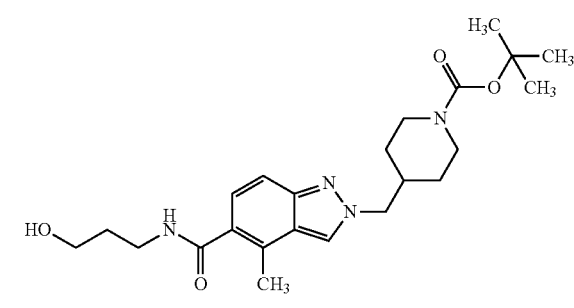 [SMILES: Cc1c(C(=O)NCCCO)ccc2nn(CC3CCN(C(=O)OC(C)(C)C)CC3)cc12]

Analogously to Example 1b, Version B, 151 mg of the title compound was obtained from 150 mg of 1d and 30 mg of 3-amino-propan-1-ol.

$^1$H-NMR (400 MHz, DMSO-d$_6$): δ [ppm]=1.01-1.30 (3H), 1.32-1.49 (10H), 1.67 (2H), 2.08-2.27 (1H), 2.52 (3H), 2.57-2.80 (2H), 3.29 (2H), 3.41-3.54 (2H), 3.81-4.00 (2H), 4.32 (2H), 4.48 (1H), 7.18 (1H), 7.42 (1H), 8.10 (1H), 8.50 (1H).

EXAMPLE 409b

N-(3-hydroxypropyl)-4-methyl-2-(4-piperidylmethyl)-2H-indazol-5-carboxamide

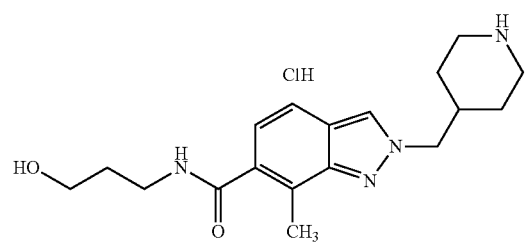 [SMILES: Cc1c(C(=O)NCCCO)ccc2cn(CC3CCNCC3)nc12 ; Cl]

Analogously to Example 1a, from 246 mg of 409a, 124 mg of the title compound was obtained, which was used in the next step without further purification.

EXAMPLE 410

2-({1-[(4'-fluorobiphenyl-4-yl)carbonyl]piperidin-4-yl}methyl)-N-(2-hydroxyethyl)-4-methyl-2H-indazol-5-carboxamide

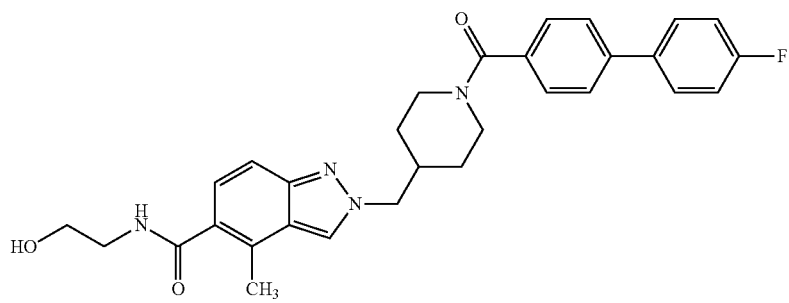 [SMILES: Cc1c(C(=O)NCCO)ccc2nn(CC3CCN(C(=O)c4ccc(-c5ccc(F)cc5)cc4)CC3)cc12]

Analogously to Example 1b, Version B, 36 mg of the title compound was obtained from 117 mg of 410b and 72 mg of 4'-fluorobiphenyl-4-carboxylic acid.

$^1$H-NMR (300 MHz, DMSO-d$_6$): δ [ppm]=1.26 (2H), 1.39-1.74 (2H), 2.21-2.40 (1H), 2.53 (3H), 2.75-3.16 (2H), 3.20-3.37 (2H), 3.43-3.74 (4H), 4.36 (3H), 7.21 (1H), 7.31 (2H), 7.38-7.52 (3H), 7.65-7.81 (4H), 8.03 (1H), 8.51 (1H).

The starting material was prepared as follows:

EXAMPLE 410a

Tert-butyl 4-({5-[N-(2-hydroxyethyl)carbamoyl]-4-methyl-2H-indazol-2-yl}-methyl)piperidin-1-carboxylate

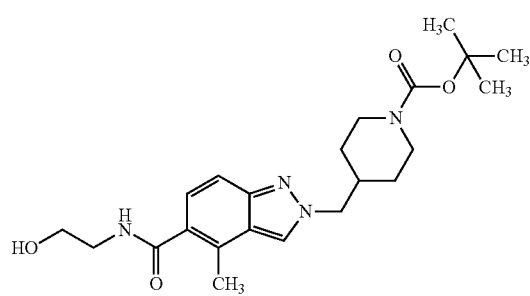 [SMILES: Cc1c(C(=O)NCCO)ccc2nn(CC3CCN(C(=O)OC(C)(C)C)CC3)cc12]

Analogously to Example 1b, Version B, 143 mg of the title compound was obtained from 150 mg of 1d) and 25 mg of 2-aminoethan-1-ol.

$^1$H-NMR (400 MHz, DMSO-d$_6$): δ [ppm]=1.01-1.30 (3H), 1.32-1.51 (10H), 2.07-2.26 (1H), 2.52-2.55 (3H), 2.58-2.82 (2H), 3.30 (2H), 3.45-3.58 (2H), 3.83-3.98 (2H), 4.32 (2H), 4.69 (1H), 7.21 (1H), 7.41 (1H), 8.05 (1H), 8.50 (1H).

EXAMPLE 410b

N-(3-hydroxypropyl)-4-methyl-2-(4-piperidylmethyl)-2H-indazol-5-carboxamide hydrochloride

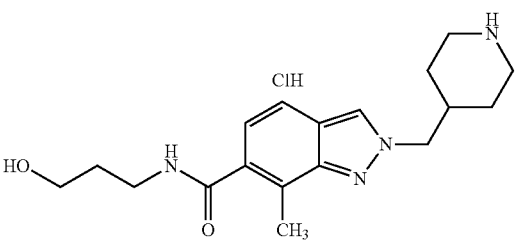 [SMILES: Cc1c(C(=O)NCCCO)ccc2cn(CC3CCNCC3)nc12 ; Cl]

Analogously to Example 1a) from 138 mg of 410a, 117 mg of the title compound was obtained, which was used in the next step without further purification.

EXAMPLE 411

(+/−)-N-(1,4-dioxan-2-ylmethyl)-2-({1-[(4'-fluorobiphenyl-4-yl)carbonyl]-piperidin-4-yl}methyl)-4-methyl-2H-indazol-5-carboxamide

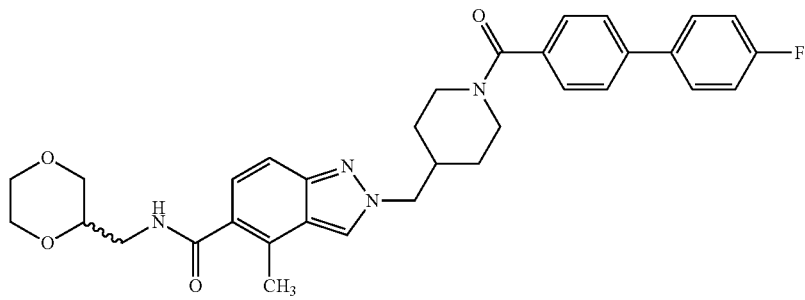 [SMILES: Cc1c(C(=O)NCC2COCCO2)ccc2nn(CC3CCN(C(=O)c4ccc(-c5ccc(F)cc5)cc4)CC3)cc12]

Analogously to Example 1b, Version B, 62 mg of the title compound was obtained from 226 mg of 411b) and 119 mg of 4'-fluorobiphenyl-4-carboxylic acid.

$^1$H-NMR (400 MHz, DMSO-d$_6$): δ [ppm]=1.19-1.34 (2H), 1.37-1.73 (2H), 2.23-2.42 (1H), 2.53 (3H), 2.69-2.90 (1H), 2.90-3.14 (1H), 3.17-3.30 (3H), 3.47 (1H), 3.58 (1H), 3.59-3.70 (3H), 3.71-3.82 (2H), 4.37 (3H), 7.19 (1H), 7.31 (2H), 7.38-7.53 (3H), 7.66-7.81 (4H), 8.18 (1H), 8.52 (1H).

The starting material was prepared as follows:

EXAMPLE 411a (+/−)-tert-butyl 4-({5-[N-(1,4-dioxan-2-ylmethyl)carbamoyl]-4-methyl-2H-indazol-2-yl}methyl)piperidin-1-carboxylate

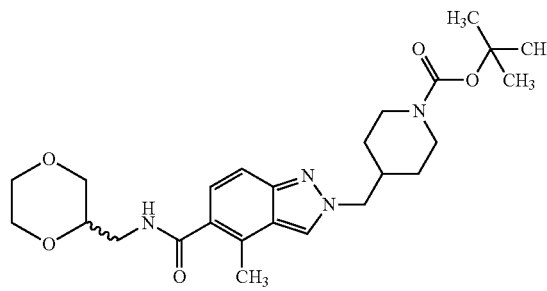

Analogously to Example 1b, Version B, 267 mg of the title compound was obtained from 250 mg of 1d and 78 mg of (+/−)-1,4-dioxan-2-ylmethylamine.

$^1$H-NMR (400 MHz, DMSO-d$_6$): δ [ppm]=0.99-1.18 (2H), 1.38 (11H), 2.09-2.24 (1H), 2.53 (3H), 3.10-3.29 (4H), 3.41-3.52 (1H), 3.53-3.70 (4H), 3.70-3.81 (2H), 3.84-3.98 (2H), 4.32 (2H), 7.18 (1H), 7.41 (1H), 8.12-8.24 (1H), 8.51 (1H).

EXAMPLE 411b (+/−)-N-(1,4-dioxan-2-ylmethyl)-4-methyl-2-(4-piperidylmethyl)-2H-indazol-5-carboxamide hydrochloride

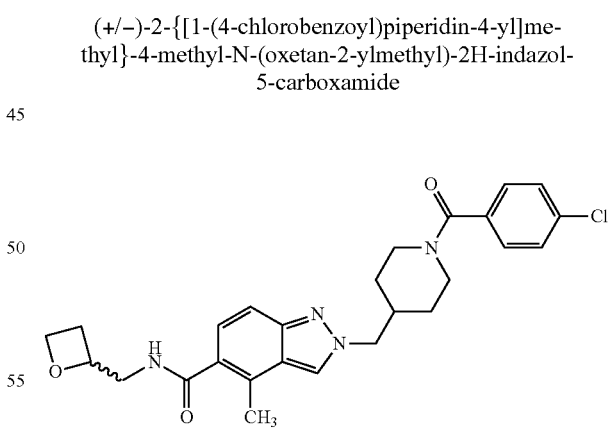

Analogously to Example 1a, from 261 mg of 411a, 226 mg of the title compound was obtained, which was used in the next step without further purification.

EXAMPLE 412

(+/−)-2-{[1-(4-chlorobenzoyl)piperidin-4-yl]methyl}-4-methyl-N-(oxetan-2-ylmethyl)-2H-indazol-5-carboxamide Analogously to Example 1b, Version B, 55 mg of the title compound was obtained from 350 mg of 238c) and 83 mg of (+/−)-oxetan-2-ylmethylamine.

$^1$H-NMR (300 MHz, DMSO-d$_6$): δ [ppm]=1.16-1.31 (2H), 1.33-1.69 (2H), 2.19-2.38 (2H), 2.53 (3H), 2.58-2.66 (1H), 2.66-2.86 (1H), 2.90-3.14 (1H), 3.38-3.64 (3H), 4.35 (5H), 4.71-4.96 (1H), 7.19 (1H), 7.33-7.45 (3H), 7.47-7.55 (2H), 8.21-8.37 (1H), 8.51 (1H).

EXAMPLE 413

(+/−)-2-{[1-(4-chlorobenzoyl)piperidin-4-yl]methyl}-N-(1,4-dioxan-2-ylmethyl)-4-methyl-2H-indazol-5-carboxamide

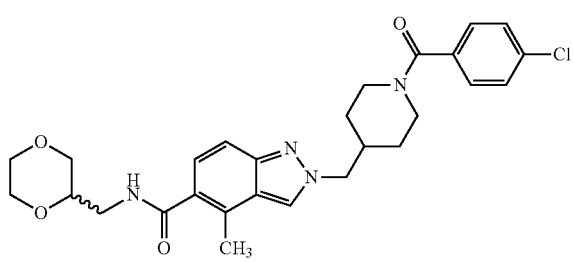

Analogously to Example 1b, Version B, 185 mg of the title compound was obtained from 376 mg of 238c and 111 mg of (+/−)-1,4-dioxan-2-ylmethylamine hydrochloride.

$^1$H-NMR (300 MHz, DMSO-d$_6$): δ [ppm]=1.19-1.32 (2H), 1.33-1.66 (2H), 2.20-2.40 (1H), 2.53 (3H), 2.71-2.86 (1H), 2.90-3.11 (1H), 3.16-3.32 (3H), 3.40-3.59 (3H), 3.60-3.70 (2H), 3.71-3.83 (2H), 4.35 (3H), 7.18 (1H), 7.31-7.46 (3H), 7.46-7.60 (2H), 8.21 (1H), 8.51 (1H).

EXAMPLE 414

(R or S)-2-{[1-(4-chlorobenzoyl)piperidin-4-yl]methyl}-N-(1,4-dioxan-2-ylmethyl)-4-methyl-2H-indazol-5-carboxamide

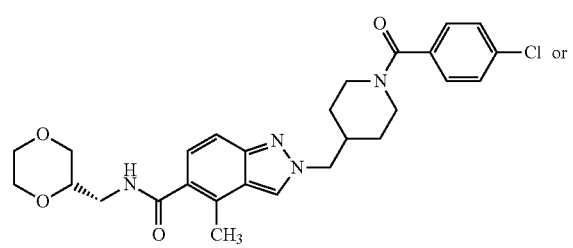

or

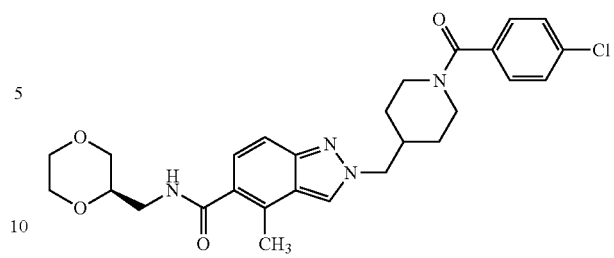

From 185 mg of the racemate prepared in Example 413, 51 mg of the title compound together with 58 mg of the slower-eluting enantiomer (Example 415) were obtained by racemate separation by means of preparative chiral HPLC (Method D).

Analytical chiral HPLC: 12.62 min

EXAMPLE 415

(S or R)-2-{[1-(4-chlorobenzoyl)piperidin-4-yl]methyl}-N-(1,4-dioxan-2-ylmethyl)-4-methyl-2H-indazol-5-carboxamide

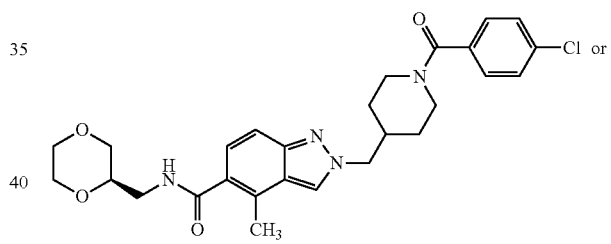

or

From 185 mg of the racemate prepared in Example 413, 58 mg of the title compound together with 51 mg of the faster-eluting enantiomer (Example 414) were obtained by racemate separation by means of preparative chiral HPLC (Method D).

Analytical chiral HPLC: 13.68 min

EXAMPLE 416

(R or S)-4-methyl-N-(3,4,5,6-tetrahydro-2H-pyran-2-ylmethyl)-2-[(1-{4-[4-(trifluoromethyl)phenoxy]benzoyl}piperidin-4-yl)methyl]-2H-indazol-5-carboxamide

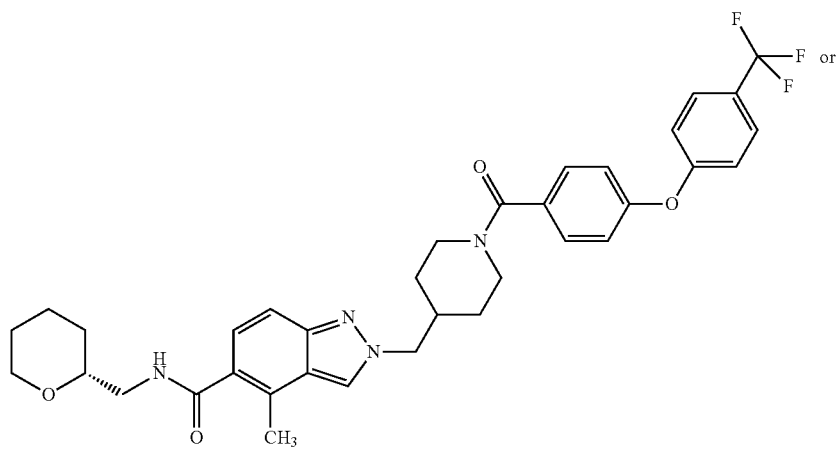

or

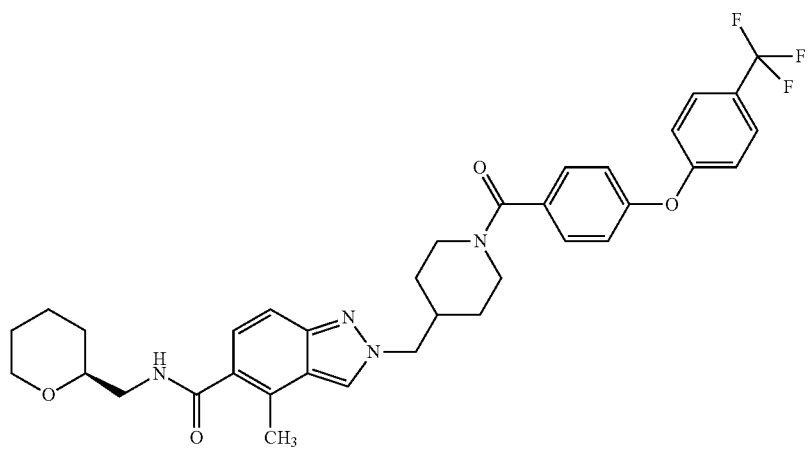

From 231 mg of the racemate prepared in Example 248, 24 mg of the title compound together with 24 mg of the slower-eluting enantiomer (Example 417) were obtained by racemate separation by means of preparative chiral HPLC (Method E).

Analytical chiral HPLC: 7.08 min

EXAMPLE 417

(S or R)-4-methyl-N-(3,4,5,6-tetrahydro-2H-pyran-2-ylmethyl)-2-[(1-{4-[4-(trifluoromethyl)phenoxy]benzoyl}piperidin-4-yl)methyl]-2H-indazol-5-carboxamide

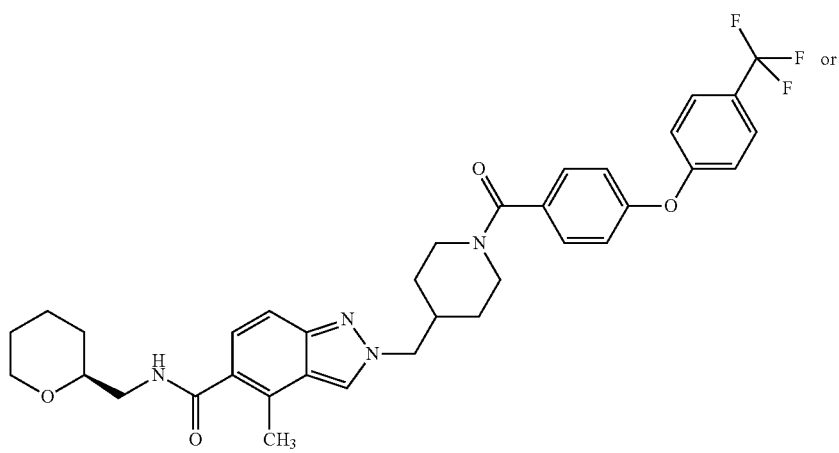

or

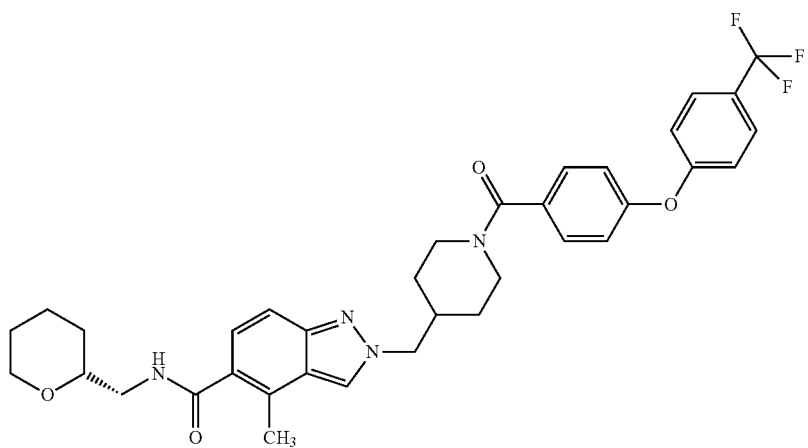

From 231 mg of the racemate prepared in Example 248, 24 mg of the title compound together with 24 mg of the faster-eluting enantiomer (Example 416) were obtained by racemate separation by means of preparative chiral HPLC (Method E).

Analytical chiral HPLC: 8.98 min

EXAMPLE 418

(R or S)—N-(1,4-dioxan-2-ylmethyl)-4-methyl-2-[(1-{4-[4-(trifluoromethyl)-phenoxy]benzoyl}piperidin-4-yl)methyl]-2H-indazol-5-carboxamide

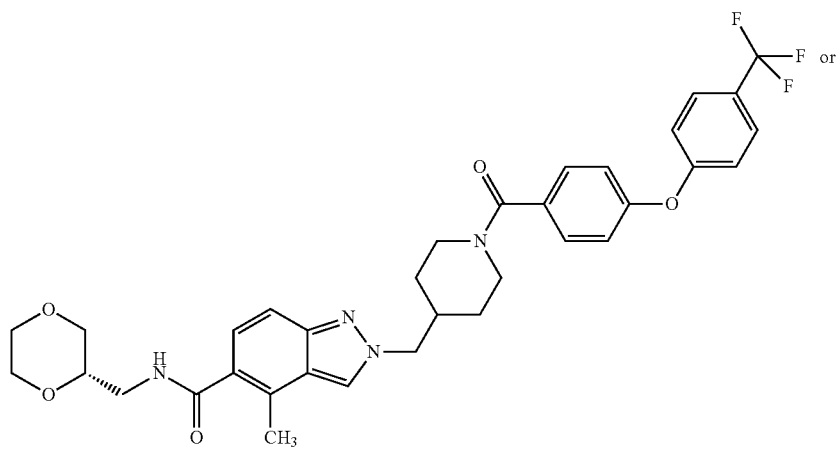

or

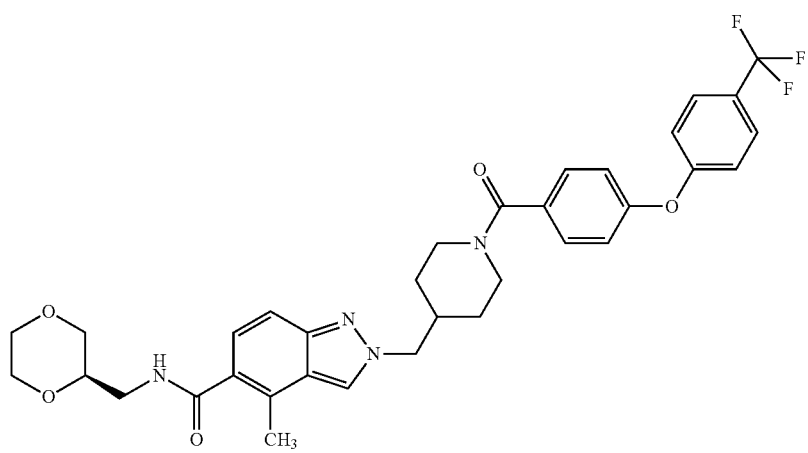

From 280 mg of the racemate prepared in Example 249, 65 mg of the title compound together with 75 mg of the slower-eluting enantiomer (Example 419) were obtained by racemate separation by means of preparative chiral HPLC (Method D (injection volume: 0.1 ml; detection: UV 210 nM)).

Analytical chiral HPLC: 13.66 min

EXAMPLE 419

(R or S)—N-(1,4-dioxan-2-ylmethyl)-4-methyl-2-[(1-{4-[4-(trifluoromethyl)-phenoxy]benzoyl}piperidin-4-yl)methyl]-2H-indazol-5-carboxamide

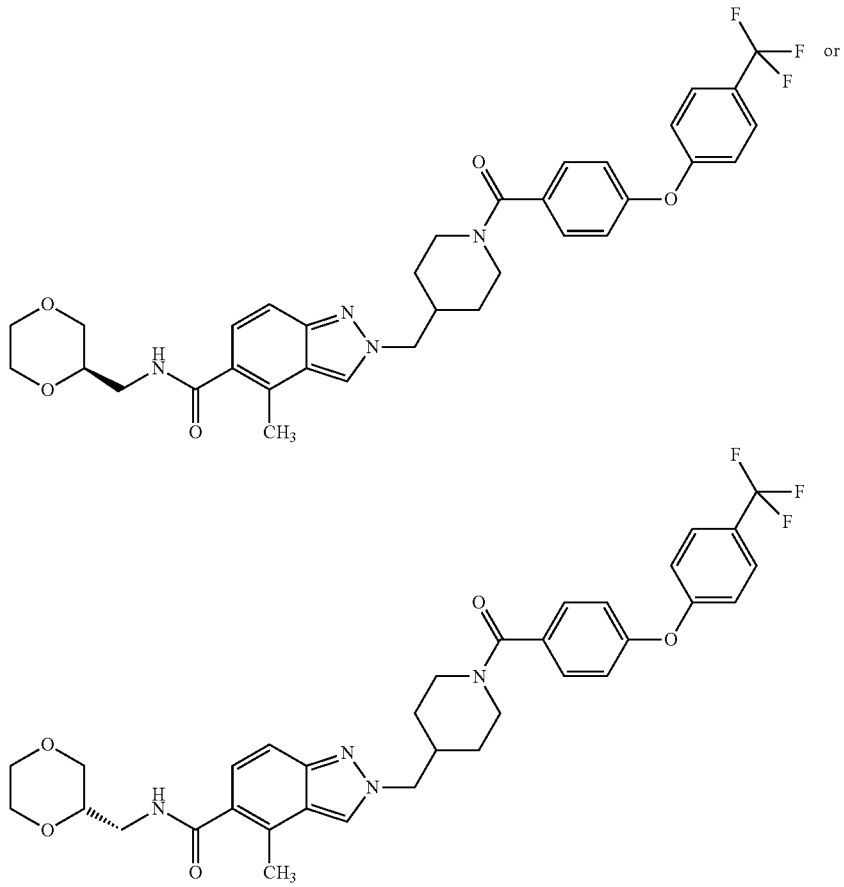

From 280 mg of the racemate prepared in Example 249, 75 mg of the title compound together with 65 mg of the faster-eluting enantiomer (Example 418) were obtained by racemate separation by means of preparative chiral HPLC (Method D (injection volume: 0.1 ml; Detection: UV 210 nM)).

Analytical chiral HPLC: 14.90 min

BIOLOGICAL EXAMPLES

1. Detection of Antagonism to the Human Prostaglandin $E_2$ (Subtype $EP_2$) Receptor Signal 1.1 Detection Principle The binding of $PGE_2$ to the $EP_2$ subtype of the human $PGE_2$ receptor induces the activation of membrane-located adenylate cyclases and leads to the formation of cAMP. In the presence of the phosphodiesterase inhibitor IBMX, the cAMP accumulated owing to this stimulation and released by cell lysis is used in a competitive detection method. In this test, the cAMP present in the lysate competes with a fluorescence-labelled cAMP (cAMP-d2) for binding to an Eu cryptate-labelled anti-cAMP antibody.

In the absence of cellular cAMP, a maximal signal is produced, which is attributable to the binding of this cAMP-d2 molecule to the antibody. After excitation of the cAMP-d2 molecule at 337 nm, there is a fluorescence resonance energy transfer (FRET) to the Eu cryptate molecules of the anti-cAMP antibody (labelled therewith), followed by a long-lasting emission signal at 665 nm (and at 620 nM). Both signals are measured in a suitable measurement instrument with a time delay, i.e. after decay of the background fluorescence. Any increase in the low FRET signal caused by prostaglandin $E_2$ administration (measured as well ratio change=$emission_{665\ nm}$/$emission_{620\ nm}$*10000) indicates the action of antagonists.

1.2. Detection Method 1.2.1. Test for Antagonism (Data Per Well of a 384-Well Plate):

To a test plate with the substance solutions already added (0.05 µl; 100% DMSO, concentration range from 0.8 nM-16.5 µM) were added 4 µl of a cAMP-d2/cell suspension (625000 cells/ml). After a 20-minute preincubation at room temperature (RT), 2 µl of a 3×PGE2 solution (1.5 nM, in PBS-IBMX) were added and incubated in the presence of the agonist for a further 60 mins at RT (volume: ~6 µl). Next the reaction was stopped by addition of 2 µl of lysis buffer and incubated for a further 20 mins at RT before the actual measurement (volume: ~8 µl).

2. Detection of Antagonism to the Human Prostaglandin E₂ (Subtype EP4) Receptor Signal

2.1 Detection Principle

The binding of $PGE_2$ to the $EP_4$ subtype of the human $PGE_2$ receptor induces the activation of membrane-located adenylate cyclases and leads to the formation of cAMP. In the presence of the phosphodiesterase inhibitor IBMX, the cAMP accumulated owing to this stimulation and released by cell lysis is used in a competitive detection method. In this test, the cAMP present in the lysate competes with a fluorescence-labelled cAMP (cAMP-d2) for binding to an Eu cryptate-labelled anti-cAMP antibody.

In the absence of cellular cAMP a maximal signal is produced, which is attributable to the binding of this cAMP-d2 molecule to the antibody. After excitation of the cAMP-d2 molecule at 337 nm, there is a fluorescence resonance energy transfer (FRET) to the Eu cryptate molecules of the anti-cAMP antibody (labelled therewith), followed by a long-lasting emission signal at 665 nm (and at 620 nM). Both signals are measured in a suitable measurement instrument with a time delay, i.e. after decay of the background fluorescence. Any increase in the low FRET signal caused by prostaglandin $E_2$ administration (measured as well ratio change=$\text{emission}_{665\ nm}/\text{emission}_{620\ nm}*10000$) indicates the action of antagonists.

2.2. Detection Method 2.2.1. Test for Antagonism (Data Per Well of a 384-Well Plate):

To a test plate with the substance solutions already added (0.05 µl; 100% DMSO, concentration range from 0.8 nM-16.5 µM) were added 4 µl of a cAMP-d2/cell suspension (312500 cells/ml). After a 20-minute preincubation at room temperature (RT), 2 µl of a 3×PGE2 solution (0.3 nM, in PBS-IBMX) were added and incubated in the presence of the agonist for a further 60 mins at RT (volume: ~6 µl). Next the reaction was stopped by addition of 2 µl of lysis buffer and incubated for a further 20 mins at RT before the actual measurement (volume: ~8 µl).

3. Detection of Antagonism to the Human Prostaglandin D Receptor Signal

3.1 Detection Principle

The binding of prostaglandin D2 to the human PGD receptor induces the activation of membrane-located adenylate cyclases and leads to the formation of cAMP. In the presence of the phosphodiesterase inhibitor IBMX, the cAMP accumulated owing to this stimulation and released by cell lysis is used in a competitive detection method. In this test, the cAMP present in the lysate competes with a fluorescence-labelled cAMP (cAMP-d2) for binding to an Eu cryptate-labelled anti-cAMP antibody.

In the absence of cellular cAMP, a maximal signal is produced, which is attributable to the binding of this cAMP-d2 molecule to the antibody. After excitation of the cAMP-d2 molecule at 337 nm, there is a fluorescence resonance energy transfer (FRET) to the Eu cryptate molecules of the anti-cAMP antibody (labelled therewith), followed by a long-lasting emission signal at 665 nm (and at 620 nM). Both signals are measured in a suitable measurement instrument with a time delay, i.e. after decay of the background fluorescence. Any increase in the low FRET signal caused by prostaglandin $E_2$ administration (measured as well ratio change=$\text{emission}_{665\ nm}/\text{emission}_{620\ nm}*10000$) indicates the action of antagonists.

3.2. Detection Method 3.2.1. Test for Antagonism (Data Per Well of a 384-Well Plate):

To a test plate with the substance solutions already added (0.05 µl; 100% DMSO, concentration range from 0.8 nM-16.5 µM) were added 4 µl of a cAMP-d2/cell suspension (625000 cells/ml). After a 20-minute preincubation at room temperature (RT), 2 µl of a 3×PGD2 solution (6 nM, in PBS-IBMX) were added and incubated in the presence of the agonist for a further 30 mins at RT (volume: ~6 µl). Next the reaction was stopped by addition of 2 µl of lysis buffer and incubated for a further 20 mins at RT before the actual measurement (volume: ~8 µl).

4. The EP₂ Subtype of the PGE₂ Receptor and the Pre-Ovulatory Cumulus Expansion

4.1. Background:

In the pre-ovulatory antral follicle, the oocyte is surrounded by cumulus cells, which form a dense cell crown around the oocyte. After the LH peak (luteinizing hormone), a series of processes is activated, which results in a marked morphological change in this cell crown of cumulus cells. During this, the cumulus cells form an extracellular matrix, which leads to the so-called cumulus expansion (Vanderhyden et al. Dev Biol. 1990 August; 140(2): 307-317) This cumulus expansion is an important component of the ovulatory process and the subsequent possibility of fertilization.

During the cumulus expansion, prostaglandins and here prostaglandin $E_2$, synthesis whereof is induced by the LH peak, are of decisive importance. Prostanoid $EP_2$ knockout mice (Hizaki et al., 1999, Proc Natl Acad Sci USA., August 31; 96(18):10501-6.) show a markedly decreased cumulus expansion and severe subfertility, which demonstrates the importance of the prostanoid $EP_2$ receptor for this process.

4.2. Cumulus Expansions Test In Vitro

In immature female mice (strain: B6D2F1 from Charles River), at an age of 14-18 days, the folliculogenesis was induced by a single administration (intraperitoneal) of 10 IU of PMSG (pregnant mare serum gonadotropin; Sigma G-4877, Lot 68H0909). 47-50 hours after the injection, the ovaries were removed and the cumulus-oocyte complexes removed. At this stage, the cumulus complex is not yet expanded.

The cumulus-oocyte complexes were now incubated for 20-24 hours with prostaglandin $E_2$ (PGE) (0.3 µM), vehicle control (ethanol) or test substances. Medium: alpha-MEM medium with 0.1 mM IBMX, pyruvate (0.23 mM), glutamine (2 mM), pen/strep 100 IU/ml pen. and 100 µg/ml strep.), HSA (8 mg/ml) and foetal bovine serum (FBS, 10%). The cumulus expansion was then established through the subdivision into four stages (after Vanderhyden et al. Dev Biol. 1990 August; 140(2):307-317).

4.3 In-Vivo Action on Post-Ovulatory In-Vitro Fertilization:

Substances can exert an influence on fertility by decreasing the fertilizability of oocytes or cumulus-oocyte complexes. In order to study such effects, substances can be administered in vivo and subjected to in vitro fertilization after ovulation of cumulus-oocyte complexes has taken place. The in-vitro fertilization rate, where no test substance is any longer present, allows conclusions as to the in-vivo effects of the test substances.

Immature female mice (strain: B6D2F1, Charles River, Suelzfeld, age: 19-25 days) were kept in Macrolon cages in rooms with controlled illumination (12 hrs darkness: 12 hrs light), fed with a standard diet and provided with drinking water ad libitum.

The mice were primed with PMSG (pregnant mare serum gonadotropin) (10 IU/animal i.p.). After 48 hours, a stimulus triggering ovulation was created in the animals by one administration of 10 IU/animal i.p. (hCG, human chorionic gonadotropin). The test substances were dissolved in benzyl benzoate/castor oil (1+4 v/v) and administered in a volume of 0.1 ml s.c. 1 hour before hCG (n=5 animals per group). Fourteen hours after hCG administration, the animals were killed. Ovulated oocytes and cumulus-oocyte complexes were obtained from the bursa ovarii and/or oviduct and subjected to in-vitro fertilization, wherein for the fertilization a sperm count of 40000 sperms/0.5 ml was used for 1 hour. Twenty-four hours after the incubation with the sperms, the number of fertilized oocytes is established and the percentage fertilization rate determined.

The results in Table 4 show that Example 17 according to the invention has a dose-dependent influence on the fertilizability of ovulated cumulus-oocyte complexes.

4.4 In-Vivo Action on Fertility in Non-Human Primates (Cynomolgus):

In order to study the effect of substances on fertility, mating studies can be performed in monkeys (Jensen et al. Contraception 81 (2010) 165-171). For this, the test substances are administered to female cynomolgus monkeys (*Macaca Fascicularis*) which are being kept in groups, then the animals are mated with a male animal. Matings are checked for by sperm detection in daily vaginal smears. Pregnancies resulting therefrom are identified by hormone determinations and ultrasound examinations. Through the changes in the serum oestradiol concentrations during the cycle, (rise before the midcycle LH peak), the fertile phase within a cycle of the individual animals can be determined Matings in this fertile period are described as "timed matings" (matings in the fertile phase). Apart from the absolute number of pregnancies occurring, the effect on the fertility can also be expressed as pregnancies per "timed matings".

To test the action of $EP_2$ receptor antagonists on fertility in monkeys, Examples 17 and 56 according to the invention were administered over 6 months, dissolved in 0.5 ml castor oil. Example 17 was administered once daily at a dosage of 10 mg/kg (n=10 animals), while Example 56 was administered twice daily at a dosage of 10 mg/kg (n=9 animals). Only the vehicle was administered to a control group (n=10 animals). In the first month of the treatment, no male animal was placed with the female animals. After this, female and male animals were kept together over 5 months, with detection of pregnancies and cycle monitoring.

Table 5 shows that both substances result in a marked reduction in the number of pregnancies occurring. These data for the first time show the strong contraceptive effect of $EP_2$ receptor antagonists in the primate. Further results of the study show that the substances have no effects on hormone levels and cycle length. This confirms that the substances produce a contraceptive effect by non-hormonal mechanisms. The reversibility of the fertility was demonstrated on some animals after discontinuation of the treatment.

5. Determination of the Pharmacokinetic Parameters after Intravenous Administration 5.1. Intravenous Administration:

For this, the substances were administered in dissolved form, compatible solubilizers such as PEG400 and/or ethanol being used in tolerable quantity. The substances were administered at a dosage of 0.1-1 mg/kg. The administration was effected in the female rat as a bolus injection. Here, at various times after bolus injection ca. 100-150 µl blood samples were withdrawn from the jugular vein via a catheter. The blood samples were treated with lithium-heparin as anticoagulant and stored refrigerated until further work-up. After centrifugation of the samples for 15 mins at 3000 rpm, an aliquot of 100 µl was withdrawn from the supernatant (plasma) and precipitated by addition of 400 µl of cold acetonitrile or methanol (absolute). The precipitated samples were frozen overnight at −20° C., then centrifuged once again for 15 mins at 3000 rpm, before 150 µl of the clear supernatant was withdrawn for the concentration determination. The analysis was performed with an Agilent 1200 HPLC system with attached LCMS/MS detection.

5.2 Calculation of the PK Parameters

The calculation was performed by means of the PK calculation software WinNonLin®, where $t_{1/2}$ means half-life within a specified interval (here: terminal $t_{1/2}$, in hrs).

TABLE 1

Examples for the biological activity of the compounds according to the invention on the $hEP_2$ receptor ($IC_{50}$ measured by cAMP antagonism test), selectivity towards hDP & $hEP_4$ ($IC_{50}$ measured by cAMP antagonism test): x: 1-10, xx: 10-100, xxx > 100:

| Example | Antagonism hEP2 $IC_{50}$ [M] | Selectivity hEP2/hDP | Selectivity hEP2/hEP4 |
|---|---|---|---|
| 1 | 1.03E−07 | xxx | xxx |
| 2 | 2.17E−08 | xxx | xxx |
| 3 | 4.91E−09 | xxx | xxx |
| 4 | 6.81E−08 | xxx | xxx |
| 5 | 5.11E−09 | xxx | xxx |
| 6 | 3.13E−07 | xx | xx |
| 7 | 2.58E−08 | xxx | xxx |
| 8 | 9.37E−09 | xxx | xxx |
| 9 | 1.72E−08 | xxx | xxx |
| 10 | 8.67E−09 | xxx | xxx |
| 11 | 8.14E−09 | xxx | xxx |
| 12 | 2.03E−08 | xxx | xxx |
| 13 | 3.59E−08 | xxx | xxx |
| 14 | 3.67E−09 | xxx | xxx |
| 15 | 4.17E−09 | xxx | xxx |
| 16 | 5.85E−09 | xxx | xxx |
| 17 | 3.44E−09 | xxx | xxx |
| 18 | 7.66E−09 | xxx | xxx |
| 19 | 8.57E−09 | xxx | xxx |
| 20 | 7.33E−09 | xxx | xxx |
| 21 | 3.58E−08 | xxx | xxx |
| 22 | 3.03E−08 | xxx | xxx |
| 23 | 1.61E−08 | xxx | xxx |
| 24 | 6.01E−08 | xxx | xxx |
| 25 | 2.52E−08 | xxx | xxx |
| 26 | 2.42E−08 | xxx | xxx |
| 27 | 1.93E−08 | xxx | xxx |
| 28 | 3.39E−08 | xxx | xxx |
| 29 | 9.31E−09 | xxx | xxx |
| 30 | 6.43E−08 | xxx | xxx |
| 31 | 3.08E−09 | xxx | xxx |
| 32 | 1.04E−08 | xxx | xxx |
| 33 | 3.42E−08 | xxx | xxx |
| 34 | 1.34E−07 | xxx | xxx |
| 35 | 6.92E−08 | xxx | xxx |
| 36 | 6.16E−08 | xxx | xxx |
| 37 | 1.04E−07 | xxx | xxx |
| 38 | 2.81E−08 | xxx | xxx |
| 39 | 1.13E−07 | xxx | xxx |
| 40 | 1.15E−08 | xxx | xxx |
| 41 | 5.62E−09 | xxx | xxx |
| 42 | 4.75E−09 | xxx | xxx |
| 43 | 4.82E−09 | xxx | xxx |
| 44 | 3.85E−09 | xxx | xxx |
| 45 | 5.51E−09 | xxx | xxx |
| 46 | 4.91E−09 | xxx | xxx |
| 47 | 5.61E−09 | xxx | xxx |
| 48 | 5.59E−09 | xxx | xxx |
| 49 | 6.44E−09 | xxx | xxx |
| 50 | 3.18E−09 | xxx | xxx |

TABLE 1-continued

Examples for the biological activity of the compounds according to the invention on the hEP$_2$ receptor (IC$_{50}$ measured by cAMP antagonism test), selectivity towards hDP & hEP$_4$ (IC$_{50}$ measured by cAMP antagonism test): x: 1-10, xx: 10-100, xxx > 100:

| Example | Antagonism hEP2 IC$_{50}$ [M] | Selectivity hEP2/hDP | Selectivity hEP2/hEP4 |
|---|---|---|---|
| 51 | 6E-08 | xxx | xxx |
| 52 | 8.3E-07 | xx | xx |
| 53 | 4.42E-08 | xxx | xxx |
| 54 | 4.74E-09 | xxx | xxx |
| 55 | 9.67E-09 | xxx | xxx |
| 56 | 1.31E-08 | xxx | xxx |
| 57 | 5.29E-09 | xxx | xxx |
| 58 | 1.08E-06 | xx | xx |
| 59 | 7.58E-07 | xx | xx |
| 60 | 1.75E-07 | xx | xx |
| 61 | 1.5E-06 | xx | xx |
| 62 | 6.74E-07 | xx | xx |
| 63 | 1.44E-06 | xx | xx |
| 64 | 4.13E-06 | x | x |
| 65 | 2.79E-06 | x | x |
| 66 | 3.21E-07 | xx | xx |
| 67 | 4.05E-07 | xx | xx |
| 68 | 1.77E-08 | xxx | xxx |
| 69 | 2.9E-08 | xxx | |
| 70 | 4.9E-08 | xxx | |
| 71 | 8.29E-08 | xxx | xxx |
| 72 | 1.2E-07 | xxx | xxx |
| 73 | 7.78E-08 | xxx | xxx |
| 74 | 9.54E-08 | xxx | xxx |
| 75 | 6.7E-08 | xxx | xxx |
| 76 | 1.79E-07 | xx | xx |
| 77 | 5.39E-08 | xxx | xxx |
| 78 | 3.17E-08 | xxx | xxx |
| 79 | 1.25E-07 | xxx | xxx |
| 80 | 8.59E-08 | xxx | xxx |
| 81 | 5.13E-07 | xx | xx |
| 82 | 2.18E-07 | xx | xx |
| 83 | 3.26E-08 | xxx | xxx |
| 84 | 1.92E-08 | xxx | xxx |
| 85 | 3.55E-08 | xxx | xxx |
| 86 | 1.54E-08 | xxx | xxx |
| 87 | 2.4E-08 | xxx | xxx |
| 88 | 1.62E-08 | xxx | xxx |
| 89 | 9.4E-09 | xxx | xxx |
| 90 | 1.48E-08 | xxx | xxx |
| 91 | 2.03E-08 | xxx | xxx |
| 92 | 1.27E-08 | xxx | xxx |
| 93 | 1.15E-08 | xxx | xxx |
| 94 | 1.28E-08 | xxx | xxx |
| 95 | 6.18E-09 | xxx | xxx |
| 96 | 9.42E-09 | xxx | xxx |
| 97 | 1.27E-08 | xxx | xxx |
| 98 | 7.07E-09 | xxx | xxx |
| 99 | 1.04E-08 | xxx | xxx |
| 100 | 6.21E-09 | xxx | xxx |
| 101 | 6.58E-09 | xxx | xxx |
| 102 | 4.1E-07 | xx | xx |
| 103 | 5.95E-07 | xx | xx |
| 104 | 5.13E-07 | xx | xx |
| 105 | 2.85E-07 | xx | xx |
| 106 | 1.5E-07 | xxx | xxx |
| 107 | 1.14E-08 | xxx | xxx |
| 108 | 6.46E-09 | xxx | xxx |
| 109 | 9.53E-09 | xxx | xxx |
| 110 | 4.4E-09 | xxx | xxx |
| 111 | 1.37E-08 | xxx | xxx |
| 112 | 1.19E-08 | xxx | xxx |
| 113 | 1.39E-08 | xxx | xxx |
| 114 | 6.08E-09 | xxx | xxx |
| 115 | 9.05E-09 | xxx | xxx |
| 116 | 5.52E-08 | xxx | xxx |
| 117 | 1.78E-08 | xxx | xxx |
| 118 | 8.17E-09 | xxx | |
| 119 | 1.32E-08 | xxx | |
| 120 | 1.55E-08 | xxx | |
| 121 | 1.55E-08 | xxx | xxx |
| 122 | 2.86E-08 | xxx | xxx |
| 123 | 8.92E-09 | xxx | xxx |
| 124 | 7.99E-09 | xxx | xxx |
| 125 | 3.66E-09 | xxx | xxx |
| 126 | 2.12E-08 | xxx | xxx |
| 127 | 5.56E-08 | xxx | xxx |
| 128 | 4.71E-07 | xx | xx |
| 129 | 3.09E-07 | xx | xx |
| 130 | 2.41E-07 | xx | xx |
| 131 | 2.28E-07 | xx | xx |
| 132 | 1.09E-07 | xxx | xxx |
| 133 | 4.19E-08 | xxx | xxx |
| 134 | 5.65E-08 | xxx | xxx |
| 135 | 1.95E-08 | xxx | xxx |
| 136 | 6.59E-09 | xxx | xxx |
| 137 | 7.65E-08 | xxx | xxx |
| 138 | 1.6E-07 | xxx | xxx |
| 139 | 4.19E-07 | xx | xx |
| 140 | 5.53E-08 | xxx | xxx |
| 141 | 1.43E-07 | xxx | xxx |
| 142 | 7.13E-07 | xx | xx |
| 143 | 3.68E-08 | xxx | xxx |
| 144 | 5.08E-08 | xxx | xxx |
| 145 | 1.88E-08 | xxx | xxx |
| 146 | 5.26E-08 | xxx | xxx |
| 147 | 5.74E-08 | xxx | xxx |
| 148 | 2.74E-08 | xxx | xxx |
| 149 | 2.96E-08 | xxx | xxx |
| 150 | 1.28E-08 | xxx | xxx |
| 151 | 4.85E-08 | xxx | xxx |
| 152 | 3.33E-08 | xxx | xxx |
| 153 | 6.08E-08 | xxx | xxx |
| 154 | 8.08E-08 | xxx | xxx |
| 155 | 2.94E-08 | xxx | xxx |
| 156 | 1.84E-07 | xx | xx |
| 157 | 1.36E-08 | xxx | xxx |
| 158 | 6.21E-08 | xxx | xxx |
| 159 | 6.24E-09 | xxx | xxx |
| 160 | 8.29E-08 | xxx | xxx |
| 161 | 9.82E-08 | xxx | xxx |
| 162 | 9.33E-09 | xxx | xxx |
| 163 | 6.8E-09 | xxx | xxx |
| 164 | 1.09E-08 | xxx | xxx |
| 165 | 3.34E-08 | xxx | xxx |
| 166 | 2.87E-09 | xxx | xxx |
| 167 | 1.35E-08 | xxx | xxx |
| 168 | 2.93E-08 | xxx | xxx |
| 169 | 2.77E-08 | xxx | xxx |
| 170 | 4.25E-09 | xxx | xxx |
| 171 | 3.88E-09 | xxx | xxx |
| 172 | 3.16E-09 | xxx | xxx |
| 173 | 2.71E-09 | xxx | xxx |
| 174 | 6.58E-09 | xxx | xxx |
| 175 | 8.05E-09 | xxx | xxx |
| 176 | 7.77E-09 | xxx | xxx |
| 177 | 1.18E-07 | xxx | xxx |
| 178 | 6.83E-08 | xxx | xxx |
| 179 | 2.61E-06 | x | x |
| 180 | 1.73E-08 | xxx | xxx |
| 181 | 3.52E-08 | xxx | xxx |
| 182 | 6.42E-08 | xxx | xxx |
| 183 | 4.66E-08 | xxx | xxx |
| 184 | 7.68E-08 | xxx | xxx |
| 185 | 2.48E-08 | xxx | xxx |
| 186 | 5.19E-08 | xxx | xxx |
| 187 | 2.35E-08 | xxx | xxx |
| 188 | 1.49E-07 | xxx | xxx |
| 189 | 3.36E-08 | xxx | xxx |
| 190 | 2.72E-07 | xx | xx |
| 191 | 4.71E-08 | xxx | xxx |
| 192 | 2.06E-07 | xx | xx |

TABLE 1-continued

Examples for the biological activity of the compounds according to the invention on the hEP$_2$ receptor (IC$_{50}$ measured by cAMP antagonism test), selectivity towards hDP & hEP$_4$ (IC$_{50}$ measured by cAMP antagonism test): x: 1-10, xx: 10-100, xxx > 100:

| Example | Antagonism hEP2 IC$_{50}$ [M] | Selectivity hEP2/hDP | Selectivity hEP2/hEP4 |
|---|---|---|---|
| 193 | 1.45E−07 | xxx | xxx |
| 194 | 4.09E−08 | xxx | xxx |
| 195 | 2.27E−07 | xx | xx |
| 196 | 5.08E−08 | xxx | xxx |
| 197 | 6.32E−08 | xxx | xxx |
| 198 | 1.53E−07 | xxx | xxx |
| 199 | 9.71E−08 | xxx | xxx |
| 200 | 1.51E−08 | xxx | xxx |
| 201 | 2.49E−08 | xxx | xxx |
| 202 | 5.06E−09 | xxx | xxx |
| 203 | 8.57E−08 | xxx | xxx |
| 204 | 1E−08 | xxx | xxx |
| 205 | 4.33E−08 | xxx | xxx |
| 206 | 4.13E−08 | xxx | xxx |
| 207 | 3.03E−08 | xxx | xxx |
| 208 | 8.06E−08 | xxx | xxx |
| 209 | 2.51E−08 | xxx | xxx |
| 210 | 1.95E−08 | xxx | xxx |
| 211 | 5.01E−08 | xxx | xxx |
| 212 | 1.06E−07 | xxx | xxx |
| 213 | 8.24E−08 | xxx | xxx |
| 214 | 6.49E−08 | xxx | xxx |
| 215 | 3.9E−08 | xxx | xxx |
| 216 | 8.61E−08 | xxx | xxx |
| 217 | 1.14E−07 | xxx | xxx |
| 218 | 1.28E−07 | xxx | xxx |
| 219 | 2.73E−07 | xx | xx |
| 220 | 1.47E−07 | xxx | xxx |
| 221 | 2.35E−07 | xx | xx |
| 222 | 4.09E−08 | xxx | xxx |
| 223 | 2E−08 | xxx | xxx |
| 224 | 5.62E−09 | xxx | xxx |
| 225 | 1.43E−08 | xxx | xxx |
| 226 | 1.19E−08 | xxx | xxx |
| 227 | 9.89E−09 | xxx | xxx |
| 228 | 8.09E−09 | xxx | xxx |
| 229 | 1.02E−08 | xxx | xxx |
| 230 | 1.37E−08 | xxx | xxx |
| 231 | 1.32E−08 | xxx | xxx |
| 232 | 3.83E−08 | xxx | xxx |
| 233 | 3.97E−08 | xxx | xxx |
| 234 | 4.77E−08 | xxx | xxx |
| 235 | 1.67E−08 | xxx | xxx |
| 236 | 5.75E−08 | xxx | xxx |
| 237 | 3.1E−08 | xxx | xxx |
| 238 | 3.24E−08 | xxx | xxx |
| 239 | 2.7E−08 | xxx | xxx |
| 240 | 2.51E−08 | xxx | xxx |
| 241 | 9.03E−09 | xxx | xxx |
| 242 | 3.05E−07 | xx | xx |
| 243 | 3.35E−07 | xx | xx |
| 244 | 4.42E−08 | xxx | xxx |
| 245 | 7.79E−09 | xxx | xxx |
| 246 | 9.23E−09 | xxx | xxx |
| 247 | 1.26E−08 | xxx | xxx |
| 248 | 1.47E−08 | xxx | xxx |
| 249 | 1.12E−08 | xxx | xxx |
| 250 | 3.06E−08 | xxx | xxx |
| 251 | 3.81E−06 | x | x |
| 252 | 2.95E−07 | xx | xx |
| 253 | 1.68E−07 | xx | xx |
| 254 | 5.52E−08 | xxx | xxx |
| 255 | 8.35E−08 | xxx | xxx |
| 256 | 1.07E−07 |  | xxx |
| 257 | 1.02E−07 | xxx | xxx |
| 258 | 1.09E−07 | xxx | xxx |
| 259 | 2.56E−08 | xxx | xxx |
| 260 | 8.02E−09 | xxx | xxx |
| 261 | 8.1E−08 | xxx | xxx |
| 262 | 3.34E−08 | xxx | xxx |
| 263 | 1.81E−07 | xx | xx |
| 264 | 1.37E−08 | xxx | xxx |
| 265 | 3.15E−08 | xxx | xxx |
| 266 | 1.89E−08 | xxx | xxx |
| 267 | 4.55E−08 | xxx | xxx |
| 268 | 2.29E−08 | xxx | xxx |
| 269 | 7.54E−09 | xxx | xxx |
| 270 | 5.31E−08 | xxx | xxx |
| 271 | 3.35E−08 | xxx | xxx |
| 272 | 2.37E−08 | xxx | xxx |
| 273 | 1.85E−08 | xxx | xxx |
| 274 | 4.46E−08 | xxx | xxx |
| 275 | 3.45E−08 | xxx | xxx |
| 276 | 2.26E−07 | xx | xx |
| 277 | 4.79E−08 | xxx | xxx |
| 278 | 1.04E−07 | xxx | xxx |
| 279 | 5.74E−08 | xxx | xxx |
| 280 | 3.07E−08 | xxx | xxx |
| 281 | 2.3E−08 | xxx | xxx |
| 282 | 2.01E−08 | xxx | xxx |
| 283 | 6.55E−08 | xxx | xxx |
| 284 | 5.64E−08 | xxx | xxx |
| 285 | 1E−07 | xxx | xxx |
| 286 | 1E−07 | xxx | xxx |
| 287 | 1.05E−06 | xx | xx |
| 288 | 4E−08 | xxx | xxx |
| 289 | 5.16E−08 | xxx | xxx |
| 290 | 4.26E−08 | xxx | xxx |
| 291 | 5.94E−09 | xxx | xxx |
| 292 | 2E−08 | xxx | xxx |
| 293 | 2.83E−08 | xxx | xxx |
| 294 | 1.32E−08 | xxx | xxx |
| 295 | 7.08E−08 | xxx | xxx |
| 296 | 2.97E−08 | xxx | xxx |
| 297 | 4.6E−07 | xx | xx |
| 298 | 3.45E−07 | xx | xx |
| 299 | 5.41E−07 | xx | xx |
| 300 | 7.98E−08 | xxx | xxx |
| 301 | 2.45E−08 | xxx | xxx |
| 302 | 1.31E−07 | xxx | xxx |
| 303 | 1.39E−08 | xxx | xxx |
| 304 | 9.98E−08 | xxx | xxx |
| 305 | 3.01E−07 | xx | xx |
| 306 | 7.66E−08 | xxx | xxx |
| 307 | 3.06E−08 | xxx | xxx |
| 308 | 2.22E−08 | xxx | xxx |
| 309 | 6.6E−08 | xxx | xxx |
| 310 | 8.06E−07 | xx | xx |
| 311 | 8.41E−08 | xxx | xxx |
| 312 | 1.58E−07 | xxx | xxx |
| 313 | 8.94E−08 | xxx | xxx |
| 314 | 2.78E−08 | xxx | xxx |
| 315 | 4.3E−08 | xxx | xxx |
| 316 | 7.9E−08 | xxx | xxx |
| 317 | 1.81E−07 | xx | xx |
| 318 | 2.63E−08 | xxx | xxx |
| 319 | 3.15E−07 | xx | xx |
| 320 | 1.56E−08 | xxx | xxx |
| 321 | 1.01E−07 | xxx | xxx |
| 322 | 7.62E−08 | xxx | xxx |
| 323 | 1.28E−07 | xxx | xxx |
| 324 | 4.6E−07 | xx | xx |
| 325 | 3.21E−07 | xx | xx |
| 326 | 4.85E−07 | xx | xx |
| 327 | 1.21E−06 | xx | xx |
| 328 | 2.56E−07 | xx | xx |
| 329 | 2.32E−07 | xx | xx |
| 330 | 9.53E−09 | xxx | xxx |
| 331 | 9.47E−09 | xxx | xxx |
| 332 | 5.47E−09 | xxx | xxx |
| 333 | 6.42E−09 | xxx | xxx |
| 334 | 7.42E−08 | xxx | xxx |

TABLE 1-continued

Examples for the biological activity of the compounds according to the invention on the hEP$_2$ receptor (IC$_{50}$ measured by cAMP antagonism test), selectivity towards hDP & hEP$_4$ (IC$_{50}$ measured by cAMP antagonism test): x: 1-10, xx: 10-100, xxx > 100:

| Example | Antagonism hEP2 IC$_{50}$ [M] | Selectivity hEP2/hDP | Selectivity hEP2/hEP4 |
|---|---|---|---|
| 335 | 5.09E−09 | xxx | xxx |
| 336 | 5.59E−09 | xxx | xxx |
| 337 | 1.81E−08 | xxx | xxx |
| 338 | 2.8E−08 | xxx | xxx |
| 339 | 7.15E−09 | xxx | xxx |
| 340 | 1.99E−08 | xxx | xxx |
| 341 | 5.53E−08 | xxx | xxx |
| 342 | 1.03E−07 | xxx | xxx |
| 343 | 4.24E−08 | xxx | xxx |
| 344 | 1.03E−08 | xxx | xxx |
| 345 | 6.26E−09 | xxx | xxx |
| 346 | 1.49E−08 | xxx | xxx |
| 347 | 7.88E−09 | xxx | xxx |
| 348 | 8.88E−09 | xxx | xxx |
| 349 | 4.82E−09 | xxx | xxx |
| 350 | 8.41E−09 | xxx | xxx |
| 351 | 6.84E−09 | xxx | xxx |
| 352 | 2.17E−08 | xxx | xxx |
| 353 | 5.02E−08 | xxx | xxx |
| 354 | 5.87E−09 | xxx | xxx |
| 355 | 5.39E−09 | xxx | xxx |
| 356 | 6.36E−08 | xxx | xxx |
| 357 | 7.36E−09 | xxx | xxx |
| 358 | 8.01E−09 | xxx | xxx |
| 359 | 6.99E−09 | xxx | xxx |
| 360 | 6.27E−09 | xxx | xxx |
| 361 | 5.11E−09 | xxx | xxx |
| 362 | 1.51E−08 | xxx | xxx |
| 363 | 5.48E−09 | xxx | xxx |
| 364 | 6.61E−09 | xxx | xxx |
| 365 | 5.3E−09 | xxx | xxx |
| 366 | 1.89E−08 | xxx | xxx |
| 367 | 5.84E−09 | xxx | xxx |
| 368 | 1.2E−08 | xxx | xxx |
| 369 | 5.66E−09 | xxx | xxx |
| 370 | 3.07E−09 | xxx | xxx |
| 371 | 6.11E−09 | xxx | xxx |
| 372 | 7.29E−09 | xxx | xxx |
| 373 | 4.07E−08 | xxx | xxx |
| 374 | 6.58E−09 | xxx | xxx |
| 375 | 5.8E−09 | xxx | xxx |
| 376 | 3.59E−09 | xxx | xxx |
| 377 | 2.73E−08 | xxx | xxx |
| 378 | 7.77E−09 | xxx | xxx |
| 379 | 6.26E−08 | xxx | xxx |
| 380 | 5.35E−09 | xxx | xxx |
| 381 | 5.84E−09 | xxx | xxx |
| 382 | 1.94E−08 | xxx | xxx |
| 383 | 5.78E−09 | xxx | xxx |
| 384 | 3.95E−09 | xxx | xxx |
| 385 | 1.31E−08 | xxx | xxx |
| 386 | 2.57E−08 | xxx | xxx |
| 387 | 1.32E−08 | xxx | xxx |
| 388 | 2.05E−08 | xxx | xxx |
| 389 | 4.51E−09 | xxx | xxx |
| 390 | 3.14E−09 | xxx | xxx |
| 391 | 6.07E−09 | xxx | xxx |
| 392 | 2.18E−08 | xxx | xxx |
| 393 | 5E−08 | xxx | xxx |
| 394 | 5.7E−09 | xxx | xxx |
| 395 | 3.04E−08 | xxx | xxx |
| 396 | 1.8E−08 | xxx | xxx |
| 397 | 1.25E−08 | xxx | xxx |
| 398 | 1.82E−08 | xxx | xxx |
| 399 | 5.93E−07 | xx | xx |
| 400 | 5.61E−08 | xxx | xxx |
| 401 | 1.55E−07 | xxx | xxx |
| 402 | 7.77E−08 | xxx | xxx |
| 403 | 9.59E−09 | xxx | xxx |
| 404 | 2.02E−08 | xxx | xxx |
| 405 | 2.14E−06 | x | x |
| 406 | 8.19E−09 | xxx | xxx |
| 407 | 1.16E−08 | xxx | xxx |
| 408 | 2.35E−08 | xxx | xxx |
| 409 | 3.18E−08 | xxx | xxx |
| 410 | 9.04E−08 | xxx | xxx |
| 411 | 1.65E−08 | xxx | xxx |
| 412 | 6.35E−08 | xxx | xxx |
| 413 | 3.78E−08 | xxx | xxx |
| 414 | 2.23E−07 | xx | xx |
| 415 | 2.13E−08 | xxx | xxx |
| 416 | 1.07E−08 | xxx | xxx |
| 417 | 9.75E−09 | xxx | xxx |
| 418 | 1.58E−08 | xxx | xxx |
| 419 | 1.09E−08 | xxx | xxx |

TABLE 2

Reduction in the cumulus expansion in percent with use of 0.3 μM PGE2 for stimulation, reference 1: example 62 from DE102009049662A1

| Example | % reduction at 1 μM | % reduction at 0.5 μm |
|---|---|---|
| Reference 1* | 79% (*reduction at 10 μM) | |
| Example 5 | 59 | 56 |
| Example 17 | 76 | 71 |
| Example 42 | 79 | 48 |
| Example 117 | 54 | 30 |
| Example 283 | 26 | 25 |
| Example 291 | 73 | 76 |
| Example 303 | 47 | 38 |
| Example 345 | 36 | 18 |

TABLE 3

Terminal half-life ($t_{1/2}$) after intravenous administration in the female rat, reference 1: example 62 from DE102009049662A1

| Example | $t_{1/2}$ [hr] |
|---|---|
| Reference 1 | 0.4 |
| Example 17 | 2.5 |
| Example 42 | 3.2 |
| Example 117 | 2.0 |
| Example 283 | 5.8 |

TABLE 4

Reduction in in-vitro fertilization rate after in-vivo administration of the test substance:

| Example | % fertilization with vehicle | % fertilization with 1 mg/kg | % fertilization with 5 mg/kg | % fertilization with 10 mg/kg |
|---|---|---|---|---|
| Example 17 | 30 ± 9 | 20 ± 10 | 9 ± 1 | 8 ± 4 |

TABLE 5

| | Reduction in the pregnancy rates in the non-human primate (Cynomolgus) | | | |
|---|---|---|---|---|
| Group | Animals per group | Number of "timed matings"* | Pregnancies | % Pregnancies/ "timed mating" |
| Control | 10 | 21 | 8 | 38 |
| Example 17 | 10 | 25 | 3 | 6 |
| Example 56 | 9 | 34 | 2 | 12 |

*Detection of vaginal sperms in the fertile phase of the cycle

The invention claimed is:

1. A compound of the general formula (I)

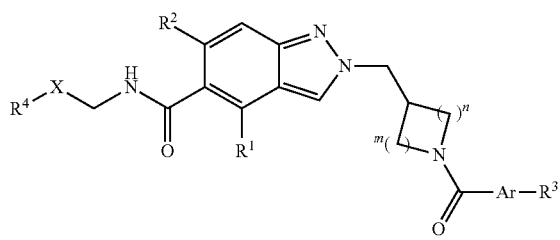

wherein
R$^1$ is H, C$_1$-C$_2$ alkyl or C$_1$-C$_2$ alkyloxy;
R$^2$ is H or methyl;
subject to the proviso that one of R$^1$ or R$^2$ equals H;
X is —(CH$_2$)$_l$—, —(CH$_2$)$_k$—O—, —CH$_2$—S—, CH$_2$—S(O)$_2$—, —CH(CH$_3$)—, —CH(CH$_3$)—O— or —C(CH$_3$)$_2$—O—, wherein k is 1 or 2; and l is 0, 1 or 2;
R$^4$ is H, C$_1$-C$_4$ alkyl, C$_3$-C$_4$ cycloalkyl or CH$_2$—C$_3$-C$_4$ cycloalkyl; and, in the case that X is —CH$_2$— or —CH(CH$_3$)—, R$^4$ is additionally a 4-6-membered heterocyclyl residue; and, in the case that X is —(CH$_2$)$_1$— or —CH(CH$_3$)—, R$^4$ is additionally CN;

or

X and R$^4$ form a 4-6-membered heterocyclyl residue via a ring carbon linkage;
m is 1 or 2;
n is 1 or 2;
Ar is a 6-10-membered aryl or 5-10-membered hetaryl residue, R$^3$ is halogen, CN, SF$_5$, C$_1$-C$_4$ alkyl, C$_3$-C$_6$ cycloalkyl, C$_4$-C$_6$ heterocyclyl, O—C$_1$-C$_4$ alkyl, O—C$_3$-C$_6$ cycloalkyl, O—C$_4$-C$_6$ heterocyclyl, S—C$_1$-C$_4$ alkyl, S(O)$_2$—C$_1$-C$_4$ alkyl, Ar', O—Ar', C(CH$_3$)$_2$—CN or C(CH$_3$)$_2$—OH; and
Ar' is an optionally singly or doubly substituted 6-membered aryl or 5-6-membered heteroaryl residue;
wherein the substituents are selected from F, Cl, CN, C$_1$-C$_4$ alkyl, O—C$_1$-C$_4$ alkyl, C(CH$_3$)$_2$—CN, C(CH$_3$)$_2$—OH and C(O)NH$_2$;
and isomers, diastereomers, enantiomers and salts or cyclodextrin clathrates thereof.

2. A compound according to claim 1, wherein
R$^1$ and R$^2$ are H or methyl;
subject to the proviso that one of R$^1$ or R$^2$ equals H;
X is —(CH$_2$)$_l$— or —(CH$_2$)$_k$—O—; wherein k is 1 or 2; and wherein l is 0, 1 or 2;
R$^4$ is C$_1$-C$_4$ alkyl, C$_3$-C$_4$ cycloalkyl or CH$_2$—C$_3$-C$_4$ cycloalkyl; and
m and n are 2.

3. A compound according to claim 1, wherein
R$^1$ and R$^2$ are H or methyl;
subject to the proviso that one of R$^1$ or R$^2$ equals H;
X is —(CH$_2$)$_l$— or —(CH$_2$)$_k$—O—; wherein k is 1 or 2; and wherein l is 0, 1 or 2;
R$^4$ is C$_1$-C$_4$ alkyl, C$_3$-C$_4$ cycloalkyl or CH$_2$—C$_3$-C$_4$ cycloalkyl; and
m and n are 1.

4. A compound according to claim 1, wherein
R$^1$ is methyl;
R$^2$ is H;
X is —(CH$_2$)$_l$— or —(CH$_2$)$_k$—O—; wherein k is 1; and wherein l is 0 or 1;
R$^4$ is C$_1$-C$_4$ alkyl, C$_3$-C$_4$ cycloalkyl or CH$_2$—C$_3$-C$_4$ cycloalkyl;
m and n are 2; and
Ar is a phenyl residue.

5. A compound according to claim 1, wherein
R$^1$ is a methyl group;
R$^2$ is H;
X is —(CH$_2$)$_l$— or —(CH$_2$)$_k$—O—; wherein k is 1; and wherein l is 0 or 1;
R$^4$ is C$_1$-C$_4$ alkyl, C$_3$-C$_4$ cycloalkyl or CH$_2$—C$_3$-C$_4$ cycloalkyl;
m and n are 1; and
Ar is a phenyl residue.

6. A compound according to claim 1 that is:
2-{[1-(4-cyano-2-fluorobenzoyl)piperidin-4-yl]methyl}-N-(2-methoxyethyl)-4-methyl-2H-indazol-5-carboxamide;
2-{[1-(4-tert-butoxybenzoyl)piperidin-4-yl]methyl}-N-(2-methoxyethyl)-4-methyl-2H-indazol-5-carboxamide;
2-({1-[4-(4-fluorophenoxyl)benzoyl]piperidin-4-yl}methyl)-N-(2-methoxyethyl)-4-methyl-2H-indazol-5-carboxamide;
N-(2-methoxyethyl)-4-methyl-2-{[1-(4-morpholinobenzoyl)piperidin-4-yl]methyl}-2H-indazol-5-carboxamide;
2-({1-[(4'-fluorobiphenyl-4-yl)carbonyl]piperidin-4-yl}methyl)-N-(2-methoxyethyl)-4-methyl-2H-indazol-5-carboxamide;
2-{[1-(2-fluoro-4-mesylbenzoyl)piperidin-4-yl]methyl}-N-(2-methoxyethyl)-4-methyl-2H-indazol-5-carboxamide;
2-{[1-(2-fluoro-4-methoxybenzoyl)piperidin-4-yl]methyl}-N-(2-methoxyethyl)-4-methyl-2H-indazol-5-carboxamide;
2-{[1-(4-bromo-2-fluorobenzoyl)piperidin-4-yl]methyl}-N-(2-methoxyethyl)-4-methyl-2H-indazol-5-carboxamide;
2-{[1-(2-fluoro-4-methylbenzoyl)piperidin-4-yl]methyl}-N-(2-methoxyethyl)-4-methyl-2H-indazol-5-carboxamide;
2-({1-[2-fluoro-4-(trifluoromethyl)benzoyl]piperidin-4-yl}methyl)-N-(2-methoxyethyl)-4-methyl-2H-indazol-5-carboxamide;
N-(2-methoxyethyl)-4-methyl-2-({1-[4-(pentafluoro-λ$^6$-sulphanyl)benzoyl]piperidin-4-yl}methyl)-2H-indazol-5-carboxamide;
N-(2-methoxyethyl)-4-methyl-2-{[1-(4-methylbenzoyl)piperidin-4-yl]methyl}-2H-indazol-5-carboxamide;
2-({1-[4-(4-chlorophenoxyl)benzoyl]piperidin-4-yl}methyl)-N-(2-methoxyethyl)-4-methyl-2H-indazol-5-carboxamide;

N-(2-methoxyethyl)-4-methyl-2-({1-[4-(4-methylphenoxyl)benzoyl]piperidin-4-yl}methyl)-2H-indazol-5-carboxamide;

2-({1-[4-(4-tert-butylphenoxy)benzoyl]piperidin-4-yl}methyl)-N-(2-methoxyethyl)-4-methyl-2H-indazol-5-carboxamide;

N-(2-methoxyethyl)-4-methyl-2-[(1-{4-[4-(trifluoromethyl)phenoxy]benzoyl}piperidin-4-yl)methyl]-2H-indazol-5-carboxamide;

N-(2-methoxyethyl)-2-({1-[4-(4-methoxyphenoxyl)benzoyl]piperidin-4-yl}methyl)-4-methyl-2H-indazol-5-carboxamide;

N-(2-methoxyethyl)-4-methyl-2-{[1-(4-phenoxybenzoyl)piperidin-4-yl]methyl}-2H-indazol-5-carboxamide;

2-{[1-(4-cyclopropylbenzoyl)piperidin-4-yl]methyl}-N-(2-methoxyethyl)-4-methyl-2H-indazol-5-carboxamide;

2-{[1-(4-methoxybenzoyl)piperidin-4-yl]methyl}-N-(2-methoxyethyl)-4-methyl-2H-indazol-5-carboxamide;

2-{[1-(4-fluorobenzoyl)piperidin-4-yl]methyl}-N-(2-methoxyethyl)-4-methyl-2H-indazol-5-carboxamide;

N-(2-methoxyethyl)-4-methyl-2-({1-[4-(trifluoromethyl)benzoyl]piperidin-4-yl}methyl)-2H-indazol-5-carboxamide;

2-{[1-(2-methoxybenzoyl)piperidin-4-yl]methyl}-N-(2-methoxyethyl)-4-methyl-2H-indazol-5-carboxamide;

N-(2-methoxyethyl)-4-methyl-2-[(1-{4-[(trifluoromethyl)sulphonyl]benzoyl}piperidin-4-yl)methyl]-2H-indazol-5-carboxamide;

N-(2-methoxyethyl)-4-methyl-2-({1-[3-(trifluoromethyl)benzoyl]piperidin-4-yl}methyl)-2H-indazol-5-carboxamide;

N-(2-methoxyethyl)-4-methyl-2-{[1-(3-methylbenzoyl)piperidin-4-yl]methyl}-2H-indazol-5-carboxamide;

2-{[1-(3-chlorobenzoyl)piperidin-4-yl]methyl}-N-(2-methoxyethyl)-4-methyl-2H-indazol-5-carboxamide;

2-({1-[4-(4-carbamoylphenoxyl)benzoyl]piperidin-4-yl}methyl)-N-(2-methoxyethyl)-4-methyl-2H-indazol-5-carboxamide;

2-({1-[4-(cyclopentyloxy)benzoyl]piperidin-4-yl}methyl)-N-(2-methoxyethyl)-4-methyl-2H-indazol-5-carboxamide;

2-({1-[4-(difluoromethyl)benzoyl]piperidin-4-yl}methyl)-N-(2-methoxyethyl)-4-methyl-2H-indazol-5-carboxamide;

2-{[1-(4-cyanobenzoyl)piperidin-4-yl]methyl}-N-(2-methoxyethyl)-4-methyl-2H-indazol-5-carboxamide;

2-({1-[4-(1H-imidazol-1-yl)benzoyl]piperidin-4-yl}methyl)-N-(2-methoxyethyl)-4-methyl-2H-indazol-5-carboxamide;

N-(2-methoxyethyl)-4-methyl-2-({1-[4-(oxazol-2-yl)benzoyl]piperidin-4-yl}methyl)-2H-indazol-5-carboxamide;

N-(2-methoxyethyl)-4-methyl-2-({1-[4-(oxazol-5-yl)benzoyl]piperidin-4-yl}methyl)-2H-indazol-5-carboxamide;

N-(2-methoxyethyl)-4-methyl-2-({1-[4-(isoxazol-5-yl)benzoyl]piperidin-4-yl}methyl)-2H-indazol-5-carboxamide;

N-(2-methoxyethyl)-4-methyl-2-({1-[4-(1H-pyrazol-1-yl)benzoyl]piperidin-4-yl}methyl)-2H-indazol-5-carboxamide;

N-(2-methoxyethyl)-4-methyl-2-({1-[4-(1H-1,2,4-triazol-1-yl)benzoyl]piperidin-4-yl}-methyl)-2H-indazol-5-carboxamide;

2-({1-[4-(difluoromethoxy)-2-fluorobenzoyl]piperidin-4-yl}methyl)-N-(2-methoxyethyl)-4-methyl-2H-indazol-5-carboxamide;

2-({1-[2-fluoro-4-(pyrrolidin-1-yl)benzoyl]piperidin-4-yl}methyl)-N-(2-methoxyethyl)-4-methyl-2H-indazol-5-carboxamide;

2-({1-[(3,4'-difluorobiphenyl-4-yl)carbonyl]piperidin-4-yl}methyl)-N-(2-methoxyethyl)-4-methyl-2H-indazol-5-carboxamide;

2-({1-[(3-fluoro-4'-methoxybiphenyl-4-yl)carbonyl]piperidin-4-yl}methyl)-N-(2-methoxyethyl)-4-methyl-2H-indazol-5-carboxamide;

2-({1-[(3-fluoro-4'-methylbiphenyl-4-yl)carbonyl]piperidin-4-yl}methyl)-N-(2-methoxy-ethyl)-4-methyl-2H-indazol-5-carboxamide;

2-[(1-{[3-fluoro-3'-(trifluoromethyl)biphenyl-4-yl]carbonyl}piperidin-4-yl)methyl]-N-(2-methoxyethyl)-4-methyl-2H-indazol-5-carboxamide;

2-[(1-{[3-fluoro-2'-(trifluoromethoxy)biphenyl-4-yl]carbonyl}piperidin-4-yl)methyl]-N-(2-methoxyethyl)-4-methyl-2H-indazol-5-carboxamide;

2-({1-[(2'-fluorobiphenyl-4-yl)carbonyl]piperidin-4-yl}methyl)-N-(2-methoxyethyl)-4-methyl-2H-indazol-5-carboxamide;

2-({1-[(2',4'-difluorobiphenyl-4-yl)carbonyl]piperidin-4-yl}methyl)-N-(2-methoxyethyl)-4-methyl-2H-indazol-5-carboxamide;

2-({1-[(2-fluorobiphenyl-4-yl)carbonyl]piperidin-4-yl}methyl)-N-(2-methoxyethyl)-4-methyl-2H-indazol-5-carboxamide;

N-(2-methoxyethyl)-4-methyl-2-({1-[(2'-methylbiphenyl-4-yl)carbonyl]piperidin-4-yl}-methyl)-2H-indazol-5-carboxamide;

N-(2-methoxyethyl)-4-methyl-2-({1-[4-(4-pyridyloxy)benzoyl]piperidin-4-yl}methyl)-2H-indazol-5-carboxamide;

N-(2-methoxyethyl)-4-methyl-2-({1-[4-(4H-1,2,4-triazol-4-yl)benzoyl]piperidin-4-yl}-methyl)-2H-indazol-5-carboxamide;

2-{[1-(2-fluoro-4-morpholinobenzoyl)piperidin-4-yl]methyl}-N-(2-methoxyethyl)-4-methyl-2H-indazol-5-carboxamide;

2-{[1-(4-bromobenzoyl)piperidin-4-yl]methyl}-N-(2-methoxyethyl)-4-methyl-2H-indazol-5-carboxamide;

N-(2-methoxyethyl)-4-methyl-2-({1-[4-(trifluoromethoxy)benzoyl]piperidin-4-yl}-methyl)-2H-indazol-5-carboxamide;

2-{[1-(4-chlorobenzoyl)piperidin-4-yl]methyl}-N-(2-methoxyethyl)-4-methyl-2H-indazol-5-carboxamide;

N-(2-methoxyethyl)-4-methyl-2-[(1-{4-[(trifluoromethyl)sulphanyl]benzoyl}piperidin-4-yl)methyl]-2H-indazol-5-carboxamide;

4-methyl-2-({1-[4-(pentafluoro-$\lambda^6$-sulphanyl)benzoyl]piperidin-4-yl}methyl)-N-(2,2,2-trifluoroethyl)-2H-indazol-5-carboxamide;

2-{[1-(4-chlorobenzoyl)piperidin-4-yl]methyl}-4-methyl-N-(2,2,2-trifluoroethyl)-2H-indazol-5-carboxamide;

4-methyl-N-(2,2,2-trifluoroethyl)-2-({1-[4-(trifluoromethoxy)benzoyl]piperidin-4-yl}methyl)-2H-indazol-5-carboxamide;

2-{[1-(4-chlorobenzoyl)piperidin-4-yl]methyl}-N-[2-(cyclopropylmethoxy)ethyl]-4-methyl-2H-indazole-5-carboxamide;

N-[2-(cyclopropylmethoxy)ethyl]-4-methyl-2-{[1-(4-methylbenzoyl)piperidin-4-yl]-methyl}-2H-indazol-5-carboxamide;

N-[2-(cyclopropylmethoxy)ethyl]-2-({1-[4-(4-fluorophenoxyl)benzoyl]piperidin-4-yl}-methyl)-4-methyl-2H-indazol-5-carboxamide;

N-[2-(cyclopropylmethoxy)ethyl]-4-methyl-2-({1-[4-(trifluoromethyl)benzoyl]piperidin-4-yl}methyl)-2H-indazol-5-carboxamide;

N-[2-(cyclopropylmethoxy)ethyl]-2-({1-[(4'-fluorobiphenyl-4-yl)carbonyl]piperidin-4-yl}methyl)-4-methyl-2H-indazol-5-carboxamide;

2-{[1-(4-cyclopropylbenzoyl)piperidin-4-yl]methyl}-N-[2-(cyclopropylmethoxy)ethyl]-4-methyl-2H-indazol-5-carboxamide;

2-{[1-(4-chlorobenzoyl)piperidin-4-yl]methyl}-4-methyl-N-[2-(2,2,2-trifluoroethoxy)-ethyl]-2H-indazol-5-carboxamide;

4-methyl-2-{[1-(4-methylbenzoyl)piperidin-4-yl]methyl}-N-[2-(2,2,2-trifluoroethoxy)-ethyl]-2H-indazol-5-carboxamide;

2-({1-[4-(4-fluorophenoxyl)benzoyl]piperidin-4-yl}methyl)-4-methyl-N-[2-(2,2,2-trifluoroethoxyl)ethyl]-2H-indazol-5-carboxamide;

4-methyl-N-[2-(2,2,2-trifluoroethoxyl)ethyl]-2-({1-[4-(trifluoromethyl)benzoyl]piperidin-4-yl}methyl)-2H-indazol-5-carboxamide;

2-({1-[(4'-fluorobiphenyl-4-yl)carbonyl]piperidin-4-yl}methyl)-4-methyl-N-[2-(2,2,2-trifluoroethoxyl)ethyl]-2H-indazol-5-carboxamide;

2-{[1-(4-cyclopropylbenzoyl)piperidin-4-yl]methyl}-4-methyl-N-[2-(2,2,2-trifluoro-ethoxy)ethyl]-2H-indazol-5-carboxamide;

2-{[1-(4-chlorobenzoyl)piperidin-4-yl]methyl}-N-(2-isopropoxyethyl)-4-methyl-2H-indazol-5-carboxamide;

N-(2-isopropoxyethyl)-4-methyl-2-{[1-(4-methylbenzoyl)piperidin-4-yl]methyl}-2H-indazol-5-carboxamide;

2-({1-[4-(4-fluorophenoxyl)benzoyl]piperidin-4-yl}methyl)-N-(2-isopropoxyethyl)-4-methyl-2H-indazol-5-carboxamide;

N-(2-isopropoxyethyl)-4-methyl-2-({1-[4-(trifluoromethyl)benzoyl]piperidin-4-yl}-methyl)-2H-indazol-5-carboxamide;

2-({1-[(4'-fluorobiphenyl-4-yl)carbonyl]piperidin-4-yl}methyl)-N-(2-isopropoxyethyl)-4-methyl-2H-indazol-5-carboxamide;

2-{[1-(4-cyclopropylbenzoyl)piperidin-4-yl]methyl}-N-(2-isopropoxyethyl)-4-methyl-2H-indazol-5-carboxamide;

2-{[1-(4-chlorobenzoyl)piperidin-4-yl]methyl}-4-methyl-N-[2-(trifluoromethoxy)ethyl]-2H-indazol-5-carboxamide;

2-({1-[4-(4-fluorophenoxyl)benzoyl]piperidin-4-yl}methyl)-4-methyl-N-[2-(trifluoro-methoxy)ethyl]-2H-indazol-5-carboxamide;

2-({1-[(4'-fluorobiphenyl-4-yl)carbonyl]piperidin-4-yl}methyl)-4-methyl-N-[2-(trifluoro-methoxy)ethyl]-2H-indazol-5-carboxamide;

4-methyl-N-[2-(trifluoromethoxy)ethyl]-2-[(1-{4-[4-(trifluoromethyl)phenoxy]benzoyl}-piperidin-4-yl)methyl]-2H-indazol-5-carboxamide;

N-(2-tert-butoxyethyl)-2-{[1-(4-chlorobenzoyl)piperidin-4-yl]methyl}-4-methyl-2H-indazol-5-carboxamide;

N-(2-tert-butoxyethyl)-2-({1-[4-(4-fluorophenoxyl)benzoyl]piperidin-4-yl}methyl)-4-methyl-2H-indazol-5-carboxamide;

N-(2-tert-butoxyethyl)-2-({1-[(4'-fluorobiphenyl-4-yl)carbonyl]piperidin-4-yl}methyl)-4-methyl-2H-indazol-5-carboxamide;

N-(2-tert-butoxyethyl)-4-methyl-2-[(1-{4-[4-(trifluoromethyl)phenoxy]benzoyl}-piperidin-4-yl)methyl]-2H-indazol-5-carboxamide;

2-{[1-(4-chlorobenzoyl)piperidin-4-yl]methyl}-4-methyl-N-{2-[($^2$H3)methyloxy]-($^2$H4)ethyl}-2H-indazol-5-carboxamide;

2-({1-[4-(4-fluorophenoxyl)benzoyl]piperidin-4-yl}methyl)-4-methyl-N-{2-[($^2$H3)methyloxy]($^2$H4)ethyl}-2H-indazol-5-carboxamide;

2-{[1-(4-chlorobenzoyl)azetidin-3-yl]methyl}-N-(2-methoxyethyl)-4-methyl-2H-indazol-5-carboxamide;

N-(2-methoxyethyl)-4-methyl-2-[(1-{4-[(trifluoromethyl)sulphanyl]benzoyl}azetidin-3-yl)methyl]-2H-indazol-5-carboxamide;

N-(2-methoxyethyl)-4-methyl-2-({1-[4-(trifluoromethoxy)benzoyl]azetidin-3-yl}methyl)-2H-indazol-5-carboxamide;

2-({1-[2-fluoro-4-(trifluoromethyl)benzoyl]azetidin-3-yl}methyl)-N-(2-methoxyethyl)-4-methyl-2H-indazol-5-carboxamide;

2-{[1-(4-chloro-2-fluorobenzoyl)azetidin-3-yl]methyl}-N-(2-methoxyethyl)-4-methyl-2H-indazol-5-carboxamide;

2-({1-[3-fluoro-4-(trifluoromethyl)benzoyl]azetidin-3-yl}methyl)-N-(2-methoxyethyl)-4-methyl-2H-indazol-5-carboxamide;

2-({1-[4-chloro-3-(trifluoromethyl)benzoyl]azetidin-3-yl}methyl)-N-(2-methoxyethyl)-4-methyl-2H-indazol-5-carboxamide;

2-{[1-(4-cyclopropylbenzoyl)azetidin-3-yl]methyl}-N-(2-methoxyethyl)-4-methyl-2H-indazol-5-carboxamide;

N-(2-methoxyethyl)-4-methyl-2-[(1-{4-[4-(trifluoromethyl)phenoxy]benzoyl}azetidin-3-yl)methyl]-2H-indazol-5-carboxamide;

2-{[1-(4-chlorobenzoyl)azetidin-3-yl]methyl}-4-methyl-N-(2,2,2-trifluoroethyl)-2H-indazol-5-carboxamide;

4-methyl-N-(2,2,2-trifluoroethyl)-2-({1-[4-(trifluoromethoxy)benzoyl]azetidin-3-yl}-methyl)-2H-indazol-5-carboxamide;

2-({1-[2-fluoro-4-(trifluoromethyl)benzoyl]azetidin-3-yl}methyl)-4-methyl-N-(2,2,2-trifluoroethyl)-2H-indazol-5-carboxamide;

4-methyl-2-({1-[4-(pentafluoro-$\lambda^6$-sulphanyl)benzoyl]azetidin-3-yl}methyl)-N-(2,2,2-trifluoroethyl)-2H-indazol-5-carboxamide;

N-[2-(cyclopropyloxy)ethyl]-4-methyl-2-({1-[4-(trifluoromethoxy)benzoyl]azetidin-3-yl}methyl)-2H-indazol-5-carboxamide;

N-[2-(cyclobutyloxy)ethyl]-4-methyl-2-({1-[4-(trifluoromethoxy)benzoyl]azetidin-3-yl}methyl)-2H-indazol-5-carboxamide;

2-{[1-(4-chlorobenzoyl)azetidin-3-yl]methyl}-N-[2-(cyclopropylmethoxy)ethyl]-4-methyl-2H-indazol-5-carboxamide;

N-[2-(cyclopropylmethoxy)ethyl]-2-({1-[4-(4-fluorophenoxyl)benzoyl]azetidin-3-yl}-methyl)-4-methyl-2H-indazol-5-carboxamide;

N-[2-(cyclopropylmethoxy)ethyl]-4-methyl-2-{[1-(4-methylbenzoyl)azetidin-3-yl]-methyl}-2H-indazol-5-carboxamide;

2-{[1-(4-chlorobenzoyl)azetidin-3-yl]methyl}-4-methyl-N-[2-(trifluoromethoxy)ethyl]-2H-indazol-5-carboxamide;

N-(2-tert-butoxyethyl)-2-{[1-(4-chlorobenzoyl)azetidin-3-yl]methyl}-4-methyl-2H-indazol-5-carboxamide;

N-[2-(cyclopropylmethoxy)ethyl]-2-({1-[(4'-fluorobiphenyl-4-yl)carbonyl]azetidin-3-yl}methyl)-4-methyl-2H-indazol-5-carboxamide;

2-({1-[(4'-fluorobiphenyl-4-yl)carbonyl]azetidin-3-yl}methyl)-N-(2-methoxyethyl)-4-methyl-2H-indazol-5-carboxamide;

2-({1-[4-(4-fluorophenoxyl)benzoyl]azetidin-3-yl}methyl)-N-(2-methoxyethyl)-4-methyl-2H-indazol-5-carboxamide;

2-({1-[4-(4-fluorophenoxyl)benzoyl]azetidin-3-yl}methyl)-4-methyl-N-(2,2,2-trifluoroethyl)-2H-indazol-5-carboxamide;

2-({1-[(4'-fluorobiphenyl-4-yl)carbonyl]azetidin-3-yl}methyl)-4-methyl-N-(2,2,2-trifluoroethyl)-2H-indazol-5-carboxamide;

2-{[1-(4-chlorobenzoyl)azetidin-3-yl]methyl}-4-methyl-N-[2-(2,2,2-trifluoroethoxy)-ethyl]-2H-indazol-5-carboxamide;

4-methyl-N-[2-(2,2,2-trifluoroethoxy)ethyl]-2-[(1-{4-[4-(trifluoromethyl)phenoxy]-benzoyl}azetidin-3-yl)methyl]-2H-indazol-5-carboxamide;

4-methyl-N-(2,2,2-trifluoroethyl)-2-[(1-{4-[4-(trifluoromethyl)phenoxy]benzoyl}-azetidin-3-yl)methyl]-2H-indazol-5-carboxamide;

2-({1-[4-(4-chlorophenoxyl)benzoyl]azetidin-3-yl}methyl)-4-methyl-N-(2,2,2-trifluoro-ethyl)-2H-indazol-5-carboxamide;

2-({1-[4-(4-chlorophenoxyl)benzoyl]azetidin-3-yl}methyl)-N-(2-methoxyethyl)-4-methyl-2H-indazol-5-carboxamide;

N-(2-methoxyethyl)-4-methyl-2-{[1-(4-{[5-(trifluoromethyl)pyridin-2-yl]oxy}-benzoyl)-azetidin-3-yl]methyl}-2H-indazol-5-carboxamide;

4-methyl-N-(2,2,2-trifluoroethyl)-2-{[1-(4-{[5-(trifluoromethyl)pyridin-2-yl]oxy}-benzoyl)azetidin-3-yl]methyl}-2H-indazol-5-carboxamide;

2-{[1-(4-chlorobenzoyl)piperidin-4-yl]methyl}-N-ethyl-4-methyl-2H-indazol-5-carboxamide;

2-({1-[4-(4-fluorophenoxyl)benzoyl]piperidin-4-yl}methyl)-4-methyl-N-(2,2,2-trifluoroethyl)-2H-indazol-5-carboxamide;

2-({1-[4-(4-chlorophenoxyl)benzoyl]piperidin-4-yl}methyl)-4-methyl-N-(2,2,2-trifluoroethyl)-2H-indazol-5-carboxamide;

4-methyl-2-({1-[4-(4-methylphenoxyl)benzoyl]piperidin-4-yl}methyl)-N-(2,2,2-trifluoroethyl)-2H-indazol-5-carboxamide;

2-({1-[(4'-fluorobiphenyl-4-yl)carbonyl]piperidin-4-yl}methyl)-4-methyl-N-(2,2,2-trifluoroethyl)-2H-indazol-5-carboxamide;

4-methyl-2-{[1-(4-morpholinobenzoyl)piperidin-4-yl]methyl}-N-(2,2,2-trifluoroethyl)-2H-indazol-5-carboxamide;

4-methyl-N-(2,2,2-trifluoroethyl)-2-[(1-{4-[(trifluoromethyl)sulphanyl]benzoyl}-piperidin-4-yl)methyl]-2H-indazol-5-carboxamide;

4-methyl-N-(2,2,2-trifluoroethyl)-2-[(1-{4-[4-(trifluoromethyl)phenoxy]benzoyl}-piperidin-4-yl)methyl]-2H-indazol-5-carboxamide;

4-methyl-N-(2,2,2-trifluoroethyl)-2-{[1-(4-{[5-(trifluoromethyl)pyridin-2-yl]oxy}-benzoyl)piperidin-4-yl]methyl}-2H-indazol-5-carboxamide;

4-methyl-N-(2,2,2-trifluoroethyl)-2-{[1-(4-{[6-(trifluoromethyl)pyridin-3-yl]oxy}-benzoyl)piperidin-4-yl]methyl}-2H-indazol-5-carboxamide;

4-methyl-N-(2,2,2-trifluoroethyl)-2-{[1-(4-{[6-(trifluoromethyl)pyridin-2-yl]oxy}-benzoyl)piperidin-4-yl]methyl}-2H-indazol-5-carboxamide;

2-({1-[4-(4-cyanophenoxyl)benzoyl]piperidin-4-yl}methyl)-4-methyl-N-(2,2,2-trifluoro-ethyl)-2H-indazol-5-carboxamide;

2-({1-[4-(3-fluorophenoxyl)benzoyl]piperidin-4-yl}methyl)-4-methyl-N-(2,2,2-trifluoro-ethyl)-2H-indazol-5-carboxamide;

4-methyl-N-(2,2,2-trifluoroethyl)-2-[(1-{4-[3-(trifluoromethyl)phenoxy]benzoyl}-piperidin-4-yl)methyl]-2H-indazol-5-carboxamide;

2-[(1-{4-[(5-cyanopyridin-2-yl)oxy]benzoyl}piperidin-4-yl)methyl]-4-methyl-N-(2,2,2-trifluoroethyl)-2H-indazol-5-carboxamide;

2-[(1-{4-[(5-chloropyridin-2-yl)oxy]benzoyl}piperidin-4-yl)methyl]-4-methyl-N-(2,2,2-trifluoroethyl)-2H-indazol-5-carboxamide;

4-methyl-N-(2,2,2-trifluoroethyl)-2-[(1-{4-[5-(trifluoromethyl)pyridin-2-yl]benzoyl}-piperidin-4-yl)methyl]-2H-indazol-5-carboxamide;

2-({1-[4(2,4-difluorophenoxy)benzoyl]piperidin-4-yl}methyl)-4-methyl-N-(2,2,2-trifluoroethyl)-2H-indazol-5-carboxamide;

2-({1-[4-(3,4-difluorophenoxy)benzoyl]piperidin-4-yl}methyl)-4-methyl-N-(2,2,2-trifluoroethyl)-2H-indazol-5-carboxamide;

4-methyl-N-(2,2,2-trifluoroethyl)-2-[(1-{[4'-(trifluoromethyl)biphenyl-4-yl]carbonyl}-piperidin-4-yl)methyl]-2H-indazol-5-carboxamide;

2 {[1-(4-bromobenzoyl)piperidin-4-yl]methyl}-4-methyl-N-(2,2,2-trifluoroethyl)-2H-indazol-5-carboxamide;

2 ({1-[4-(5-chloropyridin-2-yl)benzoyl]piperidin-4-yl}methyl)-4-methyl-N-(2,2,2-trifluoroethyl)-2H-indazol-5-carboxamide;

2-({1-[(4'-methoxy-2'-methylbiphenyl-4-yl)carbonyl]piperidin-4-yl}methyl)-4-methyl-N-(2,2,2-trifluoroethyl)-2H-indazol-5-carboxamide;

4-methyl-2-({1-[4-(6-methylpyridin-3-yl)benzoyl]piperidin-4-yl}methyl)-N-(2,2,2-trifluoroethyl)-2H-indazol-5-carboxamide;

2-({1-[(4'-fluoro-T-methoxybiphenyl-4-yl)carbonyl]piperidin-4-yl}methyl)-4-methyl-N-(2,2,2-trifluoroethyl)-2H-indazol-5-carboxamide;

4-methyl-N-(2,2,2-trifluoroethyl)-2-[(1-{4-[6-(trifluoromethyl)pyridin-3-yl]benzoyl}-piperidin-4-yl)methyl]-2H-indazol-5-carboxamide;

2-({1-[4-(6-methoxypyridin-3-yl)benzoyl]piperidin-4-yl}methyl)-4-methyl-N-(2,2,2-trifluoroethyl)-2H-indazol-5-carboxamide;

2 ({1-[4-(6-methoxypyridin-2-yl)benzoyl]piperidin-4-yl}methyl)-4-methyl-N-(2,2,2-trifluoroethyl)-2H-indazol-5-carboxamide;

4-methyl-2-({1-[4-(5-methylpyridin-2-yl)benzoyl]piperidin-4-yl}methyl)-N-(2,2,2-trifluoroethyl)-2H-indazol-5-carboxamide;

2 ({1-[4-(5-fluoropyridin-2-yl)benzoyl]piperidin-4-yl}methyl)-4-methyl-N-(2,2,2-trifluoroethyl)-2H-indazol-5-carboxamide;

2 ({1-[4-(5-methoxypyridin-2-yl)benzoyl]piperidin-4-yl}methyl)-4-methyl-N-(2,2,2-trifluoroethyl)-2H-indazol-5-carboxamide;

4-methyl-2-({1-[4-(2-methylpyrimidin-5-yl)benzoyl]piperidin-4-yl}methyl)-N-(2,2,2-trifluoroethyl)-2H-indazol-5-carboxamide;

4-methyl-N-(2,2,2-trifluoroethyl)-2-[(1-{4-[2-(trifluoromethyl)pyrimidin-5-yl]benzoyl}-piperidin-4-yl)methyl]-2H-indazol-5-carboxamide;

4 methyl-N-(2,2,2-trifluoroethyl)-2-[(1-{4-[6-(trifluoromethyl)pyridin-2-yl]benzoyl}-piperidin-4-yl)methyl]-2H-indazol-5-carboxamide;

2-({1-[4-(4-cyanophenoxy)benzoyl]piperidin-4-yl}methyl)-N-(2-methoxyethyl)-4-methyl-2H-indazol-5-carboxamide;

2-{[1-(4-bromo-3-methylbenzoyl)piperidin-4-yl]methyl}-N-(2-methoxyethyl)-4-methyl-2H-indazol-5-carboxamide;

2-{[1-(4-tert-butylbenzoyl)piperidin-4-yl]methyl}-N-(2-methoxyethyl)-4-methyl-2H-indazol-5-carboxamide;

2-({1-[4-(1-hydroxy-1-methylethyl)benzoyl]piperidin-4-yl}methyl)-N-(2-methoxy-ethyl)-4-methyl-2H-indazol-5-carboxamide;

2-{[1-(4-cyclohexylbenzoyl)piperidin-4-yl]methyl}-N-(2-methoxyethyl)-4-methyl-2H-indazol-5-carboxamide;

2-({1-[4-(1-cyano-1-methylethyl)benzoyl]piperidin-4-yl}methyl)-N-(2-methoxyethyl)-4-methyl-2H-indazol-5-carboxamide;

N-(2-methoxyethyl)-4-methyl-2-({1-[4-(pyrimidin-2-yloxy)benzoyl]piperidin-4-yl}-methyl)-2H-indazol-5-carboxamide;

N-(2-methoxyethyl)-4-methyl-2-({1-[4-(3-pyridyloxy)benzoyl]piperidin-4-yl}methyl)-2H-indazol-5-carboxamide;

N-(2-methoxyethyl)-4-methyl-2-{[1-(4-{[5-(trifluoromethyl)pyridin-2-yl]oxy}benzoyl)-piperidin-4-yl]methyl}-2H-indazol-5-carboxamide;

N-(2-methoxyethyl)-4-methyl-2-({1-[4-(2-pyridyloxy)benzoyl]piperidin-4-yl}methyl)-2H-indazol-5-carboxamide;

N-(2-methoxyethyl)-4-methyl-2-{[1-(4-{[4-(trifluoromethyl)pyrimidin-2-yl]oxy}-benzoyl)piperidin-4-yl]methyl}-2H-indazol-5-carboxamide;

N-(2-methoxyethyl)-4-methyl-2-{[1-(4-{[6-(trifluoromethyl)pyridin-3-yl]oxy}benzoyl)-piperidin-4-yl]methyl}-2H-indazol-5-carboxamide;

N-(2-methoxyethyl)-4-methyl-2-{[1-(4-{[6-(trifluoromethyl)pyridin-2-yl]oxy}benzoyl)-piperidin-4-yl]methyl}-2H-indazol-5-carboxamide;

2-({1-[(4'-methoxybiphenyl-4-yl)carbonyl]piperidin-4-yl}methyl)-N-(2-methoxyethyl)-4-methyl-2H-indazol-5-carboxamide;

N-(2-methoxyethyl)-4-methyl-2-({1-[4-(3,4,5,6-tetrahydro-2H-pyran-4-yloxy)benzoyl]-piperidin-4-yl}methyl)-2H-indazol-5-carboxamide;

N-(2-methoxyethyl)-4-methyl-2-[(1-{4-[3-(trifluoromethyl)phenoxy]benzoyl}piperidin-4-yl)methyl]-2H-indazol-5-carboxamide;

2-[(1-{4-[(5-cyanopyridin-2-yl)oxy]benzoyl}piperidin-4-yl)methyl]-N-(2-methoxy-ethyl)-4-methyl-2H-indazol-5-carboxamide;

2-[(1-{4-[(5-chloropyridin-2-yl)oxy]benzoyl}piperidin-4-yl)methyl]-N-(2-methoxy-ethyl)-4-methyl-2H-indazol-5-carboxamide;

2-({1-[4-(2,4-difluorophenoxy)benzoyl]piperidin-4-yl}methyl)-N-(2-methoxyethyl)-4-methyl-2H-indazol-5-carboxamide;

2-({1-[4-(3,4-difluorophenoxy)benzoyl]piperidin-4-yl}methyl)-N-(2-methoxyethyl)-4-methyl-2H-indazol-5-carboxamide;

N-(2-methoxyethyl)-4-methyl-2-[(1-{[4'-(trifluoromethyl)biphenyl-4-yl]carbonyl}-piperidin-4-yl)methyl]-2H-indazol-5-carboxamide;

2-({1-[4-(3-fluorophenoxy)benzoyl]piperidin-4-yl}methyl)-N-(2-methoxyethyl)-4-methyl-2H-indazol-5-carboxamide;

2-{[1-(2-fluoro-4-isopropoxybenzoyl)piperidin-4-yl]methyl}-N-(2-methoxyethyl)-4-methyl-2H-indazol-5-carboxamide;

2-({1-[(3-fluoro-3',4'-dimethylbiphenyl-4-yl)carbonyl]piperidin-4-yl}methyl)-N-(2-methoxyethyl)-4-methyl-2H-indazol-5-carboxamide;

2-({1-[(2',3-difluoro-4'-methoxybiphenyl-4-yl)carbonyl]piperidin-4-yl}methyl)-N-(2-methoxyethyl)-4-methyl-2H-indazol-5-carboxamide;

2-({1-[4-(difluoromethoxy)benzoyl]piperidin-4-yl}methyl)-N-(2-methoxyethyl)-4-methyl-2H-indazol-5-carboxamide;

2-({1-[4-(2-fluorophenoxy)benzoyl]piperidin-4-yl}methyl)-N-(2-methoxyethyl)-4-methyl-2H-indazol-5-carboxamide;

2-({1-[(4'-cyano-2'-methylbiphenyl-4-yl)carbonyl]piperidin-4-yl}methyl)-N-(2-methoxyethyl)-4-methyl-2H-indazol-5-carboxamide;

2-({1-[4-(5-chloropyridin-2-yl)benzoyl]piperidin-4-yl}methyl)-N-(2-methoxyethyl)-4-methyl-2H-indazol-5-carboxamide;

N-(2-methoxyethyl)-4-methyl-2-[(1-{4-[6-(trifluoromethyl)pyridin-2-yl]benzoyl}-piperidin-4-yl)methyl]-2H-indazol-5-carboxamide;

N-(2-methoxyethyl)-2-({1-[(4'-methoxy-2'-methylbiphenyl-4-yl)carbonyl]piperidin-4-yl}methyl)-4-methyl-2H-indazol-5-carboxamide;

2-({1-[(4'-chloro-2'-methylbiphenyl-4-yl)carbonyl]piperidin-4-yl}methyl)-N-(2-methoxyethyl)-4-methyl-2H-indazol-5-carboxamide;

2 [(1-{[4'-(1-cyano-1-methylethyl)biphenyl-4-yl]carbonyl}piperidin-4-yl)methyl]-N-(2-methoxyethyl)-4-methyl-2H-indazol-5-carboxamide;

N-(2-methoxyethyl)-2-({1-[4-(5-methoxypyridin-2-yl)benzoyl]piperidin-4-yl}methyl)-4-methyl-2H-indazol-5-carboxamide;

N-(2-methoxyethyl)-4-methyl-2-[(1-{4-[6-(trifluoromethyl)pyridin-3-yl]benzoyl}-piperidin-4-yl)methyl]-2H-indazol-5-carboxamide;

N-(2-methoxyethyl)-2-({1-[4-(6-methoxypyridin-3-yl)benzoyl]piperidin-4-yl}methyl)-4-methyl-2H-indazol-5-carboxamide;

2-({1-[(4'-fluoro-2'-methylbiphenyl-4-yl)carbonyl]piperidin-4-yl}methyl)-N-(2-methoxyethyl)-4-methyl-2H-indazol-5-carboxamide;

N-(2-methoxyethyl)-4-methyl-2-({1-[4-(6-methylpyridin-3-yl)benzoyl]piperidin-4-yl}-methyl)-2H-indazol-5-carboxamide;

N-(2-methoxyethyl)-2-({1-[4-(6-methoxypyridin-2-yl)benzoyl]piperidin-4-yl}methyl)-4-methyl-2H-indazol-5-carboxamide;

N-(2-methoxyethyl)-4-methyl-2-({1-[4-(2-methylpyrimidin-5-yl)benzoyl]piperidin-4-yl}methyl)-2H-indazol-5-carboxamide;

2-({1-[(4'-fluoro-2'-methoxybiphenyl-4-yl)carbonyl]piperidin-4-yl}methyl)-N-(2-methoxyethyl)-4-methyl-2H-indazol-5-carboxamide;

2-({1-[(4'-chloro-2'-methoxybiphenyl-4-yl)carbonyl]piperidin-4-yl}methyl)-N-(2-methoxyethyl)-4-methyl-2H-indazol-5-carboxamide;

N-(2-methoxyethyl)-4-methyl-2-[(1-{4-[2-(trifluorom-ethyl)pyrimidin-5-yl]benzoyl}-piperidin-4-yl)methyl]-2H-indazol-5-carboxamide;

2-({1-[(4'-chloro-2'-fluorobiphenyl-4-yl)carbonyl]piperidin-4-yl}methyl)-N-(2-methoxy-ethyl)-4-methyl-2H-indazol-5-carboxamide;

2-({1-[(2'-chloro-4'-fluorobiphenyl-4-yl)carbonyl]piperidin-4-yl}methyl)-N-(2-methoxy-ethyl)-4-methyl-2H-indazol-5-carboxamide;

2-({1-[4-(5-chloropyridin-3-yl)benzoyl]piperidin-4-yl}methyl)-N-(2-methoxyethyl)-4-methyl-2H-indazol-5-carboxamide;

2-({1-[4-(5-fluoropyridin-3-yl)benzoyl]piperidin-4-yl}methyl)-N-(2-methoxyethyl)-4-methyl-2H-indazol-5-carboxamide;

N-(2-methoxyethyl)-4-methyl-2-[(1-{4-[5-(trifluorom-ethyl)pyridin-3-yl]benzoyl}-piperidin-4-yl)methyl]-2H-indazol-5-carboxamide;

2-[(1-{[4'-(1-hydroxy-1-methylethyl)biphenyl-4-yl]carbonyl}piperidin-4-yl)methyl]-N-(2-methoxyethyl)-4-methyl-2H-indazol-5-carboxamide;

2-({1-[(3',5'-difluorobiphenyl-4-yl)carbonyl]piperidin-4-yl}methyl)-N-(2-methoxy-ethyl)-4-methyl-2H-indazol-5-carboxamide;

2-({1-[(4'-fluoro-2-methylbiphenyl-4-yl)carbonyl]piperidin-4-yl}methyl)-N-(2-methoxy-ethyl)-4-methyl-2H-indazol-5-carboxamide;

2-({1-[(3',5'-difluoro-2-methylbiphenyl-4-yl)carbonyl]piperidin-4-yl}methyl)-N-(2-methoxyethyl)-4-methyl-2H-indazol-5-carboxamide;

N-(2-methoxyethyl)-4-methyl-2-({1-[3-methyl-4-(3-pyridyl)benzoyl]piperidin-4-yl}-methyl)-2H-indazol-5-carboxamide;

N-(2-methoxyethyl)-4-methyl-2-({1-[3-methyl-4-(4-pyridyl)benzoyl]piperidin-4-yl}-methyl)-2H-indazol-5-carboxamide; or N-(2-methoxyethyl)-4-methyl-2-({1-[(2-methylbiphenyl-4-yl)carbonyl]piperidin-4-yl}-methyl)-2H-indazol-5-carboxamide.

7. A composition comprising a compound according to claim 1 and a COX inhibitor, wherein the COX inhibitors can be selected from the following list: aspirin, naproxen, indomethacin, meloxicam, ibuprofen, ketoprofen, piroxicam, tenoxicam, nimesulide, mefanemic acid, ketoralac, celecoxib (4-[5-(4-methylphenyl)-3-(trifluoromethyl)-1H-pyrazol-1-yl]benzenesulphonamide), parecoxib (N-[4-(5-methyl-3-phenyl-4-isoxazolyl)phenyl]sulphonylpropionamide), rofecoxib (4-(4-mesylphenyl)-3-phenylfuran-(5H)-one), valdecoxib (4-[5-methyl-3-phenyl-4-isoxazolyl)benzenesulphonamide), NS-398 (N-methyl-2-cyclohexanoxy-4-nitrobenzene-sulphonamide), lumiracoxib [2-(2'-chloro-6'-fluorophenyl)-amino-5-methylbenzene-acetic acid], ceracoxib and etoricoxib.

8. Method for the preparation of a compound according to claim 1, characterized in that a compound of the general formula (VIII)

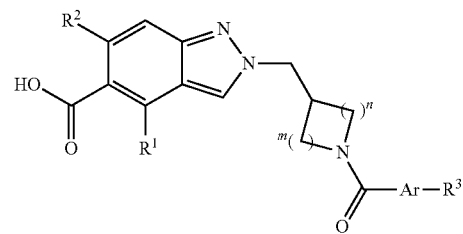

(VIII)

is reacted with an amine of the general formula (XI)

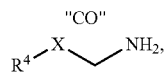

(XI)

where $R^1$, $R^2$, $R^3$, $R^4$, X, Ar, m and n have the meaning stated in claim 1;
or characterized in that
a compound of the general formula (VI)

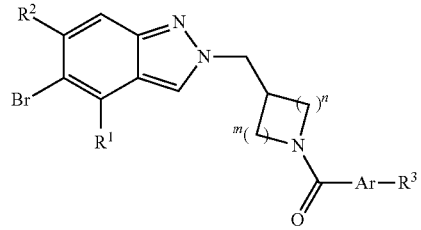

(VI)

is reacted with an amine of the general formula (XI), where $R^1$, $R^2$, $R^3$, $R^4$, X, Ar, m and n have the meaning stated in claim 1, and carbon monoxide or a carbon monoxide source such as for example molybdenum hexacarbonyl, under palladium(0) catalysis;
or characterized in that
a compound of the general formula (XV)

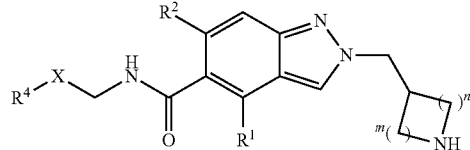

(XV)

is reacted with a carboxylic acid (Y=OH), a carboxylic acid chloride (Y=Cl) or anhydride (Y=O—C(O)—O—CH$_2$(CH$_3$)CH$_3$) of the general formula (IX)

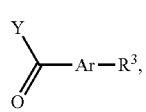

(IX)

where $R^1$, $R^2$, $R^3$, $R^4$, X, Ar, m, n have the meaning stated in claim 1;

or characterized in that
a compound of the general formula (XVI)

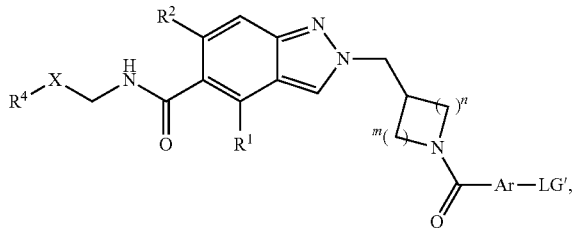

(XVI)

wherein LG' means Br or I, is reacted with a boronic acid or a boronic acid ester of the general formula (XVIII)

Met-R$^3$ (XVIII)

where R$^1$, R$^2$, R$^3$, R$^4$, X, Ar, m and n have the meaning stated in claim 1.

9. A method of fertility control/contraception; direct treatment of diseases and conditions selected from: endometriosis, menstrual problems having severe and persistent bleeding, menstrual problems having irregular bleeding and pain, fibroids, myomas, lung cancer, intestinal cancer, breast cancer, skin cancer, prostate cancer, esophageal cancer, leukemia, arteriosclerosis; a neurodegenerative disease, neuroinflammatory disease, or ischemic disease selected from Alzheimer's disease, Parkinson's disease, ALS, stroke and multiple sclerosis; polycystic kidney disease, pain, inflammatory hyperalgesia, infectious diseases of the lung, chronic obstructive pulmonary diseases, intestinal inflammatory diseases, Crohn's disease, ulcerative colitis, pathological eye diseases, Graves' disease, aneurysms, vascular damage, Kawasaki syndrome, and arthritis, comprising the step of administering a therapeutically effective amount of the compound according to claim 1 to a patient in need thereof.

* * * * *